(12) United States Patent
Biasci et al.

(10) Patent No.: US 12,285,484 B2
(45) Date of Patent: Apr. 29, 2025

(54) CANCER ASSOCIATED ANTIBODY COMPOSITIONS AND METHODS OF USE

(71) Applicant: Absci Corporation, Vancouver, WA (US)

(72) Inventors: Daniele Biasci, Cambridge, MA (US); Ines De Santiago Domingos De Jesus, Cambridge, MA (US); Berke Cagkan Toptas, Cambridge, MA (US)

(73) Assignee: ABSCI CORPORATION, Vancouver, WA (US)

( * ) Notice: Subject to any disclaimer, the term of this patent is extended or adjusted under 35 U.S.C. 154(b) by 1030 days.

(21) Appl. No.: 17/277,214

(22) PCT Filed: Sep. 19, 2019

(86) PCT No.: PCT/US2019/051967
§ 371 (c)(1),
(2) Date: Mar. 17, 2021

(87) PCT Pub. No.: WO2020/061337
PCT Pub. Date: Mar. 26, 2020

(65) Prior Publication Data
US 2022/0031841 A1 Feb. 3, 2022

Related U.S. Application Data

(60) Provisional application No. 62/733,444, filed on Sep. 19, 2018, provisional application No. 62/733,443, filed on Sep. 19, 2018, provisional application No. 62/733,435, filed on Sep. 19, 2018.

(51) Int. Cl.
| | |
|---|---|
| A61K 39/39 | (2006.01) |
| A61K 39/395 | (2006.01) |
| A61K 45/06 | (2006.01) |
| A61N 5/10 | (2006.01) |
| A61P 35/00 | (2006.01) |
| C07K 14/725 | (2006.01) |
| C07K 16/18 | (2006.01) |
| C07K 16/24 | (2006.01) |
| C07K 16/26 | (2006.01) |
| C07K 16/30 | (2006.01) |
| C07K 16/40 | (2006.01) |
| G01N 33/574 | (2006.01) |

(52) U.S. Cl.
CPC ........ *A61K 39/39575* (2013.01); *A61K 45/06* (2013.01); *A61N 5/10* (2013.01); *A61P 35/00* (2018.01); *C07K 14/7051* (2013.01); *C07K 16/18* (2013.01); *C07K 16/244* (2013.01); *C07K 16/26* (2013.01); *C07K 16/30* (2013.01); *C07K 16/3069* (2013.01); *C07K 16/40* (2013.01); *G01N 33/57484* (2013.01); *A61N 2005/1098* (2013.01); *C07K 2317/56* (2013.01); *C07K 2317/565* (2013.01)

(58) Field of Classification Search
CPC .... A61K 39/39575; A61K 45/06; A61N 5/10; A61N 2005/1098; A61P 35/00; C07K 14/7051; C07K 16/18; C07K 16/244; C07K 16/26; C07K 16/30; C07K 16/3069; C07K 16/40; C07K 2317/56; C07K 2317/565; G01N 33/57484
See application file for complete search history.

(56) References Cited

U.S. PATENT DOCUMENTS

| | | |
|---|---|---|
| 2009/0162378 A1 | 6/2009 | Lai et al. |
| 2009/0269840 A1 | 10/2009 | Popplewell et al. |
| 2009/0304590 A1 | 12/2009 | Gill et al. |
| 2010/0158922 A1 | 6/2010 | Ferlin et al. |
| 2012/0184716 A1 | 7/2012 | Fischer et al. |
| 2013/0058864 A1 | 3/2013 | Veiby et al. |
| 2016/0289727 A1 | 10/2016 | Magistrelli et al. |
| 2018/0186893 A1 | 7/2018 | Lenferink et al. |

FOREIGN PATENT DOCUMENTS

WO 2008/063346 A2 5/2008

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79):18294-18302, 2011).*
Mashidori et al., Increased alpha-taxilin protein expression is associated with the metastatic and invasive potential of renal cell cancer, Biomed. Res., 32(2): 103-110, (Apr. 2011).
Rakocevic et al., The landscape of high-affinity human antibodies against intratumoral antigens, BioRxiv, (Feb. 2021).
Akahori, et al., Homo sapiens IGL mRNA For Immunoglobulin Lambda Light Chain VLJ Region, Partial Cds, Clone: L89., National Center for Biotechnology Information, (Jul. 26, 2016).
Akahori, et al., Immunoglobulin Lambda Light Chain VLJ Region, Partial [*Homo sapiens*], National Center for Biotechnology Information, (Jul. 26, 2020).
Bolotin et al., Antigen receptor repertoire profiling from RNA-seq data, Nature Biotechnology, 35(10):908-911 (2017).
Bolotin et al., MiXCR: software for comprehensive adaptive immunity profiling, Nature Methods, 12(5):380-1 (2015).

(Continued)

*Primary Examiner* — Nelson B Moseley, II
(74) *Attorney, Agent, or Firm* — MARSHALL, GERSTEIN & BORUN LLP

(57) ABSTRACT

The disclosure herein relates to novel cancer-associated antibodies that are used in the treatment and diagnosis of a cancer. The complete polypeptide and nucleic acid consensus sequences of the antibodies disclosed herein are reconstructed in silico.

17 Claims, 46 Drawing Sheets
Specification includes a Sequence Listing.

(56) References Cited

OTHER PUBLICATIONS

Chao et al., Entropy and the species accumulation curve: a novel entropy estimator via discovery rates of new species, Methods in Ecology and Eiiolution, 4(11):1091-1100 (2013).
European Application No. 19861397.8, European Search Report and Opinion, mailed Sep. 7, 2022.
Heiden et al., pRESTO: a toolkit for processing high-throughput sequencing raw reads of lymphocyte receptor repertoires, Bioinformatics, 30(13):1930-1932 (2014).
International Application No. PCT/US19/51967, International Preliminary Report on Patentability, mailed Apr. 1, 2021.
International Application No. PCT/US19/51967, International Search Report and Written Opinion, mailed Feb. 7, 2020.
Jin, et al., *Homo sapiens* Clone IP3797 Immunoglobulin Heavy Chain mRNA, Partial Cds, National Center for Biotechnology Information, (Sep. 22, 2012).
Macarthur, Patterns Of Species Diversity, Biological reviews, 40(4):510-533 (1965).
Minici, C. et al., Distinct homotypic B-cell receptor interactions shape the outcome of chronic lymphocytic leukaemia, Nature Communications, 8(15746):1-14 (2017).
Ohtomo, N., et al., Expression of [alpha]-taxilin in hepatocellular carcinoma correlates with growth activity and malignant potential of the tumor, International Journal of Oncology, 37(6):1417-1423 (2010).
Peng, X., et al., Characteristics of a novel monoclonal antibody against interleukin-14a, Hybridoma, 28(4):235-239 (2009).
Safonova et al., IgRepertoireConstructor: a novel algorithm for antibody repertoire construction and immunoproteogenomics analysis, Bioinformatics, 31(12):i53-i61 (2015).
Sattler, M. et al., SHIP1, an SH2 Domain Containing Polyinositol-5-phosphatase, Regulates Migration through Two Critical Tyrosine Residues and Forms a Novel Signaling Complex with DOK1 and CRKL, Journal of Biological Chemistry, 276(4):2451-2458 (2001).
Shugay et al., VDJtools: Unifying Post-analysis of T Cell Receptor Repertoires, PLoS Computational Biology, 11(11):e1004503 (2015).
Stubbington et al., T cell fate and clonality inference from single cell transcriptomes, Nat Methods., 13(4):329-332, (2016).
Ye et al., IgBLAST: an immunoglobulin variable domain sequence analysis tool, Nucleic Acids Research, 41(Web Server issue):W34-40 (2013).

\* cited by examiner

```
--IGHV2-5*00--
TGGACCCTGTGGACACAGCCACATATTACTGTGCACACAGAC
||||||||||||||||||||||||||||||||||||||
TGGACCCCTGTGGACACAGCCACATATTTTGTGCACACAGAGAACAAGAGAACCTTCAGTAGTATTCGGAATGGTTCGACCCCTGGGCCCTGGGGCCAGGGCACCCTGG
                                                                              ||||||||||||||||||||  |||||
                                                                         ACAACTGGTTCGACTCCTGGGGCCAAGGAACCTGGTCACCCTCTCCTCAG
                                                                                                      --IGHJ5*00--
```

FIG. 7

| Name | Heavy V | HeavyJ | HeavyC | LightV | Light J | Light C |
|---|---|---|---|---|---|---|
| TMEL1001 | 0.07 | 0.12 | 0.01 | 0.04 | 0.13 | 0.01 |
| TMEL1002 | 0.05 | 0.17 | 0.03 | 0.06 | 0.10 | 0.01 |
| TMEL1003 | 0.03 | 0.14 | 0.01 | 0.02 | 0.10 | 0.02 |
| TMEL1004 | 0.05 | 0.19 | 0.01 | 0.03 | 0.13 | 0.01 |
| TMEL1005 | 0.06 | 0.12 | 0.01 | 0.04 | 0.08 | 0.01 |

FIG. 10

SEQUENCE LISTING

<160> NUMBER OF SEQ ID NOS: 345

<210> SEQ ID NO 1
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Cys Glu Val Gln Leu Val Glu Ser Gly Gly Gly Leu Val Lys Pro Gly
1               5                   10                  15

Gly Ser Leu Arg Leu Ser Cys Ala Ala Ser Gly Phe Thr Phe Arg Ser
            20                  25                  30

Tyr Ser Met Asn Trp Val Arg Gln Ala Pro Gly Lys Gly Leu Glu Trp
        35                  40                  45

Val Ser Ser Ile Ser Ser Ser Gly Asn Tyr Ile Tyr Tyr Ala Asp Ser
    50                  55                  60

Val Lys Gly Arg Phe Thr Leu Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Gly Gly Gly Thr Ser Trp Ser His Tyr Trp Gly Gln Gly
            100                 105                 110

Thr Leu Val Thr Val Ser Ser Ala Ser Thr Lys Gly Pro Ser Val Phe
        115                 120                 125

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Ser Glu
    210                 215
```

<210> SEQ ID NO 2
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Val Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ala Tyr Asp Ser Ser Gly Pro Asp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val
    210                 215                 220
```

<210> SEQ ID NO 3
<211> LENGTH: 225
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Ala Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Arg Ile Asp Pro Ser Asp Ser Tyr Thr Asn Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Thr Ser Asp Thr Ala Met Tyr Tyr Cys
                85                  90                  95

Ala Arg Pro Leu Gln Thr Tyr Ser Ile Ala Ser Val Gly His Trp Gly
            100                 105                 110

Gln Gly Thr Leu Val Thr Val Ser Ser Gly Ser Ala Ser Ala Pro Thr
        115                 120                 125

Leu Phe Pro Leu Val Ser Cys Glu Asn Ser Pro Ser Asp Thr Ser Ser
    130                 135                 140

Val Ala Val Gly Cys Leu Ala Gln Asp Phe Leu Pro Asp Ser Ile Thr
145                 150                 155                 160

Phe Ser Trp Lys Tyr Lys Asn Asn Ser Asp Ile Ser Ser Thr Arg Gly
                165                 170                 175

Phe Pro Ser Val Leu Arg Gly Gly Lys Tyr Ala Ala Thr Ser Gln Val
            180                 185                 190

Leu Leu Pro Ser Lys Asp Val Met Gln Gly Thr Asp Glu His Val Val
        195                 200                 205

Cys Lys Val Gln His Pro Asn Gly Asn Lys Glu Lys Asn Val Pro Leu
    210                 215                 220

Pro
225
```

<210> SEQ ID NO 4
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Thr Pro
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asp Asp Asp Lys Arg Tyr Arg Pro Ser
    50                  55                  60

Leu Glu Ser Arg Leu Thr Ile Thr Lys Asp Thr Ser Lys Asn His Val
65                  70                  75                  80

Val Leu Thr Met Thr Asn Met Asp Pro Val Asp Thr Ala Thr Tyr Phe
                85                  90                  95

Cys Ala His Lys Asn Leu Gln Tyr Ser Glu Trp Phe Asp Pro Trp Gly
```

```
                        100                 105                 110
Gln Gly Thr Leu Val Ile Val Ser Ser Ala Ser Thr Lys Gly Pro Ser
                    115                 120                 125
Val Phe Pro Leu Ala Pro Cys Ser Arg Ser Thr Ser Glu Ser Thr Ala
            130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Lys Thr Tyr Thr Cys Asn Val Asp His
                195                 200                 205
Lys Pro Ser Asn Thr Lys Val Asp Lys Arg Val
            210                 215
```

<210> SEQ ID NO 5
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Pro Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Met Ser Ile Arg
            20                  25                  30
Ser Ser Tyr Trp Gly Trp Ile Arg Gln Ser Pro Gly Lys Gly Leu Glu
        35                  40                  45
Trp Ile Gly His Ile Phe Tyr Ser Gly Ser Thr Tyr Tyr Asn Pro Ser
    50                  55                  60
Leu Gln Ser Arg Val Thr Ile Leu Val Asp Thr Ser Lys Asn Gln Phe
65                  70                  75                  80
Ser Leu Arg Leu Ser Ser Val Thr Ala Ala Asp Thr Ala Val Tyr Tyr
                85                  90                  95
Cys Val Arg Ser Phe Gly Val Ala Arg Trp Asp Phe Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val
    210                 215
```

<210> SEQ ID NO 6
<211> LENGTH: 220

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Val Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Arg Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Arg Thr His Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Glu Ile Gly Lys Tyr Gly Thr Pro Thr Leu Phe Gln His Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val
    210                 215                 220

<210> SEQ ID NO 7
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

His Val His Leu Val Gln Ser Gly Ala Glu Val Lys Lys Pro Gly Ser
1               5                   10                  15

Ser Val Lys Val Ser Cys Thr Ala Ser Gly Gly Ser Phe Ser Ser Asn
            20                  25                  30

Pro Ile Ser Trp Val Arg Gln Ala Pro Gly His Gly Leu Gln Trp Met
        35                  40                  45

Gly Gly Phe Val Pro Leu Phe Gly Thr Ala Asn Tyr Ala Pro Ser Phe
    50                  55                  60

His Gly Arg Leu Thr Ile Thr Ala Asp Glu Ser Thr Ser Thr Thr Tyr
65                  70                  75                  80

Met Glu Leu Asn Ser Leu Arg Ser Glu Asp Ser Ala Val Tyr Tyr Cys
                85                  90                  95
```

Ala Arg Asp Phe Asn Trp Asn Phe Asp Phe Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Ser Glu
            210                 215

<210> SEQ ID NO 8
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Arg Asp
            20                  25                  30

Gly Ile Ile Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Ile Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Glu Val Gly Arg Gly Met Asp Val Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Ser Glu
            210                 215

<210> SEQ ID NO 9

```
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Pro Val Gln Leu Val Gln Ser Gly Ala Glu Val Lys Lys Pro Gly Ser
1               5                   10                  15

Ser Val Lys Val Ser Cys Arg Ala Ser Gly Thr Phe Ser Asn Tyr
            20                  25                  30

Gly Leu Asn Trp Val Arg Gln Ala Pro Gly Gln Gly Leu Glu Trp Met
        35                  40                  45

Gly Gly Ile Ile Pro Ile Phe Gly Ser Val Asn Tyr Ala Gln Lys Phe
    50                  55                  60

Gln Asp Arg Val Thr Ile Thr Ala Asp Glu Ser Ser Thr Thr Tyr
65                  70                  75                  80

Met Asp Leu Asn Ser Leu Arg Ser Glu Asp Thr Ala Val Tyr Tyr Cys
                85                  90                  95

Ala Thr Glu Arg Gly His Asn Met Glu Arg Ala Phe Asp Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val
    210                 215

<210> SEQ ID NO 10
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Lys Lys Leu
    50                  55                  60

Gln Gly Arg Val Thr Met Thr Thr Asp Thr Ser Thr Ser Thr Ala Tyr
65                  70                  75                  80

Leu Glu Leu Arg Ser Leu Arg Ser Asp Asp Thr Ala Val Tyr Tyr Cys
                85                  90                  95
```

```
Ala Arg Gly Asp Gly Pro Phe Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val
    210

<210> SEQ ID NO 11
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Pro Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ser Phe Asn Trp Val Arg Gln Ala Pro Gly Gln Gly Leu Glu Trp Met
        35                  40                  45

Ala Arg Ile Ile Pro Ile Leu Gly Leu Ala Asn Tyr Ala Gln Lys Phe
    50                  55                  60

Gln Gly Arg Val Thr Leu Thr Ala Asp Glu Ser Thr Ser Thr Ala Tyr
65                  70                  75                  80

Met Glu Leu Ser Ser Leu Arg Ser Glu Asp Thr Ala Ile Phe Tyr Cys
                85                  90                  95

Ala Gly Met Val Leu Gly Gln Leu Gly Phe Asp Pro Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val
    210                 215
```

<210> SEQ ID NO 12
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Pro Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Thr Thr
            20                  25                  30

Tyr Tyr Trp Gly Trp Ile Arg Gln Pro Pro Gly Lys Gly Leu Glu Trp
        35                  40                  45

Ile Ala Ser Ile Tyr Phe Thr Gly Ser Thr Phe His Asn Pro Ser Leu
    50                  55                  60

Lys Ser Arg Val Thr Met Ser Val Asp Thr Ser Lys Asn Gln Phe Ser
65                  70                  75                  80

Leu Asn Leu Ser Ser Val Thr Ala Ala Asp Thr Ala Val Tyr Tyr Cys
                85                  90                  95

Ala Arg Arg Val Gly Asn Trp Asn Tyr Val Trp Phe Asp Pro Trp Gly
            100                 105                 110

Gln Gly Thr Leu Val Ser Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val
    210                 215
```

<210> SEQ ID NO 13
<211> LENGTH: 215
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Pro Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Asn Trp Val Arg Gln Ala Pro Gly Gln Gly Leu Glu Trp Met
        35                  40                  45

Gly Arg Ile Ile Pro Ile Leu Gly Val Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Asp Leu Ser Ser Leu Arg Ser Glu Asp Thr Ala Val Tyr Tyr Cys
```

```
                        85                  90                  95
Ala Arg Glu Trp Glu Arg Ala Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val
                210                 215

<210> SEQ ID NO 14
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Thr Met His Trp Val Arg Gln Ala Pro Gly Lys Gly Leu Glu Trp Val
            35                  40                  45

Ala Leu Ile Ser Tyr Asp Gly Ser Asn Lys Tyr Tyr Ala Asp Ser Val
        50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Asp Trp Thr Leu Gly Tyr Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Cys Ser Arg Ser Thr Ser Glu Ser Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Thr Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val
            210
```

```
<210> SEQ ID NO 15
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Glu Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Arg Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Lys Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 16
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80
```

```
Gln Ala Glu Asp Glu Ala Asp Tyr Tyr Cys Ser Ser Tyr Thr Ser Ser
                85                  90                  95

Ser Thr Leu Val Phe Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 17
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Phe Ala Val Phe Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

```
<210> SEQ ID NO 18
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Met Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Asn
            20                  25                  30

Ser Leu Ala Trp Tyr Gln Gln Arg Pro Gly Gln Thr Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Ile Ile Ser Arg Leu Glu
65                  70                  75                  80

Pro Glu Asp Phe Ala Val Tyr Phe Cys Leu Gln Tyr Asp Glu Ser Pro
                85                  90                  95

Tyr Thr Phe Gly Gln Gly Ala Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 19
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Ile Arg Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Ile Ala Thr Tyr Tyr Cys Gln Gln Tyr Asp Asn Leu Leu Leu
                85                  90                  95

Phe Thr Phe Gly Pro Gly Thr Thr Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 20
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

<210> SEQ ID NO 21
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Ser Tyr
            20                  25                  30

Asn Leu Val Ser Trp Tyr Arg Gln Tyr Pro Gly Lys Ala Pro Lys Leu
        35                  40                  45

Met Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Thr
                85                  90                  95

Thr Thr Phe Val Ile Phe Gly Arg Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Gly Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 22
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Ala Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser His Arg Phe
    50                  55                  60

Ser Gly Ser Lys Ser Gly Asn Thr Ala Ser Leu Thr Ile Ser Gly Leu
```

```
                65                  70                  75                  80

Gln Ala Glu Asp Glu Ala Asp Tyr Tyr Cys Ser Ser Tyr Thr Ile Ser
                            85                  90                  95

Ser Thr Leu Gly Val Phe Gly Pro Gly Thr Lys Val Thr Val Leu Gly
                           100                 105                 110

Gln Pro Lys Ala Asn Pro Thr Val Thr Leu Phe Pro Pro Ser Ser Glu
                           115                 120                 125

Glu Leu Gln Ala Asn Lys Ala Thr Leu Val Cys Leu Ile Ser Asp Phe
                130                 135                 140

Tyr Pro Gly Ala Val Thr Val Ala Trp Lys Ala Asp Gly Ser Pro Val
            145                 150                 155                 160

Lys Ala Gly Val Glu Thr Thr Lys Pro Ser Lys Gln Ser Asn Asn Lys
                           165                 170                 175

Tyr Ala Ala Ser Ser Tyr Leu Ser Leu Thr Pro Glu Gln Trp Lys Ser
                           180                 185                 190

His Arg Ser Tyr Ser Cys Gln Val Thr His Glu Gly Ser Thr Val Glu
                           195                 200                 205

Lys Thr Val Ala Pro Thr Glu Cys Ser
                210                 215

<210> SEQ ID NO 23
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Gln Met Thr Gln Ser Pro Ser Thr Leu Ser Ala Ser Val Gly
            1               5                   10                  15

Asp Arg Val Thr Ile Thr Cys Arg Ala Ser Gln Ser Ile Arg Arg Trp
                            20                  25                  30

Leu Ala Trp Tyr Gln Gln Lys Pro Gly Lys Ala Pro Lys Leu Leu Ile
                        35                  40                  45

Tyr Asp Ala Ser Ser Leu Glu Ser Gly Val Pro Ser Arg Phe Ser Gly
                50                  55                  60

Ser Gly Ser Gly Thr Glu Phe Thr Leu Thr Ile Ser Ser Leu Gln Pro
            65                  70                  75                  80

Asp Asp Phe Ala Thr Tyr Tyr Cys Gln Gln Tyr Asn Ser Tyr Ser Tyr
                            85                  90                  95

Thr Phe Gly Gln Gly Thr Lys Leu Glu Ile Lys Arg Thr Val Ala Ala
                           100                 105                 110

Pro Ser Val Phe Ile Phe Pro Pro Ser Asp Glu Gln Leu Lys Ser Gly
                           115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
            145                 150                 155                 160

Glu Ser Val Thr Glu Gln Asp Ser Lys Asp Ser Thr Tyr Ser Leu Ser
                           165                 170                 175

Ser Thr Leu Thr Leu Ser Lys Ala Asp Tyr Glu Lys His Lys Val Tyr
                           180                 185                 190

Ala Cys Glu Val Thr His Gln Gly Leu Ser Ser Pro Val Thr Lys Ser
                           195                 200                 205
```

Phe Asn Arg Gly Glu Cys
    210

<210> SEQ ID NO 24
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Ile Val Met Thr Gln Ser Pro Ala Thr Leu Ser Val Ser Pro Gly
1               5                   10                  15

Glu Arg Ala Thr Leu Ser Cys Trp Ala Ser Gln Ser Val Ser Ser Ser
            20                  25                  30

Leu Ala Trp Tyr Gln Gln Lys Pro Gly Gln Ala Pro Arg Leu Leu Met
        35                  40                  45

Tyr Gly Ala Ser Asn Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Lys Trp Pro Pro
                85                  90                  95

Asp Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 25
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Phe Met Leu Thr Gln Pro His Ser Val Ser Glu Ser Pro Gly Arg
1               5                   10                  15

Thr Val Thr Ile Ser Cys Thr Arg Ser Ser Gly Ser Ile Ala Arg Asn
            20                  25                  30

Tyr Val His Trp Tyr Gln His Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

```
Gly Ser Ile Asp Ser Ser Asn Ser Ala Ser Leu Thr Ile Ser Gly
 65                  70                  75                  80

Leu Lys Pro Glu Asp Glu Ala Asp Tyr Phe Cys Gln Ser Tyr Asp Ser
                 85                  90                  95

Asn Ile Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 26
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Ala Tyr Val Leu Thr Gln Pro Pro Ser Val Ser Val Ala Pro Gly Gln
 1               5                  10                  15

Thr Ala Arg Met Thr Cys Gly Gly Asn Asn Ile Gly Ser Lys Ser Val
            20                  25                  30

His Trp Tyr Arg Gln Arg Pro Gly Gln Ala Pro Val Leu Val Val Tyr
        35                  40                  45

Asp Asp Thr Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Thr Asn Ser Asp His
                 85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205
```

```
Ala Pro Thr Glu Cys Ser
    210

<210> SEQ ID NO 27
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Pro
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 28
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Val Ser Ser Glu Leu Thr Gln Asp Pro Ala Val Ser Val Ala Leu Gly
1               5                   10                  15

Gln Thr Val Arg Ile Thr Cys Gln Gly Asp Ser Leu Arg Asn Tyr Tyr
            20                  25                  30

Ala Asn Trp Tyr Gln Gln Lys Pro Gly Gln Ala Pro Ile Leu Val Ile
        35                  40                  45

Tyr Asp Lys Asn Asn Arg Pro Ser Gly Ile Pro Asp Arg Phe Ser Gly
    50                  55                  60
```

```
Ser Ser Ser Gly Asn Thr Ala Ser Leu Thr Ile Thr Gly Ala Gln Ala
 65                  70                  75                  80

Glu Asp Glu Ala Asp Tyr Tyr Cys Asn Ser Arg Asp Ser Ser Gly Tyr
                 85                  90                  95

His Leu Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Arg Gly Gly Gly Thr Ser Trp Ser His Tyr
1               5                   10

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Lys Asp Ala Tyr Asp Ser Ser Gly Pro Asp Ala Phe Asp Ile
1               5                   10                  15

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Arg Pro Leu Gln Thr Tyr Ser Ile Ala Ser Val Gly His
1               5                   10

<210> SEQ ID NO 32
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 32

Ala His Lys Asn Leu Gln Tyr Ser Glu Trp Phe Asp Pro
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Arg Pro Glu Gly Ser Gly Tyr Ser Ala Asp Ala Phe Asp Ile
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Lys Glu Ile Gly Lys Tyr Gly Thr Pro Thr Leu Phe Gln His
1               5                   10                  15

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Arg Asp Phe Asn Trp Asn Phe Asp Phe
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Arg Glu Ser Glu Val Gly Arg Gly Met Asp Val
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Thr Glu Arg Gly His Asn Met Glu Arg Ala Phe Asp Phe
1               5                   10
```

```
<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Arg Gly Asp Gly Pro Phe Asp Tyr
1               5

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Gly Met Val Leu Gly Gln Leu Gly Phe Asp Pro
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Arg Arg Val Gly Asn Trp Asn Tyr Val Trp Phe Asp Pro
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Arg Glu Trp Glu Arg Ala Phe Asp Tyr
1               5                   10

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Arg Asp Trp Thr Leu Gly Tyr
1               5

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43
```

```
Gln Ser Tyr Asp Ser Asn Asn Arg Trp Val
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Ser Tyr Thr Ser Ser Ser Thr Leu Val
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Cys Ser Tyr Ala Gly Ser Ser Thr Phe Ala Val
1               5                   10

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Gln Tyr Asp Glu Ser Pro Tyr Thr
1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Gln Tyr Asp Asn Leu Leu Leu Phe Thr
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Gln Tyr Asp Asn Leu Pro Ile Thr
1               5

<210> SEQ ID NO 49
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 49

Cys Ser Tyr Ala Gly Thr Thr Thr Phe Val Ile
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Ser Tyr Thr Ile Ser Ser Thr Leu Gly Val
1               5                   10

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Gln Tyr Asn Ser Tyr Ser Tyr Thr
1               5

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Gln Tyr Asn Lys Trp Pro Pro Asp Thr
1               5                   10

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Ser Tyr Asp Ser Asn Ile Trp Val
1               5

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Val Trp Asp Thr Asn Ser Asp His Val Val
1               5                   10
```

```
<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gln Gln Tyr Gly Asn Ser Pro Tyr Thr
1               5

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asn Ser Arg Asp Ser Ser Gly Tyr His Leu Val
1               5                   10

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ile Ser Ser Ser Gly Asn Tyr Ile
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ile Ser Gly Ser Gly Gly Ser Thr
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ile Asp Pro Ser Asp Ser Tyr Thr
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 60

Ile Tyr Trp Asp Asp Lys
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ile Phe Tyr Ser Gly Ser Thr
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ile Ser Gly Ser Gly Gly Arg Thr
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Phe Val Pro Leu Phe Gly Thr Ala
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ile Ile Pro Ile Leu Gly Ile Ala
1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ile Ile Pro Ile Phe Gly Ser Val
1               5

<210> SEQ ID NO 66
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 66

Ile Ser Ala Tyr Asn Gly Asn Thr
1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ile Ile Pro Ile Leu Gly Leu Ala
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Tyr Phe Thr Gly Ser Thr
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ile Ile Pro Ile Leu Gly Val Ala
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ile Ser Tyr Asp Gly Ser Asn Lys
1               5

<210> SEQ ID NO 71
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Glu Asp Asn
1
```

```
<210> SEQ ID NO 72
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asp Val Ser
1

<210> SEQ ID NO 73
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Glu Gly Ser
1

<210> SEQ ID NO 74
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Ala Ser
1

<210> SEQ ID NO 75
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asp Ala Ser
1

<210> SEQ ID NO 76
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asp Ala Ser
1

<210> SEQ ID NO 77
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 77

Glu Val Asn
1

<210> SEQ ID NO 78
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Val Ser
1

<210> SEQ ID NO 79
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asp Ala Ser
1

<210> SEQ ID NO 80
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Ala Ser
1

<210> SEQ ID NO 81
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Glu Asp Asp
1

<210> SEQ ID NO 82
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asp Asp Thr
1

<210> SEQ ID NO 83
<211> LENGTH: 3
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Ala Ser
1

<210> SEQ ID NO 84
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Asp Lys Asn
1

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Phe Thr Phe Arg Ser Tyr Ser
1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Phe Thr Phe Ser Ser Tyr Ala
1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Tyr Ser Phe Thr Ser Tyr Trp
1               5

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Phe Ser Leu Asn Thr Pro Gly Val Gly
```

```
1               5                   10
```

```
<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Gly Ser Met Ser Ile Arg Ser Ser Tyr
1               5                   10

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Leu Thr Phe Arg Asn Tyr Ala
1               5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Gly Ser Phe Ser Ser Asn Pro
1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Gly Thr Phe Asn Arg Asp Gly
1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Gly Thr Phe Ser Asn Tyr Gly
1               5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                          peptide

<400> SEQUENCE: 94

Gly Tyr Thr Phe Ser Ser Tyr Gly
1               5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Gly Thr Phe Ser Ser Tyr Ser
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Asp Ser Ile Thr Thr Thr Tyr Tyr
1               5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Thr Phe Ser Ser Tyr Thr
1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Phe Thr Phe Ser Ser Tyr Thr
1               5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ser Gly Ser Ile Ala Ser Asn Tyr
1               5

<210> SEQ ID NO 100
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Ser Asp Val Gly Asp Tyr Asn Tyr
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ser Ser Asp Val Gly Ser Tyr Asn Leu
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gln Ser Val Ser Arg Asn Ser
1               5

<210> SEQ ID NO 103
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gln Asn Ile Arg Asn Tyr
1               5

<210> SEQ ID NO 104
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gln Asp Ile Ser Asn Tyr
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105
```

Ser Ser Asp Ile Gly Ser Tyr Asn Leu
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ser Ser Asp Val Gly Asp Tyr Asn Tyr
1               5

<210> SEQ ID NO 107
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Ser Ile Arg Arg Trp
1               5

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gln Ser Val Ser Ser Ser
1               5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ser Gly Ser Ile Ala Arg Asn Tyr
1               5

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Asn Ile Gly Ser Lys Ser
1               5

<210> SEQ ID NO 111
<211> LENGTH: 7
<212> TYPE: PRT
<213> ORGANISM: Artificial Sequence
<220> FEATURE:

<223> OTHER INFORMATION: Description of Artificial Sequence: Synthetic
       peptide

<400> SEQUENCE: 111

Gln Ser Val Ser Ser Tyr
1               5

<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 112

Ser Leu Arg Asn Tyr Tyr
1               5

<210> SEQ ID NO 113
<211> LENGTH: 652
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 113

```
gtgtgaggtg cagctggtgg agtctggggg aggcctggtc aagcctgggg ggtccctgag      60
actctcctgt gcagcctctg gattcacctt caggagctat agcatgaact gggtccgcca     120
ggctccaggg aaggggctgg agtgggtctc atccattagt agtagtggta attacatata     180
ctacgcagac tcagtgaagg gccgattcac cctctccaga gacaacgcca agaactcact     240
gtatctgcaa atgaacagcc tgagagccga ggacacggct gtgtattact gtgcgagagg     300
tgggggtacc agctggtcgc attactgggg ccagggaacc ctggtcaccg tctcctcagc     360
ctccaccaag ggcccatcgg tcttccccct ggcaccctcc tccaagagca cctctggggg     420
cacagcggcc ctgggctgcc tggtcaagga ctacttcccc gaaccggtga cggtgtcgtg     480
gaactcaggc gccctgacca gcggcgtgca caccttcccg gctgtcctac agtcctcagg     540
actctactcc ctcagcagcg tggtgaccgt gccctccagc agcttgggca cccagaccta     600
catctgcaac gtgaatcaca agcccagcaa caccaaggtg gacaagagtg ag            652
```

<210> SEQ ID NO 114
<211> LENGTH: 660
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 114

```
gtggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaagatgca    300
tatgatagta gtggcccaga tgcttttgat atctggggcc aagggacaat ggtcaccgtc    360
tcctcagcct ccaccaaggg cccatcggtc ttccccctgg cacctcctc caagagcacc    420
```

```
tctgggggca cagcggccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagagagtg    660
```

<210> SEQ ID NO 115
<211> LENGTH: 675
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115

```
gccgtgcagc tggtgcagtc cggagcagag gtgaaaaagc ccggggagtc tctgaggatc     60
tcctgtaagg gttctggata cagctttacc agctactgga tcagctgggt gcgccagatg    120
cccgggaaag gcctggagtg gatggggagg attgatccta gtgactctta taccaactac    180
agcccgtcct tccaaggcca cgtcaccatc tcagctgaca gtccatcag cactgcctac    240 ctacagtgga gcagcctgaa gacctcggac accgccatgt attactgtgc gagaccgcta    300
caaacttata gtatagcatc agtaggacac tggggccagg gaaccctggt caccgtctcc    360
tcagggagtg catccgcccc aaccctttc ccctcgtct cctgtgagaa ttccccgtcg    420
gatacgagca gcgtggccgt tggctgcctc gcacaggact ccttcccga ctccatcact    480 ttctcctgga aatacaagaa caactctgac atcagcagca ccgggggctt ccatcagtc    540 ctgagagggg gcaagtacgc agccacctca caggtgctgc tgccttccaa ggacgtcatg    600
cagggcacag acgaacacgt ggtgtgcaaa gtccagcacc caacggcaa caaagaaaag    660 aacgtgcctc ttccg                                                    675
```

<210> SEQ ID NO 116
<211> LENGTH: 659
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116

```
cccagatcac cttgaaggag tctggtccga cgctggtgaa gcccacacag accctcacgc     60
tgacctgcac cttctctggg ttctcactca acactcctgg agtgggtgtg gctggatcc    120 gtcagccccc aggaaaggcc ctggaatggc ttgcactcat ttattgggat gatgataagc    180
gctacaggcc atctctggag agcaggctca ccatcaccaa ggacacctcc aaaaaccacg    240
ttgtccttac gatgaccaac atggaccctg tggacacagc cacatatttt tgtgcacaca    300
agaaccttca gtattcggaa tggttcgacc cctgggggcca gggcaccctg gtcattgtct    360
cctcagcctc caccaagggc ccatcggtct tccccctggc gccctgctcc aggagcacct    420
ccgagagcac agcggccctg ggctgcctgg tcaaggacta cttccccgaa ccggtgacgg    480
tgtcgtggaa ctcaggcgcc ctgaccacgc gcgtgcacac cttcccggct gtcctacagt    540
cctcaggact ctactccctc agcagcgtgg tgaccgtgcc ctccagcagc ttgggcacga    600
agacctacac ctgcaatgta gatcacaagc ccagcaacac caaggtggac aagagagtt    659
```

<210> SEQ ID NO 117

```
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
cccgtgcagc tgcaggagtc gggcccagga ctggtgaagc cttcggagac cctgtccctc      60
acctgcactg tctctggtgg ctccatgagc attaggagtt cctactgggg ctggatccgc     120
cagtcaccag ggaaggggct ggagtggatt gggcatatat tttatagtgg gagcacctac     180
tacaacccgt ccctccagag tcgagtcaca atattagtag acacgtccaa gaaccaattc     240
tccctgaggc tgagctctgt gaccgcagcg gacacggccg tgtattactg tgtgagaagt     300
tttggcgtgg ctcgatggga cttctgggc cagggaaccc tggtcaccgt ctcctcagcc      360
tccaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaggt g              651

<210> SEQ ID NO 118
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
gtggtgcagc tggtggagtc tgggggaggc ttggtacagc cggggggtc cctgagactc       60 tcctgtgcgg cctccggatt aacctttcgc aactacgcca tgagctgggt ccgccaggct     120
ccagggaagg gactggagtg ggtctcagct attagtggta gtggtggtcg cacacactac     180
gcagactccg tgaagggccg cttcaccatc tccagagaca attccaagaa cacgctgttt     240
ctgcaaatga acagcctgag agccgaggac acggccgtat attactgtgc gaaagagatt     300
ggaaaatacg ggactcctac tctttttccag cactgggggcc agggcaccct ggtcaccgtc     360
tcctcagcct ccaccaaggg cccatcggtc ttccccctgg caccctcctc caagagcacc     420
tctgggggca gcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagaaggtg     660

<210> SEQ ID NO 119
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119
cacgtgcatc tggtgcagtc tggggctgag gtgaagaaac ctgggtcctc ggtgaaggtc       60
tcctgcacgg cttctggagg ctccttcagc agtaatccaa tcagctgggt gcgtcaggcc     120
```

| | |
|---|---:|
| cctggacacg ggcttcagtg gatgggagga ttcgtccctc tctttggtac agcaaactac | 180 |
| gcaccgagtt tccacggcag actcacgatt accgcggacg aatccacgag cacaacttac | 240 |
| atggaactga atagcctgag atctgaggac tcggccgtct attattgtgc gagagatttt | 300 |
| aactggaact tcgacttctg gggccaggga accctggtca ccgtctcctc ggcctccacc | 360 |
| aagggcccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga gtgag | 645 |

<210> SEQ ID NO 120
<211> LENGTH: 653
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120

| | |
|---|---:|
| cccaggtcca gctggtgcag tctggggctg aggtgaagaa gcctgggtcc tcggtgaagg | 60 |
| tctcctgcaa ggcttctgga ggcaccttca tagggatgg tatcatctgg gtgcgacagg | 120 |
| cccctggaca agggcttgag tggatgggaa ggatcatccc tatccttggt atagcaaact | 180 |
| acgcacagaa gttccagggc agagtcacga ttatcgcgga caaatccacg agcacagcct | 240 |
| acatggaact gagcagcctg agatctgagg acacggccgt atattactgt gcgagagaat | 300 |
| cggaggtggg tcgcggtatg gacgtctggg gccaagggac cacggtcacc gtctcctcag | 360 |
| cctccaccaa gggcccatcg gtcttccccc tggcaccctc ctccaagagc acctctgggg | 420 |
| gcacagcggc cctgggctgc ctggtcaagg actactttcc cgaaccggtg acggtgtcgt | 480 |
| ggaactcagg cgccctgacc agcggcgtgc acaccttccc ggctgtccta cagtcctcag | 540 |
| gactctactc cctcagcagc gtggtgaccg tgccctccag cagcttgggc acccagacct | 600 |
| acatctgcaa cgtgaatcac aagcccagca acaccaaggt ggacaagagt gag | 653 |

<210> SEQ ID NO 121
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121

| | |
|---|---:|
| cccgtgcagc tggtgcagtc tggggctgag gtgaagaagc tgggtcctc ggtgaaggtc | 60 |
| tcctgcaggg cttctggagg caccttcagc aactatggtc tcaactgggt gcgacaggcc | 120 |
| cctggacaag gcttgagtg gatgggaggg atcatcccta tctttggttc agtaaattat | 180 |
| gcacagaagt tccaggacag agtcacgatt accgcggacg aatccacgag cactacctac | 240 |
| atggacctga cagcctgag atctgaggac acggccgtct attactgtgc gacagagcgt | 300 |
| ggacacaaca tggagagggc ttttgatttc tggggccaag ggacactggt caccgtctct | 360 |
| tcagcctcca ccaagggccc atcggtcttc cccctggcac cctcctccaa gagcacctct | 420 |
| gggggcacag cggccctggg ctgcctggtc aaggactact tccccgaacc ggtgacggtg | 480 |
| tcatggaact caggcgccct gaccagcggc gtgcacacct tcccggctgt cctacagtcc | 540 |

```
tcaggactct actccctcag cagcgtggtg accgtgccct ccagcagctt gggcacccag    600
acctacatct gcaacgtgaa tcacaagccc agcaacacca aggtggacaa gaaggtg       657
```

<210> SEQ ID NO 122
<211> LENGTH: 644
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122

```
cccaggttca gctggtgcag tctggagctg aggtgaagaa gcctggggcc tcagtgaagg     60
tctcctgcaa ggcttctggt tacacccttta gcagctatgg tatcagctgg gtgcgacagg   120
cccctggaca agggcttgag tggatgggat ggatcagcgc ttacaatggt aacacaaact   180
atgcaaagaa actccagggc agagtcacca tgaccacaga cacatccacg agtacagcct   240
acttggagtt gaggagcctg agatctgacg acacggccgt gtattactgt gcgagaggcg   300
acggtccctt tgactactgg ggccagggaa ccctggtcac cgtctcctca gcctccacca   360
agggcccatc ggtcttcccc ctggcaccct cctccaagag cacctctggg ggcacagcgg   420
ccctgggctg cctggtcaag gactacttcc ccgaaccggt gacggtgtcg tggaactcag   480
gcgccctgac cagcggcgtg cacaccttcc cggctgtcct acagtcctca ggactctact   540
ccctcagcag cgtggtgacc gtgccctcca gcagcttggg cacccagacc tacatctgca   600
acgtgaatca caagcccagc aacaccaagg tggacaagaa agtg                     644
```

<210> SEQ ID NO 123
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123

```
cccgtccagc tggtgcaatc tggggctgaa gtgaagaagc ctgggtcctc ggtgaaggtc     60
tcctgcaagg cttctggagg caccttcagc agctatagtt tcaactgggt gcgacaggcc   120
cctggacagg ggcttgagtg gatggcaagg atcatcccta ccttggtct ggcaaattac    180 gcacagaagt tccagggcag agtcacactt accgcggacg aatccacgag cacagcctac   240
atggagctga gcagcctgag atctgaagac acggccatct tttactgtgc gggaatggtc   300
ctcggccaac tggggttcga ccccctgggc cagggaaccc tggtcaccgt ctcctcagcc   360
tccaccaagg gccatcggt cttcccctg gcacctcct ccaagagcac ctctgggggc      420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga   540
ctctactccc tcagcagcgt ggtgaccgtg ccctccagca gcttgggcac ccagacctac   600
atctgcaacg tgaatcacaa gcccagcaac accaaggtgg acaagaaggt g             651
```

<210> SEQ ID NO 124
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124

```
cccctgcagc tgcaggagtc gggcccagga ctggtgaagc cttcggagac cctgtccctc    60
acctgtactg tctctggtga ctccatcact actacttact actggggctg gatccgccag   120
cccccaggga aggggctgga gtggattgcc agtatctatt ttactgggag caccttccat   180
aacccgtccc tcaagagtcg agtcacaatg tccgtggaca cgtccaagaa ccagttctcc   240
ctgaacctga gctctgtgac agccgcagac acggctgtgt attactgtgc gagacgggtg   300
ggtaactgga actacgtctg gttcgacccc tggggccagg gaaccctggt ctccgtctcc   360
tcagcctcca ccaagggccc atcggtcttc cccctggcac cctcctccaa gagcacctct   420
gggggcacag cggccctggg ctgcctggtc aaggactact tccccgaacc ggtgacggtg   480
tcgtggaact caggcgccct gaccagcggc gtgcacacct tcccggctgt cctacagtcc   540
tcaggactct actccctcag cagcgtggtg accgtgccct ccagcagctt gggcacccag   600
acctacatct gcaacgtgaa tcacaagccc agcaacacca aggtggacaa gaaagtg      657
```

<210> SEQ ID NO 125
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 125

```
cccgtccagc tggtgcaatc tggggctgag gtgaagaagc ctgggtcctc ggtgaaggtc    60
tcctgcaagg cttctggagg caccttcagc agctatacta tcaactgggt gcgacaggcc   120
cctggacaag gcttgagtg gatgggaagg atcatcccta tccttggtgt agcaaactac   180
gcacagaagt tccagggcag agtcacgatt accgcggaca atccacgag cacagcctac   240
atggacctga gcagcctgag atctgaggac acggccgtgt attactgtgc gagagagtgg   300
gagcgggcct ttgactactg gggccaggga accctggtca ccgtctcctc agcctccacc   360
aagggcccat cggtcttccc cctggcaccc tcctccaaga gcacctctgg gggcacagcg   420
gccctgggct gcctggtcaa ggactacttc cccgaaccgg tgacggtgtc gtggaactca   480
ggcgccctga ccagcggcgt gcacaccttc ccggctgtcc tacagtcctc aggactctac   540
tccctcagca gcgtggtgac cgtgccctcc agcagcttgg gcacccagac ctacatctgc   600
aacgtgaatc acaagcccag caacaccaag gtggacaaga ggtg                    645
```

<210> SEQ ID NO 126
<211> LENGTH: 639
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 126

```
tcagtgcagc tggtggagtc tgggggaggc gtggtccagc ctgggaggtc cctgagactc    60
tcctgtgcag cctctggatt caccttcagt agctatacca tgcactgggt ccgccaggct   120
ccaggcaagg gctggagtg ggtggcactt atatcatatg atggaagcaa taaatactac   180
gcagactccg tgaagggccg attcaccatc tccagagaca atcccaagaa cacgctgtat   240
ctgcaaatga acagcctgag agttgaggac acggctgtgt attactgtgc gagagattgg   300
```

```
accettgggt actggggcca gggaaccctg gtcaccgtct cctcagcctc caccaagggc      360
ccatcggtct tccccctggc gccctgctcc aggagcacct ccgagagcac agcggccctg      420
ggctgcctgg tcaaggacta cttccccgaa ccggtgacgg tgtcgtggaa ctcaggcgct      480
ctgaccagcg gcgtgcacac cttcccggct gtcctacagt cctcaggact ctactccctc      540
agcagcgtgg tgaccgtgac ctccagcaac ttcggcaccc agacctacac ctgcaacgta      600
gatcacaagc ccagcaacac caaggtggac aagacagtg                              639
```

<210> SEQ ID NO 127
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127

```
caatttatgc tgactcagcc ccactctgtg tcggagtctc cggggaagac ggtaaccatc       60
tcctgcaccc gcagcagtgg cagcattgcc agcaactatg tgcagtggta ccagcagcgc      120
ccgggcagtg cccccaccac tgtgatctat gaggataacg aaagaccctc tggggtccct      180
gatcggttct ctggctccat cgacagctcc tccaactctg cctccctcac catctctgga      240
ctgaagactg aggacgaggc tgactactac tgtcagtctt atgatagcaa caatcgttgg      300
gtgttcggcg gagggaccaa gctgaccgtc ctaggtcagc ccaaggctgc ccctcggtc       360
actctgttcc caccctcctc tgaggagctt caagccaaca aggccacact ggtgtgtctc      420
ataagtgact ctacccgggg agccgtgaca gtggcctgga aggcagatag cagccccgtc      480
aaggcgggag tggagaccac cacaccctcc aaacaaagca caacaagta cgcggccagc      540
agctacctga gcctgacgcc tgagcagtgg aagtcccaca aaagctacag ctgccaggtc      600
acgcatgaag ggagcaccgt ggagaagaca gtggccccta cagaatgttc a              651
```

<210> SEQ ID NO 128
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128

```
gcctctgccc tgactcagcc tgcctccgtg tctgggtctc ctggacagtc gatcaccatc       60
tcctgcactg gaaccagcag tgacgttggt gattataact atgtctcctg gtaccaacag      120
cacccaggca aagcccccaa actcatgatt tatgatgtca gtaatcggcc ctcaggggtt      180
tctaatcgct tctctggctc caagtctggc aacacggcct ccctgaccat ctctgggctc      240
caggctgagg acgaggctga ttattactgc agctcatata caagcagcag cactcttgta      300
ttcggcggag ggaccaagct gaccgtccta ggtcagccca aggctgcccc ctcggtcact      360
ctgttcccgc cctcctctga ggagcttcaa gccaacaagg ccacactggt gtgtctcata      420
agtgacttct acccgggagc cgtgacagtg gcctggaagg cagatagcag ccccgtcaag      480
gcgggagtgg agaccaccac accctccaaa caaagcaaca acaagtacgc ggccagcagc      540
tatctgagcc tgacgcctga gcagtggaag tcccacagaa gctacagctg ccaggtcacg      600
catgaaggga gcaccgtgga gaagacagtg gcccctacag aatgttca                   648
```

<210> SEQ ID NO 129
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129

```
gcctctgccc tgactcagcc tgcctccgtg tctgggtctc ctggacagtc gatcaccatc       60
tcctgcactg gaaccagcag tgatgttggg agttataacc ttgtctcctg gtaccaacag      120
cacccaggca aagcccccaa actcatgatt tatgagggca gtaagcggcc ctcaggggtt      180
tctaatcgct tctctggctc caagtctggc aacacggcct ccctgacaat ctctgggctc      240
caggctgagg acgaggctga ttattactgc tgctcatatg caggtagtag cactttcgcg      300
gtattcggcg gagggaccaa gctgaccgtc ctaggtcagc ccaaggctgc cccctcggtc      360
actctgttcc cgccctcctc tgaggagctt caagccaaca aggccacact ggtgtgtctc      420
ataagtgact tctacccggg agccgtgaca gtggcctgga aggcagatag cagccccgtc      480
aaggcgggag tggagaccac cacaccctcc aaacaaagca acaacaagta cgcggccagc      540
agctacctga gcctgacgcc tgagcagtgg aagtcccaca aagctacag ctgccaggtc       600 acgcatgaag ggagcaccgt ggagaagaca gtggccccta cagaatgttc a              651
```

<210> SEQ ID NO 130
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130

```
gaaatggtgt tgacgcagtc tccagccacc ctgtctttgt ctccagggga aagagccacc       60
ctctcctgca gggccagtca gagtgttagc agaaactcct tagcctggta ccagcagaga      120
cctggccaga ctcccaggct cctcatctat ggtgcctcca gcagggccac tggcatccca      180
gacaggttca gtggcagtgg gtctgggaca gacttcactc tcatcatcag cagactggag      240
cctgaagatt ttgcagtgta tttctgtctc cagtatgatg agtcaccgta cacttttggc      300
caggggccca agctggagat caaacgaact gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca aagcagacta cgagaaacac aaactctacg cctgcgaagt cacccatcag      600
ggcctgagct cgcccgtcac aaagagcttc aacaggggag agtgt                      645
```

<210> SEQ ID NO 131
<211> LENGTH: 647
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131

```
gtgacatcca gatgacccag tctccatcct ccctgtctgc atctgtagga gacagagtca       60
ccatcacttg ccaggcgagt cagaacatta ggaattattt aaattggtat cagcagaaac      120
```

```
cagggaaagc ccctaagctc ctgatctacg atgcatccaa tttgaaaaca ggggtcccat    180
caaggttcag tggaagtgga tctgggacag attttactct caccatcagc agcctgcagc    240
ctgaagatat tgcaacatat tactgtcaac agtatgataa tctcctccta ttcactttcg    300
gccctgggac cacagttgat atcaaacgaa ctgtggctgc accatctgtc ttcatcttcc    360
cgccatctga tgagcagttg aaatctggaa ctgcctctgt tgtgtgcctg ctgaataact    420
tctatcccag agaggccaaa gtacagtgga aggtggataa cgcccctcca tcgggtaact    480
cccaggagag tgtcacagag caggacagca aggacagcac ctacagcctc agcagcaccc    540
tgacgctgag caaagcagac tacgagaaac acaaagtcta cgcctgcgaa gtcacccatc    600
agggcctgag ctcgcccgtc acaaagagct tcaacagggg agagtgt                   647

<210> SEQ ID NO 132
<211> LENGTH: 644
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132
gtgacatcca gatgacccag tctccatcct ccctgtctgc atctgtagga gacagagtca    60
ccatcacttg ccaggcgagt caggacatta gcaactattt aaattggtat caacaaaaac    120
cagggaaagc ccctaaactc ctgatctacg atgcatccaa tttggaaaca ggggtcccat    180
caaggttcag tggaagtgga tctgggacag attttacttt caccatcagc agcctgcagc    240
ctgaagatat tgcaacatat tactgtcaac agtatgataa tctcccgatc accttcggcc    300
aagggacacg actggagatt aaacgaactg tggctgcacc atctgtcttc atcttcccgc    360
catctgatga gcagttgaaa tctggaactg cctctgttgt gtgcctgctg aataacttct    420
atcccagaga ggccaaagta cagtggaagg tggataacgc cctccaatcg ggtaactccc    480
aggagagtgt cacagagcag gacagcaagg acagcaccta cagcctcagc agcaccctga    540
cgctgagcaa agcagactac gagaaacaca agtctacgc ctgcgaagtc acccatcagg    600
gcctgagctc gcccgtcaca aagagcttca acaggggaga gtgt                     644

<210> SEQ ID NO 133
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133
cagtctgccc tgactcagcc tgcctccgtg tctgggtctc ctggacagtc gatcaccatc    60
tcctgcactg gaaccagcag tgatattggg agttataacc ttgtctcctg gtaccgacaa    120
tacccaggca agcccccaa actcatgatt tatgaggtca ataagcggcc ctcaggggtt    180
tctaatcgct tctctggctc caagtctggc aacacggcct ccctgacgat ctctgggctc    240
caggctgagg acgaggctga ttattactgc tgctcatatg cgggtactac tactttcgtg    300
attttcggca gagggaccaa gctgaccgtc ctaggtcagc ccaaggctgc cccctcggtc    360
actctgttcc cgccctcctc tgaggagctt caagccaaca aggccacact ggtgtgtctc    420
ataagtgact tctacccggg agccgtgaca gtggcctgga aggcagatgg cagccccgtc    480
```

```
aaggcgggag tggagaccac cacaccctcc aaacaaagca acaacaagta cgcggccagc    540
agctatctga gcctgacgcc tgagcagtgg aagtcccaca gaagctacag ctgccaggtc    600
acgcatgaag ggagcaccgt ggagaagaca gtggcccta cagaatgttc a              651
```

<210> SEQ ID NO 134
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134

```
gcctctgccc tgactcagcc tgcctccgtg tctgggtctc ctggacagtc gatcaccatc     60
tcctgcactg gaaccagcag tgacgttggt gattataact atgtctcctg gtaccaacag    120
cacccaggca agcccccaa actcatgatt tatgatgtca gtaatcggcc ctcaggggtt    180
tctcatcgct tctctggctc caagtctggc aacacggcct ccctgaccat ctctgggctc    240
caggctgagg acgaggctga ttattactgc agctcatata caatcagcag tactctagga    300
gtcttcggac ctgggaccaa ggtcaccgtc ctaggtcagc ccaaggccaa ccccactgtc    360
actctgttcc cgccctcctc tgaggagctc aagccaaca aggccacact agtgtgtctg    420
atcagtgact ctacccgggg agctgtgaca gtggcctgga aggcagatgg cagcccgtc    480 aaggcgggag tggagaccac caaaccctcc aaacagagca acaacaagta cgcggccagc    540
agctacctga gcctgacgcc cgagcagtgg aagtcccaca gaagctacag ctgccaggtc    600
acgcatgaag ggagcaccgt ggagaagaca gtggcccta cagaatgttc a              651
```

<210> SEQ ID NO 135
<211> LENGTH: 644
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135

```
gtgacatcca gatgacccag tctccttcca ccctgtctgc ttctgtagga gacagagtca     60
ccatcacttg ccgggccagt cagagtattc gtaggtggtt ggcctggtat cagcagaaac    120
cagggaaagc ccctaaactc ctgatctatg atgcctcaag tttggaaagt ggggtcccat    180
caaggttcag cggcagtgga tctgggacag aattcactct caccatcagc agcctgcagc    240
ctgatgattt tgcaacttat tactgtcaac agtataatag ttattcgtac acttttggcc    300
aggggaccaa gctggagatc aaacgaactg tggctgcacc atctgtcttc atcttcccgc    360
catctgatga gcagttgaaa tctggaactg cctctgttgt gtgcctgctg aataacttct    420
atcccagaga ggccaaagta cagtggaagg tggataacgc cctccaatcg ggtaactccc    480
aggagagtgt cacagagcag gacagcaagg acagcaccta cagcctcagc agcaccctga    540
cgctgagcaa agcagactac gagaaacaca aagtctacgc ctgcgaagtc acccatcagg    600
gcctgagctc gcccgtcaca aagagcttca cagggggaga gtgt                     644
```

<210> SEQ ID NO 136
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 136

```
gaaatagtga tgacgcagtc tccagccacc ctgtctgtgt ctccagggga aagagccacc      60
ctctcctgct gggccagtca gagtgttagc agcagcttag cctggtacca gcagaaacct     120
ggccaggctc ccaggctcct catgtatggt gcatctaaca gggccactgg tatcccagcc     180
aggttcagtg gcagtgggtc tgggacagag ttcactctca ccatcagcag cctgcagtct     240
gaagattttg cagtttatta ctgtcagcag tataataagt ggcctccgga cacttttggc     300
caggggacca agctggagat caaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacaggggag agtgt                     645
```

<210> SEQ ID NO 137
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137

```
caatttatgc tgactcagcc ccactctgtg tcggagtctc cggggaggac ggtaaccatc      60
tcctgcaccc gcagcagtgg cagcattgcc cgcaactatg tgcattggta ccagcatcgc     120
ccgggcagtt cccccaccac tgtgatctat gaggatgacc aaagaccctc tggggtccct     180
gatcggttct ctggctccat cgacagctcc tccaactctg cctccctcac catctctgga     240
ctgaaacctg aggacgaggc tgactacttc tgtcagtctt atgatagcaa catttgggtg     300
ttcggcggtg ggaccaagct gaccgtccta ggtcagccca aggctgcccc ctcggtcact     360
ctgttcccac cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca caagtacgc ggccagcagc      540
tacctgagcc tgacgcctga gcagtggaag tcccacaaaa gctacagctg ccaggtcacg     600
catgaaggga gcaccgtgga gaagacagtg gcccctacag aatgttca                  648
```

<210> SEQ ID NO 138
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138

```
gcctatgtgc tgactcagcc accctcggtg tcagtggccc cagggcagac ggccaggatg      60
acctgtgggg gaaacaacat tggaagtaaa agtgtgcatt ggtaccggca gaggccaggc     120
caggcccctg tgctggtcgt ctatgatgat accgaccggc cctcagggat ccctgagcga     180
ttctctggct ccaactctgg gaacacggcc accctgacca tcagcagggt cgaggccggg     240
gatgaggccg actattactg tcaggtgtgg gatactaata gtgatcatgt ggtattcggc     300
```

```
ggagggacca agctgaccgt cctaggtcag cccaaggctg cccctcggt cactctgttc    360 ccgccctcct ctgaggagct tcaagccaac aaggccacac tggtgtgtct cataagtgac    420
ttctacccgg gagccgtgac agtggcctgg aaggcagata gcagcccgt caaggcggga     480 gtggagacca ccacccctc caaacaaagc aacaacaagt acgcggccag cagctatctg    540
agcctgacgc ctgagcagtg gaagtcccac agaagctaca gctgccaggt cacgcatgaa    600
gggagcaccg tggagaagac agtggcccct acagaatgtt ca                      642
```

<210> SEQ ID NO 139
<211> LENGTH: 647
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 139

```
gagaaattgt gttgacgcag tctccaggca ccctgtcttt gtctccaggg gaaagagcca     60
ccctctcctg cagggccagt cagagtgtta gcagcagcta cttagcctgg taccagcaga    120
aacctggcca ggctcccagg ctcctcatct atggtgcatc cagcagggcc actggcatcc    180
cagacaggtt cagtggcagt gggtctggga cagacttcac tctcaccatc agcagactgg    240
agcctgaaga ttttgcagtg tattactgtc agcagtatgg taactcaccg tacactttg     300 gccaggggac caagctggag atcaaacgaa ctgtggctgc accatctgtc ttcatcttcc    360
cgccatctga tgagcagttg aaatctggaa ctgcctctgt tgtgtgcctg ctgaataact    420
tctatcccag agaggccaaa gtacagtgga aggtggataa cgccctccaa tcgggtaact    480
cccaggagag tgtcacagag caggacagca aggacagcac ctacagcctc agcagcaccc    540
tgacgctgag caaagcagac tacgagaaac acaaagtcta cgcctgcgaa gtcacccatc    600
agggcctgag ctcgcccgtc acaaagagct tcaacagggg agagtgt                 647
```

<210> SEQ ID NO 140
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 140

```
gtttcttctg agctgactca ggaccctgct gtgtctgtgg ccttgggaca dacagtcagg    60
atcacatgcc aaggagacag cctcagaaac tattatgcaa actggtacca gcagaagcca    120
ggacaggccc ctatacttgt catctatgat aaaaacaacc ggccctcagg gatcccagac    180
cgattctctg gctccagctc aggaaacaca gcttccttga ccatcactgg ggctcaggcg    240
gaagatgagg ctgactatta ctgtaattcc cggacagca gtggttacca tctggtgttc    300
ggcggaggga ccaagctgac cgtcctaggt cagcccaagg ctgcccctc ggtcactctg    360 ttcccgccct cctctgagga gcttcaagcc aacaaggcca cactggtgtg tctcataagt    420
gacttctacc cgggagccgt gacagtggcc tggaaggcag atagcagccc cgtcaaggcg    480
ggagtggaga ccaccacacc ctccaaacaa agcaacaaca agtacgcggc cagcagctac    540
ctgagcctga cgcctgagca gtggaagtcc cacagaagct acagctgcca ggtcacgcat    600
gaagggagca ccgtggagaa gacagtggcc cctacagaat gttca                   645
```

<210> SEQ ID NO 141
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gcgagaggtg ggggtaccag ctggtcgcat tac                                  33

<210> SEQ ID NO 142
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gcgaaagatg catatgatag tagtggccca gatgcttttg atatc                     45

<210> SEQ ID NO 143
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gcgagaccgc tacaaactta tagtatagca tcagtaggac ac                        42

<210> SEQ ID NO 144
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gcacacaaga accttcagta ttcggaatgg ttcgacccc                            39

<210> SEQ ID NO 145
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gcgagaccgg aagggagcgg ttattccgct gatgcttttg atatc                     45

<210> SEQ ID NO 146
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
gcgaaagaga ttggaaaata cgggactcct actcttttcc agcac                     45

```
<210> SEQ ID NO 147
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
gcgagagatt ttaactggaa cttcgacttc                                        30

<210> SEQ ID NO 148
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
gcgagagaat cggaggtggg tcgcggtatg gacgtc                                 36

<210> SEQ ID NO 149
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
gcgacagagc gtggacacaa catggagagg gcttttgatt tc                          42

<210> SEQ ID NO 150
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
gcgagaggcg acggtccctt tgactac                                           27

<210> SEQ ID NO 151
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
gcgggaatgg tcctcggcca actggggttc gacccc                                 36

<210> SEQ ID NO 152
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
gcgagacggg tgggtaactg gaactacgtc tggttcgacc cc                          42

<210> SEQ ID NO 153
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
gcgagagagt gggagcgggc ctttgactac                                      30

<210> SEQ ID NO 154
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
gcgagagatt ggaccttgg gtac                                             24

<210> SEQ ID NO 155
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
cagtcttatg atagcaacaa tcgttgggtg                                      30

<210> SEQ ID NO 156
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
agctcatata caagcagcag cactcttgta                                      30

<210> SEQ ID NO 157
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
tgctcatatg caggtagtag cactttcgcg gta                                  33

<210> SEQ ID NO 158
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ctccagtatg atgagtcacc gtacact                                         27

<210> SEQ ID NO 159
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
caacagtatg ataatctcct cctattcact                                      30

<210> SEQ ID NO 160
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
caacagtatg ataatctccc gatcacc                                         27

<210> SEQ ID NO 161
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
tgctcatatg cgggtactac tactttcgtg att                                  33

<210> SEQ ID NO 162
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
agctcatata caatcagcag tactctagga gtc                                  33

<210> SEQ ID NO 163
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
caacagtata atagttattc gtacact                                         27

<210> SEQ ID NO 164
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
cagcagtata ataagtggcc tccggacact                                      30

<210> SEQ ID NO 165
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 165
cagtcttatg atagcaacat ttgggtg                                          27

<210> SEQ ID NO 166
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
caggtgtggg atactaatag tgatcatgtg gta                                   33

<210> SEQ ID NO 167
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
cagcagtatg gtaactcacc gtacact                                          27

<210> SEQ ID NO 168
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
aattcccggg acagcagtgg ttaccatctg gtg                                   33

<210> SEQ ID NO 169
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
attagtagta gtggtaatta cata                                             24

<210> SEQ ID NO 170
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
attagtggta gtggtggtag caca                                             24

<210> SEQ ID NO 171
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 171
attgatccta gtgactctta tacc                                                24

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
atttattggg atgatgataa g                                                   21

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
atattttata gtgggagcac c                                                   21

<210> SEQ ID NO 174
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
attagtggta gtggtggtcg caca                                                24

<210> SEQ ID NO 175
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ttcgtccctc tctttggtac agca                                                24

<210> SEQ ID NO 176
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
atcatcccta tccttggtat agca                                                24

<210> SEQ ID NO 177
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 177
atcatcccta tctttggttc agta                                              24

<210> SEQ ID NO 178
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
atcagcgctt acaatggtaa caca                                              24

<210> SEQ ID NO 179
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
atcatcccta tccttggtct ggca                                              24

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
atctatttta ctgggagcac c                                                 21

<210> SEQ ID NO 181
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
atcatcccta tccttggtgt agca                                              24

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
atatcatatg atggaagcaa taaa                                              24

<210> SEQ ID NO 183
<211> LENGTH: 9
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 183 gaggataac                                                                  9

<210> SEQ ID NO 184
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184 gatgtcagt                                                                  9

<210> SEQ ID NO 185
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185 gagggcagt                                                                  9

<210> SEQ ID NO 186
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186 ggtgcctcc                                                                  9

<210> SEQ ID NO 187
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187 gatgcatcc                                                                  9

<210> SEQ ID NO 188
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188 gatgcatcc                                                                  9

<210> SEQ ID NO 189
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 189 gaggtcaat                                                                  9

<210> SEQ ID NO 190
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190 gatgtcagt                                                                  9

<210> SEQ ID NO 191
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191 gatgcctca                                                                  9

<210> SEQ ID NO 192
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192 ggtgcatct                                                                  9

<210> SEQ ID NO 193
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193 gaggatgac                                                                  9

<210> SEQ ID NO 194
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194 gatgatacc                                                                  9

<210> SEQ ID NO 195
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 195 ggtgcatcc                                                               9

<210> SEQ ID NO 196
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196 gataaaaac                                                               9

<210> SEQ ID NO 197
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
ggattcacct tcaggagcta tagc                                             24

<210> SEQ ID NO 198
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
ggattcacct ttagcagcta tgcc                                             24

<210> SEQ ID NO 199
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
ggatacagct ttaccagcta ctgg                                             24

<210> SEQ ID NO 200
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
gggttctcac tcaacactcc tggagtgggt                                       30

<210> SEQ ID NO 201
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
```
ggtggctcca tgagcattag gagttcctac                                        30

<210> SEQ ID NO 202
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
ggattaacct ttcgcaacta cgcc                                              24

<210> SEQ ID NO 203
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ggaggctcct tcagcagtaa tcca                                              24

<210> SEQ ID NO 204
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
ggaggcacct tcaataggga tggt                                              24

<210> SEQ ID NO 205
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
ggaggcacct tcagcaacta tggt                                              24

<210> SEQ ID NO 206
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
ggttacacct ttagcagcta tggt                                              24

<210> SEQ ID NO 207
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207

```
ggaggcacct tcagcagcta tagt                                          24

<210> SEQ ID NO 208
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
ggtgactcca tcactactac ttactac                                       27

<210> SEQ ID NO 209
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
ggaggcacct tcagcagcta tact                                          24

<210> SEQ ID NO 210
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
ggattcacct tcagtagcta tacc                                          24

<210> SEQ ID NO 211
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
agtggcagca ttgccagcaa ctat                                          24

<210> SEQ ID NO 212
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
agcagtgacg ttggtgatta taactat                                       27

<210> SEQ ID NO 213
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
agcagtgatg ttgggagtta taacctt                                       27
```

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
cagagtgtta gcagaaactc c                                              21

<210> SEQ ID NO 215
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
cagaacatta ggaattat                                                  18

<210> SEQ ID NO 216
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
caggacatta gcaactat                                                  18

<210> SEQ ID NO 217
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
agcagtgata ttgggagtta taacctt                                        27

<210> SEQ ID NO 218
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
agcagtgacg ttggtgatta taactat                                        27

<210> SEQ ID NO 219
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
cagagtattc gtaggtgg                                                  18

<210> SEQ ID NO 220
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
cagagtgtta gcagcagc                                                   18

<210> SEQ ID NO 221
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
agtggcagca ttgcccgcaa ctat                                            24

<210> SEQ ID NO 222
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
aacattggaa gtaaaagt                                                   18

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
cagagtgtta gcagcagcta c                                               21

<210> SEQ ID NO 224
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
agcctcagaa actattat                                                   18

<210> SEQ ID NO 225
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Cys Ser Ser Thr Ser Cys Tyr Ala Thr Thr Leu
            100                 105                 110

Thr Thr Gly Ala Arg Glu Pro Trp Ser Pro Ser Pro Gln Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val
210                 215                 220

<210> SEQ ID NO 226
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Tyr Tyr Tyr Asp Ser Ser Gly Tyr Tyr Tyr Cys Phe Tyr
            100                 105                 110

Leu Gly Pro Arg Asp Asn Gly His Arg Leu Phe Arg Pro Pro Pro Arg
        115                 120                 125

Ala His Arg Ser Ser Pro Trp His Pro Pro Arg Ala Pro Leu Gly
130                 135                 140

Ala Gln Arg Pro Trp Ala Ala Trp Ser Arg Thr Thr Ser Pro Asn Arg
145                 150                 155                 160

```
Arg Cys Arg Gly Thr Gln Ala Pro Pro Ala Ala Cys Thr Pro Ser Arg
                165                 170                 175

Leu Ser Tyr Ser Pro Gln Asp Ser Thr Pro Ser Ala Ala Trp Pro Cys
            180                 185                 190

Pro Pro Ala Ala Trp Ala Pro Arg Pro Thr Ser Ala Thr Ile Thr Ser
        195                 200                 205

Pro Ala Thr Pro Arg Trp Thr Arg Lys
    210                 215

<210> SEQ ID NO 227
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Arg Ile Asp Pro Ser Asp Ser Tyr Thr Asn Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Ser Ser Ser Trp Tyr Thr Thr Leu Thr Thr Gly Ala
            100                 105                 110

Arg Glu Pro Trp Ser Pro Ser Pro Gln Gly Ser Ala Ser Ala Pro Thr
        115                 120                 125

Leu Phe Pro Leu Val Ser Cys Glu Asn Ser Pro Ser Asp Thr Ser Ser
130                 135                 140

Val Ala Val Gly Cys Leu Ala Gln Asp Phe Leu Pro Asp Ser Ile Thr
145                 150                 155                 160

Leu Ser Trp Lys Tyr Lys Asn Asn Ser Asp Ile Ser Ser Thr Arg Gly
                165                 170                 175

Phe Pro Ser Val Leu Arg Gly Gly Lys Tyr Ala Ala Thr Ser Gln Val
            180                 185                 190

Leu Leu Pro Ser Lys Asp Val Met Gln Gly Thr Asp Glu His Val Val
        195                 200                 205

Cys Lys Val Gln His Pro Asn Gly Asn Lys Glu Lys Asn Val Pro Leu
    210                 215                 220

Pro
225

<210> SEQ ID NO 228
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228
```

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asp Asp Lys Arg Tyr Ser Pro Ser
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Arg Tyr Asn Arg Asn His Thr Thr Gly Ser Thr Pro
            100                 105                 110

Gly Ala Arg Glu Pro Trp Ser Pro Ser Pro Gln Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val
    210                 215                 220

<210> SEQ ID NO 229
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Tyr Tyr Asp Phe Trp Ser Gly Tyr Tyr Thr Thr Thr
            100                 105                 110

Leu Thr Thr Gly Ala Arg Glu Pro Trp Ser Pro Ser Pro Gln Ala Ser
        115                 120                 125

Thr Lys Gly Pro Ser Val Phe Pro Leu Ala Pro Ser Ser Lys Ser Thr
```

130                 135                 140
Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
210                 215                 220

<210> SEQ ID NO 230
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Tyr Cys Ser Gly Gly Ser Cys Tyr Ser Ala Glu Tyr
            100                 105                 110

Phe Gln His Trp Gly Gln Gly Thr Leu Val Thr Val Ser Ser Gly Leu
        115                 120                 125

His Gln Gly Pro Ile Gly Leu Pro Pro Gly Thr Leu Leu Gln Glu His
    130                 135                 140

Leu Trp Gly His Ser Gly Pro Gly Leu Pro Gly Gln Gly Leu Leu Pro
145                 150                 155                 160

Arg Thr Gly Asp Gly Val Val Glu Leu Arg Pro Asp Gln Arg Arg
                165                 170                 175

Ala His Leu Pro Gly Cys Pro Thr Val Leu Arg Thr Leu Leu Pro Gln
            180                 185                 190

Gln Arg Gly Asp Arg Ala Leu Gln Gln Leu Gly His Pro Asp Leu His
        195                 200                 205

Leu Gln Arg Glu Ser Gln Ala Gln Gln His Gln Gly Gly Gln Glu Ser
    210                 215                 220

<210> SEQ ID NO 231
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 231

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Leu Glu Arg His Tyr Phe Asp Tyr Trp Gly Gln Gly
            100                 105                 110

Thr Leu Val Thr Val Ser Ser Gly Leu His Gln Gly Pro Ile Gly Leu
        115                 120                 125

Pro Pro Gly Thr Leu Leu Gln Glu His Leu Trp Gly His Ser Gly Pro
    130                 135                 140

Gly Leu Pro Gly Gln Gly Leu Leu Pro Arg Thr Gly Asp Gly Val Val
145                 150                 155                 160

Glu Leu Arg Arg Pro Asp Gln Arg Ala His Leu Pro Gly Cys Pro
                165                 170                 175

Thr Val Leu Arg Thr Leu Leu Pro Gln Gln Arg Gly Asp Arg Ala Leu
            180                 185                 190

Gln Gln Leu Gly His Pro Asp Leu His Leu Gln Arg Glu Ser Gln Ala
        195                 200                 205

Gln Gln His Gln Gly Gly Gln Glu Ser
    210                 215

<210> SEQ ID NO 232
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Trp Glu Leu Leu His Tyr Tyr Tyr Tyr Gly Met
            100                 105                 110

Asp Val Trp Gly Gln Gly Thr Thr Val Thr Val Ser Ser Ala Ser Thr
        115                 120                 125
```

```
Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val
210                 215                 220
```

<210> SEQ ID NO 233
<211> LENGTH: 220
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 233

```
Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Trp Ile Gln Leu Trp Leu Leu Met Leu Leu Met Ser Gly
            100                 105                 110

Ala Lys Gly Gln Trp Ser Pro Ser Leu Gln Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Leu Gly Thr Gln Thr Tyr Ile Cys Asn Val Asn
        195                 200                 205

His Lys Pro Ser Asn Thr Lys Val Asp Lys Lys Val
210                 215                 220
```

<210> SEQ ID NO 234
<211> LENGTH: 218
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 234

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Asp Tyr Gly Asp Tyr Thr Thr Leu Thr Thr Gly Ala Arg
            100                 105                 110

Glu Pro Trp Ser Pro Ser Pro Gln Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val
    210                 215
```

<210> SEQ ID NO 235
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 235

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Thr Gly Thr Thr Gln Leu Val Arg Pro Leu Gly Pro
            100                 105                 110

Gly Asn Pro Gly His Arg Leu Leu Arg Pro Pro Arg Ala His Arg
        115                 120                 125
```

Ser Ser Pro Trp His Pro Pro Pro Arg Ala Pro Leu Gly Ala Gln Arg
        130                 135                 140

Pro Trp Ala Ala Trp Ser Arg Thr Thr Ser Pro Asn Arg Arg Cys Arg
145                 150                 155                 160

Gly Thr Gln Ala Pro Ala Ala Cys Thr Pro Ser Arg Leu Ser Tyr
                165                 170                 175

Ser Pro Gln Asp Ser Thr Pro Ser Ala Ala Trp Pro Cys Pro Pro Ala
                180                 185                 190

Ala Trp Ala Pro Arg Pro Thr Ser Ala Thr Ile Thr Ser Pro Ala Thr
                195                 200                 205

Pro Arg Trp Thr Arg Lys
    210

<210> SEQ ID NO 236
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Val Leu Glu Leu His Asn Trp Phe Asp Pro Trp Gly
            100                 105                 110

Gln Gly Thr Leu Val Thr Val Ser Ser Gly Leu His Gln Gly Pro Ile
        115                 120                 125

Gly Leu Pro Pro Gly Thr Leu Leu Gln Glu His Leu Trp Gly His Ser
    130                 135                 140

Gly Pro Gly Leu Pro Gly Gln Gly Leu Leu Pro Arg Thr Gly Asp Gly
145                 150                 155                 160

Val Val Glu Leu Arg Arg Pro Asp Gln Arg Arg Ala His Leu Pro Gly
                165                 170                 175

Cys Pro Thr Val Leu Arg Thr Leu Leu Pro Gln Gln Arg Gly Asp Arg
                180                 185                 190

Ala Leu Gln Gln Leu Gly His Pro Asp Leu His Leu Arg Glu Ser
            195                 200                 205

Gln Ala Gln Gln His Gln Gly Gly Gln Glu Ser
    210                 215

<210> SEQ ID NO 237
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 237

| Gln | Val | Gln | Leu | Val | Gln | Ser | Gly | Ala | Glu | Val | Lys | Lys | Pro | Gly | Ser |
|---|---|---|---|---|---|---|---|---|---|---|---|---|---|---|---|
| 1 | | | | 5 | | | | | 10 | | | | | 15 | |

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
            35                  40                  45

Gly Arg Ile Ile Pro Ile Leu Gly Thr Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Glu Val Trp Glu Leu Leu His Tyr Phe Asp Tyr Trp Gly Gln
                100                 105                 110

Gly Thr Leu Val Thr Val Ser Ser Gly Leu His Gln Gly Pro Ile Gly
                115                 120                 125

Leu Pro Pro Gly Thr Leu Leu Gln Glu His Leu Trp Gly His Ser Gly
 130                 135                 140

Pro Gly Leu Pro Gly Gln Gly Leu Leu Pro Arg Thr Gly Asp Gly Val
145                 150                 155                 160

Val Glu Leu Arg Arg Pro Asp Gln Arg Arg Ala His Leu Pro Gly Cys
                165                 170                 175

Pro Thr Val Leu Arg Thr Leu Leu Pro Gln Gln Arg Gly Asp Arg Ala
                180                 185                 190

Leu Gln Gln Leu Gly His Pro Asp Leu His Leu Gln Arg Glu Ser Gln
                195                 200                 205

Ala Gln Gln His Gln Gly Gly Gln Glu Ser
    210                 215

<210> SEQ ID NO 238
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Gln Val Gln Leu Val Glu Ser Gly Gly Gly Val Val Gln Pro Gly Arg
 1                   5                  10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Tyr Tyr Asp Phe Trp Thr Gly Tyr Thr Thr Thr Leu
                100                 105                 110

Thr Thr Gly Ala Arg Glu Pro Trp Ser Pro Ser Pro Gln Ala Ser Thr

```
                 115                 120                 125
Lys Gly Pro Ser Val Phe Pro Leu Ala Pro Cys Ser Arg Ser Thr Ser
            130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
            195                 200                 205

Asn Val Asp His Lys Pro Ser Asn Thr Lys Val Asp Lys Thr Val
            210                 215                 220

<210> SEQ ID NO 239
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn His Trp Val Phe Gly Gly Gly Thr Lys Leu Thr Val Leu Ala
            100                 105                 110

Gln Gly Cys Pro Leu Gly His Ser Val Pro Thr Leu Leu Gly Ala Ser
        115                 120                 125

Ser Gln Gln Gly His Thr Gly Val Ser His Lys Leu Leu Pro Gly Ser
        130                 135                 140

Arg Asp Ser Cys Leu Glu Gly Arg Gln Pro Arg Gln Gly Gly Gly Gly
145                 150                 155                 160

Asp His His Thr Leu Gln Thr Lys Gln Gln Val Arg Gly Gln Gln
                165                 170                 175

Leu Pro Glu Pro Asp Ala Ala Val Glu Val Pro Gln Lys Leu Gln Leu
            180                 185                 190

Pro Gly His Ala Arg Glu His Arg Gly Glu Asp Ser Cys Pro Tyr Gly
            195                 200                 205

Met Phe
    210

<210> SEQ ID NO 240
<211> LENGTH: 213
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 240

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Cys Gly Ile Arg Arg Arg Asp Gln Ala Asp Arg Pro Arg
            100                 105                 110

Val Ser Pro Arg Leu Pro Pro Arg Ser Leu Cys Ser Arg Pro Pro Leu
        115                 120                 125

Arg Ser Phe Lys Pro Thr Arg Pro His Trp Cys Val Ser Val Thr Ser
130                 135                 140

Thr Arg Glu Pro Gln Trp Leu Gly Lys Gln Ile Ala Ala Pro Ser Arg
145                 150                 155                 160

Arg Glu Trp Arg Pro Pro His Pro Pro Asn Lys Ala Thr Thr Ser Thr
                165                 170                 175

Arg Pro Ala Ala Ile Ala Arg Leu Ser Ser Gly Ser Pro Thr Glu Ala
            180                 185                 190

Thr Ala Ala Arg Ser Arg Met Lys Gly Ala Pro Trp Arg Gln Trp
        195                 200                 205

Pro Leu Gln Asn Val
    210

<210> SEQ ID NO 241
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Leu Val Ser Trp Tyr Gln Gln His Pro Gly Lys Ala Pro Lys Leu
            35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Phe Cys Gly Ile Arg Arg Arg Asp Gln Ala Asp Arg Pro Ser
            100                 105                 110

```
Pro Arg Leu Pro Pro Arg Ser Leu Cys Ser His Pro Leu Arg Ser
            115                 120                 125

Phe Lys Pro Thr Arg Pro His Trp Cys Val Ser Val Thr Ser Thr Arg
    130                 135                 140

Glu Pro Gln Leu Pro Gly Arg Gln Ile Ala Ala Pro Ser Arg Arg Gly
145                 150                 155                 160

Trp Arg Pro Pro His Pro Pro Asn Lys Ala Thr Thr Ser Thr Arg Pro
                165                 170                 175

Ala Ala Thr Ala Arg Leu Ser Ser Gly Ser Pro Thr Lys Ala Thr Ala
            180                 185                 190

Ala Arg Ser Arg Met Lys Gly Ala Pro Trp Arg Arg Gln Leu Pro Leu
            195                 200                 205

Arg Asn Val
    210

<210> SEQ ID NO 242
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Val His Phe Trp Pro Gly Asp Gln Ala Gly Asp Gln Thr Glu Leu
            100                 105                 110

Trp Leu His His Leu Ser Ser Ser Arg His Leu Met Ser Ser Asn
            115                 120                 125

Leu Glu Leu Pro Leu Leu Cys Ala Cys Ile Thr Ser Ile Pro Glu Arg
130                 135                 140

Pro Lys Tyr Ser Gly Arg Trp Ile Thr Pro Ser Asn Arg Val Thr Pro
145                 150                 155                 160

Arg Arg Val Ser Gln Ser Arg Thr Ala Arg Thr Ala Pro Thr Ala Ser
            165                 170                 175

Ala Ala Pro Arg Ala Lys Gln Thr Thr Arg Asn Thr Lys Ser Thr Pro
            180                 185                 190

Ala Lys Ser Pro Ile Arg Ala Ala Arg Pro Ser Gln Arg Ala Ser Thr
            195                 200                 205

Gly Glu Ser
    210

<210> SEQ ID NO 243
<211> LENGTH: 210
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 243

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Pro
                85                  90                  95

Phe Thr Phe Gly Pro Gly Thr Lys Val Asp Ile Lys Pro Asn Cys Gly
            100                 105                 110

Cys Thr Ile Cys Leu His Leu Pro Ala Ile Ala Val Glu Ile Trp Asn
        115                 120                 125

Cys Leu Cys Cys Val Pro Ala Glu Leu Leu Ser Gln Arg Gly Gln Ser
130                 135                 140

Thr Val Glu Gly Gly Arg Pro Pro Ile Gly Leu Pro Gly Glu Cys His
145                 150                 155                 160

Arg Ala Gly Gln Gln Gly Gln His Leu Gln Pro Gln Gln His Pro Asp
                165                 170                 175

Ala Glu Gln Ser Arg Leu Arg Glu Thr Gln Ser Leu Arg Leu Arg Ser
            180                 185                 190

His Pro Ser Gly Pro Glu Leu Ala Arg His Lys Glu Leu Gln Gln Gly
        195                 200                 205

Arg Val
    210

<210> SEQ ID NO 244
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Pro
                85                  90                  95

Ile Thr Phe Gly Gln Gly Thr Arg Leu Glu Ile Lys Pro Asn Cys Gly
            100                 105                 110
```

```
Cys Thr Ile Cys Leu His Leu Pro Ala Ile Ala Val Glu Ile Trp Asn
            115                 120                 125

Cys Leu Cys Cys Val Pro Ala Glu Leu Leu Ser Gln Arg Gly Gln Ser
        130                 135                 140

Thr Val Glu Gly Gly Arg Pro Pro Ile Gly Leu Pro Gly Glu Cys His
145                 150                 155                 160

Arg Ala Gly Gln Gln Gly Gln His Leu Gln Pro Gln Gln His Pro Asp
                165                 170                 175

Ala Glu Gln Ser Arg Leu Arg Glu Thr Gln Ser Leu Arg Leu Arg Ser
            180                 185                 190

His Pro Ser Gly Pro Glu Leu Ala Arg His Lys Glu Leu Gln Gln Gly
            195                 200                 205

Arg Val
    210

<210> SEQ ID NO 245
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Phe Cys Gly Ile Arg Arg Asp Gln Ala Asp Arg Pro Arg
            100                 105                 110

Val Ser Pro Arg Leu Pro Pro Arg Ser Leu Cys Ser Arg Pro Pro Leu
        115                 120                 125

Arg Ser Phe Lys Pro Thr Arg Pro His Trp Cys Val Ser Val Thr Ser
    130                 135                 140

Thr Arg Glu Pro Gln Trp Leu Gly Lys Gln Ile Ala Ala Pro Ser Arg
145                 150                 155                 160

Arg Glu Trp Arg Pro Pro His Pro Pro Asn Lys Ala Thr Thr Ser Thr
                165                 170                 175

Arg Pro Ala Ala Ile Ala Arg Leu Ser Ser Gly Ser Pro Thr Glu Ala
            180                 185                 190

Thr Ala Ala Arg Ser Arg Met Lys Gly Ala Pro Trp Arg Arg Gln Trp
        195                 200                 205

Pro Leu Gln Asn Val
    210

<210> SEQ ID NO 246
<211> LENGTH: 210
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 246

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Leu Cys Leu Arg Asn Trp Asp Gln Gly His Arg Pro Ser
            100                 105                 110

Pro Arg Pro Thr Pro Arg Ser Leu Cys Ser Arg Pro Pro Leu Arg Ser
        115                 120                 125

Ser Lys Pro Thr Arg Pro His Cys Val Ser Val Thr Ser Thr Arg Glu
130                 135                 140

Leu Gln Trp Leu Gly Arg Gln Met Ala Ala Pro Ser Arg Arg Glu Trp
145                 150                 155                 160

Arg Arg Pro Asn Pro Asn Arg Ala Thr Thr Ser Thr Arg Pro Ala
                165                 170                 175

Ala Thr Ala Arg Pro Ser Ser Gly Ser Pro Thr Glu Ala Thr Ala Ala
            180                 185                 190

Arg Ser Arg Met Lys Gly Ala Pro Trp Arg Arg Gln Trp Pro Leu Gln
        195                 200                 205

Asn Val
    210

<210> SEQ ID NO 247
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Pro
                85                  90                  95

Val His Phe Trp Pro Gly Asp Gln Ala Gly Asp Gln Thr Glu Leu Trp

```
                100             105             110
Leu His Leu Ser Ser Ser Arg His Leu Met Ser Ser Asn Leu
        115             120             125

Glu Leu Pro Leu Leu Cys Ala Cys Ile Thr Ser Ile Pro Glu Arg Pro
130             135             140

Lys Tyr Ser Gly Arg Trp Ile Thr Pro Ser Asn Arg Val Thr Pro Arg
145             150             155             160

Arg Val Ser Gln Ser Arg Thr Ala Arg Thr Ala Pro Thr Ala Ser Ala
                165             170             175

Ala Pro Arg Ala Lys Gln Thr Thr Arg Asn Thr Lys Ser Thr Pro Ala
        180             185             190

Lys Ser Pro Ile Arg Ala Ala Arg Pro Ser Gln Arg Ala Ser Thr Gly
        195             200             205

Glu Ser
    210

<210> SEQ ID NO 248
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Glu Ile Val Met Thr Gln Ser Pro Ala Thr Leu Ser Val Ser Pro Gly
1               5               10              15

Glu Arg Ala Thr Leu Ser Cys Arg Ala Ser Gln Ser Val Ser Ser Asn
            20              25              30

Leu Ala Trp Tyr Gln Gln Lys Pro Gly Gln Ala Pro Arg Leu Leu Ile
        35              40              45

Tyr Gly Ala Ser Thr Arg Ala Thr Gly Ile Pro Ala Arg Phe Ser Gly
    50              55              60

Ser Gly Ser Gly Thr Glu Phe Thr Leu Thr Ile Ser Ser Leu Gln Ser
65              70              75              80

Glu Asp Phe Ala Val Tyr Tyr Cys Gln Gln Tyr Asn Asn Trp Pro Pro
                85              90              95

Val His Phe Trp Pro Gly Asp Gln Ala Gly Asp Gln Thr Glu Leu Trp
            100             105             110

Leu His Leu Ser Ser Ser Arg His Leu Met Ser Ser Asn Leu
        115             120             125

Glu Leu Pro Leu Leu Cys Ala Cys Ile Thr Ser Ile Pro Glu Arg Pro
130             135             140

Lys Tyr Ser Gly Arg Trp Ile Thr Pro Ser Asn Arg Val Thr Pro Arg
145             150             155             160

Arg Val Ser Gln Ser Arg Thr Ala Arg Thr Ala Pro Thr Ala Ser Ala
                165             170             175

Ala Pro Arg Ala Lys Gln Thr Thr Arg Asn Thr Lys Ser Thr Pro Ala
        180             185             190

Lys Ser Pro Ile Arg Ala Ala Arg Pro Ser Gln Arg Ala Ser Thr Gly
        195             200             205

Glu Ser
    210

<210> SEQ ID NO 249
<211> LENGTH: 210
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn His Trp Val Phe Gly Gly Gly Thr Lys Leu Thr Val Leu Ala
            100                 105                 110

Gln Gly Cys Pro Leu Gly His Ser Val Pro Thr Leu Gly Ala Ser
        115                 120                 125

Ser Gln Gln Gly His Thr Gly Val Ser His Lys Leu Leu Pro Gly Ser
    130                 135                 140

Arg Asp Ser Cys Leu Glu Gly Arg Gln Pro Arg Gln Gly Gly Gly
145                 150                 155                 160

Asp His His Thr Leu Gln Thr Lys Gln Gln Val Arg Gly Gln Gln
                165                 170                 175

Leu Pro Glu Pro Asp Ala Ala Val Glu Val Pro Gln Lys Leu Gln Leu
            180                 185                 190

Pro Gly His Ala Arg Glu His Arg Gly Glu Asp Ser Cys Pro Tyr Gly
        195                 200                 205

Met Phe
    210

<210> SEQ ID NO 250
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

```
Pro Val Val Phe Gly Gly Gly Thr Lys Leu Thr Val Leu Gly Ser Ala
            100                 105                 110

Gln Gly Cys Pro Leu Gly His Ser Val Pro Ala Leu Leu Gly Ala Ser
        115                 120                 125

Ser Gln Gln Gly His Thr Gly Val Ser His Lys Leu Leu Pro Gly Ser
    130                 135                 140

Arg Asp Ser Gly Leu Glu Ser Arg Gln Pro Arg Gln Gly Gly Ser Gly
145                 150                 155                 160

Asp His His Thr Leu Gln Thr Lys Gln Gln Gln Val Arg Gly Gln Gln
                165                 170                 175

Leu Ser Glu Pro Asp Ala Ala Val Glu Val Pro Gln Lys Leu Gln Leu
            180                 185                 190

Pro Gly His Ala Arg Glu His Arg Gly Glu Asp Ser Gly Pro Tyr Arg
        195                 200                 205

Met Phe
    210

<210> SEQ ID NO 251
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Val His Phe Trp Pro Gly Asp Gln Ala Gly Asp Gln Thr Glu Leu
            100                 105                 110

Trp Leu His His Leu Ser Ser Ser Arg His Leu Met Ser Ser Asn
        115                 120                 125

Leu Glu Leu Pro Leu Leu Cys Ala Cys Ile Thr Ser Ile Pro Glu Arg
    130                 135                 140

Pro Lys Tyr Ser Gly Arg Trp Ile Thr Pro Ser Asn Arg Val Thr Pro
145                 150                 155                 160

Arg Arg Val Ser Gln Ser Arg Thr Ala Arg Thr Ala Pro Thr Ala Ser
                165                 170                 175

Ala Ala Pro Arg Ala Lys Gln Thr Thr Arg Asn Thr Lys Ser Thr Pro
            180                 185                 190

Ala Lys Ser Pro Ile Arg Ala Ala Arg Pro Ser Gln Arg Ala Ser Thr
        195                 200                 205

Gly Glu Ser
    210

<210> SEQ ID NO 252
```

<211> LENGTH: 208
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 252

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Trp Val Phe Gly Gly Gly Thr Lys Leu Thr Val Leu Ala Gln Gly
            100                 105                 110

Cys Pro Leu Gly His Ser Val Pro Thr Leu Leu Gly Ala Ser Ser Gln
        115                 120                 125

Gln Gly His Thr Gly Val Ser His Lys Leu Leu Pro Gly Ser Arg Asp
    130                 135                 140

Ser Cys Leu Glu Gly Arg Gln Pro Arg Gln Gly Gly Gly Asp His
145                 150                 155                 160

His Thr Leu Gln Thr Lys Gln Gln Val Arg Gly Gln Gln Leu Pro
                165                 170                 175

Glu Pro Asp Ala Ala Val Glu Val Pro Gln Lys Leu Gln Leu Pro Gly
            180                 185                 190

His Ala Arg Glu His Arg Gly Glu Asp Ser Cys Pro Tyr Gly Met Phe
        195                 200                 205

<210> SEQ ID NO 253
<211> LENGTH: 669
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 253
gaggtgcagc tggtggagtc tgggggaggc ctggtcaagc ctggggggtc cctgagactc      60
tcctgtgcag cctctggatt caccttcagt agctatagca tgaactgggt ccgccaggct     120
ccagggaagg ggctggagtg ggtctcatcc attagtagta gtagtagtta catatactac     180
gcagactcag tgaagggccg attcaccatc tccagagaca cgccaagaa ctcactgtat      240 ctgcaaatga acagcctgag agccgaggac acggctgtgt attactgtgc gagagaagga     300
tattgtagta gtaccagctg ctatgccact actttgacta ctggggccag ggaaccctgg     360
tcaccgtctc ctcaggcctc caccaagggc ccatcggtct tccccctggc acctcctcc      420 aagagcacct ctgggggcac agcggccctg ggctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600

```
ttgggcaccc agacctacat ctgcaacgtg aatcacaagc ccagcaacac caaggtggac    660
aagaaagtt                                                            669
```

<210> SEQ ID NO 254
<211> LENGTH: 671
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 254

```
gaggtgcagc tgttggagtc tgggggaggc ttggtacagc ctgggggggtc cctgagactc    60 tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtat attactgtgc gaaagagtat   300
tactatgata gtagtggtta ttactactga tgcttttgat atctggggcc aagggacaat   360
ggtcaccgtc tcttcaggcc tccaccaagg gcccatcggt cttccccctg gcaccctcct   420
ccaagagcac ctctgggggc acagcggccc tgggctgcct ggtcaaggac tacttccccg   480
aaccggtgac ggtgtcgtgg aactcaggcg ccctgaccag cggcgtgcac accttcccgg   540
ctgtcctaca gtcctcagga ctctactccc tcagcagcgt ggtgaccgtg ccctccagca   600
gcttgggcac ccagacctac atctgcaacg tgaatcacaa gcccagcaac accaaggtgg   660
acaagaaagt t                                                         671
```

<210> SEQ ID NO 255
<211> LENGTH: 675
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 255

```
gaagtgcagc tggtgcagtc cggagcagag gtgaaaaagc ccggggagtc tctgaggatc    60
tcctgtaagg gttctggata cagctttacc agctactgga tcagctgggt gcgccagatg   120
cccgggaaag gcctggagtg gatggggagg attgatccta gtgactctta taccaactac   180
agcccgtcct ccaaggcca cgtcaccatc tcagctgaca gtccatcag cactgcctac   240 ctgcagtgga gcagcctgaa ggcctcggac accgccatgt attactgtgc gagagggtat   300
agcagcagct ggtacactac tttgactact ggggccaggg aaccctggtc accgtctcct   360
caggggagtg catccgcccc aaccctttc cccctcgtct cctgtgagaa ttccccgtcg   420
gatacgagca gcgtggccgt tggctgcctc gcacaggact ccttcccga ctccatcact   480 ttgtcctgga atacaagaa caactctgac atcagcagta cccggggctt cccatcagtc   540
ctgagagggg gcaagtacgc agccacctca caggtgctgc tgccttccaa ggacgtcatg   600
cagggcacag acgaacacgt ggtgtgcaaa gtccagcacc ccaacggcaa caaagaaaag   660
aacgtgcctc ttcca                                                    675
```

<210> SEQ ID NO 256
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 256

```
cagatcacct tgaaggagtc tggtcctacg ctggtgaaac ccacacagac cctcacgctg      60
acctgcacct tctctgggtt ctcactcagc actagtggag tgggtgtggg ctggatccgt     120
cagcccccag gaaaggccct ggagtggctt gcactcattt attgggatga tgataagcgc     180
tacagcccat ctctgaagag caggctcacc atcaccaagg acacctccaa aaaccaggtg     240
gtccttacaa tgaccaacat ggaccctgtg gacacagcca catattactg tgcacacaga     300
cggtataacc ggaaccacac aactggttcg acccctgggg ccagggaacc ctggtcaccg     360
tctcctcagg cctccaccaa gggcccatcg gtcttccccc tggcgccctg ctccaggagc     420
acctccgaga gcacagccgc cctgggctgc ctggtcaagg actacttccc cgaaccggtg     480
acggtgtcgt ggaactcagg cgctctgacc agcggcgtgc acaccttccc agctgtccta     540
cagtcctcag gactctactc cctcagcagc gtggtgaccg tgccctccag caacttcggc     600
acccagacct acacctgcaa cgtagatcac aagcccagca acaccaaggt ggacaagaca     660
gtt                                                                   663
```

<210> SEQ ID NO 257
<211> LENGTH: 672
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 257

```
cagctgcagc tgcaggagtc gggcccagga ctggtgaagc cttcggagac cctgtccctc      60
acctgcactg tctctggtgg ctccatcagc agtagtagtt actactgggg ctggatccgc     120
cagcccccag ggaaggggct ggagtggatt gggagtatct attatagtgg gagcacctac     180
tacaacccgt ccctcaagag tcgagtcacc atatcagtag acacgtccaa gaaccagttc     240
tccctgaagc tgagctctgt gaccgccgcg gacacggccg tgtattactg tgcgagagag     300
tattacgatt tttggagtgg ttattatacc actactttga ctactggggc cagggaaccc     360
tggtcaccgt ctcctcaggc ctccaccaag ggcccatcgg tcttcccccct ggcaccctcc     420
tccaagagca cctctggggg cacagcggcc ctgggctgcc tggtcaagga ctacttcccc     480
gaaccggtga cggtgtcgtg gaactcaggc gccctgacca gcggcgtgca caccttcccg     540
gctgtcctac agtcctcagg actctactcc ctcagcagcg tggtgaccgt gccctccagc     600
agcttgggca cccagaccta catctgcaac gtgaatcaca agcccagcaa caccaaggtg     660
gacaagaaag tt                                                         672
```

<210> SEQ ID NO 258
<211> LENGTH: 673
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 258

```
gaggtgcagc tggtggagtc tgggggaggc ttggtacagc ctggggggtc cctgagactc      60
tcctgtgcag cctctggatt cacctttagc agctatgcca tgagctgggt ccgccaggct     120
```

```
ccagggaagg ggctggagtg ggtctcagct attagtggta gtggtggtag cacatactac      180
gcagactccg tgaagggccg gttcaccatc tccagagaca attccaagaa cacgctgtat      240
ctgcaaatga acagcctgag agccgaggac acggccgtat attactgtgc gaaagaagga      300
tattgtagtg gtggtagctg ctactccgct gaatacttcc agcactgggg ccagggcacc      360
ctggtcaccg tctcctcagg cctccaccaa gggcccatcg gtcttccccc tggcaccctc      420
ctccaagagc acctctgggg gcacagcggc cctgggctgc ctggtcaagg actacttccc      480
cgaaccggtg acggtgtcgt ggaactcagg cgccctgacc agcggcgtgc acaccttccc      540
ggctgtccta cagtcctcag gactctactc cctcagcagc gtggtgaccg tgccctccag      600
cagcttgggc acccagacct acatctgcaa cgtgaatcac aagcccagca acaccaaggt      660
ggacaagaaa gtt                                                         673
```

<210> SEQ ID NO 259
<211> LENGTH: 655
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 259

```
caggtgcagc tggtgcagtc tggggctgag gtgaagaagc ctgggtcctc ggtgaaggtc       60
tcctgcaagg cttctggagg caccttcagc agctatgcta tcagctgggt gcgacaggcc      120
cctggacaag ggcttgagtg gatgggaggg atcatcccta tctttggtac agcaaactac      180
gcacagaagt tccagggcag agtcacgatt accgcggacg aatccacgag cacagcctac      240
atggagctga gcagcctgag atctgaggac acggccgtgt attactgtgc gagagaggta      300
taactggaac gacactactt tgactactgg ggccagggaa ccctggtcac cgtctcctca      360
ggcctccacc aagggcccat cggtcttccc cctggcaccc cctccaagag cacctctggg      420
gggcacagcg gccctgggct gcctggtcaa ggactacttc cccgaaccgg tgacggtgtc      480
gtggaactca ggcgccctga ccagcggcgt gcacaccttc ccggctgtcc tacagtcctc      540
aggactctac tccctcagca gcgtggtgac cgtgccctcc agcagcttgg gcacccagac      600
ctacatctgc aacgtgaatc acaagcccag caacaccaag gtggacaaga aagtt          655
```

<210> SEQ ID NO 260
<211> LENGTH: 672
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 260

```
caggtccagc tggtgcagtc tggggctgag gtgaagaagc ctgggtcctc ggtgaaggtc       60
tcctgcaagg cttctggagg caccttcagc agctatgcta tcagctgggt gcgacaggcc      120
cctggacaag ggcttgagtg gatgggaagg atcatcccta tccttggtat agcaaactac      180
gcacagaagt tccagggcag agtcacgatt accgcggaca atccacgag cacagcctac       240 atggagctga gcagcctgag atctgaggac acggccgtgt attactgtgc gagagaggta      300
tagtgggagc tactacatta ctactactac tacggtatgg acgtctgggg ccaagggacc      360
acggtcaccg tctcctcagc ctccaccaag ggcccatcgg tcttcccct ggcaccctcc       420
```

| | |
|---|---|
| tccaagagca cctctggggg cacagcggcc ctgggctgcc tggtcaagga ctacttcccc | 480 |
| gaaccggtga cggtgtcgtg gaactcaggc gccctgacca gcggcgtgca caccttcccg | 540 |
| gctgtcctac agtcctcagg actctactcc ctcagcagcg tggtgaccgt gccctccagc | 600 |
| agcttgggca cccagaccta catctgcaac gtgaatcaca gcccagcaa caccaaggtg | 660 |
| gacaagaaag tt | 672 |

<210> SEQ ID NO 261
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 261

| | |
|---|---|
| caggtgcagc tggtgcagtc tggggctgag gtgaagaagc ctgggtcctc ggtgaaggtc | 60 |
| tcctgcaagg cttctggagg caccttcagc agctatgcta tcagctgggt gcgacaggcc | 120 |
| cctggacaag ggcttgagtg gatgggaggg atcatccta tctttggtac agcaaactac | 180 |
| gcacagaagt tccagggcag agtcacgatt accgcggacg aatccacgag cacagcctac | 240 |
| atggagctga gcagcctgag atctgaggac acggccgtgt attactgtgc gagagagtgg | 300 |
| atacagctat ggttactgat gcttttgatg tctggggcca agggacaatg gtcaccgtct | 360 |
| cttcaggcct ccaccaaggg cccatcggtc ttccccctgg caccctcctc caagagcacc | 420 |
| tctgggggca gcggccct gggctgcctg gtcaaggact acttcccga accggtgacg | 480 |
| gtgtcgtgga actcaggcgc cctgaccagc ggcgtgcaca ccttcccggc tgtcctacag | 540 |
| tcctcaggac tctactccct cagcagcgtg gtgaccgtgc cctccagcag cttgggcacc | 600 |
| cagacctaca tctgcaacgt gaatcacaag cccagcaaca ccaaggtgga caagaaagtt | 660 |

<210> SEQ ID NO 262
<211> LENGTH: 654
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 262

| | |
|---|---|
| caggttcagc tggtgcagtc tggagctgag gtgaagaagc ctggggcctc agtgaaggtc | 60 |
| tcctgcaagg cttctggtta caccttacc agctatggta tcagctgggt gcgacaggcc | 120 |
| cctggacaag ggcttgagtg gatgggatgg atcagcgctt acaatggtaa cacaaactat | 180 |
| gcacagaagc tccagggcag agtcaccatg accacagaca catccacgag cacagcctac | 240 |
| atggagctga ggagcctgag atctgacgac acggccgtgt attactgtgc gagagatgac | 300 |
| tacggtgact acactacttt gactactggg gccagggaac cctggtcacc gtctcctcag | 360 |
| gcctccacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag cgccctgac cagcggcgtg cacaccttcc cggctgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagaa agtt | 654 |

<210> SEQ ID NO 263
<211> LENGTH: 656

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 263
caggtccagc tggtgcaatc tggggctgag gtgaagaagc ctgggtcctc ggtgaaggtc      60
tcctgcaagg cttctggagg caccttcagc agctatacta tcagctgggt gcgacaggcc     120
cctggacaag ggcttgagtg gatgggaagg atcatcccta tccttggtat agcaaactac     180
gcacagaagt tccagggcag agtcacgatt accgcggaca atccacgag cacagcctac      240 atggagctga gcagcctgag atctgaggac acggccgtgt attactgtgc gagaggtaca     300
actggaacga cacaactggt tcgacccctg gggccaggga ccctggtca ccgtctcctc      360 aggcctccac caagggccca tcggtcttcc ccctggcacc ctcctccaag agcacctctg     420
ggggcacagc ggccctgggc tgcctggtca aggactactt ccccgaaccg gtgacggtgt     480
cgtggaactc aggcgccctg accagcggcg tgcacacctt cccggctgtc ctacagtcct     540
caggactcta ctccctcagc agcgtggtga ccgtgccctc agcagcttg ggcacccaga      600 cctacatctg caacgtgaat cacaagccca gcaacaccaa ggtggacaag aaagtt        656

<210> SEQ ID NO 264
<211> LENGTH: 661
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 264
cagctgcagc tgcaggagtc gggcccagga ctggtgaagc cttcggagac cctgtccctc      60
acctgcactg tctctggtgg ctccatcagc agtagtagtt actactgggg ctggatccgc     120
cagcccccag ggaaggggct ggagtggatt gggagtatct attatagtgg gagcacctac     180
tacaacccgt ccctcaagag tcgagtcacc atatccgtag acacgtccaa gaaccagttc     240
tccctgaagc tgagctctgt gaccgccgca gacacggctg tgtattactg tgcgagacag     300
gtataactgg aactacacaa ctggttcgac ccctggggcc agggaaccct ggtcaccgtc     360
tcctcaggcc tccaccaagg gcccatcggt cttcccctg gcaccctcct ccaagagcac      420
ctctgggggc acagcggccc tgggctgcct ggtcaaggac tacttccccg aaccggtgac     480
ggtgtcgtgg aactcaggcg ccctgaccag cggcgtgcac accttcccgg ctgtcctaca     540
gtcctcagga ctctactccc tcagcagcgt ggtgaccgtg ccctccagca gcttgggcac     600
ccagacctac atctgcaacg tgaatcacaa gcccagcaac accaaggtgg acaagaaagt     660
t                                                                    661

<210> SEQ ID NO 265
<211> LENGTH: 658
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 265
caggtccagc tggtgcaatc tggggctgag gtgaagaagc ctgggtcctc ggtgaaggtc      60
tcctgcaagg cttctggagg caccttcagc agctatacta tcagctgggt gcgacaggcc     120
```

```
cctggacaag ggcttgagtg gatgggaagg atcatcccta tccttggtac agcaaactac      180
gcacagaagt tccagggcag agtcacgatt accgcggaca aatccacgag cacagcctac      240
atggagctga gcagcctgag atctgaggac acggccgtgt attactgtgc gagagaggta      300
tagtgggagc tactcacta ctttgactac tggggccagg gaaccctggt caccgtctcc       360
tcaggcctcc accaagggcc catcggtctt ccccctggca ccctcctcca gagcacctc       420 tgggggcaca gcgccctgg gctgcctggt caaggactac ttccccgaac cggtgacggt       480
gtcgtggaac tcaggcgccc tgaccagcgg cgtgcacacc ttcccggctg tcctacagtc      540
ctcaggactc tactccctca gcagcgtggt gaccgtgccc tccagcagct gggcaccca       600 gacctacatc tgcaacgtga atcacaagcc cagcaacacc aaggtggaca gaaagtt        658
```

<210> SEQ ID NO 266
<211> LENGTH: 669
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 266

```
caggtgcagc tggtggagtc tgggggaggc gtggtccagc ctgggaggtc cctgagactc      60
tcctgtgcag cctctggatt caccttcagt agctatgcta tgcactgggt ccgccaggct      120
ccaggcaagg ggctggagtg ggtggcagtt atatcatatg atggaagcaa taaatactac      180
gcagactccg tgaagggccg attcaccatc tccagagaca attccaagaa cacgctgtat      240
ctgcaaatga acagcctgag agctgaggac acggctgtgt attactgtgc gagagagtat      300
tatgattttt ggactggtta ttataccact actttgacta ctggggccag ggaaccctgg      360
tcaccgtctc ctcaggcctc caccaagggc ccatcggtct tccccctggc gcctgctcc      420 aggagcacct ccgagagcac agccgccctg ggctgcctgg tcaaggacta cttccccgaa      480
ccggtgacgg tgtcgtggaa ctcaggcgct ctgaccagcg gcgtgcacac cttcccagct      540
gtcctacagt cctcaggact ctactccctc agcagcgtgg tgaccgtgcc ctccagcaac      600
ttcggcaccc agacctacac ctgcaacgta gatcacaagc ccagcaacac caaggtggac      660
aagacagtt                                                             669
```

<210> SEQ ID NO 267
<211> LENGTH: 646
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 267

```
aattttatgc tgactcagcc ccactctgtg tcggagtctc cggggaagac ggtaaccatc      60
tcctgcaccc gcagcagtgg cagcattgcc agcaactatg tgcagtggta ccagcagcgc      120
ccgggcagtt cccccaccac tgtgatctat gaggataacc aaagacctc tggggtccct       180 gatcggttct ctggctccat cgacagctcc tccaactctg cctccctcac catctctgga      240
ctgaagactg aggacgaggc tgactactac tgtcagtctt atgatagcag caatcattgg      300
gtgttcggcg agggaccaa gctgaccgtc ctagcccaag ctgcccccct cggtcactct       360
gttcccaccc tcctctgagg agcttcaagc caacaaggcc acactggtgt gtctcataag      420
```

```
tgacttctac ccgggagccg tgacagttgc ctggaaggca gatagcagcc ccgtcaaggc    480
gggggtggag accaccacac cctccaaaca aagcaacaac aagtacgcgg ccagcagcta    540
cctgagcctg acgcctgagc agtggaagtc ccacaaaagc tacagctgcc aggtcacgca    600
tgaagggagc accgtggaga agacagttgc ccctacggaa tgttca                  646
```

<210> SEQ ID NO 268
<211> LENGTH: 653
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 268

```
cagtctgccc tgactcagcc tgcctccgtg tctgggtctc ctggacagtc gatcaccatc     60
tcctgcactg gaaccagcag tgacgttggt ggttataact atgtctcctg gtaccaacag    120
cacccaggca aagcccccaa actcatgatt tatgaggtca gtaatcggcc ctcaggggtt    180
tctaatcgct tctctggctc caagtctggc aacacggcct ccctgaccat ctctgggctc    240
caggctgagg acgaggctga ttattactgc agctcatata agcagcag cactctctgt     300 ggtattcggc ggagggacca agctgaccgt cctagggtca gcccaaggct gccccctcgg    360
tcactctgtt cccgccctcc tctgaggagc ttcaagccaa caaggccaca ctggtgtgtc    420
tcataagtga cttctacccg ggagccgtga cagtggcttg gaaagcagat agcagccccg    480
tcaaggcggg agtggagacc accacaccct ccaaacaaag caacaacaag tacgcggcca    540
gcagctatct gagcctgacg cctgagcagt ggaagtccca cagaagctac agctgccagg    600
tcacgcatga agggagcacc gtggagaaga cagtggcccc tacagaatgt tca          653
```

<210> SEQ ID NO 269
<211> LENGTH: 647
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 269

```
cagtctgccc tgactcagcc tgcctccgtg tctgggtctc ctggacagtc gatcaccatc     60
tcctgcactg gaaccagcag tgatgttggg agttataacc ttgtctcctg gtaccaacag    120
cacccaggca aagcccccaa actcatgatt tatgagggca gtaagcggcc ctcaggggtt    180
tctaatcgct tctctggctc caagtctggc aacacggcct ccctgacaat ctctgggctc    240
caggctgagg acgaggctga ttattactgc tgctcatatg caggtagtag cactttctgt    300
ggtattcggc ggagggacca agctgaccgt cctagcccaa ggctgccccc tcggtcactc    360
tgttcccacc ctcctctgag gagcttcaag ccaacaaggc cacactggtg tgtctcataa    420
gtgacttcta cccgggagcc gtgacagttg cctggaaggc agatagcagc ccgtcaagg    480 cgggggtgga gaccaccaca ccctccaaac aaagcaacaa caagtacgcg gccagcagct    540
acctgagcct gacgcctgag cagtggaagt cccacaaaag ctacagctgc caggtcacgc    600
atgaagggag caccgtggag aagacagttg cccctacgga atgttca                 647
```

<210> SEQ ID NO 270
<211> LENGTH: 650
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 270

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacctcc tgtacacttt     300
tggccagggg accaagctgg agatcaaacc gaactgtggc tgcaccatct gtcttcatct     360
tcccgccatc tgatgagcag ttgaaatctg gaactgcctc tgttgtgtgc ctgctgaata     420
acttctatcc cagagaggcc aaagtacagt ggaaggtgga taacgccctc caatcgggta     480
actcccagga gagtgtcaca gagcaggaca gcaaggacag cacctacagc ctcagcagca     540
ccctgacgct gagcaaagca gactacgaga aacacaaagt ctacgcctgc gaagtcaccc     600
atcagggcct gagctcgccc gtcacaaaga gcttcaacag gggagagtgt                650
```

<210> SEQ ID NO 271
<211> LENGTH: 646
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 271

```
gacatccaga tgacccagtc tccatcctcc ctgtctgcat ctgtaggaga cagagtcacc      60
atcacttgcc aggcgagtca ggacattagc aactatttaa attggtatca gcagaaacca     120
gggaaagccc ctaagctcct gatctacgat gcatccaatt tggaaacagg gtcccatca     180
aggttcagtg gaagtggatc tgggacagat tttactttca ccatcagcag cctgcagcct     240
gaagatattg caacatatta ctgtcaacag tatgataatc tccctccatt cactttcggc     300
cctgggacca agtggatat caaaccgaac tgtggctgca ccatctgtct tcatcttccc     360
gccatctgat gagcagttga aatctggaac tgcctctgtt gtgtgcctgc tgaataactt     420
ctatcccaga gaggccaaag tacagtggaa ggtggataac gccctccaat cgggtaactc     480
ccaggagagt gtcacagagc aggacagcaa ggacagcacc tacagcctca gcagcaccct     540
gacgctgagc aaagcagact acgagaaaca caaagtctac gcctgcgaag tcacccatca     600
gggcctgagc tcgcccgtca caaagagctt caacagggga gagtgt                    646
```

<210> SEQ ID NO 272
<211> LENGTH: 646
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 272

```
gacatccaga tgacccagtc tccatcctcc ctgtctgcat ctgtaggaga cagagtcacc      60
atcacttgcc aggcgagtca ggacattagc aactatttaa attggtatca gcagaaacca     120
gggaaagccc ctaagctcct gatctacgat gcatccaatt tggaaacagg gtcccatca     180
aggttcagtg gaagtggatc tgggacagat tttactttca ccatcagcag cctgcagcct     240
```

```
gaagatattg caacatatta ctgtcaacag tatgataatc tccctccgat caccttcggc    300
caagggacac gactggagat taaaccgaac tgtggctgca ccatctgtct tcatcttccc    360
gccatctgat gagcagttga aatctggaac tgcctctgtt gtgtgcctgc tgaataactt    420
ctatcccaga gaggccaaag tacagtggaa ggtggataac gccctccaat cgggtaactc    480
ccaggagagt gtcacagagc aggacagcaa ggacagcacc tacagcctca gcagcaccct    540
gacgctgagc aaagcagact acgagaaaca caaagtctac gcctgcgaag tcacccatca    600
gggcctgagc tcgcccgtca caaagagctt caacagggga gagtgt                    646
```

<210> SEQ ID NO 273
<211> LENGTH: 653
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 273

```
cagtctgccc tgactcagcc tgcctccgtg tctgggtctc ctggacagtc gatcaccatc     60
tcctgcactg gaaccagcag tgatgttggg agttataacc ttgtctcctg gtaccaacag    120
cacccaggca agccccccaa actcatgatt tatgaggtca gtaagcggcc ctcaggggtt    180
tctaatcgct tctctggctc caagtctggc aacacggcct ccctgacaat ctctgggctc    240
caggctgagg acgaggctga ttattactgc tgctcatatg caggtagtag cactttctgt    300
ggtattcggc ggagggacca agctgaccgt cctaggtca gcccaaggct gccccctcgg     360
tcactctgtt cccgccctcc tctgaggagc ttcaagccaa caaggccaca ctggtgtgtc    420
tcataagtga cttctacccg ggagccgtga cagtggcttg aaagcagat agcagccccg    480 tcaaggcggg agtggagacc accacaccct ccaaacaaag caacaacaag tacgcggcca    540
gcagctatct gagcctgacg cctgagcagt ggaagtccca cagaagctac agctgccagg    600
tcacgcatga agggagcacc gtggagaaga cagtggcccc tacagaatgt tca           653
```

<210> SEQ ID NO 274
<211> LENGTH: 647
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 274

```
cagtctgccc tgactcagcc tgcctccgtg tctgggtctc ctggacagtc gatcaccatc     60
tcctgcactg gaaccagcag tgacgttggt ggttataact atgtctcctg gtaccaacag    120
cacccaggca agccccccaa actcatgatt tatgaggtca gtaatcggcc ctcaggggtt    180
tctaatcgct tctctggctc caagtctggc aacacggcct ccctgaccat ctctgggctc    240
caggctgagg acgaggctga ttattactgc agctcatata caagcagcag cactctctta    300
tgtcttcgga actgggacca aggtcaccgt cctagcccaa ggccaacccc acggtcactc    360
tgttcccgcc ctcctctgag gagctccaag ccaacaaggc cacactagtg tgtctgatca    420
gtgacttcta cccgggagct gtgacagtgg cttggaaggc agatggcagc cccgtcaagg    480
cgggagtgga gaccaccaaa ccctccaaac agagcaacaa caagtacgcg gccagcagct    540
acctgagcct gacgcccgag cagtggaagt cccacagaag ctacagctgc caggtcacgc    600
```

```
atgaaggagg caccgtggag aagacagtgg cccctacaga atgttca         647
```

<210> SEQ ID NO 275
<211> LENGTH: 647
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 275

```
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctatgat gcctccagtt tggaaagtgg ggtcccatca   180
aggttcagcg gcagtggatc tgggacagaa ttcactctca ccatcagcag cctgcagcct   240
gatgattttg caacttatta ctgccaacag tataatagtt attctcctgt acacttttgg   300
ccaggggacc aagctggaga tcaaaccgaa ctgtggctgc accatctgtc ttcatcttcc   360
cgccatctga tgagcagttg aaatctggaa ctgcctctgt tgtgtgcctg ctgaataact   420
tctatcccag agaggccaaa gtacagtgga aggtggataa cgccctccaa tcgggtaact   480
cccaggagag tgtcacagag caggacagca aggacagcac ctacagcctc agcagcaccc   540
tgacgctgag caaagcagac tacgagaaac acaaagtcta cgcctgcgaa gtcacccatc   600
agggcctgag ctcgcccgtc acaaagagct tcaacagggg agagtgt             647
```

<210> SEQ ID NO 276
<211> LENGTH: 647
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 276

```
gaaatagtga tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataact ggcctcctgt acacttttgg   300
ccaggggacc aagctggaga tcaaaccgaa ctgtggctgc accatctgtc ttcatcttcc   360
cgccatctga tgagcagttg aaatctggaa ctgcctctgt tgtgtgcctg ctgaataact   420
tctatcccag agaggccaaa gtacagtgga aggtggataa cgccctccaa tcgggtaact   480
cccaggagag tgtcacagag caggacagca aggacagcac ctacagcctc agcagcaccc   540
tgacgctgag caaagcagac tacgagaaac acaaagtcta cgcctgcgaa gtcacccatc   600
agggcctgag ctcgcccgtc acaaagagct tcaacagggg agagtgt             647
```

<210> SEQ ID NO 277
<211> LENGTH: 646
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 277

```
aattttatgc tgactcagcc ccactctgtg tcggagtctc cggggaagac ggtaaccatc    60
tcctgcaccc gcagcagtgg cagcattgcc agcaactatg tgcagtggta ccagcagcgc   120
ccgggcagtt cccccaccac tgtgatctat gaggataacc aaagaccctc tggggtccct   180
gatcggttct ctggctccat cgacagctcc tccaactctg cctccctcac catctctgga   240
ctgaagactg aggacgaggc tgactactac tgtcagtctt atgatagcag caatcattgg   300
gtgttcggcg agggaccaa gctgaccgtc ctagcccaag ctgcccctt cggtcactct    360 gttcccaccc tcctctgagg agcttcaagc caacaaggcc acactggtgt gtctcataag   420
tgacttctac ccgggagccg tgacagttgc ctggaaggca gatagcagcc ccgtcaaggc   480
gggggtggag accaccacac cctccaaaca agcaacaac aagtacgcgg ccagcagcta    540
cctgagcctg acgcctgagc agtggaagtc ccacaaaagc tacagctgcc aggtcacgca   600
tgaagggagc accgtggaga agacagttgc ccctacggaa tgttca               646

<210> SEQ ID NO 278
<211> LENGTH: 646
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 278
tcctatgtgc tgactcagcc accctcggtg tcagtggccc caggacagac ggccaggatt    60
acctgtgggg gaaacaacat tggaagtaaa agtgtgcact ggtaccagca gaagccaggc   120
caggcccctg tgctggtcgt ctatgatgat agcgaccggc cctcagggat ccctgagcga   180
ttctctggct ccaactctgg gaacacggcc accctgacca tcagcagggt cgaagccggg   240
gatgaggccg actattactg tcaggtgtgg gatagtagta gtgatcatcc tgtggtattc   300
ggcggaggga ccaagctgac cgtcctaggg tcagcccaag ctgcccctt cggtcactct    360 gttcccgccc tcctctgagg agcttcaagc caacaaggcc acactggtgt gtctcataag   420
tgacttctac ccgggagccg tgacagtggc ttggaaagca gatagcagcc ccgtcaaggc   480
gggagtggag accaccacac cctccaaaca agcaacaac aagtacgcgg ccagcagcta    540
tctgagcctg acgcctgagc agtggaagtc ccacagaagc tacagctgcc aggtcacgca   600
tgaagggagc accgtggaga agacagtggc ccctacagaa tgttca                646

<210> SEQ ID NO 279
<211> LENGTH: 650
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 279
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcacctcc tgtacacttt   300
tggccagggg accaagctgg agatcaaacc gaactgtggc tgcaccatct gtcttcatct   360
tcccgccatc tgatgagcag ttgaaatctg gaactgcctc tgttgtgtgc ctgctgaata   420
```

```
acttctatcc cagagaggcc aaagtacagt ggaaggtgga taacgccctc caatcgggta    480
actcccagga gagtgtcaca gagcaggaca gcaaggacag cacctacagc ctcagcagca    540
ccctgacgct gagcaaagca gactacgaga acacaaagt ctacgcctgc gaagtcaccc     600
atcagggcct gagctcgccc gtcacaaaga gcttcaacag gggagagtgt               650
```

<210> SEQ ID NO 280
<211> LENGTH: 640
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 280

```
tcttctgagc tgactcagga ccctgctgtg tctgtggcct gggacagac agtcaggatc      60 acatgccaag agacagcct cagaagctat tatgcaagct ggtaccagca gaagccagga    120
caggcccctg tacttgtcat ctatggtaaa acaaccggc cctcaggat cccagaccga     180 ttctctggct ccagctcagg aaacacagct tccttgacca tcactggggc tcaggcggaa    240
gatgaggctg actattactg taactcccgg gacagcagtg gtaaccatct ttgggtgttc    300
ggcggaggga ccaagctgac cgtcctagcc caaggctgcc ccctcggtca ctctgttccc    360
accctcctct gaggagcttc aagccaacaa ggccacactg gtgtgtctca taagtgactt    420
ctacccggga gccgtgacag ttgcctggaa ggcagatagc agccccgtca aggcggggt     480 ggagaccacc acaccctcca acaaagcaa caacaagtac gcggccagca gctacctgag    540
cctgacgcct gagcagtgga agtcccacaa agctacagc tgccaggtca cgcatgaagg    600
gagcaccgtg gagaagacag ttgcccctac ggaatgttca                        640
```

<210> SEQ ID NO 281
<211> LENGTH: 1189
<212> TYPE: PRT
<213> ORGANISM: Homo sapiens

<400> SEQUENCE: 281

```
Met Val Pro Cys Trp Asn His Gly Asn Ile Thr Arg Ser Lys Ala Glu
1               5                   10                  15

Glu Leu Leu Ser Arg Thr Gly Lys Asp Gly Ser Phe Leu Val Arg Ala
            20                  25                  30

Ser Glu Ser Ile Ser Arg Ala Tyr Ala Leu Cys Val Leu Tyr Arg Asn
        35                  40                  45

Cys Val Tyr Thr Tyr Arg Ile Leu Pro Asn Glu Asp Asp Lys Phe Thr
    50                  55                  60

Val Gln Ala Ser Glu Gly Val Ser Met Arg Phe Phe Thr Lys Leu Asp
65                  70                  75                  80

Gln Leu Ile Glu Phe Tyr Lys Lys Glu Asn Met Gly Leu Val Thr His
                85                  90                  95

Leu Gln Tyr Pro Val Pro Leu Glu Glu Glu Asp Thr Gly Asp Asp Pro
            100                 105                 110

Glu Glu Asp Thr Val Glu Ser Val Val Ser Pro Pro Glu Leu Pro Pro
        115                 120                 125

Arg Asn Ile Pro Leu Thr Ala Ser Ser Cys Glu Ala Lys Glu Val Pro
    130                 135                 140

Phe Ser Asn Glu Asn Pro Arg Ala Thr Glu Thr Ser Arg Pro Ser Leu
145                 150                 155                 160
```

-continued

```
Ser Glu Thr Leu Phe Gln Arg Leu Gln Ser Met Asp Thr Ser Gly Leu
                165                 170                 175

Pro Glu Glu His Leu Lys Ala Ile Gln Asp Tyr Leu Ser Thr Gln Leu
            180                 185                 190

Ala Gln Asp Ser Glu Phe Val Lys Thr Gly Ser Ser Leu Pro His
        195                 200                 205

Leu Lys Lys Leu Thr Thr Leu Leu Cys Lys Glu Leu Tyr Gly Glu Val
        210                 215                 220

Ile Arg Thr Leu Pro Ser Leu Glu Ser Leu Gln Arg Leu Phe Asp Gln
225                 230                 235                 240

Gln Leu Ser Pro Gly Leu Arg Pro Arg Pro Gln Val Pro Gly Glu Ala
                245                 250                 255

Asn Pro Ile Asn Met Val Ser Lys Leu Ser Gln Leu Thr Ser Leu Leu
                260                 265                 270

Ser Ser Ile Glu Asp Lys Val Lys Ala Leu Leu His Glu Gly Pro Glu
            275                 280                 285

Ser Pro His Arg Pro Ser Leu Ile Pro Pro Val Thr Phe Glu Val Lys
        290                 295                 300

Ala Glu Ser Leu Gly Ile Pro Gln Lys Met Gln Leu Lys Val Asp Val
305                 310                 315                 320

Glu Ser Gly Lys Leu Ile Ile Lys Lys Ser Lys Asp Gly Ser Glu Asp
                325                 330                 335

Lys Phe Tyr Ser His Lys Lys Ile Leu Gln Leu Ile Lys Ser Gln Lys
                340                 345                 350

Phe Leu Asn Lys Leu Val Ile Leu Val Glu Thr Glu Lys Glu Lys Ile
            355                 360                 365

Leu Arg Lys Glu Tyr Val Phe Ala Asp Ser Lys Lys Arg Glu Gly Phe
        370                 375                 380

Cys Gln Leu Leu Gln Gln Met Lys Asn Lys His Ser Glu Gln Pro Glu
385                 390                 395                 400

Pro Asp Met Ile Thr Ile Phe Ile Gly Thr Trp Asn Met Gly Asn Ala
                405                 410                 415

Pro Pro Pro Lys Lys Ile Thr Ser Trp Phe Leu Ser Lys Gly Gln Gly
                420                 425                 430

Lys Thr Arg Asp Asp Ser Ala Asp Tyr Ile Pro His Asp Ile Tyr Val
                435                 440                 445

Ile Gly Thr Gln Glu Asp Pro Leu Ser Glu Lys Glu Trp Leu Glu Ile
            450                 455                 460

Leu Lys His Ser Leu Gln Glu Ile Thr Ser Val Thr Phe Lys Thr Val
465                 470                 475                 480

Ala Ile His Thr Leu Trp Asn Ile Arg Ile Val Val Leu Ala Lys Pro
                485                 490                 495

Glu His Glu Asn Arg Ile Ser His Ile Cys Thr Asp Asn Val Lys Thr
            500                 505                 510

Gly Ile Ala Asn Thr Leu Gly Asn Lys Gly Ala Val Gly Val Ser Phe
        515                 520                 525

Met Phe Asn Gly Thr Ser Leu Gly Phe Val Asn Ser His Leu Thr Ser
    530                 535                 540

Gly Ser Glu Lys Lys Leu Arg Arg Asn Gln Asn Tyr Met Asn Ile Leu
545                 550                 555                 560

Arg Phe Leu Ala Leu Gly Asp Lys Lys Leu Ser Pro Phe Asn Ile Thr
                565                 570                 575
```

```
His Arg Phe Thr His Leu Phe Trp Phe Gly Asp Leu Asn Tyr Arg Val
                580                 585                 590

Asp Leu Pro Thr Trp Glu Ala Glu Thr Ile Ile Gln Lys Ile Lys Gln
            595                 600                 605

Gln Gln Tyr Ala Asp Leu Leu Ser His Asp Gln Leu Leu Thr Glu Arg
        610                 615                 620

Arg Glu Gln Lys Val Phe Leu His Phe Glu Glu Glu Ile Thr Phe
625                 630                 635                 640

Ala Pro Thr Tyr Arg Phe Glu Arg Leu Thr Arg Asp Lys Tyr Ala Tyr
                645                 650                 655

Thr Lys Gln Lys Ala Thr Gly Met Lys Tyr Asn Leu Pro Ser Trp Cys
                660                 665                 670

Asp Arg Val Leu Trp Lys Ser Tyr Pro Leu Val His Val Val Cys Gln
                675                 680                 685

Ser Tyr Gly Ser Thr Ser Asp Ile Met Thr Ser Asp His Ser Pro Val
                690                 695                 700

Phe Ala Thr Phe Glu Ala Gly Val Thr Ser Gln Phe Val Ser Lys Asn
705                 710                 715                 720

Gly Pro Gly Thr Val Asp Ser Gln Gly Gln Ile Glu Phe Leu Arg Cys
                725                 730                 735

Tyr Ala Thr Leu Lys Thr Lys Ser Gln Thr Lys Phe Tyr Leu Glu Phe
                740                 745                 750

His Ser Ser Cys Leu Glu Ser Phe Val Lys Ser Gln Glu Gly Glu Asn
                755                 760                 765

Glu Glu Gly Ser Glu Gly Glu Leu Val Val Lys Phe Gly Glu Thr Leu
770                 775                 780

Pro Lys Leu Lys Pro Ile Ile Ser Asp Pro Glu Tyr Leu Leu Asp Gln
785                 790                 795                 800

His Ile Leu Ile Ser Ile Lys Ser Ser Asp Ser Asp Glu Ser Tyr Gly
                805                 810                 815

Glu Gly Cys Ile Ala Leu Arg Leu Glu Ala Thr Glu Thr Gln Leu Pro
                820                 825                 830

Ile Tyr Thr Pro Leu Thr His His Gly Glu Leu Thr Gly His Phe Gln
        835                 840                 845

Gly Glu Ile Lys Leu Gln Thr Ser Gln Gly Lys Thr Arg Glu Lys Leu
850                 855                 860

Tyr Asp Phe Val Lys Thr Glu Arg Asp Glu Ser Gly Pro Lys Thr
865                 870                 875                 880

Leu Lys Ser Leu Thr Ser His Asp Pro Met Lys Gln Trp Glu Val Thr
                885                 890                 895

Ser Arg Ala Pro Pro Cys Ser Gly Ser Ser Ile Thr Glu Ile Ile Asn
                900                 905                 910

Pro Asn Tyr Met Gly Val Gly Pro Phe Gly Pro Met Pro Leu His
        915                 920                 925

Val Lys Gln Thr Leu Ser Pro Asp Gln Pro Thr Ala Trp Ser Tyr
        930                 935                 940

Asp Gln Pro Pro Lys Asp Ser Pro Leu Gly Pro Cys Arg Gly Glu Ser
945                 950                 955                 960

Pro Pro Thr Pro Pro Gly Gln Pro Ile Ser Pro Lys Lys Phe Leu
                965                 970                 975

Pro Ser Thr Ala Asn Arg Gly Leu Pro Pro Arg Thr Gln Glu Ser Arg
                980                 985                 990

Pro Ser Asp Leu Gly Lys Asn Ala  Gly Asp Thr Leu Pro  Gln Glu Asp
```

```
            995                 1000                1005

Leu Pro  Leu Thr  Lys Pro  Glu  Met Phe Asn  Pro  Leu Tyr Gly
    1010              1015               1020

Ser Leu  Ser Ser  Phe Pro  Lys  Pro Ala Arg  Lys  Asp Gln Glu
    1025              1030               1035

Ser Pro  Lys Met  Pro Arg  Lys  Glu Pro Pro  Cys  Pro Glu Pro
    1040              1045               1050

Gly Ile  Leu Ser  Pro Ser  Ile  Val Leu Thr  Lys  Ala Gln Glu Ala
    1055              1060               1065

Asp Arg  Gly Glu  Gly Pro  Gly  Lys Gln Val  Pro  Ala Pro Arg Leu
    1070              1075               1080

Arg Ser  Phe Thr  Cys Ser  Ser  Ser Ala Glu  Gly  Arg Ala Ala Gly
    1085              1090               1095

Gly Asp  Lys Ser  Gln Gly  Lys  Pro Lys Thr  Pro  Val Ser Ser Gln
    1100              1105               1110

Ala Pro  Val Pro  Ala Lys  Arg  Pro Ile Lys  Pro  Ser Arg Ser Glu
    1115              1120               1125

Ile Asn  Gln Gln  Thr Pro  Pro  Thr Pro Thr  Pro  Arg Pro Pro Leu
    1130              1135               1140

Pro Val  Lys Ser  Pro Ala  Val  Leu His Leu  Gln  His Ser Lys Gly
    1145              1150               1155

Arg Asp  Tyr Arg  Asp Asn  Thr  Glu Leu Pro  His  His Gly Lys His
    1160              1165               1170

Arg Pro  Glu Glu  Gly Pro  Pro  Gly Pro Leu  Gly  Arg Thr Ala Met
    1175              1180               1185

Gln

<210> SEQ ID NO 282
<211> LENGTH: 1191
<212> TYPE: PRT
<213> ORGANISM: Mus musculus

<400> SEQUENCE: 282

Met Pro Ala Met Val Pro Gly Trp Asn His Gly Asn Ile Thr Arg Ser
1               5                   10                  15

Lys Ala Glu Glu Leu Leu Ser Arg Ala Gly Lys Asp Gly Ser Phe Leu
            20                  25                  30

Val Arg Ala Ser Glu Ser Ile Pro Arg Ala Tyr Ala Leu Cys Val Leu
        35                  40                  45

Phe Arg Asn Cys Val Tyr Thr Tyr Arg Ile Leu Pro Asn Glu Asp Asp
    50                  55                  60

Lys Phe Thr Val Gln Ala Ser Glu Gly Val Pro Met Arg Phe Phe Thr
65                  70                  75                  80

Lys Leu Asp Gln Leu Ile Asp Phe Tyr Lys Lys Glu Asn Met Gly Leu
                85                  90                  95

Val Thr His Leu Gln Tyr Pro Val Pro Leu Glu Glu Asp Ala Ile
            100                 105                 110

Asp Glu Ala Glu Glu Asp Thr Val Glu Ser Val Met Ser Pro Pro Glu
        115                 120                 125

Leu Pro Pro Arg Asn Ile Pro Met Ser Ala Gly Pro Ser Glu Ala Lys
    130                 135                 140

Asp Leu Pro Leu Ala Thr Glu Asn Pro Arg Ala Pro Glu Val Thr Arg
145                 150                 155                 160

Leu Ser Leu Ser Glu Thr Leu Phe Gln Arg Leu Gln Ser Met Asp Thr
```

-continued

```
                165                 170                 175
Ser Gly Leu Pro Glu Glu His Leu Lys Ala Ile Gln Asp Tyr Leu Ser
            180                 185                 190
Thr Gln Leu Leu Leu Asp Ser Asp Phe Leu Lys Thr Gly Ser Ser Asn
        195                 200                 205
Leu Pro His Leu Lys Lys Leu Met Ser Leu Leu Cys Lys Glu Leu His
210                 215                 220
Gly Glu Val Ile Arg Thr Leu Pro Ser Leu Glu Ser Leu Gln Arg Leu
225                 230                 235                 240
Phe Asp Gln Gln Leu Ser Pro Gly Leu Arg Pro Arg Pro Gln Val Pro
                245                 250                 255
Gly Glu Ala Ser Pro Ile Thr Met Val Ala Lys Leu Ser Gln Leu Thr
            260                 265                 270
Ser Leu Leu Ser Ser Ile Glu Asp Lys Val Lys Ser Leu Leu His Glu
        275                 280                 285
Gly Ser Glu Ser Thr Asn Arg Arg Ser Leu Ile Pro Pro Val Thr Phe
290                 295                 300
Glu Val Lys Ser Glu Ser Leu Gly Ile Pro Gln Lys Met His Leu Lys
305                 310                 315                 320
Val Asp Val Glu Ser Gly Lys Leu Ile Val Lys Ser Lys Asp Gly
                325                 330                 335
Ser Glu Asp Lys Phe Tyr Ser His Lys Lys Ile Leu Gln Leu Ile Lys
            340                 345                 350
Ser Gln Lys Phe Leu Asn Lys Leu Val Ile Leu Val Glu Thr Glu Lys
        355                 360                 365
Glu Lys Ile Leu Arg Lys Glu Tyr Val Phe Ala Asp Ser Lys Lys Arg
370                 375                 380
Glu Gly Phe Cys Gln Leu Leu Gln Gln Met Lys Asn Lys His Ser Glu
385                 390                 395                 400
Gln Pro Glu Pro Asp Met Ile Thr Ile Phe Ile Gly Thr Trp Asn Met
                405                 410                 415
Gly Asn Ala Pro Pro Lys Lys Ile Thr Ser Trp Phe Leu Ser Lys
            420                 425                 430
Gly Gln Gly Lys Thr Arg Asp Asp Ser Ala Asp Tyr Ile Pro His Asp
        435                 440                 445
Ile Tyr Val Ile Gly Thr Gln Glu Asp Pro Leu Gly Glu Lys Glu Trp
450                 455                 460
Leu Glu Leu Leu Arg His Ser Leu Gln Glu Val Thr Ser Met Thr Phe
465                 470                 475                 480
Lys Thr Val Ala Ile His Thr Leu Trp Asn Ile Arg Ile Val Val Leu
                485                 490                 495
Ala Lys Pro Glu His Glu Asn Arg Ile Ser His Ile Cys Thr Asp Asn
            500                 505                 510
Val Lys Thr Gly Ile Ala Asn Thr Leu Gly Asn Lys Gly Ala Val Gly
        515                 520                 525
Val Ser Phe Met Phe Asn Gly Thr Ser Leu Gly Phe Val Asn Ser His
530                 535                 540
Leu Thr Ser Gly Ser Glu Lys Lys Leu Arg Arg Asn Gln Asn Tyr Met
545                 550                 555                 560
Asn Ile Leu Arg Phe Leu Ala Leu Gly Asp Lys Lys Leu Ser Pro Phe
                565                 570                 575
Asn Ile Thr His Arg Phe Thr His Leu Phe Trp Leu Gly Asp Leu Asn
            580                 585                 590
```

-continued

Tyr Arg Val Glu Leu Pro Thr Trp Glu Ala Glu Ala Ile Ile Gln Lys
                595                 600                 605

Ile Lys Gln Gln Gln Tyr Ser Asp Leu Leu Ala His Asp Gln Leu Leu
    610                 615                 620

Leu Glu Arg Lys Asp Gln Lys Val Phe Leu His Phe Glu Glu Glu
625                 630                 635                 640

Ile Thr Phe Ala Pro Thr Tyr Arg Phe Glu Arg Leu Thr Arg Asp Lys
                645                 650                 655

Tyr Ala Tyr Thr Lys Gln Lys Ala Thr Gly Met Lys Tyr Asn Leu Pro
                660                 665                 670

Ser Trp Cys Asp Arg Val Leu Trp Lys Ser Tyr Pro Leu Val His Val
    675                 680                 685

Val Cys Gln Ser Tyr Gly Ser Thr Ser Asp Ile Met Thr Ser Asp His
    690                 695                 700

Ser Pro Val Phe Ala Thr Phe Glu Ala Gly Val Thr Ser Gln Phe Val
705                 710                 715                 720

Ser Lys Asn Gly Pro Gly Thr Val Asp Ser Gln Gly Gln Ile Glu Phe
                725                 730                 735

Leu Ala Cys Tyr Ala Thr Leu Lys Thr Lys Ser Gln Thr Lys Phe Tyr
                740                 745                 750

Leu Glu Phe His Ser Ser Cys Leu Glu Ser Phe Val Lys Ser Gln Glu
    755                 760                 765

Gly Glu Asn Glu Glu Gly Ser Glu Gly Glu Leu Val Val Arg Phe Gly
    770                 775                 780

Glu Thr Leu Pro Lys Leu Lys Pro Ile Ile Ser Asp Pro Glu Tyr Leu
785                 790                 795                 800

Leu Asp Gln His Ile Leu Ile Ser Ile Lys Ser Ser Asp Ser Asp Glu
                805                 810                 815

Ser Tyr Gly Glu Gly Cys Ile Ala Leu Arg Leu Glu Thr Thr Glu Ala
                820                 825                 830

Gln His Pro Ile Tyr Thr Pro Leu Thr His Gly Glu Met Thr Gly
    835                 840                 845

His Phe Arg Gly Glu Ile Lys Leu Gln Thr Ser Gln Gly Lys Met Arg
    850                 855                 860

Glu Lys Leu Tyr Asp Phe Val Lys Thr Glu Arg Asp Glu Ser Ser Gly
865                 870                 875                 880

Met Lys Cys Leu Lys Asn Leu Thr Ser His Asp Pro Met Arg Gln Trp
                885                 890                 895

Glu Pro Ser Gly Arg Val Pro Ala Cys Gly Val Ser Ser Leu Asn Glu
                900                 905                 910

Met Ile Asn Pro Asn Tyr Ile Gly Met Gly Pro Phe Gly Gln Pro Leu
    915                 920                 925

His Gly Lys Ser Thr Leu Ser Pro Asp Gln Gln Leu Thr Ala Trp Ser
    930                 935                 940

Tyr Asp Gln Leu Pro Lys Asp Ser Ser Leu Gly Pro Gly Arg Gly Glu
945                 950                 955                 960

Gly Pro Pro Thr Pro Pro Ser Gln Pro Pro Leu Ser Pro Lys Lys Phe
                965                 970                 975

Ser Ser Ser Thr Ala Asn Arg Gly Pro Cys Pro Arg Val Gln Glu Ala
                980                 985                 990

Arg Pro Gly Asp Leu Gly Lys Val  Glu Ala Leu Leu Gln  Glu Asp Leu
        995                 1000                1005

```
Leu Leu Thr Lys Pro Glu Met Phe Glu Asn Pro Leu Tyr Gly Ser
    1010                1015                1020

Val Ser Ser Phe Pro Lys Leu Val Pro Arg Lys Glu Gln Glu Ser
    1025                1030                1035

Pro Lys Met Leu Arg Lys Glu Pro Pro Cys Pro Asp Pro Gly
    1040                1045                1050

Ile Ser Ser Pro Ser Ile Val Leu Pro Lys Ala Gln Glu Val Glu
    1055                1060                1065

Ser Val Lys Gly Thr Ser Lys Gln Ala Pro Val Pro Val Leu Gly
    1070                1075                1080

Pro Thr Pro Arg Ile Arg Ser Phe Thr Cys Ser Ser Ser Ala Glu
    1085                1090                1095

Gly Arg Met Thr Ser Gly Asp Lys Ser Gln Gly Lys Pro Lys Ala
    1100                1105                1110

Ser Ala Ser Ser Gln Ala Pro Val Pro Val Lys Arg Pro Val Lys
    1115                1120                1125

Pro Ser Arg Ser Glu Met Ser Gln Gln Thr Thr Pro Ile Pro Ala
    1130                1135                1140

Pro Arg Pro Pro Leu Pro Val Lys Ser Pro Ala Val Leu Gln Leu
    1145                1150                1155

Gln His Ser Lys Gly Arg Asp Tyr Arg Asp Asn Thr Glu Leu Pro
    1160                1165                1170

His His Gly Lys His Arg Gln Glu Glu Gly Leu Leu Gly Arg Thr
    1175                1180                1185

Ala Met Gln
    1190

<210> SEQ ID NO 283
<211> LENGTH: 1190
<212> TYPE: PRT
<213> ORGANISM: Rattus norvegicus

<400> SEQUENCE: 283

Met Pro Ala Met Val Pro Gly Trp Asn His Gly Asn Ile Thr Arg Ser
1               5                   10                  15

Lys Ala Glu Glu Leu Leu Ser Arg Ala Gly Lys Asp Gly Ser Phe Leu
                20                  25                  30

Val Arg Ala Ser Glu Ser Ile Pro Arg Ala Tyr Ala Leu Cys Val Leu
            35                  40                  45

Phe Arg Asn Cys Val Tyr Thr Tyr Arg Ile Leu Pro Asn Glu Asp Asp
    50                  55                  60

Lys Phe Thr Val Gln Ala Ser Glu Gly Val Pro Met Arg Phe Phe Thr
65                  70                  75                  80

Lys Leu Asp Gln Leu Ile Glu Phe Tyr Lys Lys Glu Asn Met Gly Leu
                85                  90                  95

Val Thr His Leu Gln Phe Pro Val Pro Leu Glu Glu Glu Asp Ala Ile
            100                 105                 110

Asp Glu Pro Glu Glu Asp Thr Glu Ser Val Met Ser Pro Pro Glu Leu
        115                 120                 125

Pro Pro Arg Asn Ile Pro Val Ser Gly Gly Pro Cys Glu Ala Lys Asp
    130                 135                 140

Leu Pro Leu Pro Thr Glu Asn Pro Arg Ala Pro Glu Val Thr Arg Leu
145                 150                 155                 160

Ser Leu Ser Glu Thr Leu Phe Gln Arg Leu Gln Ser Met Asp Thr Ser
                165                 170                 175
```

```
Gly Leu Pro Glu Glu His Leu Lys Ala Ile Gln Asp Tyr Leu Ser Thr
            180                 185                 190

Gln Leu Met Leu Asp Ser Asp Phe Lys Thr Gly Ser Ser Asn Leu
        195                 200                 205

Pro His Leu Lys Lys Leu Thr Ser Leu Cys Lys Glu Leu His Gly
    210                 215                 220

Glu Val Ile Arg Thr Leu Pro Ser Leu Glu Ser Leu Gln Arg Leu Phe
225                 230                 235                 240

Asp Gln Gln Leu Ser Pro Gly Leu Arg Pro Arg Pro Gln Val Pro Gly
                245                 250                 255

Glu Ala Asn Pro Ile Thr Met Val Ala Lys Leu Ser Gln Leu Thr Ser
                260                 265                 270

Leu Leu Ser Ser Ile Glu Asp Lys Val Lys Ala Leu Leu His Glu Gly
            275                 280                 285

Ser Glu Ser Thr Asn Arg Arg Ser Leu Ile Pro Pro Val Thr Phe Glu
        290                 295                 300

Val Lys Ser Glu Ser Leu Gly Ile Pro Gln Lys Met His Leu Lys Val
305                 310                 315                 320

Asp Val Glu Ser Gly Lys Leu Ile Ile Lys Ser Arg Asp Gly Ser
                325                 330                 335

Glu Asp Lys Phe Tyr Ser His Lys Lys Ile Leu Gln Leu Ile Lys Ser
                340                 345                 350

Gln Lys Phe Leu Asn Lys Leu Val Ile Leu Val Glu Thr Glu Lys Glu
            355                 360                 365

Lys Ile Leu Arg Lys Glu Tyr Val Phe Ser Asp Ser Lys Lys Arg Glu
370                 375                 380

Gly Phe Cys Gln Leu Leu Gln Gln Met Lys Asn Lys His Ser Glu Gln
385                 390                 395                 400

Ser Glu Pro Asp Met Ile Thr Ile Phe Ile Gly Thr Trp Asn Met Gly
                405                 410                 415

Asn Ala Pro Pro Pro Lys Lys Ile Thr Ser Trp Phe Leu Ser Lys Gly
                420                 425                 430

Gln Gly Lys Thr Arg Asp Asp Ser Ala Asp Tyr Ile Pro His Asp Ile
            435                 440                 445

Tyr Val Ile Gly Thr Gln Glu Asp Pro Leu Gly Glu Lys Glu Trp Leu
450                 455                 460

Glu Ile Leu Arg His Ser Leu Gln Glu Val Thr Ser Met Thr Phe Lys
465                 470                 475                 480

Thr Val Ala Ile His Thr Leu Trp Asn Ile Arg Ile Val Val Leu Ala
                485                 490                 495

Lys Pro Glu His Glu Asn Arg Ile Ser His Ile Cys Thr Asp Asn Val
                500                 505                 510

Lys Thr Gly Ile Ala Asn Thr Leu Gly Asn Lys Gly Ala Val Gly Val
            515                 520                 525

Ser Phe Met Phe Asn Gly Thr Ser Leu Gly Phe Val Asn Ser His Leu
                530                 535                 540

Thr Ser Gly Ser Glu Lys Lys Leu Arg Arg Asn Gln Asn Tyr Met Asn
545                 550                 555                 560

Ile Leu Arg Phe Leu Ala Leu Gly Asp Lys Lys Leu Ser Pro Phe Asn
                565                 570                 575

Ile Thr His Arg Phe Thr His Leu Phe Trp Leu Gly Asp Leu Asn Tyr
                580                 585                 590
```

```
Arg Val Glu Leu Pro Thr Trp Glu Ala Glu Ile Ile Gln Lys Ile
            595                 600             605

Lys Gln Gln Gln Tyr Ser Asp Leu Leu Ala His Asp Gln Leu Leu
        610                 615             620

Glu Arg Lys Glu Gln Glu Val Phe Leu His Phe Glu Glu Glu Ile
625                 630             635                 640

Thr Phe Ala Pro Thr Tyr Arg Phe Glu Arg Leu Thr Arg Asp Lys Tyr
                645             650                 655

Ala Tyr Thr Lys Gln Lys Ala Thr Gly Met Lys Tyr Asn Leu Pro Ser
            660             665                 670

Trp Cys Asp Arg Val Leu Trp Lys Ser Tyr Pro Leu Val His Val Val
            675                 680             685

Cys Gln Ser Tyr Gly Ser Thr Ser Asp Ile Met Thr Ser Asp His Ser
    690             695                 700

Pro Val Phe Ala Thr Phe Glu Ala Gly Val Thr Ser Gln Phe Val Ser
705             710                 715                 720

Lys Asn Gly Pro Gly Ala Val Asp Ser Gln Gly Gln Ile Glu Phe Leu
                725                 730                 735

Ala Cys Tyr Ala Thr Leu Lys Thr Lys Ser Gln Thr Lys Phe Tyr Leu
            740                 745                 750

Glu Leu His Ser Ser Cys Leu Glu Ser Phe Val Lys Ser Gln Glu Gly
        755                 760                 765

Glu Asn Glu Glu Gly Asp Glu Gly Leu Val Val Arg Phe Gly Glu
        770                 775             780

Thr Leu Pro Lys Leu Lys Pro Ile Ile Ser Asp Pro Glu Tyr Leu Leu
785             790                 795                 800

Asp Gln His Ile Leu Ile Ser Ile Lys Ser Ser Asp Ser Asp Glu Ser
                805                 810             815

Tyr Gly Glu Gly Cys Ile Ala Leu Arg Leu Glu Thr Thr Glu Ser Gln
            820                 825             830

Leu Pro Ile Tyr Thr Pro Leu Thr His His Gly Glu Met Thr Gly His
            835                 840             845

Phe Arg Gly Glu Ile Lys Leu Gln Thr Ser Glu Gly Lys Met Arg Glu
850                 855                 860

Lys Leu Tyr Asp Phe Val Lys Thr Glu Arg Asp Glu Ser Ser Gly Met
865                 870                 875                 880

Lys Cys Leu Lys Asn Leu Thr Ser His Asp Pro Met Arg Gln Trp Glu
            885                 890             895

Pro Ala Gly Arg Val Pro Ala Cys Gly Ile Ser Ser Leu Asn Glu Ile
                900             905                 910

Ile Asn Pro Asn Tyr Ile Gly Met Gly Pro Phe Gly Gln Pro Leu His
            915                 920             925

Gly Lys Ser Thr Leu Ser Pro Asp Gln Gln Leu Thr Ala Trp Ser Tyr
    930                 935             940

Asp Gln Leu Pro Lys Asp Ser Ser Leu Gly Pro Gly Arg Gly Glu Gly
945                 950             955                 960

Pro Pro Thr Pro Pro Ser Gln Pro Leu Ser Pro Lys Lys Phe Ser
                965             970                 975

Ser Ser Thr Ala Asn Arg Gly Ser Cys Pro Arg Val Gln Glu Thr Arg
            980             985                 990

Pro Gly Asp Leu Gly Lys Val Glu  Ala Leu Pro Gln Glu  Asp Leu Pro
        995                 1000                1005

Leu Thr  Lys Pro Glu Met Phe  Glu Asn Pro Leu Tyr  Gly Ser Val
```

```
              1010                1015                1020

Ser Pro Phe Pro Lys Leu Val Pro Arg Lys Glu Gln Glu Ser Pro
     1025                1030                1035

Lys Met Met Arg Lys Glu Pro Pro Cys Pro Asp Pro Gly Val
     1040                1045                1050

Ser Ser Pro Ser Ile Met Leu Pro Lys Ala Gln Glu Val Glu Asn
     1055                1060                1065

Val Lys Gly Thr Ser Lys Gln Ala Pro Val Pro Val Phe Gly Pro
     1070                1075                1080

Thr Pro Arg Ile Arg Ser Phe Thr Cys Ser Ser Ala Glu Gly
     1085                1090                1095

Arg Met Pro Ser Gly Asp Lys Ser Gln Gly Lys Pro Lys Ala Pro
     1100                1105                1110

Ala Ser Ser Gln Ala Pro Val Pro Val Lys Arg Pro Val Lys Pro
     1115                1120                1125

Ser Arg Ser Glu Met Ser Gln Gln Thr Thr Pro Ile Pro Ala Pro
     1130                1135                1140

Arg Pro Pro Leu Pro Val Lys Ser Pro Ala Val Leu Gln Leu Gln
     1145                1150                1155

His Ser Lys Gly Arg Asp Tyr Arg Asp Asn Thr Glu Leu Pro His
     1160                1165                1170

His Gly Lys His Arg Gln Glu Glu Ser Leu Leu Gly Arg Thr Ala
     1175                1180                1185

Met Gln
     1190

<210> SEQ ID NO 284
<211> LENGTH: 1194
<212> TYPE: PRT
<213> ORGANISM: Bos taurus

<400> SEQUENCE: 284

Met Val Pro Cys Trp Asn His Gly Asn Ile Thr Arg Ser Lys Ala Glu
1               5                   10                  15

Glu Leu Leu Ser Arg Thr Gly Lys Asp Gly Ser Phe Leu Val Arg Ala
            20                  25                  30

Ser Glu Ser Ile Ser Arg Ala Tyr Ala Leu Cys Val Leu Tyr Arg Asn
        35                  40                  45

Cys Val Tyr Thr Tyr Arg Ile Leu Pro Asn Glu Asp Asp Lys Phe Thr
    50                  55                  60

Val Gln Ala Ser Glu Gly Val Pro Met Arg Phe Phe Thr Lys Leu Asp
65                  70                  75                  80

Gln Leu Ile Glu Phe Tyr Lys Lys Glu Asn Met Gly Leu Val Thr His
                85                  90                  95

Leu Gln Tyr Pro Val Pro Leu Glu Glu Glu Asp Thr Gly Asp Glu Pro
            100                 105                 110

Glu Glu Glu Thr Glu Gly Ala Val Ser Pro Pro Glu Leu Pro Pro Arg
        115                 120                 125

Asn Ile Ile Pro Leu Pro Ala Gly Thr Cys Glu Ala Lys Glu Ala Pro
    130                 135                 140

Ala Ser Thr Glu Asn Pro Arg Ala Ala Glu Val Gly Arg Pro Ser Leu
145                 150                 155                 160

Ser Glu Thr Leu Phe Gln Arg Leu Gln Thr Met Asp Thr Ser Gly Ile
                165                 170                 175
```

```
Pro Glu Glu His Leu Lys Ala Ile Gln Asp Tyr Leu Ser Thr Gln Leu
            180                 185                 190

Ser Leu Asp Ser Asp Phe Val Lys Ser Gly Ser Ser Leu Pro His
        195                 200                 205

Leu Lys Lys Leu Thr Ala Leu Leu Cys Lys Glu Leu Tyr Gly Glu Val
    210                 215                 220

Ile Arg Ala Leu Pro Thr Leu Glu Ser Leu Gln Arg Leu Phe Asp Gln
225                 230                 235                 240

Gln Leu Ser Pro Gly Leu Arg Pro Arg Pro Gln Val Pro Gly Glu Ala
                245                 250                 255

Ser Pro Ile Asn Met Val Ala Lys Leu Ser Gln Leu Thr Ser Leu Leu
            260                 265                 270

Ser Ser Ile Glu Asp Lys Val Lys Ala Leu Leu His Glu Gly Pro Glu
    275                 280                 285

Ser Pro His Arg Arg Ser Leu Ile Pro Pro Val Thr Phe Glu Val Lys
    290                 295                 300

Ala Glu Ser Leu Gly Ile Pro Gln Lys Leu Gln Leu Lys Val Asp Val
305                 310                 315                 320

Glu Ser Gly Lys Leu Ile Ile Lys Lys Ser Lys Asp Ser Ser Glu Asp
                325                 330                 335

Lys Phe Tyr Thr His Lys Lys Ile Leu Gln Leu Ile Lys Ser Gln Lys
            340                 345                 350

Phe Leu Asn Lys Leu Val Ile Leu Val Glu Thr Glu Lys Glu Lys Thr
        355                 360                 365

Leu Arg Lys Glu Tyr Val Phe Ala Asp Ser Lys Lys Arg Glu Gly Phe
    370                 375                 380

Cys Gln Leu Leu Gln Gln Met Lys Asn Lys His Ser Glu Gln Pro Glu
385                 390                 395                 400

Pro Asp Met Ile Thr Ile Phe Ile Gly Thr Trp Asn Met Gly Asn Ala
                405                 410                 415

Pro Pro Pro Lys Lys Ile Thr Ser Trp Phe Leu Ser Lys Gly Gln Gly
            420                 425                 430

Lys Thr Arg Asp Asp Ser Ala Asp Tyr Ile Pro His Asp Ile Tyr Val
        435                 440                 445

Ile Gly Thr Gln Glu Asp Pro Leu Gly Glu Lys Glu Trp Leu Glu Ile
    450                 455                 460

Leu Lys His Ser Leu Gln Glu Val Thr Ser Met Thr Phe Lys Thr Ile
465                 470                 475                 480

Ala Ile His Thr Leu Trp Asn Ile Arg Ile Val Val Leu Ala Lys Pro
                485                 490                 495

Glu His Glu Asn Arg Ile Ser His Ile Cys Thr Asp Asn Val Lys Thr
            500                 505                 510

Gly Ile Ala Asn Thr Leu Gly Asn Lys Gly Ala Val Gly Val Ser Phe
        515                 520                 525

Met Phe Asn Gly Thr Ser Leu Gly Phe Val Asn Ser His Leu Thr Ser
    530                 535                 540

Gly Ser Glu Lys Lys Leu Arg Arg Asn Gln Asn Tyr Met Asn Ile Leu
545                 550                 555                 560

Arg Phe Leu Ala Leu Gly Asp Lys Lys Leu Ser Ser Phe Asn Ile Thr
                565                 570                 575

His Arg Phe Thr His Leu Phe Trp Leu Gly Asp Leu Asn Tyr Arg Val
            580                 585                 590

Glu Leu Pro Thr Trp Glu Ala Glu Thr Ile Ile Gln Lys Ile Arg Gln
```

-continued

Gln Gln Tyr Ala Asp Leu Leu Ser His Asp Gln Leu Leu Met Glu Arg
    610                 615                 620

Lys Glu Gln Lys Val Phe Leu His Phe Glu Glu Glu Ile Thr Phe
625                 630                 635                 640

Ala Pro Thr Tyr Arg Phe Glu Arg Met Thr Arg Asp Lys Tyr Ala Tyr
                645                 650                 655

Thr Lys Gln Lys Ala Thr Gly Met Lys Tyr Asn Leu Pro Ser Trp Cys
            660                 665                 670

Asp Arg Val Leu Trp Lys Ser Tyr Pro Leu Val His Val Cys Gln
        675                 680                 685

Ser Tyr Gly Ser Thr Ser Asp Ile Met Thr Ser Asp His Ser Pro Val
    690                 695                 700

Phe Ala Thr Phe Glu Ala Gly Val Thr Ser Gln Phe Val Ser Lys Asn
705                 710                 715                 720

Gly Pro Gly Thr Thr Asp Ser Gln Gly Gln Ile Glu Phe Leu Gly Cys
                725                 730                 735

Tyr Ala Thr Leu Lys Thr Lys Ser Gln Thr Lys Phe Tyr Leu Glu Phe
            740                 745                 750

His Ser Ser Cys Leu Glu Ser Phe Val Lys Ser Gln Glu Gly Glu Asn
        755                 760                 765

Glu Glu Gly Ser Glu Gly Glu Leu Val Val Lys Phe Gly Glu Thr Leu
    770                 775                 780

Pro Lys Leu Lys Pro Ile Ile Ser Asp Pro Glu Tyr Leu Leu Asp Gln
785                 790                 795                 800

His Ile Leu Ile Ser Ile Lys Ser Ser Asp Ser Asp Glu Ser Tyr Gly
                805                 810                 815

Glu Gly Cys Ile Ala Leu Arg Leu Glu Ala Thr Glu Thr Gln Leu Pro
            820                 825                 830

Ile Tyr Thr Pro Leu Thr His His Gly Glu Met Thr Gly His Phe Arg
        835                 840                 845

Gly Asn Ile Lys Leu Gln Thr Ser Gln Gly Lys Met Arg Glu Lys Leu
    850                 855                 860

Tyr Asp Phe Val Lys Thr Glu Arg Asp Glu Ser Ser Gly Pro Lys Ser
865                 870                 875                 880

Leu Lys Ser Leu Thr Ser His Asp Pro Met Lys Gln Trp Glu Pro Ala
                885                 890                 895

Asn Arg Val Pro Pro Cys Ser Ser Ser Ile Thr Glu Ile Ile Asn
            900                 905                 910

Pro Ser Tyr Met Gly Val Gly Asn Phe Gly His Leu Lys Gln Thr Leu
        915                 920                 925

Ser Pro Asp Gln Gln Pro Thr Ala Trp Ser Tyr Asp Pro Pro Leu Lys
    930                 935                 940

Asp Ser Thr Leu Gly Pro Gly Arg Gly Glu Ser Pro Thr Pro Pro
945                 950                 955                 960

Ser Gln Pro Pro Val Ser Pro Lys Lys Phe Thr Ser Ser Ala Thr
                965                 970                 975

Arg Gly Pro Cys Leu Arg Thr Gln Glu Ser Arg Pro Ser Asp Val Val
            980                 985                 990

Lys Ser Val Ala Glu Pro Ser Pro  Pro Glu Glu Leu Gln Leu Thr Lys
        995                 1000                 1005

Pro Glu Met Phe Glu Asn Pro  Leu Tyr Gly Ser Val  Ser Ala Phe
    1010                 1015                 1020

-continued

Pro Lys Pro Ala Pro Arg Lys Glu Gln Glu Ser Pro Lys Met Leu
    1025                1030                1035

Arg Lys Glu Pro Pro Cys Pro Asp Pro Gly Ile Met Ser Pro
    1040                1045                1050

Ser Ile Leu Leu Ser Lys Ala Gln Glu Ala Glu Gly Ser Lys Gly
    1055                1060                1065

Thr Gly Lys Pro Val Pro Pro Ala Pro Phe Leu Ser Pro Thr
    1070                1075                1080

Pro Arg Val Arg Ser Phe Thr Cys Ser Thr Ser Glu Gly Arg Pro
    1085                1090                1095

Pro Gly Gly Asp Lys Ser Gln Gly Lys Pro Lys Thr Pro Ala Gly
    1100                1105                1110

Ser Gln Val Pro Val Pro Val Pro Val Pro Val Pro Val Lys Arg
    1115                1120                1125

Pro Ile Lys Pro Ser Arg Ser Glu Leu Ser Gln Gln Pro Leu Pro
    1130                1135                1140

Ala Gln Gly Gln Arg Pro Pro Leu Pro Val Lys Ser Pro Ala Val
    1145                1150                1155

Leu His Leu Gln His Ser Lys Ser Arg Asp Tyr Arg Asp Asn Ala
    1160                1165                1170

Glu Leu Pro His His Ala Lys His Arg Pro Glu Asp Ala Pro Leu
    1175                1180                1185

Ser Arg Thr Ala Met Gln
    1190

<210> SEQ ID NO 285
<211> LENGTH: 1189
<212> TYPE: PRT
<213> ORGANISM: Macaca mulatta

<400> SEQUENCE: 285

Met Val Pro Cys Trp Asn His Gly Asn Ile Thr Arg Ser Lys Ala Glu
1               5                   10                  15

Glu Leu Leu Ser Arg Thr Gly Lys Asp Gly Ser Phe Leu Val Arg Ala
                20                  25                  30

Ser Glu Ser Ile Ser Arg Ala Tyr Ala Leu Cys Val Leu Tyr Gln Asn
            35                  40                  45

Cys Val Tyr Thr Tyr Arg Ile Leu Pro Asn Glu Asp Asp Lys Phe Thr
        50                  55                  60

Val Gln Ala Ser Glu Gly Val Pro Met Lys Phe Phe Thr Lys Leu Asp
65                  70                  75                  80

Gln Leu Ile Glu Phe Tyr Lys Lys Glu Asn Met Gly Leu Val Thr His
                85                  90                  95

Leu Gln Tyr Pro Val Pro Leu Glu Glu Glu Asp Thr Gly Asp Asp Pro
            100                 105                 110

Glu Glu Asp Thr Val Glu Ser Ile Val Ser Pro Pro Glu Leu Pro Pro
        115                 120                 125

Arg Asn Ile Pro Pro Ser Ala Gly Ser Cys Glu Ala Lys Glu Val Pro
    130                 135                 140

Leu Ser Asn Glu Asn Pro Arg Ala Thr Glu Thr Ser Arg Pro Ser Leu
145                 150                 155                 160

Ser Glu Thr Leu Phe Gln Arg Leu Gln Ser Met Asp Thr Ser Gly Leu
                165                 170                 175

Pro Glu Glu His Leu Lys Ala Ile Gln Asp Tyr Leu Ser Thr Gln Leu

-continued

```
            180                 185                 190
Ala Leu Asp Ser Glu Phe Val Lys Thr Gly Ser Ser Ser Leu Pro His
            195                 200                 205
Leu Lys Lys Leu Thr Thr Leu Leu Cys Lys Glu Leu Tyr Gly Gln Asn
            210                 215                 220
Leu Ala Leu Ser Pro Arg Leu Glu Cys Arg Asp Arg Val Val Arg Glu
225                 230                 235                 240
Asp Leu Phe Val Arg Leu Arg Pro Glu Cys Gln Val Pro Gly Glu Ala
            245                 250                 255
Asn Pro Ile Asn Met Val Ser Lys Leu Ser Gln Leu Thr Ser Leu Leu
            260                 265                 270
Ser Ser Ile Glu Asp Lys Val Lys Ala Leu Leu His Glu Gly Pro Glu
            275                 280                 285
Ser Pro His Arg Arg Ser Leu Ile Pro Pro Val Thr Phe Glu Val Lys
            290                 295                 300
Ala Glu Ser Leu Gly Ile Pro Gln Lys Met Gln Leu Lys Val Asp Val
305                 310                 315                 320
Glu Ser Gly Lys Leu Ile Ile Lys Lys Ser Lys Asp Gly Ser Glu Asp
            325                 330                 335
Lys Phe Tyr Ser His Lys Lys Ile Leu Gln Leu Ile Lys Ser Gln Lys
            340                 345                 350
Phe Leu Asn Lys Leu Val Ile Leu Val Glu Thr Glu Lys Glu Lys Ile
            355                 360                 365
Leu Arg Lys Glu Tyr Val Phe Ala Asp Ser Lys Lys Arg Glu Gly Phe
            370                 375                 380
Cys Gln Leu Leu Gln Gln Met Lys Asn Lys His Ser Glu Gln Pro Glu
385                 390                 395                 400
Pro Asp Met Ile Thr Ile Phe Ile Gly Thr Trp Asn Met Gly Asn Ala
            405                 410                 415
Pro Pro Pro Lys Lys Ile Thr Ser Trp Phe Leu Ser Lys Gly Gln Gly
            420                 425                 430
Lys Thr Arg Asp Asp Ser Ala Asp Tyr Ile Pro His Asp Ile Tyr Val
            435                 440                 445
Ile Gly Thr Gln Glu Asp Pro Leu Ser Glu Lys Glu Trp Leu Glu Ile
            450                 455                 460
Leu Lys His Ser Leu Gln Glu Ile Thr Ser Met Thr Phe Lys Thr Val
465                 470                 475                 480
Ala Ile His Thr Leu Trp Asn Ile Arg Ile Val Val Leu Ala Lys Pro
            485                 490                 495
Glu His Glu Asn Arg Ile Ser His Ile Cys Thr Asn Asn Val Lys Thr
            500                 505                 510
Gly Ile Ala Asn Thr Leu Gly Asn Lys Gly Ala Val Gly Val Ser Phe
            515                 520                 525
Met Phe Asn Gly Thr Ser Leu Gly Phe Val Asn Ser His Leu Thr Ser
            530                 535                 540
Gly Ser Glu Lys Lys Leu Arg Arg Asn Gln Asn Tyr Met Ser Ile Leu
545                 550                 555                 560
Arg Phe Leu Ala Leu Gly Asp Lys Lys Leu Ser Pro Phe Asn Ile Thr
            565                 570                 575
His Arg Phe Thr His Leu Phe Trp Phe Gly Asp Leu Asn Tyr Arg Val
            580                 585                 590
Asp Leu Pro Thr Trp Glu Ala Glu Thr Ile Ile Gln Lys Ile Lys Gln
            595                 600                 605
```

```
Gln Gln Tyr Ala Asp Leu Leu Ser His Asp Gln Leu Leu Thr Glu Arg
    610                 615                 620

Arg Glu Gln Lys Val Phe Leu His Phe Glu Glu Glu Ile Thr Phe
625                 630                 635                 640

Ala Pro Thr Tyr Arg Phe Glu Arg Leu Thr Arg Asp Lys Tyr Ala Tyr
                645                 650                 655

Thr Lys Gln Lys Ala Thr Gly Met Lys Tyr Asn Leu Pro Ser Trp Cys
            660                 665                 670

Asp Arg Val Leu Trp Lys Ser Tyr Pro Leu Val His Val Cys Gln
        675                 680                 685

Ser Tyr Gly Ser Thr Ser Asp Ile Met Thr Ser Asp His Ser Pro Val
    690                 695                 700

Phe Ala Thr Phe Glu Ala Gly Val Thr Ser Gln Phe Val Ser Lys Asn
705                 710                 715                 720

Gly Pro Gly Thr Val Asp Ser Gln Gly Gln Ile Glu Phe Leu Arg Cys
                725                 730                 735

Tyr Ala Thr Leu Lys Thr Lys Ser Gln Thr Lys Phe Tyr Leu Glu Phe
                740                 745                 750

His Ser Ser Cys Leu Glu Ser Phe Val Lys Ser Gln Glu Gly Glu Asn
            755                 760                 765

Glu Glu Gly Ser Glu Gly Glu Leu Val Val Lys Phe Gly Glu Thr Leu
770                 775                 780

Pro Lys Leu Lys Pro Ile Ile Ser Asp Pro Glu Tyr Leu Leu Asp Gln
785                 790                 795                 800

His Ile Leu Ile Ser Ile Lys Ser Ser Asp Ser Asp Gly Ser Tyr Gly
                805                 810                 815

Glu Gly Cys Ile Ala Leu Arg Leu Glu Ala Thr Glu Thr Gln Leu Pro
            820                 825                 830

Ile Tyr Thr Pro Leu Thr His His Gly Glu Leu Thr Gly His Phe Gln
                835                 840                 845

Gly Glu Ile Lys Leu Gln Thr Ser Gln Gly Lys Thr Arg Glu Lys Leu
    850                 855                 860

Tyr Asp Phe Val Lys Thr Glu Arg Asp Glu Ser Ser Gly Pro Lys Thr
865                 870                 875                 880

Leu Lys Ser Leu Thr Ser His Asp Pro Met Lys Gln Trp Glu Ala Thr
                885                 890                 895

Ser Arg Ala Pro Pro Cys Ser Gly Ser Ser Ile Thr Glu Ile Leu Asn
            900                 905                 910

Pro Asn Tyr Met Gly Val Gly Phe Gly Pro Pro Val Pro Leu His
                915                 920                 925

Val Lys Gln Thr Leu Ser Pro Asp Gln Gln Pro Thr Ala Trp Ser Tyr
    930                 935                 940

Asp Gln Pro Pro Lys Asp Ser Pro Leu Gly Pro Cys Arg Gly Glu Ser
945                 950                 955                 960

Pro Thr Thr Pro Pro Cys Gln Pro Pro Ile Ser Pro Lys Lys Phe Leu
                965                 970                 975

Pro Ser Thr Ala Asn Arg Gly Leu Pro Pro Arg Thr Gln Glu Ser Arg
            980                 985                 990

Pro Ser Asp Leu Gly Lys Asn Ala Gly Asp Thr Leu Pro Gln Glu Asp
        995                 1000                1005

Leu Pro Leu Thr Lys Pro Glu Met Phe Glu Asn Pro Leu Tyr Gly
    1010                1015                1020
```

```
Ser Val Ser Ser Phe Pro Lys Pro Ala Pro Arg Lys Asp Gln Glu
    1025                1030                1035

Ser Pro Lys Met Leu Arg Lys Glu Pro Pro Cys Pro Glu Pro
    1040                1045                1050

Ser Ile Leu Ser Pro Ser Ile Val Leu Thr Lys Ala Gln Glu Ala
    1055                1060                1065

Asp Arg Gly Glu Gly Pro Gly Lys Gln Ala Pro Ala Pro Arg Leu
    1070                1075                1080

Arg Ser Phe Thr Cys Ser Ser Ser Ala Glu Gly Arg Ala Ala Gly
    1085                1090                1095

Gly Asp Lys Ser Gln Gly Lys Pro Lys Thr Ala Ile Ser Ser Gln
    1100                1105                1110

Ala Pro Val Pro Val Lys Arg Pro Ile Lys Pro Ser Arg Ser Glu
    1115                1120                1125

Met Asn Gln Gln Thr Gln Pro Thr Pro Thr Pro Arg Pro Pro Leu
    1130                1135                1140

Pro Val Lys Ser Pro Ala Val Leu His Leu Gln His Ser Lys Ser
    1145                1150                1155

Arg Asp Tyr Arg Asp Asn Ser Glu Leu Pro Tyr His Gly Lys His
    1160                1165                1170

Arg Pro Glu Glu Gly Pro Pro Gly Pro Leu Ser Arg Thr Ala Met
    1175                1180                1185

Gln

<210> SEQ ID NO 286
<211> LENGTH: 185
<212> TYPE: PRT
<213> ORGANISM: Homo sapiens

<400> SEQUENCE: 286

Met Gly Lys Lys Gln Asn Lys Lys Val Glu Glu Val Leu Glu Glu
1               5                   10                  15

Glu Glu Glu Glu Tyr Val Val Glu Lys Val Leu Asp Arg Arg Val Val
                20                  25                  30

Lys Gly Lys Val Glu Tyr Leu Leu Lys Trp Lys Gly Phe Ser Asp Glu
                35                  40                  45

Asp Asn Thr Trp Glu Pro Glu Glu Asn Leu Asp Cys Pro Asp Leu Ile
        50                  55                  60

Ala Glu Phe Leu Gln Ser Gln Lys Thr Ala His Glu Thr Asp Lys Ser
65                  70                  75                  80

Glu Gly Gly Lys Arg Lys Ala Asp Ser Asp Ser Glu Asp Lys Gly Glu
                85                  90                  95

Glu Ser Lys Pro Lys Lys Lys Glu Glu Ser Glu Lys Pro Arg Gly
                100                 105                 110

Phe Ala Arg Gly Leu Glu Pro Glu Arg Ile Ile Gly Ala Thr Asp Ser
                115                 120                 125

Ser Gly Glu Leu Met Phe Leu Met Lys Trp Lys Asn Ser Asp Glu Ala
                130                 135                 140

Asp Leu Val Pro Ala Lys Glu Ala Asn Val Lys Cys Pro Gln Val Val
145                 150                 155                 160

Ile Ser Phe Tyr Glu Glu Arg Leu Thr Trp His Ser Tyr Pro Ser Glu
                165                 170                 175

Asp Asp Asp Lys Lys Asp Lys Asn
                180                 185
```

```
<210> SEQ ID NO 287
<211> LENGTH: 185
<212> TYPE: PRT
<213> ORGANISM: Mus musculus

<400> SEQUENCE: 287

Met Gly Lys Lys Gln Asn Lys Lys Val Glu Val Leu Glu
1               5                   10                  15

Glu Glu Glu Glu Tyr Val Val Glu Lys Val Leu Asp Arg Arg Val Val
                20                  25                  30

Lys Gly Lys Val Glu Tyr Leu Leu Lys Trp Lys Gly Phe Ser Asp Glu
            35                  40                  45

Asp Asn Thr Trp Glu Pro Glu Glu Asn Leu Asp Cys Pro Asp Leu Ile
        50                  55                  60

Ala Glu Phe Leu Gln Ser Gln Lys Thr Ala His Glu Thr Asp Lys Ser
65                  70                  75                  80

Glu Gly Gly Lys Arg Lys Ala Asp Ser Asp Ser Glu Asp Lys Gly Glu
                85                  90                  95

Glu Ser Lys Pro Lys Lys Lys Glu Glu Ser Glu Lys Pro Arg Gly
                100                 105                 110

Phe Ala Arg Gly Leu Glu Pro Glu Arg Ile Ile Gly Ala Thr Asp Ser
            115                 120                 125

Ser Gly Glu Leu Met Phe Leu Met Lys Trp Lys Asn Ser Asp Glu Ala
130                 135                 140

Asp Leu Val Pro Ala Lys Glu Ala Asn Val Lys Cys Pro Gln Val Val
145                 150                 155                 160

Ile Ser Phe Tyr Glu Glu Arg Leu Thr Trp His Ser Tyr Pro Ser Glu
                165                 170                 175

Asp Asp Asp Lys Lys Asp Asp Lys Asn
                180                 185

<210> SEQ ID NO 288
<211> LENGTH: 183
<212> TYPE: PRT
<213> ORGANISM: Rattus norvegicus

<400> SEQUENCE: 288

Met Ala Ser Asn Lys Thr Thr Leu Gln Lys Met Gly Lys Lys Gln Asn
1               5                   10                  15

Gly Lys Ser Lys Lys Val Glu Glu Ala Glu Pro Glu Glu Phe Val Val
                20                  25                  30

Glu Lys Val Leu Asp Arg Arg Val Asn Gly Lys Val Glu Tyr Phe
            35                  40                  45

Leu Lys Trp Lys Gly Phe Thr Asp Ala Asp Asn Thr Trp Glu Pro Glu
        50                  55                  60

Glu Asn Leu Asp Cys Pro Glu Leu Ile Glu Ala Phe Leu Asn Ser Gln
65                  70                  75                  80

Lys Ala Gly Lys Glu Lys Asp Gly Thr Lys Arg Lys Ser Leu Ser Asp
                85                  90                  95

Ser Glu Ser Asp Asp Ser Lys Ser Lys Lys Arg Asp Ala Ala Asp
                100                 105                 110

Lys Pro Arg Gly Phe Ala Arg Gly Leu Asp Pro Glu Arg Ile Ile Gly
            115                 120                 125

Ala Thr Asp Ser Ser Gly Glu Leu Met Phe Leu Met Lys Trp Lys Asp
130                 135                 140
```

```
Ser Asp Glu Ala Asp Leu Val Leu Ala Lys Glu Ala Asn Met Lys Cys
145                 150                 155                 160

Pro Gln Ile Val Ile Ala Phe Tyr Glu Glu Arg Leu Thr Trp His Ser
                165                 170                 175

Cys Pro Glu Asp Glu Ala Gln
                180

<210> SEQ ID NO 289
<211> LENGTH: 185
<212> TYPE: PRT
<213> ORGANISM: Bos taurus

<400> SEQUENCE: 289

Met Gly Lys Lys Gln Asn Lys Lys Val Glu Val Leu Glu Glu
1               5                   10                  15

Glu Glu Glu Glu Tyr Val Val Glu Lys Val Leu Asp Arg Arg Val Val
                20                  25                  30

Lys Gly Lys Val Glu Tyr Leu Leu Lys Trp Lys Gly Phe Ser Asp Glu
            35                  40                  45

Asp Asn Thr Trp Glu Pro Glu Glu Asn Leu Asp Cys Pro Asp Leu Ile
        50                  55                  60

Ala Glu Phe Leu Gln Ser Gln Lys Thr Ala His Glu Thr Asp Lys Ser
65                  70                  75                  80

Glu Gly Gly Lys Arg Lys Ala Asp Ser Asp Ser Glu Asp Lys Gly Glu
                85                  90                  95

Glu Ser Lys Pro Lys Lys Lys Glu Glu Ser Glu Lys Pro Arg Gly
                100                 105                 110

Phe Ala Arg Gly Leu Glu Pro Glu Arg Ile Ile Gly Ala Thr Asp Ser
            115                 120                 125

Ser Gly Glu Leu Met Phe Leu Met Lys Trp Lys Asn Ser Asp Glu Ala
        130                 135                 140

Asp Leu Val Pro Ala Lys Glu Ala Asn Val Lys Cys Pro Gln Val Val
145                 150                 155                 160

Ile Ser Phe Tyr Glu Glu Arg Leu Thr Trp His Ser Tyr Pro Ser Glu
                165                 170                 175

Asp Asp Asp Lys Lys Asp Asp Lys Asn
                180                 185

<210> SEQ ID NO 290
<211> LENGTH: 185
<212> TYPE: PRT
<213> ORGANISM: Macaca mulatta

<400> SEQUENCE: 290

Met Gly Lys Lys Gln Asn Lys Lys Val Glu Glu Val Leu Glu Glu
1               5                   10                  15

Glu Glu Glu Glu Tyr Val Val Glu Lys Val Leu Asp Arg Arg Val Val
                20                  25                  30

Lys Gly Lys Val Glu Tyr Leu Leu Lys Trp Lys Gly Phe Ser Asp Glu
            35                  40                  45

Asp Asn Thr Trp Glu Pro Glu Glu Asn Leu Asp Cys Pro Asp Leu Ile
        50                  55                  60

Ala Glu Phe Leu Gln Ser Gln Lys Thr Ala His Glu Thr Asp Lys Ser
65                  70                  75                  80

Glu Gly Gly Lys Arg Lys Ala Asp Ser Asp Ser Glu Asp Lys Gly Glu
                85                  90                  95
```

Glu Ser Lys Pro Lys Lys Lys Glu Ser Glu Lys Pro Arg Gly
                100                 105                 110

Phe Ala Arg Gly Leu Glu Pro Glu Arg Ile Ile Gly Thr Asp Ser
            115                 120                 125

Ser Gly Glu Leu Met Phe Leu Met Lys Trp Lys Asn Ser Asp Glu Ala
130                 135                 140

Asp Leu Val Pro Ala Lys Glu Ala Asn Val Lys Cys Pro Gln Val Val
145                 150                 155                 160

Ile Ser Phe Tyr Glu Arg Leu Thr Trp His Ser Tyr Pro Ser Glu
            165                 170                 175

Asp Asp Asp Lys Lys Asp Asp Lys Asn
            180                 185

<210> SEQ ID NO 291
<211> LENGTH: 183
<212> TYPE: PRT
<213> ORGANISM: Homo sapiens

<400> SEQUENCE: 291

Met Ala Ser Asn Lys Thr Thr Leu Gln Lys Met Gly Lys Lys Gln Asn
1               5                   10                  15

Gly Lys Ser Lys Lys Val Glu Glu Ala Glu Pro Glu Glu Phe Val Val
            20                  25                  30

Glu Lys Val Leu Asp Arg Arg Val Val Asn Gly Lys Val Glu Tyr Phe
        35                  40                  45

Leu Lys Trp Lys Gly Phe Thr Asp Ala Asp Asn Thr Trp Glu Pro Glu
    50                  55                  60

Glu Asn Leu Asp Cys Pro Glu Leu Ile Glu Ala Phe Leu Asn Ser Gln
65                  70                  75                  80

Lys Ala Gly Lys Glu Lys Asp Gly Thr Lys Arg Lys Ser Leu Ser Asp
                85                  90                  95

Ser Glu Ser Asp Asp Ser Lys Ser Lys Lys Lys Arg Asp Ala Ala Asp
            100                 105                 110

Lys Pro Arg Gly Phe Ala Arg Gly Leu Asp Pro Glu Arg Ile Ile Gly
        115                 120                 125

Ala Thr Asp Ser Ser Gly Glu Leu Met Phe Leu Met Lys Trp Lys Asp
    130                 135                 140

Ser Asp Glu Ala Asp Leu Val Leu Ala Lys Glu Ala Asn Met Lys Cys
145                 150                 155                 160

Pro Gln Ile Val Ile Ala Phe Tyr Glu Glu Arg Leu Thr Trp His Ser
                165                 170                 175

Cys Pro Glu Asp Glu Ala Gln
            180

<210> SEQ ID NO 292
<211> LENGTH: 183
<212> TYPE: PRT
<213> ORGANISM: Mus musculus

<400> SEQUENCE: 292

Met Ala Ser Asn Lys Thr Thr Leu Gln Lys Met Gly Lys Lys Gln Asn
1               5                   10                  15

Gly Lys Ser Lys Lys Val Glu Glu Ala Glu Pro Glu Glu Phe Val Val
            20                  25                  30

Glu Lys Val Leu Asp Arg Arg Val Val Asn Gly Lys Val Glu Tyr Phe
        35                  40                  45

```
Leu Lys Trp Lys Gly Phe Thr Asp Ala Asp Asn Thr Trp Glu Pro Glu
 50                  55                  60

Glu Asn Leu Asp Cys Pro Glu Leu Ile Glu Ala Phe Leu Asn Ser Gln
 65                  70                  75                  80

Lys Ala Gly Lys Glu Lys Asp Gly Thr Lys Arg Lys Ser Leu Ser Asp
                 85                  90                  95

Ser Glu Ser Asp Asp Ser Lys Ser Lys Lys Arg Asp Ala Ala Asp
                100                 105                 110

Lys Pro Arg Gly Phe Ala Arg Gly Leu Asp Pro Glu Arg Ile Ile Gly
            115                 120                 125

Ala Thr Asp Ser Ser Gly Glu Leu Met Phe Leu Met Lys Trp Lys Asp
130                 135                 140

Ser Asp Glu Ala Asp Leu Val Leu Ala Lys Glu Ala Asn Met Lys Cys
145                 150                 155                 160

Pro Gln Ile Val Ile Ala Phe Tyr Glu Glu Arg Leu Thr Trp His Ser
                165                 170                 175

Cys Pro Glu Asp Glu Ala Gln
            180
```

<210> SEQ ID NO 293
<211> LENGTH: 183
<212> TYPE: PRT
<213> ORGANISM: Rattus norvegicus

<400> SEQUENCE: 293

```
Met Ala Ser Asn Lys Thr Thr Leu Gln Lys Met Gly Lys Lys Gln Asn
 1               5                  10                  15

Gly Lys Ser Lys Lys Val Glu Glu Ala Glu Pro Glu Glu Phe Val Val
                20                  25                  30

Glu Lys Val Leu Asp Arg Arg Val Val Asn Gly Lys Val Glu Tyr Phe
             35                  40                  45

Leu Lys Trp Lys Gly Phe Thr Asp Ala Asp Asn Thr Trp Glu Pro Glu
 50                  55                  60

Glu Asn Leu Asp Cys Pro Glu Leu Ile Glu Ala Phe Leu Asn Ser Gln
 65                  70                  75                  80

Lys Ala Gly Lys Glu Lys Asp Gly Thr Lys Arg Lys Ser Leu Ser Asp
                 85                  90                  95

Ser Glu Ser Asp Asp Ser Lys Ser Lys Lys Arg Asp Ala Ala Asp
                100                 105                 110

Lys Pro Arg Gly Phe Ala Arg Gly Leu Asp Pro Glu Arg Ile Ile Gly
            115                 120                 125

Ala Thr Asp Ser Ser Gly Glu Leu Met Phe Leu Met Lys Trp Lys Asp
130                 135                 140

Ser Asp Glu Ala Asp Leu Val Leu Ala Lys Glu Ala Asn Met Lys Cys
145                 150                 155                 160

Pro Gln Ile Val Ile Ala Phe Tyr Glu Glu Arg Leu Thr Trp His Ser
                165                 170                 175

Cys Pro Glu Asp Glu Ala Gln
            180
```

<210> SEQ ID NO 294
<211> LENGTH: 183
<212> TYPE: PRT
<213> ORGANISM: Bos taurus

<400> SEQUENCE: 294

```
Met Ala Ser Asn Lys Thr Thr Leu Gln Lys Met Gly Lys Lys Gln Asn
1               5                   10                  15

Gly Lys Ser Lys Lys Val Glu Glu Ala Glu Pro Glu Glu Phe Val Val
            20                  25                  30

Glu Lys Val Leu Asp Arg Arg Val Val Asn Gly Lys Val Glu Tyr Phe
            35                  40                  45

Leu Lys Trp Lys Gly Phe Thr Asp Ala Asp Asn Thr Trp Glu Pro Glu
    50                  55                  60

Glu Asn Leu Asp Cys Pro Glu Leu Ile Glu Ala Phe Leu Asn Ser Gln
65                  70                  75                  80

Lys Ala Gly Lys Glu Lys Asp Gly Thr Lys Arg Lys Ser Leu Ser Asp
            85                  90                  95

Ser Glu Ser Asp Asp Ser Lys Ser Lys Lys Arg Asp Ala Ala Asp
                100                 105                 110

Lys Pro Arg Gly Phe Ala Arg Gly Leu Asp Pro Glu Arg Ile Ile Gly
            115                 120                 125

Ala Thr Asp Ser Ser Gly Glu Leu Met Phe Leu Met Lys Trp Lys Asp
            130                 135                 140

Ser Asp Glu Ala Asp Leu Val Leu Ala Lys Glu Ala Asn Met Lys Cys
145                 150                 155                 160

Pro Gln Ile Val Ile Ala Phe Tyr Glu Glu Arg Leu Thr Trp His Ser
                165                 170                 175

Cys Pro Glu Asp Glu Ala Gln
            180
```

<210> SEQ ID NO 295
<211> LENGTH: 183
<212> TYPE: PRT
<213> ORGANISM: Macaca mulatta

<400> SEQUENCE: 295

```
Met Ala Ser Asn Lys Thr Thr Leu Gln Lys Met Gly Lys Lys Gln Asn
1               5                   10                  15

Gly Lys Ser Lys Lys Val Glu Glu Ala Glu Pro Glu Glu Phe Val Val
            20                  25                  30

Glu Lys Val Leu Asp Arg Arg Val Val Asn Gly Lys Val Glu Tyr Phe
            35                  40                  45

Leu Lys Trp Lys Gly Phe Thr Asp Ala Asp Asn Thr Trp Glu Pro Glu
    50                  55                  60

Glu Asn Leu Asp Cys Pro Glu Leu Ile Glu Ala Phe Leu Asn Ser Gln
65                  70                  75                  80

Lys Ala Gly Lys Glu Lys Asp Gly Thr Lys Arg Lys Ser Leu Ser Asp
            85                  90                  95

Ser Glu Ser Asp Asp Ser Lys Ser Lys Lys Arg Asp Ala Ala Asp
                100                 105                 110

Lys Pro Arg Gly Phe Ala Arg Gly Leu Asp Pro Glu Arg Ile Ile Gly
            115                 120                 125

Ala Thr Asp Ser Ser Gly Glu Leu Met Phe Leu Met Lys Trp Lys Asp
            130                 135                 140

Ser Asp Glu Ala Asp Leu Val Leu Ala Lys Glu Ala Asn Met Lys Cys
145                 150                 155                 160

Pro Gln Ile Val Ile Ala Phe Tyr Glu Glu Arg Leu Thr Trp His Ser
                165                 170                 175

Cys Pro Glu Asp Glu Ala Gln
            180
```

<210> SEQ ID NO 296
<211> LENGTH: 191
<212> TYPE: PRT
<213> ORGANISM: Homo sapiens

<400> SEQUENCE: 296

Met Gly Lys Lys Thr Lys Arg Thr Ala Asp Ser Ser Ser Ser Glu Asp
1               5                   10                  15

Glu Glu Glu Tyr Val Val Glu Lys Val Leu Asp Arg Arg Val Val Lys
                20                  25                  30

Gly Gln Val Glu Tyr Leu Leu Lys Trp Lys Gly Phe Ser Glu Glu His
            35                  40                  45

Asn Thr Trp Glu Pro Glu Lys Asn Leu Asp Cys Pro Glu Leu Ile Ser
        50                  55                  60

Glu Phe Met Lys Lys Tyr Lys Lys Met Lys Glu Gly Glu Asn Asn Lys
65                  70                  75                  80

Pro Arg Glu Lys Ser Glu Ser Asn Lys Arg Lys Ser Asn Phe Ser Asn
                85                  90                  95

Ser Ala Asp Asp Ile Lys Ser Lys Lys Lys Arg Glu Gln Ser Asn Asp
                100                 105                 110

Ile Ala Arg Gly Phe Glu Arg Gly Leu Glu Pro Glu Lys Ile Ile Gly
            115                 120                 125

Ala Thr Asp Ser Cys Gly Asp Leu Met Phe Leu Met Lys Trp Lys Asp
        130                 135                 140

Thr Asp Glu Ala Asp Leu Val Leu Ala Lys Glu Ala Asn Val Lys Cys
145                 150                 155                 160

Pro Gln Ile Val Ile Ala Phe Tyr Glu Glu Arg Leu Thr Trp His Ala
                165                 170                 175

Tyr Pro Glu Asp Ala Glu Asn Lys Glu Lys Glu Thr Ala Lys Ser
                180                 185                 190

<210> SEQ ID NO 297
<211> LENGTH: 191
<212> TYPE: PRT
<213> ORGANISM: Mus musculus

<400> SEQUENCE: 297

Met Gly Lys Lys Thr Lys Arg Thr Ala Asp Ser Ser Ser Ser Glu Asp
1               5                   10                  15

Glu Glu Glu Tyr Val Val Glu Lys Val Leu Asp Arg Arg Met Val Lys
                20                  25                  30

Gly Gln Val Glu Tyr Leu Leu Lys Trp Lys Gly Phe Ser Glu Glu His
            35                  40                  45

Asn Thr Trp Glu Pro Glu Lys Asn Leu Asp Cys Pro Glu Leu Ile Ser
        50                  55                  60

Glu Phe Met Lys Lys Tyr Lys Lys Met Lys Glu Gly Glu Asn Asn Lys
65                  70                  75                  80

Pro Arg Glu Lys Ser Glu Gly Asn Lys Arg Lys Ser Ser Phe Ser Asn
                85                  90                  95

Ser Ala Asp Asp Ile Lys Ser Lys Lys Lys Arg Glu Gln Ser Asn Asp
                100                 105                 110

Ile Ala Arg Gly Phe Glu Arg Gly Leu Glu Pro Glu Lys Ile Ile Gly
            115                 120                 125

Ala Thr Asp Ser Cys Gly Asp Leu Met Phe Leu Met Lys Trp Lys Asp
        130                 135                 140

```
Thr Asp Glu Ala Asp Leu Val Leu Ala Lys Glu Ala Asn Val Lys Cys
145                 150                 155                 160

Pro Gln Ile Val Ile Ala Phe Tyr Glu Glu Arg Leu Thr Trp His Ala
                165                 170                 175

Tyr Pro Glu Asp Ala Glu Asn Lys Glu Lys Glu Ser Ala Lys Ser
            180                 185                 190

<210> SEQ ID NO 298
<211> LENGTH: 191
<212> TYPE: PRT
<213> ORGANISM: Rattus norvegicus

<400> SEQUENCE: 298

Met Gly Lys Lys Thr Lys Arg Thr Ala Asp Ser Ser Ser Ser Glu Asp
1               5                   10                  15

Glu Glu Glu Tyr Val Val Glu Lys Val Leu Asp Arg Arg Met Val Lys
                20                  25                  30

Gly Gln Val Glu Tyr Leu Leu Lys Trp Lys Gly Phe Ser Glu Glu His
            35                  40                  45

Asn Thr Trp Glu Pro Glu Lys Asn Leu Asp Cys Pro Glu Leu Ile Ser
50                  55                  60

Glu Phe Met Lys Lys Tyr Lys Lys Met Lys Glu Gly Glu Asn Asn Lys
65                  70                  75                  80

Pro Arg Glu Lys Ser Glu Gly Asn Lys Arg Lys Ser Ser Phe Ser Asn
                85                  90                  95

Ser Ala Asp Asp Ile Lys Ser Lys Lys Lys Arg Glu Gln Ser Asn Asp
            100                 105                 110

Ile Ala Arg Gly Phe Glu Arg Gly Leu Glu Pro Glu Lys Ile Ile Gly
        115                 120                 125

Ala Thr Asp Ser Cys Gly Asp Leu Met Phe Leu Met Lys Trp Lys Asp
    130                 135                 140

Thr Asp Glu Ala Asp Leu Val Leu Ala Lys Glu Ala Asn Val Lys Cys
145                 150                 155                 160

Pro Gln Ile Val Ile Ala Phe Tyr Glu Glu Arg Leu Thr Trp His Ala
                165                 170                 175

Tyr Pro Glu Asp Ala Glu Asn Lys Glu Lys Glu Ser Ala Lys Ser
            180                 185                 190

<210> SEQ ID NO 299
<211> LENGTH: 191
<212> TYPE: PRT
<213> ORGANISM: Bos taurus

<400> SEQUENCE: 299

Met Gly Lys Lys Thr Lys Arg Thr Ala Asp Ser Ser Ser Ser Glu Asp
1               5                   10                  15

Glu Glu Glu Tyr Val Val Glu Lys Val Leu Asp Arg Arg Val Val Lys
                20                  25                  30

Gly Gln Val Glu Tyr Leu Leu Lys Trp Lys Gly Phe Ser Glu Glu His
            35                  40                  45

Asn Thr Trp Glu Pro Glu Lys Asn Leu Asp Cys Pro Glu Leu Ile Ser
50                  55                  60

Glu Phe Met Lys Lys Tyr Lys Lys Met Lys Glu Gly Glu Asn Asn Lys
65                  70                  75                  80

Pro Arg Glu Lys Ser Glu Ser Asn Lys Arg Lys Ser Asn Phe Ser Asn
                85                  90                  95
```

```
Ser Ala Asp Asp Ile Lys Ser Lys Lys Arg Glu Gln Ser Asn Asp
            100                 105                 110

Ile Ala Arg Gly Phe Glu Arg Gly Leu Glu Pro Glu Lys Ile Ile Gly
        115                 120                 125

Ala Thr Asp Ser Cys Gly Asp Leu Met Phe Leu Met Lys Trp Lys Asp
    130                 135                 140

Thr Asp Glu Ala Asp Leu Val Leu Ala Lys Glu Ala Asn Val Lys Cys
145                 150                 155                 160

Pro Gln Ile Val Ile Ala Phe Tyr Glu Glu Arg Leu Thr Trp His Ala
                165                 170                 175

Tyr Pro Glu Asp Ala Glu Asn Lys Glu Lys Glu Thr Ala Lys Ser
            180                 185                 190

<210> SEQ ID NO 300
<211> LENGTH: 191
<212> TYPE: PRT
<213> ORGANISM: Macaca mulatta

<400> SEQUENCE: 300

Met Gly Lys Lys Thr Lys Arg Thr Ala Asp Ser Ser Ser Ser Glu Asp
1               5                   10                  15

Glu Glu Glu Tyr Val Val Glu Lys Val Leu Asp Arg Arg Val Val Lys
            20                  25                  30

Gly Gln Val Glu Tyr Leu Leu Lys Trp Lys Gly Phe Ser Glu Glu His
        35                  40                  45

Asn Thr Trp Glu Pro Glu Lys Asn Leu Asp Cys Pro Glu Leu Ile Ser
 50                 55                  60

Glu Phe Met Lys Lys Tyr Lys Lys Met Lys Glu Gly Glu Asn Asn Lys
65                  70                  75                  80

Pro Arg Glu Lys Ser Glu Ser Asn Lys Arg Lys Ser Asn Phe Ser Asn
                85                  90                  95

Ser Ala Asp Asp Ile Lys Ser Lys Lys Arg Glu Gln Ser Asn Asp
            100                 105                 110

Ile Ala Arg Gly Phe Glu Arg Gly Leu Glu Pro Glu Lys Ile Ile Gly
        115                 120                 125

Ala Thr Asp Ser Cys Gly Asp Leu Met Phe Leu Met Lys Trp Lys Asp
    130                 135                 140

Thr Asp Glu Ala Asp Leu Val Leu Ala Lys Glu Ala Asn Val Lys Cys
145                 150                 155                 160

Pro Gln Ile Val Ile Ala Phe Tyr Glu Glu Arg Leu Thr Trp His Ala
                165                 170                 175

Tyr Pro Glu Asp Ala Glu Asn Lys Glu Lys Glu Thr Ala Lys Ser
            180                 185                 190

<210> SEQ ID NO 301
<211> LENGTH: 180
<212> TYPE: PRT
<213> ORGANISM: Homo sapiens

<400> SEQUENCE: 301

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45
```

```
Gly Ala Arg Ala Ser Gly Pro Gly Gly Ala Pro Arg Gly Pro
    50              55                  60

His Gly Gly Ala Ala Ser Gly Leu Asn Gly Cys Cys Arg Cys Gly Ala
65              70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
        180

<210> SEQ ID NO 302
<211> LENGTH: 219
<212> TYPE: PRT
<213> ORGANISM: Mus musculus

<400> SEQUENCE: 302

Met Gln Asp Pro Ser Gly Asp Lys Val Cys Arg Ala Gly Gly Glu Glu
1               5                   10                  15

Asp Gly Glu Asp Gly Gln His Thr Ser Arg Val His Asp Thr Glu Ala
            20                  25                  30

Asp Pro His His Thr Glu Ala Ser Ser His Arg Thr Glu Gly Ser Ser
        35                  40                  45

His Leu Thr Glu Thr Ser Ser Arg Pro Ser Glu Ala Glu Asn Gly His
    50                  55                  60

Asp Asn Ser Pro His Val Asn Arg Ala Gln Asp Val Gly Thr Gln Ala
65              70                  75                  80

Ser Pro Gln Gly Ser Leu Asn Ser Arg Val Pro Val Glu Ala Arg Val
                85                  90                  95

Val Val Glu Glu Ala Ala Ile Ala Pro Gln Gly Glu Gln Ala Pro Ile
            100                 105                 110

Ile Pro Gly Pro Ser Gly Asp Ala Ala Thr Thr Ala Gly Ser Arg Leu
        115                 120                 125

Leu Glu Phe Ser Val Thr Val Pro Phe Arg Thr Ala Val Glu Ala Asn
    130                 135                 140

Ile Ala Cys Arg Thr Leu Ala Ser Asn Ile Gln Gln Gln Val Met
145                 150                 155                 160

Val Gln Gln Glu Phe Thr Val Asn Asp Thr Ile Leu Thr Val Arg Trp
                165                 170                 175

Thr Thr Glu Asp Pro Val Leu Phe Arg Thr Ser Ile Asn Ala Phe Leu
            180                 185                 190

Asp Gln Leu Ser Leu Val Val Arg Asn Ile Pro Arg Pro Val Phe Met
        195                 200                 205

Ala Val Phe Lys Gln Gly Arg Gly Arg Asn Asn
    210                 215
```

-continued

```
<210> SEQ ID NO 303
<211> LENGTH: 206
<212> TYPE: PRT
<213> ORGANISM: Homo sapiens

<400> SEQUENCE: 303

Met Ile Leu Val Cys Asp Arg Val Ser Glu Asp Gly Ile Asn Arg Gln
1               5                   10                  15

Lys Ala Gln Glu Trp Cys Ile Lys His Gly Phe Glu Leu Val Glu Leu
            20                  25                  30

Ser Pro Glu Glu Leu Pro Glu Asp Asp Phe Pro Glu Ser Thr
        35                  40                  45

Gly Val Lys Arg Ile Val Gln Ala Leu Asn Ala Asn Val Trp Ser Asn
    50                  55                  60

Val Val Met Lys Asn Asp Arg Asn Gln Gly Phe Ser Leu Leu Asn Ser
65                  70                  75                  80

Leu Thr Gly Thr Asn His Ser Ile Gly Ser Ala Asp Pro Cys His Pro
                85                  90                  95

Glu Gln Pro His Leu Pro Ala Ala Asp Ser Thr Glu Ser Leu Ser Asp
            100                 105                 110

His Arg Gly Gly Ala Ser Asn Thr Thr Asp Ala Gln Val Asp Ser Ile
        115                 120                 125

Val Asp Pro Met Leu Asp Leu Asp Ile Gln Glu Leu Ala Ser Leu Thr
    130                 135                 140

Thr Gly Gly Gly Asp Val Glu Asn Phe Glu Arg Leu Phe Ser Lys Leu
145                 150                 155                 160

Lys Glu Met Lys Asp Lys Ala Ala Thr Leu Pro His Glu Gln Arg Lys
                165                 170                 175

Val His Ala Glu Lys Val Ala Lys Ala Phe Trp Met Ala Ile Gly Gly
            180                 185                 190

Asp Arg Asp Glu Ile Glu Gly Leu Ser Ser Asp Glu His
        195                 200                 205

<210> SEQ ID NO 304
<211> LENGTH: 315
<212> TYPE: PRT
<213> ORGANISM: Mus musculus

<400> SEQUENCE: 304

Met Ala Ala Gly Val Pro Cys Ala Leu Val Thr Ser Cys Ser Ala Thr
1               5                   10                  15

Phe Thr Gly Asp Arg Leu Val Gln His Ile Leu Gly Thr Glu Asp Ala
            20                  25                  30

Val Val Glu Ala Thr Ser Ser Asp Ala Val Arg Phe Tyr Pro Trp Thr
        35                  40                  45

Ile Asp Asn Lys Tyr Tyr Ser Ala Glu Ile Asn Leu Cys Val Val Pro
    50                  55                  60

Ser Lys Phe Leu Val Thr Ala Glu Ile Ala Glu Ser Val Gln Ala Phe
65                  70                  75                  80

Val Val Tyr Phe Asp Ser Thr Gln Lys Ser Gly Leu Asp Ser Val Ser
                85                  90                  95

Ser Trp Leu Pro Leu Ala Glu Ala Trp Leu Ala Glu Val Met Ile Leu
            100                 105                 110

Val Cys Asp Arg Val Cys Asp Asp Gly Ile Asn Arg Gln Gln Ala Gln
        115                 120                 125

Glu Trp Cys Ile Lys His Gly Phe Glu Leu Val Glu Leu Asn Pro Glu
```

```
            130                 135                 140
Glu Leu Pro Glu Glu Asp Asp Phe Pro Glu Ser Thr Gly Val Lys
145                 150                 155                 160

Arg Ile Val Gln Ala Leu Asn Ala Asn Val Trp Ser Asn Val Val Met
                165                 170                 175

Lys Ser Asp Arg Ser Gln Gly Phe Ser Leu Leu Asn Ser Leu Ala Gly
            180                 185                 190

Ala Asn Arg Arg Val Ala Ser Ala Glu Ser Cys His Ser Glu Gln Glu
                195                 200                 205

Pro Ser Pro Thr Ala Glu Arg Thr Glu Ser Leu Pro Gly His His Ser
        210                 215                 220

Gly Ala Cys Gly Ser Ala Gly Ala Gln Val Asp Ser Ile Val Asp Pro
225                 230                 235                 240

Met Leu Asp Leu Asp Ile Gln Glu Leu Ala Ser Leu Thr Thr Gly Gly
                245                 250                 255

Gly Asp Leu Glu Asn Phe Glu Arg Leu Phe Ser Lys Leu Lys Glu Met
            260                 265                 270

Lys Asp Lys Ala Ala Thr Leu Pro His Glu Gln Arg Lys Leu His Ala
        275                 280                 285

Glu Lys Val Ala Lys Ala Phe Trp Met Ala Ile Gly Gly Asp Arg Asp
290                 295                 300

Glu Ile Glu Gly Leu Ser Ser Asp Asp Glu His
305                 310                 315

<210> SEQ ID NO 305
<211> LENGTH: 315
<212> TYPE: PRT
<213> ORGANISM: Rattus norvegicus

<400> SEQUENCE: 305

Met Ala Ala Gly Val Pro Cys Ala Leu Val Thr Ser Cys Ser Ala Thr
1               5                   10                  15

Phe Thr Gly Asp Arg Leu Val Gln His Ile Leu Gly Thr Glu Asp Ala
                20                  25                  30

Val Val Glu Ala Thr Ser Ser Asp Ala Val Arg Phe Tyr Pro Trp Thr
            35                  40                  45

Ile Asp Asn Lys Tyr Tyr Ser Ala Glu Val Asn Leu Cys Val Val Pro
50                  55                  60

Ser Lys Cys Arg Val Thr Ala Glu Ile Ala Glu Ala Val Gln Ala Phe
65                  70                  75                  80

Val Val Tyr Phe Asp Ser Thr Gln Lys Ser Gly Leu Asp Ser Val Ser
                85                  90                  95

Ser Trp Leu Pro Leu Ala Glu Thr Trp Leu Pro Glu Val Met Ile Leu
            100                 105                 110

Val Cys Asp Arg Val Cys Glu Asp Gly Ile Asn Arg Gln Gln Ala Gln
        115                 120                 125

Glu Trp Cys Ile Lys His Gly Phe Glu Leu Val Glu Leu Cys Pro Glu
    130                 135                 140

Glu Leu Pro Glu Glu Asp Asp Phe Pro Glu Ser Thr Gly Val Lys
145                 150                 155                 160

Arg Ile Val Gln Ala Leu Asn Ala Asn Val Trp Ser Asn Val Val Met
                165                 170                 175

Lys Asn Asp Arg Ser Gln Gly Phe Ser Leu Leu Asn Ser Leu Ala Gly
            180                 185                 190
```

```
Ala Ser Arg Ser Val Gly Ser Ala Glu Ser Cys Gln Cys Glu Gln Glu
            195                 200                 205

Pro Ser Pro Thr Ala Glu Arg Thr Glu Ser Leu Pro Gly His Arg Ser
210                 215                 220

Gly Ala Cys Gly Pro Ala Gly Ala Gln Val Asp Ser Ile Val Asp Pro
225                 230                 235                 240

Met Leu Asp Leu Asp Ile Gln Glu Leu Ala Ser Leu Thr Thr Gly Gly
            245                 250                 255

Gly Asp Leu Glu Asn Phe Glu Arg Phe Ser Lys Leu Lys Glu Met
            260                 265                 270

Lys Asp Lys Ala Ala Thr Leu Pro His Glu Gln Arg Lys Leu His Ala
            275                 280                 285

Glu Lys Val Ala Lys Ala Phe Trp Met Ala Ile Gly Gly Asp Arg Asp
290                 295                 300

Glu Ile Glu Gly Leu Ser Ser Asp Asp Glu His
305                 310                 315

<210> SEQ ID NO 306
<211> LENGTH: 315
<212> TYPE: PRT
<213> ORGANISM: Bos taurus

<400> SEQUENCE: 306

Met Ala Ala Gly Val Pro Cys Ala Leu Val Thr Ser Cys Ser Ser Thr
1               5                   10                  15

Phe Ser Ala Asp Arg Leu Val Gln His Ile Leu Gly Thr Glu Asp Val
            20                  25                  30

Val Val Glu Val Thr Ala Asn Asp Ala Val Arg Phe Tyr Pro Trp Thr
            35                  40                  45

Ile Asp Asn Lys Tyr Tyr Ser Ala Asp Ile Asn Leu Cys Val Val Pro
50                  55                  60

Asn Lys Phe Leu Val Thr Ala Glu Ile Ala Glu Ser Val Gln Ala Phe
65                  70                  75                  80

Val Val Tyr Phe Asp Ser Thr Gln Lys Ser Gly Leu Asp Ser Val Ser
                85                  90                  95

Ser Trp Leu Pro Leu Ala Glu Ser Trp Leu Pro Glu Val Met Ile Leu
            100                 105                 110

Val Cys Asp Arg Val Ser Glu Asn Gly Val Asn Arg Gln Lys Ala Gln
            115                 120                 125

Glu Trp Cys Ile Lys His Gly Phe Glu Leu Val Glu Leu Ser Pro Glu
130                 135                 140

Glu Leu Pro Glu Glu Asp Asp Phe Pro Glu Ser Thr Gly Val Lys
145                 150                 155                 160

Arg Ile Val Gln Ala Leu Asn Ala Asn Val Trp Ser Asn Val Val Met
            165                 170                 175

Lys Asn Glu Arg Asn Gln Gly Leu Asn Leu Leu Ser Ser Leu Thr Gly
            180                 185                 190

Ala Ser His Ser Ile Gly Ser Ala Glu Ser Cys His Ser Glu Gln Pro
            195                 200                 205

Cys Val Pro Ala Ala Glu Arg Thr Glu Ser Leu Leu Asp His Arg Gly
210                 215                 220

Ala Ala Ser Asn Thr Ala Asp Val Gln Val Asp Ser Ile Val Asp Pro
225                 230                 235                 240

Met Leu Asp Leu Asp Ile Gln Glu Leu Ala Ser Leu Thr Thr Gly Gly
            245                 250                 255
```

-continued

```
Gly Asp Leu Glu Asn Phe Glu Arg Leu Phe Ser Lys Leu Lys Glu Met
            260                 265                 270

Lys Asp Lys Ala Ala Thr Leu Pro His Glu Gln Arg Lys Met His Ala
        275                 280                 285

Glu Lys Val Ala Lys Ala Phe Trp Met Ala Ile Gly Gly Asp Arg Asp
    290                 295                 300

Glu Ile Glu Gly Leu Ser Ser Asp Glu His
305                 310                 315

<210> SEQ ID NO 307
<211> LENGTH: 206
<212> TYPE: PRT
<213> ORGANISM: Macaca mulatta

<400> SEQUENCE: 307

Met Ile Leu Val Cys Asp Arg Val Ser Glu Asp Gly Val Asn Arg Gln
1               5                   10                  15

Lys Ala Gln Glu Trp Cys Ile Arg His Gly Phe Glu Leu Val Glu Leu
            20                  25                  30

Ser Pro Glu Glu Leu Pro Glu Glu Asp Asp Phe Pro Glu Ser Thr
        35                  40                  45

Gly Val Lys Arg Ile Val Gln Ala Leu Asn Ala Asn Val Trp Ser Asn
    50                  55                  60

Val Val Met Lys Asn Asp Arg Asn Gln Gly Phe Ser Leu Leu Asn Ser
65                  70                  75                  80

Leu Thr Gly Thr Asn His Ser Ile Gly Ser Ala Asp Pro Cys His Pro
                85                  90                  95

Glu Gln Pro His Leu Pro Ala Ala Asp Arg Thr Glu Ser Leu Ser Asp
            100                 105                 110

His Arg Ser Gly Ala Ser Asn Thr Thr Asp Ala Gln Val Asp Ser Ile
        115                 120                 125

Val Asp Pro Met Leu Asp Leu Asp Ile Gln Glu Leu Ala Ser Leu Thr
    130                 135                 140

Thr Gly Gly Asp Val Glu Asn Phe Glu Arg Leu Phe Ser Lys Leu
145                 150                 155                 160

Lys Glu Met Lys Asp Lys Ala Ala Thr Leu Pro His Glu Gln Arg Lys
                165                 170                 175

Val His Ala Glu Lys Val Ala Lys Ala Phe Trp Met Ala Ile Gly Gly
            180                 185                 190

Asp Arg Asp Glu Ile Glu Gly Leu Ser Ser Asp Glu His
        195                 200                 205

<210> SEQ ID NO 308
<211> LENGTH: 619
<212> TYPE: PRT
<213> ORGANISM: Homo sapiens

<400> SEQUENCE: 308

Met Ser Gly Leu Val Leu Gly Gln Arg Asp Glu Pro Ala Gly His Arg
1               5                   10                  15

Leu Ser Gln Glu Glu Ile Leu Gly Ser Thr Arg Leu Val Ser Gln Gly
            20                  25                  30

Leu Glu Ala Leu Arg Ser Glu His Gln Ala Val Leu Gln Ser Leu Ser
        35                  40                  45

Gln Thr Ile Glu Cys Leu Gln Gln Gly Gly His Glu Glu Gly Leu Val
    50                  55                  60
```

```
His Glu Lys Ala Arg Gln Leu Arg Arg Ser Met Glu Asn Ile Glu Leu
 65                  70                  75                  80

Gly Leu Ser Glu Ala Gln Val Met Leu Ala Leu Ala Ser His Leu Ser
                 85                  90                  95

Thr Val Glu Ser Glu Lys Gln Lys Leu Arg Ala Gln Val Arg Arg Leu
                100                 105                 110

Cys Gln Glu Asn Gln Trp Leu Arg Asp Glu Leu Ala Gly Thr Gln Gln
            115                 120                 125

Arg Leu Gln Arg Ser Glu Gln Ala Val Ala Gln Leu Glu Glu Glu Lys
        130                 135                 140

Lys His Leu Glu Phe Leu Gly Gln Leu Arg Gln Tyr Asp Glu Asp Gly
145                 150                 155                 160

His Thr Ser Glu Glu Lys Glu Gly Asp Ala Thr Lys Asp Ser Leu Asp
                165                 170                 175

Asp Leu Phe Pro Asn Glu Glu Glu Asp Pro Ser Asn Gly Leu Ser
            180                 185                 190

Arg Gly Gln Gly Ala Thr Ala Ala Gln Gln Gly Gly Tyr Glu Ile Pro
        195                 200                 205

Ala Arg Leu Arg Thr Leu His Asn Leu Val Ile Gln Tyr Ala Ala Gln
    210                 215                 220

Gly Arg Tyr Glu Val Ala Val Pro Leu Cys Lys Gln Ala Leu Glu Asp
225                 230                 235                 240

Leu Glu Arg Thr Ser Gly Arg Gly His Pro Asp Val Ala Thr Met Leu
                245                 250                 255

Asn Ile Leu Ala Leu Val Tyr Arg Asp Gln Asn Lys Tyr Lys Glu Ala
            260                 265                 270

Ala His Leu Leu Asn Asp Ala Leu Ser Ile Arg Glu Ser Thr Leu Gly
        275                 280                 285

Pro Asp His Pro Ala Val Ala Ala Thr Leu Asn Asn Leu Ala Val Leu
    290                 295                 300

Tyr Gly Lys Arg Gly Lys Tyr Lys Glu Ala Glu Pro Leu Cys Gln Arg
305                 310                 315                 320

Ala Leu Glu Ile Arg Glu Lys Val Leu Gly Thr Asn His Pro Asp Val
                325                 330                 335

Ala Lys Gln Leu Asn Asn Leu Ala Leu Leu Cys Gln Asn Gln Gly Lys
            340                 345                 350

Tyr Glu Ala Val Glu Arg Tyr Tyr Gln Arg Ala Leu Ala Ile Tyr Glu
        355                 360                 365

Gly Gln Leu Gly Pro Asp Asn Pro Asn Val Ala Arg Thr Lys Asn Asn
    370                 375                 380

Leu Ala Ser Cys Tyr Leu Lys Gln Gly Lys Tyr Ala Glu Ala Glu Thr
385                 390                 395                 400

Leu Tyr Lys Glu Ile Leu Thr Arg Ala His Val Gln Glu Phe Gly Ser
                405                 410                 415

Val Asp Asp Asp His Lys Pro Ile Trp Met His Ala Glu Glu Arg Glu
            420                 425                 430

Glu Met Ser Lys Ser Arg His His Glu Gly Gly Thr Pro Tyr Ala Glu
        435                 440                 445

Tyr Gly Gly Trp Tyr Lys Ala Cys Lys Val Ser Ser Pro Thr Val Asn
    450                 455                 460

Thr Thr Leu Arg Asn Leu Gly Ala Leu Tyr Arg Arg Gln Gly Lys Leu
465                 470                 475                 480
```

```
Glu Ala Ala Glu Thr Leu Glu Glu Cys Ala Leu Arg Ser Arg Arg Gln
                485                 490                 495

Gly Thr Asp Pro Ile Ser Gln Thr Lys Val Ala Glu Leu Leu Gly Glu
            500                 505                 510

Ser Asp Gly Arg Arg Thr Ser Gln Glu Gly Pro Gly Asp Ser Val Lys
            515                 520                 525

Phe Glu Gly Gly Glu Asp Ala Ser Val Ala Val Glu Trp Ser Gly Asp
            530                 535                 540

Gly Ser Gly Thr Leu Gln Arg Ser Gly Ser Leu Gly Lys Ile Arg Asp
545                 550                 555                 560

Val Leu Arg Arg Ser Ser Glu Leu Leu Val Arg Lys Leu Gln Gly Thr
                565                 570                 575

Glu Pro Arg Pro Ser Ser Ser Asn Met Lys Arg Ala Ala Ser Leu Asn
            580                 585                 590

Tyr Leu Asn Gln Pro Ser Ala Ala Pro Leu Gln Val Ser Arg Gly Leu
            595                 600                 605

Ser Ala Ser Thr Met Asp Leu Ser Ser Ser Ser
            610                 615

<210> SEQ ID NO 309
<211> LENGTH: 619
<212> TYPE: PRT
<213> ORGANISM: Mus musculus

<400> SEQUENCE: 309

Met Ser Gly Leu Val Leu Gly Gln Arg Asp Glu Pro Ala Gly His Arg
1               5                   10                  15

Leu Ser Gln Glu Glu Ile Leu Gly Ser Thr Lys Val Val Ser Gln Gly
                20                  25                  30

Leu Glu Ala Leu His Ser Glu His Gln Ala Val Leu Gln Ser Leu Ser
            35                  40                  45

His Thr Ile Glu Cys Leu Gln Gln Gly Gly His Glu Glu Gly Leu Val
        50                  55                  60

His Glu Lys Ala Arg Gln Leu Arg Arg Ser Met Glu Asn Ile Glu Leu
65                  70                  75                  80

Gly Leu Ser Glu Ala Gln Val Met Leu Ala Leu Ala Ser His Leu Ser
                85                  90                  95

Thr Val Glu Ser Glu Lys Gln Lys Leu Arg Ala Gln Val Arg Arg Leu
            100                 105                 110

Cys Gln Glu Asn Gln Trp Leu Arg Asp Glu Leu Ala Gly Thr Gln Gln
        115                 120                 125

Arg Leu Gln Arg Ser Glu Gln Ala Val Ala Gln Leu Glu Glu Glu Lys
    130                 135                 140

Lys His Leu Glu Phe Leu Arg Gln Leu Arg Gln Tyr Asp Glu Asp Gly
145                 150                 155                 160

His Gly Met Glu Glu Lys Glu Gly Glu Ala Thr Lys Asp Ser Leu Asp
                165                 170                 175

Asp Leu Phe Pro Asn Glu Glu Glu Asp Ser Gly Asn Asp Leu Ser
            180                 185                 190

Arg Gly Gln Gly Ala Ala Ala Gln Gln Gly Gly Tyr Glu Ile Pro
        195                 200                 205

Ala Arg Leu Arg Thr Leu His Asn Leu Val Ile Gln Tyr Ala Ala Gln
    210                 215                 220

Gly Arg Tyr Glu Val Ala Val Pro Leu Cys Lys Gln Ala Leu Glu Asp
225                 230                 235                 240
```

```
Leu Glu Arg Thr Ser Gly Arg Gly His Pro Asp Val Ala Thr Met Leu
                245                 250                 255

Asn Ile Leu Ala Leu Val Tyr Arg Asp Gln Asn Lys Tyr Lys Glu Ala
            260                 265                 270

Ala His Leu Leu Asn Asp Ala Leu Ser Ile Arg Glu Ser Thr Leu Gly
            275                 280                 285

Arg Asp His Pro Ala Val Ala Thr Leu Asn Asn Leu Ala Val Leu
        290                 295                 300

Tyr Gly Lys Arg Gly Lys Tyr Lys Glu Ala Glu Pro Leu Cys Gln Arg
305                 310                 315                 320

Ala Leu Glu Ile Arg Glu Lys Val Leu Gly Thr Asp His Pro Asp Val
                325                 330                 335

Ala Lys Gln Leu Asn Asn Leu Ala Leu Leu Cys Gln Asn Gln Gly Lys
            340                 345                 350

Tyr Glu Ala Val Glu Arg Tyr Tyr Gln Arg Ala Leu Ala Ile Tyr Glu
            355                 360                 365

Ser Gln Leu Gly Pro Asp Asn Pro Asn Val Ala Arg Thr Lys Asn Asn
        370                 375                 380

Leu Ala Ser Cys Tyr Leu Lys Gln Gly Lys Tyr Ser Glu Ala Glu Ala
385                 390                 395                 400

Leu Tyr Lys Glu Ile Leu Thr Cys Ala His Val Gln Glu Phe Gly Ser
                405                 410                 415

Val Asp Asp Asp His Lys Pro Ile Trp Met His Ala Glu Glu Arg Glu
            420                 425                 430

Glu Met Ser Arg Ser Arg Pro Arg Asp Ser Ser Ala Pro Tyr Ala Glu
            435                 440                 445

Tyr Gly Gly Trp Tyr Lys Ala Cys Arg Val Ser Pro Thr Val Asn
        450                 455                 460

Thr Thr Leu Lys Asn Leu Gly Ala Leu Tyr Arg Arg Gln Gly Lys Leu
465                 470                 475                 480

Glu Ala Ala Glu Thr Leu Glu Glu Cys Ala Leu Arg Ser Arg Lys Gln
                485                 490                 495

Gly Thr Asp Pro Ile Ser Gln Thr Lys Val Ala Glu Leu Leu Gly Glu
            500                 505                 510

Gly Asp Gly Arg Lys Ala Ile Gln Glu Gly Pro Gly Asp Ser Val Lys
        515                 520                 525

Phe Glu Gly Gly Glu Asp Ala Ser Val Ala Val Glu Trp Ser Gly Asp
530                 535                 540

Gly Ser Gly Thr Leu Gln Arg Ser Gly Ser Leu Gly Lys Ile Arg Asp
545                 550                 555                 560

Val Leu Arg Arg Ser Ser Glu Leu Leu Val Arg Lys Leu Gln Gly Thr
                565                 570                 575

Glu Pro Arg Pro Ser Ser Ser Met Lys Arg Ala Ala Ser Leu Asn
            580                 585                 590

Tyr Leu Asn Gln Pro Asn Ala Ala Pro Leu Gln Val Ser Arg Gly Leu
        595                 600                 605

Ser Ala Ser Thr Val Asp Leu Ser Ser Ser Ser
    610                 615
```

<210> SEQ ID NO 310
<211> LENGTH: 619
<212> TYPE: PRT
<213> ORGANISM: Rattus norvegicus

<400> SEQUENCE: 310

```
Met Ser Gly Leu Val Leu Gly Gln Arg Asp Glu Pro Ala Gly His Arg
1               5                   10                  15
Leu Ser Gln Glu Glu Ile Leu Gly Ser Thr Arg Leu Val Ser Gln Gly
            20                  25                  30
Leu Glu Ser Leu His Ser Glu His Gln Ala Val Leu Gln Ser Leu Ser
        35                  40                  45
His Thr Ile Glu Cys Leu Gln Gln Gly His Glu Glu Gly Leu Val
    50                  55                  60
His Glu Lys Ala Arg Gln Leu Arg Arg Ser Met Glu Asn Ile Glu Leu
65                  70                  75                  80
Gly Leu Ser Glu Ala Gln Val Met Leu Ala Leu Ala Ser His Leu Ser
                85                  90                  95
Thr Val Glu Ser Glu Lys Gln Lys Leu Arg Ala Gln Val Arg Arg Leu
            100                 105                 110
Cys Gln Glu Asn Gln Trp Leu Arg Asp Glu Leu Ala Gly Thr Gln Gln
        115                 120                 125
Arg Leu Gln Arg Ser Glu Gln Ala Val Ala Gln Leu Glu Glu Glu Lys
130                 135                 140
Lys His Leu Glu Phe Leu Arg Gln Leu Arg Gln Tyr Asp Glu Asp Gly
145                 150                 155                 160
His Ser Met Glu Glu Lys Glu Gly Asp Ala Ser Lys Asp Ser Leu Asp
                165                 170                 175
Asp Leu Phe Pro Asn Glu Glu Glu Asp Ser Ser Asn Asp Leu Ser
            180                 185                 190
Arg Gly Gln Gly Ala Ala Ala Gln Gln Gly Gly Tyr Glu Ile Pro
        195                 200                 205
Ala Arg Leu Arg Thr Leu His Asn Leu Val Ile Gln Tyr Ala Ala Gln
210                 215                 220
Gly Arg Tyr Glu Val Ala Val Pro Leu Cys Lys Gln Ala Leu Glu Asp
225                 230                 235                 240
Leu Glu Arg Thr Ser Gly Arg Gly His Pro Asp Val Ala Thr Met Leu
                245                 250                 255
Asn Ile Leu Ala Leu Val Tyr Arg Asp Gln Asn Lys Tyr Lys Glu Ala
            260                 265                 270
Ala His Leu Leu Asn Asp Ala Leu Ser Ile Arg Glu Ser Thr Leu Gly
        275                 280                 285
Arg Asp His Pro Ala Val Ala Ala Thr Leu Asn Asn Leu Ala Val Leu
290                 295                 300
Tyr Gly Lys Arg Gly Lys Tyr Lys Glu Ala Glu Pro Leu Cys Gln Arg
305                 310                 315                 320
Ala Leu Glu Ile Arg Glu Lys Val Leu Gly Thr Asp His Pro Asp Val
                325                 330                 335
Ala Lys Gln Leu Asn Asn Leu Ala Leu Leu Cys Gln Asn Gln Gly Lys
            340                 345                 350
Tyr Glu Ala Val Glu Arg Tyr Tyr Gln Arg Ala Leu Ala Ile Tyr Glu
        355                 360                 365
Arg Gln Leu Gly Pro Asp Asn Pro Asn Val Ala Arg Thr Lys Asn Asn
370                 375                 380
Leu Ala Ser Cys Tyr Leu Lys Gln Gly Lys Tyr Ser Glu Ala Glu Thr
385                 390                 395                 400
Leu Tyr Lys Glu Ile Leu Thr Arg Ala His Val Gln Glu Phe Gly Ser
                405                 410                 415
```

```
Val Asp Asp Asp His Lys Pro Ile Trp Met His Ala Glu Glu Arg Glu
            420                 425                 430

Glu Met Ser Arg Ser Arg Ser Arg Glu Ser Gly Thr Pro Tyr Ala Glu
            435                 440                 445

Tyr Gly Gly Trp Tyr Lys Ala Cys Arg Val Ser Ser Pro Thr Val Asn
450                 455                 460

Thr Thr Leu Arg Asn Leu Gly Ala Leu Tyr Arg Arg Gln Gly Lys Leu
465                 470                 475                 480

Glu Ala Ala Glu Thr Leu Glu Glu Cys Ala Leu Arg Ser Arg Lys Gln
            485                 490                 495

Gly Thr Asp Pro Ile Ser Gln Thr Lys Val Ala Glu Leu Leu Gly Glu
            500                 505                 510

Gly Asp Gly Arg Lys Thr Met Gln Glu Gly Pro Gly Asp Ser Val Lys
            515                 520                 525

Phe Glu Gly Gly Glu Asp Ala Ser Val Ala Val Glu Trp Ser Gly Asp
            530                 535                 540

Gly Ser Gly Thr Leu Gln Arg Ser Gly Ser Leu Gly Lys Ile Arg Asp
545                 550                 555                 560

Val Leu Arg Arg Ser Ser Glu Leu Leu Val Arg Lys Leu Gln Gly Thr
            565                 570                 575

Glu Pro Arg Pro Ser Ser Ser Asn Met Lys Arg Ala Ala Ser Leu Asn
            580                 585                 590

Tyr Leu Asn Gln Pro Asn Ala Ala Pro Leu Gln Thr Ser Arg Gly Leu
            595                 600                 605

Ser Ala Ser Thr Val Asp Leu Ser Ser Ser
            610                 615

<210> SEQ ID NO 311
<211> LENGTH: 616
<212> TYPE: PRT
<213> ORGANISM: Bos taurus

<400> SEQUENCE: 311

Met Ser Gly Leu Val Leu Gly Gln Arg Asp Glu Pro Ala Gly His Arg
1               5                   10                  15

Leu Ser Gln Glu Glu Ile Leu Gly Ser Thr Arg Leu Val Ser Gln Gly
            20                  25                  30

Leu Glu Ala Leu His Ser Glu His Gln Ala Val Leu Gln Ser Leu Ser
            35                  40                  45

Gln Thr Ile Glu Cys Leu Gln Gln Gly Gly His Glu Glu Gly Leu Val
50                  55                  60

His Glu Lys Ala Arg Gln Leu Arg Arg Ser Met Glu Asn Ile Glu Leu
65                  70                  75                  80

Gly Leu Ser Glu Ala Gln Val Met Leu Ala Leu Ala Asn His Leu Ser
            85                  90                  95

Thr Val Glu Ser Glu Lys Gln Lys Leu Arg Ala Gln Val Arg Arg Leu
            100                 105                 110

Cys Gln Glu Asn Gln Trp Leu Arg Asp Glu Leu Ala Gly Thr Gln Gln
            115                 120                 125

Arg Leu Gln Arg Ser Glu Gln Ala Val Ala Gln Leu Glu Glu Glu Lys
            130                 135                 140

Lys His Leu Glu Phe Leu Gly Gln Leu Arg Gln Tyr Asp Glu Asp Gly
145                 150                 155                 160

His Ala Ala Glu Glu Lys Glu Gly Asp Ala Ser Lys Asp Ser Leu Asp
```

```
                  165                 170                 175
Asp Leu Phe Pro Asn Glu Glu Glu Asp Pro Ser Asn Gly Leu Ser
                180                 185                 190

Arg Gly Gln Gly Ala Gln His Ser Gly Tyr Glu Ile Pro Ala Arg Leu
            195                 200                 205

Arg Thr Leu His Asn Leu Val Ile Gln Tyr Ala Ala Gln Gly Arg Tyr
        210                 215                 220

Glu Val Ala Val Pro Leu Cys Lys Gln Ala Leu Glu Asp Leu Glu Arg
225                 230                 235                 240

Thr Ser Gly Arg Gly His Pro Asp Val Ala Thr Met Leu Asn Ile Leu
                245                 250                 255

Ala Leu Val Tyr Arg Asp Gln Asn Lys Tyr Lys Glu Ala Ala Leu Leu
            260                 265                 270

Leu Asn Asp Ala Leu Ser Ile Arg Glu Ser Thr Leu Gly Arg Asp His
        275                 280                 285

Pro Ala Val Ala Ala Thr Leu Asn Asn Leu Ala Val Leu Tyr Gly Lys
    290                 295                 300

Arg Gly Lys Tyr Lys Glu Ala Glu Pro Leu Cys Gln Arg Ala Leu Glu
305                 310                 315                 320

Ile Arg Glu Lys Val Leu Gly Thr Asn His Pro Asp Val Ala Lys Gln
                325                 330                 335

Leu Asn Asn Leu Ala Leu Leu Cys Gln Asn Gln Gly Lys Tyr Glu Ala
            340                 345                 350

Val Glu Arg Tyr Tyr Arg Arg Ala Leu Ala Ile Tyr Glu Gly Gln Leu
        355                 360                 365

Gly Pro Asp Asn Pro Asn Val Ala Arg Thr Lys Asn Asn Leu Ala Ser
    370                 375                 380

Cys Tyr Leu Lys Gln Gly Lys Tyr Ala Glu Ala Glu Thr Leu Tyr Lys
385                 390                 395                 400

Glu Ile Leu Thr Arg Ala His Val Gln Glu Phe Gly Ser Val Asp Asp
                405                 410                 415

Asp His Lys Pro Ile Trp Met His Ala Glu Glu Arg Glu Glu Met Ser
            420                 425                 430

Lys Ile Arg His Arg Glu Gly Ser Thr Pro Tyr Ala Glu Tyr Gly Gly
        435                 440                 445

Trp Tyr Lys Ala Cys Lys Val Ser Ser Pro Thr Val Asn Thr Thr Leu
    450                 455                 460

Arg Asn Leu Gly Ala Leu Tyr Arg Arg Gln Gly Lys Leu Glu Ala Ala
465                 470                 475                 480

Glu Thr Leu Glu Glu Cys Ala Leu Arg Ser Arg Lys Gln Gly Thr Asp
                485                 490                 495

Pro Ile Ser Gln Thr Lys Val Ala Glu Leu Leu Gly Glu Gly Asp Ser
            500                 505                 510

Gly Arg Thr Ser Gln Glu Gly Leu Gly Gly Ser Val Lys Phe Glu Gly
        515                 520                 525

Gly Glu Asp Ala Ser Val Ala Val Glu Trp Ser Gly Asp Gly Ser Gly
    530                 535                 540

Ala Leu Gln Arg Ser Gly Ser Leu Gly Lys Ile Arg Asp Val Leu Arg
545                 550                 555                 560

Arg Ser Ser Glu Leu Leu Val Arg Lys Leu Gln Gly Ser Glu Pro Arg
                565                 570                 575

Pro Ser Ser Ser Asn Met Lys Arg Ala Ala Ser Leu Asn Tyr Leu Asn
            580                 585                 590
```

-continued

Gln Pro Ser Ala Ala Pro Leu Gln Val Ser Arg Gly Leu Ser Ala Ser
            595                 600                 605

Ser Met Asp Leu Ser Ser Ser Ser
    610                 615

<210> SEQ ID NO 312
<211> LENGTH: 619
<212> TYPE: PRT
<213> ORGANISM: Macaca mulatta

<400> SEQUENCE: 312

Met Ser Gly Leu Val Leu Gly Gln Arg Asp Glu Pro Ala Gly His Arg
1               5                   10                  15

Leu Ser Gln Glu Glu Ile Leu Gly Ser Thr Arg Leu Val Ser Gln Gly
            20                  25                  30

Leu Glu Ala Leu His Ser Glu His Gln Ala Val Leu Gln Ser Leu Ser
        35                  40                  45

Gln Thr Ile Glu Cys Leu Gln Gln Gly Gly His Glu Glu Gly Leu Val
    50                  55                  60

His Glu Lys Ala Arg Gln Leu Arg Arg Ser Met Glu Asn Ile Glu Leu
65                  70                  75                  80

Gly Leu Ser Glu Ala Gln Val Met Leu Ala Leu Ala Ser His Leu Ser
                85                  90                  95

Thr Val Glu Ser Glu Lys Gln Lys Leu Arg Ala Gln Val Arg Arg Leu
            100                 105                 110

Cys Gln Glu Asn Gln Trp Leu Arg Asp Glu Leu Ala Gly Thr Gln Gln
        115                 120                 125

Arg Leu Gln Arg Ser Glu Gln Ala Val Ala Gln Leu Glu Glu Glu Lys
    130                 135                 140

Lys His Leu Glu Phe Leu Gly Gln Leu Arg Gln Tyr Asp Glu Asp Gly
145                 150                 155                 160

His Thr Thr Glu Glu Lys Glu Gly Asp Ala Thr Lys Asp Ser Leu Asp
                165                 170                 175

Asp Leu Phe Pro Asn Glu Glu Glu Asp Pro Ser Asn Gly Leu Ser
            180                 185                 190

Arg Gly Gln Gly Thr Ala Ala Gln Gln Gly Gly Tyr Glu Ile Pro
        195                 200                 205

Ala Arg Leu Arg Thr Leu His Asn Leu Val Ile Gln Tyr Ala Ala Gln
    210                 215                 220

Gly Arg Tyr Glu Val Ala Val Pro Leu Cys Lys Gln Ala Leu Glu Asp
225                 230                 235                 240

Leu Glu Arg Thr Ser Gly Arg Gly His Pro Asp Val Ala Thr Met Leu
                245                 250                 255

Asn Ile Leu Ala Leu Val Tyr Arg Asp Gln Asn Lys Tyr Lys Glu Ala
            260                 265                 270

Ala His Leu Leu Asn Asp Ala Leu Ser Ile Arg Glu Ser Thr Leu Gly
        275                 280                 285

Pro Asp His Pro Ala Val Ala Ala Thr Leu Asn Asn Leu Ala Val Leu
    290                 295                 300

Tyr Gly Lys Arg Gly Lys Tyr Lys Glu Ala Glu Pro Leu Cys Gln Arg
305                 310                 315                 320

Ala Leu Glu Ile Arg Glu Lys Val Leu Gly Thr Asn His Pro Asp Val
                325                 330                 335

Ala Lys Gln Leu Asn Asn Leu Ala Leu Leu Cys Gln Asn Gln Gly Lys

```
                    340             345             350
Tyr Glu Ala Val Glu Arg Tyr Tyr Gln Arg Ala Leu Ala Ile Tyr Glu
                355             360             365

Gly Gln Leu Gly Pro Asp Asn Pro Asn Val Ala Arg Thr Lys Asn Asn
        370             375             380

Leu Ala Ser Cys Tyr Leu Lys Gln Gly Lys Tyr Ala Glu Ala Glu Thr
385             390             395             400

Leu Tyr Lys Glu Ile Leu Thr Arg Ala His Val Gln Glu Phe Gly Ser
                405             410             415

Val Asp Asp Asp His Lys Pro Ile Trp Met His Ala Glu Glu Arg Glu
            420             425             430

Glu Met Ser Lys Ser Arg His His Glu Gly Gly Thr Pro Tyr Ala Glu
        435             440             445

Tyr Gly Gly Trp Tyr Lys Ala Cys Lys Val Ser Pro Thr Val Asn
        450             455             460

Thr Thr Leu Arg Asn Leu Gly Ala Leu Tyr Arg Arg Gln Gly Lys Leu
465             470             475             480

Glu Ala Ala Glu Thr Leu Glu Glu Cys Ala Gln Arg Ser Arg Arg Gln
                485             490             495

Gly Thr Asp Pro Ile Ser Gln Thr Lys Val Ala Glu Leu Leu Gly Glu
            500             505             510

Ser Asp Gly Arg Arg Thr Ser Gln Glu Gly Pro Gly Asp Ser Val Lys
        515             520             525

Phe Glu Gly Gly Glu Asp Ala Ser Val Ala Val Glu Trp Ser Gly Asp
        530             535             540

Gly Ser Gly Thr Leu Gln Arg Ser Gly Ser Leu Gly Lys Ile Arg Asp
545             550             555             560

Val Leu Arg Arg Ser Ser Glu Ile Leu Val Arg Lys Leu Gln Gly Thr
                565             570             575

Glu Pro Arg Pro Ser Ser Ser Asn Met Lys Arg Ala Ala Ser Leu Asn
            580             585             590

Tyr Leu Asn Gln Pro Ser Ala Ala Pro Leu Gln Val Ser Arg Gly Leu
        595             600             605

Ser Ala Ser Ser Met Asp Leu Ser Ser Ser Ser
        610             615

<210> SEQ ID NO 313
<211> LENGTH: 314
<212> TYPE: PRT
<213> ORGANISM: Homo sapiens

<400> SEQUENCE: 313

Met Pro Leu Glu Gln Arg Ser Gln His Cys Lys Pro Glu Glu Gly Leu
1               5               10              15

Glu Ala Arg Gly Glu Ala Leu Gly Leu Val Gly Ala Gln Ala Pro Ala
                20              25              30

Thr Glu Glu Gln Glu Ala Ala Ser Ser Ser Thr Leu Val Glu Val
                35              40              45

Thr Leu Gly Glu Val Pro Ala Ala Glu Ser Pro Asp Pro Pro Gln Ser
50              55              60

Pro Gln Gly Ala Ser Ser Leu Pro Thr Thr Met Asn Tyr Pro Leu Trp
65              70              75              80

Ser Gln Ser Tyr Glu Asp Ser Ser Asn Gln Glu Glu Glu Gly Pro Ser
                85              90              95
```

```
Thr Phe Pro Asp Leu Glu Ser Glu Phe Gln Ala Ala Leu Ser Arg Lys
            100                 105                 110

Val Ala Glu Leu Val His Phe Leu Leu Lys Tyr Arg Ala Arg Glu
        115                 120                 125

Pro Val Thr Lys Ala Glu Met Leu Gly Ser Val Val Gly Asn Trp Gln
            130                 135                 140

Tyr Phe Phe Pro Val Ile Phe Ser Lys Ala Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
            195                 200                 205

Ile Ala Arg Glu Gly Asp Cys Ala Pro Glu Glu Lys Ile Trp Glu Glu
            210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
            275                 280                 285

His Met Val Lys Ile Ser Gly Gly Pro His Ile Ser Tyr Pro Pro Leu
            290                 295                 300

His Glu Trp Val Leu Arg Glu Gly Glu Glu
305                 310

<210> SEQ ID NO 314
<211> LENGTH: 320
<212> TYPE: PRT
<213> ORGANISM: Mus musculus

<400> SEQUENCE: 314

Met Ala Asp Ser His Asn Thr Gln Tyr Cys Asn Leu Glu Glu Ser Ala
1               5                   10                  15

Gln Ala Gln Gln Glu Leu Asp Asn Asp Gln Glu Thr Met Glu Thr Ser
            20                  25                  30

Glu Glu Glu Glu Asp Thr Thr Thr Ser Asn Lys Val Tyr Gly Ser Ala
        35                  40                  45

Ile Pro Ser Pro Pro Gln Ser Pro Gln Arg Ala Tyr Ser Pro Cys Val
50                  55                  60

Ala Leu Ala Ser Ile Pro Asp Ser Pro Ser Glu Ala Ser Ile Lys
65                  70                  75                  80

Gly Ser Glu Gly Leu Glu Asp Pro Leu His Leu Leu His Asn Ala Gln
                85                  90                  95

Asn Thr Lys Val Tyr Asp Leu Val Asp Phe Leu Val Leu Asn Tyr Gln
            100                 105                 110

Met Lys Ala Phe Thr Thr Lys Ala Glu Met Leu Glu Asn Ile Gly Arg
            115                 120                 125

Glu Tyr Glu Glu Tyr Tyr Pro Leu Ile Phe Ser Glu Ala Ser Glu Cys
            130                 135                 140

Leu Lys Met Val Phe Gly Leu Asp Met Val Glu Val Asp Ser Ser Val
145                 150                 155                 160
```

```
His Thr Tyr Met Leu Val Thr Ala Leu Gly Ile Thr Tyr Asp Gly Met
                165                 170                 175

Met Thr Asp Val Gln Gly Met Pro Lys Thr Gly Ile Leu Ile Ala Val
            180                 185                 190

Leu Ser Val Ile Phe Met Lys Gly Asn Tyr Val Ser Glu Glu Ile Ile
        195                 200                 205

Trp Glu Met Leu Asn Asn Ile Gly Leu Cys Gly Gly Arg Asp Pro Tyr
    210                 215                 220

Ile His Lys Asp Pro Arg Lys Leu Ile Ser Glu Glu Phe Val Gln Glu
225                 230                 235                 240

Gly Tyr Leu Glu Tyr Arg Gln Val Pro Asn Ser Asp Pro Pro Ser Tyr
                245                 250                 255

Gly Phe Leu Trp Gly Pro Arg Ala Phe Ala Glu Thr Ser Lys Met Lys
            260                 265                 270

Val Leu Gln Phe Phe Ala Ser Ile Asn Lys Thr His Pro Arg Ala Tyr
        275                 280                 285

Pro Glu Lys Tyr Ala Glu Ala Leu Gln Asp Glu Ile Asp Arg Thr Lys
    290                 295                 300

Thr Trp Ile Leu Asn Arg Cys Ser Asn Ser Ser Asp Leu His Thr Phe
305                 310                 315                 320

<210> SEQ ID NO 315
<211> LENGTH: 289
<212> TYPE: PRT
<213> ORGANISM: Homo sapiens

<400> SEQUENCE: 315

Met Ser Gly Phe Ser Thr Glu Glu Arg Ala Ala Pro Phe Ser Leu Glu
1               5                   10                  15

Tyr Arg Val Phe Leu Lys Asn Glu Lys Gly Gln Tyr Ile Ser Pro Phe
            20                  25                  30

His Asp Ile Pro Ile Tyr Ala Asp Lys Asp Val Phe His Met Val Val
        35                  40                  45

Glu Val Pro Arg Trp Ser Asn Ala Lys Met Glu Ile Ala Thr Lys Asp
    50                  55                  60

Pro Leu Asn Pro Ile Lys Gln Asp Val Lys Lys Gly Lys Leu Arg Tyr
65                  70                  75                  80

Val Ala Asn Leu Phe Pro Tyr Lys Gly Tyr Ile Trp Asn Tyr Gly Ala
                85                  90                  95

Ile Pro Gln Thr Trp Glu Asp Pro Gly His Asn Asp Lys His Thr Gly
            100                 105                 110

Cys Cys Gly Asp Asn Asp Pro Ile Asp Val Cys Glu Ile Gly Ser Lys
        115                 120                 125

Val Cys Ala Arg Gly Glu Ile Ile Gly Val Lys Val Leu Gly Ile Leu
    130                 135                 140

Ala Met Ile Asp Glu Gly Glu Thr Asp Trp Lys Val Ile Ala Ile Asn
145                 150                 155                 160

Val Asp Asp Pro Asp Ala Ala Asn Tyr Asn Asp Ile Asn Asp Val Lys
                165                 170                 175

Arg Leu Lys Pro Gly Tyr Leu Glu Ala Thr Val Asp Trp Phe Arg Arg
            180                 185                 190

Tyr Lys Val Pro Asp Gly Lys Pro Glu Asn Glu Phe Ala Phe Asn Ala
        195                 200                 205

Glu Phe Lys Asp Lys Asp Phe Ala Ile Asp Ile Ile Lys Ser Thr His
```

```
                210               215               220
Asp His Trp Lys Ala Leu Val Thr Lys Thr Asn Gly Lys Gly Ile
225                 230                 235                 240

Ser Cys Met Asn Thr Thr Leu Ser Glu Ser Pro Phe Lys Cys Asp Pro
                    245                 250                 255

Asp Ala Ala Arg Ala Ile Val Asp Ala Leu Pro Pro Cys Glu Ser
                260                 265                 270

Ala Cys Thr Val Pro Thr Asp Val Asp Lys Trp Phe His His Gln Lys
            275                 280                 285

Asn

<210> SEQ ID NO 316
<211> LENGTH: 289
<212> TYPE: PRT
<213> ORGANISM: Mus musculus

<400> SEQUENCE: 316

Met Ser Gly Phe Ser Ser Glu Glu Arg Ala Ala Pro Phe Thr Leu Glu
1               5                   10                  15

Tyr Arg Val Phe Leu Lys Asn Glu Lys Gly Gln Tyr Ile Ser Pro Phe
                20                  25                  30

His Asp Val Pro Ile Tyr Ala Asp Lys Asp Val Phe His Met Val Val
            35                  40                  45

Glu Val Pro Arg Trp Ser Asn Ala Lys Met Glu Ile Ala Thr Lys Asp
        50                  55                  60

Pro Leu Asn Pro Ile Lys Gln Asp Val Lys Lys Gly Lys Leu Arg Tyr
65                  70                  75                  80

Val Ala Asn Leu Phe Pro Tyr Lys Gly Tyr Ile Trp Asn Tyr Gly Ala
                85                  90                  95

Ile Pro Gln Thr Trp Glu Asp Pro Gly His Ser Asp Lys His Thr Gly
            100                 105                 110

Cys Cys Gly Asp Asn Asp Pro Ile Asp Val Cys Glu Ile Gly Ser Lys
        115                 120                 125

Val Cys Ala Arg Gly Glu Ile Ile Arg Val Lys Val Leu Gly Ile Leu
    130                 135                 140

Ala Met Ile Asp Glu Gly Glu Thr Asp Trp Lys Val Ile Ala Ile Asn
145                 150                 155                 160

Val Asp Asp Pro Asp Ala Ala Asn Tyr Lys Asp Ile Ser Asp Val Glu
                165                 170                 175

Arg Leu Lys Pro Gly Tyr Leu Glu Ala Thr Val Asp Trp Phe Arg Arg
            180                 185                 190

Tyr Lys Val Pro Asp Gly Lys Pro Glu Asn Glu Phe Ala Phe Asn Ala
        195                 200                 205

Glu Phe Lys Asn Lys Asp Phe Ala Val Asp Ile Ile Lys Ser Thr His
    210                 215                 220

Asp Tyr Trp Lys Ala Leu Val Thr Lys Thr Asp Gly Lys Gly Ile
225                 230                 235                 240

Ser Cys Met Asn Thr Thr Val Ser Glu Ser Pro Phe Lys Cys Asp Pro
                    245                 250                 255

Asp Ala Ala Lys Ala Ile Val Asp Ala Leu Pro Pro Cys Glu Ser
                260                 265                 270

Ala Cys Ser Leu Pro Thr Asp Val Asp Lys Trp Phe His Gln Gln Lys
            275                 280                 285

Asn
```

<210> SEQ ID NO 317
<211> LENGTH: 289
<212> TYPE: PRT
<213> ORGANISM: Rattus norvegicus

<400> SEQUENCE: 317

Met Ser Ser Phe Ser Ser Glu Glu Arg Ala Ala Pro Phe Thr Leu Glu
1               5                   10                  15

Tyr Arg Val Phe Ile Lys Asn Glu Lys Gly Gln Tyr Ile Ser Pro Phe
            20                  25                  30

His Asp Val Pro Ile Tyr Ala Asp Lys Asp Val Phe His Met Val Val
        35                  40                  45

Glu Val Pro Arg Trp Ser Asn Ala Lys Met Glu Ile Ala Thr Lys Asp
    50                  55                  60

Pro Leu Asn Pro Ile Lys Gln Asp Val Lys Lys Gly Lys Leu Arg Tyr
65                  70                  75                  80

Val Ala Asn Leu Phe Pro Tyr Lys Gly Tyr Ile Trp Asn Tyr Gly Ala
                85                  90                  95

Ile Pro Gln Thr Trp Glu Asp Pro Gly His Ser Asp Glu His Thr Gly
            100                 105                 110

Cys Cys Gly Asp Asn Asp Pro Ile Asp Val Cys Glu Ile Gly Ser Lys
        115                 120                 125

Val Cys Ala Arg Gly Glu Ile Ile Arg Val Lys Val Leu Gly Ile Leu
    130                 135                 140

Ala Met Ile Asp Glu Gly Glu Thr Asp Trp Lys Val Ile Ala Ile Asn
145                 150                 155                 160

Val Asp Asp Pro Asp Ala Ala Asn Tyr His Asp Ile Ser Asp Val Glu
                165                 170                 175

Arg Leu Lys Pro Gly Tyr Leu Glu Ala Thr Val Asp Trp Phe Arg Arg
            180                 185                 190

Tyr Lys Val Pro Asp Gly Lys Pro Glu Asn Glu Phe Ala Phe Asn Ala
        195                 200                 205

Glu Phe Lys Asn Lys Glu Phe Ala Val Asp Ile Ile Lys Asn Thr His
    210                 215                 220

Asp Tyr Trp Lys Ala Leu Val Thr Lys Thr Asp Gly Lys Gly Ile
225                 230                 235                 240

Ser Cys Met Asn Thr Thr Val Ser Glu Ser Pro Phe Lys Cys Asp Pro
                245                 250                 255

Asp Ala Ala Lys Ala Ile Val Asp Ala Leu Pro Pro Pro Cys Glu Ser
            260                 265                 270

Ala Cys Ala Leu Pro Met Asp Val Asp Lys Trp Phe His His Gln Lys
        275                 280                 285

Asn

<210> SEQ ID NO 318
<211> LENGTH: 289
<212> TYPE: PRT
<213> ORGANISM: Bos taurus

<400> SEQUENCE: 318

Met Ser Gly Phe Ser Ser Glu Glu Arg Ala Ala Pro Phe Thr Leu Glu
1               5                   10                  15

Tyr Arg Val Phe Leu Lys Asn Glu Lys Gly Gln Tyr Ile Ser Pro Phe
            20                  25                  30

His Asp Ile Pro Ile Tyr Ala Asp Lys Glu Val Phe His Met Val Val
            35                  40                  45

Glu Val Pro Arg Trp Ser Asn Ala Lys Met Glu Ile Ala Thr Lys Asp
 50                  55                  60

Pro Leu Asn Pro Ile Lys Gln Asp Val Lys Lys Gly Lys Leu Arg Tyr
 65                  70                  75                  80

Val Ala Asn Leu Phe Pro Tyr Lys Gly Tyr Ile Trp Asn Tyr Gly Ala
                 85                  90                  95

Ile Pro Gln Thr Trp Glu Asp Pro Gly His Asn Asp Lys His Thr Gly
            100                 105                 110

Cys Cys Gly Asp Asn Asp Pro Ile Asp Val Cys Glu Ile Gly Ser Lys
            115                 120                 125

Val Cys Ala Arg Gly Glu Ile Ile Arg Val Lys Val Leu Gly Ile Leu
130                 135                 140

Ala Met Ile Asp Glu Gly Glu Thr Asp Trp Lys Val Ile Ala Ile Asn
145                 150                 155                 160

Val Glu Asp Pro Asp Ala Ala Asn Tyr Asn Asp Ile Asn Asp Val Lys
                165                 170                 175

Arg Leu Lys Pro Gly Tyr Leu Glu Ala Thr Val Asp Trp Phe Arg Arg
            180                 185                 190

Tyr Lys Val Pro Asp Gly Lys Pro Glu Asn Glu Phe Ala Phe Asn Ala
            195                 200                 205

Glu Phe Lys Asp Lys Asn Phe Ala Ile Asp Ile Glu Ser Thr His
            210                 215                 220

Asp Tyr Trp Arg Ala Leu Val Thr Lys Thr Asp Gly Lys Gly Ile
225                 230                 235                 240

Ser Cys Met Asn Thr Thr Val Ser Glu Ser Pro Phe Gln Cys Asp Pro
                245                 250                 255

Asp Ala Ala Lys Ala Ile Val Asp Ala Leu Pro Pro Cys Glu Ser
            260                 265                 270

Ala Cys Thr Ile Pro Thr Asp Val Asp Lys Trp Phe His His Gln Lys
            275                 280                 285

Asn

<210> SEQ ID NO 319
<211> LENGTH: 546
<212> TYPE: PRT
<213> ORGANISM: Homo sapiens

<400> SEQUENCE: 319

Met Lys Asn Gln Asp Lys Lys Asn Gly Ala Ala Lys Gln Ser Asn Pro
1                   5                  10                  15

Lys Ser Ser Pro Gly Gln Pro Glu Ala Gly Pro Glu Gly Ala Gln Glu
                 20                  25                  30

Arg Pro Ser Gln Ala Ala Pro Ala Val Glu Ala Glu Gly Pro Gly Ser
             35                  40                  45

Ser Gln Ala Pro Arg Lys Pro Glu Gly Ala Gln Ala Arg Thr Ala Gln
 50                  55                  60

Ser Gly Ala Leu Arg Asp Val Ser Glu Glu Leu Ser Arg Gln Leu Glu
 65                  70                  75                  80

Asp Ile Leu Ser Thr Tyr Cys Val Asp Asn Asn Gln Gly Gly Pro Gly
                 85                  90                  95

Glu Asp Gly Ala Gln Gly Glu Pro Ala Glu Pro Glu Ala Glu Lys
            100                 105                 110

```
Ser Arg Thr Tyr Val Ala Arg Asn Gly Glu Pro Glu Pro Thr Pro Val
            115                 120                 125

Val Asn Gly Glu Lys Glu Pro Ser Lys Gly Asp Pro Asn Thr Glu Glu
    130                 135                 140

Ile Arg Gln Ser Asp Glu Val Gly Asp Arg Asp His Arg Arg Pro Gln
145                 150                 155                 160

Glu Lys Lys Lys Ala Lys Gly Leu Gly Lys Glu Ile Thr Leu Leu Met
                165                 170                 175

Gln Thr Leu Asn Thr Leu Ser Thr Pro Glu Glu Lys Leu Ala Ala Leu
            180                 185                 190

Cys Lys Lys Tyr Ala Glu Leu Leu Glu Glu His Arg Asn Ser Gln Lys
        195                 200                 205

Gln Met Lys Leu Leu Gln Lys Lys Gln Ser Gln Leu Val Gln Glu Lys
    210                 215                 220

Asp His Leu Arg Gly Glu His Ser Lys Ala Val Leu Ala Arg Ser Lys
225                 230                 235                 240

Leu Glu Ser Leu Cys Arg Glu Leu Gln Arg His Asn Arg Ser Leu Lys
                245                 250                 255

Glu Glu Gly Val Gln Arg Ala Arg Glu Glu Glu Lys Arg Lys Glu
            260                 265                 270

Val Thr Ser His Phe Gln Val Thr Leu Asn Asp Ile Gln Leu Gln Met
    275                 280                 285

Glu Gln His Asn Glu Arg Asn Ser Lys Leu Arg Gln Glu Asn Met Glu
    290                 295                 300

Leu Ala Glu Arg Leu Lys Lys Leu Ile Glu Gln Tyr Glu Leu Arg Glu
305                 310                 315                 320

Glu His Ile Asp Lys Val Phe Lys His Lys Asp Leu Gln Gln Gln Leu
                325                 330                 335

Val Asp Ala Lys Leu Gln Gln Ala Gln Glu Met Leu Lys Glu Ala Glu
            340                 345                 350

Glu Arg His Gln Arg Glu Lys Asp Phe Leu Leu Lys Glu Ala Val Glu
        355                 360                 365

Ser Gln Arg Met Cys Glu Leu Met Lys Gln Gln Glu Thr His Leu Lys
    370                 375                 380

Gln Gln Leu Ala Leu Tyr Thr Glu Lys Phe Glu Glu Phe Gln Asn Thr
385                 390                 395                 400

Leu Ser Lys Ser Ser Glu Val Phe Thr Thr Phe Lys Gln Glu Met Glu
                405                 410                 415

Lys Met Thr Lys Lys Ile Lys Lys Leu Glu Lys Glu Thr Thr Met Tyr
            420                 425                 430

Arg Ser Arg Trp Glu Ser Ser Asn Lys Ala Leu Leu Glu Met Ala Glu
        435                 440                 445

Glu Lys Thr Val Arg Asp Lys Glu Leu Glu Gly Leu Gln Val Lys Ile
    450                 455                 460

Gln Arg Leu Glu Lys Leu Cys Arg Ala Leu Gln Thr Glu Arg Asn Asp
465                 470                 475                 480

Leu Asn Lys Arg Val Gln Asp Leu Ser Ala Gly Gly Gln Gly Ser Leu
                485                 490                 495

Thr Asp Ser Gly Pro Glu Arg Arg Pro Glu Gly Pro Gly Ala Gln Ala
            500                 505                 510

Pro Ser Ser Pro Arg Val Thr Glu Ala Pro Cys Tyr Pro Gly Ala Pro
        515                 520                 525

Ser Thr Glu Ala Ser Gly Gln Thr Gly Pro Gln Glu Pro Thr Ser Ala
```

Arg Ala
545

<210> SEQ ID NO 320
<211> LENGTH: 554
<212> TYPE: PRT
<213> ORGANISM: Mus musculus

<400> SEQUENCE: 320

Met Lys Asn Gln Asp Lys Lys Asn Gly Pro Ala Lys His Ser Asn Ser
1               5                   10                  15

Lys Gly Ser Pro Gly Gln Arg Glu Ala Gly Pro Glu Gly Ala His Gly
            20                  25                  30

Arg Pro Arg Gln Thr Ala Pro Gly Ala Glu Ala Glu Gly Ser Thr Ser
        35                  40                  45

Gln Ala Pro Gly Lys Thr Glu Gly Ala Arg Ala Lys Ala Ala Gln Pro
    50                  55                  60

Gly Ala Leu Cys Asp Val Ser Glu Glu Leu Ser Arg Gln Leu Glu Asp
65                  70                  75                  80

Ile Leu Ser Thr Tyr Cys Val Asp Asn Gln Gly Gly Pro Ala Glu
                85                  90                  95

Glu Gly Ala Gln Gly Glu Pro Thr Glu Pro Glu Asp Thr Glu Lys Ser
            100                 105                 110

Arg Thr Tyr Ala Ala Arg Asn Gly Glu Pro Glu Pro Gly Ile Pro Val
        115                 120                 125

Val Asn Gly Glu Lys Glu Thr Ser Lys Gly Glu Pro Gly Thr Glu Glu
    130                 135                 140

Ile Arg Ala Ser Asp Glu Val Gly Asp Arg Asp His Arg Arg Pro Gln
145                 150                 155                 160

Glu Lys Lys Lys Ala Lys Gly Leu Gly Lys Glu Ile Thr Leu Leu Met
                165                 170                 175

Gln Thr Leu Asn Thr Leu Ser Thr Pro Glu Glu Lys Leu Ala Ala Leu
            180                 185                 190

Cys Lys Lys Tyr Ala Glu Leu Leu Glu Glu His Arg Asn Ser Gln Lys
        195                 200                 205

Gln Met Lys Leu Leu Gln Lys Lys Gln Ser Gln Leu Val Gln Glu Lys
    210                 215                 220

Asp His Leu Arg Gly Glu His Ser Lys Ala Val Leu Ala Arg Ser Lys
225                 230                 235                 240

Leu Glu Ser Leu Cys Arg Glu Leu Gln Arg His Asn Arg Ser Leu Lys
                245                 250                 255

Glu Glu Gly Val Gln Arg Ala Arg Glu Glu Glu Lys Arg Lys Glu
            260                 265                 270

Val Thr Ser His Phe Gln Val Thr Leu Asn Asp Ile Gln Leu Gln Met
    275                 280                 285

Glu Gln His Asn Glu Arg Asn Ser Lys Leu Arg Gln Glu Asn Met Glu
290                 295                 300

Leu Ala Glu Arg Leu Lys Lys Leu Ile Glu Gln Tyr Glu Leu Arg Glu
305                 310                 315                 320

Glu His Ile Asp Lys Val Phe Lys His Lys Asp Leu Gln Gln Gln Leu
                325                 330                 335

Val Asp Ala Lys Leu Gln Gln Ala Gln Glu Met Leu Lys Glu Ala Glu
            340                 345                 350

```
Glu Arg His Gln Arg Glu Lys Glu Phe Leu Leu Lys Glu Ala Val Glu
            355                 360                 365

Ser Gln Arg Met Cys Glu Leu Met Lys Gln Gln Glu Thr His Leu Lys
370                 375                 380

Gln Gln Leu Ala Leu Tyr Thr Glu Lys Phe Glu Glu Phe Gln Asn Thr
385                 390                 395                 400

Leu Ser Lys Ser Ser Glu Val Phe Thr Thr Phe Lys Gln Glu Met Glu
                405                 410                 415

Lys Met Thr Lys Lys Ile Lys Lys Leu Glu Lys Glu Thr Thr Met Tyr
                420                 425                 430

Arg Ser Arg Trp Glu Ser Ser Asn Lys Ala Leu Leu Glu Met Ala Glu
            435                 440                 445

Glu Lys Thr Val Arg Asp Lys Glu Leu Glu Gly Leu Gln Val Lys Ile
450                 455                 460

Gln Arg Leu Glu Lys Leu Cys Arg Ala Leu Gln Thr Glu Arg Asn Asp
465                 470                 475                 480

Leu Asn Lys Arg Val Gln Asp Leu Thr Ala Gly Ile Thr Asp Ile
                485                 490                 495

Gly Ser Glu Arg Arg Pro Glu Ala Thr Thr Ala Ser Lys Glu Gln Gly
            500                 505                 510

Val Glu Ser Pro Gly Ala Gln Pro Ala Ser Ser Pro Arg Ala Thr Asp
            515                 520                 525

Ala Pro Cys Cys Ser Gly Ala Pro Ser Thr Gly Thr Ala Gly Gln Thr
            530                 535                 540

Gly Pro Gly Glu Pro Thr Pro Ala Thr Ala
545                 550

<210> SEQ ID NO 321
<211> LENGTH: 557
<212> TYPE: PRT
<213> ORGANISM: Rattus norvegicus

<400> SEQUENCE: 321

Met Lys Asn Gln Asp Lys Lys Asn Gly Pro Ala Lys His Ser Asn Pro
1               5                   10                  15

Lys Asn Ser Pro Gly Gln Arg Glu Ala Gly Pro Glu Gly Ala His Gly
                20                  25                  30

Arg Pro Arg Gln Thr Ala Pro Gly Ala Glu Ala Glu Gly Ser Thr Ser
            35                  40                  45

Gln Ala Pro Gly Lys Thr Glu Gly Ala Arg Ala Lys Ala Ser Gln Ser
50                  55                  60

Gly Ala Leu Cys Asp Val Ser Glu Glu Leu Ser Arg Gln Leu Glu Asp
65                  70                  75                  80

Ile Leu Ser Thr Tyr Cys Val Asp Asn Asn Gln Gly Gly Pro Gly Glu
                85                  90                  95

Glu Gly Ala Gln Gly Glu Pro Thr Glu Pro Glu Asp Thr Glu Lys Ser
            100                 105                 110

Arg Thr Tyr Ala Ala Arg Asn Gly Glu Pro Glu Pro Gly Ile Pro Val
            115                 120                 125

Val Asn Gly Glu Lys Glu Thr Ser Lys Gly Pro Gly Thr Glu Glu
            130                 135                 140

Ile Arg Ala Ser Asp Glu Val Gly Asp Arg Asp Leu Arg Arg Pro Gln
145                 150                 155                 160

Glu Lys Lys Lys Ala Lys Gly Leu Gly Lys Glu Ile Thr Leu Leu Met
                165                 170                 175
```

Gln Thr Leu Asn Thr Leu Ser Thr Pro Glu Glu Lys Leu Ala Ala Leu
                180                 185                 190

Cys Lys Lys Tyr Ala Glu Leu Glu Glu His Arg Asn Ala Gln Lys
            195                 200                 205

Gln Thr Lys Leu Leu Gln Arg Lys Gln Ser Gln Leu Val Gln Glu Lys
        210                 215                 220

Asp His Leu Arg Gly Glu His Ser Lys Ala Val Leu Ala Arg Ser Lys
225                 230                 235                 240

Leu Glu Ser Leu Cys Arg Glu Leu Gln Arg His Asn Arg Ser Leu Lys
                245                 250                 255

Glu Glu Gly Val Gln Arg Ala Arg Glu Glu Glu Lys Arg Lys Glu
            260                 265                 270

Val Thr Ser His Phe Gln Val Thr Leu Asn Asp Ile Gln Leu Gln Met
                275                 280                 285

Glu Gln His Asn Glu Arg Asn Ala Lys Leu Arg Leu Glu Asn Val Glu
        290                 295                 300

Leu Ala Glu Arg Leu Lys Lys Leu Ile Glu Gln Tyr Glu Leu Arg Glu
305                 310                 315                 320

Glu His Ile Asp Lys Val Phe Lys His Lys Asp Leu Gln Gln Leu
                325                 330                 335

Val Asp Ala Lys Leu Gln Gln Ala Gln Glu Met Leu Lys Glu Ala Glu
            340                 345                 350

Glu Arg His Gln Arg Glu Lys Glu Phe Leu Leu Lys Glu Ala Val Glu
        355                 360                 365

Ser Gln Arg Met Cys Glu Leu Met Lys Gln Gln Glu Thr His Leu Lys
            370                 375                 380

Gln Gln Leu Ala Leu Tyr Thr Glu Lys Phe Glu Glu Phe Gln Asn Thr
385                 390                 395                 400

Leu Ser Lys Ser Ser Glu Val Phe Thr Thr Phe Lys Gln Glu Met Glu
                405                 410                 415

Lys Met Thr Lys Lys Ile Lys Lys Leu Glu Lys Glu Thr Thr Val Tyr
            420                 425                 430

Arg Ser Arg Trp Glu Ser Ser Asn Lys Ala Leu Leu Glu Met Ala Glu
            435                 440                 445

Glu Lys Thr Leu Arg Asp Lys Glu Leu Glu Gly Leu Gln Val Lys Thr
        450                 455                 460

Gln Arg Leu Glu Lys Leu Cys Arg Ala Leu Gln Thr Glu Arg Asn Asp
465                 470                 475                 480

Leu Asn Lys Arg Val Gln Asp Leu Thr Ala Gly Gln Gly Ser Leu
                485                 490                 495

Thr Asp Thr Gly Ser Glu Arg Arg Pro Glu Ala Ala Thr Ala Ser Lys
            500                 505                 510

Glu Gln Gly Val Glu Ser Pro Gly Ala Gln Pro Ser Ser Pro Lys
        515                 520                 525

Ala Thr Asp Thr Pro Gly Cys Pro Gly Ala Pro Ser Thr Glu Thr Ala
            530                 535                 540

Gly Gln Thr Gly Pro Gly Glu Pro Thr Ser Ala Thr Ala
545                 550                 555

<210> SEQ ID NO 322
<211> LENGTH: 561
<212> TYPE: PRT
<213> ORGANISM: Bos taurus

<400> SEQUENCE: 322

```
Met Lys Asn Gln Asp Lys Lys Asn Gly Pro Ser Lys Gln Ser Gly Asn
1               5                   10                  15

Thr Ser Asn Pro Lys Asn Thr Pro Gly Gln Pro Glu Ala Gly Pro Glu
            20                  25                  30

Gly Ala Gln Gly Arg Pro Ser Gln Ser Ala Pro Ala Thr Glu Ala Glu
        35                  40                  45

Gly Ser Thr Ser Gln Ala Ala Gly Lys Ala Glu Gly Ala Gln Ala Lys
    50                  55                  60

Ser Ala Gln Ser Gly Ala Leu Arg Asp Val Ser Glu Glu Leu Ser Arg
65                  70                  75                  80

Gln Leu Glu Asp Ile Leu Ser Thr Tyr Cys Val Asp Asn Ser Gln Gly
                85                  90                  95

Gly Pro Gly Glu Asp Val Ala Gln Gly Glu Pro Ala Glu Pro Glu Asp
            100                 105                 110

Ala Glu Lys Ser Arg Thr Tyr Ala Ser Arg Asn Gly Glu Pro Glu Pro
        115                 120                 125

Glu Thr Pro Val Val Asn Gly Glu Lys Glu Ile Ser Lys Gly Glu Pro
    130                 135                 140

Gly Pro Asp Glu Ile Arg Thr Ser Asp Glu Val Val Asp Arg Asp His
145                 150                 155                 160

Arg Arg Pro Gln Glu Lys Lys Lys Ala Lys Gly Leu Gly Lys Glu Ile
                165                 170                 175

Thr Leu Leu Met Gln Thr Leu Asn Thr Leu Ser Thr Pro Glu Glu Lys
            180                 185                 190

Leu Ala Ala Leu Cys Lys Lys Tyr Ala Glu Leu Leu Glu Glu His Arg
        195                 200                 205

Asn Ser Gln Lys Gln Met Lys Leu Leu Gln Lys Gln Ser Gln Leu
    210                 215                 220

Val Gln Glu Lys Asp His Leu Arg Gly Glu His Ser Lys Ala Val Leu
225                 230                 235                 240

Ala Arg Ser Lys Leu Glu Ser Leu Cys Arg Glu Leu Gln Arg His Asn
                245                 250                 255

Arg Ser Leu Lys Glu Glu Gly Val Gln Arg Ala Arg Glu Glu Glu
            260                 265                 270

Lys Arg Lys Glu Val Thr Ser His Phe Gln Val Thr Leu Asn Asp Ile
        275                 280                 285

Gln Leu Gln Met Glu Gln His Asn Glu Arg Asn Ser Lys Leu Arg Gln
    290                 295                 300

Glu Asn Val Glu Leu Ala Glu Arg Leu Lys Lys Leu Ile Glu Gln Tyr
305                 310                 315                 320

Glu Leu Arg Glu Glu His Ile Asp Lys Val Phe Lys His Lys Asp Leu
                325                 330                 335

Gln Gln Gln Leu Val Asp Ala Lys Leu Gln Gln Ala Gln Glu Met Leu
            340                 345                 350

Lys Glu Ala Glu Glu Arg His Gln Arg Glu Lys Asp Phe Leu Leu Lys
        355                 360                 365

Glu Ala Val Glu Ser Gln Arg Met Cys Glu Leu Met Lys Gln Gln Glu
    370                 375                 380

Thr His Leu Lys Gln Gln Leu Ala Leu Tyr Thr Glu Lys Phe Glu Glu
385                 390                 395                 400

Phe Gln Asn Thr Leu Ser Lys Ser Ser Glu Val Phe Thr Thr Phe Lys
                405                 410                 415
```

```
Gln Glu Met Glu Lys Met Thr Lys Lys Ile Lys Lys Leu Glu Lys Glu
            420                 425                 430

Thr Thr Met Tyr Arg Ser Arg Trp Glu Ser Ser Asn Lys Ala Leu Leu
        435                 440                 445

Glu Met Ala Glu Lys Thr Leu Arg Asp Lys Glu Leu Glu Gly Leu
    450                 455                 460

Gln Val Lys Ile Gln Arg Leu Glu Lys Leu Cys Arg Ala Leu Gln Ser
465                 470                 475                 480

Glu Arg Asn Asp Leu Asn Lys Arg Val Gln Asp Leu Ser Ala Gly Ser
                485                 490                 495

Gln Ala Pro Leu Thr Asp Ser Gly Pro Glu Arg Arg Ala Glu Ala Ala
                500                 505                 510

Asn Ala Ser Lys Glu Gln Gly Ser Glu Gly Pro Arg Val Gln Thr Pro
                515                 520                 525

Ser Ser Pro Arg Ala Thr Glu Ala Pro Cys Cys Pro Gly Ala Leu Ser
                530                 535                 540

Thr Asp Pro Ser Gly Gln Thr Gly Pro Gln Glu Pro Thr Ser Ile Thr
545                 550                 555                 560

Ala

<210> SEQ ID NO 323
<211> LENGTH: 546
<212> TYPE: PRT
<213> ORGANISM: Macaca mulatta

<400> SEQUENCE: 323

Met Lys Asn Gln Asp Lys Lys Asn Gly Ala Ala Lys Gln Ser Asn Pro
1               5                   10                  15

Lys Ser Ser Pro Gly Gln Pro Glu Ala Gly Pro Glu Gly Ala Gln Glu
                20                  25                  30

Arg Pro Ser Gln Ala Ala Pro Ala Ala Glu Ala Glu Gly Pro Gly Ser
            35                  40                  45

Ser Gln Ala Pro Arg Lys Pro Glu Gly Ala Gln Ala Lys Thr Ala Gln
    50                  55                  60

Ser Gly Ala Leu Arg Asp Val Ser Glu Glu Leu Ser Arg Gln Leu Glu
65                  70                  75                  80

Asp Ile Leu Ser Thr Tyr Cys Val Asp Ser Asn Gln Gly Gly Pro Gly
                85                  90                  95

Glu Asp Gly Ala Gln Gly Glu Pro Ala Glu Pro Glu Asp Ala Glu Lys
                100                 105                 110

Ser Arg Thr Tyr Val Ala Arg Asn Gly Glu Pro Glu Pro Thr Pro Val
            115                 120                 125

Val Asn Gly Glu Lys Glu Pro Ser Lys Gly Asp Pro Gly Thr Glu Glu
    130                 135                 140

Ile Arg Gln Ser Asp Glu Val Gly Asp Arg Asp His Arg Arg Pro Gln
145                 150                 155                 160

Glu Lys Lys Lys Ala Lys Gly Leu Gly Lys Glu Ile Thr Leu Leu Met
                165                 170                 175

Gln Thr Leu Asn Thr Leu Ser Thr Pro Glu Glu Lys Leu Ala Ala Leu
                180                 185                 190

Cys Lys Lys Tyr Ala Glu Leu Leu Glu Glu His Arg Asn Ser Gln Lys
            195                 200                 205

Gln Met Lys Leu Leu Gln Lys Lys Gln Ser Gln Leu Val Gln Glu Lys
    210                 215                 220
```

```
Asp His Leu Arg Gly Glu His Ser Lys Ala Val Leu Ala Arg Ser Lys
225                 230                 235                 240

Leu Glu Ser Leu Cys Arg Glu Leu Gln Arg His Asn Arg Ser Leu Lys
            245                 250                 255

Glu Glu Gly Val Gln Arg Ala Arg Glu Glu Glu Lys Arg Lys Glu
        260                 265                 270

Val Thr Ser His Phe Gln Val Thr Leu Asn Asp Ile Gln Leu Gln Met
        275                 280                 285

Glu Gln His Asn Glu Arg Asn Ser Lys Leu Arg Gln Glu Asn Met Glu
    290                 295                 300

Leu Ala Glu Arg Leu Lys Lys Leu Ile Glu Gln Tyr Glu Leu Arg Glu
305                 310                 315                 320

Glu His Ile Asp Lys Val Phe Lys His Lys Asp Leu Gln Gln Gln Leu
                325                 330                 335

Val Asp Ala Lys Leu Gln Gln Ala Gln Glu Met Leu Lys Glu Ala Glu
                340                 345                 350

Glu Arg His Gln Arg Glu Lys Asp Phe Leu Leu Lys Glu Ala Val Glu
                355                 360                 365

Ser Gln Arg Met Cys Glu Leu Met Lys Gln Gln Glu Thr His Leu Lys
370                 375                 380

Gln Gln Leu Ala Leu Tyr Thr Glu Lys Phe Glu Glu Phe Gln Asn Thr
385                 390                 395                 400

Leu Ser Lys Ser Ser Glu Val Phe Thr Thr Phe Lys Gln Glu Met Glu
                405                 410                 415

Lys Met Thr Lys Lys Ile Lys Lys Leu Glu Lys Glu Thr Thr Met Tyr
                420                 425                 430

Arg Ser Arg Trp Glu Ser Ser Asn Lys Ala Leu Leu Glu Met Ala Glu
                435                 440                 445

Glu Lys Thr Val Arg Asp Lys Glu Leu Glu Gly Leu Gln Val Lys Ile
450                 455                 460

Gln Arg Leu Glu Lys Leu Cys Arg Ala Leu Gln Thr Glu Arg Asn Asp
465                 470                 475                 480

Leu Asn Lys Arg Val Gln Asp Leu Ser Ala Gly Gln Gly Ser Leu
                485                 490                 495

Thr Asp Ser Gly Pro Glu Arg Arg Pro Glu Gly Pro Gly Ala Gln Ala
                500                 505                 510

Pro Ser Ser Pro Arg Val Thr Glu Ala Pro Cys Tyr Pro Gly Ala Pro
                515                 520                 525

Ser Thr Glu Ala Ser Gly Gln Thr Gly Pro Gln Glu Pro Thr Ser Ala
                530                 535                 540

Arg Ala
545

<210> SEQ ID NO 324
<211> LENGTH: 1046
<212> TYPE: PRT
<213> ORGANISM: Homo sapiens

<400> SEQUENCE: 324

Met Ala Ser Ser Val Gly Asn Val Ala Asp Ser Thr Glu Pro Thr Lys
1               5                   10                  15

Arg Met Leu Ser Phe Gln Gly Leu Ala Glu Leu Ala His Arg Glu Tyr
                20                  25                  30

Gln Ala Gly Asp Phe Glu Ala Ala Glu Arg His Cys Met Gln Leu Trp
```

```
            35                  40                  45
Arg Gln Glu Pro Asp Asn Thr Gly Val Leu Leu Leu Ser Ser Ile
        50                  55                  60

His Phe Gln Cys Arg Arg Leu Asp Arg Ser Ala His Phe Ser Thr Leu
 65                  70                  75                  80

Ala Ile Lys Gln Asn Pro Leu Leu Ala Glu Ala Tyr Ser Asn Leu Gly
                85                  90                  95

Asn Val Tyr Lys Glu Arg Gly Gln Leu Gln Glu Ala Ile Glu His Tyr
               100                 105                 110

Arg His Ala Leu Arg Leu Lys Pro Asp Phe Ile Asp Gly Tyr Ile Asn
               115                 120                 125

Leu Ala Ala Ala Leu Val Ala Ala Gly Asp Met Glu Gly Ala Val Gln
        130                 135                 140

Ala Tyr Val Ser Ala Leu Gln Tyr Asn Pro Asp Leu Tyr Cys Val Arg
145                 150                 155                 160

Ser Asp Leu Gly Asn Leu Leu Lys Ala Leu Gly Arg Leu Glu Glu Ala
                165                 170                 175

Lys Ala Cys Tyr Leu Lys Ala Ile Glu Thr Gln Pro Asn Phe Ala Val
                180                 185                 190

Ala Trp Ser Asn Leu Gly Cys Val Phe Asn Ala Gln Gly Glu Ile Trp
        195                 200                 205

Leu Ala Ile His His Phe Glu Lys Ala Val Thr Leu Asp Pro Asn Phe
210                 215                 220

Leu Asp Ala Tyr Ile Asn Leu Gly Asn Val Leu Lys Glu Ala Arg Ile
225                 230                 235                 240

Phe Asp Arg Ala Val Ala Ala Tyr Leu Arg Ala Leu Ser Leu Ser Pro
                245                 250                 255

Asn His Ala Val Val His Gly Asn Leu Ala Cys Val Tyr Tyr Glu Gln
                260                 265                 270

Gly Leu Ile Asp Leu Ala Ile Asp Thr Tyr Arg Arg Ala Ile Glu Leu
        275                 280                 285

Gln Pro His Phe Pro Asp Ala Tyr Cys Asn Leu Ala Asn Ala Leu Lys
290                 295                 300

Glu Lys Gly Ser Val Ala Glu Ala Glu Asp Cys Tyr Asn Thr Ala Leu
305                 310                 315                 320

Arg Leu Cys Pro Thr His Ala Asp Ser Leu Asn Asn Leu Ala Asn Ile
                325                 330                 335

Lys Arg Glu Gln Gly Asn Ile Glu Glu Ala Val Arg Leu Tyr Arg Lys
                340                 345                 350

Ala Leu Glu Val Phe Pro Glu Phe Ala Ala Ala His Ser Asn Leu Ala
        355                 360                 365

Ser Val Leu Gln Gln Gln Gly Lys Leu Gln Glu Ala Leu Met His Tyr
        370                 375                 380

Lys Glu Ala Ile Arg Ile Ser Pro Thr Phe Ala Asp Ala Tyr Ser Asn
385                 390                 395                 400

Met Gly Asn Thr Leu Lys Glu Met Gln Asp Val Gln Gly Ala Leu Gln
                405                 410                 415

Cys Tyr Thr Arg Ala Ile Gln Ile Asn Pro Ala Phe Ala Asp Ala His
                420                 425                 430

Ser Asn Leu Ala Ser Ile His Lys Asp Ser Gly Asn Ile Pro Glu Ala
        435                 440                 445

Ile Ala Ser Tyr Arg Thr Ala Leu Lys Leu Lys Pro Asp Phe Pro Asp
450                 455                 460
```

```
Ala Tyr Cys Asn Leu Ala His Cys Leu Gln Ile Val Cys Asp Trp Thr
465                 470                 475                 480

Asp Tyr Asp Glu Arg Met Lys Lys Leu Val Ser Ile Val Ala Asp Gln
            485                 490                 495

Leu Glu Lys Asn Arg Leu Pro Ser Val His Pro His Ser Met Leu
        500                 505                 510

Tyr Pro Leu Ser His Gly Phe Arg Lys Ala Ile Ala Glu Arg His Gly
            515                 520                 525

Asn Leu Cys Leu Asp Lys Ile Asn Val Leu His Lys Pro Pro Tyr Glu
530                 535                 540

His Pro Lys Asp Leu Lys Leu Ser Asp Gly Arg Leu Arg Val Gly Tyr
545                 550                 555                 560

Val Ser Ser Asp Phe Gly Asn His Pro Thr Ser His Leu Met Gln Ser
                565                 570                 575

Ile Pro Gly Met His Asn Pro Asp Lys Phe Glu Val Phe Cys Tyr Ala
            580                 585                 590

Leu Ser Pro Asp Asp Gly Thr Asn Phe Arg Val Lys Val Met Ala Glu
        595                 600                 605

Ala Asn His Phe Ile Asp Leu Ser Gln Ile Pro Cys Asn Gly Lys Ala
610                 615                 620

Ala Asp Arg Ile His Gln Asp Gly Ile His Ile Leu Val Asn Met Asn
625                 630                 635                 640

Gly Tyr Thr Lys Gly Ala Arg Asn Glu Leu Phe Ala Leu Arg Pro Ala
                645                 650                 655

Pro Ile Gln Ala Met Trp Leu Gly Tyr Pro Gly Thr Ser Gly Ala Leu
            660                 665                 670

Phe Met Asp Tyr Ile Ile Thr Asp Gln Glu Thr Ser Pro Ala Glu Val
        675                 680                 685

Ala Glu Gln Tyr Ser Glu Lys Leu Ala Tyr Met Pro His Thr Phe Phe
690                 695                 700

Ile Gly Asp His Ala Asn Met Phe Pro His Leu Lys Lys Lys Ala Val
705                 710                 715                 720

Ile Asp Phe Lys Ser Asn Gly His Ile Tyr Asp Asn Arg Ile Val Leu
                725                 730                 735

Asn Gly Ile Asp Leu Lys Ala Phe Leu Asp Ser Leu Pro Asp Val Lys
            740                 745                 750

Ile Val Lys Met Lys Cys Pro Asp Gly Gly Asp Asn Ala Asp Ser Ser
        755                 760                 765

Asn Thr Ala Leu Asn Met Pro Val Ile Pro Met Asn Thr Ile Ala Glu
770                 775                 780

Ala Val Ile Glu Met Ile Asn Arg Gly Gln Ile Gln Ile Thr Ile Asn
785                 790                 795                 800

Gly Phe Ser Ile Ser Asn Gly Leu Ala Thr Thr Gln Ile Asn Asn Lys
                805                 810                 815

Ala Ala Thr Gly Glu Glu Val Pro Arg Thr Ile Val Thr Thr Arg
            820                 825                 830

Ser Gln Tyr Gly Leu Pro Glu Asp Ala Ile Val Tyr Cys Asn Phe Asn
        835                 840                 845

Gln Leu Tyr Lys Ile Asp Pro Ser Thr Leu Gln Met Trp Ala Asn Ile
850                 855                 860

Leu Lys Arg Val Pro Asn Ser Val Leu Trp Leu Leu Arg Phe Pro Ala
865                 870                 875                 880
```

```
Val Gly Glu Pro Asn Ile Gln Gln Tyr Ala Gln Asn Met Gly Leu Pro
                885                 890                 895

Gln Asn Arg Ile Ile Phe Ser Pro Val Ala Pro Lys Glu Glu His Val
        900                 905                 910

Arg Arg Gly Gln Leu Ala Asp Val Cys Leu Asp Thr Pro Leu Cys Asn
        915                 920                 925

Gly His Thr Thr Gly Met Asp Val Leu Trp Ala Gly Thr Pro Met Val
        930                 935                 940

Thr Met Pro Gly Glu Thr Leu Ala Ser Arg Val Ala Ala Ser Gln Leu
945                 950                 955                 960

Thr Cys Leu Gly Cys Leu Glu Leu Ile Ala Lys Asn Arg Gln Glu Tyr
                965                 970                 975

Glu Asp Ile Ala Val Lys Leu Gly Thr Asp Leu Glu Tyr Leu Lys Lys
                980                 985                 990

Val Arg Gly Lys Val Trp Lys Gln Arg Ile Ser Ser Pro Leu Phe Asn
                995                1000                1005

Thr Lys Gln Tyr Thr Met Glu Leu Glu Arg Leu Tyr Leu Gln Met
        1010                1015                1020

Trp Glu His Tyr Ala Ala Gly Asn Lys Pro Asp His Met Ile Lys
        1025                1030                1035

Pro Val Glu Val Thr Glu Ser Ala
        1040                1045

<210> SEQ ID NO 325
<211> LENGTH: 1036
<212> TYPE: PRT
<213> ORGANISM: Mus musculus

<400> SEQUENCE: 325

Met Ala Ser Ser Val Gly Asn Val Ala Asp Ser Thr Gly Leu Ala Glu
1               5                   10                  15

Leu Ala His Arg Glu Tyr Gln Ala Gly Asp Phe Glu Ala Ala Glu Arg
                20                  25                  30

His Cys Met Gln Leu Trp Arg Gln Glu Pro Asp Asn Thr Gly Val Leu
        35                  40                  45

Leu Leu Leu Ser Ser Ile His Phe Gln Cys Arg Arg Leu Asp Arg Ser
    50                  55                  60

Ala His Phe Ser Thr Leu Ala Ile Lys Gln Asn Pro Leu Leu Ala Glu
65                  70                  75                  80

Ala Tyr Ser Asn Leu Gly Asn Val Tyr Lys Glu Arg Gly Gln Leu Gln
                85                  90                  95

Glu Ala Ile Glu His Tyr Arg His Ala Leu Arg Leu Lys Pro Asp Phe
                100                 105                 110

Ile Asp Gly Tyr Ile Asn Leu Ala Ala Ala Leu Val Ala Ala Gly Asp
        115                 120                 125

Met Glu Gly Ala Val Gln Ala Tyr Val Ser Ala Leu Gln Tyr Asn Pro
130                 135                 140

Asp Leu Tyr Cys Val Arg Ser Asp Leu Gly Asn Leu Leu Lys Ala Leu
145                 150                 155                 160

Gly Arg Leu Glu Glu Ala Lys Ala Cys Tyr Leu Lys Ala Ile Glu Thr
                165                 170                 175

Gln Pro Asn Phe Ala Val Ala Trp Ser Asn Leu Gly Cys Val Phe Asn
        180                 185                 190

Ala Gln Gly Glu Ile Trp Leu Ala Ile His His Phe Glu Lys Ala Val
        195                 200                 205
```

```
Thr Leu Asp Pro Asn Phe Leu Asp Ala Tyr Ile Asn Leu Gly Asn Val
    210                 215                 220

Leu Lys Glu Ala Arg Ile Phe Asp Arg Ala Val Ala Ala Tyr Leu Arg
225                 230                 235                 240

Ala Leu Ser Leu Ser Pro Asn His Ala Val Val His Gly Asn Leu Ala
                245                 250                 255

Cys Val Tyr Tyr Glu Gln Gly Leu Ile Asp Leu Ala Ile Asp Thr Tyr
                260                 265                 270

Arg Arg Ala Ile Glu Leu Gln Pro His Phe Pro Asp Ala Tyr Cys Asn
            275                 280                 285

Leu Ala Asn Ala Leu Lys Glu Lys Gly Ser Val Ala Glu Ala Glu Asp
            290                 295                 300

Cys Tyr Asn Thr Ala Leu Arg Leu Cys Pro Thr His Ala Asp Ser Leu
305                 310                 315                 320

Asn Asn Leu Ala Asn Ile Lys Arg Glu Gln Gly Asn Ile Glu Glu Ala
                325                 330                 335

Val Arg Leu Tyr Arg Lys Ala Leu Glu Val Phe Pro Glu Phe Ala Ala
                340                 345                 350

Ala His Ser Asn Leu Ala Ser Val Leu Gln Gln Gln Gly Lys Leu Gln
            355                 360                 365

Glu Ala Leu Met His Tyr Lys Glu Ala Ile Arg Ile Ser Pro Thr Phe
            370                 375                 380

Ala Asp Ala Tyr Ser Asn Met Gly Asn Thr Leu Lys Glu Met Gln Asp
385                 390                 395                 400

Val Gln Gly Ala Leu Gln Cys Tyr Thr Arg Ala Ile Gln Ile Asn Pro
                405                 410                 415

Ala Phe Ala Asp Ala His Ser Asn Leu Ala Ser Ile His Lys Asp Ser
                420                 425                 430

Gly Asn Ile Pro Glu Ala Ile Ala Ser Tyr Arg Thr Ala Leu Lys Leu
            435                 440                 445

Lys Pro Asp Phe Pro Asp Ala Tyr Cys Asn Leu Ala His Cys Leu Gln
450                 455                 460

Ile Val Cys Asp Trp Thr Asp Tyr Asp Glu Arg Met Lys Lys Leu Val
465                 470                 475                 480

Ser Ile Val Ala Glu Gln Leu Glu Lys Asn Arg Leu Pro Ser Val His
                485                 490                 495

Pro His His Ser Met Leu Tyr Pro Leu Ser His Gly Phe Arg Lys Ala
                500                 505                 510

Ile Ala Glu Arg His Gly Asn Leu Cys Leu Asp Lys Ile Asn Val Leu
            515                 520                 525

His Lys Pro Pro Tyr Glu His Pro Lys Asp Leu Lys Leu Ser Asp Gly
530                 535                 540

Arg Leu Arg Val Gly Tyr Val Ser Ser Asp Phe Gly Asn His Pro Thr
545                 550                 555                 560

Ser His Leu Met Gln Ser Ile Pro Gly Met His Asn Pro Asp Lys Phe
                565                 570                 575

Glu Val Phe Cys Tyr Ala Leu Ser Pro Asp Asp Gly Thr Asn Phe Arg
                580                 585                 590

Val Lys Val Met Ala Glu Ala Asn His Phe Ile Asp Leu Ser Gln Ile
            595                 600                 605

Pro Cys Asn Gly Lys Ala Ala Asp Arg Ile His Gln Asp Gly Ile His
610                 615                 620
```

-continued

```
Ile Leu Val Asn Met Asn Gly Tyr Thr Lys Gly Ala Arg Asn Glu Leu
625                 630                 635                 640

Phe Ala Leu Arg Pro Ala Pro Ile Gln Ala Met Trp Leu Gly Tyr Pro
            645                 650                 655

Gly Thr Ser Gly Ala Leu Phe Met Asp Tyr Ile Ile Thr Asp Gln Glu
            660                 665                 670

Thr Ser Pro Ala Glu Val Ala Glu Gln Tyr Ser Glu Lys Leu Ala Tyr
        675                 680                 685

Met Pro His Thr Phe Phe Ile Gly Asp His Ala Asn Met Phe Pro His
    690                 695                 700

Leu Lys Lys Lys Ala Val Ile Asp Phe Lys Ser Asn Gly His Ile Tyr
705                 710                 715                 720

Asp Asn Arg Ile Val Leu Asn Gly Ile Asp Leu Lys Ala Phe Leu Asp
                725                 730                 735

Ser Leu Pro Asp Val Lys Ile Val Lys Met Lys Cys Pro Asp Gly Gly
            740                 745                 750

Asp Asn Pro Asp Ser Ser Asn Thr Ala Leu Asn Met Pro Val Ile Pro
        755                 760                 765

Met Asn Thr Ile Ala Glu Ala Val Ile Glu Met Ile Asn Arg Gly Gln
    770                 775                 780

Ile Gln Ile Thr Ile Asn Gly Phe Ser Ile Ser Asn Gly Leu Ala Thr
785                 790                 795                 800

Thr Gln Ile Asn Asn Lys Ala Ala Thr Gly Glu Glu Val Pro Arg Thr
                805                 810                 815

Ile Ile Val Thr Thr Arg Ser Gln Tyr Gly Leu Pro Glu Asp Ala Ile
            820                 825                 830

Val Tyr Cys Asn Phe Asn Gln Leu Tyr Lys Ile Asp Pro Ser Thr Leu
        835                 840                 845

Gln Met Trp Ala Asn Ile Leu Lys Arg Val Pro Asn Ser Val Leu Trp
    850                 855                 860

Leu Leu Arg Phe Pro Ala Val Gly Glu Pro Asn Ile Gln Gln Tyr Ala
865                 870                 875                 880

Gln Asn Met Gly Leu Pro Gln Asn Arg Ile Ile Phe Ser Pro Val Ala
                885                 890                 895

Pro Lys Glu Glu His Val Arg Arg Gly Gln Leu Ala Asp Val Cys Leu
            900                 905                 910

Asp Thr Pro Leu Cys Asn Gly His Thr Thr Gly Met Asp Val Leu Trp
        915                 920                 925

Ala Gly Thr Pro Met Val Thr Met Pro Gly Glu Thr Leu Ala Ser Arg
    930                 935                 940

Val Ala Ala Ser Gln Leu Thr Cys Leu Gly Cys Leu Glu Leu Ile Ala
945                 950                 955                 960

Lys Ser Arg Gln Glu Tyr Glu Asp Ile Ala Val Lys Leu Gly Thr Asp
                965                 970                 975

Leu Glu Tyr Leu Lys Lys Ile Arg Gly Lys Val Trp Lys Gln Arg Ile
            980                 985                 990

Ser Ser Pro Leu Phe Asn Thr Lys  Gln Tyr Thr Met Glu  Leu Glu Arg
        995                  1000                 1005

Leu Tyr  Leu Gln Met Trp Glu  His Tyr Ala Ala Gly  Asn Lys Pro
     1010                 1015                 1020

Asp His  Met Ile Lys Pro Val  Glu Val Thr Glu Ser  Ala
     1025                 1030                 1035
```

<210> SEQ ID NO 326
<211> LENGTH: 1036
<212> TYPE: PRT
<213> ORGANISM: Rattus norvegicus

<400> SEQUENCE: 326

```
Met Ala Ser Ser Val Gly Asn Val Ala Asp Ser Thr Gly Leu Ala Glu
1               5                   10                  15

Leu Ala His Arg Glu Tyr Gln Ala Gly Asp Phe Glu Ala Ala Glu Arg
            20                  25                  30

His Cys Met Gln Leu Trp Arg Gln Glu Pro Asp Asn Thr Gly Val Leu
        35                  40                  45

Leu Leu Leu Ser Ser Ile His Phe Gln Cys Arg Arg Leu Asp Arg Ser
50                  55                  60

Ala His Phe Ser Thr Leu Ala Ile Lys Gln Asn Pro Leu Leu Ala Glu
65                  70                  75                  80

Ala Tyr Ser Asn Leu Gly Asn Val Tyr Lys Glu Arg Gly Gln Leu Gln
                85                  90                  95

Glu Ala Ile Glu His Tyr Arg His Ala Leu Arg Leu Lys Pro Asp Phe
            100                 105                 110

Ile Asp Gly Tyr Ile Asn Leu Ala Ala Ala Leu Val Ala Ala Gly Asp
        115                 120                 125

Met Glu Gly Ala Val Gln Ala Tyr Val Ser Ala Leu Gln Tyr Asn Pro
130                 135                 140

Asp Leu Tyr Cys Val Arg Ser Asp Leu Gly Asn Leu Leu Lys Ala Leu
145                 150                 155                 160

Gly Arg Leu Glu Glu Ala Lys Ala Cys Tyr Leu Lys Ala Ile Glu Thr
                165                 170                 175

Gln Pro Asn Phe Ala Val Ala Trp Ser Asn Leu Gly Cys Val Phe Asn
            180                 185                 190

Ala Gln Gly Glu Ile Trp Leu Ala Ile His His Phe Glu Lys Ala Val
        195                 200                 205

Thr Leu Asp Pro Asn Phe Leu Asp Ala Tyr Ile Asn Leu Gly Asn Val
210                 215                 220

Leu Lys Glu Ala Arg Ile Phe Asp Arg Ala Val Ala Ala Tyr Leu Arg
225                 230                 235                 240

Ala Leu Ser Leu Ser Pro Asn His Ala Val Val His Gly Asn Leu Ala
                245                 250                 255

Cys Val Tyr Tyr Glu Gln Gly Leu Ile Asp Leu Ala Ile Asp Thr Tyr
            260                 265                 270

Arg Arg Ala Ile Glu Leu Gln Pro His Phe Pro Asp Ala Tyr Cys Asn
        275                 280                 285

Leu Ala Asn Ala Leu Lys Glu Lys Gly Ser Val Ala Glu Ala Glu Asp
290                 295                 300

Cys Tyr Asn Thr Ala Leu Arg Leu Cys Pro Thr His Ala Asp Ser Leu
305                 310                 315                 320

Asn Asn Leu Ala Asn Ile Lys Arg Glu Gln Gly Asn Ile Glu Glu Ala
                325                 330                 335

Val Arg Leu Tyr Arg Lys Ala Leu Glu Val Phe Pro Glu Phe Ala Ala
            340                 345                 350

Ala His Ser Asn Leu Ala Ser Val Leu Gln Gln Gln Gly Lys Leu Gln
        355                 360                 365

Glu Ala Leu Met His Tyr Lys Glu Ala Ile Arg Ile Ser Pro Thr Phe
370                 375                 380
```

```
Ala Asp Ala Tyr Ser Asn Met Gly Asn Thr Leu Lys Glu Met Gln Asp
385                 390                 395                 400

Val Gln Gly Ala Leu Gln Cys Tyr Thr Arg Ala Ile Gln Ile Asn Pro
            405                 410                 415

Ala Phe Ala Asp Ala His Ser Asn Leu Ala Ser Ile His Lys Asp Ser
        420                 425                 430

Gly Asn Ile Pro Glu Ala Ile Ala Ser Tyr Arg Thr Ala Leu Lys Leu
    435                 440                 445

Lys Pro Asp Phe Pro Asp Ala Tyr Cys Asn Leu Ala His Cys Leu Gln
450                 455                 460

Ile Val Cys Asp Trp Thr Asp Tyr Asp Glu Arg Met Lys Lys Leu Val
465                 470                 475                 480

Ser Ile Val Ala Glu Gln Leu Glu Lys Asn Arg Leu Pro Ser Val His
            485                 490                 495

Pro His His Ser Met Leu Tyr Pro Leu Ser His Gly Phe Arg Lys Ala
        500                 505                 510

Ile Ala Glu Arg His Gly Asn Leu Cys Leu Asp Lys Ile Asn Val Leu
    515                 520                 525

His Lys Pro Pro Tyr Glu His Pro Lys Asp Leu Lys Leu Ser Asp Gly
530                 535                 540

Arg Leu Arg Val Gly Tyr Val Ser Ser Asp Phe Gly Asn His Pro Thr
545                 550                 555                 560

Ser His Leu Met Gln Ser Ile Pro Gly Met His Asn Pro Asp Lys Phe
            565                 570                 575

Glu Val Phe Cys Tyr Ala Leu Ser Pro Asp Asp Gly Thr Asn Phe Arg
        580                 585                 590

Val Lys Val Met Ala Glu Ala Asn His Phe Ile Asp Leu Ser Gln Ile
    595                 600                 605

Pro Cys Asn Gly Lys Ala Ala Asp Arg Ile His Gln Asp Gly Ile His
610                 615                 620

Ile Leu Val Asn Met Asn Gly Tyr Thr Lys Gly Ala Arg Asn Glu Leu
625                 630                 635                 640

Phe Ala Leu Arg Pro Ala Pro Ile Gln Ala Met Trp Leu Gly Tyr Pro
            645                 650                 655

Gly Thr Ser Gly Ala Leu Phe Met Asp Tyr Ile Ile Thr Asp Gln Glu
        660                 665                 670

Thr Ser Pro Ala Glu Val Ala Glu Gln Tyr Ser Glu Lys Leu Ala Tyr
    675                 680                 685

Met Pro His Thr Phe Phe Ile Gly Asp His Ala Asn Met Phe Pro His
690                 695                 700

Leu Lys Lys Lys Ala Val Ile Asp Phe Lys Ser Asn Gly His Ile Tyr
705                 710                 715                 720

Asp Asn Arg Ile Val Leu Asn Gly Ile Asp Leu Lys Ala Phe Leu Asp
            725                 730                 735

Ser Leu Pro Asp Val Lys Ile Val Lys Met Lys Cys Pro Asp Gly Gly
        740                 745                 750

Asp Asn Ala Asp Thr Thr Asn Thr Ala Leu Asn Met Pro Val Ile Pro
    755                 760                 765

Met Asn Thr Ile Ala Glu Ala Val Ile Glu Met Ile Asn Arg Gly Gln
770                 775                 780

Ile Gln Ile Thr Ile Asn Gly Phe Ser Ile Ser Asn Gly Leu Ala Thr
785                 790                 795                 800

Thr Gln Ile Asn Asn Lys Ala Ala Thr Gly Glu Glu Val Pro Arg Thr
```

```
                    805                 810                 815
Ile Ile Val Thr Thr Arg Ser Gln Tyr Gly Leu Pro Glu Asp Ala Ile
                820                 825                 830

Val Tyr Cys Asn Phe Asn Gln Leu Tyr Lys Ile Asp Pro Ser Thr Leu
                835                 840                 845

Gln Met Trp Ala Asn Ile Leu Lys Arg Val Pro Asn Ser Val Leu Trp
            850                 855                 860

Leu Leu Arg Phe Pro Ala Val Gly Pro Asn Ile Gln Gln Tyr Ala
865                 870                 875                 880

Gln Asn Met Gly Leu Pro Gln Asn Arg Ile Ile Phe Ser Pro Val Ala
                885                 890                 895

Pro Lys Glu Glu His Val Arg Arg Gly Gln Leu Ala Asp Val Cys Leu
                900                 905                 910

Asp Thr Pro Leu Cys Asn Gly His Thr Thr Gly Met Asp Val Leu Trp
                915                 920                 925

Ala Gly Thr Pro Met Val Thr Met Pro Gly Glu Thr Leu Ala Ser Arg
            930                 935                 940

Val Ala Ala Ser Gln Leu Thr Cys Leu Gly Cys Leu Glu Leu Ile Ala
945                 950                 955                 960

Lys Ser Arg Gln Glu Tyr Glu Asp Ile Ala Val Lys Leu Gly Thr Asp
                965                 970                 975

Leu Glu Tyr Leu Lys Lys Ile Arg Gly Lys Val Trp Lys Gln Arg Ile
            980                 985                 990

Ser Ser Pro Leu Phe Asn Thr Lys  Gln Tyr Thr Met Glu  Leu Glu Arg
            995                 1000                1005

Leu Tyr  Leu Gln Met Trp Glu  His Tyr Ala Ala Gly  Asn Lys Pro
    1010                1015                1020

Asp His  Met Ile Lys Pro Val  Glu Val Thr Glu Ser  Ala
    1025                1030                1035

<210> SEQ ID NO 327
<211> LENGTH: 1036
<212> TYPE: PRT
<213> ORGANISM: Bos taurus

<400> SEQUENCE: 327

Met Ala Ser Ser Val Gly Asn Val Ala Asp Ser Thr Gly Leu Ala Glu
1               5                   10                  15

Leu Ala His Arg Glu Tyr Gln Ala Gly Asp Phe Glu Ala Ala Glu Arg
                20                  25                  30

His Cys Met Gln Leu Trp Arg Gln Glu Pro Asp Asn Thr Gly Val Leu
            35                  40                  45

Leu Leu Leu Ser Ser Ile His Phe Gln Cys Arg Arg Leu Asp Arg Ser
        50                  55                  60

Ala His Phe Ser Thr Leu Ala Ile Lys Gln Asn Pro Leu Leu Ala Glu
65              70                  75                  80

Ala Tyr Ser Asn Leu Gly Asn Val Tyr Lys Glu Arg Gly Gln Leu Gln
                85                  90                  95

Glu Ala Ile Glu His Tyr Arg His Ala Leu Arg Leu Lys Pro Asp Phe
            100                 105                 110

Ile Asp Gly Tyr Ile Asn Leu Ala Ala Ala Leu Val Ala Ala Gly Asp
        115                 120                 125

Met Glu Gly Ala Val Gln Ala Tyr Val Ser Ala Leu Gln Tyr Asn Pro
    130                 135                 140
```

-continued

```
Asp Leu Tyr Cys Val Arg Ser Asp Leu Gly Asn Leu Leu Lys Ala Leu
145                 150                 155                 160

Gly Arg Leu Glu Glu Ala Lys Ala Cys Tyr Leu Lys Ala Ile Glu Thr
            165                 170                 175

Gln Pro Asn Phe Ala Val Ala Trp Ser Asn Leu Gly Cys Val Phe Asn
            180                 185                 190

Ala Gln Gly Glu Ile Trp Leu Ala Ile His His Phe Glu Lys Ala Val
        195                 200                 205

Thr Leu Asp Pro Asn Phe Leu Asp Ala Tyr Ile Asn Leu Gly Asn Val
    210                 215                 220

Leu Lys Glu Ala Arg Ile Phe Asp Arg Ala Val Ala Ala Tyr Leu Arg
225                 230                 235                 240

Ala Leu Ser Leu Ser Pro Asn His Ala Val Val His Gly Asn Leu Ala
            245                 250                 255

Cys Val Tyr Tyr Glu Gln Gly Leu Ile Asp Leu Ala Ile Asp Thr Tyr
            260                 265                 270

Arg Arg Ala Ile Glu Leu Gln Pro His Phe Pro Asp Ala Tyr Cys Asn
        275                 280                 285

Leu Ala Asn Ala Leu Lys Glu Lys Gly Ser Val Ala Glu Ala Glu Asp
    290                 295                 300

Cys Tyr Asn Thr Ala Leu Arg Leu Cys Pro Thr His Ala Asp Ser Leu
305                 310                 315                 320

Asn Asn Leu Ala Asn Ile Lys Arg Glu Gln Gly Asn Ile Glu Glu Ala
            325                 330                 335

Val Arg Leu Tyr Arg Lys Ala Leu Glu Val Phe Pro Glu Phe Ala Ala
            340                 345                 350

Ala His Ser Asn Leu Ala Ser Val Leu Gln Gln Gln Gly Lys Leu Gln
        355                 360                 365

Glu Ala Leu Met His Tyr Lys Glu Ala Ile Arg Ile Ser Pro Thr Phe
    370                 375                 380

Ala Asp Ala Tyr Ser Asn Met Gly Asn Thr Leu Lys Glu Met Gln Asp
385                 390                 395                 400

Val Gln Gly Ala Leu Gln Cys Tyr Thr Arg Ala Ile Gln Ile Asn Pro
            405                 410                 415

Ala Phe Ala Asp Ala His Ser Asn Leu Ala Ser Ile His Lys Asp Ser
            420                 425                 430

Gly Asn Ile Pro Glu Ala Ile Ala Ser Tyr Arg Thr Ala Leu Lys Leu
        435                 440                 445

Lys Pro Asp Phe Pro Asp Ala Tyr Cys Asn Leu Ala His Cys Leu Gln
    450                 455                 460

Ile Val Cys Asp Trp Thr Asp Tyr Asp Glu Arg Met Lys Lys Leu Val
465                 470                 475                 480

Ser Ile Val Ala Asp Gln Leu Glu Lys Asn Arg Leu Pro Ser Val His
            485                 490                 495

Pro His His Ser Met Leu Tyr Pro Leu Ser His Gly Phe Arg Lys Ala
            500                 505                 510

Ile Ala Glu Arg His Gly Asn Leu Cys Leu Asp Lys Ile Asn Val Leu
        515                 520                 525

His Lys Pro Pro Tyr Glu His Pro Lys Asp Leu Lys Leu Ser Asp Gly
    530                 535                 540

Arg Leu Arg Val Gly Tyr Val Ser Ser Asp Phe Gly Asn His Pro Thr
545                 550                 555                 560

Ser His Leu Met Gln Ser Ile Pro Gly Met His Asn Pro Asp Lys Phe
```

```
                565                 570                 575
Glu Val Phe Cys Tyr Ala Leu Ser Pro Asp Gly Thr Asn Phe Arg
                580                 585                 590

Val Lys Val Met Ala Glu Ala Asn His Phe Ile Asp Leu Ser Gln Ile
                595                 600                 605

Pro Cys Asn Gly Lys Ala Ala Asp Arg Ile His Gln Asp Gly Ile His
                610                 615                 620

Ile Leu Val Asn Met Asn Gly Tyr Thr Lys Gly Ala Arg Asn Glu Leu
625                 630                 635                 640

Phe Ala Leu Arg Pro Ala Pro Ile Gln Ala Met Trp Leu Gly Tyr Pro
                645                 650                 655

Gly Thr Ser Gly Ala Leu Phe Met Asp Tyr Ile Ile Thr Asp Gln Glu
                660                 665                 670

Thr Ser Pro Ala Glu Val Ala Glu Gln Tyr Ser Glu Lys Leu Ala Tyr
                675                 680                 685

Met Pro His Thr Phe Phe Ile Gly Asp His Ala Asn Met Phe Pro His
                690                 695                 700

Leu Lys Lys Lys Ala Val Ile Asp Phe Lys Ser Asn Gly His Ile Tyr
705                 710                 715                 720

Asp Asn Arg Ile Val Leu Asn Gly Ile Asp Leu Lys Ala Phe Leu Asp
                725                 730                 735

Ser Leu Pro Asp Val Lys Ile Val Lys Met Lys Cys Pro Asp Gly Gly
                740                 745                 750

Asp Asn Val Asp Ser Ser Asn Thr Ala Leu Asn Met Pro Val Ile Pro
                755                 760                 765

Met Asn Thr Ile Ala Glu Ala Val Ile Glu Met Ile Asn Arg Gly Gln
770                 775                 780

Ile Gln Ile Thr Ile Asn Gly Phe Ser Ile Ser Asn Gly Leu Ala Thr
785                 790                 795                 800

Thr Gln Ile Asn Asn Lys Ala Ala Thr Gly Glu Glu Val Pro Arg Thr
                805                 810                 815

Ile Ile Val Thr Thr Arg Ser Gln Tyr Gly Leu Pro Glu Asp Ala Ile
                820                 825                 830

Val Tyr Cys Asn Phe Asn Gln Leu Tyr Lys Ile Asp Pro Ser Thr Leu
                835                 840                 845

Gln Met Trp Ala Asn Ile Leu Lys Arg Val Pro Asn Ser Val Leu Trp
                850                 855                 860

Leu Leu Arg Phe Pro Ala Val Gly Glu Pro Asn Ile Gln Gln Tyr Ala
865                 870                 875                 880

Gln Asn Met Gly Leu Pro Gln Asn Arg Ile Ile Phe Ser Pro Val Ala
                885                 890                 895

Pro Lys Glu Glu His Val Arg Arg Gly Gln Leu Ala Asp Val Cys Leu
                900                 905                 910

Asp Thr Pro Leu Cys Asn Gly His Thr Thr Gly Met Asp Val Leu Trp
                915                 920                 925

Ala Gly Thr Pro Met Val Thr Met Pro Gly Glu Thr Leu Ala Ser Arg
                930                 935                 940

Val Ala Ala Ser Gln Leu Thr Cys Leu Gly Cys Leu Glu Leu Ile Ala
945                 950                 955                 960

Lys Asn Arg Gln Glu Tyr Glu Asp Ile Ala Val Lys Leu Gly Thr Asp
                965                 970                 975

Leu Glu Tyr Leu Lys Lys Ile Arg Gly Lys Val Trp Lys Gln Arg Ile
                980                 985                 990
```

-continued

Ser Ser Pro Leu Phe Asn Thr Lys Gln Tyr Thr Met Glu Leu Glu Arg
                995                1000               1005

Leu Tyr Leu Gln Met Trp Glu His Tyr Ala Ala Gly Asn Lys Pro
    1010                1015               1020

Asp His Met Ile Lys Pro Val Glu Val Thr Glu Ser Ala
    1025                1030               1035

<210> SEQ ID NO 328
<211> LENGTH: 1036
<212> TYPE: PRT
<213> ORGANISM: Macaca mulatta

<400> SEQUENCE: 328

Met Ala Ser Ser Val Gly Asn Val Ala Asp Ser Thr Gly Leu Ala Glu
1               5                   10                  15

Leu Ala His Arg Glu Tyr Gln Ala Gly Asp Phe Glu Ala Ala Glu Arg
            20                  25                  30

His Cys Met Gln Leu Trp Arg Gln Glu Pro Asp Asn Thr Gly Val Leu
        35                  40                  45

Leu Leu Leu Ser Ser Ile His Phe Gln Cys Arg Arg Leu Asp Arg Ser
    50                  55                  60

Ala His Phe Ser Thr Leu Ala Ile Lys Gln Asn Pro Leu Leu Ala Glu
65              70                  75                  80

Ala Tyr Ser Asn Leu Gly Asn Val Tyr Lys Glu Arg Gly Gln Leu Gln
                85                  90                  95

Glu Ala Ile Glu His Tyr Arg His Ala Leu Arg Leu Lys Pro Asp Phe
            100                 105                 110

Ile Asp Gly Tyr Ile Asn Leu Ala Ala Ala Leu Val Ala Ala Gly Asp
        115                 120                 125

Met Glu Gly Ala Val Gln Ala Tyr Val Ser Ala Leu Gln Tyr Asn Pro
    130                 135                 140

Asp Leu Tyr Cys Val Arg Ser Asp Leu Gly Asn Leu Leu Lys Ala Leu
145                 150                 155                 160

Gly Arg Leu Glu Glu Ala Lys Ala Cys Tyr Leu Lys Ala Ile Glu Thr
                165                 170                 175

Gln Pro Asn Phe Ala Val Ala Trp Ser Asn Leu Gly Cys Val Phe Asn
            180                 185                 190

Ala Gln Gly Glu Ile Trp Leu Ala Ile His His Phe Glu Lys Ala Val
        195                 200                 205

Thr Leu Asp Pro Asn Phe Leu Asp Ala Tyr Ile Asn Leu Gly Asn Val
    210                 215                 220

Leu Lys Glu Ala Arg Ile Phe Asp Arg Ala Val Ala Ala Tyr Leu Arg
225                 230                 235                 240

Ala Leu Ser Leu Ser Pro Asn His Ala Val Val His Gly Asn Leu Ala
                245                 250                 255

Cys Val Tyr Tyr Glu Gln Gly Leu Ile Asp Leu Ala Ile Asp Thr Tyr
            260                 265                 270

Arg Arg Ala Ile Glu Leu Gln Pro His Phe Pro Asp Ala Tyr Cys Asn
        275                 280                 285

Leu Ala Asn Ala Leu Lys Glu Lys Gly Ser Val Ala Glu Ala Glu Asp
    290                 295                 300

Cys Tyr Asn Thr Ala Leu Arg Leu Cys Pro Thr His Ala Asp Ser Leu
305                 310                 315                 320

Asn Asn Leu Ala Asn Ile Lys Arg Glu Gln Gly Asn Ile Glu Glu Ala

```
                325                 330                 335
Val Arg Leu Tyr Arg Lys Ala Leu Glu Val Phe Pro Glu Phe Ala Ala
                340                 345                 350

Ala His Ser Asn Leu Ala Ser Val Leu Gln Gln Gly Lys Leu Gln
                355                 360                 365

Glu Ala Leu Met His Tyr Lys Glu Ala Ile Arg Ile Ser Pro Thr Phe
                370                 375                 380

Ala Asp Ala Tyr Ser Asn Met Gly Asn Thr Leu Lys Glu Met Gln Asp
385                 390                 395                 400

Val Gln Gly Ala Leu Gln Cys Tyr Thr Arg Ala Ile Gln Ile Asn Pro
                405                 410                 415

Ala Phe Ala Asp Ala His Ser Asn Leu Ala Ser Ile His Lys Asp Ser
                420                 425                 430

Gly Asn Ile Pro Glu Ala Ile Ala Ser Tyr Arg Thr Ala Leu Lys Leu
                435                 440                 445

Lys Pro Asp Phe Pro Asp Ala Tyr Cys Asn Leu Ala His Cys Leu Gln
                450                 455                 460

Ile Val Cys Asp Trp Thr Asp Tyr Asp Glu Arg Met Lys Lys Leu Val
465                 470                 475                 480

Ser Ile Val Ala Asp Gln Leu Glu Lys Asn Arg Leu Pro Ser Val His
                485                 490                 495

Pro His His Ser Met Leu Tyr Pro Leu Ser His Gly Phe Arg Lys Ala
                500                 505                 510

Ile Ala Glu Arg His Gly Asn Leu Cys Leu Asp Lys Ile Asn Val Leu
                515                 520                 525

His Lys Pro Pro Tyr Glu His Pro Lys Asp Leu Lys Leu Ser Asp Gly
                530                 535                 540

Arg Leu Arg Val Gly Tyr Val Ser Ser Asp Phe Gly Asn His Pro Thr
545                 550                 555                 560

Ser His Leu Met Gln Ser Ile Pro Gly Met His Asn Pro Asp Lys Phe
                565                 570                 575

Glu Val Phe Cys Tyr Ala Leu Ser Pro Asp Asp Gly Thr Asn Phe Arg
                580                 585                 590

Val Lys Val Met Ala Glu Ala Asn His Phe Ile Asp Leu Ser Gln Ile
                595                 600                 605

Pro Cys Asn Gly Lys Ala Ala Asp Arg Ile His Gln Asp Gly Ile His
                610                 615                 620

Ile Leu Val Asn Met Asn Gly Tyr Thr Lys Gly Ala Arg Asn Glu Leu
625                 630                 635                 640

Phe Ala Leu Arg Pro Ala Pro Ile Gln Ala Met Trp Leu Gly Tyr Pro
                645                 650                 655

Gly Thr Ser Gly Ala Leu Phe Met Asp Tyr Ile Ile Thr Asp Gln Glu
                660                 665                 670

Thr Ser Pro Ala Glu Val Ala Glu Gln Tyr Ser Glu Lys Leu Ala Tyr
                675                 680                 685

Met Pro His Thr Phe Phe Ile Gly Asp His Ala Asn Met Phe Pro His
                690                 695                 700

Leu Lys Lys Lys Ala Val Ile Asp Phe Lys Ser Asn Gly His Ile Tyr
705                 710                 715                 720

Asp Asn Arg Ile Val Leu Asn Gly Ile Asp Leu Lys Ala Phe Leu Asp
                725                 730                 735

Ser Leu Pro Asp Val Lys Ile Val Lys Met Lys Cys Pro Asp Gly Gly
                740                 745                 750
```

Asp Asn Ala Asp Ser Ser Asn Thr Ala Leu Asn Met Pro Val Ile Pro
            755                 760                 765

Met Asn Thr Ile Ala Glu Ala Val Ile Glu Met Ile Asn Arg Gly Gln
        770                 775                 780

Ile Gln Ile Thr Ile Asn Gly Phe Ser Ile Ser Asn Gly Leu Ala Thr
785                 790                 795                 800

Thr Gln Ile Asn Asn Lys Ala Ala Thr Gly Glu Glu Val Pro Arg Thr
                805                 810                 815

Ile Ile Val Thr Thr Arg Ser Gln Tyr Gly Leu Pro Glu Asp Ala Ile
            820                 825                 830

Val Tyr Cys Asn Phe Asn Gln Leu Tyr Lys Ile Asp Pro Ser Thr Leu
        835                 840                 845

Gln Met Trp Ala Asn Ile Leu Lys Arg Val Pro Asn Ser Val Leu Trp
    850                 855                 860

Leu Leu Arg Phe Pro Ala Val Gly Glu Pro Asn Ile Gln Gln Tyr Ala
865                 870                 875                 880

Gln Asn Met Gly Leu Pro Gln Asn Arg Ile Ile Phe Ser Pro Val Ala
                885                 890                 895

Pro Lys Glu Glu His Val Arg Arg Gly Gln Leu Ala Asp Val Cys Leu
            900                 905                 910

Asp Thr Pro Leu Cys Asn Gly His Thr Thr Gly Met Asp Val Leu Trp
        915                 920                 925

Ala Gly Thr Pro Met Val Thr Met Pro Gly Glu Thr Leu Ala Ser Arg
    930                 935                 940

Val Ala Ala Ser Gln Leu Thr Cys Leu Gly Cys Leu Glu Leu Ile Ala
945                 950                 955                 960

Lys Asn Arg Gln Glu Tyr Glu Asp Ile Ala Val Lys Leu Gly Thr Asp
                965                 970                 975

Leu Glu Tyr Leu Lys Lys Ile Arg Gly Lys Val Trp Lys Gln Arg Ile
            980                 985                 990

Ser Ser Pro Leu Phe Asn Thr Lys  Gln Tyr Thr Met Glu  Leu Glu Arg
        995                 1000                1005

Leu Tyr  Leu Gln Met Trp Glu  His Tyr Ala Ala Gly  Asn Lys Pro
    1010                1015                1020

Asp His  Met Ile Lys Pro Val  Glu Val Thr Glu Ser  Ala
    1025                1030                1035

<210> SEQ ID NO 329
<211> LENGTH: 289
<212> TYPE: PRT
<213> ORGANISM: Macaca mulatta

<400> SEQUENCE: 329

Met Ser Gly Phe Ser Thr Glu Glu Arg Ala Ala Pro Phe Ser Leu Glu
1               5                   10                  15

Tyr Arg Val Phe Leu Lys Asn Glu Lys Gly Gln Tyr Ile Ser Pro Phe
            20                  25                  30

His Asp Ile Pro Ile Tyr Ala Asp Lys Asp Val Phe His Met Val Val
        35                  40                  45

Glu Val Pro Arg Trp Ser Asn Ala Lys Met Glu Ile Ala Thr Lys Asp
    50                  55                  60

Pro Leu Asn Pro Ile Lys Gln Asp Val Lys Lys Gly Lys Leu Arg Tyr
65                  70                  75                  80

Val Ala Asn Leu Phe Pro Tyr Lys Gly Tyr Ile Trp Asn Tyr Gly Ala

-continued

```
                    85                  90                  95
Ile Pro Gln Thr Trp Glu Asp Pro Gly His Asn Asp Lys His Thr Gly
            100                 105                 110

Cys Cys Gly Asp Asn Asp Pro Ile Asp Val Cys Glu Ile Gly Ser Lys
            115                 120                 125

Val Cys Ala Arg Gly Glu Ile Ile Gly Val Lys Val Leu Gly Ile Leu
        130                 135                 140

Ala Met Ile Asp Glu Gly Glu Thr Asp Trp Lys Val Ile Ala Ile Asn
145                 150                 155                 160

Val Asp Asp Pro Asp Ala Ala Asn Tyr Asn Asp Ile Asn Asp Val Lys
                165                 170                 175

Arg Leu Lys Pro Gly Tyr Leu Glu Ala Thr Val Asp Trp Phe Arg Arg
            180                 185                 190

Tyr Lys Val Pro Asp Gly Lys Pro Glu Asn Glu Phe Ala Phe Asn Ala
        195                 200                 205

Glu Phe Lys Asp Lys Asp Phe Ala Ile Asp Ile Ile Lys Ser Thr His
    210                 215                 220

Asp His Trp Lys Ala Leu Val Thr Lys Thr Asn Gly Lys Gly Ile
225                 230                 235                 240

Ser Cys Met Asn Thr Thr Val Ser Glu Ser Pro Phe Lys Cys Asp Pro
                245                 250                 255

Asp Ala Ala Arg Ala Ile Val Asp Ala Leu Pro Pro Pro Cys Glu Ser
            260                 265                 270

Ala Cys Thr Val Pro Thr Asp Val Asp Lys Trp Phe His His Gln Lys
        275                 280                 285

Asn

<210> SEQ ID NO 330
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-4 "Gly Gly Gly
      Gly Ser" repeating units

<400> SEQUENCE: 330

Gly Gly Gly Gly Ser Gly Gly Gly Ser Gly Gly Gly Gly Ser Gly
1               5                   10                  15

Gly Gly Gly Ser
            20

<210> SEQ ID NO 331
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
tggaccctgt ggacacagcc acatattact gtgcacacag ac                          42

<210> SEQ ID NO 332
<211> LENGTH: 90
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 332
tggaccctgt ggacacagcc acatattttt gtgcacacaa gaaccttcag tattcggaat    60
ggttcgaccc ctggggccag ggcaccctgg                                     90

<210> SEQ ID NO 333
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
acaactggtt cgactcctgg ggccaaggaa ccctggtcac cgtctcctca g              51

<210> SEQ ID NO 334
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Gly Gly Gly Gly Ser Gly Gly Gly Gly Ser Gly Gly Gly Gly Ser
1               5                  10                  15

<210> SEQ ID NO 335
<211> LENGTH: 6
<212> TYPE: PRT
<213> ORGANISM: Homo sapiens

<400> SEQUENCE: 335

Glu Leu Leu Gly Gly Pro
1               5

<210> SEQ ID NO 336
<211> LENGTH: 4
<212> TYPE: PRT
<213> ORGANISM: Homo sapiens

<400> SEQUENCE: 336

Cys Pro Ser Cys
1

<210> SEQ ID NO 337
<211> LENGTH: 4
<212> TYPE: PRT
<213> ORGANISM: Homo sapiens

<400> SEQUENCE: 337

Cys Pro Pro Cys
1

<210> SEQ ID NO 338
<211> LENGTH: 4
<212> TYPE: PRT
<213> ORGANISM: Homo sapiens

<400> SEQUENCE: 338
```

```
Leu Leu Gly Gly
1

<210> SEQ ID NO 339
<211> LENGTH: 9
<212> TYPE: PRT
<213> ORGANISM: Unknown
<220> FEATURE:
<223> OTHER INFORMATION: Description of Unknown:
      integrin binding peptide

<400> SEQUENCE: 339

Cys Tyr Gly Gly Arg Gly Asp Thr Pro
1               5

<210> SEQ ID NO 340
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Gly Gly Gly Gly Ser
1               5

<210> SEQ ID NO 341
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 2-4 "Gly Gly Gly
      Gly Ser" repeating units

<400> SEQUENCE: 341

Gly Gly Gly Gly Ser Gly Gly Gly Gly Ser Gly Gly Gly Gly Ser Gly
1               5                   10                  15

Gly Gly Gly Ser
            20

<210> SEQ ID NO 342
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: This sequence may encompass 1-3 "Gly Gly Gly
      Gly Ser" repeating units

<400> SEQUENCE: 342

Gly Gly Gly Gly Ser Gly Gly Gly Gly Ser Gly Gly Gly Gly Ser
1               5                   10                  15

<210> SEQ ID NO 343
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
        peptide

<400> SEQUENCE: 343

Gly Gly Gly Gly Ser Gly Gly Gly Gly Ser
1               5                   10

<210> SEQ ID NO 344
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
ggtggcggag gttctggagg tggaggttcc                                      30

<210> SEQ ID NO 345
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Gly Gly Gly Gly Ser Gly Gly Gly Gly Ser Gly Gly Gly Gly Ser Gly
1               5                   10                  15

Gly Gly Gly Ser
            20
```

CANCER ASSOCIATED ANTIBODY COMPOSITIONS AND METHODS OF USE

CROSS-REFERENCE

This application is a U.S. National Phase of International Patent Application No. PCT/US2019/051967 filed Sep. 19, 2019, which claims the benefit of U.S. Provisional Application No. 62/733,444 filed Sep. 19, 2018, U.S. Provisional Application No. 62/733,443, filed Sep. 19, 2018, and U.S. Provisional Application No. 62/733,435, filed Sep. 19, 2018; which are incorporated herein by reference in their entirety.

BACKGROUND OF THE INVENTION

While the role of cytotoxic T cells in mediating immune responses against cancer is well established, the role of B cells is less known. In particular, the effect of antibodies identified in cancer patients is still unclear: while some studies suggested that such antibodies might promote tumor progression, others have reported that they might stimulate anti-tumor immunity.

SUMMARY OF THE INVENTION

In one aspect provided herein is an antibody or antigen-binding fragment thereof comprising at least one of: a complementarity-determining region heavy chain 1 (CDR-H1), a CDR-H2 and a CDR-H3, wherein the CDR-H1 comprises a reconstructed polypeptide consensus sequence selected from any one of SEQ ID NOS: 85-98, the CDR-H2 comprises a reconstructed polypeptide consensus sequence selected from any one of SEQ ID NOS: 57-70, and the CDR-H3 comprises a reconstructed polypeptide consensus sequence selected from any one of SEQ ID NOS: 29-42.

In one aspect provided herein is an antibody or antigen-binding fragment thereof that comprising at least one of: a complementarity-determining region light chain 1 (CDR-L1), a CDR-L2 and a CDR-L3, wherein the CDR-L1 comprises a reconstructed polypeptide consensus sequence selected from any one of SEQ ID NOS: 99-112, the CDR-L2 comprises a reconstructed polypeptide consensus sequence selected from any one of SEQ ID NOS: 71-84, and the CDR-L3 comprises a reconstructed polypeptide consensus sequence selected from any one of SEQ ID NOS: 43-56.

In one aspect provided herein is an antibody or antigen-binding fragment thereof comprising: a complementarity-determining region heavy chain 1 (CDR-H1), a CDR-H2 and a CDR-H3, wherein the CDR-H1 comprises a reconstructed polypeptide consensus sequence selected from any one of SEQ ID NOS: 85-98, the CDR-H2 comprises a reconstructed polypeptide consensus sequence selected from any one of SEQ ID NOS: 57-70, and the CDR-H3 comprises a reconstructed polypeptide consensus sequence selected from any one of SEQ ID NOS: 29-42, and a complementarity-determining region light chain 1 (CDR-L1), a CDR-L2 and a CDR-L3, wherein the CDR-L1 comprises a reconstructed polypeptide consensus sequence selected from any one of SEQ ID NOS: 99-112, the CDR-L2 comprises a reconstructed polypeptide consensus sequence selected from any one of SEQ ID NOS: 71-84, and the CDR-L3 comprises a reconstructed polypeptide consensus sequence selected from any one of SEQ ID NOS: 43-56.

In some embodiments, the antibody is an IgG, IgA, or IgM antibody. In some embodiments, the IgG is IgG1, IgG2, IgG3, IgG4, IgGA1, or IgGA2. In some embodiments, the antibody is a chimeric antibody, a humanized antibody, a human antibody, a monoclonal antibody, a deimmunized antibody, a bispecific antibody, a multispecific antibody, or a combination thereof. In some embodiments, the antibody is a monoclonal antibody. In some embodiments, the antibody is a multispecific antibody. In some embodiments, the antibody is a multivalent antibody. In some embodiments, the antigen-binding fragment comprises a Fab, Fab', Fab'-SH, Fv, scFv, F(ab')2, a diabody, a linear antibody, a single domain antibodies (sdAb), a camelid VHH domain, or a multi-specific antibody formed from antibody fragments. In some embodiments, the antibody or antigen-binding fragment thereof is recombinant or synthetic.

In some embodiments, the antibody or antigen-binding fragment thereof further comprises an enzyme, a substrate, cofactor, a fluorescent marker, a chemiluminescent marker, a peptide tag, a magnetic particle, a drug, a toxin, a radionuclide, a binding site for secondary antibodies, a metal binding domain, or a combination thereof. In some embodiments, the antibody or antigen-binding fragment thereof is cytolytic to tumor cells or cancer cells. In some embodiments, the antibody or antigen-binding fragment thereof inhibits tumor growth or cancer cell growth. In some embodiments, the antibody or antigen binding fragment thereof is useful for treating a skin cancer. In some embodiments, the skin cancer is basal cell carcinoma, squamous cell carcinoma, cutaneous melanoma, merkel cell carcinoma, atypical fibroxanthoma, cutaneous lymphoma, or dermatofibrosarcoma. In some embodiments, the cutaneous melanoma is superficial spreading melanoma, nodular melanoma, acral lentiginous melanoma, subungual melanoma, lentigo maligna melanoma, desmoplastic melanoma, mucosal melanoma, or polyploid melanoma.

In one aspect provided herein is an antibody or antigen-binding fragment thereof comprising: (a) a variable heavy chain, wherein the variable heavy chain comprises a reconstructed polypeptide consensus sequence having at least 95% identity to an amino acid sequence selected from any one of SEQ ID NOS: 1-14, (b) a variable light chain, wherein the variable light chain comprises a reconstructed polypeptide consensus sequence having at least 95% sequence identity to an amino acid sequence selected from any one of SEQ ID NOS: 15-28, or (c) the variable heavy chain as in (a) and the variable light chain as in (b).

In one aspect provided herein is a hybridoma that produces the antibody or antigen-binding fragment of any one of aspects above.

In one aspect provided herein is a fusion protein that comprises the antibody or antigen-binding fragment of any one of aspects above.

Provided herein is a chimeric antigen receptor or a T cell receptor fusion protein that comprises: (a) an antigen-binding fragment of any one of aspects disclosed above, (b) a transmembrane domain, and (c) an intracellular signaling domain.

Provided herein is a T cell receptor fusion protein that comprises: (i) the antibody or antigen-binding fragment thereof of any one of aspects disclosed above, and (ii) a T cell receptor (TCR) subunit. In some embodiments, the antibody or antigen binding fragment thereof comprises a human or humanized anti-cancer antigen binding domain. In some embodiments, the TCR subunit comprises; (i) at least a portion of a TCR extracellular domain, (ii) a transmembrane domain, and (iii) a TCR intracellular domain comprising a stimulatory domain from an intracellular signaling domain. In some embodiments, the extracellular, the transmembrane, and the intracellular signaling domains of the TCR subunit are either derived from only CD3 epsilon or only CD3 gamma. In some embodiments, the antibody or antigen-binding fragment thereof and the TCR extracellular domain are connected by a linker sequence. In some embodiments, the linker sequence comprises the sequence of (G4S).n, wherein G is glycine, S is serine, and n=1 to 4.

Provided herein is an isolated nucleic acid molecule encoding the T cell receptor fusion protein of any one of aspects above.

Provided herein is a vector comprising the isolated nucleic acid molecule described above.

Provided herein is a host cell comprising the isolated nucleic acid molecule or the vector described above. In some embodiments, the host cell is a T cell.

In one aspect provided herein is a T cell expressing the T cell receptor fusion protein described above. In some embodiments, the T cell receptor fusion protein is functionally integrated with an endogenous T cell receptor. In some embodiments, the T cell is a CD8+ or CD4+ T-cell.

Provided herein is an immunoconjugate comprising the antibody or the antigen binding fragment thereof of any one of aspects above, and a therapeutic agent.

Provided herein is a pharmaceutical composition or a medicament comprising the antibody or antigen-binding fragment thereof described above and a pharmaceutically acceptable carrier. In some embodiments, the pharmaceutical composition further comprises a second therapeutic agent. In some embodiments, the second therapeutic agent comprises an anti-cancer agent, a cytotoxic agent, a NSAID, a corticosteroid, a dietary supplement such as an antioxidant, or a combination thereof. In some embodiments, the anti-cancer agent is an anti-cancer antibody or a chemotherapeutic agent.

In some embodiments, the pharmaceutical composition is formulated for administration via a subcutaneous, intravenous, intradermal, intraperitoneal, intramuscular, intracerebroventricular, intracranial, intracelial, or intracerebellar administration route. In some embodiments, the pharmaceutical composition in an aqueous or in a lyophilized form. In some embodiments, the pharmaceutical composition is contained in a delivery device selected from the group consisting of a syringe, a blunt tip syringe, a catheter, and an implantable pump.

Provided herein is use of the antibody or antigen binding fragment of any one of aspects above for treating a cancer. In some embodiments the antibody or antigen binding fragment thereof immunoconjugate described above is used in the manufacture of a medicament. In some embodiments, the medicament is for treatment of a cancer.

In one aspect. provided herein is a method for treating a subject suffering from a cancer, the method comprising administering to the subject a therapeutically effective amount of the antibody or antigen-binding fragment thereof of any one of aspects above. In some embodiments, the antibody or antigen-binding fragment thereof is cytolytic to tumor cells. In some embodiments, the antibody or antigen-binding fragment thereof inhibits tumor growth. In some embodiments, the cancer is skin cancer. In some embodiments, the skin cancer is basal cell carcinoma, squamous cell carcinoma, cutaneous melanoma, merkel cell carcinoma, atypical fibroxanthoma, cutaneous lymphoma, or dermatofibrosarcoma. In some embodiments, the cutaneous melanoma is superficial spreading melanoma, nodular melanoma, acral lentiginous melanoma, subungual melanoma, lentigo maligna melanoma, desmoplastic melanoma, mucosal melanoma, or polyploid melanoma.

In some embodiments, the antibody or antigen-binding fragment thereof is administered subcutaneously, intravenously, intradermally, intraperitoneally, orally, intramuscularly or intracranially. In some embodiments, the antibody or antigen-binding fragment thereof is administered to the subject in combination with a second therapeutic agent. In some embodiments, the second therapeutic agent comprises an anti-cancer agent, radiation therapy, a cytotoxic agent, a NSAID, a corticosteroid, a dietary supplement such as an antioxidant, or a combination thereof. In some embodiments, the anti-cancer agent is an anti-cancer antibody or a chemotherapeutic agent. In some embodiments, the second therapeutic agent is administered prior to, concurrently, or after administering the antibody or antigen binding fragment.

Provided herein is an isolated nucleic acid molecule comprising at least one of, (a) a nucleic acid sequence encoding a CDR-H1, wherein the nucleic acid sequence is selected from SEQ ID NOS: 197-210, (b) a nucleic acid sequence encoding a CDR-H2, wherein the nucleic acid sequence is selected from SEQ ID NOS: 169-182, (c) a nucleic acid sequence encoding a CDR-H3, wherein the nucleic acid sequence is selected from SEQ ID NOS: 141-154, (d) a nucleic acid sequence encoding a CDR-L1, wherein the nucleic acid sequence is selected from SEQ ID NOS: 211-224, (e) a nucleic acid sequence encoding a CDR-L2, wherein the nucleic acid sequence is selected from SEQ ID NOS: 183-196, and (f) a nucleic acid sequence encoding a CDR-L3, wherein the nucleic acid sequence is selected from SEQ ID NOS: 155-168.

Provided herein is an isolated nucleic acid molecule comprising a nucleic acid sequence encoding a heavy chain polypeptide of an antibody, wherein the nucleic acid sequence is selected from any one of SEQ ID NOS: 113-126.

Provided herein is an isolated nucleic acid molecule comprising a nucleic acid sequence encoding a light chain polypeptide of an antibody, wherein the nucleic acid sequence is selected from any one of SEQ ID NOS: 127-140.

Provided herein is a vector comprising the isolated nucleic acid molecule described above. In some embodiments the isolated nucleic acid molecule is operably linked to a regulatory control sequence.

Provided herein is a host cell comprising the vector or the isolated nucleic acid molecule described above. In some embodiments, a method of producing an antibody or an antigen binding fragment thereof, the method comprising, (a) culturing the host cell described above in a medium under conditions permitting expression of a polypeptide encoded by the isolated nucleic acid molecule and assembling of the antibody or an antigen binding fragment thereof, and (b) purifying the antibody or antigen binding fragment thereof from the cultured cell or the medium of the cell.

Provided herein a kit comprising (a) a therapeutically effective amount of at least one of the antibody or antigen binding fragment thereof described above. In some embodiments, the kit further comprises a therapeutically effective amount of a second therapeutic agent. In some embodiments, the second therapeutic agent is an anti-cancer agent, radiation therapy, a cytotoxic agent, a NSAID, a corticosteroid, a dietary supplement such as an antioxidant, or a combination thereof. In some embodiments, the anti-cancer agent is an anti-cancer antibody or a chemotherapeutic agent. In some embodiments, the antibody or antigen binding fragment thereof is in a lyophilized or an aqueous form. In some embodiments, further comprises a reconstitution solution or a diluent.

In one aspect provided herein is an antibody or an antigen binding fragment thereof that binds to a Src homology 2

(SH2) domain containing inositol polyphosphate 5-phosphatase 1 (SHIP1) protein or a variant thereof, comprising at least one of (a) a variable heavy chain region, wherein the variable heavy chain region comprises a complementarity-determining region heavy chain 1 (CDR-H1) of SEQ ID NO 85, CDR-H2 of SEQ ID NO: 57, and CDR-H3 of SEQ ID NO: 29, (b) a variable light chain region, wherein the variable light chain region comprises a complementarity-determining region light chain 1 (CDR-L1) of SEQ ID NO 99, CDR-L2 of SEQ ID NO: 71, and CDR-L3 of SEQ ID NO: 43, or (c) the variable heavy chain of (a) and the variable light chain of (b).

In some embodiments, the variable heavy chain comprises a polypeptide sequence having at least 95% sequence identity to the amino acid sequence of SEQ ID NO 1, and the variable light chain comprises a polypeptide consensus sequence having at least 95% sequence identity to the amino acid sequence of SEQ ID NO 15. In some embodiments, the antibody or antigen binding fragment thereof binds a human SHIP1, mouse SHIP1, rat SHIP1, bovine SHIP1, cynomolgus monkey SHIP1. In some embodiments, the human SHIP1 comprises a sequence of SEQ ID NO: 281.

In one aspect provided herein is an antibody that competes with an antibody or antigen binding fragment of described above for binding to SHIP1, wherein the antibody binds to human SHIP1 and mouse SHIP1.

In one aspect provided herein is an antibody or an antigen binding fragment thereof that binds to a Chromobox protein (CBX) or a variant thereof, comprising at least one of (a) a variable heavy chain region, wherein the variable heavy chain region comprises a complementarity-determining region heavy chain 1 (CDR-H1) of SEQ ID NO: 87, CDR-H2 of SEQ ID NO: 59, and CDR-H3 of SEQ ID NO: 31, (b) a variable light chain region, wherein the variable light chain region comprises a complementarity-determining region light chain 1 (CDR-L1) of SEQ ID NO: 101, CDR-L2 of SEQ ID NO: 73, and CDR-L3 of SEQ ID NO: 45; or (c) the variable heavy chain of (a) and the variable light chain of (b). In some embodiments, the variable heavy chain comprises a polypeptide consensus sequence having at least 95% sequence identity to the amino acid sequence of SEQ ID NO: 3, and the variable light chain comprises a polypeptide consensus sequence having at least 95% sequence identity to the amino acid sequence of SEQ ID NO: 17. In some embodiments, the antibody or antigen binding fragment thereof binds a human CBX, mouse CBX, rat CBX, bovine CBX, or cynomolgus monkey CBX.

In some embodiments, the chromobox (CBX) protein is Chromobox protein homolog 1, Chromobox protein homolog 3, or Chromobox protein homolog 5. In some embodiments, the CBX protein is a human CBX 1 comprising a sequence of SEQ ID NO: 286. In some embodiments, the CBX protein is a human CBX 3 comprising a sequence of SEQ ID NO: 291. In some embodiments, the CBX protein is a human CBX 5 comprising a sequence of SEQ ID NO: 296.

Provided herein is an antibody that competes with an antibody or antigen binding fragment of any one of aspects above for binding to CBX protein, wherein the antibody binds to human CBX and mouse CBX.

Provided herein is an antibody or an antigen binding fragment thereof that selectively binds to a Cancer/Testis Antigen 1B (CTAG1A) or a variant thereof, comprising at least one of (a) a variable heavy chain region, wherein the variable heavy chain region comprises a complementarity-determining region heavy chain 1 (CDR-H1) of SEQ ID NO: 89, CDR-H2 of SEQ ID NO: 61, and CDR-H3 of SEQ ID NO: 33, (b) a variable light chain region, wherein the variable light chain region comprises a complementarity-determining region light chain 1 (CDR-L1) of SEQ ID NO: 103, CDR-L2 of SEQ ID NO: 75, and CDR-L3 of SEQ ID NO: 47; or (c) the variable heavy chain of (a) and the variable light chain of (b). In some embodiments, the variable heavy chain comprises a polypeptide consensus sequence having at least 95% sequence identity to the amino acid sequence of SEQ ID NO: 5, and the variable light chain comprises a polypeptide consensus sequence having at least 95% sequence identity to the amino acid sequence of SEQ ID NO: 19. In some embodiments, the antibody or antigen binding fragment thereof binds a human CTAG1A, mouse CTAG1A, rat CTAG1A, bovine CTAG1A, cynomolgus monkey CTAG1A. In some embodiments, the human CTAG1A comprises a sequence of SEQ ID NO: 301.

In one aspect provided herein is an antibody that competes with an antibody or antigen binding fragment described above for binding to CTAG1A, wherein the antibody binds to human CTAG1A and mouse CTAG1A.

In one aspect provided herein is an antibody or an antigen binding fragment thereof that selectively binds to an Alpha and Gamma Adaptin Binding Protein (AAGAB) or a variant thereof, comprising at least one of
(a) a variable heavy chain region, wherein the variable heavy chain region comprises a complementarity-determining region heavy chain 1 (CDR-H1) of SEQ ID NO: 90, CDR-H2 of SEQ ID NO: 62, and CDR-H3 of SEQ ID NO: 34, (b) a variable light chain region, wherein the variable light chain region comprises a complementarity-determining region light chain 1 (CDR-L1) of SEQ ID NO: 104, CDR-L2 of SEQ ID NO: 76, and CDR-L3 of SEQ ID NO: 48; or (c) the variable heavy chain of (a) and the variable light chain of (b). In some embodiments, the variable heavy chain comprises a polypeptide consensus sequence having at least 95% sequence identity to the amino acid sequence of SEQ ID NO: 6, and the variable light chain comprises a polypeptide consensus sequence having at least 95% sequence identity to the amino acid sequence of SEQ ID NO: 20. In some embodiments, the antibody or antigen binding fragment thereof binds a human AAGAB, mouse AAGAB, rat AAGAB, bovine AAGAB, cynomolgus monkey AAGAB. In some embodiments, the human AAGAB comprises a sequence of SEQ ID NO: 303.

Provided herein is an antibody that competes with an antibody or antigen binding fragment described above for binding to AAGAB, wherein the antibody binds to human AAGAB and mouse AAGAB.

In one aspect provided herein is an antibody or an antigen binding fragment thereof that selectively binds to Kinesin light chain 4 protein (KLC4) or a variant thereof, comprising at least one of (a) a variable heavy chain region, wherein the variable heavy chain region comprises a complementarity-determining region heavy chain 1 (CDR-H1) of SEQ ID NO: 91, CDR-H2 of SEQ ID NO: 63, and CDR-H3 of SEQ ID NO: 35, (b) a variable light chain region, wherein the variable light chain region comprises a complementarity-determining region light chain 1 (CDR-L1) of SEQ ID NO: 105, CDR-L2 of SEQ ID NO: 77, and CDR-L3 of SEQ ID NO: 49, or (c) the variable heavy chain of (a) and the variable light chain of (b). In some embodiments, the variable heavy chain comprises a polypeptide consensus sequence having at least 95% sequence identity to the amino acid sequence of SEQ ID NO: 7, and the variable light chain comprises a polypeptide consensus sequence having at least 95% sequence identity to the amino acid sequence of SEQ ID NO: 21. In some embodiments, the antibody or antigen binding fragment thereof binds a human KLC4, mouse KLC4, rat KLC4, bovine KLC4, cynomolgus monkey KLC4. In some embodiments, the human KLC4 comprises a sequence of SEQ ID NO: 308.

Provided herein is an antibody that competes with an antibody or antigen binding fragment described above for binding to KLC4, wherein the antibody binds to human KLC4 and mouse KLC4.

Provided herein is an antibody or an antigen binding fragment thereof that selectively binds to Melanoma-associated antigen 3 (MAGE-A3) or a variant thereof, comprising at least one of (a) a variable heavy chain region, wherein the variable heavy chain region comprises a complementarity-determining region heavy chain 1 (CDR-H1) of SEQ ID NO: 92, CDR-H2 of SEQ ID NO: 64, and CDR-H3 of SEQ ID NO: 36, (b) a variable light chain region, wherein the variable light chain region comprises a complementarity-determining region light chain 1 (CDR-L1) of SEQ ID NO: 106, CDR-L2 of SEQ ID NO: 78, and CDR-L3 of SEQ ID NO: 50; or (c) the variable heavy chain of (a) and the variable light chain of (b). In some embodiments, the variable heavy chain comprises a polypeptide consensus sequence having at least 95% sequence identity to the amino acid sequence of SEQ ID NO: 8, and the variable light chain comprises a polypeptide consensus sequence having at least 95% sequence identity to the amino acid sequence of SEQ ID NO: 22. In some embodiments, the antibody or antigen binding fragment thereof binds a human MAGE-A3, mouse MAGE-A3, rat MAGE-A3, bovine MAGE-A3, cynomolgus monkey MAGE-A3. In some embodiments, the human MAGE-A3 comprises a sequence of SEQ ID NO: 313.

In one aspect provided herein is an antibody that competes with an antibody or antigen binding fragment of any one of aspects above for binding to MAGE-A3, wherein the antibody binds to human MAGE-A3 and mouse MAGE-A3.

Provided herein is an antibody or an antigen binding fragment thereof that selectively binds to Inorganic pyrophosphatase (PPA1) or a variant thereof, comprising at least one of (a) a variable heavy chain region, wherein the variable heavy chain region comprises a complementarity-determining region heavy chain 1 (CDR-H1) of SEQ ID NO: 94, CDR-H2 of SEQ ID NO: 66, and CDR-H3 of SEQ ID NO: 38, (b) a variable light chain region, wherein the variable light chain region comprises a complementarity-determining region light chain 1 (CDR-L1) of SEQ ID NO: 108, CDR-L2 of SEQ ID NO: 80, and CDR-L3 of SEQ ID NO: 52; or (c) the variable heavy chain of (a) and the variable light chain of (b). In some embodiments, the variable heavy chain comprises a polypeptide consensus sequence having at least 95% sequence identity to the amino acid sequence of SEQ ID NO: 10, and the variable light chain comprises a polypeptide consensus sequence having at least 95% sequence identity to the amino acid sequence of SEQ ID NO: 24.

In some embodiments, the antibody or antigen binding fragment thereof binds a human PPA1, mouse PPA1, rat PPA1, bovine PPA1, cynomolgus monkey PPA1. In some embodiments, the human PPA1 comprises a sequence of SEQ ID NO: 315.

Provided herein is an antibody that competes with an antibody or antigen binding fragment of aspects above for binding to PPA1, wherein the antibody binds to human PPA1 and mouse PPA1.

Provided herein is an antibody or an antigen binding fragment thereof that selectively binds to interleukin-14A (IL-14A) or a variant thereof, comprising at least one of (a) a variable heavy chain region, wherein the variable heavy chain region comprises a complementarity-determining region heavy chain 1 (CDR-H1) of SEQ ID NO: 95, CDR-H2 of SEQ ID NO: 67, and CDR-H3 of SEQ ID NO: 39, (b) a variable light chain region, wherein the variable light chain region comprises a complementarity-determining region light chain 1 (CDR-L1) of SEQ ID NO: 109, CDR-L2 of SEQ ID NO: 81, and CDR-L3 of SEQ ID NO: 53, or (c) the variable heavy chain of (a) and the variable light chain of (b). In some embodiments, the variable heavy chain comprises a polypeptide consensus sequence having at least 95% sequence identity to the amino acid sequence of SEQ ID NO: 11, and the variable light chain comprises a polypeptide consensus sequence having at least 95% sequence identity to the amino acid sequence of SEQ ID NO: 25. In some embodiments, the antibody or antigen binding fragment thereof binds a human IL-14A, mouse IL-14A, rat IL-14A, bovine IL-14A, cynomolgus monkey IL-14A. In some embodiments, the human IL-14A comprises a sequence of SEQ ID NO: 319.

Provided herein is an antibody that competes with an antibody or antigen binding fragment of aspects above for binding to IL-14A, wherein the antibody binds to human IL-14A and mouse IL-14A.

Provided herein is an antibody or an antigen binding fragment thereof that selectively binds to O-linked N-acetylglucosamine (GlcNAc) transferase (OGT) or a variant thereof, comprising at least one of (a) a variable heavy chain region, wherein the variable heavy chain region comprises a complementarity-determining region heavy chain 1 (CDR-H1) of SEQ ID NO: 98, CDR-H2 of SEQ ID NO: 70, and CDR-H3 of SEQ ID NO: 42, (b) a variable light chain region, wherein the variable light chain region comprises a complementarity-determining region light chain 1 (CDR-L1) of SEQ ID NO: 112, CDR-L2 of SEQ ID NO: 84, and CDR-L3 of SEQ ID NO: 56, or (c) the variable heavy chain of (a) and the variable light chain of (b). In some embodiments, the variable heavy chain comprises a polypeptide consensus sequence having at least 95% sequence identity to the amino acid sequence of SEQ ID NO: 14, and the variable light chain comprises a polypeptide consensus sequence having at least 95% sequence identity to the amino acid sequence of SEQ ID NO: 28. In some embodiments, the antibody or antigen binding fragment thereof binds a human OGT, mouse OGT, rat OGT, bovine OGT, cynomolgus monkey OGT. In some embodiments, the human OGT comprises a sequence of SEQ ID NO: 324.

Provided herein is an antibody that competes with an antibody or antigen binding fragment of any one of aspects above for binding to OGT, wherein the antibody binds to human OGT and mouse OGT.

In one aspect provided herein is an immunohistochemical assay comprising, (a) contacting a sample with the antibody or antigen binding fragment thereof of any one of aspects above under conditions permitting selective binding of the antibody or antigen binding fragment thereof with an antigen, to form an antibody-antigen complex, (b) detecting the presence or absence of the antibody-antigen complex by an immunodetection method. In some embodiments, the sample is a blood sample or a tissue sample. In some embodiments, the sample is from a subject suspected to be suffering from cancer or diagnosed with cancer.

Provided herein is a method for diagnosing or treating a Src homology 2 (SH2) domain containing inositol polyphosphate 5-phosphatase 1 (SHIP1) related condition in a cell, tissue, organ or subject comprising:

contacting or administering an effective amount of at least one antibody or antigen binding fragment thereof of any one aspects above, with or to, the cell, tissue, organ or subject. In some embodiments, the antibody or antigen binding fragment thereof comprises at least one of (a) a variable heavy chain region, wherein the variable heavy chain region comprises a complementarity-determining region heavy chain 1 (CDR-H1) of SEQ ID NO 85, CDR-H2 of SEQ ID NO: 57, and CDR-H3 of SEQ ID NO: 29, (b) a variable light chain region, wherein the variable light chain region comprises a complementarity-determining region light chain 1 (CDR-L1) of SEQ ID NO 99, CDR-L2 of SEQ ID NO: 71, and CDR-L3 of SEQ ID NO: 43, or (c) the variable heavy chain of (a) and the variable light chain of (b). In some embodiments, the variable heavy chain comprises a polypeptide sequence having at least 95% sequence identity to the amino acid sequence of SEQ ID NO 1, and the variable light chain comprises a polypeptide consensus sequence having at least 95% sequence identity to the amino acid sequence of SEQ ID NO 15.

Provided herein is a method for diagnosing or treating a Chromobox protein (CBX) or a variant thereof related condition in a cell, tissue, organ or subject comprising:

contacting or administering an effective amount of at least one antibody or antigen binding fragment thereof of any one of aspects above, with or to, the cell, tissue, organ or subject. In some embodiments, the antibody or antigen binding fragment thereof comprises at least one of (a) a variable heavy chain region, wherein the variable heavy chain region comprises a complementarity-determining region heavy chain 1 (CDR-H1) of SEQ ID NO: 87, CDR-H2 of SEQ ID NO: 59, and CDR-H3 of SEQ ID NO: 31, (b) a variable light chain region, wherein the variable light chain region comprises a complementarity-determining region light chain 1 (CDR-L1) of SEQ ID NO: 101, CDR-L2 of SEQ ID NO: 73, and CDR-L3 of SEQ ID NO: 45, or (c) the variable heavy chain of (a) and the variable light chain of (b). In some embodiments, the variable heavy chain comprises a polypeptide consensus sequence having at least 95% sequence identity to the amino acid sequence of SEQ ID NO: 3, and the variable light chain comprises a polypeptide consensus sequence having at least 95% sequence identity to the amino acid sequence of SEQ ID NO: 17. In some embodiments, the chromobox protein (CBX) is Chromobox protein homolog 1, Chromobox protein homolog 3, or Chromobox protein homolog 5.

Provided herein is a method for diagnosing or treating a Cancer/Testis Antigen 1B (CTAG1A) thereof related condition in a cell, tissue, organ or subject comprising, contacting or administering an effective amount of at least one antibody or antigen binding fragment thereof of any one of aspects above, with or to, the cell, tissue, organ or subject. In some embodiments, the antibody or antigen binding fragment thereof comprises at least one of at least one of: (a) a variable heavy chain region, wherein the variable heavy chain region comprises a complementarity-determining region heavy chain 1 (CDR-H1) of SEQ ID NO: 89, CDR-H2 of SEQ ID NO: 61, and CDR-H3 of SEQ ID NO: 33, (b) a variable light chain region, wherein the variable light chain region comprises a complementarity-determining region light chain 1 (CDR-L1) of SEQ ID NO: 103, CDR-L2 of SEQ ID NO: 75, and CDR-L3 of SEQ ID NO: 47, or (c) the variable heavy chain of (a) and the variable light chain of (b). In some embodiments, the variable heavy chain comprises a polypeptide consensus sequence having at least 95% sequence identity to the amino acid sequence of SEQ ID NO: 5, and the variable light chain comprises a polypeptide consensus sequence having at least 95% sequence identity to the amino acid sequence of SEQ ID NO: 19.

Provided herein is a method for diagnosing or treating an Alpha and Gamma Adaptin Binding Protein (AAGAB) thereof related condition in a cell, tissue, organ or subject comprising: contacting or administering an effective amount of at least one antibody or antigen binding fragment thereof of any one of aspects above, with or to, the cell, tissue, organ or subject. In some embodiments, the antibody or antigen binding fragment thereof comprises at least one of comprising at least one of (a) a variable heavy chain region, wherein the variable heavy chain region comprises a complementarity-determining region heavy chain 1 (CDR-H1) of SEQ ID NO: 90, CDR-H2 of SEQ ID NO: 62, and CDR-H3 of SEQ ID NO: 34, (b) a variable light chain region, wherein the variable light chain region comprises a complementarity-determining region light chain 1 (CDR-L1) of SEQ ID NO: 104, CDR-L2 of SEQ ID NO: 76, and CDR-L3 of SEQ ID NO: 48, or (c) the variable heavy chain of (a) and the variable light chain of (b). In some embodiments, the variable heavy chain comprises a polypeptide consensus sequence having at least 95% sequence identity to the amino acid sequence of SEQ ID NO: 6, and the variable light chain comprises a polypeptide consensus sequence having at least 95% sequence identity to the amino acid sequence of SEQ ID NO: 20.

Provided herein is a method for diagnosing or treating an Kinesin light chain 4 protein (KLC4) thereof related condition in a cell, tissue, organ or subject comprising: contacting or administering an effective amount of at least one antibody or antigen binding fragment thereof of any one of aspects above, with or to, the cell, tissue, organ or subject. In some embodiments, the antibody or antigen binding fragment thereof comprises at least one of comprising at least one of: (a) a variable heavy chain region, wherein the variable heavy chain region comprises a complementarity-determining region heavy chain 1 (CDR-H1) of SEQ ID NO: 91, CDR-H2 of SEQ ID NO: 63, and CDR-H3 of SEQ ID NO: 35, (b) a variable light chain region, wherein the variable light chain region comprises a complementarity-determining region light chain 1 (CDR-L1) of SEQ ID NO: 105, CDR-L2 of SEQ ID NO: 77, and CDR-L3 of SEQ ID NO: 49, or (c) the variable heavy chain of (a) and the variable light chain of (b). In some embodiments, the variable heavy chain comprises a polypeptide consensus sequence having at least 95% sequence identity to the amino acid sequence of SEQ ID NO: 7, and the variable light chain comprises a polypeptide consensus sequence having at least 95% sequence identity to the amino acid sequence of SEQ ID NO: 21.

Provided herein is a method for diagnosing or treating Melanoma-associated antigen 3 (MAGE-A3) thereof related condition in a cell, tissue, organ or subject comprising: contacting or administering an effective amount of at least one antibody or antigen binding fragment thereof of any one of aspects above, with or to, the cell, tissue, organ or subject. In some embodiments, the antibody or antigen binding fragment thereof comprises at least one of comprising at least one of: (a) a variable heavy chain region, wherein the variable heavy chain region comprises a complementarity-determining region heavy chain 1 (CDR-H1) of SEQ ID NO: 92, CDR-H2 of SEQ ID NO: 64, and CDR-H3 of SEQ ID NO: 36, (b) a variable light chain region, wherein the variable light chain region comprises a complementarity-determining region light chain 1 (CDR-L1) of SEQ ID NO: 106, CDR-L2 of SEQ ID NO: 78, and CDR-L3 of SEQ ID NO: 50, or (c) the variable heavy chain of (a) and the variable light chain of (b). In some embodiments, the variable heavy chain comprises a polypeptide consensus sequence having at least 95% sequence identity to the amino acid sequence of SEQ ID NO: 8, and the variable light chain comprises a polypeptide consensus sequence having at least 95% sequence identity to the amino acid sequence of SEQ ID NO: 22.

Provided herein is a method for diagnosing or treating Inorganic pyrophosphatase (PPA1) thereof related condition in a cell, tissue, organ or subject comprising: contacting or administering an effective amount of at least one antibody or antigen binding fragment thereof of any one of aspects above, with or to, the cell, tissue, organ or subject. In some embodiments, the antibody or antigen binding fragment thereof comprises at least one of comprising at least one of, (a) a variable heavy chain region, wherein the variable heavy chain region comprises a complementarity-determining region heavy chain 1 (CDR-H1) of SEQ ID NO: 94, CDR-H2 of SEQ ID NO: 66, and CDR-H3 of SEQ ID NO: 38, (b) a variable light chain region, wherein the variable light chain region comprises a complementarity-determining region light chain 1 (CDR-L1) of SEQ ID NO: 108, CDR-L2 of SEQ ID NO: 80, and CDR-L3 of SEQ ID NO: 52, or (c) the variable heavy chain of (a) and the variable light chain of (b). In some embodiments, the variable heavy chain comprises a polypeptide consensus sequence having at least 95% sequence identity to the amino acid sequence of SEQ ID NO: 10, and the variable light chain comprises a polypeptide consensus sequence having at least 95% sequence identity to the amino acid sequence of SEQ ID NO: 24.

Provided herein is a method for diagnosing or treating interleukin-14A (IL-14A) thereof related condition in a cell, tissue, organ or subject comprising: contacting or administering an effective amount of at least one antibody or antigen binding fragment thereof of any one of aspects above, with or to, the cell, tissue, organ or subject. In some embodiments, the antibody or antigen binding fragment thereof comprises at least one of comprising at least one of, (a) a variable heavy chain region, wherein the variable heavy chain region comprises a complementarity-determining region heavy chain 1 (CDR-H1) of SEQ ID NO: 95, CDR-H2 of SEQ ID NO: 67, and CDR-H3 of SEQ ID NO: 39, (b) a variable light chain region, wherein the variable light chain region comprises a complementarity-determining region light chain 1 (CDR-L1) of SEQ ID NO: 109, CDR-L2 of SEQ ID NO: 81, and CDR-L3 of SEQ ID NO: 53, or (c) the variable heavy chain of (a) and the variable light chain of (b). In some embodiments, the variable heavy chain comprises a polypeptide consensus sequence having at least 95% sequence identity to the amino acid sequence of SEQ ID NO: 11, and the variable light chain comprises a polypeptide consensus sequence having at least 95% sequence identity to the amino acid sequence of SEQ ID NO: 25.

Provided herein is a method for diagnosing or treating O-linked N-acetylglucosamine (GlcNAc) transferase (OGT) thereof related condition in a cell, tissue, organ or subject comprising: contacting or administering an effective amount of at least one antibody or antigen binding fragment thereof of any one of aspects above, with or to, the cell, tissue, organ or subject. In some embodiments, the antibody or antigen binding fragment thereof comprises at least one of comprising at least one of: (a) a variable heavy chain region, wherein the variable heavy chain region comprises a complementarity-determining region heavy chain 1 (CDR-H1) of SEQ ID NO: 98, CDR-H2 of SEQ ID NO: 70, and CDR-H3 of SEQ ID NO: 42, (b) a variable light chain region, wherein the variable light chain region comprises a complementarity-determining region light chain 1 (CDR-L1) of SEQ ID NO: 112, CDR-L2 of SEQ ID NO: 84, and CDR-L3 of SEQ ID NO: 56, or (c) the variable heavy chain of (a) and the variable light chain of (b). In some embodiments, the variable heavy chain comprises a polypeptide consensus sequence having at least 95% sequence identity to the amino acid sequence of SEQ ID NO: 14, and the variable light chain comprises a polypeptide consensus sequence having at least 95% sequence identity to the amino acid sequence of SEQ ID NO: 28.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A-3J shows alignment visualization of 5 patients and immunoglobulin sequences. Individual reads obtained from RNA-seq are shown for the 5 selected patients. The aligned germline VDJ segments are shown at the bottom of each track. IGV colors paired-end alignments that deviate from expectations (horizontal colored lines) and the mismatched bases are displayed as vertical lines in darker shades of gray.

FIG. 7 shows assembly visualization of a heavy D segment.

FIG. 10 shows exemplary antibodies identified using the methods described herein show strong evidence of somatic hypermutation.

FIG. 15A shows experimental replicate 1 and FIG. 15B shows experimental replicate 2.

FIG. 16A shows experimental replicate 1 and FIG. 16B shows experimental replicate 2.

FIG. 17A shows experimental replicate 1 and FIG. 17B shows experimental replicate 2.

FIG. 18A shows experimental replicate 1 and FIG. 18B shows experimental replicate 2.

FIG. 19A shows experimental replicate 1 and FIG. 19B shows experimental replicate 2.

FIG. 20A shows experimental replicate 1 and FIG. 20B shows experimental replicate 2.

FIG. 21A shows experimental replicate 1 and FIG. 21B shows experimental replicate 2.

FIG. 22A shows experimental replicate 1 and FIG. 22B shows experimental replicate 2.

FIG. 23A shows experimental replicate 1 and FIG. 23B shows experimental replicate 2.

FIG. 24A shows experimental replicate 1, FIG. 24E shows experimental replicate 5.

DETAILED DESCRIPTION OF THE INVENTION

Figure 1:
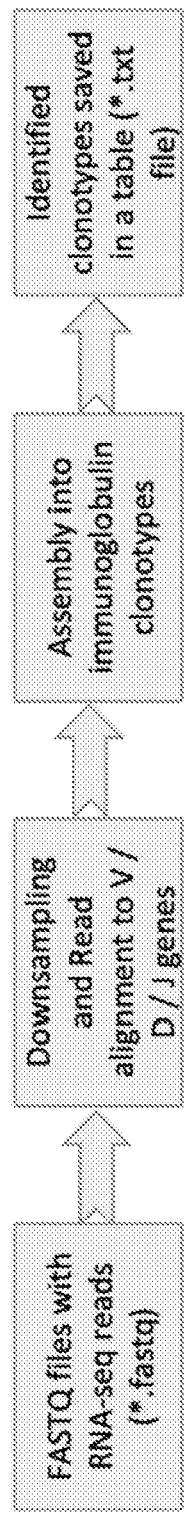
FIG. 1 shows an exemplary scheme of computational pipeline used for identifying immunoglobulin clonotypes.

It is to be understood that this application is not limited to particular formulations or process parameters, as these may, of course, vary. It is also to be understood that the terminology used herein is for the purpose of describing particular embodiments only, and is not intended to be limiting. Further, it is understood that a number of methods and materials similar or equivalent to those described herein can be used in the practice of the present inventions.

In accordance with the present application, there may be employed conventional molecular biology, microbiology, and recombinant DNA techniques as explained fully in the art.

The following definitions supplement those in the art and are directed to the current application and are not to be imputed to any related or unrelated case, e.g., to any commonly owned patent or application. Accordingly, the terminology used herein is for the purpose of describing particular embodiments only, and is not intended to be limiting.

In this application, the use of the singular includes the plural unless specifically stated otherwise. It must be noted that, as used in the specification, the singular forms "a," "an" and "the" include plural referents unless the context clearly dictates otherwise. Furthermore, use of the term "including" as well as other forms, such as "include", "includes," and "included," is not limiting.

The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C."

The term "or" can be used conjunctively or disjunctively, unless the context specifically refers to a disjunctive use.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the invention, and vice versa. Furthermore, compositions of the invention can be used to achieve methods of the invention.

As used herein the term "consisting essentially of" refers to those elements required for a given embodiment. The term permits the presence of elements that do not materially affect the basic and novel or functional characteristic(s) of that embodiment of the invention.

As used herein the term "consisting of" refers to compositions, methods, and respective components thereof as described herein, which are exclusive of any element not recited in that description of the embodiment.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the inventions.

The terms "disease", "disorder", or "condition" are used interchangeably herein, refer to any alternation in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, or affectation.

The term "in need thereof" when used in the context of a therapeutic or prophylactic treatment, means having a disease, being diagnosed with a disease, or being in need of preventing a disease, e.g., for one at risk of developing the disease. Thus, a subject in need thereof can be a subject in need of treating or preventing a disease.

As used herein, the term "administering," refers to the placement of a compound (e.g., an antibody or antigen binding fragment thereof as disclosed herein) into a subject by a method or route that results in at least partial delivery of the agent at a desired site. Pharmaceutical compositions comprising an antibody or antigen binding fragment thereof, disclosed herein can be administered by any appropriate route which results in an effective treatment in the subject, including but not limited to intravenous, intraarterial, injection or infusion directly into a tissue parenchyma, etc. Where necessary or desired, administration can include, for example, intracerebroventricular ("icv") administration, intranasal administration, intracranial administration, intracelial administration, intracerebellar administration, or intrathecal administration.

The term "cancer" refers to a disease characterized by the rapid and uncontrolled growth of aberrant cells. Cancer cells can spread locally or through the bloodstream and lymphatic system to other parts of the body.

The term "anti-tumor effect" refers to a biological effect which can be manifested by various means, including but not limited to, e.g., a decrease in tumor volume, a decrease in the number of tumor cells, a decrease in the number of metastases, an increase in life expectancy, decrease in tumor cell proliferation, decrease in tumor cell survival, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, a "subject", "patient", "individual" and like terms are used interchangeably and refers to a vertebrate, a mammal, a primate, or a human. Mammals include, without limitation, humans, primates, rodents, wild or domesticated animals, including feral animals, farm animals, sport animals, and pets. Primates include, for example, chimpanzees, cynomolgous monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, and canine species, e.g., dog, fox, wolf, avian species, e.g., chicken, emu, ostrich, and fish, e.g., trout, catfish and salmon. The terms, "individual," "patient" and "subject" are used interchangeably herein. A subject can be male or female.

In some embodiments, the subject is a mammal. The mammal can be a human, non-human primate, mouse, rat, dog, cat, horse, or cow, but is not limited to these examples. Mammals other than humans can be advantageously used as subjects that represent animal models of conditions or disorders associated with uncontrolled cell growth (e.g., a cancer). Non-limiting examples include murine tumor models. In addition, the compositions and methods described herein can be used to treat domesticated animals and/or pets. A subject can be one who has been previously diagnosed with or identified as suffering from a cancer. A subject can be one who is diagnosed and currently being treated for, or seeking treatment, monitoring, adjustment or modification of an existing therapeutic treatment, or is at a risk of developing a given disorder (e.g., cancer).

A "cytotoxic agent" refers to an agent that has a cytotoxic and/or cytostatic effect on a cell. A "cytotoxic effect" refers to the depletion, elimination and/or the killing of a target cell(s). A "cytostatic effect" refers to the inhibition of cell proliferation.

As used herein, the terms "protein", "peptide" and "polypeptide" are used interchangeably to designate a series of amino acid residues connected to each other by peptide bonds between the alpha-amino and carboxy groups of adjacent residues. The terms "protein", "peptide" and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein", "peptide" and "polypeptide" are used interchangeably herein when referring to a gene product and fragments thereof. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric. A polypeptide can have the amino acid sequence of naturally occurring polypeptide from any mammal. Such native sequence polypeptide can be isolated from nature or can be produced by recombinant or synthetic means. In some embodiments, the polypeptide is a "variant". "Variant" means a biologically active polypeptide having at least about 80% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about 80% amino acid sequence identity. In some embodiments, a variant will have at least about 90% amino acid sequence identity. In some embodiments, a variant will have at least about 95% amino acid sequence identity with the native sequence polypeptide. A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation The terms "increased", "increase", or "enhance" are all used herein to generally mean an increase by a staticaly significant amount; for the avoidance of doubt, the terms "increased", "increase", or "enhance", mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "fusion protein" as used herein refers to a polypeptide that comprises an amino acid sequence of an antibody or fragment thereof and an amino acid sequence of a heterologous polypeptide (i.e., an unrelated polypeptide).

The terms, "decrease", "reduce", "reduction", "lower" or "lowering," or "inhibit" are all used herein generally to mean a decrease by a statistically significant amount. For example, "decrease", "reduce", "reduction", or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., tumor size after treatment as compared to a reference level prior to the treatment), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease. Reduce or inhibit can refer to, for example, the symptoms of the disorder being treated, the presence or size of metastases or micrometastases, the size of the primary tumor, the presence or the size of the dormant tumor.

The terms "synthetic polynucleotide," "synthetic gene" or "synthetic polypeptide," as used herein, mean that the corresponding polynucleotide sequence or portion thereof, or amino acid sequence or portion thereof, is derived, from a sequence that has been designed, or synthesized de novo, or modified, compared to an equivalent naturally-occurring sequence. Synthetic polynucleotides (antibodies or antigen-binding fragments) or synthetic genes can be prepared by methods known in the art, including but not limited to, the chemical synthesis of nucleic acid or amino acid sequences. Synthetic genes are typically different from naturally-occurring genes, either at the amino acid, or polynucleotide level, (or both) and are typically located within the context of synthetic expression control sequences. Synthetic gene polynucleotide sequences, may not necessarily encode proteins with different amino acids, compared to the natural gene; for example, they can also encompass synthetic polynucleotide sequences that incorporate different codons but which encode the same amino acid (i.e., the nucleotide changes represent silent mutations at the amino acid level).

Antibody Terminology

As used herein, the term "antibody" refers to an immunoglobulin (Ig) whether natural or partly or wholly synthetically produced. The term also covers any polypeptide or protein having a binding domain which is, or is homologous to, an antigen-binding domain. The term further includes "antigen-binding fragments" and other interchangeable terms for similar binding fragments such as described below.

An antibody includes, but is not be limited to, any specific binding member, immunoglobulin class and/or isotype (e.g., IgG1, IgG2, IgG3, IgG4, IgM, IgA, IgD, IgE and IgM); and biologically relevant fragment or specific binding member thereof. Thus, an antibody includes, for example, monoclonal antibodies, chimeric antibodies, humanized antibodies, human antibodies, recombinant antibodies, chemically engineered antibodies, deimmunized antibodies, affinity-matured antibodies, multispecific antibodies (for example, bispecific antibodies and polyreactive antibodies), heteroconjugate antibodies, antibody fragments, and combinations thereof (e.g., a monoclonal antibody that is also deimmunized, a humanized antibody that is also deimmunized, etc.).

The present disclosure provides cancer associated antibodies that find use in treating and/or diagnosing cancer. The term "cancer associated antibody" as used herein refers to an antibody specific for a cancer associated antigen. In some embodiments, the cancer associated antibody comprises at least one antigen-binding region specific for a cancer associated antigen. Disclosed herein are the complete reconstructed nucleic acid consensus sequences and complete reconstructed polypeptide consensus sequences of the variable heavy chain (VH) and variable light chain (VL) of the antibodies. The nucleic acid and polypeptide sequences of the CDR1, CDR2, and CDR3 of the VH and the VL are also provided.

Native antibodies and native immunoglobulins are usually heterotetrameric glycoproteins of about 150,000 Daltons, composed of two identical light (L) chains and two identical heavy (H) chains. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ("VH") followed by a number of constant domains ("CH"). Each light chain has a variable domain at one end ("VL") and a constant domain ("CL") at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The antibodies or antigen-binding fragment thereof of the present disclosure can comprise a deletion at an end of a light chain. The antibodies or antigen-binding fragment thereof of the invention can comprise a deletion of 3 or more amino acids at an end of the light chain. The antibodies or antigen-binding fragment thereof of the invention can comprise a deletion of 7 or less amino acids at an end of the light chain. The antibodies or antigen-binding fragment thereof of the invention can comprise a deletion of 3, 4, 5, 6, or 7 amino acids at an end of the light chain.

The antibodies or antigen-binding fragment thereof of the present disclosure can comprise an insertion in a light chain. The antibodies or antigen-binding fragment thereof of the invention can comprise an insertion of 1, 2, 3, 4, 5, 6, 7, 8, 9, or 10, or more amino acids in the light chain. The antibodies or antigen-binding fragment thereof of the invention can comprise an insertion of 3 amino acids in the light chain.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made by the hybridoma method first described by Kohler and Milstein, 1975, Nature, 256:495, or may be made by recombinant DNA methods. The monoclonal antibodies may also be isolated from phage libraries generated using the techniques described in McCafferty et al., 1990, Nature, 348:552-554, for example.

As used herein, "humanized" antibodies refer to forms of non-human (e.g. murine) antibodies that are specific chimeric immunoglobulins, immunoglobulin chains, or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Other forms of humanized antibodies have one or more CDRs (one, two, three, four, five, six) which are altered with respect to the original antibody, which are also termed one or more CDRs "derived from" one or more CDRs from the original antibody.

As used herein, an "isolated antibody" is one that has been separated and/or recovered from a component of its natural environment. Contaminant components of its natural environment are materials that would interfere with diagnostic or therapeutic uses of the antibody, and may include enzymes, hormones, and other proteinaceous or non-proteinaceous components. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity as shown by SDS-PAGE under reducing or non-reducing conditions and using Coomassie blue or, preferably, silver staining. Isolated antibody includes the antibody in situ within recombinant cells since at least one component of the antibody's natural environment will not be present. Ordinarily, however, isolated antibody will be prepared by at least one purification step.

As used herein, the term "Complementarity Determining Regions" (CDRs, i.e., CDR1, CDR2, and CDR3) refers to the amino acid residues of an antibody variable domain the presence of which are necessary for antigen binding. Each variable domain typically has three CDR regions identified as CDR1, CDR2 and CDR3. The CDRs of variable heavy chain can be CDR-H1, CDR-H2 and CDR-H3. The CDRs of variable light chain can be CDR-L1, CDR-L2 and CDR-L3. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987)). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (Kabat et al., Sequences of Proteins of Immunological Interest, 5th ed. (1991)). Thus, the HVs may be comprised within the corresponding CDRs and references herein to the "hypervariable loops" of VH and VL domains should be interpreted as also encompassing the corresponding CDRs, and vice versa, unless otherwise indicated. The more highly conserved regions of variable domains are called the framework region (FR), as defined below. The variable domains of native heavy and light chains each comprise four FRs (FR1, FR2, FR3 and FR4, respectively), largely adopting a [beta]-sheet configuration, connected by the three hypervariable loops. The hypervariable loops in each chain are held together in close proximity by the FRs and, with the hypervariable loops from the other chain, contribute to the formation of the antigen-binding site of antibodies. Structural analysis of antibodies revealed the relationship between the sequence and the shape of the binding site formed by the complementarity determining regions (Chothia et al., J. Mol. Biol. 227: 799-817 (1992)); Tramontano et al., J. Mol. Biol, 215: 175-182 (1990)). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Allazikani et al (1997) J. Molec. Biol. 273:927-948)). A CDR may refer to CDRs defined by either approach or by a combination of both approaches.

A "constant region" of an antibody refers to the constant region of the antibody light chain or the constant region of the antibody heavy chain, either alone or in combination. The constant region does not vary with respect to antigen specificity.

As used herein, the term "heavy chain region" includes amino acid sequences derived from the constant domains of an immunoglobulin heavy chain. A polypeptide comprising a heavy chain region comprises at least one of: a CH1 domain, a hinge (e.g., upper, middle, and/or lower hinge region) domain, a CH2 domain, a CH3 domain, or a variant or fragment thereof. In an embodiment, an antibody or an antigen-binding fragment thereof may comprise the Fc region of an immunoglobulin heavy chain (e.g., a hinge portion, a CH2 domain, and a CH3 domain). In another embodiment, an antibody or an antigen-binding fragment thereof lacks at least a region of a constant domain (e.g., all or part of a CH2 domain). In certain embodiments, at least one, and preferably all, of the constant domains are derived from a human immunoglobulin heavy chain. For example, in one preferred embodiment, the heavy chain region comprises a fully human hinge domain. In other preferred embodiments, the heavy chain region comprising a fully human Fc region (e.g., hinge, CH2 and CH3 domain sequences from a human immunoglobulin). In certain embodiments, the constituent constant domains of the heavy chain region are from different immunoglobulin molecules. For example, a heavy chain region of a polypeptide may comprise a domain derived from an IgG1 molecule and a hinge region derived from an IgG3 or IgG4 molecule. In other embodiments, the constant domains are chimeric domains comprising regions of different immunoglobulin molecules. For example, a hinge may comprise a first region from an IgG1 molecule and a second region from an IgG3 or IgG4 molecule. As set forth above, it will be understood by one of ordinary skill in the art that the constant domains of the heavy chain region may be modified such that they vary in amino acid sequence from the naturally occurring (wild-type) immunoglobulin molecule. That is, the polypeptides of the invention disclosed herein may comprise alterations or modifications to one or more of the heavy chain constant domains (CH1, hinge, CH2 or CH3) and/or to the light chain constant domain (CL). Exemplary modifications include additions, deletions or substitutions of one or more amino acids in one or more domains.

The antibodies or antigen-binding fragment thereof of the present disclosure can comprise a CDR3 region that is a length of at least about 10, 11, 12, 13, 14, 15, 16, 17, 18, 19, 20, 21, 22, 23, 24, 25, 26, 27, 28, 29, or 30 amino acids in length. The antibodies or antigen-binding fragment thereof of the present disclosure can comprise a CDR3 region that is at least about 18 amino acids in length.

As used herein, the term "hinge region" includes the region of a heavy chain molecule that joins the CH1 domain to the CH2 domain. The hinge region can comprise approximately 25 residues and is flexible, thus allowing the two N-terminal antigen binding regions to move independently. Hinge regions can be subdivided into three distinct domains: upper, middle, and lower hinge domains (Roux et al. J. Immunol. 1998161:4083).

As used herein, the term "Fv" is the minimum antibody fragment that contains a complete antigen-recognition and -binding site. This fragment consists of a dimer of one heavy- and one light-chain variable region domain in tight, non-covalent association.

From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Heavy chain variable region" or "VH" with regard to an antibody refers to the fragment of the heavy chain that contains three CDRs interposed between flanking stretches known as framework regions, these framework regions are generally more highly conserved than the CDRs and form a scaffold to support the CDRs.

Six hypervariable loops (three loops each from the H and L chain) contribute the amino acid residues for antigen-binding and confer antigen-binding specificity to the antibody. However, even a single variable domain (or half of an Fv comprising only three CDRs specific for an antigen) has the ability to recognize and bind antigen, although at a lower affinity than the entire binding site.

"Framework" or FR residues are those variable domain residues other than the hypervariable region residues.

It is understood in the art that an antibody is a glycoprotein having at least two heavy (H) chains and two light (L) chains interconnected by disulfide bonds, or an antigen-binding portion thereof. A heavy chain is comprised of a heavy chain variable region (VH) and a heavy chain constant region (CH1, CH2 and CH3). A light chain is comprised of a light chain variable region (VL) and a light chain constant region (CL). The variable regions of both the heavy and light chains comprise framework regions (FRs or FWRs) and hypervariable regions (HVRs). The HVRs are the amino acid residues of an antibody that are responsible for antigen binding. The hypervariable region generally comprises amino acid residues from a complementarity determining region (CDR), which have the highest sequence variability and/or involved in antigen recognition. With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See, e.g., Fransson, Front. Biosci. 13:1619-1633 (2008))

Unless otherwise indicated, HVR residues and other residues in the variable domain (e.g., FR residues) are numbered herein according to Kabat et al., supra. A variable region is a domain of an antibody heavy or light chain that is involved in binding the antibody to antigen. (See, e.g., Kindt et al. Kuby Immunology, 6th ed., W.H. Freeman and Co., p. 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. (See, e.g., Portolano et al., J. Immunol. 150:880-887 (1993); Clarkson et al., Nature 352:624-628 (1991)). The four FWR regions are typically more conserved while CDR regions (CDR1, CDR2 and CDR3) represent hypervariable regions and are arranged from NH2 terminus to the COOH terminus as follows: FWR1, CDR1, FWR2, CDR2, FWR3, CDR3, and FWR4. The variable regions of the heavy and light chains contain a binding domain that interacts with an antigen while, depending of the isotype, the constant region(s) may mediate the binding of the immunoglobulin to host tissues or factors. An antibody also includes chimeric antibodies, humanized antibodies, and recombinant antibodies, human antibodies generated from a transgenic non-human animal, as well as antibodies selected from libraries using enrichment technologies available to the artisan.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa ("κ") and lambda ("λ") light chains refer to the two major antibody light chain isotypes.

An antibody or antigen-binding fragment thereof "specifically binds" or "preferentially binds" to a target if it binds with greater affinity and/or avidity than it binds to epitopes on unrelated polypeptides. The specificity of an antibody or antigen-binding fragment or portion thereof can be determined based on affinity and/or avidity. Methods to determine such specific binding are also well known in the art. According to certain embodiments of the present disclosure, the antibodies or antigen-binding fragment thereof can bind to a human cancer antigen but not to a cancer antigen from other species. Alternatively, the antibodies or antigen-binding fragment thereof, in certain embodiments, bind to human cancer antigen and to cancer antigen from one or more non-human species. For example, the antibodies or antigen-binding fragment thereof can bind to human cancer antigen and can bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee cancer antigen.

The affinity, represented by the equilibrium constant for the dissociation ($K_D$) of an antigen with an antigen-binding protein, is a measure for the binding strength between an antigenic determinant and an antigen-binding site on the antigen-binding protein: the lesser the value of the $K_D$, the stronger the binding strength between an antigenic determinant and the antigen-binding molecule. Alternatively, the affinity can also be expressed as the affinity constant ($K_A$), which is $1/K_D$. As will be clear to the skilled person, affinity can be determined in a manner known per se, depending on the specific antigen of interest. Accordingly, an antibody or antigen-binding fragment thereof as defined herein is said to be "specific for" a first target or antigen compared to a second target or antigen when it binds to the first antigen with an affinity (as described above, and suitably expressed, for example as a $K_D$ value) that is at least 50 times, such as at least 100 times, and preferably at least 1000 times, and up to 10,000 times or more better than the affinity with which said amino acid sequence or polypeptide binds to another target or polypeptide. Preferably, when an antibody or antigen-binding fragment thereof is "specific for" a target or antigen, compared to another target or antigen, it can bind the target or antigen, but does not bind the other target or antigen. However, as understood by one of ordinary skill in the art, in some embodiments, where a binding site on a target is shared or partially shared by multiple, different ligands, an antibody or antigen-binding fragment thereof can specifically bind to a target, such as cancer associated antigen, and have the functional effect of, for example, inhibiting/preventing tumor progression.

In some embodiments, an antibody provided herein has a dissociation constant ($K_D$) of about 1 μM, 100 nM, 10 nM, 5 nM, 2 nM, 1 nM, 0.5 nM, 0.1 nM, 0.05 nM, 0.01 nM, or 0.001 nM or less (e.g., $10^{-8}$M or less, e.g., from $10^{-8}$M to $10^{-13}$M, e.g., from $10^{-9}$M to $10^{-13}$ M). Another aspect of the invention provides for an antibody or antigen-binding fragment thereof with an increased affinity for its target, for example, an affinity matured antibody. An affinity matured antibody is an antibody with one or more alterations in one or more hypervariable regions (HVRs), compared to a parent antibody which does not possess such alterations, such alterations resulting in an improvement in the affinity of the antibody for antigen. These antibodies can bind to antigen with a $K_D$ of about $5\times10^{-9}$ M, $2\times10^{-9}$ M, $1\times10^{-9}$ M, $5\times10^{-10}$ M, $2\times10^{-10}$ M, $1\times10^{-10}$ M, $5\times10^{-11}$ M, $1\times10^{-11}$ M, $5\times10^{-12}$ M, $1\times10^{-12}$ M, or less. In some embodiments, the present disclosure provides an antibody or antigen-binding fragment thereof which has an increased affinity of at least 1.5 fold, 2 fold, 2.5 fold, 3 fold, 4 fold, 5 fold, 10 fold, 20 fold or greater as compared to a germline antibody containing the heavy chain sequence and light chain sequence, or both. In other embodiments, an antibody is provided that competes for binding to the same epitope as an antibody as described herein. In some embodiments, the antibody or antigen-binding fragment thereof that binds to the same epitope, and/or competes for binding to the same epitope as an antibody exhibits effector function activities, such as, for example, Fc-mediated cellular cytotoxicity, including ADCC activity.

$K_D$ can be measured by any suitable assay. For example, $K_D$ can be measured by a radiolabeled antigen-binding assay (RIA) (See, e.g., Chen et al., J. Mol. Biol. 293:865-881 (1999); Presta et al., Cancer Res. 57:4593-4599 (1997)). For example, KD can be measured using a surface plasmon resonance assay (e.g., using a BIACORE®-2000 or a BIACORE®-3000). For example, $K_D$ can be measured using a competitive ELISA.

Avidity is the measure of the strength of binding between an antigen-binding molecule and the pertinent antigen. Avidity is related to both the affinity between an antigenic determinant and its antigen-binding site on the antigen-binding molecule, and the number of pertinent binding sites present on the antigen-binding molecule. Typically, antigen-binding proteins will bind to their cognate or specific antigen with a dissociation constant ($K_D$ of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ M$^{-1}$) is generally considered to indicate non-specific binding. The $K_D$ for biological interactions which are considered meaningful (e.g., specific) are typically in the range of $10^{-10}$ M (0.1 nM) to $10^{-5}$ M (10000 nM). The stronger an interaction is, the lower is its $K_D$. Preferably, a binding site on an anti-LAP antibody or antigen-binding fragment thereof described herein will bind with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

The term "kon", as used herein, is intended to refer to the rate constant for association of an antibody or antigen-binding fragment thereof to an antigen.

The term "Koff", as used herein, is intended to refer to the rate constant for dissociation of an antibody or antigen-binding fragment thereof from the antibody/antigen complex.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from reconstructed immunoglobulin consensus sequences, disclosed herein. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human immunoglobulin VH and VL sequences, may not naturally exist within the human antibody germline repertoire in vivo.

In the context of an antibody or antigen-binding fragment thereof, the term "specificity" or "specific for" refers to the number of different types of antigens or antigenic determinants to which a particular antibody or antigen-binding fragment thereof can bind. The specificity of an antibody or antigen-binding fragment or portion thereof can be determined based on affinity and/or avidity. The affinity, represented by the equilibrium constant for the dissociation ($K_D$) of an antigen with an antigen-binding protein, is a measure for the binding strength between an antigenic determinant and an antigen-binding site on the antigen-binding protein: the lesser the value of the $K_D$, the stronger the binding strength between an antigenic determinant and the antigen-binding molecule. Alternatively, the affinity can also be expressed as the affinity constant ($K_A$), which is $1/K_D$. As will be clear to the skilled person, affinity can be determined in a manner known per se, depending on the specific antigen of interest. Accordingly, an antibody or antigen-binding fragment thereof as defined herein is said to be "specific for" a first target or antigen compared to a second target or antigen when it binds to the first antigen with an affinity (as described above, and suitably expressed, for example as a $K_D$ value) that is at least 50 times, such as at least 100 times, and preferably at least 1000 times, and up to 10,000 times or more better than the affinity with which said amino acid sequence or polypeptide binds to another target or polypeptide. Preferably, when an antibody or antigen-binding fragment thereof is "specific for" a target or antigen, compared to another target or antigen, it can bind the target or antigen, but does not bind the other target or antigen.

However, as understood by one of ordinary skill in the art, in some embodiments, where a binding site on a target is shared or partially shared by multiple, different ligands, an antibody or antigen binding fragment thereof can specifically bind to a target, such as cancer associated antigen, and have the functional effect of, for example, inhibiting/preventing tumor progression.

Avidity is the measure of the strength of binding between an antigen-binding molecule and the pertinent antigen. Avidity is related to both the affinity between an antigenic determinant and its antigen binding site on the antigen-binding molecule, and the number of pertinent binding sites present on the antigen-binding molecule. Typically, antigen-binding proteins will bind to their cognate or specific antigen with a dissociation constant ($K_D$ of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ M$^{-1}$) is generally considered to indicate non-specific binding. The $K_D$ for biological interactions which are considered meaningful (e.g., specific) are typically in the range of $10^{-10}$ M (0.1 nM) to $10^{-5}$ M (10000 nM). The stronger an interaction is, the lower is its $K_D$. Preferably, a binding site on an anti-LAP antibody or antigen-binding fragment thereof described herein will bind with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

The term "fusion protein" as used herein refers to a polypeptide that comprises an amino acid sequence of an antibody or fragment thereof and an amino acid sequence of a heterologous polypeptide (i.e., an unrelated polypeptide).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

In some embodiments, the antibody or antigen binding fragment thereof of the present disclosure is a single domain antibody. The expression "single domain antibody" (sdAbs) or "single variable domain (SVD) antibody" generally refers to a single variable region (VH or ') wherein the antibody-antigen binding can be imparted. In other words, single variable domain does not need to recognize the target antigen by interacting with another variable region. A single domain antibody monomers single arm antigen binding by each antibody variable region (VH*VJ composition. Examples of single domain antibodies include those derived from camelids (camels and llamas) and cartilaginous fish (e.g. nurse sharks) antibodies and those antibodies (Ward et al from human and mouse antibodies by recombinant methods, Nature (1989) 341: 544-546; Dooley and Flajnik, Dev Comp Immunol (2006) 30: 43-56; Muyldermans et, Trend-Biochem Sci (2001) 26: 230-235; Holt et, Trends Biotechnol (2003): 21: 484-490; WO 2005/035572; TO 03/035694; Davies and Riechmann, Febs Lett (1994) 339: 285-290; W000/29004; W0 02/051870) and a single variable region of an antibody can be other than a single domain antibody variable regions or variable domains are present in an antigen binding arm (e.g., homo- or hetero-multimer together).

Computationally Reconstructed Antibodies

Provided herein are reconstructed polypeptide and nucleic acid consensus sequences for cancer associated antibodies. The consensus sequences are reconstructed in silico. The term "polypeptide consensus sequence" as used herein refers to an amino acid sequence which comprises the most frequently occurring amino acid residues at each location in all immunoglobulins of any particular subclass or subunit structure. The polypeptide consensus sequence may be based on immunoglobulins of a particular species or of many species. A polypeptide "consensus" sequence, "consensus" structure, or "consensus" antibody is understood to encompass a human polypeptide consensus sequence as described in certain embodiments provided herein, and to refer to an amino acid sequence which comprises the most frequently occurring amino acid residues at each location in all human immunoglobulins of any particular subclass or subunit structure. The embodiments herein provide consensus human structures and consensus structures, which consider other species in addition to human.

The term, "nucleic acid consensus sequence" as used herein refers to a nucleic acid sequence, which comprises the most frequently occurring nucleotide residues at each location in all immunoglobulin nucleic acid sequence of any particular subclass or subunit structure. The nucleic acid consensus sequence may be based on immunoglobulins of a particular species or of many species. A nucleic acid "consensus" sequence, or "consensus" structure, is understood to encompass a human nucleic acid consensus sequence as described in certain embodiments of this invention, and to refer to a nucleic acid sequence which comprises the most frequently occurring nucleotide residues at each location in all human immunoglobulins nucleic acid of any particular subclass or subunit structure.

Provided herein are consensus human structures and consensus structures of other species in addition to human. Methods to computationally reconstruct the consensus sequences from RNA seq data are described in the examples herein. Non limiting examples of computational tools known in the art for reconstructing full-length antibody repertoires including MIGEC (Shugay et al. 2014), PRESTO (Vander Heiden et al. 2014), MiXCR (Bolotin et al. 2015), and IGREPERTOIRECONSTRUCTOR (Safonova et al. 2015). In some embodiments, the TraCeR pipeline by Stubbington and Teichmann is implemented, which uses de novo assembly after a pre-filtering step against a custom database containing in silico combinations for all known human V and J gene segments/alleles in the International Immunogenetics Information System (IMGT) repository. In some embodiments, another pipeline, VDJPuzzle, is implemented which filters in reads by mapping to TCR genes followed by a Trinity-based assembly; whereby the total reads are then mapped back to the assemblies in order to retrieve reads missed in the initial mapping step, followed by another round of assembly with Trinity. An exemplary method for computationally reconstructing consensus sequences can comprise somatic sequence identification, manual IGV investigation and (if necessary) correction of somatic vdj sequence and identification of germline sequence and CDR regions.

In some embodiments, RNA-seq FASTQ files retrieved for patients e.g., a cancer patient are recorded and analysed. Kallisto, BWA, MiXCR or other known tools can be used, in some embodiments, to perform a first alignment of RNA-seq samples to reference V, D and J genes of immunoglobulins in order to identify the repertoire present in the samples. In further embodiments, identical CDR3 sequences are identified and grouped in clonotypes (Bolotin D A et al., Nature Methods, 2015; Bolotin D A et al. Nature biotechnology, 2017). VDJtools are used, in some embodiments, (Shugay M. et al. PLoS computational biology, 2015) to filter out non-functional (non-coding) clonotypes and to compute basic diversity statistics. In further embodiments, non-functional clonotypes are identified as those containing a stop codon or frameshift in their receptor sequence. In some embodiments, the diversity of the Ig repertoire is obtained based on the effective number of species which is calculated as the exponent of the Shannon-Wiener Entropy index (MacArthur RH. Biological reviews. 1965).

In some embodiments, further alignments against the immunoglobulin segments present in the samples are performed for viewing the results to explore the frequency distribution of sequence mismatches along the V, D, J gene segments and, in particular in the CDR3 region length statistics. This alignment step can be useful, for example, for summarizing repertoires, as well as offering a detailed view of rearrangements and region alignments for individual query sequences. Exemplary methodology for alignment and assembly is described in the examples herein.

In some embodiments, the immunoglobulin segments present in the samples are identified using IMGT reference files or equivalent. In some instances, the heavy D segment and light V-J junction sequences can be assembled using an assembler. Non limiting examples of assembler known in the art include Trinity and V'DJer. A FASTA file with corrected heavy D and light V-J junction sequences can be generated for each sample in some embodiments. In addition to the assembled FASTA files, germline FASTA files can be generated, for example, by using IgBLAST v1.9.0 (Ye J, et al Nucleic Acids Research, 2013) and the IMGT database. In further embodiments, the somatic FASTA sequence can be input to IgBLAST to obtain the closest segment ids for the heavy and light chain. The germline FASTA can be generated by merging corresponding segment sequences from the IMGT database. The final assembled FASTA sequences can serve as 'reference' sequences for the alignment and visualisation steps.

In further embodiments, using the reference files generated from the assembly step, the FASTQs can be aligned in BowTie2 default mode. Other alignment tools, known in the art, for example STAR or TopHat2 can also be used. The output BAM file can be used for IGV visualization and mutations in the patient can be observed.

In further embodiments, the identification of the CDR3 region and corresponding V, D, and J chains from the final assembled FASTA sequences can be done, for example with IgBLAST. The standardized output using version v.1.9.0 of IgBLAST can be delivered by wrapping IgBLASTn with default parameters in some instances. In other instances, the output from the IgBLAST service can be extracted using a purpose-built parser tool designed to extract the CDR1, CDR2 and CDR3 nucleotide and amino acid sequences.

Exemplary Cancer Associated Antibodies or Antigen Binding Fragments Thereof

In another aspect, the present disclosure provides cancer associated antibodies comprising in silico reconstructed consensus sequence. In some embodiments, the antibodies or antigen binding fragment thereof induce lysis of cancer cells. Lysis can be induced by any mechanism, such as by mediating an effector function, such as C1q binding and complement dependent cytotoxicity (CDC); Fc receptor binding; antibody-dependent cell-mediated cytotoxicity (ADCC); phagocytosis, or direct induction of cell apoptosis.

In some embodiments, an antibody or antigen binding fragment thereof, disclosed herein, is engineered to have at least one increase in effector function as compared to the non-engineered parent antibody or antigen binding fragment thereof. Effector functions are biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis. For example, an antibody or antigen binding fragment thereof, disclosed herein can be glycoengineered to have at least one increase in effector function as compared to the non-glycoengineered parent. Antibody-dependent cellular cytotoxicity (ADCC) is the result of the formation of a complex between the IgG Fab portion of the antibody with the viral protein on the cell surface and binding of the Fc portion to the Fc receptors (FcγRs), on effector cells. The increase in effector function can be increased binding affinity to an Fc receptor, increased ADCC; increased cell mediated immunity; increased binding to cytotoxic CD8 T cells; increased binding to NK cells; increased binding to macrophages; increased binding to polymorphonuclear cells; increased binding to monocytes; increased binding to macrophages; increased binding to large granular lymphocytes; increased binding to granulocytes; direct signaling inducing apoptosis; increased dendritic cell maturation; or increased T cell priming.

TMEL1001-TMEL1014

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of any one of SEQ ID NO: 1, 2, 3, 4, 5, 6, 7, 8, 9, 10, 11, 12, 13, and 14. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody comprising that sequence retains the ability to bind to same antigen as of the parent (e.g., cancer associated antigen). In some embodiments, a total of 1 to 10 amino acids have been substituted, inserted and/or deleted in the amino acid sequence of any one of SEQ ID NO: 1, 2, 3, 4, 5, 6, 7, 8, 9, 10, 11, 12, 13, and 14. In some embodiments, substitutions, insertions, or deletions occur in regions outside the CDRs (e.g., in the FRs). Optionally, the antibody comprises the VH sequence of the amino acid sequence of SEQ ID NO: 1, 2, 3, 4, 5, 6, 7, 8, 9, 10, 11, 12, 13, or 14, including one or more post-translational modifications of that sequence. In a particular embodiment, the VH comprises one, two or three CDRs selected from: (a) CDR-H1 comprising the amino acid sequence of any one of SEQ ID NO: 85, 86, 87, 88, 89, 90, 91, 92, 93, 94, 95, 96, 97, and 98, (b) CDR-H2 comprising the amino acid sequence of any one of SEQ ID NO: 57, 58, 59, 60, 61, 62, 63, 64, 65, 66, 67, 68, 69, and 70, and (c) CDR-H3 comprising the amino acid sequence of any one of SEQ ID NO: 29, 30, 31, 32, 33, 34, 35, 36, 37, 38, 39, 40, 41, and 42.

In one aspect, an antibody or antigen-binding fragment thereof, is provided, wherein the antibody or antigen-binding fragment thereof comprises a light chain variable domain (VL) having at least 90%, 91%, 92%, 93%, 94%, 95%, 96%, 97%, 98%, 99%, or 100% sequence identity to the amino acid sequence of any one of SEQ ID NO: 15, 16, 17, 18, 19, 20, 21, 22, 23, 24, 25, 26, 27, and 28. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to same antigen as the parent (e.g., cancer associated antigen). In some embodiments, a total of 1 to 10 amino acids have been substituted, inserted and/or deleted in any one of the amino acid sequence of any one of SEQ ID NO: 15, 16, 17, 18, 19, 20, 21, 22, 23, 24, 25, 26, 27, and 28. In some embodiments, the substitutions, insertions, or deletions occur in regions outside the CDRs (e.g., in the FRs). Optionally, the antibody or antigen-binding fragment thereof comprises the VL sequence of any one of SEQ ID NO: 15, 16, 17, 18, 19, 20, 21, 22, 23, 24, 25, 26, 27, and 28, including post-translational modifications of that sequence. In a particular embodiment, the VL comprises one, two or three CDRs selected from (a) CDR-L1 comprising the amino acid sequence of any one of SEQ ID NOS: 99, 100, 101, 102, 103, 104, 105, 106, 107, 108, 109, 110, 111, and 112; (b) CDR-L2 comprising the amino acid sequence of any one of SEQ ID NOS: 71, 72, 73, 74, 75, 76, 77, 78, 79, 80, 81, 82, 83, and 84; and (c) CDR-L3 comprising the amino acid sequence of any one of SEQ ID NOS: 43, 44, 45, 46, 47, 48, 49, 50, 51, 52, 53, 54, 55, and 56.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody or antigen-binding fragment thereof comprises a VH and a VL, wherein the VH comprises the amino acid sequence of any one of SEQ ID NOS: 1, 2, 3, 4, 5, 6, 7, 8, 9, 10, 11, 12, 13, and 14, and wherein the VL comprises the amino acid sequence in any one of SEQ ID NOS: 15, 16, 17, 18, 19, 20, 21, 22, 23, 24, 25, 26, 27, and 28, and optionally including post-translational modifications of those sequences.

In one aspect, an antibody or antigen-binding fragment thereof is provided, wherein the antibody or antigen-binding fragment thereof comprises a VH selected from any VH in Table 1. In one aspect, an antibody or antigen-binding fragment thereof is provided, wherein the antibody or antigen-binding fragment thereof comprises a VL selected from any VL in Table 1. In one aspect, an antibody or antigen-binding fragment thereof is provided, wherein the antibody or antigen-binding fragment thereof comprises a VH selected from any VH in Table 1 and a VL selected from any VL in Table 1. In one aspect, an antibody or antigen-binding fragment thereof is provided, wherein the antibody or antigen-binding fragment thereof comprises a VH selected from any VH in Table 1 and a VL selected from any VL in Table 1, wherein the selected VH and VL are paired according to Table 7. In one aspect, an antibody or antigen-binding fragment thereof is provided, wherein the antibody or antigen-binding fragment thereof comprises a CDR-H3 selected from any CDR-H3 in Table 2 and a CDR-L3 selected from any CDRL3 in Table 2, wherein the selected CDR-H3 and CDRL3 are paired according to Table 7. In one aspect, an antibody or antigen-binding fragment thereof is provided, wherein the antibody or antigen-binding fragment thereof comprises a CDR-H2 selected from any CDR-H2 in Table 2 and a CDR-L2 selected from any CDR-L2 in Table 2, wherein the selected CDR-H2 and CDR-L2 are paired according to Table 7. In one aspect, an antibody or antigen-binding fragment thereof is provided, wherein the antibody or antigen-binding fragment thereof comprises a CDR-H1 selected from any CDR-H1 in Table 2 and a CDR-L1 selected from any CDR-L1 in Table 2, wherein the selected CDR-H1 and CDR-L1 are paired according to Table 7. In one aspect, an antibody or antigen-binding fragment thereof is provided, wherein the antibody or antigen-binding fragment thereof comprises a CDR-H1, a CDR-H2, and a CDR-H3 selected from any CDR-H1, a CDR-H2, and a CDR-H3 in Table 2 and a CDR-L1, a CDR-L2, and a CDR-L3 selected from any CDR-L1, CDR-L2, or CDR-L3 in Table 2, wherein the selected CDR-H1, CDR-H2, CDR-H3, CDR-L1, CDR-L2, and CDR-L3 are paired according to Table 7.

TMEL1001

In one aspect, the present disclosure provides an antibody or antigen-binding fragment thereof comprises one or more variable regions selected from the group consisting of (a) VH comprising the amino acid sequence of SEQ ID NO: 1, (b) VL comprising the amino acid sequence of SEQ ID NO: 15, and (c) a combination thereof.

In one aspect, the present disclosure provides an antibody or antigen-binding fragment thereof comprising at least one, two, three, four, five, or six CDRs selected from (a) CDR-H1 comprising the amino acid sequence of SEQ ID NO: 85; (b) CDR-H2 comprising the amino acid sequence of SEQ ID NO: 57; (c) CDR-H3 comprising the amino acid sequence of SEQ ID NO: 29; (d) CDR-L1 comprising the amino acid sequence of SEQ ID NO: 99; (e) CDR-L2 comprising the amino acid sequence of SEQ ID NO: 71; and (f) CDR-L3 comprising the amino acid sequence of SEQ ID NO: 43.

In one aspect, the present disclosure provides an antibody or antigen-binding fragment thereof comprising at least one, at least two, or all three VH CDR sequences selected from (a) CDR-H1 comprising the amino acid sequence of SEQ ID NO: 85; (b) CDR-H2 comprising the amino acid sequence of SEQ ID NO: 57; and (c) CDR-H3 comprising the amino acid sequence of SEQ ID NO: 29; and (d) a VL comprising the amino acid sequence of SEQ ID NO: 15.

In one aspect, the present disclosure provides an antibody or antigen-binding fragment thereof comprising at least one, at least two, or all three VL CDR sequences selected from (a) CDR-L1 comprising the amino acid sequence of SEQ ID NO: 99; (b) CDR-L2 comprising the amino acid sequence of SEQ ID NO: 71; and (c) CDR-L3 comprising the amino acid sequence of SEQ ID NO: 43; and a VH comprising the amino acid sequence of SEQ ID NO: 1.

In one aspect, the present disclosure provides an antibody or antigen-binding fragment thereof comprising the CDRs: CDR-H3 comprising the amino acid sequence of SEQ ID NO: 29; and CDR-L3 comprising the amino acid sequence of SEQ ID NO: 43.

In one aspect, the disclosure herein provides an antibody or antigen-binding fragment thereof comprising at least one, at least two, or all three VL CDR sequences selected from (a) CDR-L1 comprising the amino acid sequence of SEQ ID NO: 99; (b) CDR-L2 comprising the amino acid sequence of SEQ ID NO: 71 and (c) CDR-L3 comprising the amino acid sequence of SEQ ID NO: 43. In one aspect, the disclosure provides an antibody or antigen-binding fragment thereof comprising at least one, at least two, or all three VH CDR sequences selected from (a) CDR-H1 comprising the amino acid sequence of SEQ ID NO: 85; (b) CDR-H2 comprising the amino acid sequence of SEQ ID NO: 57 and (c) CDR-H3 comprising the amino acid sequence of SEQ ID NO: 29.

In one aspect, the disclosure provides an antibody or antigen-binding fragment thereof comprising the CDRs: (a) CDR-H1 comprising the amino acid sequence of SEQ ID NO: 85; (b) CDR-H2 comprising the amino acid sequence of SEQ ID NO: 57; (c) CDR-H3 comprising the amino acid sequence of SEQ ID NO: 29; (d) CDR-L1 comprising the amino acid sequence of SEQ ID NO: 99; (e) CDR-L2 comprising the amino acid sequence of SEQ ID NO: 71; and (f) CDR-L3 comprising the amino acid sequence of SEQ ID NO: 43.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 1. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 1. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 1, including post-translational modifications of that sequence. In a particular embodiment, the VH comprises one, two or three CDRs selected from: (a) CDR-H1 comprising the amino acid sequence of SEQ ID NO: 85, (b) CDR-H2 comprising the amino acid sequence of SEQ ID NO: 57, and (c) CDR-H3 comprising the amino acid sequence of SEQ ID NO: 29.

In one aspect, an antibody or antigen-binding fragment thereof is provided, wherein the antibody or antigen-binding fragment thereof comprises a light chain variable domain (VL) having at least 90%, 91%, 92%, 93%, 94%, 95%, 96%, 97%, 98%, 99%, or 100% sequence identity to the amino acid sequence of SEQ ID NO: 15. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 15. In some embodiments, the substitutions, insertions, or deletions occur in regions outside the CDRs (e.g., in the FRs). Optionally, the antibody or antigen-binding fragment thereof comprises the VL sequence of SEQ ID NO: 15, including post-translational modifications of that sequence. In a particular embodiment, the VL comprises one, two or three CDRs selected from (a) CDR-L1 comprising the amino acid sequence of SEQ ID NO: 99; (b) CDR-L2 comprising the amino acid sequence of SEQ ID NO: 71; and (c) CDR-L3 comprising the amino acid sequence of SEQ ID NO: 43.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 1, and a VL sequence in SEQ ID NO: 15, including post-translational modifications of those sequences.

TMEL1002

In one aspect, the present disclosure provides an antibody or antigen-binding fragment thereof comprises one or more variable regions selected from the group consisting of (a) VH comprising the amino acid sequence of SEQ ID NO: 2, (b) VL comprising the amino acid sequence of SEQ ID NO: 16, and (c) a combination thereof.

In one aspect, the present disclosure provides an antibody or antigen-binding fragment thereof comprising at least one, two, three, four, five, or six CDRs selected from (a) CDR-H1 comprising the amino acid sequence of SEQ ID NO: 86; (b) CDR-H2 comprising the amino acid sequence of SEQ ID NO: 58; (c) CDR-H3 comprising the amino acid sequence of SEQ ID NO: 30; (d) CDR-L1 comprising the amino acid sequence of SEQ ID NO: 100; (e) CDR-L2 comprising the amino acid sequence of SEQ ID NO: 72; and (f) CDR-L3 comprising the amino acid sequence of SEQ ID NO: 44.

In one aspect, the present disclosure provides an antibody or antigen-binding fragment thereof comprising at least one, at least two, or all three VH CDR sequences selected from (a) CDR-H1 comprising the amino acid sequence of SEQ ID NO: 86; (b) CDR-H2 comprising the amino acid sequence of SEQ ID NO: 58; and (c) CDR-H3 comprising the amino acid sequence of SEQ ID NO: 30; and (d) a VL comprising the amino acid sequence of SEQ ID NO: 16.

In one aspect, the present disclosure provides an antibody or antigen-binding fragment thereof comprising at least one, at least two, or all three VL CDR sequences selected from (a) CDR-L1 comprising the amino acid sequence of SEQ ID NO: 100; (b) CDR-L2 comprising the amino acid sequence of SEQ ID NO: 72; and (c) CDR-L3 comprising the amino acid sequence of SEQ ID NO: 44; and a VH comprising the amino acid sequence of SEQ ID NO: 2.

In one aspect, the present disclosure provides an antibody or antigen-binding fragment thereof comprising the CDRs: CDR-H3 comprising the amino acid sequence of SEQ ID NO: 30; and CDR-L3 comprising the amino acid sequence of SEQ ID NO: 44.

In one aspect, the disclosure herein provides an antibody or antigen-binding fragment thereof comprising at least one, at least two, or all three VL CDR sequences selected from (a) CDR-L1 comprising the amino acid sequence of SEQ ID NO: 100; (b) CDR-L2 comprising the amino acid sequence of SEQ ID NO: 72 and (c) CDR-L3 comprising the amino acid sequence of SEQ ID NO: 44. In one aspect, the disclosure provides an antibody or antigen-binding fragment thereof comprising at least one, at least two, or all three VH CDR sequences selected from (a) CDR-H1 comprising the amino acid sequence of SEQ ID NO: 86; (b) CDR-H2 comprising the amino acid sequence of SEQ ID NO: 58 and (c) CDR-H3 comprising the amino acid sequence of SEQ ID NO: 30.

In one aspect, the disclosure provides an antibody or antigen-binding fragment thereof comprising the CDRs: (a) CDR-H1 comprising the amino acid sequence of SEQ ID NO: 86; (b) CDR-H2 comprising the amino acid sequence of SEQ ID NO: 58; (c) CDR-H3 comprising the amino acid sequence of SEQ ID NO: 30; (d) CDR-L1 comprising the amino acid sequence of SEQ ID NO: 100; (e) CDR-L2 comprising the amino acid sequence of SEQ ID NO: 72; and (f) CDR-L3 comprising the amino acid sequence of SEQ ID NO: 44.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 2. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 2. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 2, including post-translational modifications of that sequence. In a particular embodiment, the VH comprises one, two or three CDRs selected from: (a) CDR-H1 comprising the amino acid sequence of SEQ ID NO: 86, (b) CDR-H2 comprising the amino acid sequence of SEQ ID NO: 58, and (c) CDR-H3 comprising the amino acid sequence of SEQ ID NO: 30.

In one aspect, an antibody or antigen-binding fragment thereof is provided, wherein the antibody or antigen-binding fragment thereof comprises a light chain variable domain (VL) having at least 90%, 91%, 92%, 93%, 94%, 95%, 96%, 97%, 98%, 99%, or 100% sequence identity to the amino acid sequence of SEQ ID NO: 16. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 16. In some embodiments, the substitutions, insertions, or deletions occur in regions outside the CDRs (e.g., in the FRs). Optionally, the antibody or antigen-binding fragment thereof comprises the VL sequence of SEQ ID NO: 16, including post-translational modifications of that sequence. In a particular embodiment, the VL comprises one, two or three CDRs selected from (a) CDR-L1 comprising the amino acid sequence of SEQ ID NO: 100; (b) CDR-L2 comprising the amino acid sequence of SEQ ID NO: 72; and (c) CDR-L3 comprising the amino acid sequence of SEQ ID NO: 44.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 2, and a VL sequence in SEQ ID NO: 16, including post-translational modifications of those sequences.

TMEL1003

In one aspect, the present disclosure provides an antibody or antigen-binding fragment thereof comprises one or more variable regions selected from the group consisting of (a) VH comprising the amino acid sequence of SEQ ID NO: 3, (b) VL comprising the amino acid sequence of SEQ ID NO: 17, and (c) a combination thereof.

In one aspect, the present disclosure provides an antibody or antigen-binding fragment thereof comprising at least one, two, three, four, five, or six CDRs selected from (a) CDR-H1 comprising the amino acid sequence of SEQ ID NO: 87; (b) CDR-H2 comprising the amino acid sequence of SEQ ID NO: 59; (c) CDR-H3 comprising the amino acid sequence of SEQ ID NO: 31; (d) CDR-L1 comprising the amino acid sequence of SEQ ID NO: 101; (e) CDR-L2 comprising the amino acid sequence of SEQ ID NO: 73; and (f) CDR-L3 comprising the amino acid sequence of SEQ ID NO: 45.

In one aspect, the present disclosure provides an antibody or antigen-binding fragment thereof comprising at least one, at least two, or all three VH CDR sequences selected from (a) CDR-H1 comprising the amino acid sequence of SEQ ID NO: 87; (b) CDR-H2 comprising the amino acid sequence of SEQ ID NO: 59; and (c) CDR-H3 comprising the amino acid sequence of SEQ ID NO: 31; and (d) a VL comprising the amino acid sequence of SEQ ID NO: 17.

In one aspect, the present disclosure provides an antibody or antigen-binding fragment thereof comprising at least one, at least two, or all three VL CDR sequences selected from (a) CDR-L1 comprising the amino acid sequence of SEQ ID NO: 101; (b) CDR-L2 comprising the amino acid sequence of SEQ ID NO: 73; and (c) CDR-L3 comprising the amino acid sequence of SEQ ID NO: 45; and a VH comprising the amino acid sequence of SEQ ID NO: 3.

In one aspect, the present disclosure provides an antibody or antigen-binding fragment thereof comprising the CDRs: CDR-H3 comprising the amino acid sequence of SEQ ID NO: 31; and CDR-L3 comprising the amino acid sequence of SEQ ID NO: 45.

In one aspect, the disclosure herein provides an antibody or antigen-binding fragment thereof comprising at least one, at least two, or all three VL CDR sequences selected from (a) CDR-L1 comprising the amino acid sequence of SEQ ID NO: 101; (b) CDR-L2 comprising the amino acid sequence of SEQ ID NO: 73 and (c) CDR-L3 comprising the amino acid sequence of SEQ ID NO: 45. In one aspect, the disclosure provides an antibody or antigen-binding fragment thereof comprising at least one, at least two, or all three VH CDR sequences selected from (a) CDR-H1 comprising the amino acid sequence of SEQ ID NO: 87; (b) CDR-H2 comprising the amino acid sequence of SEQ ID NO: 59 and (c) CDR-H3 comprising the amino acid sequence of SEQ ID NO: 31.

In one aspect, the disclosure provides an antibody or antigen-binding fragment thereof comprising the CDRs: (a) CDR-H1 comprising the amino acid sequence of SEQ ID NO: 87; (b) CDR-H2 comprising the amino acid sequence of SEQ ID NO: 59; (c) CDR-H3 comprising the amino acid sequence of SEQ ID NO: 31; (d) CDR-L1 comprising the amino acid sequence of SEQ ID NO: 101; (e) CDR-L2 comprising the amino acid sequence of SEQ ID NO: 73; and (f) CDR-L3 comprising the amino acid sequence of SEQ ID NO: 45.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 3. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 3. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 3, including post-translational modifications of that sequence. In a particular embodiment, the VH comprises one, two or three CDRs selected from: (a) CDR-H1 comprising the amino acid sequence of SEQ ID NO: 87, (b) CDR-H2 comprising the amino acid sequence of SEQ ID NO: 59, and (c) CDR-H3 comprising the amino acid sequence of SEQ ID NO: 31.

In one aspect, an antibody or antigen-binding fragment thereof is provided, wherein the antibody or antigen-binding fragment thereof comprises a light chain variable domain (VL) having at least 90%, 91%, 92%, 93%, 94%, 95%, 96%, 97%, 98%, 99%, or 100% sequence identity to the amino acid sequence of SEQ ID NO: 17. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 17. In some embodiments, the substitutions, insertions, or deletions occur in regions outside the CDRs (e.g., in the FRs). Optionally, the antibody or antigen-binding fragment thereof comprises the VL sequence of SEQ ID NO: 17, including post-translational modifications of that sequence. In a particular embodiment, the VL comprises one, two or three CDRs selected from (a) CDR-L1 comprising the amino acid sequence of SEQ ID NO: 101; (b) CDR-L2 comprising the amino acid sequence of SEQ ID NO: 73; and (c) CDR-L3 comprising the amino acid sequence of SEQ ID NO: 45.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 3, and a VL sequence in SEQ ID NO: 17, including post-translational modifications of those sequences.

TMEL1004

In one aspect, the present disclosure provides an antibody or antigen-binding fragment thereof comprises one or more variable regions selected from the group consisting of (a) VH comprising the amino acid sequence of SEQ ID NO: 4, (b) VL comprising the amino acid sequence of SEQ ID NO: 18, and (c) a combination thereof.

In one aspect, the present disclosure provides an antibody or antigen-binding fragment thereof comprising at least one, two, three, four, five, or six CDRs selected from (a) CDR-H1 comprising the amino acid sequence of SEQ ID NO: 88; (b) CDR-H2 comprising the amino acid sequence of SEQ ID NO: 60; (c) CDR-H3 comprising the amino acid sequence of SEQ ID NO: 32; (d) CDR-L1 comprising the amino acid sequence of SEQ ID NO: 102; (e) CDR-L2 comprising the amino acid sequence of SEQ ID NO: 74; and (f) CDR-L3 comprising the amino acid sequence of SEQ ID NO: 46.

In one aspect, the present disclosure provides an antibody or antigen-binding fragment thereof comprising at least one, at least two, or all three VH CDR sequences selected from (a) CDR-H1 comprising the amino acid sequence of SEQ ID NO: 88; (b) CDR-H2 comprising the amino acid sequence of SEQ ID NO: 60; and (c) CDR-H3 comprising the amino acid sequence of SEQ ID NO: 32; and (d) a VL comprising the amino acid sequence of SEQ ID NO: 18.

In one aspect, the present disclosure provides an antibody or antigen-binding fragment thereof comprising at least one, at least two, or all three VL CDR sequences selected from (a) CDR-L1 comprising the amino acid sequence of SEQ ID NO: 102; (b) CDR-L2 comprising the amino acid sequence of SEQ ID NO: 74; and (c) CDR-L3 comprising the amino acid sequence of SEQ ID NO: 46; and a VH comprising the amino acid sequence of SEQ ID NO: 4.

In one aspect, the present disclosure provides an antibody or antigen-binding fragment thereof comprising the CDRs: CDR-H3 comprising the amino acid sequence of SEQ ID NO: 32; and CDR-L3 comprising the amino acid sequence of SEQ ID NO: 46.

In one aspect, the disclosure herein provides an antibody or antigen-binding fragment thereof comprising at least one, at least two, or all three VL CDR sequences selected from (a) CDR-L1 comprising the amino acid sequence of SEQ ID NO: 102; (b) CDR-L2 comprising the amino acid sequence of SEQ ID NO: 74 and (c) CDR-L3 comprising the amino acid sequence of SEQ ID NO: 46. In one aspect, the disclosure provides an antibody or antigen-binding fragment thereof comprising at least one, at least two, or all three VH CDR sequences selected from (a) CDR-H1 comprising the amino acid sequence of SEQ ID NO: 88; (b) CDR-H2 comprising the amino acid sequence of SEQ ID NO: 60 and (c) CDR-H3 comprising the amino acid sequence of SEQ ID NO: 32.

In one aspect, the disclosure provides an antibody or antigen-binding fragment thereof comprising the CDRs: (a) CDR-H1 comprising the amino acid sequence of SEQ ID NO: 88; (b) CDR-H2 comprising the amino acid sequence of SEQ ID NO: 60; (c) CDR-H3 comprising the amino acid sequence of SEQ ID NO: 32; (d) CDR-L1 comprising the amino acid sequence of SEQ ID NO: 102; (e) CDR-L2 comprising the amino acid sequence of SEQ ID NO: 74; and (f) CDR-L3 comprising the amino acid sequence of SEQ ID NO: 46.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 4. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 4. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 4, including post-translational modifications of that sequence. In a particular embodiment, the VH comprises one, two or three CDRs selected from: (a) CDR-H1 comprising the amino acid sequence of SEQ ID NO: 88, (b) CDR-H2 comprising the amino acid sequence of SEQ ID NO: 60, and (c) CDR-H3 comprising the amino acid sequence of SEQ ID NO: 32.

In one aspect, an antibody or antigen-binding fragment thereof is provided, wherein the antibody or antigen-binding fragment thereof comprises a light chain variable domain (VL) having at least 90%, 91%, 92%, 93%, 94%, 95%, 96%, 97%, 98%, 99%, or 100% sequence identity to the amino acid sequence of SEQ ID NO: 18. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 18. In some embodiments, the substitutions, insertions, or deletions occur in regions outside the CDRs (e.g., in the FRs). Optionally, the antibody or antigen-binding fragment thereof comprises the VL sequence of SEQ ID NO: 18, including post-translational modifications of that sequence. In a particular embodiment, the VL comprises one, two or three CDRs selected from (a) CDR-L1 comprising the amino acid sequence of SEQ ID NO: 102; (b) CDR-L2 comprising the amino acid sequence of SEQ ID NO: 74; and (c) CDR-L3 comprising the amino acid sequence of SEQ ID NO: 46.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 4, and a VL sequence in SEQ ID NO: 18, including post-translational modifications of those sequences.

TMEL1005

In one aspect, the present disclosure provides an antibody or antigen-binding fragment thereof comprises one or more variable regions selected from the group consisting of (a) VH comprising the amino acid sequence of SEQ ID NO: 5, (b) VL comprising the amino acid sequence of SEQ ID NO: 19, and (c) a combination thereof.

In one aspect, the present disclosure provides an antibody or antigen-binding fragment thereof comprising at least one, two, three, four, five, or six CDRs selected from (a) CDR-H1 comprising the amino acid sequence of SEQ ID NO: 89; (b) CDR-H2 comprising the amino acid sequence of SEQ ID NO: 61; (c) CDR-H3 comprising the amino acid sequence of SEQ ID NO: 33; (d) CDR-L1 comprising the amino acid sequence of SEQ ID NO: 103; (e) CDR-L2 comprising the amino acid sequence of SEQ ID NO: 75; and (f) CDR-L3 comprising the amino acid sequence of SEQ ID NO: 47.

In one aspect, the present disclosure provides an antibody or antigen-binding fragment thereof comprising at least one, at least two, or all three VH CDR sequences selected from (a) CDR-H1 comprising the amino acid sequence of SEQ ID NO: 89; (b) CDR-H2 comprising the amino acid sequence of SEQ ID NO: 61; and (c) CDR-H3 comprising the amino acid sequence of SEQ ID NO: 33; and (d) a VL comprising the amino acid sequence of SEQ ID NO: 19.

In one aspect, the present disclosure provides an antibody or antigen-binding fragment thereof comprising at least one, at least two, or all three VL CDR sequences selected from (a) CDR-L1 comprising the amino acid sequence of SEQ ID NO: 103; (b) CDR-L2 comprising the amino acid sequence of SEQ ID NO: 75; and (c) CDR-L3 comprising the amino acid sequence of SEQ ID NO: 47; and a VH comprising the amino acid sequence of SEQ ID NO: 5.

In one aspect, the present disclosure provides an antibody or antigen-binding fragment thereof comprising the CDRs: CDR-H3 comprising the amino acid sequence of SEQ ID NO: 33; and CDR-L3 comprising the amino acid sequence of SEQ ID NO: 47.

In one aspect, the disclosure herein provides an antibody or antigen-binding fragment thereof comprising at least one, at least two, or all three VL CDR sequences selected from (a) CDR-L1 comprising the amino acid sequence of SEQ ID NO: 103; (b) CDR-L2 comprising the amino acid sequence of SEQ ID NO: 75 and (c) CDR-L3 comprising the amino acid sequence of SEQ ID NO: 47. In one aspect, the disclosure provides an antibody or antigen-binding fragment thereof comprising at least one, at least two, or all three VH CDR sequences selected from (a) CDR-H1 comprising the amino acid sequence of SEQ ID NO: 89; (b) CDR-H2 comprising the amino acid sequence of SEQ ID NO: 61 and (c) CDR-H3 comprising the amino acid sequence of SEQ ID NO: 33.

In one aspect, the disclosure provides an antibody or antigen-binding fragment thereof comprising the CDRs: (a) CDR-H1 comprising the amino acid sequence of SEQ ID NO: 89; (b) CDR-H2 comprising the amino acid sequence of SEQ ID NO: 61; (c) CDR-H3 comprising the amino acid sequence of SEQ ID NO: 33; (d) CDR-L1 comprising the amino acid sequence of SEQ ID NO: 103; (e) CDR-L2 comprising the amino acid sequence of SEQ ID NO: 75; and (f) CDR-L3 comprising the amino acid sequence of SEQ ID NO: 47.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 5. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 5. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 5, including post-translational modifications of that sequence. In a particular embodiment, the VH comprises one, two or three CDRs selected from: (a) CDR-H1 comprising the amino acid sequence of SEQ ID NO: 89, (b) CDR-H2 comprising the amino acid sequence of SEQ ID NO: 61, and (c) CDR-H3 comprising the amino acid sequence of SEQ ID NO: 33.

In one aspect, an antibody or antigen-binding fragment thereof is provided, wherein the antibody or antigen-binding fragment thereof comprises a light chain variable domain (VL) having at least 90%, 91%, 92%, 93%, 94%, 95%, 96%, 97%, 98%, 99%, or 100% sequence identity to the amino acid sequence of SEQ ID NO: 19. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 19. In some embodiments, the substitutions, insertions, or deletions occur in regions outside the CDRs (e.g., in the FRs). Optionally, the antibody or antigen-binding fragment thereof comprises the VL sequence of SEQ ID NO: 19, including post-translational modifications of that sequence. In a particular embodiment, the VL comprises one, two or three CDRs selected from (a) CDR-L1 comprising the amino acid sequence of SEQ ID NO: 103; (b) CDR-L2 comprising the amino acid sequence of SEQ ID NO: 75; and (c) CDR-L3 comprising the amino acid sequence of SEQ ID NO: 47.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 5, and a VL sequence in SEQ ID NO: 19, including post-translational modifications of those sequences.

TMEL1006

In one aspect, the present disclosure provides an antibody or antigen-binding fragment thereof comprises one or more variable regions selected from the group consisting of (a) VH comprising the amino acid sequence of SEQ ID NO: 6, (b) VL comprising the amino acid sequence of SEQ ID NO: 20, and (c) a combination thereof.

In one aspect, the present disclosure provides an antibody or antigen-binding fragment thereof comprising at least one, two, three, four, five, or six CDRs selected from (a) CDR-H1 comprising the amino acid sequence of SEQ ID NO: 90; (b) CDR-H2 comprising the amino acid sequence of SEQ ID NO: 62; (c) CDR-H3 comprising the amino acid sequence of SEQ ID NO: 34; (d) CDR-L1 comprising the amino acid sequence of SEQ ID NO: 104; (e) CDR-L2 comprising the amino acid sequence of SEQ ID NO: 76; and (f) CDR-L3 comprising the amino acid sequence of SEQ ID NO: 48.

In one aspect, the present disclosure provides an antibody or antigen-binding fragment thereof comprising at least one, at least two, or all three VH CDR sequences selected from (a) CDR-H1 comprising the amino acid sequence of SEQ ID NO: 90; (b) CDR-H2 comprising the amino acid sequence of SEQ ID NO: 62; and (c) CDR-H3 comprising the amino acid sequence of SEQ ID NO: 34; and (d) a VL comprising the amino acid sequence of SEQ ID NO: 20.

In one aspect, the present disclosure provides an antibody or antigen-binding fragment thereof comprising at least one, at least two, or all three VL CDR sequences selected from (a) CDR-L1 comprising the amino acid sequence of SEQ ID NO: 104; (b) CDR-L2 comprising the amino acid sequence of SEQ ID NO: 76; and (c) CDR-L3 comprising the amino acid sequence of SEQ ID NO: 48; and a VH comprising the amino acid sequence of SEQ ID NO: 6.

In one aspect, the present disclosure provides an antibody or antigen-binding fragment thereof comprising the CDRs: CDR-H3 comprising the amino acid sequence of SEQ ID NO: 34; and CDR-L3 comprising the amino acid sequence of SEQ ID NO: 48.

In one aspect, the disclosure herein provides an antibody or antigen-binding fragment thereof comprising at least one, at least two, or all three VL CDR sequences selected from (a) CDR-L1 comprising the amino acid sequence of SEQ ID NO: 104; (b) CDR-L2 comprising the amino acid sequence of SEQ ID NO: 76 and (c) CDR-L3 comprising the amino acid sequence of SEQ ID NO: 48. In one aspect, the disclosure provides an antibody or antigen-binding fragment thereof comprising at least one, at least two, or all three VH CDR sequences selected from (a) CDR-H1 comprising the amino acid sequence of SEQ ID NO: 90; (b) CDR-H2 comprising the amino acid sequence of SEQ ID NO: 62 and (c) CDR-H3 comprising the amino acid sequence of SEQ ID NO: 34.

In one aspect, the disclosure provides an antibody or antigen-binding fragment thereof comprising the CDRs: (a) CDR-H1 comprising the amino acid sequence of SEQ ID NO: 90; (b) CDR-H2 comprising the amino acid sequence of SEQ ID NO: 62; (c) CDR-H3 comprising the amino acid sequence of SEQ ID NO: 34; (d) CDR-L1 comprising the amino acid sequence of SEQ ID NO: 104; (e) CDR-L2 comprising the amino acid sequence of SEQ ID NO: 76; and (f) CDR-L3 comprising the amino acid sequence of SEQ ID NO: 48.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 6. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 6. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 6, including post-translational modifications of that sequence. In a particular embodiment, the VH comprises one, two or three CDRs selected from: (a) CDR-H1 comprising the amino acid sequence of SEQ ID NO: 90, (b) CDR-H2 comprising the amino acid sequence of SEQ ID NO: 62, and (c) CDR-H3 comprising the amino acid sequence of SEQ ID NO: 34.

In one aspect, an antibody or antigen-binding fragment thereof is provided, wherein the antibody or antigen-binding fragment thereof comprises a light chain variable domain (VL) having at least 90%, 91%, 92%, 93%, 94%, 95%, 96%, 97%, 98%, 99%, or 100% sequence identity to the amino acid sequence of SEQ ID NO: 20. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 20. In some embodiments, the substitutions, insertions, or deletions occur in regions outside the CDRs (e.g., in the FRs). Optionally, the antibody or antigen-binding fragment thereof comprises the VL sequence of SEQ ID NO: 20, including post-translational modifications of that sequence. In a particular embodiment, the VL comprises one, two or three CDRs selected from (a) CDR-L1 comprising the amino acid sequence of SEQ ID NO: 104; (b) CDR-L2 comprising the amino acid sequence of SEQ ID NO: 76; and (c) CDR-L3 comprising the amino acid sequence of SEQ ID NO: 48.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 6, and a VL sequence in SEQ ID NO: 20, including post-translational modifications of those sequences.

TMEL1007

In one aspect, the present disclosure provides an antibody or antigen-binding fragment thereof comprises one or more variable regions selected from the group consisting of (a) VH comprising the amino acid sequence of SEQ ID NO: 7, (b) VL comprising the amino acid sequence of SEQ ID NO: 21, and (c) a combination thereof.

In one aspect, the present disclosure provides an antibody or antigen-binding fragment thereof comprising at least one, two, three, four, five, or six CDRs selected from (a) CDR-H1 comprising the amino acid sequence of SEQ ID NO: 91; (b) CDR-H2 comprising the amino acid sequence of SEQ ID NO: 63; (c) CDR-H3 comprising the amino acid sequence of SEQ ID NO: 35; (d) CDR-L1 comprising the amino acid sequence of SEQ ID NO: 105; (e) CDR-L2 comprising the amino acid sequence of SEQ ID NO: 77; and (f) CDR-L3 comprising the amino acid sequence of SEQ ID NO: 49.

In one aspect, the present disclosure provides an antibody or antigen-binding fragment thereof comprising at least one, at least two, or all three VH CDR sequences selected from (a) CDR-H1 comprising the amino acid sequence of SEQ ID NO: 91; (b) CDR-H2 comprising the amino acid sequence of SEQ ID NO: 63; and (c) CDR-H3 comprising the amino acid sequence of SEQ ID NO: 35; and (d) a VL comprising the amino acid sequence of SEQ ID NO: 21.

In one aspect, the present disclosure provides an antibody or antigen-binding fragment thereof comprising at least one, at least two, or all three VL CDR sequences selected from (a) CDR-L1 comprising the amino acid sequence of SEQ ID NO: 105; (b) CDR-L2 comprising the amino acid sequence of SEQ ID NO: 77; and (c) CDR-L3 comprising the amino acid sequence of SEQ ID NO: 49; and a VH comprising the amino acid sequence of SEQ ID NO: 7.

In one aspect, the present disclosure provides an antibody or antigen-binding fragment thereof comprising the CDRs: CDR-H3 comprising the amino acid sequence of SEQ ID NO: 35; and CDR-L3 comprising the amino acid sequence of SEQ ID NO: 49.

In one aspect, the disclosure herein provides an antibody or antigen-binding fragment thereof comprising at least one, at least two, or all three VL CDR sequences selected from (a) CDR-L1 comprising the amino acid sequence of SEQ ID NO: 105; (b) CDR-L2 comprising the amino acid sequence of SEQ ID NO: 77 and (c) CDR-L3 comprising the amino acid sequence of SEQ ID NO: 49. In one aspect, the disclosure provides an antibody or antigen-binding fragment thereof comprising at least one, at least two, or all three VH CDR sequences selected from (a) CDR-H1 comprising the amino acid sequence of SEQ ID NO: 91; (b) CDR-H2 comprising the amino acid sequence of SEQ ID NO: 63 and (c) CDR-H3 comprising the amino acid sequence of SEQ ID NO: 35.

In one aspect, the disclosure provides an antibody or antigen-binding fragment thereof comprising the CDRs: (a) CDR-H1 comprising the amino acid sequence of SEQ ID NO: 91; (b) CDR-H2 comprising the amino acid sequence of SEQ ID NO: 63; (c) CDR-H3 comprising the amino acid sequence of SEQ ID NO: 35; (d) CDR-L1 comprising the amino acid sequence of SEQ ID NO: 105; (e) CDR-L2 comprising the amino acid sequence of SEQ ID NO: 77; and (f) CDR-L3 comprising the amino acid sequence of SEQ ID NO: 49.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 7. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 7. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 7, including post-translational modifications of that sequence. In a particular embodiment, the VH comprises one, two or three CDRs selected from: (a) CDR-H1 comprising the amino acid sequence of SEQ ID NO: 91, (b) CDR-H2 comprising the amino acid sequence of SEQ ID NO: 63, and (c) CDR-H3 comprising the amino acid sequence of SEQ ID NO: 35.

In one aspect, an antibody or antigen-binding fragment thereof is provided, wherein the antibody or antigen-binding fragment thereof comprises a light chain variable domain (VL) having at least 90%, 91%, 92%, 93%, 94%, 95%, 96%, 97%, 98%, 99%, or 100% sequence identity to the amino acid sequence of SEQ ID NO: 21. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 21. In some embodiments, the substitutions, insertions, or deletions occur in regions outside the CDRs (e.g., in the FRs). Optionally, the antibody or antigen-binding fragment thereof comprises the VL sequence of SEQ ID NO: 21, including post-translational modifications of that sequence. In a particular embodiment, the VL comprises one, two or three CDRs selected from (a) CDR-L1 comprising the amino acid sequence of SEQ ID NO: 105; (b) CDR-L2 comprising the amino acid sequence of SEQ ID NO: 77; and (c) CDR-L3 comprising the amino acid sequence of SEQ ID NO: 49.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 7, and a VL sequence in SEQ ID NO: 21, including post-translational modifications of those sequences.

TMEL1008

In one aspect, the present disclosure provides an antibody or antigen-binding fragment thereof comprises one or more variable regions selected from the group consisting of (a) VH comprising the amino acid sequence of SEQ ID NO: 8, (b) VL comprising the amino acid sequence of SEQ ID NO: 22, and (c) a combination thereof.

In one aspect, the present disclosure provides an antibody or antigen-binding fragment thereof comprising at least one, two, three, four, five, or six CDRs selected from (a) CDR-H1 comprising the amino acid sequence of SEQ ID NO: 92; (b) CDR-H2 comprising the amino acid sequence of SEQ ID NO: 64; (c) CDR-H3 comprising the amino acid sequence of SEQ ID NO: 36; (d) CDR-L1 comprising the amino acid sequence of SEQ ID NO: 106; (e) CDR-L2 comprising the amino acid sequence of SEQ ID NO: 78; and (f) CDR-L3 comprising the amino acid sequence of SEQ ID NO: 50.

In one aspect, the present disclosure provides an antibody or antigen-binding fragment thereof comprising at least one, at least two, or all three VH CDR sequences selected from (a) CDR-H1 comprising the amino acid sequence of SEQ ID NO: 92; (b) CDR-H2 comprising the amino acid sequence of SEQ ID NO: 64; and (c) CDR-H3 comprising the amino acid sequence of SEQ ID NO: 36; and (d) a VL comprising the amino acid sequence of SEQ ID NO: 22.

In one aspect, the present disclosure provides an antibody or antigen-binding fragment thereof comprising at least one, at least two, or all three VL CDR sequences selected from (a) CDR-L1 comprising the amino acid sequence of SEQ ID NO: 106; (b) CDR-L2 comprising the amino acid sequence of SEQ ID NO: 78; and (c) CDR-L3 comprising the amino acid sequence of SEQ ID NO: 50; and a VH comprising the amino acid sequence of SEQ ID NO: 8.

In one aspect, the present disclosure provides an antibody or antigen-binding fragment thereof comprising the CDRs: CDR-H3 comprising the amino acid sequence of SEQ ID NO: 36; and CDR-L3 comprising the amino acid sequence of SEQ ID NO: 50.

In one aspect, the disclosure herein provides an antibody or antigen-binding fragment thereof comprising at least one, at least two, or all three VL CDR sequences selected from (a) CDR-L1 comprising the amino acid sequence of SEQ ID NO: 106; (b) CDR-L2 comprising the amino acid sequence of SEQ ID NO: 78 and (c) CDR-L3 comprising the amino acid sequence of SEQ ID NO: 50. In one aspect, the disclosure provides an antibody or antigen-binding fragment thereof comprising at least one, at least two, or all three VH CDR sequences selected from (a) CDR-H1 comprising the amino acid sequence of SEQ ID NO: 92; (b) CDR-H2 comprising the amino acid sequence of SEQ ID NO: 64 and (c) CDR-H3 comprising the amino acid sequence of SEQ ID NO: 36.

In one aspect, the disclosure provides an antibody or antigen-binding fragment thereof comprising the CDRs: (a) CDR-H1 comprising the amino acid sequence of SEQ ID NO: 92; (b) CDR-H2 comprising the amino acid sequence of SEQ ID NO: 64; (c) CDR-H3 comprising the amino acid sequence of SEQ ID NO: 36; (d) CDR-L1 comprising the amino acid sequence of SEQ ID NO: 106; (e) CDR-L2 comprising the amino acid sequence of SEQ ID NO: 78; and (f) CDR-L3 comprising the amino acid sequence of SEQ ID NO: 50.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 8. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 8. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 8, including post-translational modifications of that sequence. In a particular embodiment, the VH comprises one, two or three CDRs selected from: (a) CDR-H1 comprising the amino acid sequence of SEQ ID NO: 92, (b) CDR-H2 comprising the amino acid sequence of SEQ ID NO: 64, and (c) CDR-H3 comprising the amino acid sequence of SEQ ID NO: 36.

In one aspect, an antibody or antigen-binding fragment thereof is provided, wherein the antibody or antigen-binding fragment thereof comprises a light chain variable domain (VL) having at least 90%, 91%, 92%, 93%, 94%, 95%, 96%, 97%, 98%, 99%, or 100% sequence identity to the amino acid sequence of SEQ ID NO: 22. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 22. In some embodiments, the substitutions, insertions, or deletions occur in regions outside the CDRs (e.g., in the FRs). Optionally, the antibody or antigen-binding fragment thereof comprises the VL sequence of SEQ ID NO: 22, including post-translational modifications of that sequence. In a particular embodiment, the VL comprises one, two or three CDRs selected from (a) CDR-L1 comprising the amino acid sequence of SEQ ID NO: 106; (b) CDR-L2 comprising the amino acid sequence of SEQ ID NO: 78; and (c) CDR-L3 comprising the amino acid sequence of SEQ ID NO: 50.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 8, and a VL sequence in SEQ ID NO: 22, including post-translational modifications of those sequences.

TMEL1009

In one aspect, the present disclosure provides an antibody or antigen-binding fragment thereof comprises one or more variable regions selected from the group consisting of (a) VH comprising the amino acid sequence of SEQ ID NO: 9, (b) VL comprising the amino acid sequence of SEQ ID NO: 23, and (c) a combination thereof.

In one aspect, the present disclosure provides an antibody or antigen-binding fragment thereof comprising at least one, two, three, four, five, or six CDRs selected from (a) CDR-H1 comprising the amino acid sequence of SEQ ID NO: 93; (b) CDR-H2 comprising the amino acid sequence of SEQ ID NO: 65; (c) CDR-H3 comprising the amino acid sequence of SEQ ID NO: 37; (d) CDR-L1 comprising the amino acid sequence of SEQ ID NO: 107; (e) CDR-L2 comprising the amino acid sequence of SEQ ID NO: 79; and (f) CDR-L3 comprising the amino acid sequence of SEQ ID NO: 51.

In one aspect, the present disclosure provides an antibody or antigen-binding fragment thereof comprising at least one, at least two, or all three VH CDR sequences selected from (a) CDR-H1 comprising the amino acid sequence of SEQ ID NO: 93; (b) CDR-H2 comprising the amino acid sequence of SEQ ID NO: 65; and (c) CDR-H3 comprising the amino acid sequence of SEQ ID NO: 37; and (d) a VL comprising the amino acid sequence of SEQ ID NO: 23.

In one aspect, the present disclosure provides an antibody or antigen-binding fragment thereof comprising at least one, at least two, or all three VL CDR sequences selected from (a) CDR-L1 comprising the amino acid sequence of SEQ ID NO: 107; (b) CDR-L2 comprising the amino acid sequence of SEQ ID NO: 79; and (c) CDR-L3 comprising the amino acid sequence of SEQ ID NO: 51; and a VH comprising the amino acid sequence of SEQ ID NO: 9.

In one aspect, the present disclosure provides an antibody or antigen-binding fragment thereof comprising the CDRs: CDR-H3 comprising the amino acid sequence of SEQ ID NO: 37; and CDR-L3 comprising the amino acid sequence of SEQ ID NO: 51.

In one aspect, the disclosure herein provides an antibody or antigen-binding fragment thereof comprising at least one, at least two, or all three VL CDR sequences selected from (a) CDR-L1 comprising the amino acid sequence of SEQ ID NO: 107; (b) CDR-L2 comprising the amino acid sequence of SEQ ID NO: 79 and (c) CDR-L3 comprising the amino acid sequence of SEQ ID NO: 51. In one aspect, the disclosure provides an antibody or antigen-binding fragment thereof comprising at least one, at least two, or all three VH CDR sequences selected from (a) CDR-H1 comprising the amino acid sequence of SEQ ID NO: 93; (b) CDR-H2 comprising the amino acid sequence of SEQ ID NO: 65 and (c) CDR-H3 comprising the amino acid sequence of SEQ ID NO: 37.

In one aspect, the disclosure provides an antibody or antigen-binding fragment thereof comprising the CDRs: (a) CDR-H1 comprising the amino acid sequence of SEQ ID NO: 93; (b) CDR-H2 comprising the amino acid sequence of SEQ ID NO: 65; (c) CDR-H3 comprising the amino acid sequence of SEQ ID NO: 37; (d) CDR-L1 comprising the amino acid sequence of SEQ ID NO: 107; (e) CDR-L2 comprising the amino acid sequence of SEQ ID NO: 79; and (f) CDR-L3 comprising the amino acid sequence of SEQ ID NO: 51.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 9. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 9. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 9, including post-translational modifications of that sequence. In a particular embodiment, the VH comprises one, two or three CDRs selected from: (a) CDR-H1 comprising the amino acid sequence of SEQ ID NO: 93, (b) CDR-H2 comprising the amino acid sequence of SEQ ID NO: 65, and (c) CDR-H3 comprising the amino acid sequence of SEQ ID NO: 37.

In one aspect, an antibody or antigen-binding fragment thereof is provided, wherein the antibody or antigen-binding fragment thereof comprises a light chain variable domain (VL) having at least 90%, 91%, 92%, 93%, 94%, 95%, 96%, 97%, 98%, 99%, or 100% sequence identity to the amino acid sequence of SEQ ID NO: 23. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 23. In some embodiments, the substitutions, insertions, or deletions occur in regions outside the CDRs (e.g., in the FRs). Optionally, the antibody or antigen-binding fragment thereof comprises the VL sequence of SEQ ID NO: 23, including post-translational modifications of that sequence. In a particular embodiment, the VL comprises one, two or three CDRs selected from (a) CDR-L1 comprising the amino acid sequence of SEQ ID NO: 107; (b) CDR-L2 comprising the amino acid sequence of SEQ ID NO: 79; and (c) CDR-L3 comprising the amino acid sequence of SEQ ID NO: 51.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 9, and a VL sequence in SEQ ID NO: 23, including post-translational modifications of those sequences.

TMEL1010

In one aspect, the present disclosure provides an antibody or antigen-binding fragment thereof comprises one or more variable regions selected from the group consisting of (a) VH comprising the amino acid sequence of SEQ ID NO: 10, (b) VL comprising the amino acid sequence of SEQ ID NO: 24, and (c) a combination thereof.

In one aspect, the present disclosure provides an antibody or antigen-binding fragment thereof comprising at least one, two, three, four, five, or six CDRs selected from (a) CDR-H1 comprising the amino acid sequence of SEQ ID NO: 94; (b) CDR-H2 comprising the amino acid sequence of SEQ ID NO: 66; (c) CDR-H3 comprising the amino acid sequence of SEQ ID NO: 38; (d) CDR-L1 comprising the amino acid sequence of SEQ ID NO: 108; (e) CDR-L2 comprising the amino acid sequence of SEQ ID NO: 80; and (f) CDR-L3 comprising the amino acid sequence of SEQ ID NO: 52.

In one aspect, the present disclosure provides an antibody or antigen-binding fragment thereof comprising at least one, at least two, or all three VH CDR sequences selected from (a) CDR-H1 comprising the amino acid sequence of SEQ ID NO: 94; (b) CDR-H2 comprising the amino acid sequence of SEQ ID NO: 66; and (c) CDR-H3 comprising the amino acid sequence of SEQ ID NO: 38; and (d) a VL comprising the amino acid sequence of SEQ ID NO: 24.

In one aspect, the present disclosure provides an antibody or antigen-binding fragment thereof comprising at least one, at least two, or all three VL CDR sequences selected from (a) CDR-L1 comprising the amino acid sequence of SEQ ID NO: 108; (b) CDR-L2 comprising the amino acid sequence of SEQ ID NO: 80; and (c) CDR-L3 comprising the amino acid sequence of SEQ ID NO: 52; and a VH comprising the amino acid sequence of SEQ ID NO: 10.

In one aspect, the present disclosure provides an antibody or antigen-binding fragment thereof comprising the CDRs: CDR-H3 comprising the amino acid sequence of SEQ ID NO: 38; and CDR-L3 comprising the amino acid sequence of SEQ ID NO: 52.

In one aspect, the disclosure herein provides an antibody or antigen-binding fragment thereof comprising at least one, at least two, or all three VL CDR sequences selected from (a) CDR-L1 comprising the amino acid sequence of SEQ ID NO: 108; (b) CDR-L2 comprising the amino acid sequence of SEQ ID NO: 80 and (c) CDR-L3 comprising the amino acid sequence of SEQ ID NO: 52. In one aspect, the disclosure provides an antibody or antigen-binding fragment thereof comprising at least one, at least two, or all three VH CDR sequences selected from (a) CDR-H1 comprising the amino acid sequence of SEQ ID NO: 94; (b) CDR-H2 comprising the amino acid sequence of SEQ ID NO: 66 and (c) CDR-H3 comprising the amino acid sequence of SEQ ID NO: 38.

In one aspect, the disclosure provides an antibody or antigen-binding fragment thereof comprising the CDRs: (a) CDR-H1 comprising the amino acid sequence of SEQ ID NO: 94; (b) CDR-H2 comprising the amino acid sequence of SEQ ID NO: 66; (c) CDR-H3 comprising the amino acid sequence of SEQ ID NO: 38; (d) CDR-L1 comprising the amino acid sequence of SEQ ID NO: 108; (e) CDR-L2 comprising the amino acid sequence of SEQ ID NO: 80; and (f) CDR-L3 comprising the amino acid sequence of SEQ ID NO: 52.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 10. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 10. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 10, including post-translational modifications of that sequence. In a particular embodiment, the VH comprises one, two or three CDRs selected from: (a) CDR-H1 comprising the amino acid sequence of SEQ ID NO: 94, (b) CDR-H2 comprising the amino acid sequence of SEQ ID NO: 66, and (c) CDR-H3 comprising the amino acid sequence of SEQ ID NO: 38.

In one aspect, an antibody or antigen-binding fragment thereof is provided, wherein the antibody or antigen-binding fragment thereof comprises a light chain variable domain (VL) having at least 90%, 91%, 92%, 93%, 94%, 95%, 96%, 97%, 98%, 99%, or 100% sequence identity to the amino acid sequence of SEQ ID NO: 24. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 24. In some embodiments, the substitutions, insertions, or deletions occur in regions outside the CDRs (e.g., in the FRs). Optionally, the antibody or antigen-binding fragment thereof comprises the VL sequence of SEQ ID NO: 24, including post-translational modifications of that sequence. In a particular embodiment, the VL comprises one, two or three CDRs selected from (a) CDR-L1 comprising the amino acid sequence of SEQ ID NO: 108; (b) CDR-L2 comprising the amino acid sequence of SEQ ID NO: 80; and (c) CDR-L3 comprising the amino acid sequence of SEQ ID NO: 52.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 10, and a VL sequence in SEQ ID NO: 24, including post-translational modifications of those sequences.

TMEL1011

In one aspect, the present disclosure provides an antibody or antigen-binding fragment thereof comprises one or more variable regions selected from the group consisting of (a) VH comprising the amino acid sequence of SEQ ID NO: 11, (b) VL comprising the amino acid sequence of SEQ ID NO: 25, and (c) a combination thereof.

In one aspect, the present disclosure provides an antibody or antigen-binding fragment thereof comprising at least one, two, three, four, five, or six CDRs selected from (a) CDR-H1 comprising the amino acid sequence of SEQ ID NO: 95; (b) CDR-H2 comprising the amino acid sequence of SEQ ID NO: 67; (c) CDR-H3 comprising the amino acid sequence of SEQ ID NO: 39; (d) CDR-L1 comprising the amino acid sequence of SEQ ID NO: 109; (e) CDR-L2 comprising the amino acid sequence of SEQ ID NO: 81; and (f) CDR-L3 comprising the amino acid sequence of SEQ ID NO: 53.

In one aspect, the present disclosure provides an antibody or antigen-binding fragment thereof comprising at least one, at least two, or all three VH CDR sequences selected from (a) CDR-H1 comprising the amino acid sequence of SEQ ID NO: 95; (b) CDR-H2 comprising the amino acid sequence of SEQ ID NO: 67; and (c) CDR-H3 comprising the amino acid sequence of SEQ ID NO: 39; and (d) a VL comprising the amino acid sequence of SEQ ID NO: 25.

In one aspect, the present disclosure provides an antibody or antigen-binding fragment thereof comprising at least one, at least two, or all three VL CDR sequences selected from (a) CDR-L1 comprising the amino acid sequence of SEQ ID NO: 109; (b) CDR-L2 comprising the amino acid sequence of SEQ ID NO: 81; and (c) CDR-L3 comprising the amino acid sequence of SEQ ID NO: 53; and a VH comprising the amino acid sequence of SEQ ID NO: 11.

In one aspect, the present disclosure provides an antibody or antigen-binding fragment thereof comprising the CDRs: CDR-H3 comprising the amino acid sequence of SEQ ID NO: 39; and CDR-L3 comprising the amino acid sequence of SEQ ID NO: 53.

In one aspect, the disclosure herein provides an antibody or antigen-binding fragment thereof comprising at least one, at least two, or all three VL CDR sequences selected from (a) CDR-L1 comprising the amino acid sequence of SEQ ID NO: 109; (b) CDR-L2 comprising the amino acid sequence of SEQ ID NO: 81 and (c) CDR-L3 comprising the amino acid sequence of SEQ ID NO: 53. In one aspect, the disclosure provides an antibody or antigen-binding fragment thereof comprising at least one, at least two, or all three VH CDR sequences selected from (a) CDR-H1 comprising the amino acid sequence of SEQ ID NO: 95; (b) CDR-H2 comprising the amino acid sequence of SEQ ID NO: 67 and (c) CDR-H3 comprising the amino acid sequence of SEQ ID NO: 39.

In one aspect, the disclosure provides an antibody or antigen-binding fragment thereof comprising the CDRs: (a) CDR-H1 comprising the amino acid sequence of SEQ ID NO: 95; (b) CDR-H2 comprising the amino acid sequence of SEQ ID NO: 67; (c) CDR-H3 comprising the amino acid sequence of SEQ ID NO: 39; (d) CDR-L1 comprising the amino acid sequence of SEQ ID NO: 109; (e) CDR-L2 comprising the amino acid sequence of SEQ ID NO: 81; and (f) CDR-L3 comprising the amino acid sequence of SEQ ID NO: 53.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 11. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 11. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 11, including post-translational modifications of that sequence. In a particular embodiment, the VH comprises one, two or three CDRs selected from: (a) CDR-H1 comprising the amino acid sequence of SEQ ID NO: 95, (b) CDR-H2 comprising the amino acid sequence of SEQ ID NO: 67, and (c) CDR-H3 comprising the amino acid sequence of SEQ ID NO: 39.

In one aspect, an antibody or antigen-binding fragment thereof is provided, wherein the antibody or antigen-binding fragment thereof comprises a light chain variable domain (VL) having at least 90%, 91%, 92%, 93%, 94%, 95%, 96%, 97%, 98%, 99%, or 100% sequence identity to the amino acid sequence of SEQ ID NO: 25. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 25. In some embodiments, the substitutions, insertions, or deletions occur in regions outside the CDRs (e.g., in the FRs). Optionally, the antibody or antigen-binding fragment thereof comprises the VL sequence of SEQ ID NO: 25, including post-translational modifications of that sequence. In a particular embodiment, the VL comprises one, two or three CDRs selected from (a) CDR-L1 comprising the amino acid sequence of SEQ ID NO: 109; (b) CDR-L2 comprising the amino acid sequence of SEQ ID NO: 81; and (c) CDR-L3 comprising the amino acid sequence of SEQ ID NO: 53.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 11, and a VL sequence in SEQ ID NO: 25, including post-translational modifications of those sequences.

TMEL1012

In one aspect, the present disclosure provides an antibody or antigen-binding fragment thereof comprises one or more variable regions selected from the group consisting of (a) VH comprising the amino acid sequence of SEQ ID NO: 12, (b) VL comprising the amino acid sequence of SEQ ID NO: 26, and (c) a combination thereof.

In one aspect, the present disclosure provides an antibody or antigen-binding fragment thereof comprising at least one, two, three, four, five, or six CDRs selected from (a) CDR-H1 comprising the amino acid sequence of SEQ ID NO: 96; (b) CDR-H2 comprising the amino acid sequence of SEQ ID NO: 68; (c) CDR-H3 comprising the amino acid sequence of SEQ ID NO: 40; (d) CDR-L1 comprising the amino acid sequence of SEQ ID NO: 110; (e) CDR-L2 comprising the amino acid sequence of SEQ ID NO: 82; and (f) CDR-L3 comprising the amino acid sequence of SEQ ID NO: 54.

In one aspect, the present disclosure provides an antibody or antigen-binding fragment thereof comprising at least one, at least two, or all three VH CDR sequences selected from (a) CDR-H1 comprising the amino acid sequence of SEQ ID NO: 96; (b) CDR-H2 comprising the amino acid sequence of SEQ ID NO: 68; and (c) CDR-H3 comprising the amino acid sequence of SEQ ID NO: 40; and (d) a VL comprising the amino acid sequence of SEQ ID NO: 26.

In one aspect, the present disclosure provides an antibody or antigen-binding fragment thereof comprising at least one, at least two, or all three VL CDR sequences selected from (a) CDR-L1 comprising the amino acid sequence of SEQ ID NO: 110; (b) CDR-L2 comprising the amino acid sequence of SEQ ID NO: 82; and (c) CDR-L3 comprising the amino acid sequence of SEQ ID NO: 54; and a VH comprising the amino acid sequence of SEQ ID NO: 12.

In one aspect, the present disclosure provides an antibody or antigen-binding fragment thereof comprising the CDRs: CDR-H3 comprising the amino acid sequence of SEQ ID NO: 40; and CDR-L3 comprising the amino acid sequence of SEQ ID NO: 54.

In one aspect, the disclosure herein provides an antibody or antigen-binding fragment thereof comprising at least one, at least two, or all three VL CDR sequences selected from (a) CDR-L1 comprising the amino acid sequence of SEQ ID NO: 110; (b) CDR-L2 comprising the amino acid sequence of SEQ ID NO: 82 and (c) CDR-L3 comprising the amino acid sequence of SEQ ID NO: 54. In one aspect, the disclosure provides an antibody or antigen-binding fragment thereof comprising at least one, at least two, or all three VH CDR sequences selected from (a) CDR-H1 comprising the amino acid sequence of SEQ ID NO: 96; (b) CDR-H2 comprising the amino acid sequence of SEQ ID NO: 68 and (c) CDR-H3 comprising the amino acid sequence of SEQ ID NO: 40.

In one aspect, the disclosure provides an antibody or antigen-binding fragment thereof comprising the CDRs: (a) CDR-H1 comprising the amino acid sequence of SEQ ID NO: 96; (b) CDR-H2 comprising the amino acid sequence of SEQ ID NO: 68; (c) CDR-H3 comprising the amino acid sequence of SEQ ID NO: 40; (d) CDR-L1 comprising the amino acid sequence of SEQ ID NO: 110; (e) CDR-L2 comprising the amino acid sequence of SEQ ID NO: 82; and (f) CDR-L3 comprising the amino acid sequence of SEQ ID NO: 54.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 12. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 12. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 12, including post-translational modifications of that sequence. In a particular embodiment, the VH comprises one, two or three CDRs selected from: (a) CDR-H1 comprising the amino acid sequence of SEQ ID NO: 96, (b) CDR-H2 comprising the amino acid sequence of SEQ ID NO: 68, and (c) CDR-H3 comprising the amino acid sequence of SEQ ID NO: 40.

In one aspect, an antibody or antigen-binding fragment thereof is provided, wherein the antibody or antigen-binding fragment thereof comprises a light chain variable domain (VL) having at least 90%, 91%, 92%, 93%, 94%, 95%, 96%, 97%, 98%, 99%, or 100% sequence identity to the amino acid sequence of SEQ ID NO: 26. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 26. In some embodiments, the substitutions, insertions, or deletions occur in regions outside the CDRs (e.g., in the FRs). Optionally, the antibody or antigen-binding fragment thereof comprises the VL sequence of SEQ ID NO: 26, including post-translational modifications of that sequence. In a particular embodiment, the VL comprises one, two or three CDRs selected from (a) CDR-L1 comprising the amino acid sequence of SEQ ID NO: 110; (b) CDR-L2 comprising the amino acid sequence of SEQ ID NO: 82; and (c) CDR-L3 comprising the amino acid sequence of SEQ ID NO: 54.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 12, and a VL sequence in SEQ ID NO: 26, including post-translational modifications of those sequences.

TMEL1013

In one aspect, the present disclosure provides an antibody or antigen-binding fragment thereof comprises one or more variable regions selected from the group consisting of (a) VH comprising the amino acid sequence of SEQ ID NO: 13, (b) VL comprising the amino acid sequence of SEQ ID NO: 27, and (c) a combination thereof.

In one aspect, the present disclosure provides an antibody or antigen-binding fragment thereof comprising at least one, two, three, four, five, or six CDRs selected from (a) CDR-H1 comprising the amino acid sequence of SEQ ID NO: 97; (b) CDR-H2 comprising the amino acid sequence of SEQ ID NO: 69; (c) CDR-H3 comprising the amino acid sequence of SEQ ID NO: 41; (d) CDR-L1 comprising the amino acid sequence of SEQ ID NO: 111; (e) CDR-L2 comprising the amino acid sequence of SEQ ID NO: 83; and (f) CDR-L3 comprising the amino acid sequence of SEQ ID NO: 55.

In one aspect, the present disclosure provides an antibody or antigen-binding fragment thereof comprising at least one, at least two, or all three VH CDR sequences selected from (a) CDR-H1 comprising the amino acid sequence of SEQ ID NO: 97; (b) CDR-H2 comprising the amino acid sequence of SEQ ID NO: 69; and (c) CDR-H3 comprising the amino acid sequence of SEQ ID NO: 41; and (d) a VL comprising the amino acid sequence of SEQ ID NO: 27.

In one aspect, the present disclosure provides an antibody or antigen-binding fragment thereof comprising at least one, at least two, or all three VL CDR sequences selected from (a) CDR-L1 comprising the amino acid sequence of SEQ ID NO: 111; (b) CDR-L2 comprising the amino acid sequence of SEQ ID NO: 83; and (c) CDR-L3 comprising the amino acid sequence of SEQ ID NO: 55; and a VH comprising the amino acid sequence of SEQ ID NO: 13.

In one aspect, the present disclosure provides an antibody or antigen-binding fragment thereof comprising the CDRs: CDR-H3 comprising the amino acid sequence of SEQ ID NO: 41; and CDR-L3 comprising the amino acid sequence of SEQ ID NO: 55.

In one aspect, the disclosure herein provides an antibody or antigen-binding fragment thereof comprising at least one, at least two, or all three VL CDR sequences selected from (a) CDR-L1 comprising the amino acid sequence of SEQ ID NO: 111; (b) CDR-L2 comprising the amino acid sequence of SEQ ID NO: 83 and (c) CDR-L3 comprising the amino acid sequence of SEQ ID NO: 55. In one aspect, the disclosure provides an antibody or antigen-binding fragment thereof comprising at least one, at least two, or all three VH CDR sequences selected from (a) CDR-H1 comprising the amino acid sequence of SEQ ID NO: 97; (b) CDR-H2 comprising the amino acid sequence of SEQ ID NO: 69 and (c) CDR-H3 comprising the amino acid sequence of SEQ ID NO: 41.

In one aspect, the disclosure provides an antibody or antigen-binding fragment thereof comprising the CDRs: (a) CDR-H1 comprising the amino acid sequence of SEQ ID NO: 97; (b) CDR-H2 comprising the amino acid sequence of SEQ ID NO: 69; (c) CDR-H3 comprising the amino acid sequence of SEQ ID NO: 41; (d) CDR-L1 comprising the amino acid sequence of SEQ ID NO: 111; (e) CDR-L2 comprising the amino acid sequence of SEQ ID NO: 83; and (f) CDR-L3 comprising the amino acid sequence of SEQ ID NO: 55.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 13. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 13. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 13, including post-translational modifications of that sequence. In a particular embodiment, the VH comprises one, two or three CDRs selected from: (a) CDR-H1 comprising the amino acid sequence of SEQ ID NO: 97, (b) CDR-H2 comprising the amino acid sequence of SEQ ID NO: 69, and (c) CDR-H3 comprising the amino acid sequence of SEQ ID NO: 41.

In one aspect, an antibody or antigen-binding fragment thereof is provided, wherein the antibody or antigen-binding fragment thereof comprises a light chain variable domain (VL) having at least 90%, 91%, 92%, 93%, 94%, 95%, 96%, 97%, 98%, 99%, or 100% sequence identity to the amino acid sequence of SEQ ID NO: 27. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 27. In some embodiments, the substitutions, insertions, or deletions occur in regions outside the CDRs (e.g., in the FRs). Optionally, the antibody or antigen-binding fragment thereof comprises the VL sequence of SEQ ID NO: 27, including post-translational modifications of that sequence. In a particular embodiment, the VL comprises one, two or three CDRs selected from (a) CDR-L1 comprising the amino acid sequence of SEQ ID NO: 111; (b) CDR-L2 comprising the amino acid sequence of SEQ ID NO: 83; and (c) CDR-L3 comprising the amino acid sequence of SEQ ID NO: 55.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 13, and a VL sequence in SEQ ID NO: 27, including post-translational modifications of those sequences.

TMEL1014

In one aspect, the present disclosure provides an antibody or antigen-binding fragment thereof comprises one or more variable regions selected from the group consisting of (a) VH comprising the amino acid sequence of SEQ ID NO: 14, (b) VL comprising the amino acid sequence of SEQ ID NO: 28, and (c) a combination thereof.

In one aspect, the present disclosure provides an antibody or antigen-binding fragment thereof comprising at least one, two, three, four, five, or six CDRs selected from (a) CDR-H1 comprising the amino acid sequence of SEQ ID NO: 98; (b) CDR-H2 comprising the amino acid sequence of SEQ ID NO: 70; (c) CDR-H3 comprising the amino acid sequence of SEQ ID NO: 42; (d) CDR-L1 comprising the amino acid sequence of SEQ ID NO: 112; (e) CDR-L2 comprising the amino acid sequence of SEQ ID NO: 84; and (f) CDR-L3 comprising the amino acid sequence of SEQ ID NO: 56.

In one aspect, the present disclosure provides an antibody or antigen-binding fragment thereof comprising at least one, at least two, or all three VH CDR sequences selected from (a) CDR-H1 comprising the amino acid sequence of SEQ ID NO: 98; (b) CDR-H2 comprising the amino acid sequence of SEQ ID NO: 70; and (c) CDR-H3 comprising the amino acid sequence of SEQ ID NO: 42; and (d) a VL comprising the amino acid sequence of SEQ ID NO: 28.

In one aspect, the present disclosure provides an antibody or antigen-binding fragment thereof comprising at least one, at least two, or all three VL CDR sequences selected from (a) CDR-L1 comprising the amino acid sequence of SEQ ID NO: 112; (b) CDR-L2 comprising the amino acid sequence of SEQ ID NO: 84; and (c) CDR-L3 comprising the amino acid sequence of SEQ ID NO: 56; and a VH comprising the amino acid sequence of SEQ ID NO: 14.

In one aspect, the present disclosure provides an antibody or antigen-binding fragment thereof comprising the CDRs: CDR-H3 comprising the amino acid sequence of SEQ ID NO: 42; and CDR-L3 comprising the amino acid sequence of SEQ ID NO: 56.

In one aspect, the disclosure herein provides an antibody or antigen-binding fragment thereof comprising at least one, at least two, or all three VL CDR sequences selected from (a) CDR-L1 comprising the amino acid sequence of SEQ ID NO: 112; (b) CDR-L2 comprising the amino acid sequence of SEQ ID NO: 84 and (c) CDR-L3 comprising the amino acid sequence of SEQ ID NO: 56. In one aspect, the disclosure provides an antibody or antigen-binding fragment thereof comprising at least one, at least two, or all three VH CDR sequences selected from (a) CDR-H1 comprising the amino acid sequence of SEQ ID NO: 98; (b) CDR-H2 comprising the amino acid sequence of SEQ ID NO: 70 and (c) CDR-H3 comprising the amino acid sequence of SEQ ID NO: 42.

In one aspect, the disclosure provides an antibody or antigen-binding fragment thereof comprising the CDRs: (a) CDR-H1 comprising the amino acid sequence of SEQ ID NO: 98; (b) CDR-H2 comprising the amino acid sequence of SEQ ID NO: 70; (c) CDR-H3 comprising the amino acid sequence of SEQ ID NO: 42; (d) CDR-L1 comprising the amino acid sequence of SEQ ID NO: 112; (e) CDR-L2 comprising the amino acid sequence of SEQ ID NO: 84; and (f) CDR-L3 comprising the amino acid sequence of SEQ ID NO: 56.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 14. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 14. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 14, including post-translational modifications of that sequence. In a particular embodiment, the VH comprises one, two or three CDRs selected from: (a) CDR-H1 comprising the amino acid sequence of SEQ ID NO: 98, (b) CDR-H2 comprising the amino acid sequence of SEQ ID NO: 70, and (c) CDR-H3 comprising the amino acid sequence of SEQ ID NO: 42.

In one aspect, an antibody or antigen-binding fragment thereof is provided, wherein the antibody or antigen-binding fragment thereof comprises a light chain variable domain (VL) having at least 90%, 91%, 92%, 93%, 94%, 95%, 96%, 97%, 98%, 99%, or 100% sequence identity to the amino acid sequence of SEQ ID NO: 28. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 28. In some embodiments, the substitutions, insertions, or deletions occur in regions outside the CDRs (e.g., in the FRs). Optionally, the antibody or antigen-binding fragment thereof comprises the VL sequence of SEQ ID NO: 28, including post-translational modifications of that sequence. In a particular embodiment, the VL comprises one, two or three CDRs selected from (a) CDR-L1 comprising the amino acid sequence of SEQ ID NO: 112; (b) CDR-L2 comprising the amino acid sequence of SEQ ID NO: 84; and (c) CDR-L3 comprising the amino acid sequence of SEQ ID NO: 56.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 14, and a VL sequence in SEQ ID NO: 28, including post-translational modifications of those sequences.

Antibodies

As described above, the antibodies of the present disclosure are referred to as TMEL1001, TMEL1002, TMEL1003, TMEL1004, TMEL1005, TMEL1006, TMEL1007, TMEL1008, TMEL1009, TMEL1010, TMEL1011, TMEL1012, TMEL1013, and TMEL1014. A sequence listing which facilitates identification of individual amino acid sequences and nucleic acid sequences for a particular antibody and their CDR is provided herein. Tables 1-4 discloses the sequences and the preferred pairing of sequences for individual antibody is summarized in Table 7. Provided herein are compositions comprising at least one of the antibody or antigen binding fragment thereof disclosed herein, for example, comprising the specified polypeptide sequences or having a sequence that is at least 80%, 85%, 90%, 95% or more identical to the specified sequence, and Nucleic acid. The present disclosure provides cancer associated antibodies that find use in treating, preventing and/or diagnosing a cancer. The term "cancer associated antibody" as used herein refers to an antibody specific for a cancer associated antigen. In some embodiments, the cancer associated antibody comprises at least one antigen binding region specific for a cancer associated antigen. Disclosed herein are the complete reconstructed nucleic acid consensus sequences and complete reconstructed polypeptide consensus sequences of the variable heavy chain (VH) and variable light chain (VL) of the antibodies. The nucleic acid and polypeptide sequences of the CDR1, CDR2 and CDR3 of the VH and the VL are also provided.

An antibody includes, for example, monoclonal antibodies, chimeric antibodies, humanized antibodies, human antibodies, recombinant antibodies, chemically engineered antibodies, deimmunized antibodies, affinity-matured antibodies, multispecific antibodies (for example, bispecific antibodies and polyreactive antibodies), heteroconjugate antibodies, antibody fragments, and combinations thereof (e.g., a monoclonal antibody that is also deimmunized, a humanized antibody that is also deimmunized, etc.). An antibody includes, but not be limited to, any specific binding member, immunoglobulin class and/or isotype (e.g., IgG1, IgG2, IgG3, IgG4, IgM, IgA, IgD, IgE and IgM); and biologically relevant fragment or specific binding member thereof, including but not limited to Fab, F(ab')2, Fv, and scFv (single chain or related entity). A monoclonal antibody is obtained from a population of substantially homogeneous antibodies, i.e., the individual antibodies comprising the population are identical except for possible naturally occurring mutations that may be present in minor amounts. A polyclonal antibody is a preparation that includes different antibodies directed against different determinants (epitopes).

It is understood in the art that an antibody is a glycoprotein having at least two heavy (H) chains and two light (L) chains interconnected by disulfide bonds, or an antigen binding portion thereof. A heavy chain is comprised of a heavy chain variable region (VH) and a heavy chain constant region (CH1, CH2 and CH3). A light chain is comprised of a light chain variable region (VL) and a light chain constant region (CL). The variable regions of both the heavy and light chains comprise framework regions (FRs or FWRs) and hypervariable regions (HVRs). The HVRs are the amino acid residues of an antibody that are responsible for antigen binding. The hypervariable region generally comprises amino acid residues from a complementarity determining region (CDR), which have the highest sequence variability and/or involved in antigen recognition. With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See, e.g., Fransson, Front. Biosci. 13:1619-1633 (2008).)

Unless otherwise indicated, HVR residues and other residues in the variable domain (e.g., FR residues) are numbered herein according to Kabat et al., supra. A variable region is a domain of an antibody heavy or light chain that is involved in binding the antibody to antigen. (See, e.g., Kindt et al. Kuby Immunology, 6th ed., W.H. Freeman and Co., p. 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. (See, e.g., Portolano et al., J. Immunol. 150:880-887 (1993); Clarkson et al., Nature 352:624-628 (1991)). The four FWR regions are typically more conserved while CDR regions (CDR1, CDR2 and CDR3) represent hypervariable regions and are arranged from NH2 terminus to the COOH terminus as follows: FWR1, CDR1, FWR2, CDR2, FWR3, CDR3, and FWR4. The variable regions of the heavy and light chains contain a binding domain that interacts with an antigen while, depending of the isotype, the constant region(s) may mediate the binding of the immunoglobulin to host tissues or factors. An antibody also includes chimeric antibodies, humanized antibodies, and recombinant antibodies, human antibodies generated from a transgenic non-human animal, as well as antibodies selected from libraries using enrichment technologies available to the artisan.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B

Antibody Properties
Mutation Frequency

The antibodies or antigen binding fragment thereof of the present disclosure can comprise a heavy chain sequence with a mutation frequency of at least about 5%, 6%, 7%, 8%, 9%, 10%, 11%, 12%, 13%, 14%, 15%, 16%, 17%, 18%, 19%, or 20%, or higher from a germline sequence. In some embodiments, the reconstructed germline polypeptide sequences of the antibodies or antigen binding fragment thereof of the disclosure can be selected from Table 5. In some embodiments, the reconstructed germline polypeptide sequence of the variable heavy chain can be selected from sequences set forth in SEQ ID NOs: 225-238. In some embodiments, the reconstructed germline polypeptide sequence of the variable light chain can be selected from SEQ ID NOs.: 239-252. In some embodiments, the reconstructed germline nucleic acid sequence of the antibodies or antigen binding fragment thereof of the present disclosure can be selected from Table 6. In some embodiments, the reconstructed germline nucleic acid sequence of the variable heavy chain can be selected from SEQ ID NOs.: 253-266. In some embodiments, the reconstructed germline nucleic acid sequence of the variable light chain is selected from SEQ ID NOs.: 267-280. The antibodies of the present disclosure can comprise a CDR3 region that is a light chain sequence with a mutation frequency of at least about 5%, 6%, 7%, 8%, 9%, 10%, 11%, 12%, 13%, 14%, 15%, 16%, 17%, 18%, 19%, or 20%, or higher from a germline sequence. The antibodies or antigen binding fragment thereof of the invention can comprise a heavy chain and a light chain sequence with a mutation frequency of at least about 5%, 6%, 7%, 8%, 9%, 10%, 11%, 12%, 13%, 14%, 15%, 16%, 17%, 18%, 19%, or 20%, or higher from a germline sequence. The antibodies or antigen binding fragment thereof of the invention can comprise a $V_H$ region from a $V_H$ family selected from the group consisting of any one of $V_H$ family 4-59.

Heavy and Light Chain Lengths

The antibodies or antigen binding fragment thereof of the present disclosure can comprise a CDR1, CDR2, and/or CDR3 region that is a length of at least about 10, 11, 12, 13, 14, 15, 16, 17, 18, 19, 20, 21, 22, 23, 24, 25, 26, 27, 28, 29, or 30 amino acids in length. The antibodies or antigen binding fragment thereof of the present disclosure can comprise a CDR1, CDR2, and/or CDR3 region that is at least about 18 amino acids in length.

The antibodies or antigen binding fragment thereof of the present disclosure can comprise a deletion at an end of a light chain. The antibodies or antigen binding fragment thereof of the invention can comprise a deletion of 3 or more amino acids at an end of the light chain. The antibodies or antigen binding fragment thereof of the invention can comprise a deletion of 7 or less amino acids at an end of the light chain. The antibodies or antigen binding fragment thereof of the invention can comprise a deletion of 3, 4, 5, 6, or 7 amino acids at an end of the light chain.

The antibodies or antigen binding fragment thereof of the present disclosure can comprise an insertion in a light chain. The antibodies or antigen binding fragment thereof of the invention can comprise an insertion of 1, 2, 3, 4, 5, 6, 7, 8, 9, or 10, or more amino acids in the light chain. The antibodies or antigen binding fragment thereof of the invention can comprise an insertion of 3 amino acids in the light chain

Affinity

Affinity is the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($k_d$). Affinity can be measured by common methods known in the art, including those described herein. Specific illustrative and exemplary embodiments for measuring binding affinity are described in the following.

In some embodiments, an antibody provided herein has a dissociation constant ($K_D$) of about 1 μM, 100 nM, 10 nM, 5 nM, 2 nM, 1 nM, 0.5 nM, 0.1 nM, 0.05 nM, 0.01 nM, or 0.001 nM or less (e.g., $10^{-8}$M or less, e.g., from $10^{-8}$M to $10^{-13}$M, e.g., from $10^{-9}$M to $10^{-13}$ M). Another aspect of the invention provides for an antibody or antigen binding fragment thereof with an increased affinity for its target, for example, an affinity matured antibody. An affinity matured antibody is an antibody with one or more alterations in one or more hypervariable regions (HVRs), compared to a parent antibody which does not possess such alterations, such alterations resulting in an improvement in the affinity of the antibody for antigen. These antibodies can bind to antigen with a $K_D$ of about $5\times10^{-9}$M, $2\times10^{-9}$M, $1\times10^{-9}$M, $5\times10^{-10}$ M, $2\times10^{-9}$M, $1\times10^{-10}$ M, $5\times10^{-11}$M, $1\times10^{-11}$M, $5\times10^{-12}$ M, $1\times10^{-12}$ M, or less. In some embodiments, the present disclosure provides an antibody or antigen binding fragment thereof which has an increased affinity of at least 1.5 fold, 2 fold, 2.5 fold, 3 fold, 4 fold, 5 fold, 10 fold, 20 fold or greater as compared to a germline antibody containing the heavy chain sequence and light chain sequence, or both. In other embodiments, an antibody is provided that competes for binding to the same epitope as an antibody as described herein. In some embodiments, the antibody or antigen binding fragment thereof that binds to the same epitope, and/or competes for binding to the same epitope as an antibody exhibits effector function activities, such as, for example, Fc-mediated cellular cytotoxicity, including ADCC activity.

$K_D$ can be measured by any suitable assay. For example, $K_D$ can be measured by a radiolabeled antigen binding assay (RIA) (See, e.g., Chen et al., J. Mol. Biol. 293:865-881 (1999); Presta et al., Cancer Res. 57:4593-4599 (1997)). For example, $K_D$ can be measured using surface plasmon resonance assays (e.g., using a BIACORE®-2000 or a BIACORE®-3000).

Antigen-Binding Fragments

The terms "antibody fragment," "antigen-binding fragment," or "antibody binding domain" refer to at least one portion of an antibody, or recombinant variants thereof, that contains the antigen-binding domain, i.e., an antigenic determining variable region of an intact antibody, that is sufficient to confer recognition and specific binding of the antibody fragment to a target, such as an antigen and its defined epitope. Examples of antigen-binding fragments include, but are not limited to, Fab, Fab', F(ab')$_2$, and Fv fragments, single-chain (sc)Fv ("scFv") antibody fragments, linear antibodies, single domain antibodies such as sdAb (either $V_L$ or $V_H$), camelid $V_{HH}$ domains, and multi-specific antibodies formed from antibody fragments. In another embodiment, the antibody is a full length antibody, e.g., an intact IgG1 antibody or other antibody class or isotype as described herein. (See, e.g., Hudson et al. Nat. Med. 9:129-134 (2003); Pluckthiin, The Pharmacology of Monoclonal Antibodies, vol. 113, pp. 269-315 (1994); Hollinger et al., Proc. Natl. Acad. Sci. USA 90: 6444-6448 (1993)). A full length antibody, intact antibody, or whole antibody is an antibody having a structure substantially similar to a native antibody structure or having heavy chains that contain an Fc region as defined herein. Antibody fragments can be made by various techniques, including but not limited to proteolytic digestion of an intact antibody as well as production by recombinant host cells (e.g., *E. coli* or phage), as described herein.

An Fv is the minimum antibody fragment that contains a complete antigen-recognition and antigen-binding site. This fragment contains a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable region (or half of an Fv comprising only three CDRs specific for an antigen) has the ability to recognize and bind antigen, although at a lower affinity than the entire binding site.

The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single polypeptide chain, and wherein the scFv retains the specificity of the intact antibody from which it is derived. Unless specified, as used herein a scFv may have the VL and VH variable regions in either order, e.g., with respect to the N-terminal and C-terminal ends of the polypeptide, the scFv may comprise VL-linker-VH or may comprise VH-linker-VL.

A diabody is a small antibody fragment prepared by constructing an sFv fragment with a short linker (about 5-10 residues) between the $V_H$ and $V_L$ domains such that interchain but not intra-chain pairing of the V domains is achieved, resulting in a bivalent fragment. Bispecific diabodies are heterodimers of two crossover sFv fragments in which the $V_H$ and $V_L$ domains of the two antibodies are present on different polypeptide chains. (See, e.g., Hollinger et al, Proc. Natl. Acad. Sci. USA, 90:6444-6448 (1993)).

Domain antibodies (dAbs), which can be produced in fully human form, are the smallest known antigen-binding fragments of antibodies, ranging from about 11 kDa to about 15 kDa. DAbs are the robust variable regions of the heavy and light chains of immunoglobulins ($V_H$ and $V_L$, respectively). They are highly expressed in microbial cell culture, show favorable biophysical properties including, for example, but not limited to, solubility and temperature stability, and are well suited to selection and affinity maturation by in vitro selection systems such as, for example, phage display. DAbs are bioactive as monomers and, owing to their small size and inherent stability can be formatted into larger molecules to create drugs with prolonged serum half-lives or other pharmacological activities.

Fv and scFv are the only species with intact combining sites that are devoid of constant regions. Thus, they are suitable for reduced nonspecific binding during in vivo use. scFv fusion proteins can be constructed to yield fusion of an effector protein at either the amino or the carboxy terminus of an scFv. The antibody fragment also can be a "linear antibody. Such linear antibody fragments can be monospecific or bispecific.

Chimeric Antibodies

In some embodiments, an antibody provided herein is a chimeric. As used herein the term, "chimeric antibody" refers to an antibody in which a portion of the heavy and/or light chain is derived from a particular source or species, while the remainder of the heavy and/or light chain is derived from a different source or species. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof. For details, see, for example, Jones et al., Nature 321: 522-525 (1986); Reichmann et al., Nature 332: 323-329 (1988); Presta, Curr. Op. Struct. Biol., 2: 593-596 (1992); and Morrison et al., Proc. Natl. Acad. Sci. USA, 81:6851-6855 (1984).

Humanized Antibodies

In some embodiments, an antibody provided herein is a humanized antibody. In one embodiment, a humanized antibody is an antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. See, e.g., Almagro and Fransson, Front. Biosci. 13:1619-1633 (2008); Riechmann et al., Nature 332:323-329 (1988); Queen et al., Proc. Nat'l Acad. Sci. USA 86:10029-10033 (1989); Kashmiri et al., Methods 36:25-34 (2005); Padlan, Mol. Immunol. 28:489-498 (1991); Dall'Acqua et al., Methods 36:43-60 (2005); Osbourn et al., Methods 36:61-68 (2005); and Klimka et al., Br. J. Cancer, 83:252-260 (2000).

A non-human antibody can be humanized to reduce immunogenicity to humans, while retaining the specificity and affinity of the parental non-human antibody. A humanized antibody can comprise one or more variable domains comprising one or more CDRs, or portions thereof, derived from a non-human antibody. A humanized antibody can comprise one or more variable domains comprising one or more FRs, or portions thereof, derived from human antibody sequences. A humanized antibody can optionally comprise at least a portion of a human constant region. In some embodiments, one or more FR residues in a humanized antibody are substituted with corresponding residues from a non-human antibody (e.g., the antibody from which the CDR residues are derived), e.g., to restore or improve antibody specificity or affinity.

Human framework regions that may be used for humanization include but are not limited to: framework regions selected using a "best-fit" method; framework regions derived from the consensus sequence of human antibodies of a particular subgroup of light or heavy chain variable regions; human mature (somatically mutated) framework regions or human germline framework regions; and framework regions derived from screening FR libraries (See, e.g., Sims et al., J. Immunol. 151:2296 (1993); Carter et al. Proc. Natl. Acad. Sci. USA, 89:4285 (1992); Presta et al., J. Immunol., 151:2623 (1993); Baca et al., J. Biol. Chem. 272:10678-10684 (1997); and Rosok et al., J. Biol. Chem. 271:22611-22618 (1996)).

Human Antibodies

In some embodiments, an antibody provided herein is a human antibody. Human antibodies can be produced using various techniques known in the art (See, e.g., van Dijk and van de Winkel, Curr. Opin. Pharmacol. 5: 368-74 (2001); and Lonberg, Curr. Opin. Immunol. 20:450-459 (2008)). A human antibody is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. Human antibodies may be prepared by administering an immunogen (e.g., a cancer cell antigen) to a transgenic animal that has been modified to produce intact human antibodies or intact antibodies with human variable regions in response to antigenic challenge. (See, e.g., Lonberg, *Nat. Biotech.* 23:1117-1125 (2005)). Human variable regions from intact antibodies generated by such animals may be further modified, e.g., by combining with a different human constant region.

Human antibodies can also be made by hybridoma-based methods. For example, human antibodies can be produced from human myeloma and mouse-human heteromyeloma cell lines, using human B-cell hybridoma technology, and other methods (See, e.g., Kozbor J. Immunol., 133: 3001 (1984); Brodeur et al., Monoclonal Antibody Production Techniques and Applications, pp. 51-63 (1987); Boerner et al., J. Immunol., 147: 86 (1991); Li et al., Proc. Natl. Acad., 103:3557-3562 (2006); Ni, Xiandai Mianyixue, 26(4):265-268 (2006); Vollmers and Brandlein, Histology and Histopathology, 20(3):927-937 (2005); and Vollmers and Brandlein, Methods and Findings in Experimental and Clinical *Pharmacology*, 27(3):185-91 (2005)). Human antibodies may also be generated by isolating Fv clone variable domain sequences selected from human-derived phage display libraries. Such variable domain sequences may then be combined with a desired human constant domain.

Deimmunized Antibodies

An antibody or an antigen-binding fragment thereof described herein can be optionally assessed for immunogenicity and, as needed, be deimmunized (i.e., the antibody is made less immunoreactive by altering one or more T cell epitopes). As used herein, a "deimmunized antibody" means that one or more T cell epitopes in an antibody sequence have been modified such that a T cell response after administration of the antibody to a subject is reduced compared to an antibody that has not been deimmunized, yet the antibody retains its binding activity. Analysis of immunogenicity and T-cell epitopes present in the antibodies and antigen-binding fragments described herein can be carried out via the use of software and specific databases known in the art. Exemplary software and databases include iTope™ developed by Antitope of Cambridge, England. iTope™, is an in silico technology for analysis of peptide binding to human MHC class II alleles. The iTope™ software predicts peptide binding to human MHC class II alleles and thereby provides an initial screen for the location of such "potential T cell epitopes." iTope™ software predicts favorable interactions between amino acid side chains of a peptide and specific binding pockets within the binding grooves of 34 human MHC class II alleles. The location of key binding residues is achieved by the in silico generation of 9 mer peptides that overlap by one amino acid spanning the test antibody variable region sequence. Each 9 mer peptide can be tested against each of the 34 MHC class II allotypes and scored based on their potential "fit" and interactions with the MHC class II binding groove. Peptides that produce a high mean binding score (>0.55 in the iTope™ scoring function) against >50% of the MHC class II alleles are considered as potential T cell epitopes. In such regions, the core 9 amino acid sequence for peptide binding within the MHC class II groove is analyzed to determine the MHC class II pocket residues (P1, P4, P6, P7 and P9) and the possible T cell receptor (TCR) contact residues (P-1, P2, P3, P5, P8). After identification of any T-cell epitopes, amino acid residue changes, substitutions, additions, and/or deletions can be introduced to remove the identified T-cell epitope. Such changes can be made so as to preserve antibody structure and function while still removing the identified epitope. Exemplary changes can include, but are not limited to, conservative amino acid changes.

Multispecific Antibodies and Antigen-Binding Fragments

In some embodiments, an antibody provided herein is a multispecific antibody, e.g., a bispecific antibody. Multispecific antibodies are monoclonal antibodies that have binding specificities for at least two different sites. In some embodiments, one of the binding specificities is for cancer associated antigen and the other is for any other antigen. In some embodiments, bispecific antibodies may bind to two different epitopes of antigen. Bispecific antibodies may also be used to localize cytotoxic agents to cancer cells. Bispecific antibodies can be prepared as full length antibodies or antibody fragments.

Exemplary techniques for making multispecific antibodies include recombinant co-expression of two immunoglobulin heavy chain-light chain pairs having different specificities, engineering electrostatic steering effects for making antibody Fc-heterodimeric molecules, cross-linking two or more antibodies or fragments, using leucine zippers to produce bi-specific antibodies, using "diabody" technology for making bispecific antibody fragments, using single-chain Fv (sFv) dimers, preparing trispecific antibodies, and "knob-in-hole" engineering (See, e.g., Milstein and Cuello, Nature 305: 537 (1983); Traunecker et al., EMBO J. 10: 3655 (1991); U.S. Pat. Nos. 4,676,980 and 5,731,168; Brennan et al., Science, 229: 81 (1985); Kostelny et al., J. Immunol., 148(5):1547-1553 (1992); Hollinger et al., Proc. Natl. Acad. Sci. USA, 90:6444-6448 (1993); Gruber et al., J. Immunol., 152:5368 (1994)); and Tutt et al. J. Immunol. 147: 60 (1991)). Engineered antibodies with three or more functional antigen binding sites are also contemplated.

Variants

In another aspect, provided herein are variants of antibodies or antigen-binding fragments thereof.

Substitution, Insertion, and Deletion Variants

In some embodiments, amino acid sequence variants of the antibodies provided herein are contemplated. A variant typically differs from a polypeptide specifically disclosed herein in one or more substitutions, deletions, additions and/or insertions. Such variants can be naturally occurring or can be synthetically generated, for example, by modifying one or more of the above polypeptide sequences of the invention and evaluating one or more biological activities of the polypeptide as described herein and/or using any of a number of techniques well known in the art. For example, it may be desirable to improve the binding affinity and/or other biological properties of the antibody amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In some embodiments, antibody variants or antigen binding fragment thereof having one or more amino acid substitutions are provided. Sites of interest for mutagenesis by substitution include the CDRs and FRs. Amino acid substitutions may be introduced into an antibody of interest and the products screened for a desired activity, e.g., retained/improved antigen binding, decreased immunogenicity, or improved ADCC or CDC function.

| Original Residue | Exemplary Conserved Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Hydrophobic amino acids include: Norleucine, Met, Ala, Val, Leu, and Ile. Neutral hydrophilic amino acids include: Cys, Ser, Thr, Asn, and Gln. Acidic amino acids include: Asp and Glu. Basic amino acids include: His, Lys, and Arg. Amino acids with residues that influence chain orientation include: Gly and Pro. Aromatic amino acids include: Trp, Tyr, and Phe.

In some embodiments, substitutions, insertions, or deletions may occur within one or more CDRs, wherein the substitutions, insertions, or deletions do not substantially reduce antibody binding to antigen. For example, conservative substitutions that do not substantially reduce binding affinity may be made in CDRs. Such alterations may be outside of CDR "hotspots" or SDRs. In some embodiments of the variant $V_H$ and $V_L$ sequences, each CDR either is unaltered, or contains no more than one, two or three amino acid substitutions.

Alterations (e.g., substitutions) may be made in CDRs, e.g., to improve antibody affinity. Such alterations may be made in CDR encoding codons with a high mutation rate during somatic maturation (See, e.g., Chowdhury, Methods Mol. Biol. 207:179-196 (2008)), and the resulting variant can be tested for binding affinity. Affinity maturation (e.g., using error-prone PCR, chain shuffling, randomization of CDRs, or oligonucleotide-directed mutagenesis) can be used to improve antibody affinity (See, e.g., Hoogenboom et al. in Methods in Molecular Biology 178:1-37 (2001)). CDR residues involved in antigen binding may be specifically identified, e.g., using alanine scanning mutagenesis or modeling (See, e.g., Cunningham and Wells Science, 244:1081-1085 (1989)). CDR-H3 and CDR-L3 in particular are often targeted. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions and deletions include amino- and/or carboxyl-terminal fusions ranging in length from one residue to polypeptides containing a hundred or more residues, as well as intrasequence insertions and deletions of single or multiple amino acid residues. Examples of terminal insertions include an antibody with an N-terminal methionyl residue. Other insertional variants of the antibody molecule include the fusion to a polypeptide which increases serum half life of the antibody, for example, at the N-terminus or C-terminus. The term "epitope tagged" refers to the antibody fused to an epitope tag. The epitope tag polypeptide has enough residues to provide an epitope against which an antibody there against can be made, yet is short enough such that it does not interfere with activity of the antibody. The epitope tag preferably is sufficiently unique so that the antibody there against does not substantially cross-react with other epitopes. Suitable tag polypeptides generally have at least 6 amino acid residues and usually between about 8-50 amino acid residues (preferably between about 9-30 residues). Examples include the flu HA tag polypeptide and its antibody 12CA5 [Field et al., Mal. Cell. Biol. 8: 2159-2165 (1988)]; the c-myc tag and the 8F9, 3C7, 6E10, G4, B7 and 9E10 antibodies thereto [Evan et al., Mal. Cell. Biol. 5(12): 3610-3616 (1985)]; and the Herpes Simplex virus glycoprotein D (gD) tag and its antibody [Paborsky et al., Protein Engineering 3(6): 547-553 (1990)]. Other exemplary tags are a poly-histidine sequence, generally around six histidine residues, that permits isolation of a compound so labeled using nickel chelation. Other labels and tags, such as the FLAG® tag (Eastman Kodak, Rochester, N.Y.), well known and routinely used in the art, are embraced by the invention.

Other insertional variants of the antibody molecule include the fusion to the N- or C-terminus of the antibody to an enzyme (e.g., for ADEPT) or a polypeptide which increases the serum half-life of the antibody. Examples of intrasequence insertion variants of the antibody molecules include an insertion of 3 amino acids in the light chain. Examples of terminal deletions include an antibody with a deletion of 7 or less amino acids at an end of the light chain.

Glycosylation Variants

In some embodiments, the antibodies are altered to increase or decrease their glycosylation (e.g., by altering the amino acid sequence such that one or more glycosylation sites are created or removed). A carbohydrate attached to an Fc region of an antibody may be altered. Native antibodies from mammalian cells typically comprise a branched, biantennary oligosaccharide attached by an N-linkage to Asn297 of the CH2 domain of the Fc region (See, e.g., Wright et al. TIBTECH 15:26-32 (1997)). The oligosaccharide can be various carbohydrates, e.g., mannose, N-acetyl glucosamine (GlcNAc), galactose, sialic acid, fucose attached to a GlcNAc in the stem of the biantennary oligosaccharide structure. Modifications of the oligosaccharide in an antibody can be made, for example, to create antibody variants with certain improved properties. Antibody glycosylation variants can have improved ADCC and/or CDC function.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn297 (See, e.g., WO 08/077546). Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants can have improved ADCC function (See, e.g. Okazaki et al. *J. Mol. Biol.* 336:1239-1249 (2004); and Yamane-Ohnuki et al. Biotech. Bioeng. 87: 614 (2004)). Cell lines, e.g., knockout cell lines and methods of their use can be used to produce defucosylated antibodies, e.g., Lec13 CHO cells deficient in protein fucosylation and alpha-1,6-fucosyltransferase gene (FUT8) knockout CHO cells (See, e.g., Ripka et al. Arch. Biochem. Biophys. 249:533-545 (1986); Yamane-Ohnuki et al. Biotech. Bioeng. 87: 614 (2004); Kanda, Y. et al., Biotechnol. Bioeng., 94(4):680-688 (2006). Other antibody glycosylation variants are also contemplated.

In still another embodiment, the glycosylation of an antibody is modified. For example, an aglycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al. Conservative substitutions involve replacing an amino acid with another member of its class. Non-conservative substitutions involve replacing a member of one of these classes with a member of another class.

Accordingly, the antibodies or antigen binding fragment thereof of the present disclosure can be produced by a host cell with one or more of exogenous and/or high endogenous glycosyltransferase activities. Genes with glycosyltransferase activity include β(1,4)-N-acetylglucosaminyltransferase III (GnTII), α-mannosidase II (ManII), β(1,4)-galactosyltransferase (GalT), β(1,2)-N-acetylglucosaminyltransferase I (GnTI), and β(1,2)-N-acetylglucosaminyltransferase II (GnTII). The glycotranferases can comprise a fusion comprising a Golgi localization domain (See, e.g., Lifely et al., Glycobiology 318:813-22 (1995); Schachter, Biochem. Cell Biol. 64:163-81 (1986)). In some embodiments, an antibody can be expressed in a host cell comprising a disrupted or deactivated glycosyltransferase gene. Accordingly, in some embodiments, the present disclosure is directed to a host cell comprising (a) an isolated nucleic acid comprising a sequence encoding a polypeptide having a glycosyltransferase activity; and (b) an isolated polynucleotide encoding an antibody or antigen binding fragment thereof of the present disclosure. In some embodiments, the modified antibody produced by the host cell has an IgG constant region or a fragment thereof comprising the Fc region. In another particular embodiment the antibody is a humanized antibody or a fragment thereof comprising an Fc region. An isolated nucleic acid is a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

Antibodies with altered glycosylation produced by the host cells of the invention can exhibit increased Fc receptor binding affinity (e.g., increased binding to a Fcγ activating receptor, such as the FcγRIIIa receptor) and/or increased effector function. The increased effector function can be an increase in one or more of the following: increased antibody-dependent cellular cytotoxicity, increased antibody-dependent cellular phagocytosis (ADCP), increased cytokine secretion, increased immune-complex-mediated antigen uptake by antigen-presenting cells, increased Fc-mediated cellular cytotoxicity, increased binding to NK cells, increased binding to macrophages, increased binding to polymorphonuclear cells (PMNs), increased binding to monocytes, increased crosslinking of target-bound antibodies, increased direct signaling inducing apoptosis, increased dendritic cell maturation, and increased T cell priming. Accordingly, in one aspect, the present invention provides glycoforms of an antibody having increased effector function as compared to the antibody that has not been glycoengineered. (See, e.g., Tang et al., J. Immunol. 179:2815-2823 (2007)).

The present disclosure is also directed to a method for producing an antibody or antigen binding fragment thereof, described herein having modified oligosaccharides, comprising (a) culturing a host cell engineered to express at least one nucleic acid encoding a polypeptide having glycosyltransferase activity under conditions which permit the production of an antibody according to the present disclosure, wherein said polypeptide having glycosyltransferase activity is expressed in an amount sufficient to modify the oligosaccharides in the Fc region of said antibody produced by said host cell; and (b) isolating said antibody. In another embodiment, there are two polypeptides having glycosyltransferase activity. The antibodies or antigen binding fragment thereof produced by the methods of the present invention can have increased Fc receptor binding affinity and/or increased effector function.

In some embodiments, the percentage of bisected N-linked oligosaccharides in the Fc region of the antibody is at least about 10% to about 100%, specifically at least about 50%, more specifically, at least about 60%, at least about 70%, at least about 80%, or at least about 90-95% of the total oligosaccharides. In yet another embodiment, the antibody produced by the methods of the invention has an increased proportion of nonfucosylated oligosaccharides in the Fc region as a result of the modification of its oligosaccharides by the methods of the present invention. In some embodiments, the percentage of nonfucosylated oligosaccharides is at least about 20% to about 100%, specifically at least about 50%, at least about 60% to about 70%, and more specifically, at least about 75%. The nonfucosylated oligosaccharides may be of the hybrid or complex type. In yet another embodiment, the antibody or antigen binding fragment thereof produced by the methods of the invention has an increased proportion of bisected oligosaccharides in the Fc region as a result of the modification of its oligosaccharides by the methods of the present invention. In some embodiments, the percentage of bisected oligosaccharides is at least about 20% to about 100%, specifically at least about 50%, at least about 60% to about 70%, and more specifically, at least about 75%.

In another embodiment, the present invention is directed to an antibody or antigen binding fragment thereof engineered to have increased effector function and/or increased Fc receptor binding affinity, produced by the methods of the disclosure. In some embodiments, the antibody is an intact antibody. In some embodiments, the antibody is an antibody fragment containing the Fc region, or a fusion protein that includes a region equivalent to the Fc region of an immunoglobulin.

In one aspect, the present disclosure provides host cell expression systems for the generation of the antibodies or antigen binding fragment thereof of the present disclosure having modified glycosylation patterns. In particular, the present disclosure provides host cell systems for the generation of glycoforms of the antibodies or antigen binding fragment thereof, disclosed herein, having an improved therapeutic value. Therefore, the present disclosure provides host cell expression systems selected or engineered to express a polypeptide having a glycosyltransferase activity. Generally, any type of cultured cell line, including the cell lines discussed above, can be used as a background to engineer the host cell lines of the present invention. In some embodiments, CHO cells, BHK cells, NS0 cells, SP2/0 cells, YO myeloma cells, P3X63 mouse myeloma cells, PER cells, PER.C6 cells or hybridoma cells, other mammalian cells, yeast cells, insect cells, or plant cells are used as the background cell line to generate the engineered host cells of the invention.

The host cells which contain the coding sequence of an antibody or antigen binding fragment thereof of the invention and which express the biologically active gene products may be identified by at least four general approaches; (a) DNA-DNA or DNA-RNA hybridization; (b) the presence or absence of "marker" gene functions; (c) assessing the level of transcription as measured by the expression of the respective mRNA transcripts in the host cell; and (d) detection of the gene product as measured by immunoassay or by its biological activity.

Fc Region Variants

In some embodiments, one or more amino acid modifications may be introduced into the Fc region of an antibody provided herein, thereby generating an Fc region variant. Mutation of residues within Fc receptor binding sites can result in altered effector function, such as altered ADCC, CDC activity, and/or altered half-life. Mutations include, for example, insertion, deletion, and/or substitution of one or more residues as described in more detail above, including substitution with alanine, a conservative substitution, a non-conservative substitution, and/or replacement with a corresponding amino acid residue at the same position from a different IgG subclass (e.g., replacing an IgG1 residue with a corresponding IgG2 residue at that position).

An Fc region herein is a C-terminal region of an immunoglobulin heavy chain that contains at least a portion of the constant region. An Fc region includes native sequence Fc regions and variant Fc regions. The Fc region variant may comprise a human Fc region sequence (e.g., a human IgG1, IgG2, IgG3 or IgG4 Fc region) comprising an amino acid modification (e.g., a substitution) at one or more amino acid positions.

Previous studies mapped the binding site on human and murine IgG for FcγR primarily to the lower hinge region composed of IgG residues 233-239. Other studies proposed additional broad segments, e.g., Gly316-Lys338 for human Fc gamma receptor I, Lys274-Arg301 and Tyr407Arg416 for human Fc gamma receptor III, or found a few specific residues outside the lower hinge, e.g., Asn297 and Glu318 for murine IgG2b interacting with murine Fc gamma receptor II. The report of the 3.2-A crystal structure of the human IgG Fc fragment with human Fc gamma receptor IIIA delineated IgG1 residues Leu234-Ser239, Asp265-Glu269, Asn297-Thr299, and Ala327-Ile332 as involved in binding to Fc receptor γIIIA. It has been suggested based on crystal structure that in addition to the lower hinge (Leu234-Gly237), residues in IgG CH2 domain loops FG (residues 326-330) and BC (residues 265-271) might play a role in binding to Fc gamma receptor IIA. See Shields et al., J. Biol. Chem., 276(9):6591-6604 (2001). Shields et al. reported that IgG1 residues involved in binding to all human Fc receptors are located in the CH2 domain proximal to the hinge and fall into two categories as follows: 1) positions that may interact directly with all FcR include Leu234-Pro238, Ala327, and Pro329 (and possibly Asp265); 2) positions that influence carbohydrate nature or position include Asp265 and Asn297.

In some embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the effect of one or more Fc amino acid modifications on CDC and/or ADCC activities. For example, Fc receptor (FcR) binding assays can be conducted to ensure that the antibody lacks FcγR binding (hence likely lacking ADCC activity), but retains FcRn binding ability.

Fc Variants with Altered Binding to an Fc Gamma Receptor

In some instances, exhibits altered affinity for one or more Fc gamma receptors (FcγR). For example, an Fc variant exhibits increased affinity for one or more Fc gamma receptors (FcγR), decreased affinity for one or more Fc gamma receptors (FcγR), or a combination thereof. In one instance, an Fc variant exhibits increased ADCC activity. In yet another example, the Fc region is modified to increase the ability of the antibody to mediate antibody dependent cellular cytotoxicity (ADCC). The binding sites on human IgG1 for Fc gamma RI (FcγRI), Fc gamma RII (FcγRII), Fc gamma RIII (FcγRIII), and FcRn have been mapped and variants with altered binding have been described. Non-limiting examples of such modifications are described in, for example, U.S. Pat. No. 6,737,056; PCT Publication WO 00/42072 by Presta; Shields, R. L. et al. (2001) J. Biol. Chem. 276:6591-6604; U.S. Pat. No. 7,332,581, etc. In some embodiments, the constant region of the antibodies disclosed herein is replaced with an IGHG1.

In some embodiments, an Fc variant provided herein that exhibits improved ADCC activity comprises an Fc region with a mutation at amino acid position 298, 333, and/or 334 of the Fc region (using Kabat numbering).

In one instance, provided herein is an Fc variant with altered effector and/or Fc-gamma-receptor binding that contain at least one mutation in a human IgG Fc region at amino acid position 238, 239, 248, 249, 252, 254, 255, 256, 258, 265, 267, 268, 269, 270, 272, 276, 278, 280, 283, 285, 286, 289, 290, 292, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438, and/or 439 (using Kabat numbering), which variant displays a receptor binding profile associated with altered ADCC or CDC activity.

In one instance, provided herein is an Fc variant that displays reduced binding to a FcγRI, which comprises an amino acid modification at amino acid position 238, 265, 269, 270, 327, and/or 329 (utilizing Kabat numbering).

In one instance, provided herein is an Fc variant that displays reduced binding to a FcγRII, that contains an amino acid modification at amino acid position 238, 265, 269, 270, 292, 294, 295, 298, 303, 324, 327, 329, 333, 335, 338, 373, 376, 414, 416, 419, 435, 438, and/or 439 (utilizing Kabat numbering).

In one instance, provided herein is an Fc variant that displays increased binding to FcγRII that contains an amino acid modification at amino acid position 255, 256, 258, 267, 268, 272, 276, 280, 283, 285, 286, 290, 301, 305, 307, 309, 312, 315, 320, 322, 326, 330, 331, 337, 340, 378, 398, and/or 430 (utilizing Kabat numbering).

In one instance, provided herein is an Fc variant that exhibits altered binding to a FcγRII that contains an amino acid modification at amino acid position Arg255, Thr256, Glu258, His268, Ser267, Asp270, Asn276, Glu272, Asp280, His285, Asn286, Lys290, Arg292, Gln295, Ser298, Arg301, Thr307, Leu309, Asn315, Lys322, Lys326, Pro331, Ser337, Ala339, Ala378, and/or Lys414 (utilizing Kabat numbering).

In one instance, provided herein is an Fc variant that exhibits reduced binding to a FcγRII that contains an amino acid modification at amino acid position A327Q, A327S, P329A, D265A, and/or D270A (utilizing Kabat numbering).

In one instance, provided herein is an Fc variant that displays reduced binding to a FcγRIII, that contains an amino acid modification at amino acid position 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435, and/or 437 (utilizing Kabat numbering).

In one instance, provided herein is an Fc variant that displays improved binding to FcγRII and FcγRIIIA that contains an amino acid modification at amino acid position T256A and/or K290A (using Kabat numbering).

In one instance, provided herein is an Fc variant that displays reduced binding to FcγRII and FcγRIIIA that contains an amino acid modification at amino acid position D270A, Q295A, and/or A327S (using Kabat numbering).

In one instance, provided herein is an Fc variant that displays improved binding to FcγRII and no effect FcγRIIIA that contains an amino acid modification at amino acid position Kabat numbering).

In one instance, provided herein is an Fc variant that displays reduced binding to FcγRII and improved binding to FcγRIIIA that contains an amino acid modification at amino acid position S298A (using Kabat numbering).

In one instance, provided herein is an Fc variant that displays improved binding to FcγRII and reduced binding to FcγRIIIA that contains an amino acid modification at amino acid position H268A, R301A, and/or K322A (using Kabat numbering).

In one instance, provided herein is an Fc variant that displays reduced binding to FcγRII and no effect on FcγRIIIA that contains an amino acid modification at amino acid position R292A and/or K414A (using Kabat numbering).

In one instance, provided herein is an Fc variant that displays no effect on FcγRII and reduced binding to FcγRIIIA that contains an amino acid modification at amino acid position S239A, E269A, E293A, V296F, V303A, A327G, K338A, and/or D376A (using Kabat numbering).

In one instance, provided herein is an Fc variant that displays increased binding to FcγRIIIA that contains an amino acid modification at amino acid position E333A, K334A, and/or A339T (using Kabat numbering).

An Fc variant that displays improved binding to a FcγR may also be made and may comprise an amino acid modification at amino acid position 255, 256, 258, 267, 268, 272, 276, 280, 283, 285, 286, 290, 298, 301, 305, 307, 309, 312, 315, 320, 322, 326, 330, 331, 333, 334, 337, 340, 360, 378, 398, and/or 430 (utilizing Kabat numbering). In one instance, provided herein is an Fc variant that displays improved binding to a FcγRIII, and optionally may further display decreased binding to FcγRII, which variant comprises an amino acid modification at amino acid position 298 and/or 333 of an Fc region (utilizing Kabat numbering).

In one instance, provided herein is an Fc variant that displays improved binding to a FcγRII that contains an amino acid modification at amino acid position 255, 256, 258, 267, 268, 272, 276, 280, 283, 285, 286, 290, 301, 305, 307, 309, 312, 315, 320, 322, 326, 330, 331, 337, 340, 378, 398 and/or 430 (utilizing Kabat numbering). Such variant may further display decreased binding to FcγRIII if it includes an Fc region amino acid modification at any one or more of amino acid positions 268, 272, 298, 301, 322 or 340 (utilizing Kabat numbering).

In one instance, a variant described herein contains a mutation at amino acid positions 240, 243, 245, 247, 262, 263, 266, 299, 313, 325, 328, and/or 332 (using Kabat numbering); or at amino acid positions 234, 235, 239, 240, 241, 243, 244, 245, 247, 262, 263, 264, 265, 266, 267, 269, 296, 297, 298, 299, 313, 325, 327, 328, 329, 330, and/or 332 (using Kabat numbering), of which mutations at positions 234, 235, 239, 240, 241, 243, 244, 245, 247, 262, 263, 264, 265, 266, 267, 269, 296, 297, 298, 299, 313, 325, 327, 328, 329, 330, or 332 may reduce ADCC activity or reduce binding to an Fc gamma receptor. In one instant, an Fc variant described herein contains a mutation at amino acid position 234, 235, 239, 240, 243, 264, 266, 328, 330, 332, and/or 325 (using Kabat numbering) that increases ADCC activity, and wherein the Fc variant comprises at least one substitution selected from the group consisting of 234E, 234Y, 234I, 235D, 235S, 235Y, 235I, 239D, 239E, 239N, 239Q, 239T, 240I, 240M, 243L, 264I, 264T, 264Y, 266I, 328M, 328I, 328Q, 328D, 328V, 328T, 330Y, 330L, 330I, 332D, 332E, 332N, 332Q, and 325T.

In one instance, provided herein is an Fc variant that exhibits altered binding to a FcγRII that contains an amino acid modification at amino acid position Arg255, Thr256, Glu258, His268, Ser267, Asp270, Asn276, Glu272, Asp280, His285, Asn286, Lys290, Arg292, Gln295, Ser298, Arg301, Thr307, Leu309, Asn315, Lys322, Lys326, Pro331, Ser337, Ala339, Ala378, and/or Lys414 (utilizing Kabat numbering).

In one instance, provided herein is an Fc variant that exhibits reduced binding to a FcγRII that contains an amino acid modification at amino acid position A327Q, A327S, P329A, D265A, and/or D270A (utilizing Kabat numbering).

In one instance, provided herein is an Fc variant that exhibits reduced binding to a FcγRIIIA that contains an amino acid modification at amino acid position Ser239, Ser267 (Gly only), His268, Glu293, Gln295, Tyr296, Arg301, Val303, Lys338, and/or Asp376 (utilizing Kabat numbering).

In one instance, provided herein is an Fc variant that exhibits reduced binding to a FcγRIIA and FcγRIIB that contains an amino acid modification at amino acid position Lys414 (utilizing Kabat numbering).

In one instance, provided herein is an Fc variant that exhibits reduced binding to a FcγRIIA and FcγRIIIA that contains an amino acid modification at amino acid position Arg416 (utilizing Kabat numbering).

In one instance, provided herein is an Fc variant that exhibits reduced binding to a FcγRIIA and FcγRIIB that contains an amino acid modification at amino acid position Gln419 (utilizing Kabat numbering).

In one instance, provided herein is an Fc variant that exhibits improved (increased) binding to a FcγRIIIA that contains an amino acid modification at amino acid position Lys360 (utilizing Kabat numbering).

Armour et al. (Mol Immunol. 2003; 40(9):585-93) identified IgG1 variants which react with the activating receptor, FcγRIIa, at least 10-fold less efficiently than wildtype IgG1, but whose binding to the inhibitory receptor, FcγRIIb, is only four-fold reduced. Mutations were made in the region of amino acids 233-236 and/or at amino acid positions 327, 330 and 331. See also WO 99/58572.

Non-limiting examples of in vitro assays to assess ADCC activity of a molecule of interest are described, for example, in U.S. Pat. Nos. 5,500,362 and 5,821,337. Alternatively, non-radioactive assays methods may be employed (e.g., ACTI™ and CYTOTOX 96® non-radioactive cytotoxicity assays). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model (See, e.g., Clynes et al., Proc. Nat'l Acad. Sci. USA 95:652-656 (1998)).

Fc Variants with Decreased C1q Binding

In another instance, an Fc variant exhibits reduced C1q binding. C1q binding assays may also be carried out to confirm that the antibody is able or unable bind C1q and, hence, contains or lacks CDC activity (Idusogie et al., J. Immunol. 164: 4178-4184 (2000)). To assess complement activation, a CDC assay may be performed (See, e.g., Gazzano-Santoro et al., J. Immunol. Methods 202:163 (1996); Cragg, M. S. et al., Blood 101:1045-1052 (2003); and Cragg et al., Blood 103:2738-2743 (2004)).

In another example, one or more amino acids can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al. In another example, one or more amino acid residues are altered to thereby alter the ability of the antibody to fix complement. This approach is described further in PCT Publication WO 94/29351 by Bodmer et al. In one instance, an Fc variant provided herein can contain a mutation at amino acid position 329, 331, and/or 322 (using Kabat numbering), and exhibits reduced C1q binding and/or CDC activity. In some instances, C1q binding activity and/or CDC activity of an antibody can be reduced by mutating amino acid residue 318, 320, and/or 322 (using Kabat numbering) of a heavy chain; replacing residue 297 (Asn) may result in removal of lytic activity of an antibody.

Cytophilic activity of IgG1 is a property of its heavy chain CH2 domain. In one instance, where an Fc variant is an IgG, amino acid residues 234-237 are maintained as wild type to preserve cytophilic activity of the molecule. An IgG2 antibody containing the entire ELLGGP sequence (residues 233-238) may, in some instances, be more active than wild-type IgG1.

In some instances, C1q binding activity and/or lytic activity of an IgG1 antibody can be reduced by mutating amino acid residue Pro331 to Ser. In other instances, C1q binding activity and/or lytic activity of an IgG4 antibody can be reduced by mutating amino acid residue Pro for Ser331 (Xu et al., J Biol Chem. 1994; 269(5):3469-74).

Fc Variants with Interchain Disulfide Binds or Dual Fc Regions

In yet another embodiment, it may be desirable to modify the antibody of the invention with respect to effector function, so as to enhance the effectiveness of the antibody in treating cancer, for example. For example, one or more cysteine residue(s) may be introduced in the Fc region, thereby allowing interchain disulfide bond formation in this region. The homodimeric antibody thus generated may have improved internalization capability, increased complement-mediated cell killing, and/or antibody-dependent cellular cytotoxicity (ADCC). See Caron et al., J. Exp Med. 176: 1191-1195 (1992) and Shapes, B. J. Immunol. 148: 2918-2922 (1992). Homodimeric antibodies with enhanced antitumor activity may also be prepared using heterobifunctional cross-linkers as described in Wolff et al., Cancer Research 53: 2560-2565 (1993).

Alternatively, an antibody can be engineered which has dual Fc regions and may thereby have enhanced complement lysis and/or ADCC capabilities. See, Stevenson et al., Anti-Cancer Drug Design 3: 219-230 (1989).

Fc Variants with Increased FcRn Binding and In Vivo Half-Life

Fc region variants with altered binding affinity for the neonatal receptor (FcRn) are also contemplated herein. Fc region variants with improved affinity for FcRn are anticipated to have longer serum half-lives, and such variants are useful in methods of treating subjects where long half-life of the administered polypeptide is desired, e.g., to treat a chronic disease or disorder. Fc region variants with decreased FcRn binding affinity, on the contrary, are expected to have shorter half-lives, and such variants may be administered to a subject where a shortened circulation time may be preferred, e.g. for in vivo diagnostic imaging or for antibodies which have toxic side effects when left circulating in the blood stream for extended periods, etc.

Fc region variants with altered binding affinity for FcRn include those that contains an amino acid modification at amino acid position 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439, and/or 447 (utilizing Kabat numbering).

Fc region variants with decreased FcRn binding affinity are less likely to cross the placenta and, therefore, may be utilized in the treatment of diseases or disorders in pregnant women. In one instance, provided herein is an Fc variant that exhibits reduced binding to FcRn that contains an amino acid modification at amino acid position 252, 253, 254, 255, 288, 309, 386, 388, 400, 415, 433, 435, 436, 439, and/or 447 (utilizing Kabat numbering).

In one instance, provided herein is an Fc variant that exhibits increased binding to a FcRn that contains an amino acid modification at amino acid position 238, 256, 265, 272, 286, 303, 305, 307, 311, 312, 317, 340, 356, 360, 362, 376, 378, 380, 382, 413, 424, and/or 434 (utilizing Kabat numbering).

In one instance, provided herein is an Fc variant that exhibits increased binding to a FcRn that contains an amino acid of Pro238Ala, Thr256Ala, Thr307Ala, Gln311Ala, Asp312Ala, Glu380Ala, Glu382Ala, and/or Asn434Ala (utilizing Kabat numbering).

In one instance, provided herein is an Fc variant that exhibits reduced binding to a FcRn that contains a modification at amino acid position Glu233-Gly236, Arg255, Lys288, Ser415, and/or His433 (utilizing Kabat numbering).

In one instance, provided herein is an Fc variant that exhibits abrogated binding to a FcRn that contains a modification at amino acid position Ile253, Ser254, His435, and/or Tyr436 (utilizing Kabat numbering).

Schuurman et al., Mol Immunol. 2001; 38(1):1-8, incorporated by reference herein in its entirety, report that mutating one of the hinge cysteines involved in the inter-heavy chain bond formation, Cys226, to serine resulted in a more stable inter-heavy chain linkage. Mutating the IgG4 hinge sequence Cys-Pro-Ser-Cys to the IgG1 hinge sequence Cys-Pro-Pro-Cys also markedly stabilizes the covalent interaction between the heavy chains. Angal et al., Mol Immunol. 1993; 30(1):105-8, incorporated by reference herein in its entirety, report that mutating the serine at amino acid position 241 in IgG4 to praline (found at that position in IgG1 and IgG2) led to the production of a homogeneous antibody, as well as extending serum half-life and improving tissue distribution compared to the original chimeric IgG4. Other such examples of Fc region variants are also contemplated (See, e.g., Duncan & Winter, Nature 322:738-40 (1988); Chan C A and Carter P J (2010) Nature Rev Immunol 10:301-316); and Shields et al., J. Biol. Chem. 9(2): 6591-6604 (2001).

Determination of FcRn binding and in vivo clearance/half-life can be performed using methods known in the art (See, e.g., Petkova, S. B. et al., Int'l. Immunol. 18(12):1759-1769 (2006)).

Variants of Antibody Fragments and Salvage Receptor Binding Epitopes

In certain embodiments of the invention, it may be desirable to use an antibody fragment, rather than an intact antibody, to increase tumor penetration, for example. In this case, it may be desirable to modify the antibody fragment in order to increase its serum half-life, for example, adding molecules such as PEG or other water soluble polymers, including polysaccharide polymers, to antibody fragments to increase the half-life.

This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, e.g., WO 96/32478). The salvage receptor binding epitope preferably constitutes a region wherein any one or more amino acid residues from one or two loops of an Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CHI, CH3, or VH region, or more than one such region, of the antibody. Alternatively, the epitope is taken from the CH2 domain of the Fc region and transferred to the CL region or VL region, or both, of the antibody fragment. See, also, International applications WO 97/34631 and WO 96/32478.

Thus, antibodies of the invention may comprise a human Fc portion, a human consensus Fc portion, or a variant thereof that retains the ability to interact with the Fc salvage receptor, including variants in which cysteines involved in disulfide bonding are modified or removed, and/or in which the a Met is added at the N-terminus and/or one or more of the N-terminal 20 amino acids are removed, and/or regions that interact with complement, such as the C1q binding site, are removed.

Isaacs et al., J Immunol. 1998; 161(8):3862-9, incorporated herein by reference in its entirety, report that mutations within a motif critical for FcγR binding (glutamate 233 to praline, leucine/phenylalanine 234 to valine, and leucine 235 to alanine) completely prevented depletion of target cells. The mutation glutamate 318 to alanine eliminated effector function of mouse IgG2b and also reduced the potency of human IgG4.

Cysteine Engineered Antibody Variants

In some embodiments, it may be desirable to create cysteine engineered antibodies or antigen binding fragment thereof, e.g., "thioMAbs," in which one or more residues of an antibody are substituted with cysteine residues. In some embodiments, the substituted residues occur at accessible sites of the antibody. Reactive thiol groups can be positioned at sites for conjugation to other moieties, such as drug moieties or linker-drug moieties, to create an immunoconjugate. In some embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described.

Any cysteine residue not involved in maintaining the proper conformation of the monoclonal, human, humanized, or variant antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Antibody Derivatives

In some embodiments, an antibody or antigen binding fragment thereof provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if two or more polymers are attached, they can be the same or different molecules.

In another embodiment, conjugates of an antibody and nonproteinaceous moiety that may be selectively heated by exposure to radiation are provided. In some embodiments, the nonproteinaceous moiety is a carbon nanotube (See, e.g., Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Bispecific Antibodies

In some embodiments, it may be desirable to generate multispecific (e.g. bispecific) monoclonal antibody including monoclonal, human, humanized, or variant antibodies having binding specificities for at least two different epitopes. In some embodiments, the antibodies disclosed herein are multispecific. Exemplary bispecific antibodies may bind to two different epitopes of an antigen (e.g., cancer associated antigen). Alternatively, an antigen binding region may be combined with a region which binds to a triggering molecule on a leukocyte such as a T-cell receptor molecule (e.g., CD2 or CD3), or Fe receptors for IgG (FcγR), such as FcγRI (CD64), FcγRII (CD32) and FcγRIII (CD16) so as to focus cellular defense mechanisms to the antigen-expressing cell. Bispecific antibodies may also be used to localize cytotoxic agents to cells which express desired antigen. These antibodies possess an antigen-binding arm and an arm which binds the cytotoxic agent (e.g., saporin, anti-interferon-60, vinca alkaloid, ricin A chain, methotrexate or radioactive isotope hapten). Bispecific antibodies can be prepared as full length antibodies or antibody fragments (e.g., F(ab')$_2$ bispecific antibodies).

According to another approach for making bispecific antibodies, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are contemplated, along with a number of cross-linking techniques.

Techniques for generating bispecific antibodies from antibody fragments have also been described in the literature. For example, bispecific antibodies can be prepared using chemical linkage. Brennan et al., Science 229: 81 (1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. In yet a further embodiment, Fab'-SH fragments directly recovered from *E. coli* can be chemically coupled in vitro to form bispecific antibodies. (Shalaby et al., J. Exp. Med. 175:217-225 (1992))

Monoclonal Antibodies

In some embodiments, the antibodies of the present disclosure are monoclonal. Monoclonal antibodies may be made using the hybridoma method first described by Kohler et al., Nature, 256:495 (1975), or may be made by recombinant DNA methods.

In the hybridoma method, a mouse or other appropriate host animal, such as a hamster or macaque monkey, is immunized as herein described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferred myeloma cells are those that fuse efficiently, support stable high-level production of antibody by the selected antibody-producing cells, and are sensitive to a medium. Human myeloma and mouse-human heteromyeloma cell lines also have been described for the production of human monoclonal antibodies (Kozbor, J. Immunol., 133: 3001 (1984); Brodeur et al., Monoclonal Antibody Production Techniques and Applications, pp. 51-63 (Marcel Dekker, Inc., New York, 1987)). Exemplary murine myeloma lines include those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA. Culture medium in which hybridoma cells are growing is assayed for production of monoclonal antibodies directed against the antigen. Accordingly, in one aspect the present disclosure provides a hybridoma producing the antibody or antigen binding fragment thereof, described herein. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by Scatchard analysis (Munson et al., Anal. Biochem., 107:220 (1980)).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Engineered and Modified Antibodies

An antibody according to at least some embodiments of the invention further can be prepared using an antibody having one or more of the VH and/or VL sequences derived from an antibody or antigen binding fragment thereof, disclosed herein, starting material to engineer a modified antibody, which modified antibody may have altered properties from the starting antibody. Provided herein are complete reconstructed amino acid and nucleic acid consensus sequences of VH and VL chain regions of antibodies disclosed herein. Also provided herein, are the amino acid and nucleic acid sequences of the CDR3 regions of the VH and VL of the antibodies, described herein. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant regions, for example to alter the effector functions of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific antibodies by constructing expression vectors that include CDR sequences from the specific antibody (e.g. antibodies disclosed herein) grafted onto framework sequences from a different antibody with different properties (see, e.g., Riechmann, L. et al. (1998) Nature 332:323-327; Jones, P. et al. (1986) Nature 321:522-525; Queen, C. et al. (1989) Proc. Natl. Acad. See. U.S.A. 86:10029-10033; U.S. Pat. No. 5,225,539 to Winter, and U.S. Pat. Nos. 5,530,101; 5,585,089; 5,693,762 and 6,180,370 to Queen et al.)

Suitable framework sequences can be obtained from public DNA databases or published references that include germline antibody gene sequences. For example, germline DNA sequences for human heavy and light chain variable region genes can be found in the "VBase" human germline sequence database (available on the Internet), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline VH Sequences Reveals about Fifty Groups of VH Segments with Different Hypervariable Loops" J. Mol. Biol. 227:776-798; and Cox, J. P. L. et al. (1994) "A Directory of Human Germ-line VH Segments Reveals a Strong Bias in their Usage" Eur. J. Immunol. 24:827-836; the contents of each of which are expressly incorporated herein by reference.

Another type of variable region modification is to mutate amino acid residues within the VH and/or VL CDR 1, CDR2 and/or CDR3 regions to thereby improve one or more binding properties (e.g., affinity) of the antibody of interest. Site-directed mutagenesis or PCR-mediated mutagenesis can be performed to introduce the mutations and the effect on antibody binding, or other functional property of interest, can be evaluated in appropriate in vitro or in vivo assays. Preferably conservative modifications (as discussed above) are introduced. The mutations may be amino acid substitutions, additions or deletions, but are preferably substitutions. Moreover, typically no more than one, two, three, four or five residues within a CDR region are altered.

Engineered antibodies according to at least some embodiments of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

In addition or alternative to modifications made within the framework or CDR regions, antibodies according to at least some embodiments of the disclosure may be engineered to include modifications within the Fc region, typically to alter one or more functional properties of the antibody, such as serum half-life, complement fixation, Fc receptor binding, and/or antigen-dependent cellular cytotoxicity. Furthermore, an antibody according to at least some embodiments of the invention may be chemically modified (e.g., one or more chemical moieties can be attached to the antibody) or be modified to alter its glycosylation, again to alter one or more functional properties of the antibody. Such embodiments are described above. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody. In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. In another example, one or more amino acids can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al. In another example, one or more amino acid residues are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for Fc gamma RI, Fc gamma RII, Fc gammaRIII and FcRn have been mapped and variants with improved binding have been described (see Shields, R. L. et al. (2001) J. Biol. Chem. 276:6591-6604). Specific mutations at positions are shown to improve binding to FcγRIII. Furthermore, specific mutations such as may improve binding to FcRn and increase antibody circulation half-life (see Chan C A and Carter P J (2010) Nature Rev Immunol 10:301-316). In some embodiments, the constant region of the antibodies disclosed herein are replaced with IGHG1.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al. Conservative substitutions involve replacing an amino acid with another member of its class. Non-conservative substitutions involve replacing a member of one of these classes with a member of another class.

Any cysteine residue not involved in maintaining the proper conformation of the monoclonal, human, humanized, or variant antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Other modifications of the antibody are contemplated. For example, it may be desirable to modify the antibody of the invention with respect to effector function, so as to enhance the effectiveness of the antibody in treating cancer, for example. For example cysteine residue(s) may be introduced in the Fe region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176: 1191-1195 (1992) and Shapes, B. J. Immunol. 148: 2918-2922 (1992). Homodimeric antibodies with enhanced anti-tumor activity may also be prepared using heterobifunctional cross-linkers as described in Wolff et al., Cancer Research 53: 2560-2565 (1993). Alternatively, an antibody can be engineered which has dual Fe regions and may thereby have enhanced complement lysis and ADCC capabilities. See Stevenson et al., *Anti-Cancer Drug Design* 3: 219-230 (1989). In addition, it has been shown that sequences within the CDR can cause an antibody to bind to MHC Class II and trigger an unwanted helper T-cell response. A conservative substitution can allow the antibody to retain binding activity yet lose its ability to trigger an unwanted T-cell response. Also see Steplewski et al., Proc Natl Acad Sci USA. 1988; 85(13):4852-6, incorporated herein by reference in its entirety, which described chimeric antibodies wherein a murine variable region was joined with human gamma 1, gamma 2, gamma 3, and gamma 4 constant regions.

In certain embodiments of the invention, it may be desirable to use an antibody fragment, rather than an intact antibody, to increase tumor penetration, for example. In this case, it may be desirable to modify the antibody fragment in order to increase its serum half-life, for example, adding molecules such as PEG or other water soluble polymers, including polysaccharide polymers, to antibody fragments to increase the half-life. This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, e.g., W096/32478).

The salvage receptor binding epitope preferably constitutes a region wherein any one or more amino acid residues from one or two loops of a Fe domain are transferred to an analogous position of the antibody fragment. Even more preferably, three or more residues from one or two loops of the Fe domain are transferred. Still more preferred, the epitope is taken from the CH2 domain of the Fe region (e.g., of an igG) and transferred to the CHI, CH3, or VH region, or more than one such region, of the antibody. Alternatively, the epitope is taken from the CH2 domain of the Fe region and transferred to the CL region or VL region, or both, of the antibody fragment. See also International applications WO 97/34631 and WO 96/32478 which describe Fe variants and their interaction with the salvage receptor.

Thus, antibodies of the invention may comprise a human Fe portion, a human consensus Fe portion, or a variant thereof that retains the ability to interact with the Fe salvage receptor, including variants in which cysteines involved in disulfide bonding are modified or removed, and/or in which the a met is added at the N-terminus and/or one or more of the N-terminal 20 amino acids are removed, and/or regions that interact with complement, such as the C1 q binding site, are removed, and/or the ADCC site is removed [see, e.g., Malec. Immunol. 29 (5): 633-9 (1992)].

Previous studies mapped the binding site on human and murine IgG for FcR primarily to the lower hinge region composed of lgG residues 233-239. Other studies proposed additional broad segments, e.g. Gly316-Lys338 for human Fe receptor I, Lys274-Arg301 and Tyr407-Arg416 for human Fe receptor III, or found a few specific residues outside the lower hinge, e.g. Asn297 and Glu318 for murine IgG2b interacting with murine Fe receptor II. The report of the 3.2-A crystal structure of the human IgG Fe fragment with human Fe receptor IIIA delineated IgG1 residues Leu234-Ser239, Asp265-Glu269, Asn297-Thr299, and Ala327-Ile332 as involved in binding to Fee receptor IIIA. It has been suggested based on crystal structure that in addition to the lower hinge (Leu234-Gly237), residues in IgG CH2 domain loops FG (residues 326-330) and BC (residues 265-271) might play a role in binding to Fe receptor IIA. See Shields et al., J. Biol. Chem., 276(9):6591-6604 (2001), incorporated by reference herein in its entirety. Mutation of residues within Fe receptor binding sites can result in altered effector function, such as altered ADCC or CDC activity, or altered half-life. As described above, potential mutations include insertion, deletion or substitution of one or more residues, including substitution with alanine, a conservative substitution, a non-conservative substitution, or replacement with a corresponding amino acid residue at the same position from a different IgG subclass (e.g. replacing an IgG1 residue with a corresponding IgG2 residue at that position).

Shields et al. reported that IgG1 residues involved in binding to all human Fe receptors are located in the CH2 domain proximal to the hinge and fall into two categories as follows: 1) positions that may interact directly with all FcR include Leu234-Pro238, Ala327, and Pro329 (and possibly Asp265); 2) positions that influence carbohydrate nature or position include Asp265 and Asn297. The additional IgG 1 residues that affected binding to Fe receptor II are as follows: (largest effect) Arg255, Thr256, Glu258, Ser267, Asp270, Glu272, Asp280, Arg292, Ser298, and (less effect) His268, Asn276, His285, Asn286, Lys290, Gln295, Arg301, Thr307, Leu309, Asn315, Lys322, Lys326, Pro331, Ser337, Ala339, Ala378, and Lys414. A327Q, A327S, P329A, D265A and D270A reduced binding. In addition to the residues identified above for all FcR, additional IgG 1 residues that reduced binding to Fc receptor IIIA by 40% or more are as follows: Ser239, Ser267 (Gly only), His268, Glu293, Gln295, Tyr296, Arg301, Val303, Lys338, and Asp376. Variants that improved binding to FcRIIIA include T256A, K290A, S298A, E333A, K334A, and A339T.

Lys414 showed a 40% reduction in binding for FcRIIA and FcRIIB, Arg416 a 30% reduction for FcRIIA and FcRIIIA, Gln419 a 30% reduction to FcRIIA and a 40% reduction to FcRIIB, and Lys360 a 23% improvement to FcRIIIA. See also Presta et al., Biochem. Soc. Trans. (2001) 30, 487-490.

For example, U.S. Pat. No. 6,194,551, incorporated herein by reference in its entirety, describes variants with altered effector function containing mutations in the human IgG Fc region, at amino acid position 329, 331 or 322 (using Kabat numbering), some of which display reduced C1q binding or CDC activity. As another example, U.S. Pat. No. 6,737,056, incorporated herein by reference in its entirety, describes variants with altered effector or Fc-gamma-receptor binding containing mutations in the human IgG Fc region, at amino acid position 238, 239, 248, 249, 252, 254, 255, 256, 258, 265, 267, 268, 269, 270, 272, 276, 278, 280, 283, 285, 286, 289, 290, 292, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439 (using Kabat numbering), some of which display receptor binding profiles associated with reduced ADCC or CDC activity. Of these, a mutation at amino acid position 238, 265, 269, 270, 327 or 329 are stated to reduce binding to FcRI, a mutation at amino acid position 238, 265, 269, 270, 292, 294, 295, 298, 303, 324, 327, 329, 333, 335, 338, 373, 376, 414, 416, 419, 435, 438 or 439 are stated to reduce binding to FcRII, and a mutation at amino acid position 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 is stated to reduce binding to FcRIII.

U.S. Pat. No. 5,624,821, incorporated by reference herein in its entirety, reports that C1q binding activity of an murine antibody can be altered by mutating amino acid residue 318, 320 or 322 of the heavy chain and that replacing residue 297 (Asn) results in removal of lytic activity.

U.S. Application Publication No. 20040132101, incorporated by reference herein in its entirety, describes variants with mutations at amino acid positions 240, 24 245, 247, 262, 263, 266, 299, 313, 325, 328, or 332 (using Kabat numbering) or positions 234, 235, 239, 240, 241, 243, 244, 245, 247, 262, 263, 264, 265, 266, 267, 269, 296, 297, 298, 299, 313, 325, 327, 328, 329, 330, or 332 (using Kabat numbering), of which mutations at positions 234, 235, 239, 240, 241, 243, 244, 245, 247, 262, 263, 264, 265, 266, 267, 269, 296, 297, 298, 299, 313, 325, 327, 328, 329, 330, or 332 may reduce ADCC activity or reduce binding to an Fc gamma receptor.

Chappel et al., Proc Natl Acad Sci USA. 1991; 88(20): 9036-40, incorporated herein by reference in its entirety, report that cytophilic activity of IgG 1 is an intrinsic property of its heavy chain CH2 domain. Single point mutations at any of amino acid residues 234-237 of IgG1 significantly lowered or abolished its activity. Substitution of all of IgG1 residues 234-237 (LLGG) into IgG2 and IgG4 were required to restore full binding activity. An IgG2 antibody containing the entire ELLGGP sequence (residues 233-238) was observed to be more active than wild-type IgG1.

Isaacs et al., J Immunol. 1998; 161(8):3862-9, incorporated herein by reference in its entirety, report that mutations within a motif critical for Fc gammaR binding (glutamate 233 to praline, leucine/phenylalanine 234 to valine, and leucine 235 to alanine) completely prevented depletion of target cells. The mutation glutamate 318 to alanine eliminated effector function of mouse IgG2b and also reduced the potency of human IgG4.

Armour et al., Mol Immunol. 2003; 40(9):585-93, incorporated by reference herein in its entirety, identified IgG 1 variants which react with the activating receptor, FcgammaRIIa, at least 10-fold less efficiently than wildtype IgG1 but whose binding to the inhibitory receptor, FcgammaRIIb, is only four-fold reduced. Mutations were made in the region of amino acids 233-236 and/or at amino acid positions 327, 330 and 331. See also WO 99/58572, incorporated by reference herein in its entirety. Xu et al., J Biol Chem. 1994; 269(5):3469-74, incorporated by reference herein in its entirety, report that mutating IgG1 Pro331 to Ser markedly decreased C1q binding and virtually eliminated lytic activity. In contrast, the substitution of Pro for Ser331 in IgG4 bestowed partial lytic activity (40%) to the IgG4 Pro331 variant.

Schuurman et al., Mol Immunol. 2001; 38(1):1-8, incorporated by reference herein in its entirety, report that mutating one of the hinge cysteines involved in the inter-heavy chain bond formation, Cys226, to serine resulted in a more stable inter-heavy chain linkage. Mutating the IgG4 hinge sequence Cys-Pro-Ser-Cys to the IgG1 hinge sequence Cys-Pro-Pro-Cys also markedly stabilizes the covalent interaction between the heavy chains. Angal et al., Mol Immunol. 1993; 30(1):105-8, incorporated by reference herein in its entirety, report that mutating the serine at amino acid position 241 in IgG4 to praline (found at that position in IgG1 and IgG2) led to the production of a homogeneous antibody, as well as extending serum half-life and improving tissue distribution compared to the original chimeric IgG4.

Affinity Maturation

Affinity maturation involves preparing and screening antibody variants that have substitutions within the CDRs of a parent antibody and selecting variants that have improved biological properties such as binding affinity relative to the parent antibody. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity).

Alanine scanning mutagenesis can be performed to identify hypervariable region residues that contribute significantly to antigen binding. Alternatively, or in addition, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Altered Glycosylation

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Embodiments encompassing glycosylated antibodies or antigen binding fragments thereof have been described in above sections. Such carbohydrate modifications can be accomplished by, for example, expressing the antibody in a host cell with altered glycosylation machinery. Cells with altered glycosylation machinery have been described in the art and can be used as host cells in which to express recombinant antibodies according to at least some embodiments of the disclosure to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8.−/− cell lines are created by the targeted disruption of the FUT8 gene in CHO/DG44 cells using two replacement vectors (see U.S. Patent Publication No. 20040110704 by Yamane et al. and Yamane-Ohnuki et al. (2004) Biotechnol Bioeng 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) J. Biol. Chem. 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) Biochem. 14:5516-23).

Pegylation

Another modification of the antibodies herein that is contemplated by the present disclosure is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies according to at least some embodiments of the invention. See for example, EP 0154316 by Nishimura et al. and EP 0401384 by Ishikawa et al.

Other Covalent Modifications

Covalent modifications of the antibody are also included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues.

Cysteinyl residues most commonly are reacted with a haloacetate (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-(5 imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0. Lysinyl and amino-terminal residues are reacted with succinic or other carboxylic acid anhydrides. Derivatization with these agents has the effect of reversing the charge of the lysinyl residues. Other suitable reagents for derivatizing alpha amino-containing residues include imidoesters such as methyl picolinimidate, pyridoxal phosphate, pyridoxal, chloroborohydride, trinitrobenzenesulfonic acid, methylisourea, 2,4-pentanedione, and transaminase-catalyzed reaction with glyoxylate.

Arginyl residues are modified by reaction with one or several conventional reagents, among them phenylgly-oxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form 0-acetyl tyrosyl species and 3-nitro derivatives, respectively. Tyrosyl residues are iodinated using 125I or 131I to prepare labeled proteins for use in radioimmunoassay. Carboxyl side groups (aspartyl or glutamyl) are selectively modified by reaction with carbodiimides (R—N. dbd.C.dbd.N—R'), where R and R' are different alkyl groups, such as 1-cyclohexyl-3-(2-morpholinyl-4-ethyl) carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention. Other modifications include hydroxylation of proline and lysine, phosphorylation of hydroxyl groups of seryl or threonyl residues, methylation of the alpha amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO87I 05330 published 11 Sep. 1987, and in Aplin and Wriston, CRC Crit. Rev. Biochem., pp. 259-306 (1981).

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Hakimuddin, et al. Arch. Biochem. Biophys. 259: 52 (1987) and by Edge et al. Anal. Biochem., 118: 131 (1981). Enzymatic cleavage of carbohydrate moieties on antibodies can be achieved by the use of a variety of endo- and exoglycosidases as described by Thotakura et al. Meth. Enzymol. 138: 350 (1987).

Another type of covalent modification of the antibody comprises linking the antibody to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art, see, e.g. U.S. Pat. Nos. 4,640,835; 4,496,689; 4,301,144; 4,670,417; 4,791,192, 4,179,337, 4,766,106, 4,179,337, 4,495,285, 4,609,546 or EP 315456.

Competitive Antibody

In some embodiments, antibodies which compete with the antibodies provided herein for binding to specified antigens (e.g., antigen in Table 9 and Table 10) are provided. In some embodiments, antibodies compete with the antibodies provided herein for binding to an epitope on the specified antigen.

In some embodiments, competition assays may be used to identify a monoclonal antibody that competes with an antibody described herein. Competition assays can be used to determine whether two antibodies bind the same epitope by recognizing identical or sterically overlapping epitopes or one antibody competitively inhibits binding of another antibody to the antigen. In some embodiments, such a competing antibody binds to the same epitope that is bound by an antibody described herein. Exemplary competition assays include, but are not limited to, routine assays such as those provided in Harlow and Lane (1988) Antibodies: A Laboratory Manual ch. 14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). In some embodiments, two antibodies are said to bind to the same epitope if each blocks binding of the other by 50% or more. In some embodiments, the antibody that competes with an antibody described herein is a chimeric, humanized or human antibody. In some embodiments, an antibody that competes with a chimeric, humanized, or human antibody as described herein is provided.

In some embodiments, antibodies that bind to any one or more of the epitopes that the antibodies provided herein are provided. In some embodiments, antibodies that bind and overlap an epitope to which the present antibodies bind to are provided. In some embodiments, an antibody is provided that competes with at least one of the antibodies provided herein. In some embodiments, an antibody is provided that competes with at least two of the antibodies provided herein. In some embodiments, an antibody is provided that competes with at least three of the antibodies provided herein. In some embodiments, the antibody binds to an overlapping epitope as an antibody described in the examples herein. In some embodiments, the entire epitope is bound and/or obstructed by the competing antibody. In some embodiments, a part of the epitope is bound and/or obstructed by the competing antibody. In some embodiments, the competing antibody's paratope binds to at least a part of the epitope of an antibody provided herein. In some embodiments, the competing antibody's paratope binds the target, and a different section of the competing antibody's structure obstruct at least a part of the epitope of an antibody provided herein.

The term "competition" or "cross-competition" refers to the ability of an antibody molecule, e.g., an antibody molecule that interferes with the binding of an antibody the invention to a target, eg, antigens in Table 9 and Table 10; is used interchangeably herein. Interference to binding may be direct or indirect (e.g., through allosteric modulation of the antibody molecule or target). The degree to which antibody molecules can interfere with the binding of other antibody molecules to the target and thus whether they can compete can be determined using competitive binding assays, such as FACS analysis, ELISA or BIACORE analysis. In some embodiments, the competitive binding assay is a quantitative competitive assay. In some embodiments, the first antibody molecule has a binding of the first antibody molecule to a target that is greater than or equal to 10%, such as greater than or equal to 20% (e. G., Greater than or equal to 10%, 30% or more, 40% or more, 50% or more, 55% or more, 60% or more, 65% or more, 70% or more, 75% or more, 80% or more, 85% or more, 90% %, More than 99%, compared to the antibody of the second antibody molecule.

Methods of Making Antibodies

The antibodies or antigen binding fragment thereof of the present disclosure can be obtained using the in silico reconstructed, complete nucleic acid sequences and amino acid sequences of cancer associated antibodies or antigen binding fragment thereof disclosed herein. In some embodiments, antibodies or antigen binding fragment thereof prepared by the methods described below are provided. In some embodiments, the antibody or antigen binding fragment thereof is prepared in a host cell. In some embodiments, the antibody or antigen binding fragment thereof is isolated from a host cell. In some embodiments, the antibody or antigen binding fragment thereof is prepared in a cell-free system. In some embodiments, the antibody or antigen binding fragment thereof is purified. The present invention also provides a method of producing an antibody molecule of the invention, said method generally comprising the steps of: Culturing a host cell comprising an expression vector comprising a nucleic acid encoding an antibody molecule of the invention under conditions permitting the formation of an antibody of the invention; isolating the antibody molecule expressed by the host cell from the culture; And Optionally, further purifying and/or modifying and/or formulating an antibody molecule of the invention.

Nucleic acid molecules encoding the antibodies or antigen binding fragment thereof of the present disclosure can be isolated, for example, from mature mammalian B lymphocyte or when fused with an immortalized cell as part of a hybridoma culture, using conventional procedures (e.g., by using oligonucleotide probes that are capable of binding specifically to genes encoding the heavy and light chains of a desired antibody). The disclosure provides isolated nucleic acid molecule comprising a nucleic acid sequence encoding an antibody polypeptide or antigen binding fragment thereof. Isolated nucleic acid molecule comprising the sequences disclosed herein can be prepared using (a) recombinant methods, (b) synthetic techniques, (c) purification techniques, and/or (d) combinations thereof, as is well known in the art and discussed below.

Messenger RNA coding for the antibodies or antigen binding fragment thereof (e.g., heavy or light chain) can be isolated from a suitable source, either mature B cells or a hybridoma culture, employing standard techniques of RNA isolation, and the use of oligo-dT cellulose chromatography to segregate the poly-A mRNA. The poly-A mRNA may, further, be fractionated to obtain sequences of sufficient size to code for the amino acid sequences in the light or heavy chain of the desired antibody as the case may be.

For example, a cDNA library may be constructed by reverse transcription of polyA+mRNA, preferably membrane-associated mRNA, and the library screened using a suitable primer, preferably a nucleic acid sequence which is characteristic of the desired cDNA. Such a primer can be easily hypothesized and synthesized based on the cDNA or the amino acid sequence of an antibody if the sequence is known, for example, the primer can be synthesized based on the nucleic acid sequence or the amino acid sequence of the antibodies disclosed herein.

In some embodiments, however, the polymerase chain reaction (PCR) using the primers described above is used to amplify cDNAs (or portions of full-length cDNAs) encoding one or more immunoglobulin gene segment of interest (e.g., a light chain variable segment). The amplified sequences can be readily cloned into any suitable vector, e.g., expression vectors, minigene vectors, or phage display vectors. In some embodiments, the nucleic acid sequence of the antibodies or antigen binding fragment thereof, of the present disclosure can be readily cloned into any suitable vector, e.g., expression vectors, minigene vectors, or phage display vectors. Cloning is carried out using standard techniques (see, e.g., Sambrook et al. (1989) Molecular Cloning: A Laboratory Guide, Vols 1-3, Cold Spring Harbor Press, which is incorporated herein by reference). It will be appreciated that the particular method of cloning used not critical, so long as it is possible to determine the sequence of some portion of the immunoglobulin polypeptide of interest.

One source for RNA used for cloning and isolating nucleic acid sequence encoding a desired antibody or antigen-binding fragment thereof, is a hybridoma produced by fusing a B cell producing the antibody to an immortal cell. An advantage of using hybridomas is that they can be easily screened, and a hybridoma that produces the antibody of interest selected. Alternatively, RNA can be isolated from antibody-producing cells (e.g., B-cells) from the peripheral blood or, preferably the spleen or lymph nodes, or whole spleen, of a subject (e.g., humans or other suitable animals). In some embodiments, the human or suitable animal has been immunized against a target antigen (e.g., antigen in Tables 9 and table 10). Recombinant antigens or fragments thereof can be used to immunize mice to generate the hybridomas that produce the antibodies of the instant disclosure. In some embodiments, provided herein is a hybridoma generating the antibodies or the present disclosure. The antigen may include an antigenic polypeptide, a fusion protein or variants thereof. Depending upon the nature of the polypeptides (i.e., percent hydrophobicity, percent hydrophilicity, stability, net charge, isoelectric point etc.), it may be useful to conjugate the antigen to a protein known to be immunogenic in the mammal being immunized. As it relates to the present disclosure, the subject can be one suffering from a cancer.

Based on the in silico reconstructed nucleic acid and amino acid sequences of the cancer associated antibody, the isolated nucleic acid molecule encoding a cancer associated antibody or an antigen binding fragment thereof, can also be prepared by direct chemical synthesis by known methods (see, e.g., Ausubel et al., Supra, WO1999014318A1). Chemical synthesis generally produces a single stranded oligonucleotide, which can become dsDNA by hybridization with a complementary sequence, or by polymerization with a DNA polymerase using the single strand as a template. One skilled in the art will recognize that while chemical synthesis of DNA can be limited to sequences of about 100 or more bases, longer sequences may be obtained by the ligation of shorter sequences.

In some embodiments, the isolated nucleic acid molecule comprises a nucleic acid sequence encoding a heavy chain polypeptide of an antibody. In some embodiments, the nucleic acid sequence encoding a heavy chain polypeptide is selected from SEQ ID NOs.: 113-126. In some embodiments, the isolated nucleic acid molecule comprises a nucleic acid sequence encoding a light chain polypeptide of an antibody. In some embodiments, the nucleic acid sequence encoding a light chain polypeptide is selected from SEQ ID NOs.: 127-140. In some embodiments, the isolated nucleic acid molecule comprises a nucleic acid sequence encoding a CDR1 polypeptide of a variable heavy chain. In some embodiments, the isolated nucleic acid molecule comprises a nucleic acid sequence encoding a CDR2 polypeptide of a variable heavy chain. In some embodiments, the isolated nucleic acid molecule comprises a nucleic acid sequence encoding a CDR3 polypeptide of a variable heavy chain. In some embodiments, the nucleic acid sequence encoding the CDR1 polypeptide of a variable heavy chain (CDR-H1) comprises a sequence selected from SEQ ID NOs.:197-210. In some embodiments, the nucleic acid sequence encoding the CDR2 polypeptide of a variable heavy chain (CDR-H2) comprises a sequence selected from SEQ ID NOs.:169-182. In some embodiments, the nucleic acid sequence encoding the CDR3 polypeptide of a variable heavy chain (CDR-H3) comprises a sequence selected from SEQ ID NOs.:141-154. In some embodiments, the isolated nucleic acid molecule comprises a nucleic acid sequence encoding a CDR1 polypeptide of a variable light chain. In some embodiments, the isolated nucleic acid molecule comprises a nucleic acid sequence encoding a CDR2 polypeptide of a variable light chain. In some embodiments, the isolated nucleic acid molecule comprises a nucleic acid sequence encoding a CDR3 polypeptide of a variable light chain. In some, embodiments, the nucleic acid sequence encoding the CDR1 region of a variable light chain polypeptide (CDR-L1) comprises a sequence selected from SEQ ID NOs: 211-224. In some embodiments, the nucleic acid sequence encoding the CDR2 region of a variable light chain polypeptide (CDR-L2) comprises a sequence selected from SEQ ID NOs: 183-196. In some, embodiments, the nucleic acid sequence encoding the CDR3 region of a variable light chain polypeptide (CDR-L3) comprises a sequence selected from SEQ ID NOs: 155-168.

The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides.

As used herein, an "isolated" nucleic acid molecule or "isolated" nucleic acid sequence is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined, is considered isolated. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells. "Isolated nucleic acid", as used herein, is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man. The term "polypeptide" is used in its conventional meaning, i.e., as a sequence of amino acids.

An isolated nucleic acid molecule encoding the antibody, portion or polypeptide of the present disclosure can be recombined with vector DNA (e.g., expression vector) in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., Molecular Cloning, Lab. Manual (Cold Spring Harbor Lab. Press, N Y, 1982 and 1989), and Ausubel, 1987, 1993, and can be used to construct nucleic acid sequences which encode an antibody molecule or antigen binding region thereof. Accordingly, the disclosure provides for a vector or expression vector comprising the isolated nucleic acids set forth herein. In one embodiment, the nucleic acid coding for the light chain and that coding for the heavy chain are isolated separately by the procedures outlined above. In one embodiment, the isolated nucleic acid encoding the light chain and that coding for the heavy chain may be inserted into separate expression plasmids, or together in the same plasmid, so long as each is under suitable promoter and translation control.

Once the isolated nucleic acid molecule is placed into an expression vector, they are then transfected into host cells such as E. coli cells, simian COS cells, human embryonic kidney 293 cells (e.g., 293E cells), Chinese hamster ovary (CHO) cells, or myeloma cells that do not otherwise produce immunoglobulin protein, to obtain the synthesis of the antibody or an antigen-binding fragment thereof in the recombinant host cells. Recombinant production of antibodies is well known in the art. Many vectors are available. The vector components generally include, but are not limited to, one or more of the following: a signal sequence, an origin of replication, one or more selective marker genes, an enhancer element, a promoter, and a transcription termination sequence.

The isolated nucleic acid molecules are operably linked to an expression control sequence in the vector DNA. Expression control sequence refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

Nucleic acid is operably linked when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and/or can contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Cell, cell line, and cell culture are often used interchangeably and all such designations herein include progeny. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context. In an alternative embodiment, suitable encoding nucleic acid sequences can be designed according to a universal codon table, based on the known amino acid sequence of an immunoglobulin of interest.

Amino acid sequence variants of the desired antibody may be prepared by introducing appropriate nucleotide changes into the encoding DNA, or by peptide synthesis. Such variants include, for example, deletions from, and/or insertions into and/or substitutions of, residues within the amino acid sequences of the antibodies. Any combination of deletion, insertion, and substitution is made to arrive at the final construct, provided that the final construct possesses the desired characteristics. The amino acid changes also may alter post-translational processes of the monoclonal, human, humanized, or variant antibody, such as changing the number or position of glycosylation sites.

Nucleic acid molecules encoding amino acid sequence variants of the antibody are prepared by various methods. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

The present disclosure also provides isolated nucleic acid molecules encoding for antibodies or antigen binding fragment thereof, described herein, optionally operably linked to regulatory control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium.

For recombinant production of an antibody or antigen binding fragment thereof, the nucleic acid molecule encoding it can be isolated and inserted into a replicable vector for further cloning (amplification of the DNA) or for expression. Accordingly provided herein are isolated antibody or antigen binding fragment thereof. In some embodiments, the antibodies or the present disclosure or antigen binding fragment thereof can be recombinant antibody. The term "recombinant antibody" refers to an antibody that is expressed from a cell or cell line transfected with an expression vector (or possibly more than one expression vector, typically two expression vectors) comprising the coding sequence of the antibody, where said coding sequence is not naturally associated with the cell. In one embodiment, a recombinant antibody has a glycosylation pattern that is different than the glycosylation pattern of an antibody having the same sequence if it were to exist in nature. In one embodiment, a recombinant antibody is expressed in a mammalian host cell which is not a human host cell. Notably, individual mammalian host cells have unique glycosylation patterns In some embodiments, the antibodies or antigen binding fragment thereof of the present disclosure are isolated. With regards to the an isolated antibody polypeptide or an antigen binding fragment polypeptide; "isolated" is referred to when the polypeptide is separated from at least some of the components of the cell (e.g., host cell) in which it was produced. Where a polypeptide is secreted by a host cell after expression, physically separating the supernatant containing the polypeptide from the host cell that produced it is considered to be "isolating" the polypeptide. The term "isolated" refers to a protein (e.g., an antibody) that is substantially free of other cellular material and/or chemicals. In one embodiment, an isolated antibody is substantially free of other proteins from the same species. In one embodiment, an isolated antibody is expressed by a cell from a different species and is substantially free of other proteins from the difference species. A protein may be rendered substantially free of naturally associated components (or components associated with the cellular expression system used to produce the antibody) by isolation, using protein purification techniques well known in the art.

In some embodiments, the antibody or antigen binding fragment thereof disclosed herein is produced in a cell-free system. Nonlimiting exemplary cell-free systems are described, for example, in Sitaraman et al., Methods Mol. Biol. 498: 229-44 (2009); Spirin, Trends Biotechnol. 22: 538-45 (2004); Endo et al., Biotechnol. Adv. 21: 695-713 (2003). For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system. Antibody polypeptides can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis. In some embodiments, the antibodies or antigen binding fragment of the present disclosure is synthetic. The polypeptides of the present disclosure can be purified by isolation/purification methods for proteins generally known in the field of protein chemistry.

When sources other than hybridomas are used to obtain antibodies, it may be desirable to screen for sequences encoding immunoglobulins or immunoglobulin polypeptides with specific binding characteristics. One method for such screening is the use of phage display technology. Phage display is described in e.g., Dower et al., McCafferty et al., and Caton and Koprowski, Proc. Natl. Acad. Sci. USA, 87:6450-6454 (1990), each of which is incorporated herein by reference. In one embodiment using phage display technology, cDNA from an immunized transgenic mouse (e.g., total spleen cDNA) is isolated, the polymerase chain reaction is used to amplify a cDNA sequences that encode a portion of an immunoglobulin polypeptide, e.g., CDR regions, and the amplified sequences are inserted into a phage vector. cDNAs encoding peptides of interest, e.g., variable region peptides with desired binding characteristics are identified by standard techniques such as panning. The sequence of the amplified or cloned nucleic acid is then determined. Typically the sequence encoding an entire variable region of the immunoglobulin polypeptide is determined, however, it will sometimes be adequate to sequence only a portion of a variable region, for example, the CDR-encoding portion. Typically the portion sequenced will be at least 30 bases in length, more often based coding for at least about one-third or at least about one-half of the length of the variable region will be sequenced.

Sequencing can be carried out on clones isolated from a cDNA library, or, when PCR is used, after subcloning the amplified sequence or by direct PCR sequencing of the amplified segment. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Selection and Transformation of Host Cells

In one aspect, provided herein is a host cell comprising the isolated nucleic acid molecules described herein or a vector comprising said isolated nucleic acid molecules described herein. The vector can be a cloning vector or an expression vector. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1 776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia* pastors (EP 183,070); *Candida*; *Trichoderma* reesia (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NP\7, and such viruses may be used as the virus herein according to the present invention, particularly for transfection of *Spodoptera frugiperda* cells.

Plant cell cultures of cotton, coal, potato, soybean, *petunia*, tomato, tobacco, *lemna*, and other plant cells can also be utilized as hosts. However, interest has been greatest in vertebrate cells, and propagation of vertebrate cells in culture (tissue culture) has become routine procedure. Examples of useful mammalian host cell lines are Chinese hamster ovary cells, including CHOK1 cells (ATCC CCL61), DXB-11, DG-44, and Chinese hamster ovary cells/-DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, [Graham et al., *J. Gen Viral.* 36: 59 (1977)]; baby hamster kidney cells (BHK, ATCC CCL 10); mouse sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y Acad. Sci. 383: 44-68 (1982)); MRC 5 cells; FS4 cells; and a human hepatoma line (Hep G2).

Host cells are transformed or transfected with the above-described expression or cloning vectors for antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of antibodies, described herein.

For transfection of the expression vectors and production of the chimeric, humanized, or composite human antibodies described herein, the recipient cell line can be a myeloma cell. Myeloma cells can synthesize, assemble and secrete immunoglobulins encoded by transfected immunoglobulin nucleic acid sequences and possess the mechanism for glycosylation of the immunoglobulin. For example, in some embodiments, the recipient cell is the recombinant Ig-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells. An expression vector carrying a chimeric, humanized, or composite human antibody construct or antibody polypeptide described herein can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et al., 240 Science 1538 (1988), as known to one of ordinary skill in the art.

Yeast provides certain advantages over bacteria for the production of immunoglobulin H and L chains Yeasts carry out post-translational peptide modifications including glycosylation. A number of recombinant DNA strategies exist that utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 11th Intl. Conf. Yeast, Genetics & Molec. Biol. (Montpelier, France, 1982). Yeast gene expression systems can be routinely evaluated for the levels of production, secretion and the stability of antibody polypeptide or antigen binding fragment peptide thereof, and assembled chimeric, humanized, or composite human antibodies, fragments and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast.

Bacterial strains can also be utilized as hosts for the production of the antibody molecules or fragments thereof described herein, E. coli K12 strains such as E. coli W3110 (ATCC 27325), Bacillus species, enterobacteria such as Salmonella typhimurium or Serratia marcescens, and various Pseudomonas species can be used. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of chimeric, humanized, or composite humanized antibodies and fragments thereof encoded by the cloned immunoglobulin cDNAs or CDRs in bacteria {see Glover, 1985; Ausubel, 1987, 1993; Sambrook, 1989; Colligan, 1992-1996).

Host mammalian cells can be grown in vitro or in vivo. Mammalian cells provide post-translational modifications to immunoglobulin protein molecules including leader peptide removal, folding and assembly of H and L chains, glycosylation of the antibody molecules, and secretion of functional antibody protein. Mammalian cells which can be useful as hosts for the production of antibody proteins, in addition to the cells of lymphoid origin described above, include cells of fibroblast origin, such as Vero (ATCC CRL 81) or CHO-K1 (ATCC CRL 61) cells. Exemplary eukaryotic cells that can be used to express polypeptides include, but are not limited to, COS cells, including COS 7 cells; 293 cells, including 293-6E cells; CHO cells, including CHO-S and DG44 cells; PER.C6® cells (Crucell); and NSO cells. In some embodiments, a particular eukaryotic host cell is selected based on its ability to make desired post-translational modifications to the variable heavy chains and/or variable light chains. For example, in some embodiments, CHO cells produce polypeptides that have a higher level of sialylation than the same polypeptide produced in 293 cells.

In some embodiments, polypeptides of the antibodies or antigen binding fragment thereof, disclosed herein can be produced in vivo in an animal that has been engineered or transfected with one or more nucleic acid molecules encoding the polypeptides, according to any suitable method.

In some embodiments, an antibody or antigen binding fragment thereof is produced in a cell-free system. Nonlimiting exemplary cell-free systems are described, e.g., in Sitaraman et al., Methods Mol. Biol. 498: 229-44 (2009); Spirin, Trends Biotechnol. 22: 538-45 (2004); Endo et al., Biotechnol. Adv. 21: 695-713 (2003).

Many vector systems are available for the expression of H and L chain nucleic acid sequence in mammalian cells (see Glover, 1985). Different approaches can be followed to obtain complete $H_2L_2$ antibodies. As discussed above, it is possible to co-express H and L chains in the same cells to achieve intracellular association and linkage of H and L chains into complete tetrameric $H_2L_2$ antibodies and/or antigen binding fragment peptides. The co-expression can occur by using either the same or different plasmids in the same host. Genes for both H and L chains and/or CDR3 regions peptides can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing antigen binding peptide fragments and/or $H_2L_2$ molecules via either route could be transfected with plasmids encoding additional copies of peptides, H, L, or H plus L chains in conjunction with additional selectable markers to generate cell lines with enhanced properties, such as higher production of assembled $H_2L_2$ antibody molecules or enhanced stability of the transfected cell lines.

Additionally, plants have emerged as a convenient, safe and economical alternative main-stream expression systems for recombinant antibody production, which are based on large scale culture of microbes or animal cells. Antibodies can be expressed in plant cell culture, or plants grown conventionally. The expression in plants may be systemic, limited to sub-cellular plastids, or limited to seeds (endosperms). Several plant-derived antibodies have reached advanced stages of development (see, e.g., Biolex, NC).

In some aspects, provided herein are methods and systems for the production of a humanized antibody, which is prepared by a process which comprises maintaining a host transformed with a first expression vector which encodes the light chain of the humanized antibody and with a second expression vector which encodes the heavy chain of the humanized antibody under such conditions that each chain is expressed and isolating the humanized antibody formed by assembly of the thus-expressed chains. The first and second expression vectors can be the same vector. Also provided herein are DNA sequences encoding the light chain or the heavy chain of the humanized antibody; an expression vector which incorporates a said DNA sequence; and a host transformed with a said expression vector. Generating a humanized antibody from the sequences and information provided herein can be practiced by those of ordinary skill in the art without undue experimentation. In one approach, there are four general steps employed to humanize a monoclonal antibody. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Purification

The term "isolated" means altered or removed from the natural state. For example, a nucleic acid or a polypeptide (e.g. antibodies or antigen binding fragment thereof disclosed herein) naturally present in a living animal is not "isolated," but the same nucleic acid or polypeptide partially or completely separated from the coexisting materials of its natural state is "isolated." An isolated nucleic acid molecule or polypeptide can exist in substantially purified form, or can exist in a non-native environment such as, for example, a host cell. An isolated polypeptide is one that has been separated and/or recovered from a component of its natural environment. Contaminant components of its natural environment are materials that would interfere with diagnostic or therapeutic uses of the polypeptide, and may include enzymes, hormones, and other proteinaceous or non-proteinaceous components. In some embodiments, the antibodies or antigen binding fragments thereof of the instant disclosure can be purified by a suitable method. In preferred embodiments, the polypeptide is purified: (1) to greater than 95% by weight of polypeptide as determined by the Lowry method, and most preferably more than 99% by weight; (2) to a degree sufficient to obtain at least 15 residues of N-terminal or internal amino acid sequence by use of a spinning cup sequenator; or (3) to homogeneity as shown by SDS-PAGE under reducing or non-reducing conditions and using Coomassie blue or, preferably, silver staining. Isolated antibody includes the polypeptide in situ within recombinant cells since at least one component of the polypeptide's natural environment will not be present. Ordinarily, however, isolated polypeptide will be prepared by at least one purification step. In one aspect, disclosed herein is a purified antibody or antigen-binding fragment as provided herein.

Once expressed, the whole antibodies, their dimers, individual light and heavy chains, or other immunoglobulin forms of the present invention can be recovered and purified by known techniques, e.g., immunoabsorption or immunoaffinity chromatography, chromatographic methods such as HPLC (high performance liquid chromatography), ammonium sulfate precipitation, gel electrophoresis, or any combination of these. See generally, Scopes, PROTEIN PURIF. (Springer-Verlag, NY, 1982). Substantially pure immunoglobulins of at least about 90% to 95% homogeneity are advantageous, as are those with 98% to 99% or more homogeneity, particularly for pharmaceutical uses. When using recombinant techniques, the antibody can be produced intracellularly, in the periplasmic space, or directly secreted into the medium, including from microbial cultures. If the antibody is produced intracellularly, as a first step, the particulate debris, either host cells or lysed fragments, is removed, for example, by centrifugation or ultrafiltration. Better et al. Science 240: 1041-1043 (1988); ICSU Short Reports 10: 105 (1990); and Proc. Natl. Acad. Sci. USA 90: 457-461 (1993) describe a procedure for isolating antibodies which are secreted to the periplasmic space of $E.\ coli$. (See also, [Carter et al., Bio/Technology 10: 163-167 (1992)].

The antibody composition isolated from microbial or mammalian cells can be purified using, for example, hydroxylapatite chromatography cation or avian exchange chromatography, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., $J.\ Immunol.\ Meth.$ 62: 1-13 (1983)). Protein G is recommended for all mouse isotypes and for human γ3 (Guss et al., EMBO J. 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH 3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered. Once purified, partially or to homogeneity as desired, a humanized or composite human antibody can then be used therapeutically or in developing and performing assay procedures, immunofluorescent staining, and the like. See generally, Vols. I & II Immunol. Meth. (Lefkovits & Pernis, eds., Acad. Press, N Y, 1979 and 1981).

Functional activities of an antibody or antigen-binding fragment disclosed herein. Such functional activities include biological activity and ability to bind to a cancer cell antigen. Additionally, a polypeptide having functional activity means the polypeptide exhibits activity similar, but not necessarily identical to, an activity of an antibody described herein, including mature forms, as measured in a particular assay, such as, for example, a biological assay, with or without dose dependency. In the case where dose dependency does exist, it need not be identical to that of the antibodies of the disclosure, but rather substantially similar to the dose-dependence in a given activity as compared to the antibodies set forth herein (i.e., the candidate polypeptide will exhibit greater activity, or not more than about 25-fold less, about 10-fold less, or about 3-fold less activity relative to the antibodies described herein).

Library-Derivation

Antibodies or antigen binding fragment thereof of the present disclosure may be isolated by screening combinatorial libraries for antibodies with the desired activity or activities. (See, e.g., in Hoogenboom et al., Methods in Molecular Biology 178:1-37 (2001); McCafferty et al., Nature 348:552-554; Clackson et al., Nature 352: 624-628 (1991); Marks et al., J. Mol. Biol. 222: 581-597 (1992); Marks and Bradbury, Methods in Molecular Biology 248: 161-175 (2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004)). Repertoires of VH and VL genes can be cloned separately (e.g., by PCR) and recombined randomly in libraries (e.g., phage libraries), and screened (See, e.g., Winter et al., Ann. Rev. Immunol., 12: 433-455 (1994)). Alternatively, the naive repertoire can be cloned (e.g., from human) to provide a single source of antibodies to a wide range of non-self and also self-antigens without any immunization (See, e.g., Griffiths et al., EMBO J, 12: 725-734 (1993). Alternatively, naive libraries can be synthetically made by cloning unrearranged V-gene segments from stem cells, and encoding the CDR3 regions using random primers or to rearrange the V-gene segments in vitro (See, e.g., Hoogenboom and Winter, J. Mol. Biol., 227: 381-388 (1992)). Antibodies or antibody fragments isolated from human antibody libraries are considered human antibodies or human antibody fragments herein.

Nucleic Acid Molecules Encoding Antibodies

Using the information provided herein, for example, the reconstructed nucleic acid and amino acid sequences of the cancer associated antibodies; a nucleic acid molecule encoding the antibodies or antigen-binding fragment thereof can be obtained. Such a nucleic acid molecule can be obtained, for example, using conventional methods disclosed in the art. Nucleic acid molecules of the present disclosure may be in the form of RNA, such as mRNA, hnRNA, tRNA or any other form, or in the form of DNA, including but not limited to, cDNA and genomic DNA obtained by cloning or produced synthetically, or any combinations thereof. The DNA may be triplex, duplex or single-stranded, or any combination thereof. Any portion of at least one strand of the DNA or RNA may be the coding strand, also known as the sense strand, or it can be the antisense strand, also known as the antisense strand.

"Polynucleotide," or "nucleic acid molecule," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A nucleic acid molecule can comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azidoribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including isolated nucleic acid, RNA and DNA.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine. In some embodiments, the nucleic acid molecule comprises an isolated nucleic acid.

The nucleic acids can be present in whole cells, in a cell lysate, or in a partially purified or substantially pure form. A nucleic acid molecule is "isolated" or "rendered substantially pure" when purified away from other cellular components or other contaminants, e.g., other cellular nucleic acids or proteins, by standard techniques, including, but not limited to alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid according to at least some embodiments of the disclosure can be, for example, DNA or RNA and may or may not contain intronic sequences. In a preferred embodiment, the nucleic acid is a cDNA molecule.

Another aspect of the present disclosure pertains to nucleic acid molecules comprising reconstructed consensus nucleic acid sequences that encode the antibody polypeptide, described herein or antigen-binding fragment thereof. In some embodiments, the isolated nucleic acid molecule comprises a nucleic acid sequence encoding a heavy chain polypeptide of an antibody. In some embodiments, the nucleic acid sequence encoding a heavy chain polypeptide is selected from SEQ ID NOs.: 113-126. In some embodiments, the isolated nucleic acid molecule comprises a nucleic acid sequence encoding a light chain polypeptide of an antibody. In some embodiments, the nucleic acid sequence encoding a light chain polypeptide is selected from SEQ ID NOs.: 127-140. In some embodiments, the isolated nucleic acid molecule comprises a nucleic acid sequence encoding a CDR1 polypeptide of a variable heavy chain. In some embodiments, the isolated nucleic acid molecule comprises a nucleic acid sequence encoding a CDR2 polypeptide of a variable heavy chain. In some embodiments, the isolated nucleic acid molecule comprises a nucleic acid sequence encoding a CDR3 polypeptide of a variable heavy chain. In some embodiments, the nucleic acid sequence encoding the CDR1 polypeptide of a variable heavy chain (CDR-H1) comprises a sequence selected from SEQ ID NOs.:197-210. In some embodiments, the nucleic acid sequence encoding the CDR2 polypeptide of a variable heavy chain (CDR-H2) comprises a sequence selected from SEQ ID NOs.:169-182. In some embodiments, the nucleic acid sequence encoding the CDR3 polypeptide of a variable heavy chain (CDR-H3) comprises a sequence selected from SEQ ID NOs.:141-154. In some embodiments, the isolated nucleic acid molecule comprises a nucleic acid sequence encoding a CDR1 polypeptide of a variable light chain. In some embodiments, the isolated nucleic acid molecule comprises a nucleic acid sequence encoding a CDR2 polypeptide of a variable light chain. In some embodiments, the isolated nucleic acid molecule comprises a nucleic acid sequence encoding a CDR3 polypeptide of a variable light chain. In some, embodiments, the nucleic acid sequence encoding the CDR1 region of a variable light chain polypeptide (CDR-L1) comprises a sequence selected from SEQ ID NOs: 211-224. In some embodiments, the nucleic acid sequence encoding the CDR2 region of a variable light chain polypeptide (CDR-L2) comprises a sequence selected from SEQ ID NOs: 183-196. In some, embodiments, the nucleic acid sequence encoding the CDR3 region of a variable light chain polypeptide (CDR-L3) comprises a sequence selected from SEQ ID NOs: 155-168.

Nucleic acid molecules according to at least some embodiments of the present disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame. The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence (Gly-4-Ser)3, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Nucleic acid molecules isolated from the present disclosure can include nucleic acid molecules comprising an open reading frame (ORF), optionally with one or more introns, e.g., but not limited to, at least one specified portion of at least a CDR, as CDR1, CDR2 and/or CDR3 of at least one light chain (e.g., SEQ ID NOS:127-140) or at least one heavy chain (e.g., SEQ ID NOs:113-126); nucleic acid molecules comprising the coding sequence of a cancer associated antibody disclosed herein or variable region e.g., variable regions of the light chain (SEQ ID NOS: 127-140) and variable regions of the heavy chain SEQ ID NO: 113-126); and nucleic acid molecules comprising a nucleotide sequence substantially different from those described above but which, due to the degeneracy of the genetic code, still encode at least antibody or antigen binding fragment thereof as described herein and/or as it is known in the art. Of course, the genetic code is well known in the art. Therefore, it would be routine for one skilled in the art to generate such degenerate nucleic acid variants encoding specific antibodies of the present disclosure. See for example, Ausubel et al., Supra, and such nucleic acid variants are included in the present invention.

Nucleic acid molecules comprising nucleic acid sequence that encode one or more chains of an antibody are provided herein. In some embodiments, a nucleic acid molecule comprises a nucleic acid sequence that encodes a heavy chain or a light chain of an antibody. In some embodiments, a nucleic acid molecule comprises both a nucleic acid sequence that encodes a heavy chain and a nucleic acid sequence that encodes a light chain, of an antibody. In some embodiments, a first nucleic acid molecule comprises a first nucleic acid sequence that encodes a heavy chain and a second nucleic acid molecule comprises a second nucleic acid sequence that encodes a light chain.

In some embodiments, the heavy chain and the light chain are expressed from one nucleic acid molecule, or from two separate nucleic acid molecules, as two separate polypeptides. In some embodiments, such as when an antibody is an scFv, a single nucleic acid sequence encodes a single polypeptide comprising both a heavy chain and a light chain linked together.

In some embodiments, a nucleic acid sequence encoding a heavy chain or light chain of an antibody disclosed herein comprises a nucleic acid sequence that encodes at least one of the CDRs provided herein. In some embodiments, a nucleic acid sequence encoding a heavy chain or light chain of an antibody disclosed herein comprises a sequence that encodes at least 3 of the CDRs provided herein. In some embodiments, a nucleic acid sequence encoding a heavy chain or light chain of an antibody comprises a sequence that encodes at least 6 of the CDRs provided herein. In some embodiments, a nucleic acid sequence encoding a heavy chain or light chain of an antibody comprises a nucleotide sequence that encodes a leader sequence, which, when translated, is located at the N terminus of the heavy chain or light chain. The leader sequence may be the native heavy or light chain leader sequence, or may be another heterologous leader sequence. The term "leader sequence" refers to a sequence of amino acid residues located at the N-terminus of a polypeptide that facilitates secretion of a polypeptide from a mammalian cell. A leader sequence can be cleaved upon export of the polypeptide from the mammalian cell, forming a mature protein. Leader sequences can be natural or synthetic, and they can be heterologous or homologous to the protein to which they are attached.

In some embodiments, the nucleic acid molecule is one that encodes for any of the amino acid sequences for the antibodies in the Tables 1-2 herein. In some embodiments, the nucleic acid sequence is one that is at least 80% identical to a nucleic acid encoding any of the amino acid sequences for the antibodies in the in the Tables 1-2 herein, for example, at least 80, 85, 90, 91, 92, 93, 94, 95, 96, 97, 98, or 99% identical. In some embodiments, the nucleic acid is one that hybridizes to any one or more of the nucleic acid sequences provided herein. In some of the embodiments, the hybridization is under moderate conditions. In some embodiments, the hybridization is under highly stringent conditions, such as: at least about 6×SSC and 1% SDS at 65° C., with a first wash for 10 minutes at about 42° C. with about 20% (v/v) formamide in 0.1×SSC, and with a subsequent wash with 0.2×SSC and 0.1% SDS at 65° C.

Nucleic acid molecules can be constructed using recombinant DNA techniques conventional in the art. In some embodiments, a nucleic acid molecule is placed in an expression vector that is suitable for expression in a selected host cell.

Vectors comprising nucleic acid molecules that encode the antibodies or antigen binding fragment herein are provided. Vectors comprising nucleic acid molecules that encode a heavy chains and/or a light chains are also provided. Such vectors include, but are not limited to, DNA vectors, phage vectors, viral vectors, retroviral vectors, etc. In one embodiment, the nucleic acid coding for the light chain and that coding for the heavy chain are isolated separately by the procedures outlined above. In one embodiment, the isolated nucleic acid encoding the light chain and that coding for the heavy chain may be inserted into separate expression plasmids, or together in the same plasmid, so long as each is under suitable promoter and translation control. In some embodiments, the heavy chain and light chain are expressed as part of a single polypeptide, such as, for example, when the antibody is an scFv.

In some embodiments, a first vector comprises a nucleic acid molecule that encodes a heavy chain and a second vector comprises a nucleic acid molecule that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used. In some embodiments, a vector is selected that is optimized for expression of polypeptides in CHO or CHO-derived cells, or in NSO cells. Exemplary such vectors are described, for example, in Running Deer et al., Biotechnol. Prog. 20:880-889 (2004).

In one aspect, the present disclosure provides methods for treatment or prevention of cancer comprising administering nucleic acid molecules, wherein the nucleic acid molecules encode for a VH, VL, CDR3 region of VH or CDR 3 region of VL or antigen binding fragment thereof, wherein the nucleic acid molecule comprises a sequence disclosed herein (e.g. Table 3 or Table 4) by way of gene therapy. Gene therapy refers to therapy performed by the administration to a subject of an expressed or expressible nucleic acid. In this embodiment of the invention, the nucleic acids produce their encoded protein that mediates a prophylactic or therapeutic effect. Any of the methods for gene therapy available in the art can be used according to the embodiments herein.

For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5): 155-215 Methods. commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY. Delivery of a therapeutic antibody to appropriate cells can be effected via gene therapy ex vivo, in situ, or in vivo by use of any suitable approach known in the art, including by use of physical DNA transfer methods (e.g., liposomes or chemical treatments) or by use of viral vectors (e.g., adenovirus, adeno-associated virus, or a retrovirus). For example, for in vivo therapy, a nucleic acid encoding the desired antibody, either alone or in conjunction with a vector, liposome, or precipitate may be injected directly into the subject, and in some embodiments, may be injected at the site where the expression of the antibody compound is desired. For ex vivo treatment, the subject's cells are removed, the nucleic acid is introduced into these cells, and the modified cells are returned to the subject either directly or, for example, encapsulated within porous membranes which are implanted into the patient. See, e.g. U.S. Pat. Nos. 4,892,538 and 5,283,187. There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, and calcium phosphate precipitation. A commonly used vector for ex vivo delivery of a nucleic acid is a retrovirus.

The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

Other in vivo nucleic acid transfer techniques include transfection with viral vectors (such as adenovirus, Herpes simplex I virus, or adeno-associated virus) and lipid-based systems. The nucleic acid and transfection agent are optionally associated with a microparticle. Exemplary transfection agents include calcium phosphate or calcium chloride co-precipitation, DEAE-dextran-mediated transfection, quaternary ammonium amphiphile DOTMA ((dioleoyloxypropyl) trimethylammonium bromide, commercialized as Lipofectin by GIBCO-BRL)) (Felgner et al, (1987) Proc. Natl. Acad. Sci. USA 84, 7413-7417; Malone et al. (1989) Proc. Natl Acad. Sci. USA 866077-6081); lipophilic glutamate diesters with pendent trimethylammonium heads (Ito et al. (1990) Biochem. Biophys. Acta 1023, 124-132); the metabolizable parent lipids such as the cationic lipid dioctadecylamido glycylspermine (DOGS, Transfectam, Promega) and dipalmitoylphosphatidyl ethanolamylspermine (DPPES) (J. P. Behr (1986) Tetrahedron Lett. 27, 5861-5864; J. P. Behr et al. (1989) Proc. Natl. Acad. Sci. USA 86, 6982-6986); metabolizable quaternary ammonium salts (DOTB, N-(1-[2, 3-dioleoyloxy]propyl)-N,N,N-trimethylammonium methylsulfate (DOTAP) (Boehringer Mannheim), polyethyleneimine (PEI), dioleoyl esters, ChoTB, ChoSC, DOSC) (Leventis et al. (1990) Biochim. Inter. 22, 235-241); 3beta [N—(N',N'-dimethylaminoethane)-carbamoyl]cholesterol (DC-Chol), dioleoylphosphatidyl ethanolamine (DOPE)/ 3beta[N—(N',N' dimethylaminoethane)-carbamoyl] cholesterolDC-Chol in one to one mixtures (Gao et al., (1991) Biochim. Biophys. Acta 1065, 8-14), spermine, spermidine, lipopolyamines (Behr et al., Bioconjugate Chem, 1994, 5: 382-389), lipophilic polylysines (LPLL) (Zhou et al., (1991) Biochim. Biophys. Acta 939, 8-18), [[(1,1,3,3 tetramethylbutyl)cresoxy]ethoxy]ethyl]dimethylbnzylammonium hydroxide (DEBDA hydroxide) with excess phosphatidylcholine/cholesterol (Ballas et al., (1988) Biochim. Biophys. Acta 939, 8-18), cetyltrimethylammonium bromide (CTAB)/DOPE mixtures (Pinnaduwage et al, (1989) Biochim. Biophys. Acta 985, 33-37), lipophilic diester of glutamic acid (TMAG) with DOPE, CTAB, DEBDA, didodecylammonium bromide (DDAB), and stearylamine in admixture with phosphatidylethanolamine (Rose et al., (1991) Biotechnique 10, 520-525), DDAB/DOPE (TransfectACE, GIBCO BRL), and oligogalactose bearing lipids. Exemplary transfection enhancer agents that increase the efficiency of transfer include, for example, DEAE-dextran, polybrene, lysosome-disruptive peptide (Ohmori N I et al, Biochem Biophys Res Commun Jun. 27, 1997; 235(3):726-9), chondroitan-based proteoglycans, sulfated proteoglycans, polyethylenimine, polylysine (Pollard H et al. J Biol Chem, 1998273 (13):7507-11), integrin-binding peptide CYGGRGDTP, linear dextran nonasaccharide, glycerol, cholesteryl groups tethered at the 3'-terminal internucleoside link of an oligonucleotide (Letsinger, R. L. 1989 Proc Natl Acad Sci USA 86: (17):6553-6), lysophosphatide, lysophosphatidylcholine, lysophosphatidylethanolamine, and 1-oleoyl lysophosphatidylcholine.

In some situations, it may be desirable to deliver the nucleic acid with an agent that directs the nucleic acid containing vector to target cells. Such "targeting" molecules include antibodies specific for a cell-surface membrane protein on the target cell, or a ligand for a receptor on the target cell. Where liposomes are employed, proteins which bind to a cell-surface membrane protein associated with endocytosis may be used for targeting and/or to facilitate uptake. Examples of such proteins include capsid proteins and fragments thereof tropic for a particular cell type, antibodies for proteins which undergo internalization in cycling, and proteins that target intracellular localization and enhance intracellular half-life. In other embodiments, receptor-mediated endocytosis can be used. Such methods are described, for example, in Wu et al., 1987 or Wagner et al., 1990. For review of the currently known gene marking and gene therapy protocols, see Anderson 1992. See also WO 93/25673 and the references cited therein.

Fusion Proteins

In one aspect, provided herein is a fusion protein comprising an antibody or an antigen binding fragment, disclosed herein. In some embodiments, fusion protein comprises one or more antibody or antigen binding fragment thereof, disclosed herein, and an immunomodulator or toxin moiety. Methods of making antibody fusion proteins are known. Antibody fusion proteins comprising an interleukin-2 moiety are described by Boleti et al., Ann. Oneal. 6:945 (1995), Nicolet et al., Cancer Gene Ther. 2:161 (1995), Becker et al., Proc. Natl Acad. Sci. USA 93:7826 (1996), Hank et al., Clin. Cancer Res. 2:1951 (1996), and Hu et al., Cancer Res. 56:4998 (1996). In addition, Yang et al., Hum. Antibodies Hybridomas 6:129 (1995), describe a fusion protein that includes an F(ab')2 fragment and a tumor necrosis factor alpha moiety.

Methods of making antibody-toxin fusion proteins in which a recombinant molecule comprises one or more antibody components and a toxin or chemotherapeutic agent also are known to those of skill in the art. For example, antibody-*Pseudomonas* exotoxin A fusion proteins have been described by Chaudhary et al., Nature 339:394 (1989), Brinkmann et al., Proc. Nat'l Acad. Sci. USA 88:8616 (1991), Batra et al., Proc. Natl Acad. Sci. USA 89:5867 (1992), Friedman et al., J. Immunol. 150:3054 (1993), Weis et al., Int. J. Can. 60:137 (1995), Fominaya et al., J. Biol. Chem. 271:10560 (1996), Kuan et al., Biochemistry 35:2872 (1996), and Schmidt et al., Int. J. Can. 65:538 (1996). Antibody toxin fusion proteins containing a diphtheria toxin moiety have been described by Kreitman et al., Leukemia 7:553 (1993), Nicholls et al., J. Biol. Chem. 268:5302 (1993), Thompson et al., J. Biol. Chem. 270:28037 (1995), and Vallera et al., Blood 88:2342 (1996). Deonarain et al., Tumor Targeting 1:177 (1995), have described an antibody-toxin fusion protein having an RNase moiety, while Linardou et al., Cell Biophys. 24-25:243 (1994), produced an antibody-toxin fusion protein comprising a DNase I component. Gelonin was used as the toxin moiety in the antibody-toxin fusion protein of Wang et al., Abstracts of the 209th ACS National Meeting, Anaheim, Calif., Apr. 2-6, 1995, Part 1, BIOT005. As a further example, Dohlsten et al., Proc. Natl Acad. Sci. USA 91:8945 (1994), reported an antibody-toxin fusion protein comprising Staphylococcal enterotoxin-A.

Illustrative of toxins which are suitably employed in the preparation of such conjugates are ricin, abrin, ribonuclease, DNase I, Staphylococcal enterotoxin-A, pokeweed antiviral protein, gelonin, diphtherin toxin, *Pseudomonas* exotoxin, and *Pseudomonas* endotoxin. See, for example, Pastan et al., Cell 47:641 (1986), and Goldenberg, C A-A Cancer Journal for Clinicians 44:43 (1994). Other suitable toxins are known to those of skill in the art.

Antibodies or antigen binding fragment thereof, disclosed herein, may also be used in ADEPT by conjugating the antibody to a prodrug-activating enzyme which converts a prodrug (e.g., a peptidyl chemotherapeutic agent, See W081/01145) to an active anti-cancer drug. See, for example, W088/07378 and U.S. Pat. No. 4,975,278. The enzyme component of the immunoconjugate useful for ADEPT includes any enzyme capable of acting on a prodrug in such a way so as to convert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *Serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as galactosidase and neuraminidase useful for converting glycosylated prodrugs into free drugs; lactamase useful for converting drugs derivatized with lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as abzymes, can be used to convert the prodrugs of the invention into free active drugs (See, e.g., Massey, Nature 328:457-458 (1987)). Antibody-abzyme conjugates can be prepared as described herein for delivery of the abzyme to a tumor cell population.

The enzymes of this invention can be covalently bound to the antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (See, e.g., Neuberger et al., Nature 312: 604-608 (1984)).

Chimeric Antigen Receptors

In one aspect, the disclosure herein, provides a chimeric antigen receptor comprising, an antigen binding fragment, disclosed herein, a transmembrane domain, and an intracellular signaling domain. The term "chimeric Antigen Receptor" (CAR), "artificial T cell receptor", "chimeric T cell receptor", or "chimeric immunoreceptor" as used herein refers to an engineered receptor, which grafts an arbitrary specificity onto an immune effector cell. CARs typically have an extracellular domain (ectodomain), which comprises an antigen-binding domain, a transmembrane domain, and an intracellular (endodomain) domain. The term "signaling domain" refers to the functional portion of a protein which acts by transmitting information within the cell to regulate cellular activity via defined signaling pathways by generating second messengers or functioning as effectors by responding to such messengers.

An "intracellular signaling domain," as the term is used herein, refers to an intracellular portion of a molecule. The intracellular signaling domain generates a signal that promotes an immune effector function of the CAR containing cell, e.g., a CART cell. Examples of immune effector function, e.g., in a CART cell, include cytolytic activity and helper activity, including the secretion of cytokines.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, FcR gamma, FcR beta, CD3 gamma, CD3 delta, CD3 epsilon, CD5, CD22, CD79a, CD79b, and CD66d DAP10 and DAP12.

The term "zeta" or alternatively "zeta chain", "CD3-zeta" or "TCR-zeta" is defined as the protein provided as GenBan Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain that are sufficient to functionally transmit an initial signal necessary for T cell activation. In one aspect the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof.

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to, an MHC class I molecule, BTLA and a Toll ligand receptor, as well as OX40, CD2, CD27, CD28, CD5, ICAM-1, LFA-1 (CD11a/CD18) and 4-1BB (CD137).

A costimulatory intracellular signaling domain can be derived from the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, and a ligand that specifically binds with CD83, and the like.

The intracellular signaling domain can comprise the entire intracellular portion, or the entire native intracellular signaling domain, of the molecule from which it is derived, or a functional fragment thereof.

In another aspect, the antigen binding fragment comprises a humanized antibody or antibody fragment. In one embodiment, the antigen binding fragment comprises one or more (e.g., one, two, or all three) light chain complementary determining region 1 (CDR-L1), light chain complementary determining region 2 (CDR-L2), and light chain complementary determining region 3 (CDR-L3) of an antibody described herein, and one or more (e.g., one, two, or all three) heavy chain complementary determining region 1 (CDR-H1), heavy chain complementary determining region 2 (CDR-H2), and heavy chain complementary determining region 3 (CDR-H3) of an antibody described herein. In one embodiment, the CDR-L1 comprises a sequence selected from any one of SEQ ID NOS: 99-112. In one embodiment, the CDR-L2 comprises a sequence selected from any one of SEQ ID NOS: 71-84. In one embodiment, the CDR-L3 comprises a sequence selected from any one of SEQ ID NOS: 43-56. In one embodiment, the CDR-H1 comprises a sequence selected from any one of SEQ ID NOS: 85-98. In one embodiment, the CDR-H2 comprises a sequence selected from any one of SEQ ID NOS: 57-70. In one embodiment, the CDR-H3 comprises a sequence selected from any one of SEQ ID NOS: 29-42. In one embodiment, the antigen-binding fragment comprises a light chain variable region described herein and/or a heavy chain variable region described herein. In some embodiments, the light chain variable region comprises a sequence selected from any one of SEQ ID NOS: 15-28. In some embodiments, the heavy chain variable region comprises a sequence selected from any one of SEQ ID NOS: 1-14. In one embodiment, the antigen-binding fragment is a scFv comprising a light chain variable region and a heavy chain variable region of an amino acid sequence, e.g., a light chain variable region and heavy chain variable region described herein. In an embodiment, the antigen-binding fragment (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided herein, or a sequence with 85-99% (e.g., 90-99%, or 95-99%) identity to an amino acid sequence provided herein; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided herein, or a sequence with 85-99% (e.g., 90-99%, or 95-99%) identity to an amino acid sequence provided herein.

Transmembrane Domain

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR is used. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the CAR T-cell surface. In a different aspect, the amino acid sequence of the transmembrane domain may be modified or substituted so as to minimize interactions with the binding domains of the native binding partner present in the same CAR T-cell.

The transmembrane domain may be derived either from a natural or from a recombinant source. Where the source is natural, the domain may be derived from any membrane-bound or transmembrane protein. In one aspect the transmembrane domain is capable of signaling to the intracellular domain(s) whenever the CAR has bound to a target. A transmembrane domain, for example, can include at least the transmembrane region(s) of e.g., the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154.

In some instances, the transmembrane domain can be attached to the extracellular region of the CAR, e.g., the antigen-binding domain of the CAR, via a hinge, e.g., a hinge from a human protein. For example, in one embodiment, the hinge can be a human Ig (immunoglobulin) hinge, e.g., an IgG4 hinge, or a CD8a hinge. In one aspect, the hinge or spacer comprises an IgG4 hinge.

Cytoplasmic Domain

The cytoplasmic domain or region of the CAR includes an intracellular signaling domain. An intracellular signaling domain is generally responsible for activation of at least one of the normal effector functions of the immune cell in which the CAR has been introduced. The term "effector function" refers to a specialized function of a cell. Effector function of a T cell, for example, may be cytolytic activity or helper activity including the secretion of cytokines. The term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic signaling domain, e.g., a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of TCR zeta, FcR gamma, FcR beta, CD3 gamma, CD3 delta, CD3 epsilon, CD5, CD22, CD79a, CD79b, and CD66d. In one embodiment, a CAR of the invention, e.g., a CAR comprises a intracellular signaling domain, e.g., a primary signaling domain, of CD3-zeta. In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

The intracellular signaling domain of the CAR can comprise the CD3-zeta signaling domain by itself or it can be combined with any other desired intracellular signaling domain(s) useful in the context of a CAR of the invention. For example, the intracellular signaling domain of the CAR can comprise a CD3 zeta chain portion and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human CART cells in vitro and augments human T cell persistence and antitumor activity in vivo (Song et al. Blood. 2012; 119(3):696-706).

The intracellular signaling sequences within the cytoplasmic portion of a CAR of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequence. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

In some embodiments, CAR does not actually recognize the entire antigen; instead it binds to only a portion of the antigen's surface, an area called the antigenic determinant or epitope.

In some embodiments, a CAR described herein include (including functional portions and functional variants thereof) glycosylated, amidated, carboxylated, phosphorylated, esterified, N-acylated, cyclized via, e.g., a disulfide bridge, or converted into an acid addition salt and/or optionally dimerized or polymerized, or conjugated.

T Cell Receptor Fusion Proteins (TFP)

As used herein, a "T-cell receptor (TCR) fusion protein" or "TFP" includes a recombinant polypeptide derived from the various polypeptides comprising the TCR that is generally capable of i) binding to a surface antigen on target cells and ii) interacting with other polypeptide components of the intact TCR complex, typically when co-located in or on the surface of a T-cell. Non-limiting examples of TFPs are illustrated in FIGS. 11-14.

In one aspect, provided herein is an isolated TFP molecule that comprises a human or humanized anti-cancer antigen (anti-CAg) binding domain, a TCR extracellular domain, a transmembrane domain, and an intracellular domain.

In one aspect, provided herein is an isolated TFP molecule that comprises a human or humanized anti-CAg binding domain, a TCR extracellular domain, a transmembrane domain, and an intracellular signaling domain, wherein the TFP molecule is capable of functionally interacting with an endogenous TCR complex and/or at least one endogenous TCR polypeptide.

In one aspect, provided herein is an isolated TFP molecule that comprises a human or humanized anti-CAg binding domain, a TCR extracellular domain, a transmembrane domain, and an intracellular signaling domain, wherein the TFP molecule is capable of functionally integrating into an endogenous TCR complex In some instances, the isolated TFP molecule comprises an antibody or antibody fragment that comprises a human or humanized anti-CAg binding domain, a TCR extracellular domain, a transmembrane domain, and an intracellular domain. In some instances, the anti-CAg binding domain is a scFv or a VH domain. In some instances, the anti-CAg binding domain comprises a heavy chain with 95-100% identity to an amino acid sequence of SEQ ID NOs: 1-14, a functional fragment thereof, or an amino acid sequence thereof having at least one but not more than 30 modifications. In some instances, the anti-CAg binding domain comprises a light chain with 95-100% identity to an amino acid sequence of SEQ ID NOs: 15-28, a functional fragment thereof, or an amino acid sequence thereof having at least one but not more than 30 modifications. In some instances, the isolated TFP molecule comprises a TCR extracellular domain that comprises an extracellular domain or portion thereof of a protein selected from the group consisting of a TCR alpha chain, a TCR beta chain, a CD3 epsilon TCR subunit, a CD3 gamma TCR subunit, a CD3 delta TCR subunit, functional fragments thereof, and amino acid sequences thereof having at least one but not more than 20 modifications. In some instances, the anti-CAg binding domain is connected to the TCR extracellular domain by a linker sequence. In some instances, the linker region comprises $(G_4S)_n$, wherein n=1 to 4.

In one aspect, provided herein is a vector that comprises a nucleic acid molecule encoding a TFP provided herein. In some instances, the vector is selected from the group consisting of a DNA, a RNA, a plasmid, a lentivirus vector, adenoviral vector, a Rous sarcoma viral (RSV) vector, or a retrovirus vector. In some instances, the vector further comprises a promoter. In some instances, the vector is an in vitro transcribed vector. In some instances, a nucleic acid sequence in the vector further comprises a poly(A) tail. In some instances, a nucleic acid sequence in the vector further comprises a 3'UTR.

In one aspect, provided herein is a host cell that comprises a vector provided herein. In some instances, the host cell is a human T-cell. In some instances, the T-cell is a CD8+ or CD4+ T-cell. In some embodiments, the host cell is a human effector cell. "Human effector cell" are leukocytes which express one or more FcRs and perform effector functions. In some embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, for example, from blood. In some instances, the host cell further comprises a nucleic acid encoding an inhibitory molecule that comprises a first polypeptide that comprises at least a portion of an inhibitory molecule, associated with a second polypeptide that comprises a positive signal from an intracellular signaling domain. In some instances, the inhibitory molecule comprise first polypeptide that comprises at least a portion of PD1 and a second polypeptide comprising a costimulatory domain and primary signaling domain.

In one aspect, provided herein is a human CD8+ or CD4+ T-cell that comprises at least two TFP molecules, the TFP molecules comprising a human or humanized anti-CAg binding domain, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human CD8+ or CD4+ T-cell.

In one aspect, provided herein is a protein complex that comprises: a TFP molecule comprising a human or humanized anti-CAg binding domain, a TCR extracellular domain, a transmembrane domain, and an intracellular domain; and at least one endogenous TCR complex.

In some instances, the TCR comprises an extracellular domain or portion thereof of a protein selected from the group consisting of TCR alpha chain, a TCR beta chain, a CD3 epsilon TCR subunit, a CD3 gamma TCR subunit, and a CD3 delta TCR subunit. In some instances, the anti-CAg binding domain is connected to the TCR extracellular domain by a linker sequence. In some instances, the linker region comprises $(G_4S)_n$, wherein n=1 to 4.

In some instances, the disease associated with the cancer antigen expression is selected from the group consisting of a proliferative disease, a cancer, a malignancy, myelodysplasia, a myelodysplastic syndrome, a preleukemia, a non-cancer related indication associated with expression of the cancer antigen. In some instances, the disease is a cancer or a metastasis thereof. In some instances, the cells expressing a TFP molecule are administered in combination with an agent that increases the efficacy of a cell expressing a TFP molecule.

In one aspect, an isolated nucleic acid molecule provided herein, an isolated polypeptide molecule provided herein, an isolated TFP provided herein, a complex provided herein, a vector provided herein, or a cell provided herein, is for use as a medicament.

The term "stimulation" refers to a primary response induced by binding of a stimulatory domain or stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, and/or reorganization of cytoskeletal structures, and the like.

Methods of making, expressing and isolating TFPs are known in the art in, for example, U.S. Pre-Grant Publication No. 20170166622 A1, which methods are hereby incorporated by reference.

Antigen-Binding Domain

In one aspect, the TFP of the invention comprises a target-specific binding element otherwise referred to as an antigen-binding domain. The choice of moiety depends upon the type and number of target antigen that define the surface of a target cell. For example, the antigen-binding domain may be chosen to recognize a target antigen that acts as a cell surface marker on target cells associated with a particular disease state. Thus examples of cell surface markers that may act as target antigens for the antigen-binding domain in a TFP of the invention include those associated with cancerous diseases (e.g., malignant diseases).

In one aspect, the TFP-mediated T-cell response can be directed to an antigen of interest by way of engineering an antigen-binding domain into the TFP that specifically binds a desired antigen. In one aspect, the portion of the TFP comprising the antigen-binding domain comprises an antigen-binding domain that targets a cancer antigen (CAg). In one aspect, the antigen-binding domain targets human CAg.

The antigen-binding domain can be any domain that binds to the CAg including but not limited to a monoclonal antibody, a polyclonal antibody, a recombinant antibody, a human antibody, a humanized antibody, and a functional fragment thereof, including but not limited to a single-domain antibody such as a heavy chain variable domain ($V_H$), a light chain variable domain ($V_L$) and a variable domain ($V_{HH}$) of a camelid derived nanobody, and to an alternative scaffold known in the art to function as antigen-binding domain, such as a recombinant fibronectin domain, anticalin, DARPIN, and the like. Likewise a natural or synthetic ligand specifically recognizing and binding the target CAg can be used as antigen-binding domain for the TFP. In some instances, it is beneficial for the antigen-binding domain to be derived from the same species in which the TFP will ultimately be used in. For example, for use in humans, it may be beneficial for the antigen-binding domain of the TFP to comprise human or humanized residues for the antigen-binding domain of an antibody or antibody fragment.

The portion of the TFP composition of the invention comprising an antibody or antibody fragment thereof may exist in a variety of forms where the antigen-binding domain is expressed as part of a contiguous polypeptide chain including, for example, a single domain antibody fragment (sdAb), a single chain antibody (scFv) derived from a murine, humanized or human antibody (Harlow et al., 1999, In: Using Antibodies: A Laboratory Manual, Cold Spring Harbor Laboratory Press, N.Y.; Harlow et al., 1989, In: Antibodies: A Laboratory Manual, Cold Spring Harbor, N.Y.; Houston et al., 1988, *Proc. Natl. Acad. Sci. USA* 85:5879-5883; Bird et al., 1988, Science 242:423-426). In one aspect, the antigen-binding domain of a TFP composition of the invention comprises an antibody fragment. In a further aspect, the TFP comprises an antibody fragment that comprises a scFv or a sdAb.

In another aspect, the antigen-binding domain comprises a humanized antibody or antigen-binding domain. In one embodiment, the antigen-binding domain comprises one or more (e.g., one, two, or all three) light chain complementary determining region 1 (CDR-L1), light chain complementary determining region 2 (CDR-L2), and light chain complementary determining region 3 (CDR-L3) of an antibody described herein, and one or more (e.g., one, two, or all three) heavy chain complementary determining region 1 (CDR-H1), heavy chain complementary determining region 2 (CDR-H2), and heavy chain complementary determining region 3 (CDR-H3) of an antibody described herein. In one embodiment, the CDR-L1 comprises a sequence selected from any one of SEQ ID NOS: 99-112. In one embodiment, the CDR-L2 comprises a sequence selected from any one of SEQ ID NOS: 71-84. In one embodiment, the CDR-L3 comprises a sequence selected from any one of SEQ ID NOS: 43-56. In one embodiment, the CDR-H1 comprises a sequence selected from any one of SEQ ID NOS: 85-98. In one embodiment, the CDR-H2 comprises a sequence selected from any one of SEQ ID NOS: 57-70. In one embodiment, the CDR-H3 comprises a sequence selected from any one of SEQ ID NOS: 29-42. In one embodiment, the antigen-binding domain comprises a light chain variable region described herein and/or a heavy chain variable region described herein. In some embodiments, the light chain variable region comprises a sequence selected from any one of SEQ ID NOS: 15-28. In some embodiments, the heavy chain variable region comprises a sequence selected from any one of SEQ ID NOS: 1-14. In one embodiment, the antigen-binding domain is a scFv comprising a light chain variable region and a heavy chain variable region of an amino acid sequence, e.g., a light chain variable region and heavy chain variable region described herein. In an embodiment, the antigen-binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided herein, or a sequence with 85-99% (e.g., 90-99%, or 95-99%) identity to an amino acid sequence provided herein; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided herein, or a sequence with 85-99% (e.g., 90-99%, or 95-99%) identity to an amino acid sequence provided herein.

The term "stimulatory molecule" or "stimulatory domain" refers to a molecule or portion thereof expressed by a T-cell that provides the primary cytoplasmic signaling sequence(s) that regulate primary activation of the TCR complex in a stimulatory way for at least some aspect of the T-cell signaling pathway. In one aspect, the primary signal is initiated by, for instance, binding of a TCR/CD3 complex with an MHC molecule loaded with peptide, and which leads to mediation of a T-cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif (ITAM). Examples of an ITAM containing primary cytoplasmic signaling sequence that is of particular use in the invention includes, but is not limited to, those derived from TCR zeta, FcR gamma, FcR beta, CD3 gamma, CD3 delta, CD3 epsilon, CD5, CD22, CD79a, CD79b, CD278 (also known as "ICOS") and CD66d.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. The intracellular signaling domain generates a signal that promotes an immune effector function of the TFP containing cell, e.g., a TFP-expressing T-cell. Examples of immune effector function, e.g., in a TFP-expressing T-cell, include cytolytic activity and T helper cell activity, including the secretion of cytokines. In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation.

A primary intracellular signaling domain can comprise an ITAM ("immunoreceptor tyrosine-based activation motif"). Examples of ITAM containing primary cytoplasmic signaling sequences include, but are not limited to, those derived from CD3 zeta, FcR gamma, FcR beta, CD3 gamma, CD3 delta, CD3 epsilon, CD5, CD22, CD79a, CD79b, and CD66d DAP10 and DAP12.

The term "costimulatory molecule" refers to the cognate binding partner on a T-cell that specifically binds with a costimulatory ligand, thereby mediating a costimulatory response by the T-cell, such as, but not limited to, proliferation. Costimulatory molecules are cell surface molecules other than antigen receptors or their ligands that are required for an efficient immune response. Costimulatory molecules include, but are not limited to an MHC class 1 molecule, BTLA and a Toll ligand receptor, as well as OX40, CD2, CD27, CD28, CDS, ICAM-1, LFA-1 (CD11a/CD18) and 4-1BB (CD137). A costimulatory intracellular signaling domain can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, and a ligand that specifically binds with CD83, and the like. The intracellular signaling domain can comprise the entire intracellular portion, or the entire native intracellular signaling domain, of the molecule from which it is derived, or a functional fragment thereof. The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank Acc. No. AAA62478.2, or the equivalent residues from a non-human species, e.g., mouse, rodent, monkey, ape and the like.

Extracellular Domain

The extracellular domain may be derived either from a natural or from a recombinant source. Where the source is natural, the domain may be derived from any protein, but in particular a membrane-bound or transmembrane protein. In one aspect the extracellular domain is capable of associating with the transmembrane domain. An extracellular domain of particular use in this invention may include at least the extracellular region(s) of e.g., the alpha, beta or zeta chain of the T-cell receptor, or CD3 epsilon, CD3 gamma, or CD3 delta, or in alternative embodiments, CD28, CD45, CD4, CD5, CD8, CD9, CD16, CD22, CD33, CD37, CD64, CD80, CD86, CD134, CD137, CD154.

Transmembrane Domain

In general, a TFP sequence contains an extracellular domain and a transmembrane domain encoded by a single genomic sequence. In alternative embodiments, a TFP can be designed to comprise a transmembrane domain that is heterologous to the extracellular domain of the TFP. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 or up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 or up to 15 amino acids of the intracellular region). In one aspect, the transmembrane domain is one that is associated with one of the other domains of the TFP is used. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another TFP on the TFP-T-cell surface. In a different aspect the amino acid sequence of the transmembrane domain may be modified or substituted so as to minimize interactions with the binding domains of the native binding partner present in the same TFP.

The transmembrane domain may be derived either from a natural or from a recombinant source. Where the source is natural, the domain may be derived from any membrane-bound or transmembrane protein. In one aspect the transmembrane domain is capable of signaling to the intracellular domain(s) whenever the TFP has bound to a target. A transmembrane domain of particular use in this invention may include at least the transmembrane region(s) of e.g., the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154.

In some instances, the transmembrane domain can be attached to the extracellular region of the TFP, e.g., the antigen-binding domain of the TFP, via a hinge, e.g., a hinge from a human protein. For example, in one embodiment, the hinge can be a human immunoglobulin (Ig) hinge, e.g., an IgG4 hinge, or a CD8a hinge.

Linkers

Optionally, a linker may form the linkage between the transmembrane domain and the cytoplasmic region of the TFP. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

For example, a short oligo- or polypeptide linker, between 2 and 10 amino acids in length may form the linkage between the transmembrane domain and the cytoplasmic region of the TFP. In some instances, a linker can be about 10, 11, 12, 13, 14, 15 or greater than 15 residues between VL and VH regions. The linker sequence may comprise any naturally occurring amino acid. Variation in the linker length may retain or enhance activity, giving rise to superior efficacy in activity studies.

In one aspect, a linker comprises amino acids glycine and serine with an optimized length and/or amino acid composition. The linker length can greatly affect how the variable regions of a polypeptide fold and interact. In fact, if a short polypeptide linker is employed (e.g., between 5-10 amino acids) intra-chain folding is prevented. Inter-chain folding is also required to bring the two variable regions together to form a functional epitope binding site. In some embodiments, the linker sequence comprises sets of glycine and serine repeats such as $(Gly_4Ser)_n$, where n is a positive integer equal to or greater than 1. In some instances, the linker sequence comprises a long linker (LL) sequence. In some instances, the long linker sequence comprises $(G_4S)_n$, wherein n=2 to 4. In some instances, the linker sequence comprises a short linker (SL) sequence. In some instances, the short linker sequence comprises $(G_4S)_n$, wherein n=1 to 3. A glycine-serine doublet provides a particularly suitable linker. For example, in one aspect, the linker comprises the amino acid sequence of GGGGSGGGGS. In some embodiments, the linker is encoded by a nucleotide sequence of GGTGGCGGAGGTTCTGGAGGTGGAGGTTCC. In one embodiment, the linker can be $(Gly_4Ser)_4$ or $(Gly_4Ser)_3$.

Methods of Engineering Antibodies

As discussed above, antibodies having VH and VL sequences disclosed herein can be used to create new antibodies, respectively, by modifying the VH and/or VL sequences, or the constant regions attached thereto. Thus, in another aspect according to at least some embodiments of the present disclosure, the structural features of an antibody disclosed herein according to at least some embodiments of the disclosure, are used to create structurally related antibodies that retain at least one functional property of the parent antibodies according to at least some embodiments of the disclosure herein, such as binding to human cancer cell antigen, respectively. For example, one or more CDR regions of one antibody disclosed herein or mutations thereof, can be combined recombinantly with known framework regions and/or other CDRs to create additional, recombinantly-engineered, antibodies according to at least some embodiments of the disclosure, as discussed above. Other types of modifications include those described in the previous section. The starting material for the engineering method is one or more of the VH and/or VL sequences provided herein, or one or more CDR regions thereof, or one or more of the CDR1, CDR2 and CDR3 region sequences provided herein. To create the engineered antibody, it is not necessary to actually prepare (i.e., express as a protein) an antibody having one or more of the VH and/or VL sequences provided herein, or one or more CDR regions thereof. Rather, the information contained in the sequences is used as the starting material to create a "second generation" sequences derived from the original sequences and then the "second generation" sequences is prepared and expressed as a protein.

Standard molecular biology techniques can be used to prepare and express altered antibody sequence. Preferably, the antibody encoded by the altered antibody sequences is one that retains one, some or all of the functional properties of the antibodies disclosed herein, respectively, produced by methods and with sequences provided herein, which functional properties include binding to a cancer cell antigen with a specific KD level or less and/or modulating immune stimulation and/or selectively binding to desired target cells such as for example, that express cancer associated antigen.

The functional properties of the altered antibodies can be assessed using standard assays available in the art and/or described herein. In some embodiments, mutations can be introduced randomly or selectively along all or part of an antibody coding sequence disclosed herein and the resulting modified antibodies can be screened for binding activity and/or other desired functional properties. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Species Selectivity and Species Cross-Reactivity

According to certain embodiments of the present disclosure, the antibodies or antigen binding fragment thereof can bind to human cancer antigen but not to cancer antigen from other species. Alternatively, the antibodies or antigen binding fragment thereof, in certain embodiments, bind to human cancer antigen and to cancer antigen from one or more non-human species. For example, the antibodies or antigen binding fragment thereof can bind to human cancer antigen and can bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee cancer antigen.

Identification of Target Antigens

Screening Methods

Antibodies may be screened for binding affinity by methods known in the art. For example, gel-shift assays, Western blots, radiolabeled competition assay, co-fractionation by chromatography, co-precipitation, cross linking, ELISA, and the like may be used, which are described in, for example, Current Protocols in Molecular Biology (1999) John Wiley & Sons, NY, which is incorporated herein by reference in its entirety.

To initially screen for antibodies which bind to the desired epitope on an antigen (e.g., a cancer associated antigen), a routine cross-blocking assay such as that described in Antibodies, A Laboratory Manual, Cold Spring Harbor Laboratory, Ed Harlow and David Lane (1988), can be performed. Routine competitive binding assays may also be used, in which the unknown antibody is characterized by its ability to inhibit binding of antigen to an antigen specific antibody of the invention. Intact antigen, fragments thereof, or linear epitopes can be used. Epitope mapping is described in Champe et al., J. Biol. Chem. 270: 1388-1394 (1995).

The antibodies or antigen binding fragment thereof, described herein, may also be useful in preventing or treating cancer. The effectiveness of a candidate antibody or antigen binding fragment thereof in preventing or treating cancer metastasis may be screened using a human anmionic basement membrane invasion model as described in Filderman et al., Cancer Res 52: 36616, 1992. In addition, any of the animal model systems for metastasis of various types of cancers may also be used. Such model systems include, but are not limited to, those described in Wenger et al., Clin. Exp. Metastasis 19: 169 73, 2002; Yi et al., Cancer Res. 62: 91723, 2002; Tsutsumi et al., Cancer Lett 169: 77-85, 2001; Tsingotjidou et al., Anticancer Res. 21: 9718, 2001; Wakabayashi et al., Oncology 59: 7580, 2000; Culp and Kogerman, Front Biosci. 3:D67283, 1998; Runge et al., Invest Radiol. 32: 2127; Shioda et al., J. Surg. Oneal. 64: 1226, 1997; Ma et al., Invest Ophthalmol Vis Sci. 37: 2293301, 1996; Kuruppu et al., J Gastroenterol Hepatol. 11: 2632, 1996. In the presence of an effective antibody, cancer metastases may be prevented, or inhibited to result in fewer and/or smaller metastases.

The anti-tumor activity of a particular antibody, or combination of antibodies, or fragment thereof may be evaluated in vivo using a suitable animal model. For example, xenogenic lymphoma cancer models wherein human lymphoma cells are introduced into immune com-promised animals, such as nude or SCID mice. Efficacy may be predicted using assays which measure inhibition of tumor formation, tumor regression or metastasis, and the like.

In one variation of an in vitro assay, the present disclosure provides a method comprising the steps of (a) contacting an immobilized antigen with a candidate antibody and (b) detecting binding of the candidate antibody to the antigen. In an alternative embodiment, the candidate antibody is immobilized and binding of antigen is detected. Immobilization is accomplished using any of the methods well known in the art, including covalent bonding to a support, a bead, or a chromatographic resin, as well as non-covalent, high affinity interaction such as antibody binding, or use of streptavidin/biotin binding wherein the immobilized compound includes a biotin moiety. Detection of binding can be accomplished (i) using a radioactive label on the compound that is not immobilized, (ii) using a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well known and routinely practiced in the art.

Antibodies that modulate (i.e., increase, decrease, or block) the activity or expression of desired target may be identified by incubating a putative modulator with a cell expressing the desired target and determining the effect of the putative modulator on the activity or expression of the target. The selectivity of an antibody that modulates the activity of a target polypeptide or polynucleotide can be evaluated by comparing its effects on the target polypeptide or polynucleotide to its effect on other related compounds. Selective modulators may include, for example, antibodies and other proteins, peptides, or organic molecules which specifically bind to target polypeptides or to a nucleic acid encoding a target polypeptide. Modulators of target activity will be therapeutically useful in treatment of diseases and physiological conditions in which normal or aberrant activity of target polypeptide is involved. The target can be a for example, but not limited to a cancer associated antigen.

The invention also comprehends high throughput screening (HTS) assays to identify antibodies that interact with or inhibit biological activity (i.e., inhibit enzymatic activity, binding activity, etc.) of an antigen. HTS assays permit screening of large numbers of compounds in an efficient manner. Cell-based HTS systems are contemplated to investigate the interaction between antibodies and their target antigen and their binding partners. HTS assays are designed to identify "hits" or "lead compounds" having the desired property, from which modifications can be designed to improve the desired property. Chemical modification of the "hit" or "lead compound" is often based on an identifiable structure/activity relationship between the "hit" and target antigen.

Another aspect of the present invention is directed to methods of identifying antibodies which modulate (i.e., decrease) activity of a target antigen comprising contacting a target antigen with an antibody, and determining whether the antibody modifies activity of the antigen. The activity in the presence of the test antibody is compared to the activity in the absence of the test antibody. Where the activity of the sample containing the test antibody is lower than the activity in the sample lacking the test antibody, the antibody will have inhibited activity.

A variety of heterologous systems is available for functional expression of recombinant polypeptides that are well known to those skilled in the art. Such systems include bacteria (Strosberg, et al., Trends in Pharmacological Sciences (1992) 13:95-98), yeast (Pausch, Trends in Biotechnology (1997) 15:487-494), several kinds of insect cells (Vanden Broeck, Int. Rev. Cytology (1996) 164:189-268), amphibian cells (Jayawickreme et al., Current Opinion in Biotechnology (1997) 8: 629-634) and several mammalian cell lines (CHO, HEK293, COS, etc.; see Gerhardt, et al., Eur. J. Pharmacology (1997) 334:1-23). These examples do not preclude the use of other possible cell expression systems, including cell lines obtained from nematodes (PCT application WO 98/37177).

In one embodiment of the invention, methods of screening for antibodies which modulate the activity of target antigen comprise contacting antibodies with a target antigen polypeptide and assaying for the presence of a complex between the antibody and the target antigen. In such assays, the ligand is typically labeled. After suitable incubation, free ligand is separated from that present in bound form, and the amount of free or uncomplexed label is a measure of the ability of the particular antibody to bind to the target antigen.

The present disclosure encompasses the use of HTS to identify and characterize target antigens. A HTS can be protein arrays (e.g., antibody arrays, antibody microarrays, protein microarray). The array can comprise one or more antibodies or antigen binding fragment thereof, disclosed herein, immobilized on a solid support. Methods of production and use of such arrays are known well known in art (e.g., (Buessow et al., 1998, Lueking et al., 2003; Angenendt et al., 2002, 2003 a,b, 2004a, 2004b, 2006) In some embodiments, very small amounts (e.g., 1 to 500 µg) of antibody or antigen binding fragment thereof is immobilized. In some embodiments, there will be from 1 µg to 100 µg, from 1 µg to 50 µg, from 1 µg to 20 µg, from 3 µg to 100 µg, from 3 µg to 50 µg, from 3 µg to 20, from 5 µg to 100 µg, from 5 µg to 50 µg, from 5 µg to 20 µg of antibody present in a single sample. In one aspect, at least one of the samples in a plurality of samples will have from 1 µg to 100 µg, from 1 µg to 50 µg, from 1 µg to 20 µg, from 3 µg to 100 µg, from 3 µg to 50 µg, from 3 µg to 20, from 5 µg to 100 µg, from 5 µg to 50 µg, from 5 µg to 20 µg of antibody present. A solid support refers to an insoluble, functionalized material to which the antibodies can be reversibly attached, either directly or indirectly, allowing them to be separated from unwanted materials, for example, excess reagents, contaminants, and solvents. Examples of solid supports include, for example, functionalized polymeric materials, e.g., agarose, or its bead form Sepharose®, dextran, polystyrene and polypropylene, or mixtures thereof; compact discs comprising microfluidic channel structures; protein array chips; pipet tips; membranes, e.g., nitrocellulose or PVDF membranes; and microparticles, e.g., paramagnetic or non-paramagnetic beads. In some embodiments, an affinity medium will be bound to the solid support and the antibody will be indirectly attached to solid support via the affinity medium. In one aspect, the solid support comprises a protein A affinity medium or protein G affinity medium. A "protein A affinity medium" and a "protein G affinity medium" each refer to a solid phase onto which is bound a natural or synthetic protein comprising an Fc-binding domain of protein A or protein G, respectively, or a mutated variant or fragment of an Fc-binding domain of protein A or protein G, respectively, which variant or fragment retains the affinity for an Fc-portion of an antibody. Antibody arrays can be fabricated by the transfer of antibodies onto the solid surface in an organized high-density format followed by chemical immobilization. Representative techniques for fabrication of an array include photolithography, ink jet and contact printing, liquid dispensing and piezoelectrics. The patterns and dimensions of antibody arrays are to be determined by each specific application. The sizes of each antibody spot may be easily controlled by the users. Antibodies may be attached to various kinds of surfaces via diffusion, adsorption/absorption, or covalent cross-linking and affinity. Antibodies may be directly spotted onto a plain glass surface. To keep antibodies in a wet environment during the printing process, high percent glycerol (e.g., 30-40%) may be used in sample buffer and the spotting is carried out in a humidity-controlled environment.

The surface of a substrate may be modified to achieve better binding capacity. For example, the glass surface may be coated with a thin nitrocellulose membrane or poly-L-lysine such that antibodies can be passively adsorbed to the modified surface through non-specific interactions. Antibodies may be immobilized onto a support surface either by chemical ligation through a covalent bond or non-covalent binding. There are many known methods for covalently immobilizing antibodies onto a solid support. For example, MacBeath et al., (1999) J. Am. Chem. Soc. 121:7967-7968) use the Michael addition to link thiol-containing compounds to maleimide-derivatized glass slides to form a microarray of small molecules. See also, Lam & Renil (2002) Current Opin. Chemical Biol. 6:353-358. Depending upon, if the potential antigen is associated with a specific type of cancer, an antibody specific to a further biomarker may be included in the antibody array. Representative examples of biomarkers include, TROP/TNFRSF19, IL-1 sRI, uPAR, IL-10, VCAM-1 (CD106), IL-10 receptor-β, VE-cadherin, IL-13 receptor-α1, VEGF, IL-13 receptor-α2, VEGF R2 (KDR), IL-17, VEGF R3

The arrays can employ single-antibody (label-base) detection or 2-antibody (sandwich-based) detection. In some embodiments, an ELISA (also known as an antibody sandwich assay) may be performed following standard techniques as follows. Antibodies used as the capture antibodies for an antigen disposed on (e.g., coated onto) a solid support, which may then be washed at least once (e.g., with water and/or a buffer such as PBS-t), followed by a standard blocking buffer, and then at least one more wash. The solid support may then be brought into contact with the sample/biosample under conditions to allow antibody-antigen complexes to form (e.g., incubating from 1 hour to about 24 hours at a temperature from about 4° C. to about room temperature). As used herein, "biosample" and "sample" are used interchangeably and embrace both fluids (also referred to herein as fluid samples and biofluids) and tissue obtained from the subject. The term "biofluid" as used herein refers to a biological fluid sample such as blood samples, cerebral spinal fluid (CSF), urine and other liquids obtained from the subject, or a solubilized preparation of such fluids wherein the cell components have been lysed to release intra-cellular contents into a buffer or other liquid medium. The definition also includes samples that have been manipulated in any way after their procurement, such as by treatment with reagents, or enrichment for certain components, such as proteins or polynucleotides. The term "blood sample" embraces whole blood, plasma, and serum. Solid tissue samples include biopsy specimens and tissue cultures or cells derived therefrom, and the progeny thereof. A sample may comprise a single cell or more than a single cell. The biosample may also be a cultured population of cells derived from the subject human or animal. However, whenever the biosample comprises a population of cells, the method will first require that the constituents of the cells be solubilized by lysing the cells, and removing solid cell debris, thereby providing a solution of the biomarkers. Samples can be prepared by methods known in the art such as lysing, fractionation, purification, including affinity purification, FACS, laser capture micro-dissection or iospycnic centrifugation. The support may then be washed at least once (e.g., with a buffer such as PBS-t). To detect the complexation between the capture antibodies and the antigen that may be present in the sample, secondary or "detection" antibodies are applied to the solid support (e.g., diluted in blocking buffer) under conditions to allow complexation between the secondary antibodies and the respective biomarkers (e.g., at room temperature for at least one hour). The secondary antibodies are selected so as to bind a different epitope on the antigen than the capture antibody. The optimum concentrations of capture and detection antibodies are determined using standard techniques such as the "criss-cross" method of dilutions. The detection antibody may be conjugated, directly or indirectly, to a detectable label.

The term "detectable label" as used herein refers to labeling moieties known in the art. Said moiety may be, for example, a radiolabel (e.g., $^3H$, $^{125}I$, $^{35}S$, $^{14}C$, $^{32}P$, etc.), detectable enzyme (e.g., horse radish peroxidase (HRP), alkaline phosphatase etc.), a dye (e.g., a fluorescent dye), a colorimetric label such as colloidal gold or colored glass or plastic (e.g., polystyrene, polypropylene, latex, etc.), beads, or any other moiety capable of generating a detectable signal such as a colorimetric, fluorescent, chemiluminescent or electrochemiluminescent (ECL) signal. The term "dye" as used herein refers to any reporter group whose presence can be detected by its light absorbing or light emitting properties. For example, Cy5 is a reactive water-soluble fluorescent dye of the cyanine dye family. Cy5 is fluorescent in the red region (about 650 to about 670 nm). It may be synthesized with reactive groups on either one or both of the nitrogen side chains so that they can be chemically linked to either nucleic acids or protein molecules. Labeling is done for visualization and quantification purposes. Cy5 is excited maximally at about 649 nm and emits maximally at about 670 nm, in the far red part of the spectrum; quantum yield is 0.28 (FW=792). Suitable fluorophores (chromes) for the probes of the disclosure may be selected from, but not intended to be limited to, fluorescein isothiocyanate (FITC, green), cyanine dyes Cy2, Cy3, Cy3.5, Cy5, Cy5.5 Cy7, Cy7.5 (ranging from green to near-infrared), Texas Red, and the like. Derivatives of these dyes for use in the embodiments of the disclosure may be, but are not limited to, Cy dyes (Amersham Bioscience), Alexa Fluors (Molecular Probes Inc.), HILYTE™ Fluors (AnaSpec), and DYLITE™ Fluors (Pierce, Inc). In some embodiments, the detectable label is a chromogenic label such as biotin, in which case the detection antibody-biotin conjugate is detected using Streptavidin/Horseradish Peroxidase (HRP) or the equivalent. The streptavidin may be diluted in an appropriate block and incubated for 30 minutes at room temperature. Other detectable labels suitable for use in the present invention include fluorescent labels and chemiluminescent labels.

The support may then be washed and the label (e.g., HRP enzymatic conjugate on the streptavidin) is detected using the following standard protocols such as a chromogenic system (the SIGMA FAST™ OPD system), a fluorescent system or a chemiluminescent system. The amounts of antigen present in the sample may then be read on an ELISA plate reader (e.g., SpectraMax 384 or the equivalent). The concentration of each of the antigens may then be back-calculated (e.g., by using the standard curve generated from purified antigens and multiplied by the dilution factor following standard curve fitting methods), and then compared to a control (generated from tissue samples obtained from healthy subjects).

In one embodiment, a biosample, e.g., a biofluid, is contacted with a system of reagents, well-known in the art, that can attach biotin moieties to some or all of the constituent components of the sample, and especially to the protein or peptide constituents thereof, including the biomarkers. Following this biotinylation step, the biotinylated biosample may then be contacted with the antibody array that contains an array of antibodies specific to each of the antigens.

After an adequate incubation period, readily selected to allow the binding of any antigen in the sample to its corresponding antibody of the array, the fluid sample is washed from the array. The array is then contacted with a biotin-binding polypeptide such as avidin or streptavidin, that has been conjugated with a detectable label (as described above in connection with the ELISA). Detection of the label on the array (relative to a control) will indicate which of the biomarkers captured by the respective antibody is present in the sample.

Regardless of the specific assay format, the biotin-label-based array methods are relatively advantageous from several standpoints. Biotin-label can be used as signal amplification. Biotin is the most common method for labeling protein and the label process can be highly efficient. Furthermore, biotin can be detected using fluorescence-streptavidin and, therefore, visualized via laser scanner, or HRP-streptavidin using chemiluminescence. Using biotin-label-based antibody arrays, most targeted proteins can be detected at pg/ml levels. The detection sensitivity of the present methods can be further enhanced by using 3-DNA detection technology or rolling circle amplification (Schweitzer et al., (2000) Proc. Natl. Acad. Sci. U.S.A. 97:10113-10119; Horie et al., (1996) Int. J. Hematol. 63:303-309).

As it relates to the present disclosure, the sample can be obtained from a subject having disease (e.g., cancer) and a healthy subject.

In some embodiments, protein arrays can be used where protein antigens with known identities are immobilized on a solid support as capture molecules and one seeks to determine whether the known antigens binds to a candidate antibody. The antigen can be labeled with a tag that allows detection or immunoprecipitation after capture by an immobilized antibody. Protein antigens can be obtained, for example, from a cancer patient or a cancer cell. A number of commercial protein arrays are available e.g., ProtoArray®, Kinex™, RayBio® Human RTK Phosphorylation Antibody Array. The antibody-antigen complexes can be obtained by methods known in the art (e.g., immunoprecipitation or Western blot). For reviews on Protein array and antibody array that can be of interest in this study, see Reymond Sutandy, et al. 2013; Liu, B. C.-S., et al. 2012; Haab B B, 2005.

In an exemplary immunoprecipitation method, an antibody or antigen binding fragment thereof, described herein is added first to a sample comprising an antigen, and incubated to allow antigen-antibody complexes to form. Subsequently, the antigen-antibody complexes are or with protein A/G-coated beads to allow them to absorb the complexes. In a modified approach, the antibody or antigen binding fragment thereof is fused to a His tag or other tags (e.g., FLAG tag, Biotin Tag) by recombinant DNA techniques, and immunoprecipitated using an antibody to the tag (pull-down assay). The beads are then thoroughly washed, and the antigen is eluted from the beads by an acidic solution or SDS. The eluted sampled can be analyzed using Mass Spectrometry or SDS page to identify and confirm the antigen. Methods to analyze antibody-antigen complexes formed on a protein microarray and identify the antigen via mass spec are known.

In one aspect, the antibodies or antigen binding fragment thereof, disclosed herein, are contemplated as therapeutic antibodies for treatment of cancer. Accordingly, the antibodies or antigen binding fragment thereof, can be further screened in an antibody-dependent cell-mediated cytotocity (ADCC) assay and/or Complement-dependent cytotoxicity (CDC) assay. "ADCC activity" refers to the ability of an antibody to elicit an ADCC reaction. ADCC is a cell-mediated reaction in which antigen-nonspecific cytotoxic cells that express FcRs (e.g., natural killer (NK) cells, neutrophils, and macrophages) recognize antibody bound to the surface of a target cell and subsequently cause lysis of (i.e., "kill") the target cell (e.g., cancer cell). The primary mediator cells are natural killer (NK) cells. NK cells express FcγRIII only, with FcγRIIIA being an activating receptor and FcγRIIIB an inhibiting one; monocytes express FcγRI, FcγRII and FcγRIII (Ravetch et al. (1991) Annu. Rev. Immunol., 9:457-92). ADCC activity can be assessed directly using an in vitro assay, e.g., a $^{51}$Cr release assay using peripheral blood mononuclear cells (PBMC) and/or NK effector cells as described in the Examples and Shields et al. (2001) J. Biol. Chem., 276:6591-6604, or another suitable method known in the art. ADCC activity may be expressed as a concentration of antibody at which the lysis of target cells is half-maximal. Accordingly, in some embodiments, the concentration of an antibody or antigen binding fragment thereof of the disclosure, at which the lysis level is the same as the half-maximal lysis level by the wild-type control, is at least 2-, 3-, 5-, 10-, 20-, 50-, 100-fold lower than the concentration of the wild-type control itself.

Additionally, in some embodiments, the antibody or antigen binding fragment thereof of the present disclosure may exhibit a higher maximal target cell lysis as compared to the wild-type control. For example, the maximal target cell lysis of an antibody or Fc fusion protein of the invention may be 10%, 15%, 20%, 25% or more higher than that of the wild-type control. "Complement dependent cytotoxicity" or "CDC" refer to the ability of a molecule to lyse a target (e.g. cancer cell) in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods 202:163 (1996), may be performed.

Epitope Mapping

The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

Various techniques known to persons of ordinary skill in the art can be used to determine whether an antigen-binding domain of an antibody "interacts with one or more amino acids" within a polypeptide or protein. Exemplary techniques include, e.g., routine cross-blocking assay such as that described Antibodies, Harlow and Lane (Cold Spring Harbor Press, Cold Spring Harb., NY), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antigen-binding domain of an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues, which correspond to the specific amino acids with which the antibody interacts. See, e.g., Ehring (1999) Analytical Biochemistry 267(2):252-259; Engen and Smith (2001) Anal. Chem. 73:256A-265A. X-ray crystallography of the antigen/antibody complex may also be used for epitope mapping purposes.

The epitope on an antigen to which the antibody or antigen binding fragment, disclosed herein, bind may consist of a single contiguous sequence of 3 or more (e.g., 3, 4, 5, 6, 7, 8, 9, 10, 11, 12, 13, 14, 15, 16, 17, 18, 19, 20 or more) amino acids of the antigen. Alternatively, the epitope may consist of a plurality of non-contiguous amino acids (or amino acid sequences) of antigen.

Antigens

In some embodiments, the antibodies or antigen biding fragment thereof, disclosed herein, are directed to a cancer associated antigen. In some embodiments, the cancer associated antigen is a tumor antigen, i.e., a part of a tumor cell such as a protein or peptide expressed in a tumor cell which may be derived from the cytoplasm, the cell surface or the cell nucleus, in particular those which primarily occur intracellularly or as surface antigens of tumor cells. For example, tumor antigens include the carcinoembryonal antigen, α1-fetoprotein, isoferritin, and fetal sulphoglycoprotein, α2-H-ferroprotein and γ-fetoprotein. The term "cancer associated antigen" as used herein can be any type of cancer antigen that may be associated with a cancer (e.g., produced or overexpressed in cancer cells or is known in the art to be associated with cancer) and includes antigens found on the cell surface, including tumor cells, as well as soluble cancer antigens. Several cell surface antigens on tumors and normal cells have soluble counterparts. A cancer associated antigen can be a cell surface antigen or a soluble cancer antigen located in the tumor microenvironment or otherwise in close proximity to the tumor being treated. Such antigens include, but are not limited to those found on cancer-associated fibroblasts (CAFs), tumor endothelial cells (TEC) and tumor-associated macrophages (TAM). Examples of cancer-associated fibroblasts (CAFs) target antigens include but are not limited to: carbonic anhydrase IX (CAIX); fibroblast activation protein alpha (FAPα); and matrix metalloproteinases (MMPs) including MMP-2 and MMP-9. Examples of Tumor endothelial cell (TECs) target antigens include, but are not limited to vascular endothelial growth factor (VEGF) including VEGFR-1, 2, and 3; CD-105 (endoglin), tumor endothelia markers (TEMs) including TEM1 and TEM8; MMP-2; Survivin; and prostate-specific membrane antigen (PMSA). Examples of tumor associated macrophage antigens include, but are not limited to: CD105; MMP-9; VEGFR-1, 2, 3 and TEM8. In one embodiment, the cancer associated antibody specific for a cancer associated antigen may be specific for cancer antigens located on non-tumor cells, for example, VEGFR-2, MMPs, Survivin, TEM8 and PMSA. The cancer associated antigen may be an epithelial cancer antigen, (e.g., breast, gastrointestinal, lung), a prostate specific cancer antigen (PSA) or prostate specific membrane antigen (PSMA), a bladder cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, or a head and neck cancer antigen. A cancer antigen can also be a lymphoma antigen (e.g., non-Hodgkin's lymphoma or Hodgkin's lymphoma), a B-cell lymphoma cancer antigen, a leukemia antigen, a myeloma (i.e., multiple myeloma or plasma cell myeloma) antigen, an acute lymphoblastic leukemia antigen, a chronic myeloid leukemia antigen, or an acute myelogenous leukemia antigen. According to the present invention, a cancer associated antigen preferably comprises any antigen which is expressed in and optionally characteristic with respect to type and/or expression level for tumors or cancers as well as for tumor or cancer cells. In one embodiment, the term "tumor antigen" or "tumor-associated antigen" or "cancer antigen" or "cancer associated antigen" relates to proteins that are under normal conditions specifically expressed in a limited number of tissues and/or organs or in specific developmental stages, for example, the cancer associated antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2. The cancer associated antigen in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. Preferably, the cancer associated antigen or the aberrant expression of the cancer associated antigen identifies cancer cells. In the context of the present invention, the cancer associated antigen that is expressed by a cancer cell in a subject, e.g., a patient suffering from a cancer disease, is preferably a self-protein in said subject. In preferred embodiments, the cancer associated antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. A "cancer associated antigen", as used herein can be any antigenic substance produced or overexpressed in tumor cells. It can, for example, trigger an immune response in the host. Alternatively, for purposes of this disclosure, cancer associated antigens can be proteins that are expressed by both healthy and tumor cells, but because they identify a certain tumor type, they can be a suitable therapeutic target. Non-limiting examples of the cancer associated antigen is CD19, CD20, CD30, CD33, CD38, Her2/neu, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), high molecular weight-melanoma associated antigen (HMW-MAA), MAGE-A1, IL-13R-a2, GD2, or any combination thereof. In some embodiments, the cancer associated antigen is 1p19q, ABL1, AKT1, ALK, APC, AR, ATM, BRAF, BRCA1, BRCA2, cKIT, cMET, CSF1R, CTNNB1, EGFR, EGFRvIII, ER, ERBB2 (HER2), FGFR1, FGFR2, FLT3, GNA11, GNAQ, GNAS, HER2, HRAS, IDH1, IDH2, JAK2, KDR (VEGFR2), KRAS, MGMT, MGMT-Me, MLH1, MPL, NOTCH1, NRAS, PDGFRA, Pgp, PIK3CA, PR, PTEN, RET, RRM1, SMO, SPARC, TLE3, TOP2A, TOPO1, TP53, TS, TUBB3, VHL, CDH1, ERBB4, FBXW7, HNF1A, JAK3, NPM1, PTPN11, RB1, SMAD4, SMARCB1, STK1, MLH1, MSH2, MSH6, PMS2, microsatellite instability (MSI), ROS1, ERCC1, or any combination thereof. According to the invention, the terms "cancer associated antigen", "tumor antigen", "tumor expressed antigen", "cancer antigen" "cancer associated antigen" and "cancer expressed antigen" are equivalents and are used interchangeably herein.

Src Homology 2 (SH2) Domain Containing Inositol Polyphosphate 5-Phosphatase 1 (SHIP1)

In some embodiments, the antibody disclosed herein or an antigen binding fragment thereof binds to a Src homology 2 (SH2) domain containing inositol polyphosphate 5-phosphatase 1 (SHIP1) polypeptide. The term "SHIP1", as used herein, refers, to any native or variant (whether native or synthetic) SHIP1 polypeptide. The term "native sequence" specifically encompasses naturally occurring truncated or secreted forms (e.g., an extracellular domain sequence), naturally occurring variant forms (e.g., alternatively spliced forms) and naturally-occurring allelic variants. SHIP1 is an enzyme with phosphatase activity. SHIP1 is structured by multiple domain and is encoded by the INPP5D gene in humans, as described by Sandra Fernandes et al. Ann N Y Acad Sci. 2013 March; 1280(1): 6-10. The term "SHIP1" as used herein refers to the 1189 amino acid polypeptide together with the naturally occurring allelic and processed forms thereof. As used herein, the term "SHIP1" refers to a full length SHIP1 polypeptide or to a fragment or derivative thereof. The SHIP1 polypeptide can be full length human FGF1 and/or functional fragments thereof, a species homologue and/or functional fragments thereof, an ortholog of human SHIP1 and/or functional fragments thereof. The SHIP1 polypeptide can be a mammalian SHIP1 polypeptide. The SHIP1 polypeptide can also be a functional isoform of the full length SHIP1 or fragment thereof.

In some embodiments, the SHIP1 polypeptide includes or is derived from human SHIP1 having the following amino acid sequence of SEQ ID NO: 281 (NCBI reference sequence number: NP_001017915.1, which is incorporated herein in its entirety. The polypeptide and coding nucleic acid sequences of SHIP1 and of other members of the family of human origin and those of a number of animals are publicly available, e.g., from the NCBI website. The term "SHIP1" also refers to SHIP1 from non-human species such as mouse (e.g., NCBI: NP_034696.2—SEQ ID NO: 282); rat (e.g., NCBI ref: NP_062184.1; SEQ ID NO: 283), bovine (e.g., NCBI NP_001095352.1; SEQ ID NO: 284) or monkey (e.g., EHH21775.1; SEQ ID NO: 285).

The term "SHIP1" is also used to refer to truncated forms of the 1189-amino acid human SHIP1. The term "SHIP1 variant" as used herein refers to a SHIP1 polypeptide which includes one or more amino acid mutations in the native SHIP1 sequence. Optionally, the one or more amino acid mutations include amino acid substitution(s). In some embodiments, at least one of the antibodies disclosed herein or antigen binding fragment thereof binds to SHIP1. In some embodiments, the antibody or antigen binding fragment thereof binding the SHIP1 comprises a complementarity-determining region heavy chain 1 (CDR-H1) of SEQ ID NO 85, CDR-H2 of SEQ ID NO: 57, and CDR-H3 of SEQ ID NO: 29. In some embodiments, the antibody or antigen binding fragment thereof that binds SHIP1 comprises a complementarity-determining region light chain 1 (CDR-L1) of SEQ ID NO 99, CDR-L2 of SEQ ID NO: 71, and CDR-L3 of SEQ ID NO: 43. In some embodiments, the antibody or antigen-binding fragment thereof that binds SHIP1 comprises a variable heavy chain comprising a polypeptide sequence having at least 95% sequence identity to the amino acid sequence of SEQ ID NO 1. In some embodiments, the antibody or antigen-binding fragment thereof that binds SHIP1 comprises a variable light chain comprising a polypeptide consensus sequence having at least 95% sequence identity to the amino acid sequence of SEQ ID NO 15.

Chromobox Homolog 1

In some embodiments, the antibody disclosed herein or an antigen binding fragment thereof binds to a Chromobox protein homolog 1 (CBX1) polypeptide. The term "CBX1" as used herein, refers, to any native or variant (whether native or synthetic) CBX1. The term "native sequence" specifically encompasses naturally occurring truncated or secreted forms (e.g., an extracellular domain sequence), naturally occurring variant forms (e.g., alternatively spliced forms) and naturally-occurring allelic variants. CBX1 belongs to the HP1 family of proteins and is known to localize to the heterochromatin, as described by lombrek et al. Genome Biology volume 7, Article number: 228 (2006). The term "CBX1" as used herein refers to the 185 amino acid polypeptide together with the naturally occurring allelic and processed forms thereof. As used herein, the term "CBX1" refers to a full length CBX1 polypeptide or to a fragment or derivative thereof. The CBX1 polypeptide can be full length human CBX1 and/or functional fragments thereof, a species homologue and/or functional fragments thereof, an ortholog of human CBX1 and/or functional fragments thereof. The CBX1 polypeptide can be a mammalian CBX1 polypeptide. The CBX1 polypeptide can also be a functional isoform of the full length CBX1 or fragment thereof.

In some embodiments, the CBX1 polypeptide includes or is derived from human CBX1 having the following amino acid sequence of SEQ ID NO: 286 (NCBI reference sequence number: NP_001120700.1, which is incorporated herein in its entirety. The polypeptide and coding nucleic acid sequences of CBX1 and of other members of the family of human origin and those of a number of animals are publicly available, e.g., from the NCBI website. The term "CBX1" also refers to CBX1 from non-human species such as mouse (e.g., NCBI: NP_001349489.1—SEQ ID NO: 287); rat (e.g., NCBI ref: NP_001008314.2; SEQ ID NO: 288), bovine (e.g., NCBI NP_001193344.1; SEQ ID NO: 289) or monkey (e.g., AFH30900.1; SEQ ID NO: 290).

The term "CBX1" is also used to refer to truncated forms of the 185-amino acid human CBX1. The term "CBX1 variant" as used herein refers to a CBX1 polypeptide which includes one or more amino acid mutations in the native CBX1 sequence. Optionally, the one or more amino acid mutations include amino acid substitution(s).

Chromobox Homolog 3

In some embodiments, the antibody disclosed herein or an antigen binding fragment thereof binds to a Chromobox protein homolog 3 (CBX3) polypeptide. The term "CBX3" as used herein, refers, to any native or variant (whether native or synthetic) CBX3. The term "native sequence" specifically encompasses naturally occurring truncated or secreted forms (e.g., an extracellular domain sequence), naturally occurring variant forms (e.g., alternatively spliced forms) and naturally-occurring allelic variants. CBX3 belongs to the HP1 family of proteins and is known to localize to the heterochromatin, as described by lombrek et al. Genome Biology volume 7, Article number: 228 (2006). The term "CBX3" as used herein refers to the 183 amino acid polypeptide together with the naturally occurring allelic and processed forms thereof. As used herein, the term "CBX3" refers to a full length CBX3 polypeptide or to a fragment or derivative thereof. The CBX3 polypeptide can be full length human CBX3 and/or functional fragments thereof, a species homologue and/or functional fragments thereof, an ortholog of human CBX3 and/or functional fragments thereof. The CBX3 polypeptide can be a mammalian CBX3 polypeptide. The CBX3 polypeptide can also be a functional isoform of the full length CBX3 or fragment thereof.

In some embodiments, the CBX3 polypeptide includes or is derived from human CBX3 having the following amino acid sequence of SEQ ID NO: 291 (NCBI reference sequence number: NP_009207.2, which is incorporated herein in its entirety. The polypeptide and coding nucleic acid sequences of CBX3 and of other members of the family of human origin and those of a number of animals are publicly available, e.g., from the NCBI website. The term "CBX3" also refers to CBX3 from non-human species such as mouse (e.g., NCBI: AAH59831.1—SEQ ID NO: 292); rat (e.g., NCBI ref: NP_001008314.2; SEQ ID NO: 293), bovine (e.g., NCBI AAI47956.1; SEQ ID NO: 294) or monkey (e.g., NP_001180536.1; SEQ ID NO: 295).

The term "CBX3" is also used to refer to truncated forms of the 183-amino acid human CBX3. The term "CBX3 variant" as used herein refers to a CBX3 polypeptide which includes one or more amino acid mutations in the native CBX3 sequence. Optionally, the one or more amino acid mutations include amino acid substitution(s).

Chromobox Homolog 5

In some embodiments, the antibody disclosed herein or an antigen binding fragment thereof binds to a Chromobox protein homolog 5 (CBX5) polypeptide. The term "CBX5" as used herein, refers, to any native or variant (whether native or synthetic) CBX5. The term "native sequence" specifically encompasses naturally occurring truncated or secreted forms (e.g., an extracellular domain sequence), naturally occurring variant forms (e.g., alternatively spliced forms) and naturally-occurring allelic variants. CBX5 belongs to the HP1 family of proteins and is known to localize to the heterochromatin, as described by lombrek et al. Genome Biology volume 7, Article number: 228 (2006). The term "CBX5" as used herein refers to the 191 amino acid polypeptide together with the naturally occurring allelic and processed forms thereof. As used herein, the term "CBX5" refers to a full length CBX5 polypeptide or to a fragment or derivative thereof. The CBX5 polypeptide can be full length human CBX5 and/or functional fragments thereof, a species homologue and/or functional fragments thereof, an ortholog of human CBX5 and/or functional fragments thereof. The CBX5 polypeptide can be a mammalian CBX5 polypeptide. The CBX5 polypeptide can also be a functional isoform of the full length CBX5 or fragment thereof.

In some embodiments, the CBX5 polypeptide includes or is derived from human CBX5 having the following amino acid sequence of SEQ ID NO: 296 (NCBI reference sequence number: NP_001120793.1, which is incorporated herein in its entirety. The polypeptide and coding nucleic acid sequences of CBX5 and of other members of the family of human origin and those of a number of animals are publicly available, e.g., from the NCBI website. The term "CBX5" also refers to CBX5 from non-human species such as mouse (e.g., NCBI: NP_001345879.1—SEQ ID NO: 297); rat (e.g., NCBI ref: NP_001100267.1; SEQ ID NO: 298), bovine (e.g., NCBI NP_001180142.1; SEQ ID NO: 299) or monkey (e.g., NP_001253841.1; SEQ ID NO: 300).

The term "CBX5" is also used to refer to truncated forms of the 191-amino acid human CBX5. The term "CBX5 variant" as used herein refers to a CBX5 polypeptide which includes one or more amino acid mutations in the native CBX5 sequence. Optionally, the one or more amino acid mutations include amino acid substitution(s).

In some embodiments, the antibody or antigen binding fragment thereof disclosed herein binds a chromobox protein (e.g, CBX1, CBX 2, CBX3). In some embodiments, the antibody or antigen binding fragment thereof that binds a chromobox protein comprises a complementarity-determining region heavy chain 1 (CDR-H1) of SEQ ID NO: 87, CDR-H2 of SEQ ID NO: 59, and CDR-H3 of SEQ ID NO: 31. In some embodiments, the antibody or antigen binding fragment thereof that binds a chromobox protein comprises a complementarity-determining region light chain 1 (CDR-L1) of SEQ ID NO: 101, CDR-L2 of SEQ ID NO: 73, and CDR-L3 of SEQ ID NO: 45. In some embodiments, the antibody or antigen binding fragment thereof that binds chromobox protein comprises a variable heavy chain comprising a polypeptide consensus sequence having at least 95% sequence identity to the amino acid sequence of SEQ ID NO: 3. In some embodiments, the antibody or antigen binding fragment thereof that binds chromobox protein comprises a variable light chain comprising a polypeptide consensus sequence having at least 95% sequence identity to the amino acid sequence of SEQ ID NO: 17.

Cancer/Testis Antigen 1A

In some embodiments, the antibody disclosed herein or an antigen binding fragment thereof binds to a Cancer/Testis Antigen 1A (CTAG1A) polypeptide. The term "CTAG1A" can be used interchangeably with "NY-ESO-1" as used herein, refers, to any native or variant (whether native or synthetic) CTAG1A. The term "native sequence" specifically encompasses naturally occurring truncated or secreted forms (e.g., an extracellular domain sequence), naturally occurring variant forms (e.g., alternatively spliced forms) and naturally-occurring allelic variants. CTAG1A is a protein belonging to the family of Cancer Testis Antigens (CTA), as described by martins et. al. Cancer Cell International volume 5, Article number: 4 (2005). The term "CTAG1A" as used herein refers to the 180 amino acid polypeptide together with the naturally occurring allelic and processed forms thereof. As used herein, the term "CTAG1A" refers to a full length CTAG1A polypeptide or to a fragment or derivative thereof. The CTAG1A polypeptide can be full length human CTAG1A and/or functional fragments thereof, a species homologue and/or functional fragments thereof, an ortholog of human CTAG1A and/or functional fragments thereof. The CTAG1A polypeptide can be a mammalian CTAG1A polypeptide. The CTAG1A polypeptide can also be a functional isoform of the full length CTAG1A or fragment thereof.

In some embodiments, the CTAG1A polypeptide includes or is derived from human CTAG1A having the following amino acid sequence of SEQ ID NO: 301 (e.g., NCBI reference sequence number: NP_640343.1, which is incorporated herein in its entirety. The polypeptide and coding nucleic acid sequences of CBX5 and of other members of the family of human origin and those of a number of animals are publicly available, e.g., from the NCBI website. The term "CTAG1A" also refers to CTAG1A from non-human species such as mouse (e.g., NCBI: NP_081578.1—SEQ ID NO: 302); rat, bovine or monkey.

The term "CTAG1A" is also used to refer to truncated forms of the 180-amino acid human CTAG1A. The term "CTAG1A variant" as used herein refers to a CTAG1A polypeptide which includes one or more amino acid mutations in the native CTAG1A sequence. Optionally, the one or more amino acid mutations include amino acid substitution(s). In some the antibody or antigen binding fragment that binds CTAG1A comprises a complementarity-determining region heavy chain 1 (CDR-H1) of SEQ ID NO: 90, CDR-H2 of SEQ ID NO: 62, and CDR-H3 of SEQ ID NO: 34. In some the antibody or antigen binding fragment that binds CTAG1A comprises a complementarity-determining region light chain 1 (CDR-L1) of SEQ ID NO: 103, CDR-L2 of SEQ ID NO: 75, and CDR-L3 of SEQ ID NO: 47. In some embodiments, the antibody or antigen binding fragment thereof that binds CTAG1A comprises variable heavy chain comprises a polypeptide consensus sequence having at least 95% sequence identity to the amino acid sequence of SEQ ID NO: 5. In some embodiments, the antibody or antigen binding fragment thereof that binds CTAG1A comprises variable light chain comprises a polypeptide consensus sequence having at least 95% sequence identity to the amino acid sequence of SEQ ID NO: 19. In some embodiments, the antibody or antigen binding fragment thereof binds to a CTAG1B polypeptide.

Alpha and Gamma Adaptin Binding Protein

In some embodiments, the antibody disclosed herein or an antigen binding fragment thereof binds to an Alpha And Gamma Adaptin Binding Protein (AAGAB) polypeptide. The term "AAGAB" as used herein, refers, to any native or variant (whether native or synthetic) AAGAB. The term "native sequence" specifically encompasses naturally occurring truncated or secreted forms (e.g., an extracellular domain sequence), naturally occurring variant forms (e.g., alternatively spliced forms) and naturally-occurring allelic variants. AAGAB interacts with the gamma-adaptin subunit of AP1 and with the alpha-adaptin subunit of AP2, as described by Pohler et al. Nature Genet. 44: 1272-1276, 2012. The term "AAGAB" as used herein refers to the 206 amino acid polypeptide together with the naturally occurring allelic and processed forms thereof. As used herein, the term "AAGAB" refers to a full length AAGAB polypeptide or to a fragment or derivative thereof. The AAGAB polypeptide can be full length human AAGAB and/or functional fragments thereof, a species homologue and/or functional fragments thereof, an ortholog of human AAGAB and/or functional fragments thereof. The AAGAB polypeptide can be a mammalian AAGAB polypeptide. The AAGAB polypeptide can also be a functional isoform of the full length AAGAB or fragment thereof.

In some embodiments, the AAGAB polypeptide includes or is derived from human AAGAB having the following amino acid sequence of SEQ ID NO: 303 (NCBI reference sequence number: NP_001258814.1, which is incorporated herein in its entirety. The polypeptide and coding nucleic acid sequences of AAGAB and of other members of the family of human origin and those of a number of animals are publicly available, e.g., from the NCBI website. The term "AAGAB" also refers to AAGAB from non-human species such as mouse (e.g., NCBI: NP_001344252.1—SEQ ID NO: 304); rat (e.g., NCBI ref: NP_599225.1; SEQ ID NO: 305), bovine (e.g., NCBI NP_001092366.1; SEQ ID NO: 306) or monkey (e.g., XP_014998028.1; SEQ ID NO: 307).

The term "AAGAB" is also used to refer to truncated forms of the 206-amino acid human AAGAB. The term "AAGAB variant" as used herein refers to an AAGAB polypeptide which includes one or more amino acid mutations in the native AAGAB sequence. Optionally, the one or more amino acid mutations include amino acid substitution(s). In some embodiments, the antibody or antigen binding fragment thereof that binds AAGAB comprises a complementarity-determining region heavy chain 1 (CDR-H1) of SEQ ID NO: 90, CDR-H2 of SEQ ID NO: 62, and CDR-H3 of SEQ ID NO: 34.

Kinesin Light Chain 4 Protein

In some embodiments, the antibody disclosed herein or an antigen binding fragment thereof binds to an Kinesin light chain 4 protein (KLC4) polypeptide. The term "KLC4" as used herein, refers, to any native or variant (whether native or synthetic) KLC4. The term "native sequence" specifically encompasses naturally occurring truncated or secreted forms (e.g., an extracellular domain sequence), naturally occurring variant forms (e.g., alternatively spliced forms) and naturally-occurring allelic variants. Kinesin is a microtubule-associated force-producing protein that may play a role in organelle transport. The light chain may function in coupling of cargo to the heavy chain or in the modulation of its ATPase activity. The term "KLC4" as used herein refers to the 619 amino acid polypeptide together with the naturally occurring allelic and processed forms thereof. As used herein, the term "KLC4" refers to a full length KLC4 polypeptide or to a fragment or derivative thereof. The KLC4 polypeptide can be full length human KLC4 and/or functional fragments thereof, a species homologue and/or functional fragments thereof, an ortholog of human KLC4 and/or functional fragments thereof. The KLC4 polypeptide can be a mammalian KLC4 polypeptide. The KLC4 polypeptide can also be a functional isoform of the full length KLC4 or fragment thereof.

In some embodiments, the KLC4 polypeptide includes or is derived from human KLC4 having the following amino acid sequence of SEQ ID NO: 308 (NCBI reference sequence number: NP_001275963.1, which is incorporated herein in its entirety. The polypeptide and coding nucleic acid sequences of KLC4 and of other members of the family of human origin and those of a number of animals are publicly available, e.g., from the NCBI website. The term "KLC4" also refers to KLC4 from non-human species such as mouse (e.g., NCBI: NP_001344059.1—SEQ ID NO: 309); rat (e.g., NCBI ref: NP_001009601.1; SEQ ID NO: 310), bovine (e.g., NCBI XP 024839789.1; SEQ ID NO: 311) or monkey (e.g., XP_028703383.1; SEQ ID NO: 312).

The term "KLC4" is also used to refer to truncated forms of the 619-amino acid human KLC4. The term "KLC4 variant" as used herein refers to an KLC4 polypeptide which includes one or more amino acid mutations in the native KLC4 sequence. Optionally, the one or more amino acid mutations include amino acid substitution(s). In some embodiments, the antibody or antigen binding fragment thereof that binds KLC4 comprises a complementarity-determining region heavy chain 1 (CDR-H1) of SEQ ID NO: 91, CDR-H2 of SEQ ID NO: 63, and CDR-H3 of SEQ ID NO: 35. In some embodiments, the antibody or antigen binding fragment thereof that binds KLC4 comprises a complementarity-determining region light chain 1 (CDR-L1) of SEQ ID NO: 105, CDR-L2 of SEQ ID NO: 77, and CDR-L3 of SEQ ID NO: 49. In some embodiments, the antibody or antigen binding fragment thereof that binds KLC4 comprises a variable heavy chain comprising a polypeptide consensus sequence having at least 95% sequence identity to the amino acid sequence of SEQ ID NO: 7. In some embodiments, the antibody or antigen binding fragment thereof that binds KLC4 comprises a variable light chain comprising a polypeptide consensus sequence having at least 95% sequence identity to the amino acid sequence of SEQ ID NO: 21.

Melanoma-Associated Antigen 3

In some embodiments, the antibody disclosed herein or an antigen binding fragment thereof binds to an Melanoma-associated antigen 3 (MAGE-A3) polypeptide. The term "MAGE-A3" as used herein, refers, to any native or variant (whether native or synthetic) MAGE-A3. The term "native sequence" specifically encompasses naturally occurring truncated or secreted forms (e.g., an extracellular domain sequence), naturally occurring variant forms (e.g., alternatively spliced forms) and naturally-occurring allelic variants. MAGE-A3 is a member of a large, highly conserved group of proteins that share a common MAGE homology domain. The term "MAGE-A3" as used herein refers to the 314 amino acid polypeptide together with the naturally occurring allelic and processed forms thereof. As used herein, the term "MAGE-A3" refers to a full length MAGE-A3 polypeptide or to a fragment or derivative thereof. The MAGE-A3 polypeptide can be full length human MAGE-A3 and/or functional fragments thereof, a species homologue and/or functional fragments thereof, an ortholog of human MAGE-A3 and/or functional fragments thereof. The MAGE-A3 polypeptide can be a mammalian MAGE-A3 polypeptide. The MAGE-A3 polypeptide can also be a functional isoform of the full length MAGE-A3 or fragment thereof.

In some embodiments, the MAGE-A3 polypeptide includes or is derived from human MAGE-A3 having the following amino acid sequence of SEQ ID NO: 313 (NCBI reference sequence number: NP_005353.1, which is incorporated herein in its entirety. The polypeptide and coding nucleic acid sequences of MAGEA-3 and of other members of the family of human origin and those of a number of animals are publicly available, e.g., from the NCBI website. The term "MAGE-A3" also refers to MAGE-A3 from non-human species such as mouse (e.g., NCBI: NP_064401.2—SEQ ID NO: 314); rat, bovine or monkey.

The term "MAGE-A3" is also used to refer to truncated forms of the 314-amino acid human MAGE-A3. The term "MAGE-A3 variant" as used herein refers to a MAGE-A3 polypeptide which includes one or more amino acid mutations in the native MAGE-A3 sequence. Optionally, the one or more amino acid mutations include amino acid substitution(s). In some embodiments, the antibody or antigen binding fragment thereof that binds MAGE-A3 comprises a complementarity-determining region heavy chain 1 (CDR-H1) of SEQ ID NO: 92, CDR-H2 of SEQ ID NO: 64, and CDR-H3 of SEQ ID NO: 36. In some embodiments, the antibody or antigen binding fragment thereof that binds MAGE-A3 comprises a complementarity-determining region light chain 1 (CDR-L1) of SEQ ID NO: 106, CDR-L2 of SEQ ID NO: 78, and CDR-L3 of SEQ ID NO: 50. In some embodiments, the antibody or antigen binding fragment thereof that binds MAGE-A3 comprises a variable heavy chain comprising a polypeptide consensus sequence having at least 95% sequence identity to the amino acid sequence of SEQ ID NO: 8. In some embodiments, the antibody or antigen binding fragment thereof that binds MAGE-A3 comprises a variable light chain comprising a polypeptide consensus sequence having at least 95% sequence identity to the amino acid sequence of SEQ ID NO: 22.

Inorganic Pyrophosphatase

In some embodiments, the antibody disclosed herein or an antigen binding fragment thereof binds to an Inorganic pyrophosphatase (PPA1) polypeptide. The term "PPA1" as used herein, refers, to any native or variant (whether native or synthetic) PPA1. The term "native sequence" specifically encompasses naturally occurring truncated or secreted forms (e.g., an extracellular domain sequence), naturally occurring variant forms (e.g., alternatively spliced forms) and naturally-occurring allelic variants. PPA1 is an enzyme that catalyzes the conversion of one ion of pyrophosphate to two phosphate ions. The term "PPA1" as used herein refers to the 289 amino acid polypeptide together with the naturally occurring allelic and processed forms thereof. As used herein, the term "PPA1" refers to a full length PPA1 polypeptide or to a fragment or derivative thereof. The PPA1 polypeptide can be full length human PPA1 and/or functional fragments thereof, a species homologue and/or functional fragments thereof, an ortholog of human PPA1 and/or functional fragments thereof. The PPA1 polypeptide can be a mammalian PPA1 polypeptide. The PPA1 polypeptide can also be a functional isoform of the full length PPA1 or fragment thereof.

In some embodiments, the PPA1 polypeptide includes or is derived from human PPA1 having the following amino acid sequence of SEQ ID NO: 315 (NCBI reference sequence number: NP_066952.1, which is incorporated herein in its entirety. The polypeptide and coding nucleic acid sequences of PPA1 and of other members of the family of human origin and those of a number of animals are publicly available, e.g., from the NCBI website. The term "PPA1" also refers to PPA1 from non-human species such as mouse (e.g., NCBI: NP_080714.2—SEQ ID NO: 316); rat (e.g., NCBI ref: NP_001094304.1; SEQ ID NO: 317), bovine (e.g., NCBI NP_001068586.1; SEQ ID NO: 318) or monkey (e.g., NCBI XP_015002942.1; SEQ ID NO: 329)

The term "PPA1" is also used to refer to truncated forms of the 289-amino acid human PPA1. The term "PPA1 variant" as used herein refers to an PPA1 polypeptide which includes one or more amino acid mutations in the native PPA1 sequence. Optionally, the one or more amino acid mutations include amino acid substitution(s). In some embodiments, the antibody or antigen binding fragment thereof that binds PPA1 comprises a complementarity-determining region heavy chain 1 (CDR-H1) of SEQ ID NO: 94, CDR-H2 of SEQ ID NO: 66, and CDR-H3 of SEQ ID NO: 38. In some embodiments, the antibody or antigen binding fragment thereof that binds PPA1 comprises a complementarity-determining region light chain 1 (CDR-L1) of SEQ ID NO: 108, CDR-L2 of SEQ ID NO: 80, and CDR-L3 of SEQ ID NO: 52. In some embodiments, the antibody or antigen binding fragment thereof that binds PPA1 comprises a variable heavy chain comprising a polypeptide consensus sequence having at least 95% sequence identity to the amino acid sequence of SEQ ID NO: 10. In some embodiments, the antibody or antigen binding fragment thereof that binds PPA1 comprises a variable light chain comprising a polypeptide consensus sequence having at least 95% sequence identity to the amino acid sequence of SEQ ID NO: 24.

Interleukin-14A

In some embodiments, the antibody disclosed herein or an antigen binding fragment thereof binds to an interleukin-14A (IL-14A) polypeptide. The term "IL-14A" as used herein, refers, to any native or variant (whether native or synthetic) IL-14A. The term "native sequence" specifically encompasses naturally occurring truncated or secreted forms (e.g., an extracellular domain sequence), naturally occurring variant forms (e.g., alternatively spliced forms) and naturally-occurring allelic variants. IL-14A is a cytokine that induces B-cell proliferation, inhibits antibody secretion, and expands selected B-cell subgroups. The term "IL-14A" as used herein refers to the 546 amino acid polypeptide together with the naturally occurring allelic and processed forms thereof. As used herein, the term "IL-14A" refers to a full length IL-14A polypeptide or to a fragment or derivative thereof. The IL-14A polypeptide can be full length human IL-14A and/or functional fragments thereof, a species homologue and/or functional fragments thereof, an ortholog of human IL-14A and/or functional fragments thereof. The IL-14A polypeptide can be a mammalian IL-14A polypeptide. The IL-14A polypeptide can also be a functional isoform of the full length IL-14A or fragment thereof.

In some embodiments, the IL-14A polypeptide includes or is derived from human IL-14A having the following amino acid sequence of SEQ ID NO: 319 (NCBI reference sequence number: NP_787048.1, which is incorporated herein in its entirety. The polypeptide and coding nucleic acid sequences of IL-14A and of other members of the family of human origin and those of a number of animals are publicly available, e.g., from the NCBI website. The term "IL-14A" also refers to IL-14A from non-human species such as mouse (e.g., NCBI: NP_001005506.2—SEQ ID NO: 320); rat (e.g., NCBI ref: NP_001121105.1; SEQ ID NO: 321), bovine (e.g., NCBI XP_024852996.1; SEQ ID NO: 322) or monkey (e.g., AFH31416.1; SEQ ID NO: 323).

The term "IL-14A" is also used to refer to truncated forms of the 546-amino acid human IL-14A. The term "IL-14A variant" as used herein refers to an IL-14A polypeptide which includes one or more amino acid mutations in the native IL-14A sequence. Optionally, the one or more amino acid mutations include amino acid substitution(s). In some embodiments, the antibody or antigen binding fragment thereof that binds IL-14A a complementarity-determining region heavy chain 1 (CDR-H1) of SEQ ID NO: 95, CDR-H2 of SEQ ID NO: 67, and CDR-H3 of SEQ ID NO: 39. In some embodiments, the antibody or antigen binding fragment thereof that binds IL-14A comprises a complementarity-determining region light chain 1 (CDR-L1) of SEQ ID NO: 109, CDR-L2 of SEQ ID NO: 81, and CDR-L3 of SEQ ID NO: 53. In some embodiments, the antibody or antigen binding fragment thereof that binds IL-14A comprises a variable heavy chain comprising a polypeptide consensus sequence having at least 95% sequence identity to the amino acid sequence of SEQ ID NO: 11. In some embodiments, the antibody or antigen binding fragment thereof that binds IL-14A comprises a variable light chain comprising a polypeptide consensus sequence having at least 95% sequence identity to the amino acid sequence of SEQ ID NO: 25.

O-Linked N-Acetylglucosamine (GlcNAc) Transferase

In some embodiments, the antibody disclosed herein or an antigen binding fragment thereof binds to an O-linked N-acetylglucosamine (GlcNAc) transferase (OGT) polypeptide. The term "OGT" as used herein, refers, to any native or variant (whether native or synthetic) OGT. The term "native sequence" specifically encompasses naturally occurring truncated or secreted forms (e.g., an extracellular domain sequence), naturally occurring variant forms (e.g., alternatively spliced forms) and naturally-occurring allelic variants. OGT catalyzes the addition of a single N-acetylglucosamine in O-glycosidic linkage to serine or threonine residues of intracellular proteins. The term "OGT" as used herein refers to the 1046 amino acid polypeptide together with the naturally occurring allelic and processed forms thereof. As used herein, the term "OGT" refers to a full length OGT polypeptide or to a fragment or derivative thereof. The OGT polypeptide can be full length human OGT and/or functional fragments thereof, a species homologue and/or functional fragments thereof, an ortholog of human OGT and/or functional fragments thereof. The OGT polypeptide can be a mammalian OGT polypeptide. The OGT polypeptide can also be a functional isoform of the full length OGT or fragment thereof.

In some embodiments, the OGT polypeptide includes or is derived from human OGT having the following amino acid sequence of SEQ ID NO: 324 (NCBI reference sequence number: NP_858058.1, which is incorporated herein in its entirety. The polypeptide and coding nucleic acid sequences of OGT and of other members of the family of human origin and those of a number of animals are publicly available, e.g., from the NCBI website. The term "OGT" also refers to OGT from non-human species such as mouse (e.g., NCBI: NP_001277464.1—SEQ ID NO: 325); rat (e.g., NCBI ref: NP_058803.2; SEQ ID NO: 326), bovine (e.g., NCBI NP_001091539.1; SEQ ID NO: 327) or monkey (e.g., XP_014983153.1; SEQ ID NO: 328).

The term "OGT" is also used to refer to truncated forms of the 1046-amino acid human OGT. The term "OGT variant" as used herein refers to an OGT polypeptide which includes one or more amino acid mutations in the native OGT sequence. Optionally, the one or more amino acid mutations include amino acid substitution(s). In some embodiments, the antibody or antigen binding fragment thereof that binds the OGT comprises a complementarity-determining region heavy chain 1 (CDR-H1) of SEQ ID NO: 98, CDR-H2 of SEQ ID NO: 70, and CDR-H3 of SEQ ID NO: 42. In some embodiments, the antibody or antigen binding fragment thereof comprises a complementarity-determining region light chain 1 (CDR-L1) of SEQ ID NO: 112, CDR-L2 of SEQ ID NO: 84, and CDR-L3 of SEQ ID NO: 56. In some embodiments, the antibody or antigen binding fragment thereof comprises a variable heavy chain comprising a polypeptide consensus sequence having at least 95% sequence identity to the amino acid sequence of SEQ ID NO: 14. In some embodiments, the antibody or antigen binding fragment thereof comprises a variable light chain comprising a polypeptide consensus sequence having at least 95% sequence identity to the amino acid sequence of SEQ ID NO: 28.

Immunoconjugates

In one aspect of the present disclosure, the antibodies or antigen binding fragment thereof, disclosed herein, can initiate a potent immune response against the tumor and/or are capable of direct cytotoxicity. In this regard, the antibodies or antigen binding fragment thereof herein may elicit tumor cell lysis by either complement-mediated or antibody-dependent cell cytotoxicity (ADCC) mechanisms, both of which require an intact Fe portion of the immunoglobulin molecule for interaction with effector cell Fe receptor sites or complement proteins. In addition, antibodies that exert a direct biological effect on tumor growth are useful in the practice of the disclosure. Potential mechanisms by which such directly cytotoxic antibodies may act include inhibition of cell growth, modulation of cellular differentiation, modulation of tumor angiogenesis factor profiles, and the induction of apoptosis. The mechanism by which a particular antibody or an antigen binding fragment thereof, disclosed herein, exerts an anti-tumor effect may be evaluated using any number of in vitro assays designed to determine ADCC, ADMMC, complement-mediated cell lysis, and so forth, as is generally known in the art.

The antibodies or antigen binding fragment thereof, disclosed herein, may be administered in their "naked" or unconjugated form, or may have therapeutic agents conjugated to them. In one embodiment, antibodies or antigen binding fragment thereof are used as a radiosensitizer. In such embodiments, the antibodies or antigen binding fragment are conjugated to a radiosensitizing agent. The term "radiosensitizer," as used herein, is defined as a molecule, preferably a low molecular weight molecule, administered to animals in therapeutically effective amounts to increase the sensitivity of the cells to be radiosensitized to electromagnetic radiation and/or to promote the treatment of diseases that are treatable with electromagnetic radiation. Diseases that are treatable with electromagnetic radiation include neoplastic diseases, benign and malignant tumors, and cancerous cells.

The terms "electromagnetic radiation" and "radiation" as used herein include, but are not limited to, radiation having the wavelength of 10-20 to 100 meters. Preferred embodiments of the present disclosure can employ for example, the electro-magnetic radiation of: gamma-radiation c$10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1.0 mm), and microwave radiation (1 mm to 30 cm).

Radiosensitizers are known to increase the sensitivity of cancerous cells to the toxic effects of electromagnetic radiation. Many cancer treatment protocols currently employ radiosensitizers activated by the electromagnetic radiation of X-rays. Examples of X-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromode-oxyuridine (BUdR), 5-iododeoxyuridine (IUdR), bromode-oxycytidine, fluorodeoxyuridine (FUdR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

In another embodiment, the antibody may be conjugated to a receptor (such streptavidin) for utilization in tumor pretargeting wherein the antibody-receptor conjugate is administered to the patient, followed by removal of unbound conjugate from the circulation using a clearing agent and then administration of a ligand (e.g., avidin) which is conjugated to a cytotoxic agent (e.g., a radionuclide).

The present disclosure further provides the above-described antibodies or antigen binding thereof in detectably labeled form. Antibodies can be detectably labeled through the use of radioisotopes, affinity labels (such as biotin, avidin, etc.), enzymatic labels (such as horseradish peroxidase, alkaline phosphatase, etc.) fluorescent or luminescent or bioluminescent labels (such as FITC or rhodamine, etc.), paramagnetic atoms, and the like. Procedures for accomplishing such labeling are well known in the art; for example, see (Sternberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

"Label" refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable. Alternatively, the label may not be detectable on its own but may be an element that is bound by another agent that is detectable (e.g. an epitope tag or one of a binding partner pair such as biotin-avidin, etc.). Thus, the antibody may comprise a label or tag that facilitates its isolation, and methods of the invention to identify antibodies include a step of isolating the antigen/antibody through interaction with the label or tag.

Exemplary therapeutic immunoconjugates comprise the antibody described herein conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate). Fusion proteins are described in further detail below.

In some embodiments, antibodies and antigen binding fragments thereof disclosed herein can be conjugated to a therapeutic agent such as a chemotherapeutic cytotoxin, such as a cytostatic or cytocidal agent (e.g., paclitaxol, cytochalasin B or diphtheria toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracindione, mitoxantrone, mithramycin, actinomycin D, 1-dehydrotestosterone, glucocorticoids, procaine, tetracaine, lidocaine, propranolol, and puromycin and analogs or homologs thereof), antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents, a thrombotic or anti-angiogenic agent or a radioactive label. Examples of suitable cytotoxic agents and chemotherapeutic agents for forming immunoconjugates are known in the art, see for example, WO 05/103081). In another embodiment, antibodies and antigen binding fragments thereof disclosed herein are conjugated to a detectable substrate such as, e.g., an enzyme, fluorescent marker, chemiluminescent marker, bioluminescent material, or radioactive material. In some embodiments of the aspects described herein, the antibody and antibody fragments thereof disclosed herein are conjugated to a toxin (e.g., an enzymatically active toxin of bacterial, fungal, plant or animal origin, or fragments thereof), a small molecule, an siRNA, a nanoparticle, a targeting agent (e.g., a microbubble), or a radioactive isotope (i.e., a radioconjugate). Such conjugates are referred to herein as "immunoconjugates". Such immunoconjugates can be used, for example, in diagnostic, theranostic, or targeting methods.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. A variety of radioisotopes are available for the production of radioconjugate antibodies. Examples include, but are not limited to, 212 Bi, 131 I, 131 In, 90Y and 186Re.

Conjugates of the antibodies or antigen binding fragments thereof described herein and a cytotoxic agent can be made using any of a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., 238 Science 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026.

In other embodiments, the antibody or portion thereof can be conjugated to a "receptor" (e.g., streptavidin) for utilization in tumor pretargeting wherein the antibody-receptor conjugate is administered to the subject, followed by removal of unbound conjugate from the circulation using a clearing agent and then administration of a "ligand" (e.g., avidin) which is conjugated to a cytotoxic agent (e.g. a radionucleotide). In some embodiments, the antibody or antibody fragment thereof can be conjugated to biotin, and the biotin conjugated antibody or antibody fragment thereof can be further conjugated or linked to a streptavidin-bound or -coated agent, such as a streptavidin-coated microbubble, for use in, for example, molecular imaging of angiogenesis.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62: 119-58 (1982).

Production of immunoconjugates is described in U.S. Pat. No. 6,306,393. Immunoconjugates can be pre-pared by indirectly conjugating a therapeutic agent to an antibody component. General techniques are described in Shih et al., Int. J. Cancer 41:832-839 (1988); Shih et al., Int. J. Cancer 46:1101-1106 (1990); and Shih et al., U.S. Pat. No. 5,057,313. The general method involves reacting an antibody component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate.

The carrier polymer is preferably an aminodextran or polypeptide of at least 50 amino acid residues, although other substantially equivalent polymer carriers can also be used. Preferably, the final immunoconjugate is soluble in an aqueous solution, such as mammalian serum, for ease of administration and effective targeting for use in therapy. Thus, solubilizing functions on the carrier polymer will enhance the serum solubility of the final immunoconjugate. In particular, an aminodextran will be preferred.

The process for preparing an immunoconjugate with an aminodextran carrier typically begins with a dextran polymer, advantageously a dextran of average molecular weight of about 10,000-100,000. The dextran is reacted with an oxidizing agent to affect a controlled oxidation of a portion of its carbohydrate rings to generate aldehyde groups. The oxidation is conveniently affected with glycolytic chemical reagents such as NaI04, according to conventional procedures.

The oxidized dextran is then reacted with a polyamine, preferably a diamine, and more preferably, a mono- or polyhydroxy diamine. Suitable amines include ethylene diamine, propylene diamine, or other like polymethylene diamines, diethylene triamine or like polyamines, 1,3-diamino-2-hydroxypropane, or other like hydroxylated diamines or polyamines, and the like. An excess of the amine relative to the aldehyde groups of the dextran is used to ensure substantially complete conversion of the aldehyde functions to Schiff base groups.

A reducing agent, such as NaBH4, NaBH 3CN or the like, is used to effect reductive stabilization of the resultant Schiff base intermediate. The resultant adduct can be purified by passage through a conventional sizing column to remove cross-linked dextrans. Other conventional methods of derivatizing a dextran to introduce amine functions can also be used, e.g., reaction with cyanogen bromide, followed by reaction with a diamine. The anminodextran is then reacted with a derivative of the particular drug, toxin, chelator, immunomodulator, boron addend, or other therapeutic agent to be loaded, in an activated form, preferably, a carboxyl-activated derivative, prepared by conventional means, e.g., using dicyclohexylcarbodiimide (DCC) or a water soluble variant thereof, to form an intermediate adduct.

Alternatively, polypeptide toxins such as poke-weed antiviral protein or ricin A-chain, and the like, can be coupled to aminodextran by glutaraldehyde condensation or by reaction of activated carboxyl groups on the protein with amines on the aminodextran. Chelators for radiometals or magnetic resonance enhancers are well-known in the art. Typical are derivatives of ethylenediaminetetraacetic acid (EDTA) and diethylen-etriaminepentaacetic acid (DTPA). These chelators typically have groups on the side chain by which the chelator can be attached to a carrier. Such groups include, e.g., benzylisothiocyanate, by which the DTPA or EDTA can be coupled to the amine group of a carrier. Alternatively, carboxyl groups or amine groups on a chelator can be coupled to a carrier by activation or prior derivatization and then coupling, all by well-known means.

Boron addends, such as carboranes, can be attached to antibody components by conventional methods. For example, carboranes can be prepared with carboxyl functions on pendant side chains, as is well known in the art. Attachment of such carboranes to a carrier, e.g., aminodextran, can be achieved by activation of the carboxyl groups of the carboranes and condensation with amines on the carrier to produce an intermediate conjugate. Such intermediate conjugates are then attached to antibody components to produce therapeutically useful immunoconjugates, as described below.

A polypeptide carrier can be used instead of aminodextran, but the polypeptide carrier should have at least 50 amino acid residues in the chain, preferably 100-5000 amino acid residues. At least some of the amino acids should be lysine residues or glutamate or aspartate residues. The pendant amines of lysine residues and pendant carboxylates of glutamine and aspartate are convenient for attaching a drug, toxin, immunomodulator, chelator, boron addend or other therapeutic agent. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier and immunoconjugate.

Conjugation of the intermediate conjugate with the antibody component is effected by oxidizing the carbohydrate portion of the antibody component and reacting the resulting aldehyde (and ketone) carbonyls with amine groups remaining on the carrier after loading with a drug, toxin, chelator, immunomodulator, boron addend, or other therapeutic agent. Alternatively, an intermediate conjugate can be attached to an oxidized antibody component via amine groups that have been introduced in the intermediate conjugate after loading with the therapeutic agent. Oxidation is conveniently effected either chemically, e.g., with NaIO4 or other glycolytic reagent, or enzymatically, e.g., with neuraminidase and galactose oxidase. In the case of an aminodextran carrier, not all of the amines of the aminodextran are typically used for loading a therapeutic agent. The remaining amines of aminodextran condense with the oxidized antibody component to form Schiff base adducts, which are then reductively stabilized, normally with a borohydride reducing agent.

Analogous procedures are used to produce other immunoconjugates according to the invention. Loaded polypeptide carriers preferably have free lysine residues remaining for condensation with the oxidized carbohydrate portion of an antibody component. Carboxyls on the polypeptide carrier can, if necessary, be converted to amines by, e.g., activation with DCC and reaction with an excess of a diamme.

The final immunoconjugate is purified using conventional techniques, such as sizing chromatography on Sephacryl S-300 or affinity chromatography using one or more CD84Hy epitopes. Alternatively, immunoconjugates can be prepared by directly conjugating an antibody component with a therapeutic agent. The general procedure is analogous to the indirect method of conjugation except that a therapeutic agent is directly attached to an oxidized antibody component. It will be appreciated that other therapeutic agents can be substituted for the chelators described herein. Those of skill in the art will be able to devise conjugation schemes without undue experimentation.

As a further illustration, a therapeutic agent can be attached at the hinge region of a reduced antibody component via disulfide bond formation. For example, the tetanus toxoid peptides can be constructed with a single cysteine residue that is used to attach the peptide to an antibody component. As an alternative, such peptides can be attached to the antibody component using a heterobifunctional cross-linker, such as N-succinyl 3-(2-pyridyldithio)proprionate (SPDP). Yu et al., Int. J. Cancer 56:244 (1994). General techniques for such conjugation are well-known in the art. See, for example, Wong, Chemistry Of Protein Conjugation and Cross-Linking (CRC Press 1991); Upeslacis et al., "Modification of Antibodies by Chemical Methods," in Monoclonal Antibodies: Principles and Applications, Birch et al. (eds.), pages 187-230 (Wiley-Liss, Inc. 1995); Price, "Production and Characterization of Synthetic Peptide-Derived Antibodies," in Monoclonal Antibodies: Production, Engineering and Clinical Application, Ritter et al. (eds.), pages 60-84 (Cambridge University Press 1995).

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azido-benzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methy ldiethylene triaminepentaacetic acid (MX-DTPA) is an exemplary chelating agent for conjugation of radionuclide to the antibody (see, e.g., W094/11026).

As described above, carbohydrate moieties in the Fe region of an antibody can be used to conjugate a therapeutic agent. However, the Fe region may be absent if an antibody fragment is used as the antibody component of the immunoconjugate. Nevertheless, it is possible to introduce a carbohydrate moiety into the light chain variable region of an antibody or antibody fragment. See, for example, Leung et al., J. Immunol. 154:5919 (1995); Hansen et al., U.S. Pat.

No. 5,443,953. The engineered carbohydrate moiety is then used to attach a therapeutic agent. [0404] In addition, those of skill in the art will recognize numerous possible variations of the conjugation methods. For example, the carbohydrate moiety can be used to attach polyethyleneglycol in order to extend the half-life of an intact antibody, or antigen-binding fragment thereof, in blood, lymph, or other extracellular fluids. Moreover, it is possible to construct a "divalent immunoconjugate" by attaching therapeutic agents to a carbohydrate moiety and to a free sulfhydryl group. Such a free sulfhydryl group may be located in the hinge region of the antibody component.

In some embodiments, provided herein is a method for diagnosing or treating a condition associated with an antigen disclosed herein (e.g., antigens listed in Tables 9-10). In some embodiments, the condition associated with the antigen results due to an increase in the expression or biological activity of the antigen. In some embodiments, the condition associated with the antigen results due to a decrease in the expression or biological activity of the antigen. In some embodiments, the antibody or antigen-binding fragment thereof disclosed herein binds an antigen (e.g., antigen listed in Table 9-10) and, thereby, partially or substantially inhibits the expression and/or at least one biological activity of the antigen. An antibody, or specified portion or variant thereof, that partially or preferably substantially inhibits the expression and/or at least one biological activity of an antigen disclosed herein can bind the protein antigen or fragment thereof and thereby inhibit activities mediated through the antigen e.g., binding of antigen to one or more receptor or ligand known in the art to bind a particular antigen. In some embodiments, the antibody can inhibit an antigen activity by about 20-120%, preferably by at least about 10, 20, 30, 40, 50, 55, 60, 65, 70, 75, 80, 85, 90, 91, 92, 93, 94, 95, 96, 97, 98, 99, 100% or more. An antibody, or specified portion or variant thereof, that partially or preferably substantially increases the expression and/or at least one biological activity of an antigen disclosed herein can bind the protein antigen or fragment thereof and thereby increase activities mediated through the antigen. In some embodiments, the antibody can increase an antigen activity by about 20-120%, preferably by at least about 10, 20, 30, 40, 50, 55, 60, 65, 70, 75, 80, 85, 90, 91, 92, 93, 94, 95, 96, 97, 98, 99, 100% or more.

The capacity of an antibody to increase an antigen-dependent activity is preferably assessed by at least one suitable assay, as described herein and/or as known in the art. In some embodiments, the antigen related condition can be an immune related disease, a cardiovascular disease, an infectious disease, a malignant disease or a neurologic disease.

Pharmaceutical Compositions and Medicaments

The antibodies or antigen binding fragment thereof, or the compositions, described herein can be used screening for a disease, detecting a presence or a severity of a disease, providing prognosis of a disease, monitoring disease progression or relapse, as well as assessment of treatment efficacy and/or relapse of a disease, disorder or condition, as well as selecting a therapy and/or a treatment for a disease, optimization of a given therapy for a disease, monitoring the treatment of a disease, and/or predicting the suitability of a therapy for specific patients or subpopulations or determining the appropriate dosing of a therapeutic product in patients or subpopulations. In some embodiments, the disease is cancer.

For the clinical use of the methods described herein, administration of the antibodies or antigen binding fragments thereof of the present disclosure, can include formulation into pharmaceutical compositions or pharmaceutical formulations, or medicaments for administration, e.g., subcutaneous, intravenous, intradermal, intraperitoneal, oral, intramuscular, intracranial or other routes of administration. In some embodiments, the antibodies or antigen binding fragments thereof, described herein can be administered along with any pharmaceutically acceptable carrier, excipient, or diluent, which results in an effective treatment in the subject. Thus, in one aspect, the present disclosure provides pharmaceutical compositions comprising one or more antibodies or antigen binding fragment thereof, described herein, in combination with one or more pharmaceutically acceptable carrier, excipient, or diluent.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, an antibody or antigen binding fragment thereof of the present disclosure. Examples include, but are not limited to, any of a number of standard pharmaceutical carriers such as sterile phosphate buffered saline solutions, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like. Each carrier must be "acceptable" in the sense of being compatible with the other ingredients of the formulation and not injurious to the patient. The terms "excipient", "carrier", "pharmaceutically acceptable carrier", or the like are used interchangeably herein. The compositions of the present disclosure may further comprise one or more pharmaceutically acceptable carriers, excipients, and other agents that are incorporated into formulations to provide improved transfer, delivery, tolerance, and the like (herein collectively referred to as "pharmaceutically acceptable carriers or diluents"). A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA, 1998, J Pharm Sci Technol 52:238-311.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Optionally, the formulations comprising the compositions described herein contain a pharmaceutically acceptable salt, typically, e.g., sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are examples of preservatives. Optionally, the formulations of the invention can include a pharmaceutically acceptable surfactant at a concentration of 0.005 to 0.02%.

The compositions described herein can be specially formulated for administration of the antibody or antigen binding fragment thereof to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (7) nasally. Additionally, an antibody or antigen binding fragment thereof, or compositions of the present disclosure can be implanted into a patient or injected using a drug delivery system. See, e.g., Urquhart et al., 24 Ann. Rev. Pharmacol. Toxicol. 199 (1984); *Controlled Release of Pesticides & Pharmaceuticals* (Lewis, ed., Plenum Press, New York, 1981); U.S. Pat. Nos. 3,773,919, 3,270,960.

The compositions disclosed herein, comprising an antibody or antigen binding fragment, described herein, can also contain more than one active compound as necessary for the particular indication being treated, preferably those with complementary activities that do not adversely affect each other. For example, the composition can further comprise a cytotoxic agent, cytokine, growth inhibitory agent and/or an angiogenesis inhibitor such as a VEGFR antagonist. Such molecules are suitably present in combination in amounts that are effective for the purpose intended. The active ingredients of the compositions comprising an antibody or antigen binding fragment thereof described herein can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microparticle, microemulsions, nano-particles and nanocapsules) or in macroemulsions. Such techniques are disclosed in Remington's Pharmaceutical Sciences (16th ed., Osol, ed., 1980). The pharmaceutical composition can be also delivered in a vesicle, in particular a liposome (see Langer 1990 Science 249:1527-1533; Treat et al. (1989) in Liposomes in the Therapy of Infectious Disease and Cancer, Lopez-Berestein and Fidler (eds.), Liss, New York, pp. 353-365; Lopez-Berestein, ibid., pp. 317-327; see generally ibid.). Liposomes include emulsions, foams, micelles, insoluble monolayers, phospholipid dispersions, lamellar layers and the like, and can serve as vehicles to target the M-CSF antibodies to a particular tissue as well as to increase the half life of the composition. A variety of methods are available for preparing liposomes, as described in, e.g., U.S. Pat. Nos. 4,837,028 and 5,019,369, which patents are incorporated herein by reference.

Liposomes containing the antibody are prepared by methods known in the art, such as described in Epstein et al., Proc. Natl. Acad. Sci. USA 82: 3688 (1985); Hwang et al., Proc. Natl Acad. Sci. USA 77: 4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257: 286-288 (1982) via a disulfide interchange reaction. A chemotherapeutic agent (such as Doxorubicin) is optionally contained within the liposome [see, e.g., Gabizon et al., J. National Cancer Inst. 81(19): 1484 (1989)].

In some embodiments, sustained-release preparations can be used. Suitable examples of sustained-release preparations include semipermeable matrices of solid hydrophobic polymers containing an antibody or antigen binding fragment of the present disclosure, in which the matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they can denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thiodisulfide interchange, stabilization can be achieved by modifying sulfhydryl residues, lyophilizing from acidic solutions, controlling moisture content, using appropriate additives, and developing specific polymer matrix compositions. In certain situations, the pharmaceutical composition can be delivered in a controlled release system. In one embodiment, a pump may be used (see Langer, supra; Sefton 1987 CRC Crit. Ref. Biomed. Eng. 14:201). In another embodiment, polymeric materials can be used. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138).

A pharmaceutical composition of the present disclosure can be delivered, e.g., subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded. Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN70130™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition include, but certainly are not limited to the SOLOSTAR™ pen (Sanofi-Aventis), the FLEXPEN™ (Novo Nordisk), and the KWIKPEN™ (Eli Lilly).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Compositions of the present disclosure can be in the form of, for example, granules, powders, tablets, capsules, syrup, suppositories, injections, emulsions, elixirs, suspensions or solutions. The amount of the aforesaid antibody contained can be about 5 to about 500 mg per dosage form in a unit dose; especially in the form of injection, it is preferred that the aforesaid antibody is contained in about 5 to about 100 mg and in about 10 to about 250 mg for the other dosage forms.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. In some embodiments, pharmaceutical formulations and medicaments may be prepared as liquid suspensions or aqueous solutions, for example, using a sterile liquid, such as, but not limited to, an oil, water, an alcohol, and combinations of these. In some embodiments, pharmaceutical compositions can be prepared in a lyophilized form. The lyophilized preparations can comprise a cryoprotectant known in the art. The term "cryoprotectants" as used herein generally includes agents, which provide stability to the protein from freezing-induced stresses. Examples of cryoprotectants include polyols such as, for example, mannitol, and include saccharides such as, for example, sucrose, as well as including surfactants such as, for example, polysorbate, poloxamer or polyethylene glycol, and the like. Cryoprotectants also contribute to the tonicity of the formulations. Pharmaceutically suitable surfactants, suspending agents, emulsifying agents, may be added for oral or par-enteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, iso-propyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For nasal administration, the pharmaceutical formulations and medicaments may be a spray or aerosol containing an appropriate solvent(s) and optionally other compounds such as, but not limited to, stabilizers, antimicrobial agents, antioxidants, pH modifiers, surfactants, bio-availability modifiers and combinations of these. A propellant for an aerosol formulation may include compressed air, nitrogen, carbon dioxide, or a hydrocarbon based low boiling solvent.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent.

Acceptable solvents or vehicles include sterilized water, Ringer's solution, or an isotonic aqueous saline solution. Alternatively, sterile oils may be employed as solvents or suspending agents. Preferably, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

For rectal administration, the pharmaceutical formulations and medicaments may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

The concentration of an antibody or an antigen binding fragment thereof in these compositions can vary widely, i.e., from less than about 10%, usually at least about 25% to as much as 75% or 90% by weight and will be selected primarily by fluid volumes, viscosities, etc., in accordance with the particular mode of administration selected. Actual methods for preparing orally, topically and parenterally administrable compositions will be known or apparent to those skilled in the art and are described in detail in, for example, Remington's Pharmaceutical Science, 19th ed., Mack Publishing Co., Easton, Pa. (1995), which is incorporated herein by reference.

In another embodiment of the invention, an article of manufacture containing materials useful for the treatment of the diseases, disorders or conditions described above is provided, including for treatment of cancer. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody of the invention. The label on or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use. Pharmaceutical compositions and medicaments described herein are useful in treating a cancerous disease.

Methods of Treatment

The disclosure provides methods for treatment or prevention of a cancer, including, but not limited to, neoplasms, tumors, metastases, or any disease or disorder characterized by uncontrolled cell growth, by the administration of an antibody or antigen binding fragment thereof disclosed herein, to a patient in an amount effective to treat the patient.

In some embodiments, the cancer can be a carcinoma, a sarcoma, a lymphoma, a leukemia, germ cell tumor, a blastoma, or a melanoma. In some embodiments, the cancer can be a cancer from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In some embodiments, the cancer may be a neoplasm, malignant carcinoma, carcinoma, undifferentiated, giant and spindle cell carcinoma, small cell carcinoma, papillary carcinoma, squamous cell carcinoma, lymphoepithelial carcinoma, basal cell carcinoma, pilomatrix carcinoma, transitional cell carcinoma, papillary transitional cell carcinoma, adenocarcinoma; gastrinoma, cholangiocarcinoma, hepatocellular carcinoma, combined hepatocellular carcinoma and cholangiocarcinoma, trabecular adenocarcinoma, adenoid cystic carcinoma, adenocarcinoma in adenomatous polyp, adenocarcinoma, Familial adenomatous polyposis, solid carcinoma, carcinoid tumor, branchiolo-alveolar adenocarcinoma, papillary adenocarcinoma, chromophobe carcinoma, acidophil carcinoma, oxyphilic adenocarcinoma, basophil carcinoma, clear cell adenocarcinoma, granular cell carcinoma, follicular adenocarcinoma, papillary and follicular adenocarcinoma, nonencapsulating sclerosing carcinoma, adrenal cortical carcinoma, endometroid carcinoma, skin appendage carcinoma, apocrine adenocarcinoma, sebaceous adenocarcinoma, ceruminous adenocarcinoma, mucoepidermoid carcinoma, cystadenocarcinoma, papillary cystadenocarcinoma, papillary serous cystadenocarcinoma, mucinous cystadenocarcinoma, mucinous adenocarcinoma, signet ring cell carcinoma, infiltrating duct carcinoma, medullary carcinoma, lobular carcinoma, inflammatory carcinoma, paget's disease, mammary acinar cell carcinoma, adenosquamous carcinoma, adenocarcinoma w/squamous metaplasia, thymoma, ovarian stromal tumor, thecoma, granulosa cell tumor, androblastoma, sertoli cell carcinoma, leydig cell tumor, lipid cell tumor, paraganglioma, extra-mammary paraganglioma, pheochromocytoma, glomangiosarcoma, melanoma, Lentigo maligna, Lentigo maligna melanoma, Acral lentiginous melanoma, mucosal melanoma, nodular melanoma, polyploid melanoma, desmoplastic melanoma, skin cutaneous melanoma, amelanotic melanoma, superficial spreading melanoma, melanoma in giant pigmented nevus, epithelioid cell melanoma, blue nevus, sarcoma, fibrosarcoma, fibrous histiocytoma, myxosarcoma, liposarcoma, leiomyosarcoma, rhabdomyosarcoma, embryonal rhabdomyosarcoma, alveolar rhabdomyosarcoma, stromal sarcoma, mixed tumor, mullerian mixed tumor, nephroblastoma, hepatoblastoma, carcinosarcoma, mesenchymoma, brenner tumor, phyllodes tumor, synovial sarcoma, mesothelioma, dysgerminoma, embryonal carcinoma, teratoma, struma ovarii, choriocarcinoma, mesonephroma, hemangiosarcoma, hemangioendothelioma, kaposi's sarcoma, hemangiopericytoma, lymphangiosarcoma, osteosarcoma, juxtacortical osteosarcoma, chondrosarcoma, chondroblastoma, mesenchymal chondrosarcoma, giant cell tumor of bone, ewing's sarcoma, odontogenic tumor, ameloblastic odontosarcoma, ameloblastoma, ameloblastic fibrosarcoma, pinealoma, chordoma glioma, ependymoma, astrocytoma, protoplasmic astrocytoma, fibrillary astrocytoma, astroblastoma, glioblastoma, oligodendroglioma, oligodendroblastoma, primitive neuroectodermal, cerebellar sarcoma, ganglioneuroblastoma, neuroblastoma, retinoblastoma, olfactory neurogenic tumor, meningioma, neurofibrosarcoma, neurilemmoma, granular cell tumor, malignant lymphoma, hodgkin's disease, hodgkin's, paragranuloma, lymphoma, small lymphocytic, malignant lymphoma, Diffuse large B-cell lymphoma, follicular lymphoma, mycosis fungoides, other specified non-hodgkin's lymphomas, histiocytosis, multiple myeloma, mast cell sarcoma, immunoproliferative small intestinal disease, leukemia, lymphoid leukemia, plasma cell leukemia, erythroleukemia, lymphosarcoma cell leukemia, myeloid leukemia, basophilic leukemia, eosinophilic leukemia, monocytic leukemia, mast cell leukemia, megakaryoblastic leukemia, myeloid sarcoma, or hairy cell leukemia. In some embodiments, the cancer is skin cancer. In some embodiments, the skin cancer is basal cell carcinoma, squamous cell carcinoma, cutaneous melanoma, merkel cell carcinoma, atypical fibroxanthoma, cutaneous lymphoma, or dermatofibrosarcoma. In some embodiments, the cutaneous melanoma is superficial spreading melanoma, nodular melanoma, acral lentiginous melanoma, subungual melanoma, lentigo maligna melanoma, desmoplastic melanoma, mucosal melanoma, or polyploid melanoma.

An antibody of the present disclosure may be administered to a subject per se or in the form of a pharmaceutical composition disclosed herein for the treatment or prevention of diseases, e.g., cancer. The antibodies or antigen binding fragment thereof or the compositions described herein may be administered alone or in combination a second therapeutic agent or therapy useful for treating cancer. Examples of second therapy useful for treating cancer can include, but not limited to radiotherapy, cryotherapy, antibody therapy, chemotherapy, photodynamic therapy, surgery, hormonal therapy, immunotherapy, cytokine therapy, or a combination therapy with conventional drugs. In some embodiments, a second therapeutic agent, can be a cytotoxic drug, tumor vaccine, a peptide, a pepti-body, a small molecule, a cytotoxic agent, a cytostatic agent, immunological modifier, interferon, interleukin, immunostimulatory growth hormone, cytokine, vitamin, mineral, aromatase inhibitor, RNAi, Histone Deacetylase Inhibitor, proteasome inhibitor, a cancer chemotherapeutic agent, Tregs targeting agent, another antibody, Immunostimulatory antibody, a NSAID, a corticosteroid, a dietary supplement such as an antioxidant, cisplatin, ifosfamide, paclitaxel, taxanes, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, and taxol. In some embodiments, the second therapeutic agent is a chemotherapeutic agent selected from a group consisting of platinum based compounds, antibiotics with anti-cancer activity, Anthracyclines, Anthracenediones, alkylating agents, antimetabolites, Antimitotic agents, Taxanes, Taxoids, microtubule inhibitors, Vinca alkaloids, Folate antagonists, Topoisomerase inhibitors, Antiestrogens, Antiandrogens, Aromatase inhibitors, GnRh analogs, and inhibitors of 5α-reductase, biphosphonates.

In some embodiments, the second therapeutic agent can be a PD-1 inhibitor, histone deacetylase (HDAC) inhibitor, proteasome inhibitor, mTOR pathway inhibitor, JAK2 inhibitor, tyrosine kinase inhibitor (TKIs), PI3K inhibitor, Protein kinase inhibitor, Inhibitor of serine/threonine kinases, inhibitor of intracellular signaling, inhibitors of Ras/Raf signaling, MEK inhibitor, AKT inhibitor, inhibitor of survival signaling proteins, cyclin dependent kinase inhibitor, therapeutic monoclonal antibodies, TRAIL pathway agonist, anti-angiogenic agent, metalloproteinase inhibitor, cathepsin inhibitor, inhibitor of urokinase plasminogen activator receptor function, immunoconjugate, antibody drug conjugate, antibody fragments bispecific antibodies, bispecific T cell engagers (BiTEs). In some embodiments, the another antibody is selected from cetuximab, panitumumab, nimotuzumab, trastuzumab, pertuzumab, rituximab, ofatumumab, veltuzumab, alemtuzumab, labetuzumab, adecatumumab, oregovomab, onartuzumab; apomab, mapatumumab, lexatumumab, conatumumab, tigatuzumab, catumaxomab, blinatumomab, ibritumomab triuxetan, tositumomab, brentuximab vedotin, gemtuzumab ozogamicin, clivatuzumab tetraxetan, pemtumomab, trastuzumab emtansine, bevacizumab, etaracizumab, volociximab, ramucirumab, aflibercept. In yet another embodiment, the second therapeutic agent can be antibodies currently used for the treatment of cancer. Examples of such antibodies include, but are not limited to, Herceptin®, Retuxan®, OvaRex, Panorex, BEC2, IMC-C225, Vitaxin, Campath I/H, Smart MI95, LymphoCide, Smart I D10, and Oncolym. In some embodiments, the another antibody is an immunostimulatory antibody is selected from antagonistic antibodies targeting one or more of CTLA4, PD-1, PDL-1, LAG-3, TIM-3, BTLA, B7-H4, B7-H3, VISTA, and/or Agonistic antibodies targeting one or more of CD40, CD137, OX40, GITR, CD27, CD28, ICOS or a combination thereof. In some embodiments, the second therapeutic agent targeting immunosuppressive cells Tregs and/or MDSCs is selected from antimitotic drugs, cyclophosphamide, gemcitabine, mitoxantrone, fludarabine, thalidomide, thalidomide derivatives, COX-2 inhibitors, depleting or killing antibodies that directly target Tregs through recognition of Treg cell surface receptors, anti-CD25 daclizumab, basiliximab, ligand-directed toxins, denileukin diftitox (Ontak)—a fusion protein of human IL-2 and diphtheria toxin, or LMB-2—a fusion between an scFv against CD25 and the *Pseudomonas* exotoxin, antibodies targeting Treg cell surface receptors, TLR modulators, agents that interfere with the adenosinergic pathway, ectonucleotidase inhibitors, or inhibitors of the A2A adenosine receptor, TGF-β inhibitors, chemokine receptor inhibitors, retinoic acid, all-trans retinoic acid (ATRA), Vitamin D3, phosphodiesterase 5 inhibitors, sildenafil, ROS inhibitors and nitroaspirin. In some embodiments, the second therapeutic agent is cytokine therapy selected from one or more of the following cytokines such as IL-2, IL-7, IL-12, IL-15, IL-17, IL-18 and IL-21, IL23, IL-27, GM-CSF, IFNα (interferon alpha), IFNα-2b, IFNβ, IFNγ, and their different strategies for delivery. In some embodiments, the second therapeutic agent is a therapeutic cancer vaccine selected from a group consisting of exogenous cancer vaccines including proteins or peptides used to mount an immunogenic response to a tumor antigen, recombinant virus and bacteria vectors encoding tumor antigens, DNA-based vaccines encoding tumor antigens, proteins targeted to dendritic cell-based vaccines, whole tumor cell vaccines, gene modified tumor cells expressing GM-CSF, ICOS and/or Flt3-ligand, oncolytic virus vaccines.

In some embodiments, the second therapeutic agent include EPO, G-CSF, ganciclovir; antibiotics, leuprolide; meperidine; zidovudine (AZT); interleukins 1 through 18, including mutants and analogues; interferons or cytokines, such as interferons a, ' and y hormones, such as luteinizing hormone releasing hormone (LHRH) and analogues and, gonadotropin releasing hormone (GnRH); growth factors, such as transforming growth factor, fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), and insulin growth factor (IGF); tumor necrosis factor-alpha (TNF-α); invasion inhibiting factor-2 (IIF-2); bone morphogenetic proteins 1-7 (BMP 1-7); somatostatin; thymosin-a-1; y-globulin; superoxide dismutase (SOD); complement factors; anti-angiogenesis factors; antigenic materials; and pro-drugs.

Prodrug refers to a precursor or derivative form of a pharmaceutically active substance that is less cytotoxic or non-cytotoxic to tumor cells compared to the parent drug and is capable of being enzymatically activated or converted into an active or the more active parent form. See, e.g., Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, lactam-containing prodrugs, optionally substituted phenoxyacetamide-containing prodrugs or optionally substituted phenylacetamide-containing prodrugs, 5-fluorocyto-sine and other 5-fluorouridine prodrugs which can be converted into the more active cytotoxic free drug. Examples of cytotoxic drugs that can be derivatized into a prodrug form for use herein include, but are not limited to, those chemotherapeutic agents described above.

In another embodiment, the antibodies or antigen binding fragment thereof disclosed herein are administered, for the prevention or treatment of cancer prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the second therapeutic agent. In another embodiment, the second therapeutic agent can be antibodies immunospecific for one or more cancer cell antigens. In some embodiments, the cancer is refractory to other anti-cancer treatments or a second therapeutic agent. In some embodiments, the cancer is in remission. In some embodiments, one or more antibodies disclosed herein or antigen binding fragments thereof are administered to an animal, preferably a mammal and most preferably a human. In some embodiments, the antibodies disclosed herein or antigen binding fragment thereof are administered after surgical resection of cancer. The method and compositions of the present disclosure contemplate single antibody or antigen binding fragment thereof, disclosed herein, as well as combinations, or "cocktails", of more than one antibody or antigen binding fragment thereof, disclosed herein. In some embodiments, more than one antibody comprises at least 2, at least 3, at least 4, all 5 antibodies or antigen binding fragment thereof, disclosed herein. Such antibody cocktails may have certain advantages inasmuch as they contain antibodies which exploit different effector mechanisms or combine directly cytotoxic antibodies with antibodies that rely on immune effector functionality.

Antibody Based Gene Therapy

In another aspect of the disclosure, nucleic acids molecules comprising sequences encoding antibodies or antigen binding fragment thereof, are administered to treat, inhibit or prevent a disease or disorder by way of gene therapy. In some embodiments, the disease is a cancer. In some embodiments, the disease is a skin cancer. In some embodiments, the disease is a skin cutaneous melanoma. In some embodiments, the disease is associated with aberrant expression and/or activity of an antigen that the antibody binds. Gene therapy refers to therapy performed by the administration to a subject of an expressed or expressible nucleic acid molecule. In this embodiment of the disclosure, the nucleic acid molecules produce their encoded protein (e.g., an antibody or antigen binding fragment disclosed herein) that mediates a therapeutic effect. Any of the methods for gene therapy available can be used according to the present invention. Exemplary methods are described below. For general reviews of the methods of gene therapy, see Goldspiel et al., Clinical Pharmacy 12:488-505 (1993); Wu and Wu, Biotherapy 3:87-95 (1991);

In a one aspect, the nucleic acid molecule comprising nucleic acid sequences encoding an antibody, said nucleic acid molecule being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific.

In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijistra et al., Nature 342:435-438 (1989). In some embodiments, the expressed antibody is a single chain antibody; alternatively, the nucleic acid sequences include sequences encoding both the heavy and light chains, or fragments thereof, of the antibody.

Delivery of the nucleic acid molecules into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid molecules are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijistra et al., Nature 342:435-438 (1989)).

In a specific embodiment, viral vectors that contain nucleic acid sequences encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid molecules encoding the antibody to be used in gene therapy are cloned into one or more vectors, which facilitates the delivery of the gene into a patient. More detail about retroviral vectors can be found in Boesen et al., Biotherapy 6:291-302 (1994).

Adenoviruses may also be used in the present invention. Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid molecule is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny. The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a one embodiment, the cell used for gene therapy is autologous to the patient. Nucleic acid sequences encoding an antibody of the present invention are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)).

Dosages

Provided herein are compositions comprising antibodies or antigen binding fragment thereof for treatment (including prevention) of cancer. In some embodiments, the compositions are pharmaceutical compositions comprising a pharmaceutically acceptable carrier. The compositions are administered in an amount effective for treatment (including prophylaxis) of cancer. In some embodiments, the compositions (e.g., the antibodies or the antigen binding fragment thereof or the nucleic acid molecules encoding said antibody or antigen binding fragment thereof) are administered in an amount effective for enhancing an immune response and/or increasing T cell activation in a subject. The compositions are to be used for in vivo administration to a subject by any available means, such as parenteral administration. For administration to a subject, a composition or medicament comprising the antibodies or antigen binding fragment thereof described herein can be sterile, which can readily accomplished by filtration through sterile filtration membranes, or other methods known to those of skill in the art. In one embodiment, a composition or medicament has been treated to be free of pyrogens or endotoxins. Testing pharmaceutical compositions or medicaments for pyrogens or endotoxins and preparing pharmaceutical compositions or medicaments free of pyrogens or endotoxins or preparing pharmaceutical compositions or medicaments that have endotoxins at a clinically-acceptable level, are well understood to one of ordinary skill in the art. Commercial kits are available to test pharmaceutical compositions or medicaments for pyrogens or endotoxins.

The compositions to be used for in vivo administration, such as parenteral administration, in the methods described herein can be sterile, which is readily accomplished by filtration through sterile filtration membranes, or other methods known to those of skill in the art.

The antibodies or antigen binding fragments thereof, describe herein, are formulated, dosed, and administered in a fashion consistent with good medical practice. Factors for consideration in this context include the particular disorder being treated, the particular subject being treated, the clinical condition of the individual subject, the cause of the disorder, the site of delivery of the agent, the method of administration, the scheduling of administration, and other factors known to medical practitioners. A "therapeutically effective amount" of a substance/molecule, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations. A therapeutically effective amount refers to an amount effective, at dosages and for periods of time necessary, to achieve the desired therapeutic and/or prophylactic result. The "therapeutically effective amount" to be administered will be governed by such considerations, and refers to the minimum amount necessary to ameliorate, treat, or stabilize, the cancer; to increase the time until progression (duration of progression free survival) or to treat or prevent the occurrence or recurrence of a tumor, a dormant tumor, or a micrometastases. The antibodies or antigen binding fragment thereof, disclosed herein, is optionally formulated with one or more additional therapeutic agents currently used to prevent or treat cancer or a risk of developing a cancer. The effective amount of such other agents depends on the amount of antibody or antigen binding fragment thereof present in the formulation, the type of disorder or treatment, and other factors discussed above. These are generally used in the same dosages and with administration routes as used herein before or about from 1 to 99% of the heretofore employed dosage.

The dose of antibody may vary depending upon the age and the size of a subject to be administered, target disease, conditions, route of administration, and the like. The preferred dose is typically calculated according to body weight or body surface area. When an antibody or antigen binding fragment thereof disclosed herein is used for treating a condition or disease in an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg, about 5 mg/kg, about 7.5 mg/kg, about 10 mg/kg, or about 15 mg/kg body weight. Depending on the severity of the condition, the frequency and the duration of the treatment can be adjusted. Effective dosages and schedules for administering may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351). In some embodiments, the compositions herein can comprise a prophylactically effective amount, eg., when administering to a subject at a risk of cancer or in earlier stages of a disease. A "prophylactically effective amount" refers to an amount effective, at dosages and for periods of time necessary, to achieve the desired prophylactic result. Typically, since a prophylactic dose is used in subjects prior to or at an earlier stage of disease, the prophylactic dose is lower than the therapeutic dose.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

The administration can be, for example, by one or more separate administrations, or by continuous infusion. For repeated administrations over several days or longer, depending on the condition, the treatment is sustained until, for example, the cancer is treated, as measured by the methods known in the art. However, other dosage regimens can be useful. In one non-limiting example, an antibody or antigen binding fragment thereof, disclosed herein is administered once every week, every two weeks, or every three weeks, at a dose range from about 5 mg/kg to about 15 mg/kg, including but not limited to 5 mg/kg, 7.5 mg/kg, 10 mg/kg or 15 mg/kg. The progress of using the methods described herein can be easily monitored by conventional techniques and assays. The duration of a therapy using the methods described herein will continue for as long as medically indicated or until a desired therapeutic effect (e.g., those described herein) is achieved. In certain embodiments, the administration of one or more antibodies or antigen binding fragment thereof, or compositions, described herein, is continued for 1 month, 2 months, 4 months, 6 months, 8 months, 10 months, 1 year, 2 years, 3 years, 4 years, 5 years, 10 years, 20 years, or for a period of years up to the lifetime of the subject.

Efficacy of Treatment

The efficacy of the treatment methods for cancer, comprising administering the antibodies or antigen binding fragment thereof, or pharmaceutical compositions of the present disclosure can be measured by various endpoints commonly used in evaluating cancer treatments, including but not limited to, tumor regression, tumor weight or size shrinkage, time to progression, duration of survival, progression free survival, overall response rate, duration of response, and quality of life. The antibodies or antigen binding fragments thereof disclosed herein can require unique measures and definitions of clinical responses to drugs. In the case of cancers, the therapeutically effective amount of the antibodies, antigen binding fragments thereof disclosed herein or compositions comprising the same can reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the antibodies or antigen binding fragment thereof, disclosed herein, act to prevent growth and/or kill existing cancer cells; it can be cytostatic and/or cytotoxic. For cancer therapy, efficacy in vivo can, for example, be measured by assessing the duration of survival, duration of progression free survival (PFS), the response rates (RR), duration of response, and/or quality of life.

In those embodiments related to the treatment or prevention of skin cancer (e.g., cutaneous melanoma). Symptoms of melanoma include but are not limited to changes to the shape or color of existing moles or, in the case of nodular melanoma, the appearance of a new lump anywhere on the skin. At later stages, the mole may itch, ulcerate or bleed. Early signs of melanoma are summarized by asymmetry, borders (irregular with edges and corners), color (variegated), diameter (greater than 6 mm (0.24 in), about the size of a pencil eraser), evolving over time, funny looking. Nodular melanoma, appears elevated above the skin surface, firm to the touch and growing. Metastatic melanoma may cause nonspecific paraneoplastic symptoms, including loss of appetite, nausea, vomiting and fatigue. Metastasis of early melanoma is possible, but relatively rare: less than a fifth of melanomas diagnosed early become metastatic. Brain metastases are particularly common in patients with metastatic melanoma. It can also spread to the liver, bones, abdomen or distant lymph nodes. In some embodiments, one or more symptoms of skin cancer (e.g., cutaneous melanoma) are inhibited or treated using the compositions and methods described herein.

In other embodiments, described herein are methods for increasing progression free survival of a human subject susceptible to or diagnosed with a cancer, for example, skin cancer, such as cutaneous melanoma. Time to disease progression is defined as the time from administration of the drug until disease progression or death. In a preferred embodiment, the combination treatment of the invention using an antibody or antigen binding fragment thereof, disclosed herein, and one or more chemotherapeutic agents may significantly increase progression free survival by at least about 1 month, 1.2 months, 2 months, 2.4 months, 2.9 months, 3.5 months, such as by about 1 to about 5 months, when compared to a treatment with chemotherapy alone. In another embodiment, the methods described herein may significantly increase response rates in a group of human subjects susceptible to or diagnosed with a cancer that are treated with various therapeutics. Response rate is defined as the percentage of treated subjects who responded to the treatment. In one embodiment, the combination treatment described herein using an antibody or antigen binding fragment thereof, disclosed herein, such as a recombinant antibody or antigen binding fragment thereof, and one or more chemotherapeutic agents significantly increases response rate in the treated subject group compared to the group treated with chemotherapy alone.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a chronic immune condition, such as, but not limited to, a chronic infection or a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

For example, in some embodiments, the methods described herein comprise administering an effective amount of the antibodies or antigen binding fragment thereof, described herein, to a subject in order to alleviate a symptom of a cancer. As used herein, "alleviating a symptom of a cancer" is ameliorating or reducing any condition or symptom associated with the cancer. As compared with an equivalent untreated control, such reduction or degree of prevention is at least 5%, 10%, 20%, 40%, 50%, 60%, 80%, 90%, 95%, or 100% as measured by any standard technique. Ideally, the cancer is completely cleared as detected by any standard method known in the art, in which case the cancer is considered to have been treated. A patient who is being treated for a cancer is one who a medical practitioner has diagnosed as having such a condition. Diagnosis can be by any suitable means. Diagnosis and monitoring can involve, for example, detecting the level of cancer cells in a biological sample (for example, a tissue or lymph node biopsy, blood test, or urine test), detecting the level of a surrogate marker of the cancer in a biological sample, detecting symptoms associated with the specific cancer, or detecting immune cells involved in the immune response typical of such a cancer.

The term "effective amount" as used herein refers to the amount of an antibody or antigen binding fragment thereof or composition comprising the same needed to alleviate at least one or more symptom of the disease or disorder, and relates to a sufficient amount of pharmacological composition to provide the desired effect. The term "therapeutically effective amount" therefore refers to an amount of an antibody or antigen binding fragment thereof disclosed herein, that is sufficient to effect a particular effect when administered to a typical subject. An effective amount as used herein would also include an amount sufficient to delay the development of a symptom of the disease, alter the course of a symptom disease (for example but not limited to, slow the progression of a symptom of the disease), or reverse a symptom of the disease. Thus, it is not possible to specify the exact "effective amount". For any given case, however, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dosage can vary depending upon the dosage form employed and the route of administration utilized. The dose ratio between toxic and therapeutic effects is the therapeutic index and can be expressed as the ratio $LD_{50}/ED_{50}$— Compositions and methods that exhibit large therapeutic indices are preferred. A therapeutically effective dose can be estimated initially from cell culture assays. Also, a dose can be formulated in animal models to achieve a circulating plasma concentration range that includes the $IC_{50}$ (i.e., the concentration of the antibody or antigen binding fragment thereof), which achieves a half-maximal inhibition of symptoms as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

The treatment and/or prevention of cancer includes, but is not limited to, alleviating symptoms associated with cancer, the inhibition of the progression of cancer, the promotion of the regression of cancer, the promotion of the immune response, inhibition of tumor growth, inhibition of tumor size, inhibition of metastasis, inhibition of cancer cell growth, inhibition of cancer cell proliferation, or cause cancer cell death.

Modes of Administration

The antibodies or antigen binding fragment thereof, described herein, can be administered to a subject in need thereof by any appropriate route which results in an effective treatment in the subject. As used herein, the terms "administering," and "introducing" are used interchangeably and refer to the placement of an antibody or antibody portion thereof into a subject by a method or route which results in at least partial localization of such agents at a desired site, such as a site of inflammation or cancer, such that a desired effect(s) is produced.

In some embodiments, the antibodies or antigen binding fragment thereof, described herein, or compositions comprising the same is administered to a subject having a cancer, to be inhibited by any mode of administration that delivers the agent systemically or to a desired surface or target, and can include, but is not limited to, injection, infusion, instillation, and inhalation administration. Oral administration forms are also contemplated herein. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intracranial, intraspinal, intracerebro spinal, and intrasternal injection and infusion.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of the bispecific or multispecific polypeptide agent other than directly into a target site, tissue, or organ, such as a tumor site, such that it enters the subject's circulatory system and, thus, is subject to metabolism and other like processes.

In some embodiments, the antibodies, or antigen binding fragment thereof, described herein, or compositions comprising the same can be administered via intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration, for example, to a tumor or cancer site where angiogenesis is occurring, is particularly desired if extensive side effects or toxicity is associated with the use of the antibodies, or antigen binding fragment thereof, described herein, or compositions comprising the same. An ex vivo strategy can also be used for therapeutic applications in some embodiments. Ex vivo strategies involve transfecting or transducing cells obtained from a subject with a nucleic acid sequence, disclosed herein. The transfected or transduced cells are then returned to the subject. The cells can be any of a wide range of types including, without limitation, hematopoietic cells (e.g., bone marrow cells, macrophages, monocytes, dendritic cells, T cells, or B cells), fibroblasts, epithelial cells, endothelial cells, keratinocytes, or muscle cells.

In some embodiments, an antibody or antigen binding fragment thereof, disclosed herein, or a composition comprising the same is administered by any suitable means, including parenteral, subcutaneous, intraperitoneal, intrapulmonary, and intranasal, and, if desired for local immunosuppressive treatment, intralesional administration.

Parenteral infusions include intramuscular, intravenous, intraarterial, intraperitoneal, or subcutaneous administration. In some embodiments, the antibody or antigen binding fragment thereof or compositions of the disclosure are suitably administered by pulse infusion, particularly with declining doses of the antibody. Preferably the dosing is given by injections, most preferably intravenous or subcutaneous injections, depending in part on whether the administration is brief or chronic. In some embodiments, the antibody or antigen binding fragment thereof or compositions of the disclosure are administered locally, e.g., by direct injections, when the disorder or location of the tumor permits, and the injections can be repeated periodically. In some embodiments, the antibody or antigen binding fragment thereof or compositions of the disclosure can also be delivered systemically to the subject or directly to the tumor cells, e.g., to a tumor or a tumor bed following surgical excision of the tumor, in order to prevent or reduce local recurrence or metastasis, for example of a dormant tumor or micrometastases.

Antibody-targeted sonoporation methods are contemplated for use in some embodiments of the methods for inhibiting tumors described herein, in order to enhance the efficacy and potency of the therapeutic compositions comprising antibodies and antigen binding fragment thereof provided herein. As used herein, "sonoporation" refers to the use of sound, preferably at ultrasonic frequencies, or the interaction of ultrasound with contrast agents (e.g., stabilized microbubbles) for temporarily modifying the permeability of cell plasma membranes, thus allowing uptake of large molecules, such as therapeutic agents. The membrane permeability caused by the sonoporation is transient, leaving the agents trapped inside the cell after the ultrasound exposure. Sonoporation employs acoustic cavitation of microbubbles to enhance delivery of large molecules.

Accordingly, in some embodiments of the methods, the antibody or antigen binding fragment thereof described herein, mixed with ultrasound contrast agents, such as microbubbles, can be injected locally or systemically into a subject in need of treatment for cancer, and ultrasound can be coupled and even focused into the defined area, e.g., tumor site, to achieve targeted delivery. In some embodiments, the methods use focused ultrasound methods to achieve targeted delivery. As used herein, HIFU or "High Intensity Focused Ultrasound" refers to a non-invasive therapeutic method using high-intensity ultrasound to heat and destroy malignant or pathogenic tissue without causing damage to overlying or surrounding health tissue. As described in Khaibullina et al., 49 J. Nucl. Med. 295 (2008), and WO 2010127369, HIFU can also be used as a means of delivery of therapeutic agents, such as antibodies or antibody fragments thereof.

Methods using contrast-enhanced ultrasound (CEUS) are also contemplated for use with an antibody or antigen binding fragment thereof, described herein. Contrast-enhanced ultrasound (CEUS) refers to the application of ultrasound contrast medium and ultrasound contrast agents to traditional medical sonography. Ultrasound contrast agents refer to agents that rely on the different ways in which sound waves are reflected from interfaces between substances. A variety of microbubble contrast agents are available for use with the compositions and methods described herein. Microbubbles can differ in their shell makeup, gas core makeup, and whether or not they are targeted. Targeting ligands that bind to receptors characteristic of angiogenic disorders, can be conjugated to microbubbles, enabling the microbubble complex to accumulate selectively in areas of interest, such as diseased or abnormal tissues. This form of molecular imaging, known as targeted contrast-enhanced ultrasound, will only generate a strong ultrasound signal if targeted microbubbles bind in the area of interest. Targeted contrast-enhanced ultrasound has many applications in both medical diagnostics and medical therapeutics. In some embodiments, an antibody or antigen binding fragment thereof, described herein, is administered to a subject in need of treatment for a cancer or a tumor, using a targeted ultrasound delivery.

Diagnostic and Other Uses

Provided herein are methods of using the antibodies for detection, diagnosis and monitoring of a disease, disorder or condition associated with the antigen expression (either increased or decreased relative to a normal sample, and/or inappropriate expression, such as presence of expression in tissues(s) and/or cell(s) that normally lack the epitope expression). Provided herein are methods of determining whether a patient will respond to antibody therapy.

In some embodiments, the method comprises detecting whether the patient has cells that express target antigen using an antibody disclosed herein. In some embodiments, the method of detection comprises contacting the sample with an antibody or antigen binding fragment thereof of the disclosure, and determining whether the level of binding differs from that of a reference or comparison sample (such as a control). In some embodiments, the method may be useful to determine whether the antibodies or polypeptides described herein are an appropriate treatment for the subject.

In some embodiments, the cells or cell/tissue lysate are contacted with an antibody and the binding between the antibody and the cell is determined. When the test cells show binding activity as compared to a reference cell of the same tissue type, it may indicate that the subject would benefit from treatment with an antibody. In some embodiments, the test cells are from human tissues. In some embodiments, the test cells are from human blood.

Various methods known in the art for detecting specific antibody-antigen binding can be used. Exemplary immunoassays which can be conducted include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected so as to meet the needs of various uses of the method which are often dictated by the availability of assay equipment and compatible immunoassay procedures.

Appropriate labels include, without limitation, radionuclides (for example 125I, 131I, 35S, 3H, or 32P), enzymes (for example, alkaline phosphatase, horseradish peroxidase, luciferase, or β-galactosidase), fluorescent moieties or proteins (for example, fluorescein, rhodamine, phycoerythrin, GFP, or BFP), or luminescent moieties (for example, Qdot™ nanoparticles supplied by the Quantum Dot Corporation, Palo Alto, Calif.). General techniques to be used in performing the various immunoassays noted above are known to those of ordinary skill in the art.

For purposes of diagnosis, the antibodies or antigen binding fragment thereof can be labeled with a detectable moiety including but not limited to radioisotopes, fluorescent labels, and various enzyme-substrate labels know in the art. Methods of conjugating labels to an antibody are known in the art.

In some embodiments, the antibodies need not be labeled, and the presence thereof can be detected using a second labeled antibody which binds to the first antibody. The antibodies or antigen binding fragment thereof of the present invention may be used as affinity purification agents for a cancer associated antigen or in diagnostic assays for a cancer associated antigen protein, e.g., detecting its expression in specific cells, tissues, or serum. The antibodies or antigen binding fragment thereof, disclosed herein, may also be used for in vivo diagnostic assays. Generally, for these purposes the antibody is labeled with a radionuclide (such as u1In, 99Tc, 14C, 131I, 12sI, 3H, 32p or 3sS) so that the tumor can be localized using immunoscintiography.

The antibodies of the present invention may be employed in any known assay method, such as competitive binding assays, direct and indirect sandwich assays, such as ELISAs, and immunoprecipitation assays. Zola, Monoclonal Antibodies: A Manual of Techniques, pp. 147-158 (CRC Press, Inc. 1987). The antibodies may also be used for immunohistochemistry, to label tumor samples using methods known in the art. As a matter of convenience, the antibody of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Kits

Provided herein are also kits, medicines, compositions, and unit dosage forms for use in any of the methods described herein. Provided herein is a kit comprising a therapeutically effective amount of at least one of the antibody or antigen binding fragment thereof disclosed herein. In some embodiments, the kit further comprises a second therapeutic agent (e.g., a chemotherapeutic agent). In some embodiments, the antibody or antigen binding fragment thereof is an aqueous form or a lyophilized form. The kit further comprises a diluent or a reconstitution solution.

Kits can include one or more containers comprising an antibody (or unit dosage forms and/or articles of manufacture). In some embodiments, a unit dosage is provided wherein the unit dosage contains a predetermined amount of a composition comprising an antibody (e.g., a therapeutically effective amount), with or without one or more additional agents. In some embodiments, such a unit dosage is supplied in single-use prefilled syringe for injection. In some embodiments, the composition comprising the antibody or antigen binding fragment thereof can comprise saline, sucrose, or the like; a buffer, such as phosphate, or the like; and/or be formulated within a stable and effective pH range. In some embodiments, the antibody or antigen binding fragment thereof can be provided as a lyophilized powder that may be reconstituted upon addition of an appropriate liquid, for example, sterile water. In some embodiments, the antibody or antigen binding fragment thereof further comprises one or more substances that inhibit protein aggregation, including, but not limited to, sucrose and arginine. In some embodiments, the antibody or antigen binding fragment thereof further comprises heparin and/or a proteoglycan.

In some embodiments, kits further comprise instructions for use in the treatment of cancer in accordance with any of the methods described herein. The kit may further comprise a description of selection an individual suitable or treatment. Instructions supplied in the kits are typically written instructions on a label or package insert (for example, a paper sheet included in the kit), but machine-readable instructions (for example, instructions carried on a magnetic or optical storage disk) are also acceptable. In some embodiments, the kit further comprises another therapeutic agent (e.g., an anti-cancer antibody or a chemotherapeutic agent)

The kits are in suitable packaging. Suitable packaging includes, but is not limited to, vials, bottles, jars, flexible packaging (for example, sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

EXAMPLES

Provided below are exemplary methods for in silico reconstruction of consensus sequences of cancer associated antibodies. Also described herein are computational analytical approaches for estimation of immunoglobulin repertoire diversity and the identification of clonal rearranged immunoglobulin CDR3 sequences present in the repertoire. The approaches are contemplated for the reconstruction of complete consensus sequences of the variable heavy chain, variable light chain and the respective CDR3 of said immunoglobulins.

Example 1: Estimation of the Immunoglobulin Repertoire Diversity

RNA-seq FASTQ files for 473 TCGA Skin Cutaneous Melanoma (SKCM) patients collected by TCGA consortium (The Cancer Genome Atlas, NCI & NHGRI) were recorded and analysed. RNA-seq samples (n=473) were aligned to reference V, D and J genes of immunoglobulins in order to identify the repertoire present in the samples. Then, identical CDR3 sequences were identified and grouped in clonotypes. The information was exported into a tab-delimited and understandable text file (FIG. 1). From the initial 473 samples, 178 samples were eliminated for which there were no reads aligning to immunoglobulin heavy chain genes or the number of reads was lower than the downsampling threshold and an additional 25 samples corresponding to lymph nodes. In total, the information on immunoglobulin (Ig) diversity from 270 melanoma samples was collected and analysed.

VDJtools were used to filter out non-functional (non-coding) clonotypes and to compute basic diversity statistics. Non-functional clonotypes were identified as those containing a stop codon or frameshift in their receptor sequence. The diversity of the Ig repertoire was based on the effective number of species which is calculated as the exponent of the Shannon-Wiener Entropy index such that a community of S species with species frequencies p1, ... pi, ... ps, then the diversity (D) is the exponent of the Shannon-Wiener Entropy index (H) given by:

$$D = \exp(H) = \exp\left(-\sum_{i=1}^{S} p_i \ln p_i\right). \quad \text{Equation 1}$$

Figure 2:
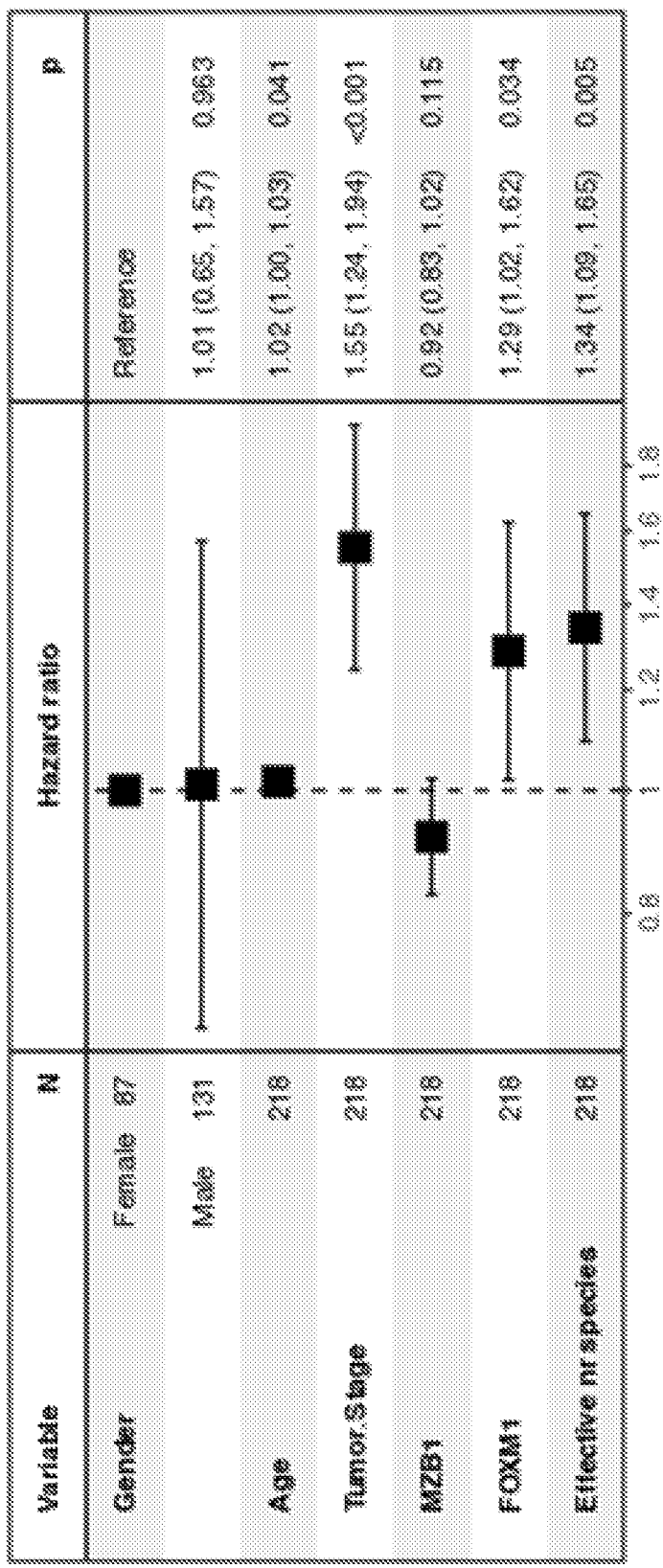
FIG. 2 demonstrates Multivariate Cox proportional hazards regression analysis for the TCGA-SKCM cohort, with covariates including patient gender, age at diagnosis, tumor stage (TMN system) and the expression of MZB1 and FOXM1 genes. Squares represent the hazard ratio (HR) and the horizontal bars extend from the lower limit to the upper limit of the 95% confidence interval of the estimate of the hazard ratio. The plot also shows the number of considered events (N) and Wald test p-values (p) for the interaction between survival and any covariate.
Figure 3A:
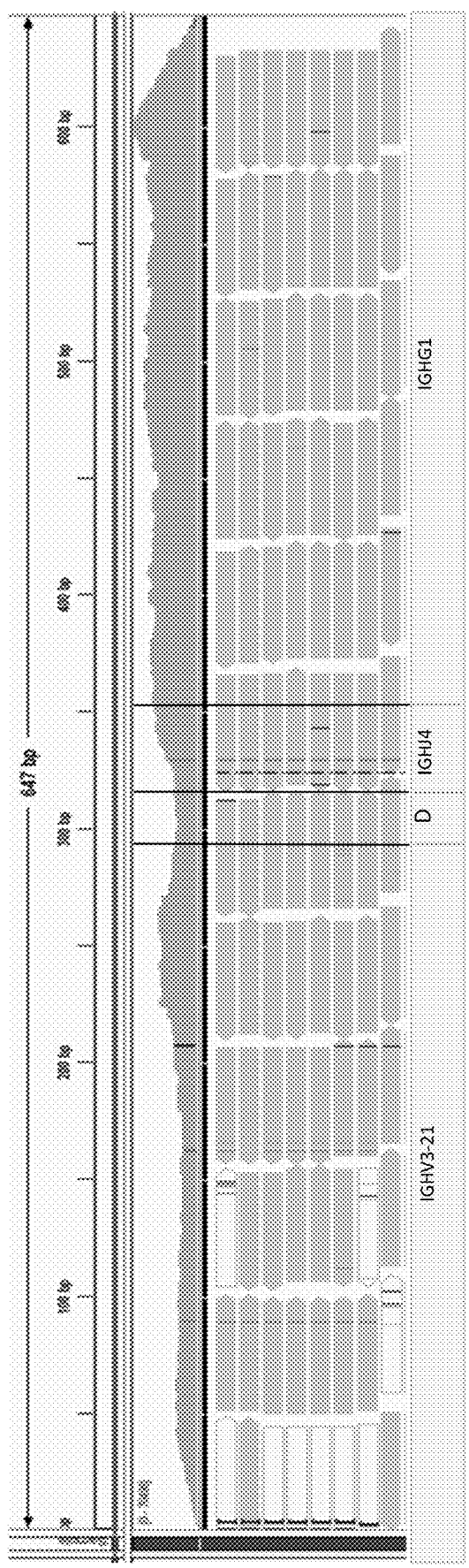
Figure 3B:
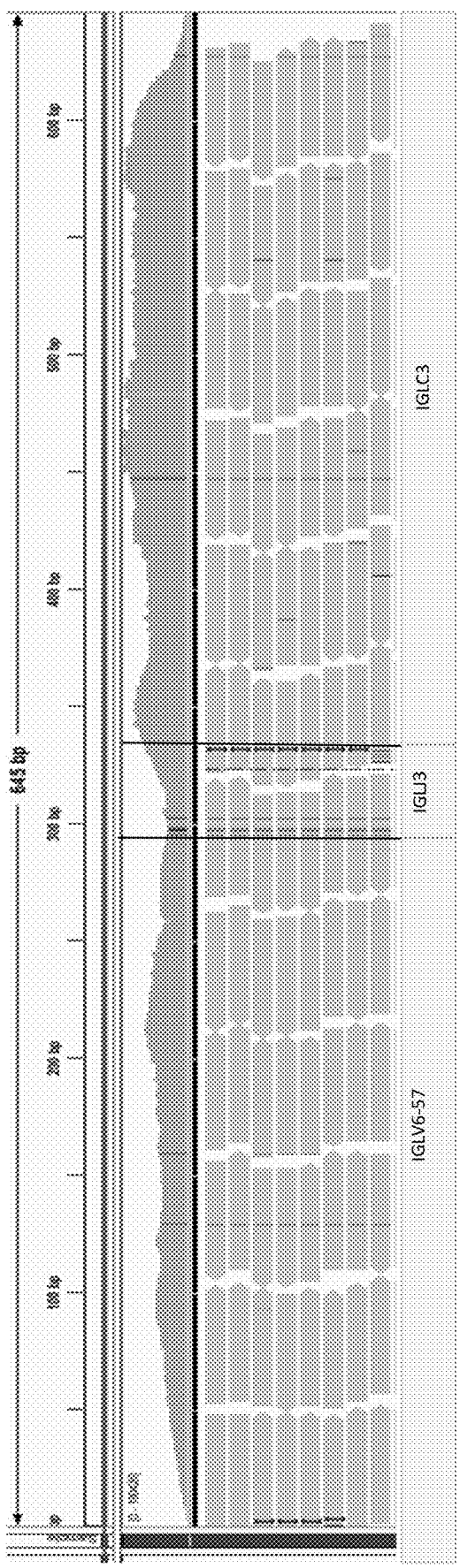
Figure 3C:
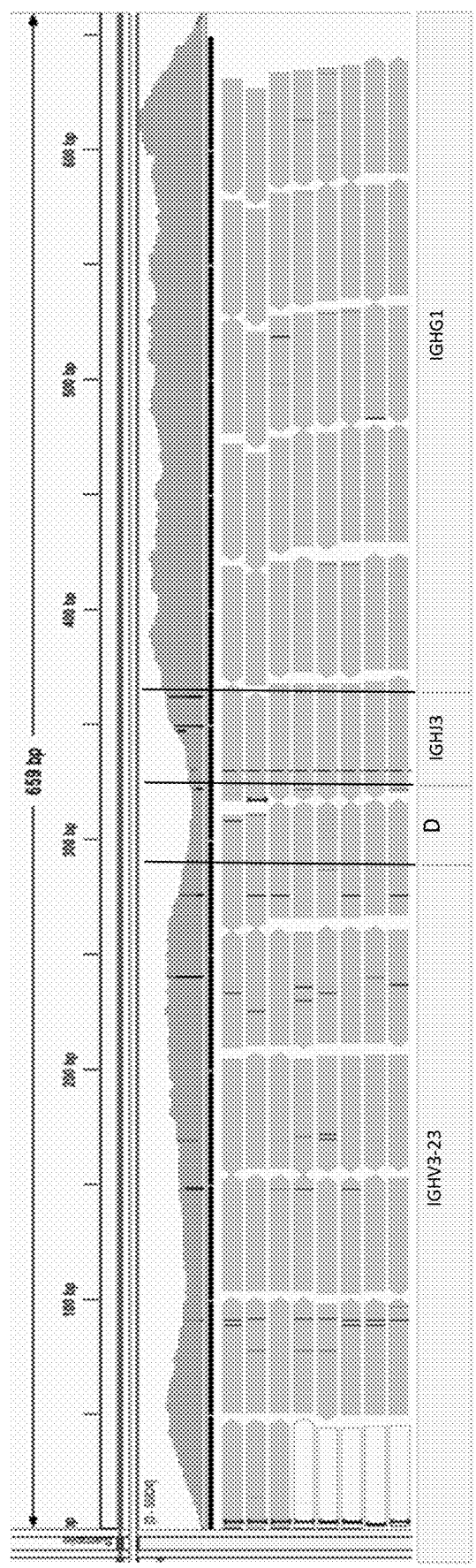
Figure 3D:
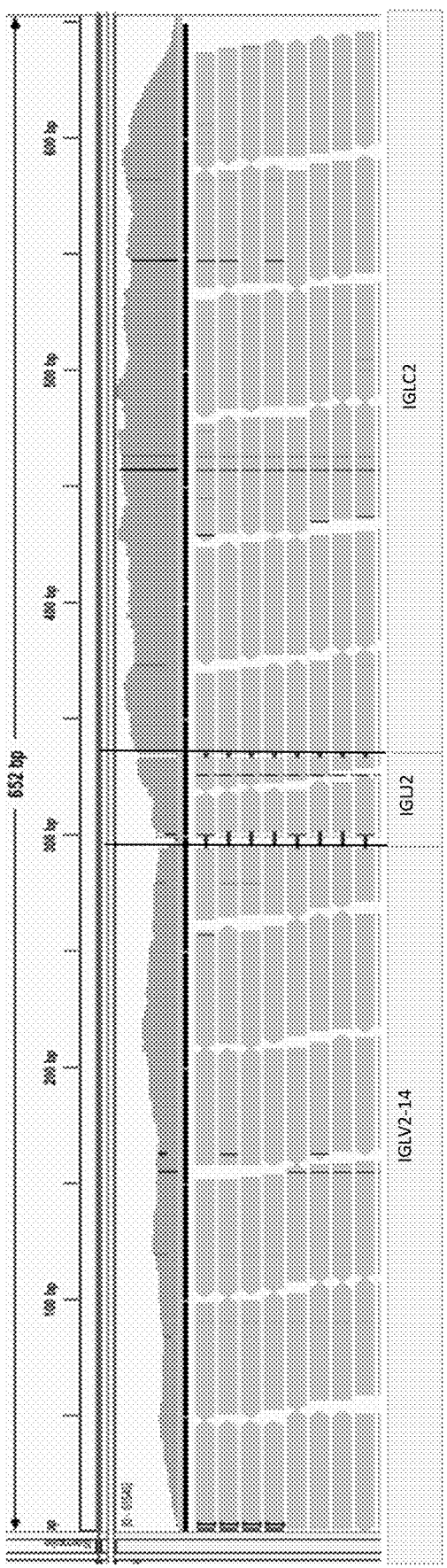
Figure 3E:
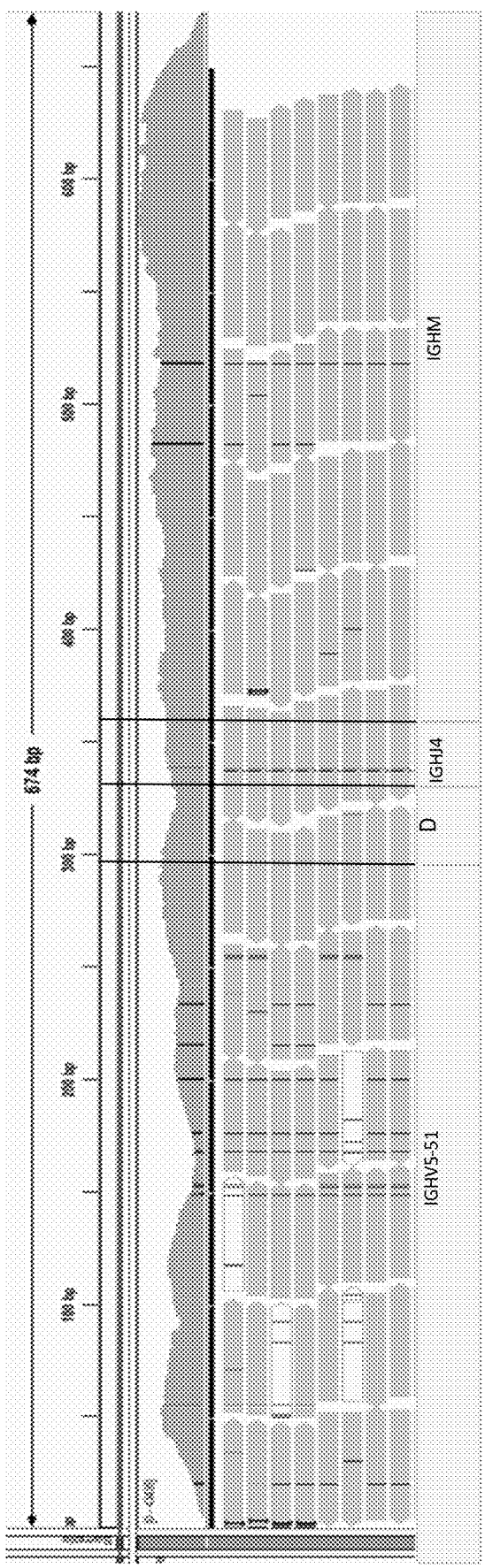
Figure 3F:
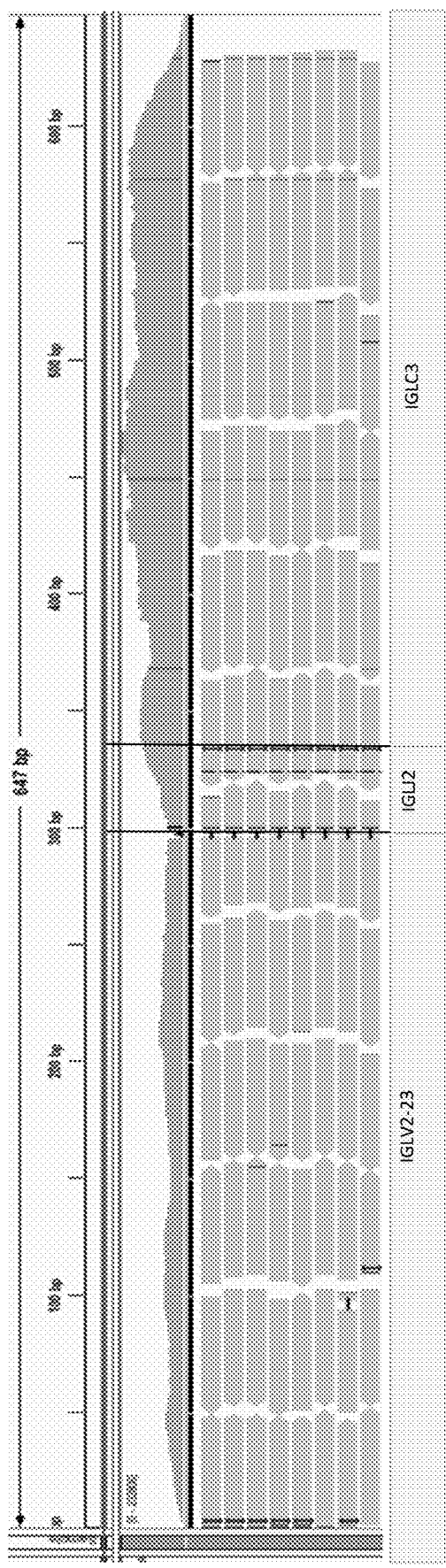
Figure 3G:
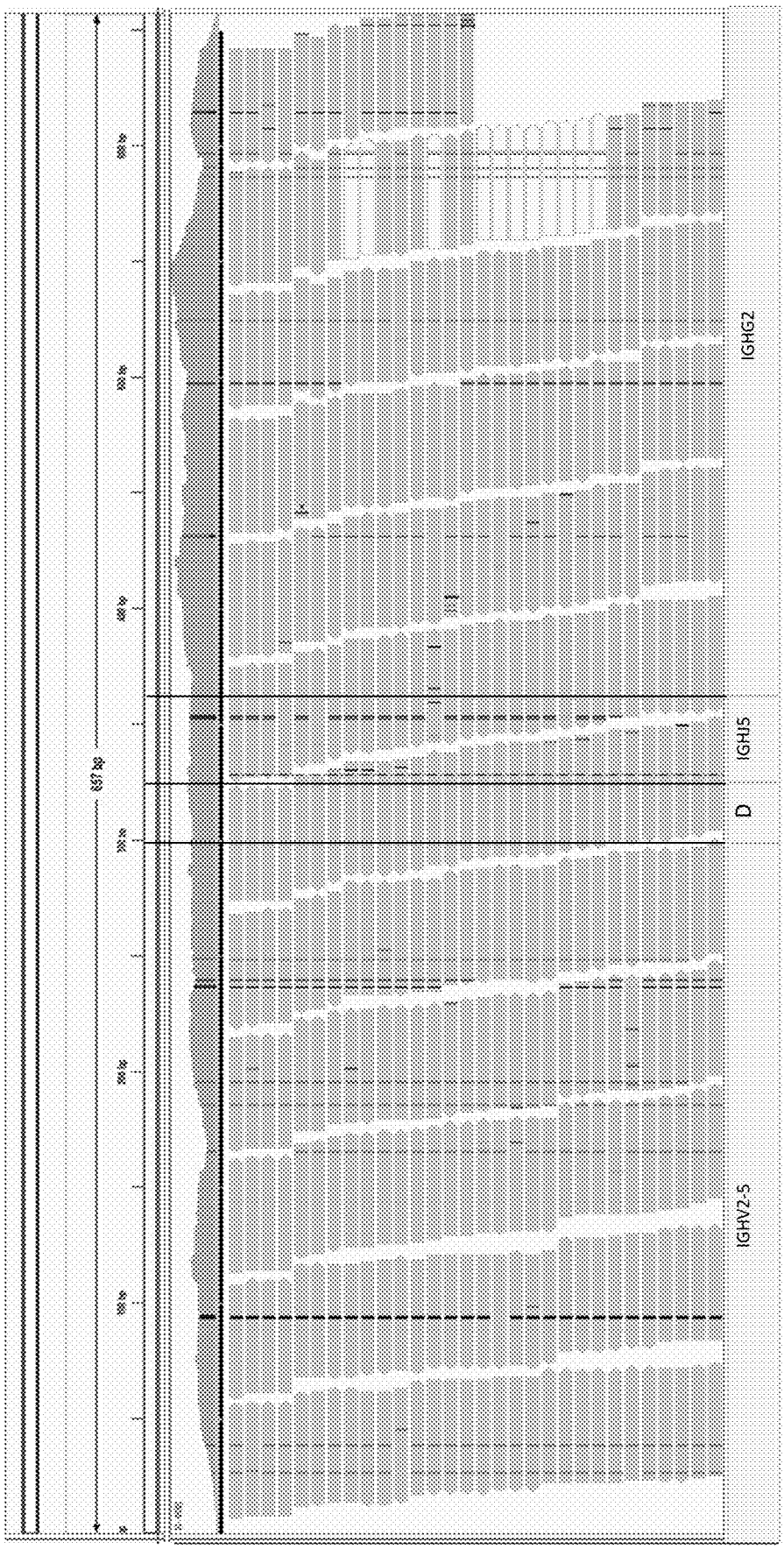
Figure 3H:
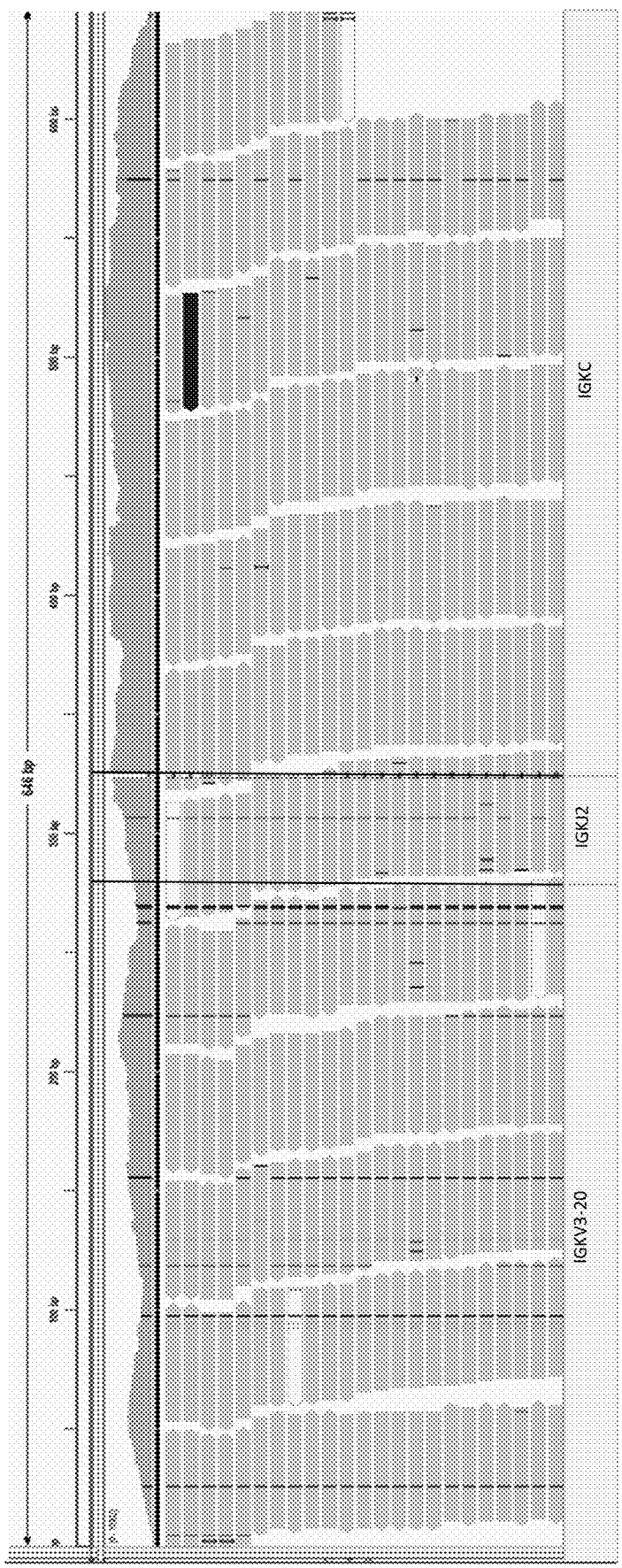
Figure 31:
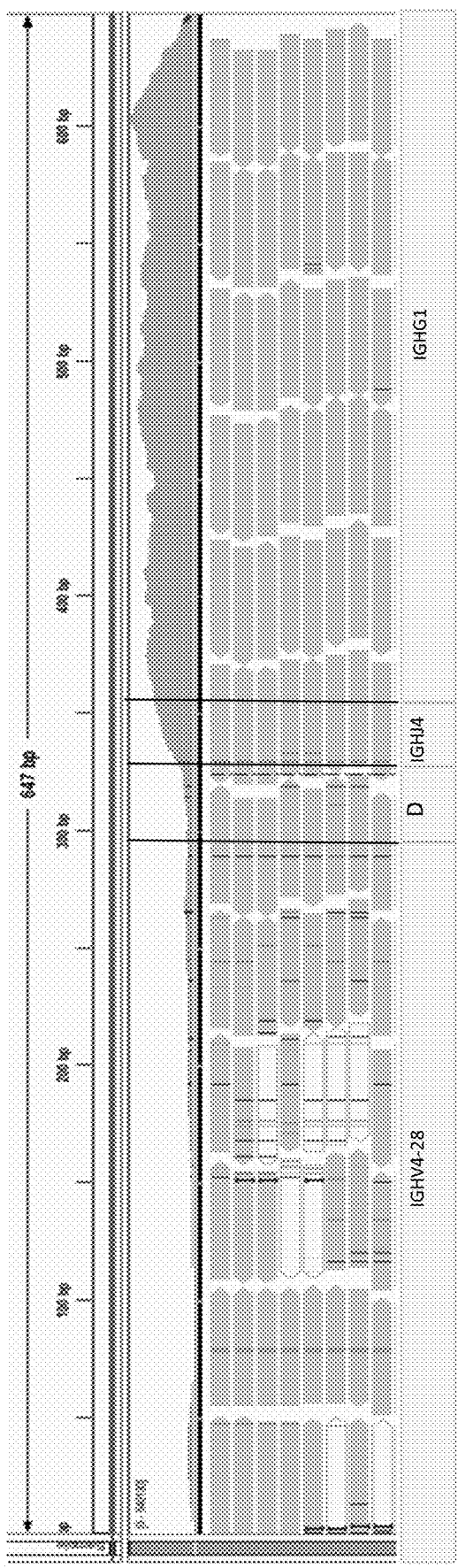
Figure 3J:
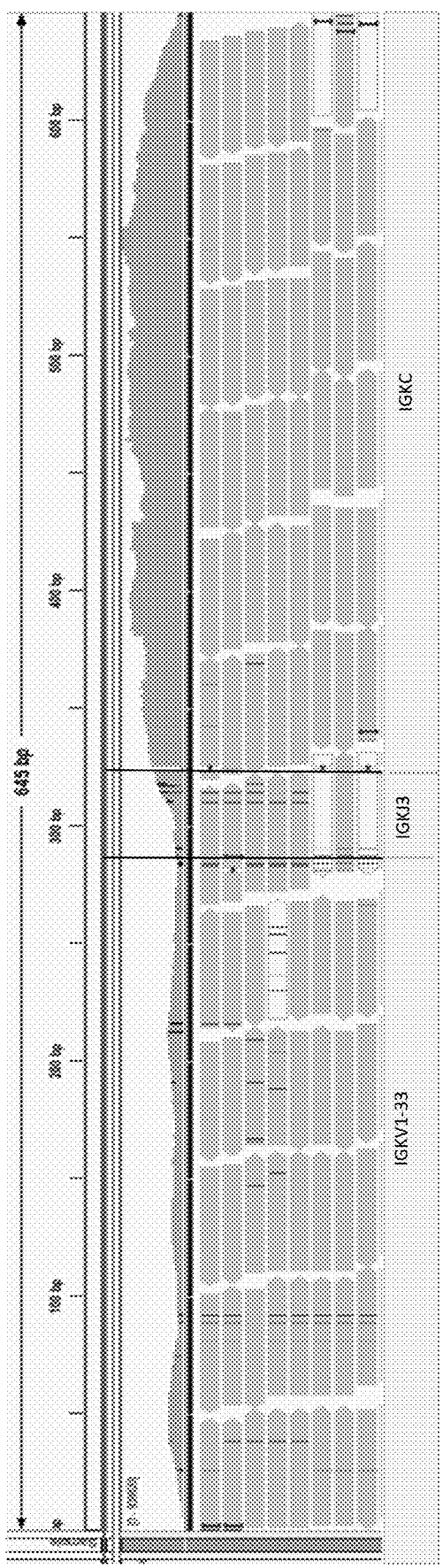

The R software was used on the files obtained from the first alignment step to analyse the relationship between diversity of CDR3 sequences and patients' overall survival. Out of the 270 samples, 50 had no information about the tumour stage and 2 had no information on survival time. Multivariable Cox regression was performed to investigate whether immunoglobulin repertoire diversity was correlated to disease survival, using age, gender, tumor stage, and expression of MZB1 and FOXM1 genes as covariates. A P-value less than 0.05 was set as the significant difference for all the Cox regression analyses (FIG. 2).

Example 2: Identification of Clonal Immunoglobulin Sequences

The top 50 patients (highly clonal patients) were chosen to investigate their immunoglobulin sequences in more detail. Manual curation of immunoglobulin predictions and corresponding read alignments led to the selection of 14 patients for further alignment investigation. The Table 8 below shows the clinical and clonality information for selected patients:

TABLE 8

| sample_id | OS survival time (months) | Status | Eff nr species |
|---|---|---|---|
| 1 | 20.76 | alive | 1.551084969 |
| 2 | 111.01 | dead | 1.827143864 |
| 3 | 180.26 | alive | 2.004177897 |
| 4 | 170.07 | alive | 2.044512649 |
| 5 | 62.02 | alive | 2.26857309 |
| 6 | 148.92 | alive | 5.616622449 |
| 7 | 176.41 | dead | 6.172934019 |
| 8 | 19.38 | alive | 6.880520052 |
| 9 | 92.9 | alive | 7.563366072 |
| 10 | 133.71 | alive | 7.834202032 |
| 11 | 135.64 | alive | 8.488138592 |
| 12 | 241.2 | alive | 9.05109639 |
| 13 | 160.87 | alive | 9.384014312 |
| 14 | 21.19 | alive | 10.11978853 |

Example 3: Alignment and Assembly of V D J Sequences

Alignments were performed against the immunoglobulin segments identified by the first alignment step for viewing the results, allowing the exploration of the frequency distribution of sequence mismatches along the V, D, J gene segments and in particular in the CDR3 region length statistics. This alignment step was useful for summarizing repertoires, as well as offering a detailed view of rearrangements and region alignments for individual query sequences. More details about the alignment and assembly methodology are given in the Example 5 below.

In brief, the identified segments by first alignment step from IMGT were first provided using the reference files provided in the BraCeR tool. The heavy D segment and light V-J junction sequences were then reconstructed using an in-house built assembler (see Example 5 for detailed description). A FASTA file with corrected heavy D and light V-J junction sequences was generated for each sample. In addition to the assembled FASTA files germline FASTA files using IgBLAST v1.9.0 and IMGT database were also generated. The somatic FASTA sequence was inputted to IgBLAST and to obtain the closest segment ids for the heavy and light chain. Then, the germline FASTA were generated by merging corresponding segment sequences from the IMGT database. The final assembled FASTA sequences served as 'reference' sequences for the alignment and visualisation steps described below. All final 'reconstructed' nucleotide and amino acid consensus sequences are provided herein (Tables 1-4).

Quality-Control and Visual Confirmation of Alignments

Using the reference files generated from the assembly step, the FASTQs were aligned in BowTie2 default mode. The output BAM file can be used for IGV visualization and mutations in the patient can be observed.

Example alignments and corresponding hypermutations using BowTie2 with default parameters for 4 exemplary patients are shown in FIG. 3A-3J. The D segments of the heavy chain was identified using a custom local assembly tool and edited the corresponding part of the FASTA file, therefore, no mutations are shown in D segments of IGV plots.

Example 4: Identification of Rearranged Immunoglobulin CDR3 Amino Acid Sequences The identification of the CDR3 region and corresponding V, D, and J chains from the final assembled FASTA sequences was achieved with IgBLAST. The standardized output using version v.1.9.0 of IgBLAST was delivered by wrapping IgBLASTn with default parameters. The output from the IgBLAST service is extracted using a purpose-built parser tool designed to extract the CDR1, CDR2 and CDR3 nucleotide and amino acid sequences. Summary of identified nucleotide and amino acid consensus sequences for CDR3 for the selected tumor samples are provided herein (e.g., Table 2 and Table 4).

Example 5: VDJ Sequence Identification Workflow

Figure 4:
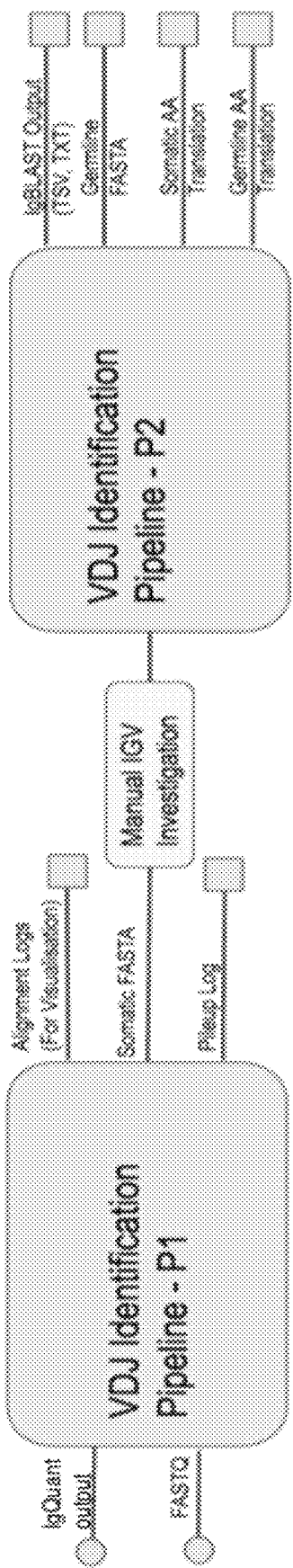
FIG. 4 depicts an exemplary schema of VDJ identification pipeline.

VDJ Sequence identification workflow was used to determine somatic and germline sequences of given patient and information such as CDR regions and mutation rates. The exemplary pipeline comprised of 3 steps (FIG. 4):
1. Somatic Sequence identification
2. Manual IGV investigation and (if necessary) correction of somatic vdj sequence
3. Germline Sequence and CDR regions identification The workflow accepted 2 inputs for each target patient: (1) the TCGA Archive File: TCGA archive file of the patient. Prefixes of all output files were determined based on metadata (i.e. aliquot id) of patients' archive file; and (2) the preliminary alignment Output File: IG clones output of preliminary alignment were used to obtain initial segment id predictions. This text file included both heavy and light chain results.

By completing all three steps of the pipeline, the following output files were obtained:
Somatic Sequence: A FASTA file for a given patient's identified VDJ sequence
Germline Sequence: A FASTA file for a given patient's predicted germline sequence using the IMGT database.
The amino acid translation of Somatic and Germline FASTA files
IgBLAST output log for somatic FASTA file: Contains CDR regions
Alignment Logs: Visual text representation of the heavy D region and light V-J junction of somatic sequence (For validation purpose).
Pileup logs: Contains somatic mutation rate of segments and V-C segment coverage ratio of heavy and light chain which we use as an internal quality control metric.

Step 1: Somatic Sequence Identification

Figure 5:
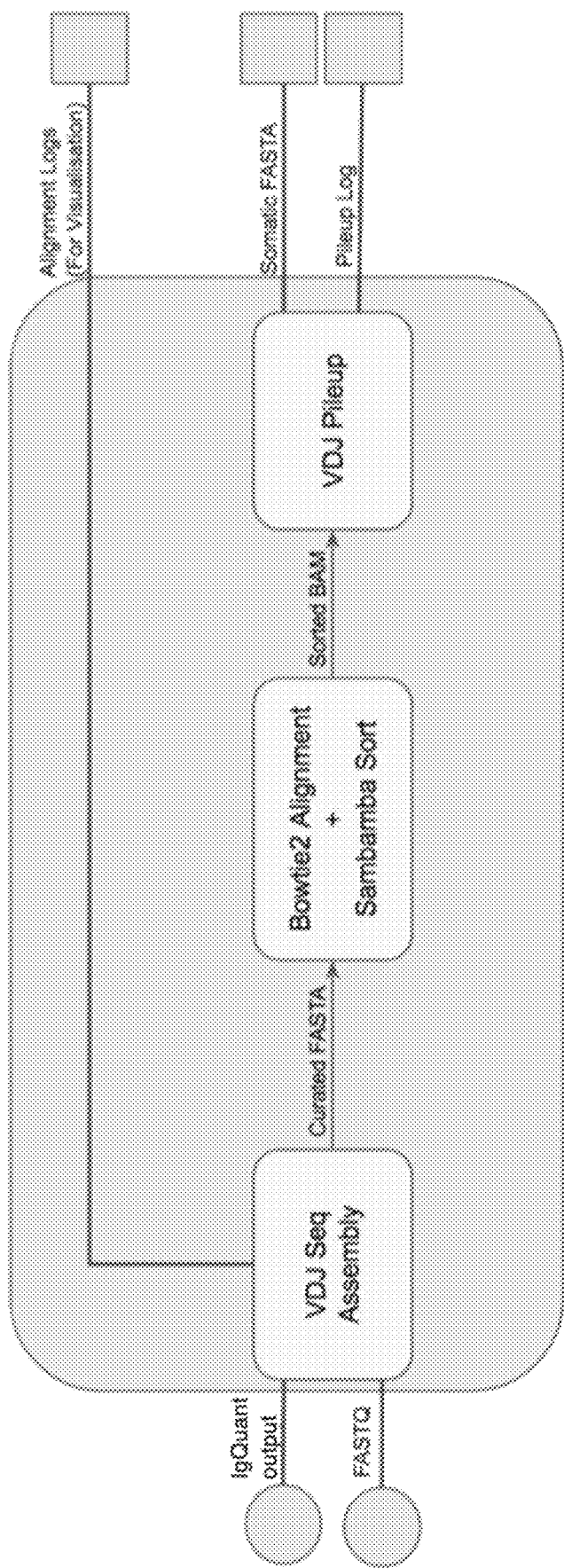
FIG. 5 shows a detailed schema of Somatic VDJ sequence identification.

The first step of the VDJ sequence identification workflow was the somatic sequence identification. For this purpose, two input were initially taken, which were the IG segments id identified during the first alignment step and the FASTQ file of the patient. Somatic sequence identification was performed in 3 substages (FIG. 5):

The Assembly Stage

During the preliminary alignment step, the vdjc segment ids were identified for both heavy and light chain. Then with use of the segment ids and IMGT database, the heavy and light chain sequences were generated by appending segment sequences to form V(D)JC structure.

Figure 6A:
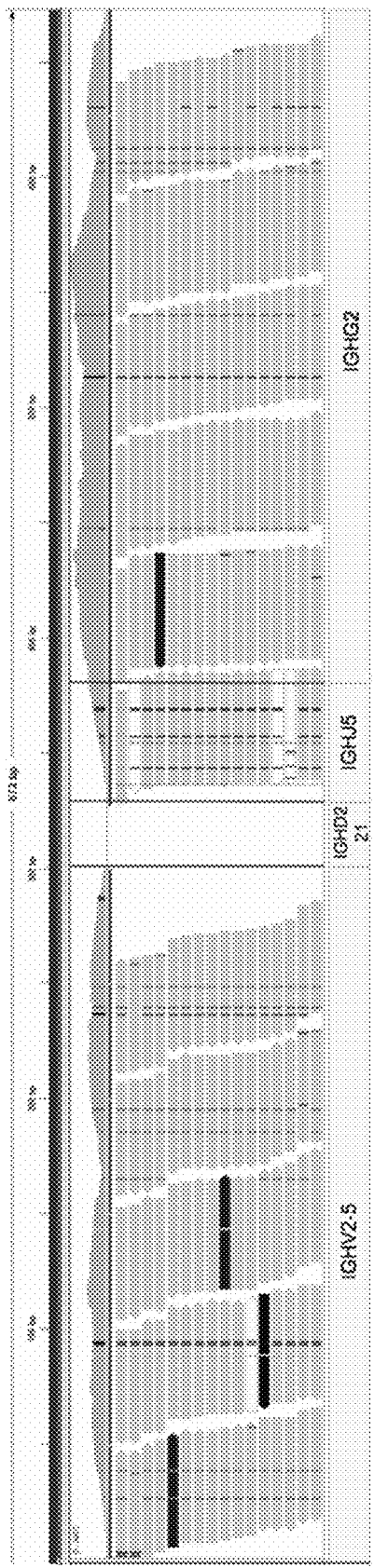
FIG. 6A shows heavy chain and FIG. 6B shows light chain refined alignment for selected patient compared to the initial alignment. Sudden coverage drop can be observed at D segment of heavy chain and the V-J junction of the light chain.
Figure 6B:
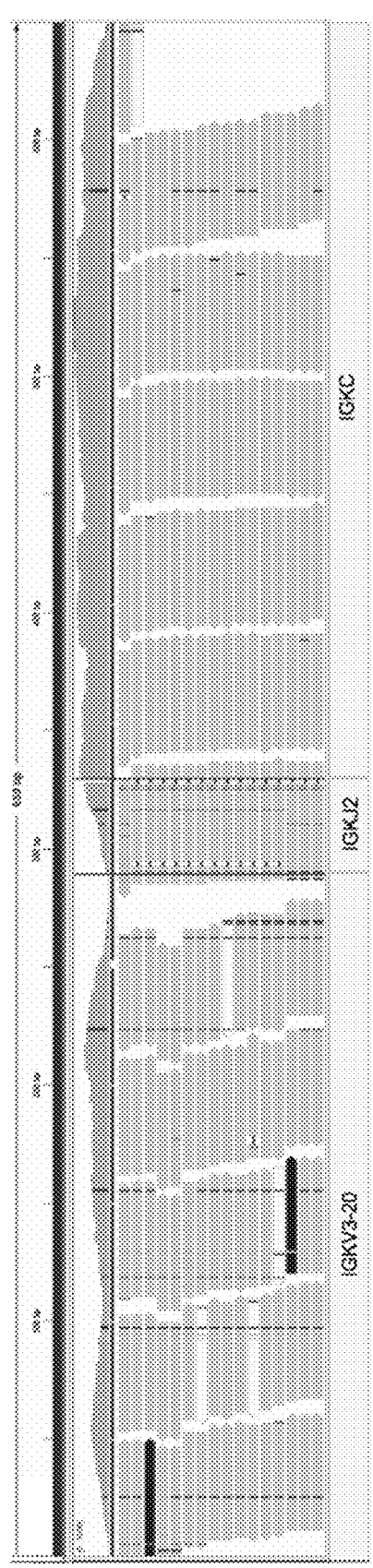

When the FASTQ of a patient was aligned with the reference FASTA generated by the first alignment step, it was often observed that D segment of the heavy chain (FIG. 6A) and V-J junction of the light chain (FIG. 6B) did not properly align. One reason of observing a low coverage in these areas could be the high mutation rate of antibody construction. Somatic mutations in these two regions are high enough that during the alignment against IMGT reference, many reads were eliminated. In addition, sizes of the reads were typically small for TCGA patients (ie. 50 bp for Melanoma dataset) which was harder to align to difficult (mutated) regions.

In order to identify the correct sequence in heavy D and light V-J junction, a custom assembly based algorithm was implemented. From the VDJ segments identified during the first alignment step, a 22 bp seed sequence was selected from the ending of V segments. From the end of V segment, the read length was read backwards. From that index, the next 22 bp was selected as the initial seed.

Once the seed sequence was selected, the FASTQ file was searched for the reads that contain this seed sequence. Since somatic mutations could occur, a fuzzy pattern searching algorithm was used (i.e. bitap algorithm) by allowing matches up to 4 edit distance penalty.

After the reads were selected in the first iteration, the unrelated ones were eliminated by comparing the whole read with V segment. The match ratio was checked of the intersection of reads and the V segment identified during the first alignment step. If the match ratio is less than 0.84, then the read was removed. Once the unrelated reads were removed, the reads were sorted descending by their match ratios and selected the first half of reads for pile up processing.

Using the selected reads, the bases were piled up and formed a single sequence. From the generated sequence, another 22 bp seed was selected and started a new iteration. For the following iterations, the maximum edit distance penalty was decreased to 1 and a read elimination was not performed in contrast to the first iteration. The iteration continued until a long enough final assembled sequence that covers more than half of the J segment was obtained (FIG. 7).

Once the assembled Heavy D region and Light V-J junction were obtained, the corresponding part of the reference was edited and produced an intermediate FASTA file for the alignment stage.

b. Alignment Stage

Figure 8:
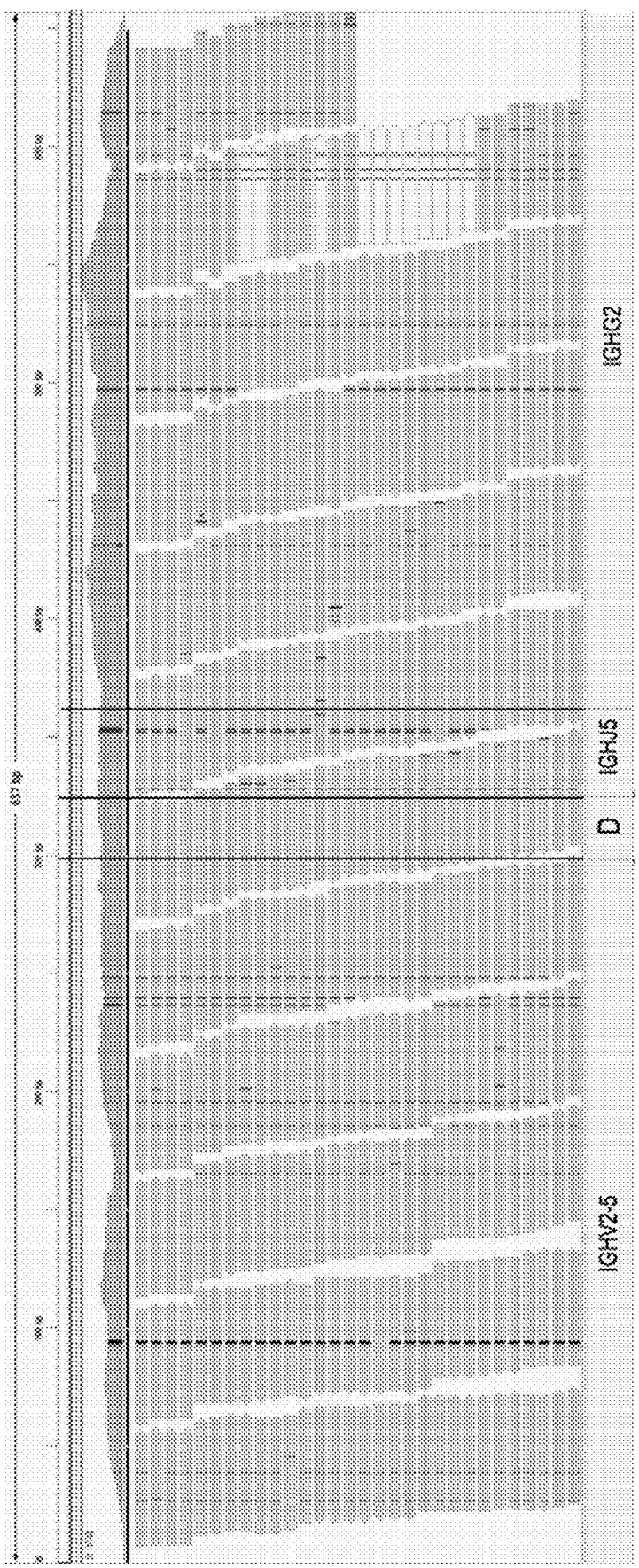
FIG. 8 shows an IGV plot of heavy chain with a corrected D segment after the alignment stage.

After the difficult regions (i.e. heavy D and light V-J junction) were identified using a custom assembly method, the aim was to correct the remaining variants (i.e. variants seen in FIG. 8) by using a standard variant calling pipeline which involved aligning reads followed by variant calling operation. For this purpose, BowTie22.2.6 with default parameters was used. To decrease the size of the output BAM file, the unaligned reads were discarded from the BAM file. After that, Sambamba 0.5.9 was used to sort the output BAM file.

c. Pileup Stage

In the third stage, rather than using a variant caller, the BAM file was used from the alignment stage do a pile-up processing to identify and correct variants in the reference file. For each position in the alignment, SNPs and INDELs were checked. Reads less than 20 quality threshold were ignored. In order to identify a variant in a specific position, 0.5 as the minimum ratio was applied, which meant that at least half of the total reads should contained that variant for the position. The variants in positions were also ignored where the total coverage is less than 200 reads. It was mostly observed that low coverage value in the first few base pairs of V segments and at the ending few base pairs of C segment.

Mutation Rate Calculation

Once a final sequence was obtained, the sequence was compared with the initial reference file which the BAM file was generated from. The mutation rate was calculated as the Levenshtein Distance between segments divided by the Alignment Length of segments (i.e. Python Levenshtein.ratio (seq1, seq2)).

Coverage Ratio Between V and C Segments

The average coverage was checked between V and C segments of both chains as an internal quality control step to ensure that the patient was high clonal. In the pileup log file, if the coverage ratio was over 0.3 then this suggested high clonality. A high V/C ratio might not always mean that the patient is highly clonal. However, a low V/C ratio could be a strong sign for low clonality.

Step 2: Manual IGV Inspection & Somatic Sequence Correction

Once the somatic FASTA files were obtained through step 1, the FASTA file was manually inspected using IGV browser. The IGV browser was check on whether it showed a variant in our somatic reference file. Bases were mostly corrected which were previously skipped due to the low number of reads in pileup stage of step 1.

Step 3: Germline Sequence and CDR Regions Identification

Figure 9:
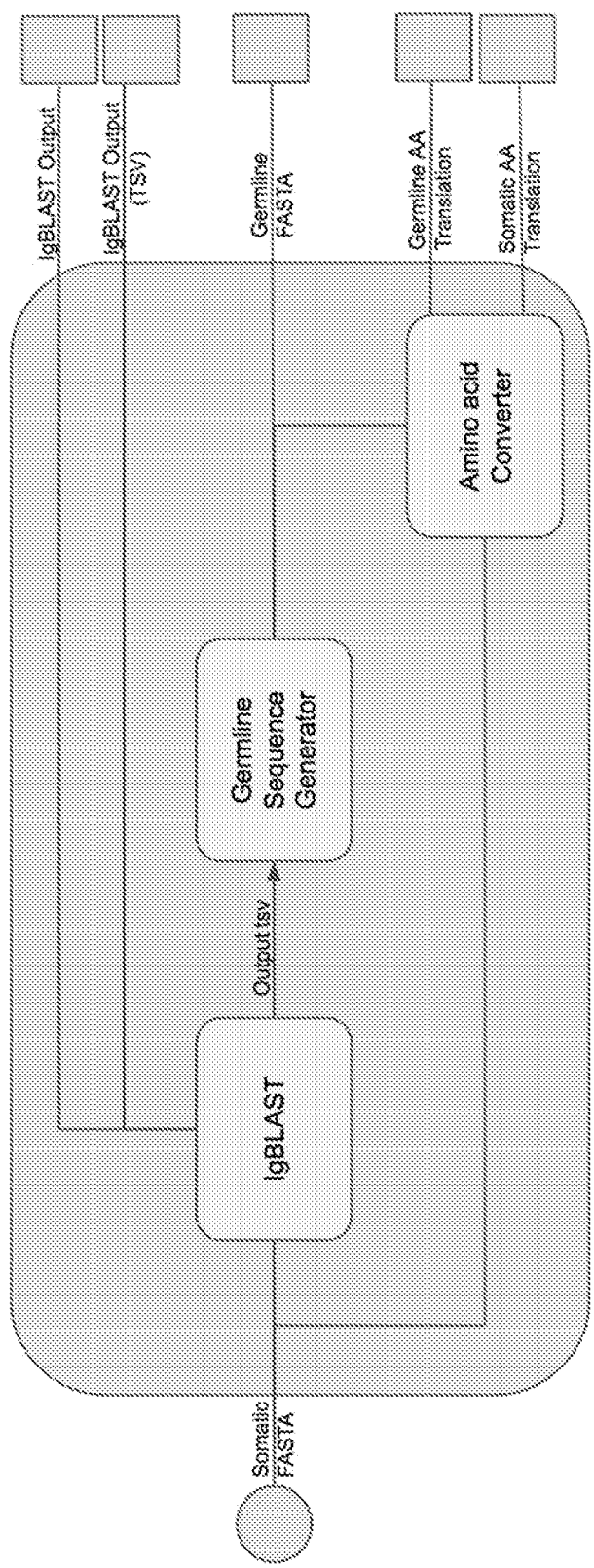
FIG. 9 illustrates a detailed schema of Germline and CDR sequence identification.
Figure 11:
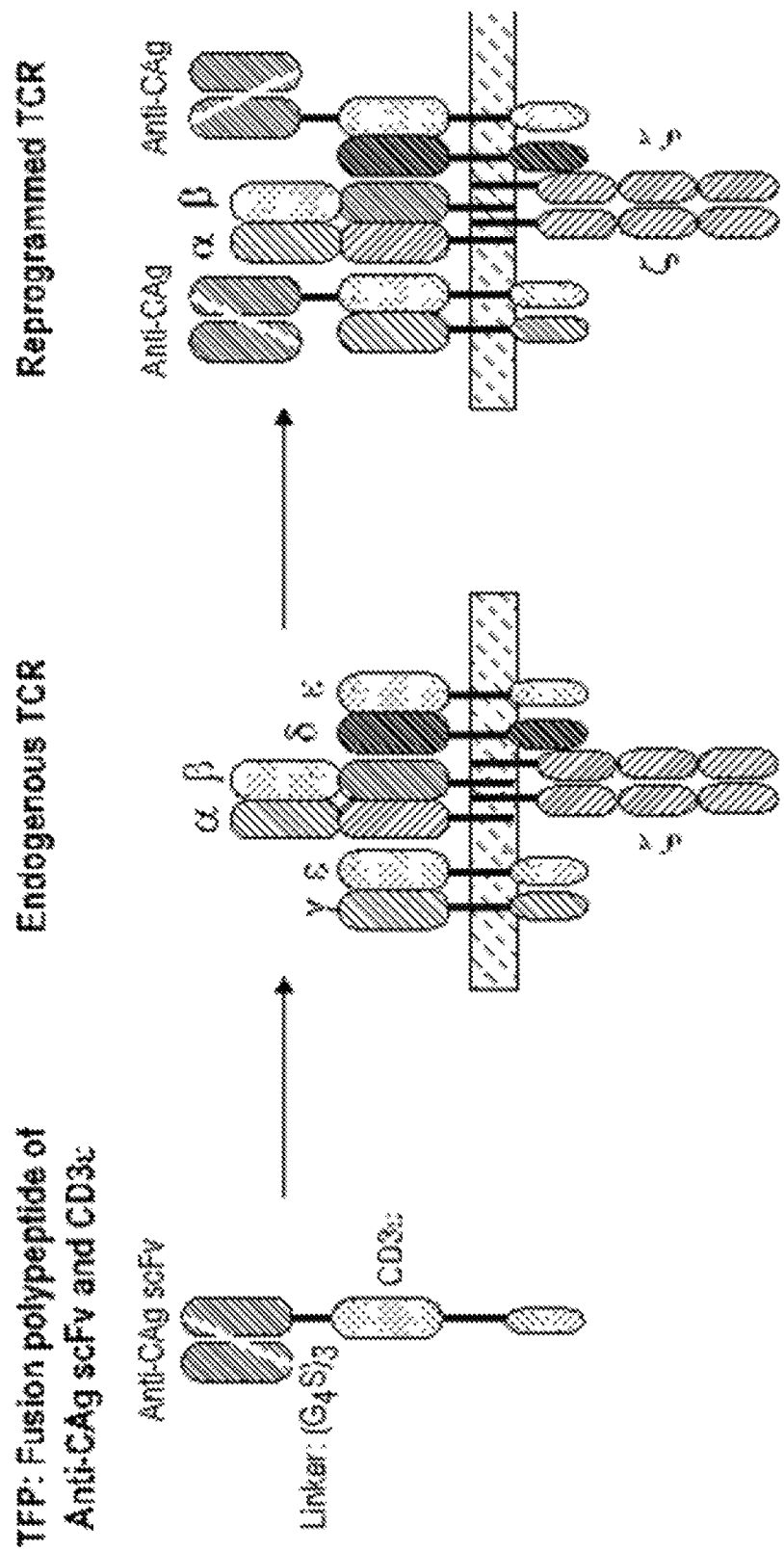
FIG. 11 is a schematic illustration demonstrating the use of T-cell receptor fusion polypeptides (TFPs) of the invention. An exemplary TFP contains an anti-cancer antigen (CAg) scFv and a full-length CD3 epsilon polypeptide fused via a (G4S)3 linker sequence. When produced by or introduced into a T-cell, the TFP associates with other polypeptides of the endogenous T-cell receptor (TCR) (shown to include two CD3 epsilon polypeptides, one CD3 gamma polypeptide, one CD3 delta polypeptide, two CD3 zeta polypeptides, one TCR alpha subunit and one TCR beta subunit, where the horizontal grey segment represents the plasma membrane) to form a reprogrammed TCR in which one or both of the endogenous CD3 epsilon polypeptides are substituted by the TFP.
Figures 12A, 12B, 12C, 12D:
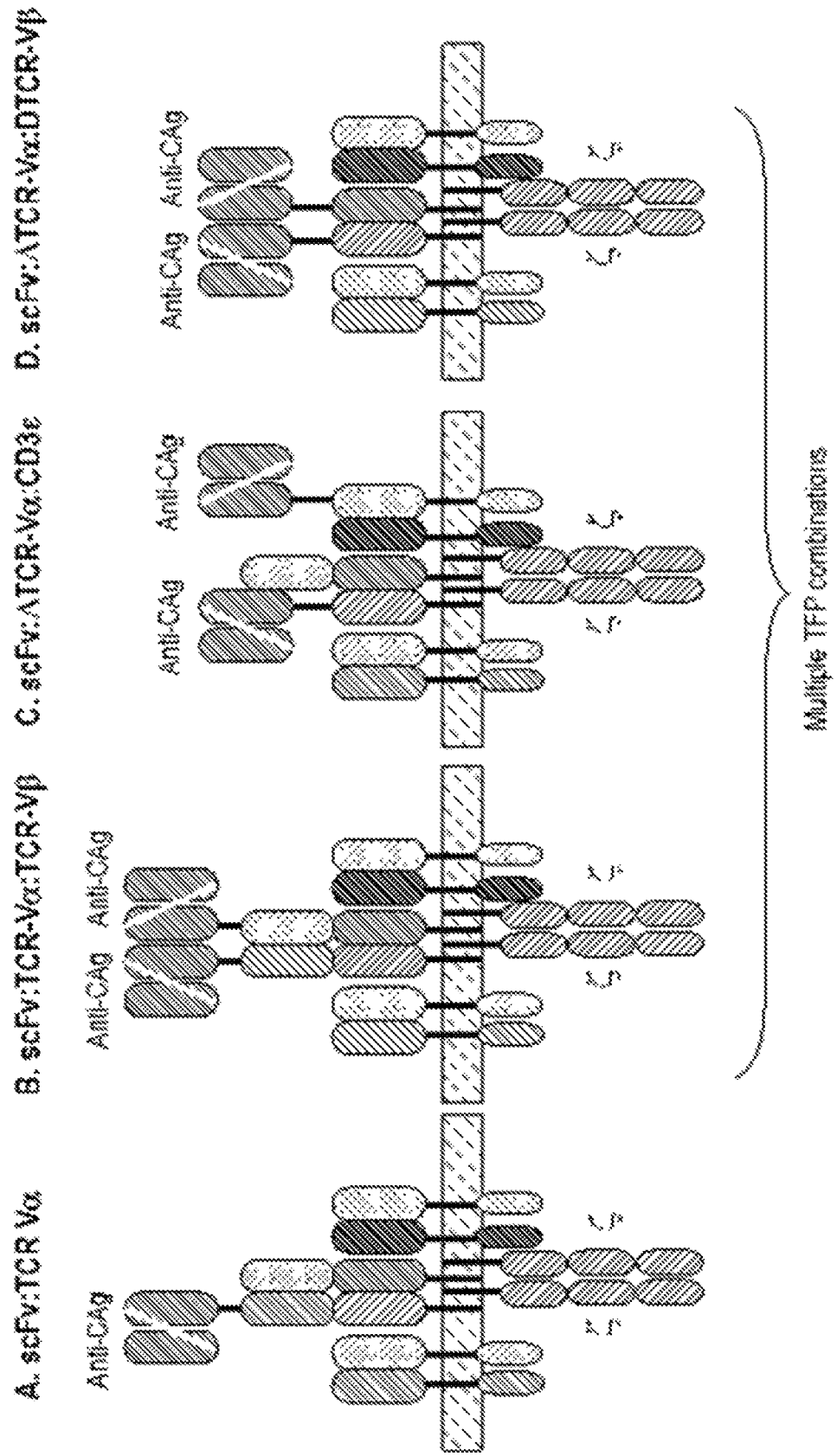
FIG. 12A represents schematic illustrations demonstrating exemplary variations of reprogrammed T-cell receptor fusion polypeptides (TFPs) of the invention. An exemplary reprogrammed TCR containing a TFP that contains an anti-CAg scFv and a full-length TCR Vα polypeptide fused via a (G4S)3 linker sequence is illustrated.
FIG. 12B illustrates a series of exemplary reprogrammed TCRs that contain multiple TFPs including i) an anti-CAg scFv and a full-length TCR Vα polypeptide fused via a (G4S)3 linker sequence and ii) an anti-CAg scFv and a full-length TCR Vβ polypeptide fused via a (G4S)3 linker sequence.
FIG. 12C illustrates an exemplary reprogrammed TCR that contains multiple TFPs including i) an anti-CAg scFv and a truncated (Δ) TCR polypeptide fused via a (G4S)3 linker sequence and ii) an anti-CAg scFv and a full-length CD3 epsilon polypeptide fused via a (G4S)3 linker sequence. The truncated (Δ) TCR polypeptide is truncated by the deletion of the Vα.
FIG. 12D illustrates an exemplary reprogrammed TCR that contains multiple TFPs including i) an anti-CAg scFv and a truncated (Δ) TCR Vα polypeptide fused via a (G4S)3 linker sequence and ii) an anti-CAg scFv and a truncated (Δ) TCR Vβ polypeptide fused via a (G4S)3 linker sequence. The truncated (Δ) TCR polypeptide is truncated by the deletion of the Vβ.
Figure 13:
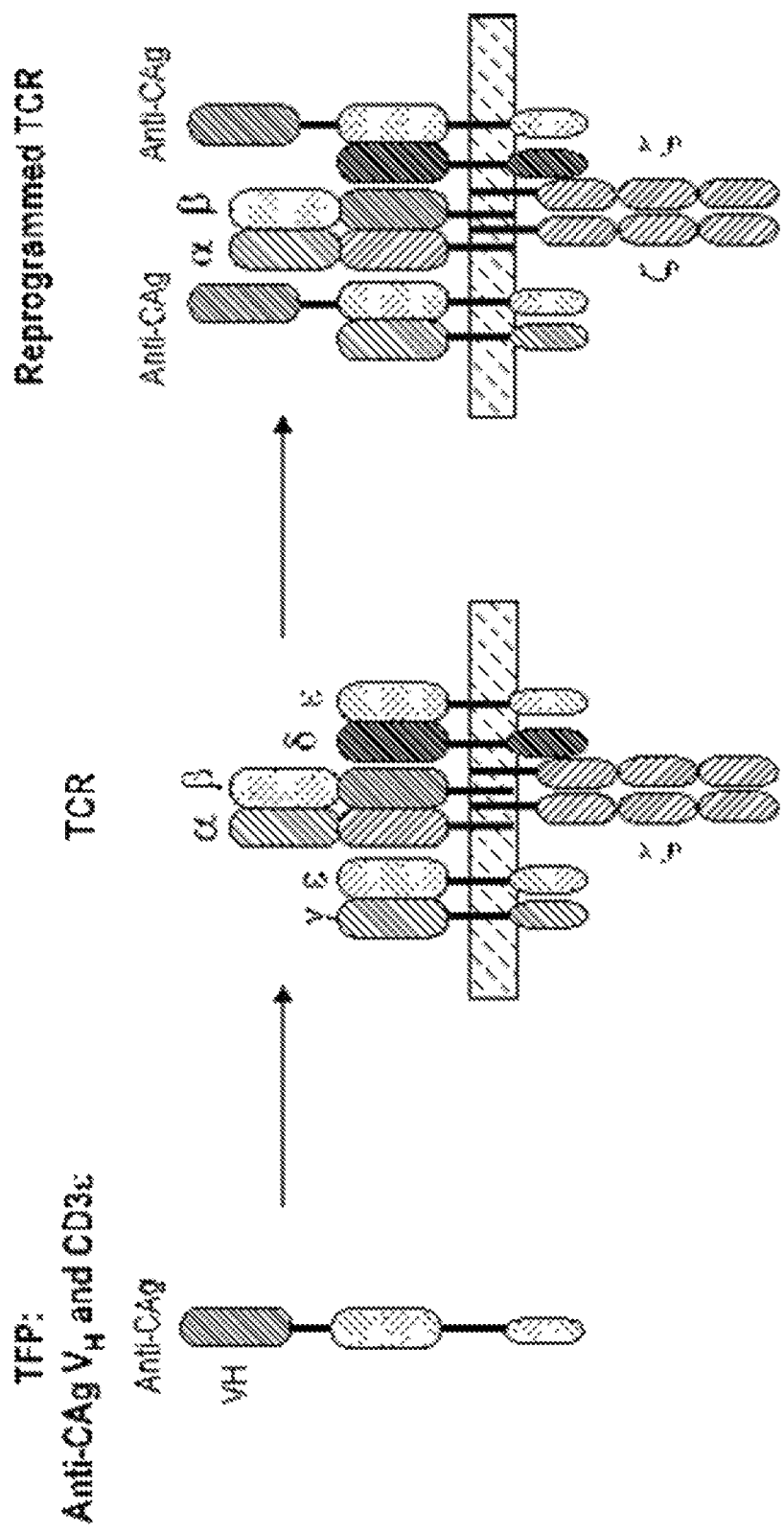
FIG. 13 is a schematic illustration demonstrating the use of T-cell receptor fusion polypeptides (TFPs) of the invention. An exemplary TFP contains an anti-CAg VH domain and a full-length CD3 epsilon polypeptide fused via a (G4S)3 linker sequence. When produced by a T-cell or introduced into a T-cell, the TFP associates with other polypeptides of the endogenous T-cell receptor (TCR) (shown to include two CD3 epsilon polypeptides, one CD3 gamma polypeptide, one CD3 delta polypeptide, two CD3 zeta polypeptides, one TCR alpha subunit and one TCR beta subunit, where the horizontal grey segment represents the plasma membrane) to form a reprogrammed TCR in which one or both of the endogenous CD3 epsilon polypeptides are substituted by the TFP.
Figure 14:
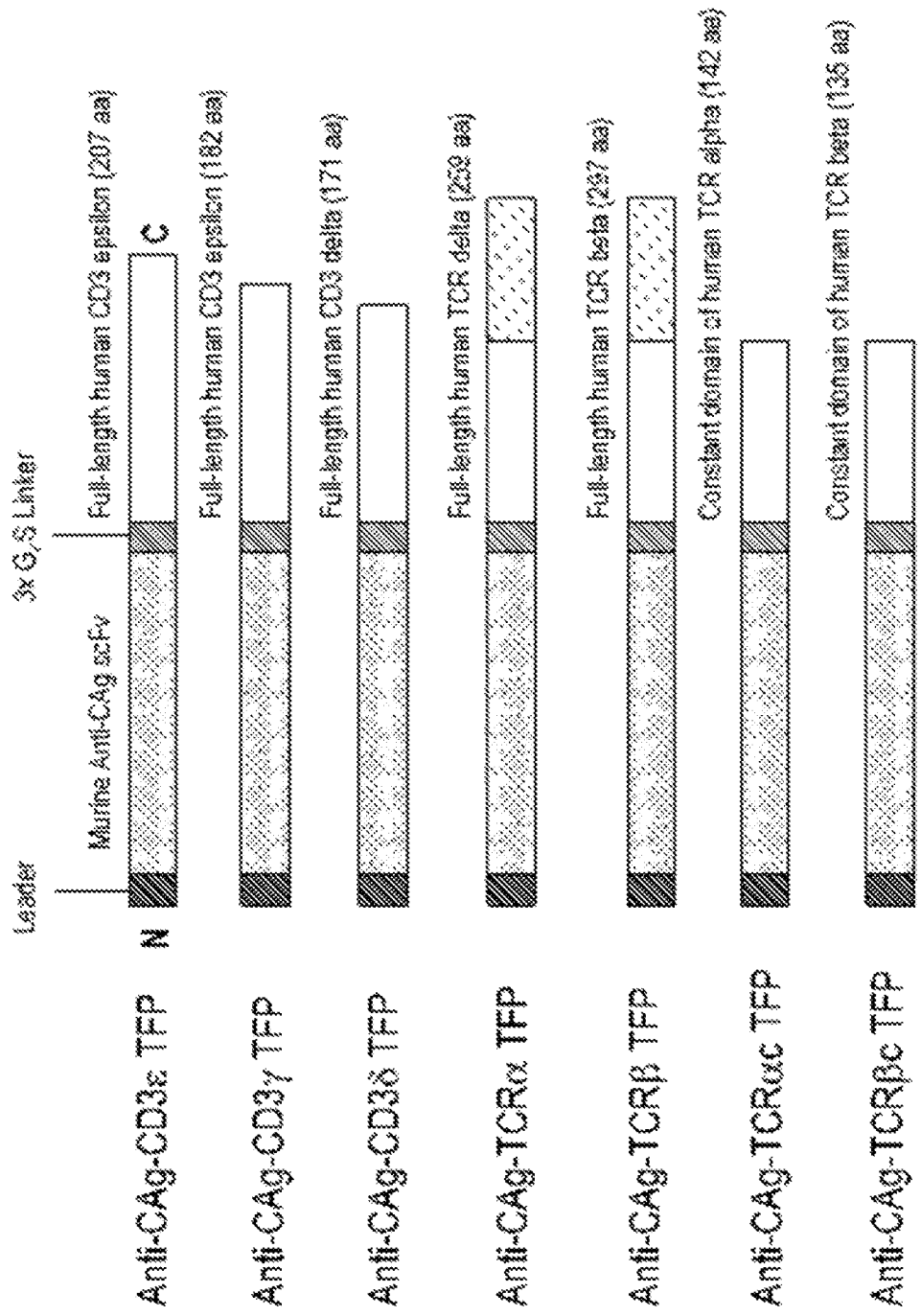
FIG. 14 is a series of schematic illustrations demonstrating DNA constructs encoding various TFPs.
Figure 15A:
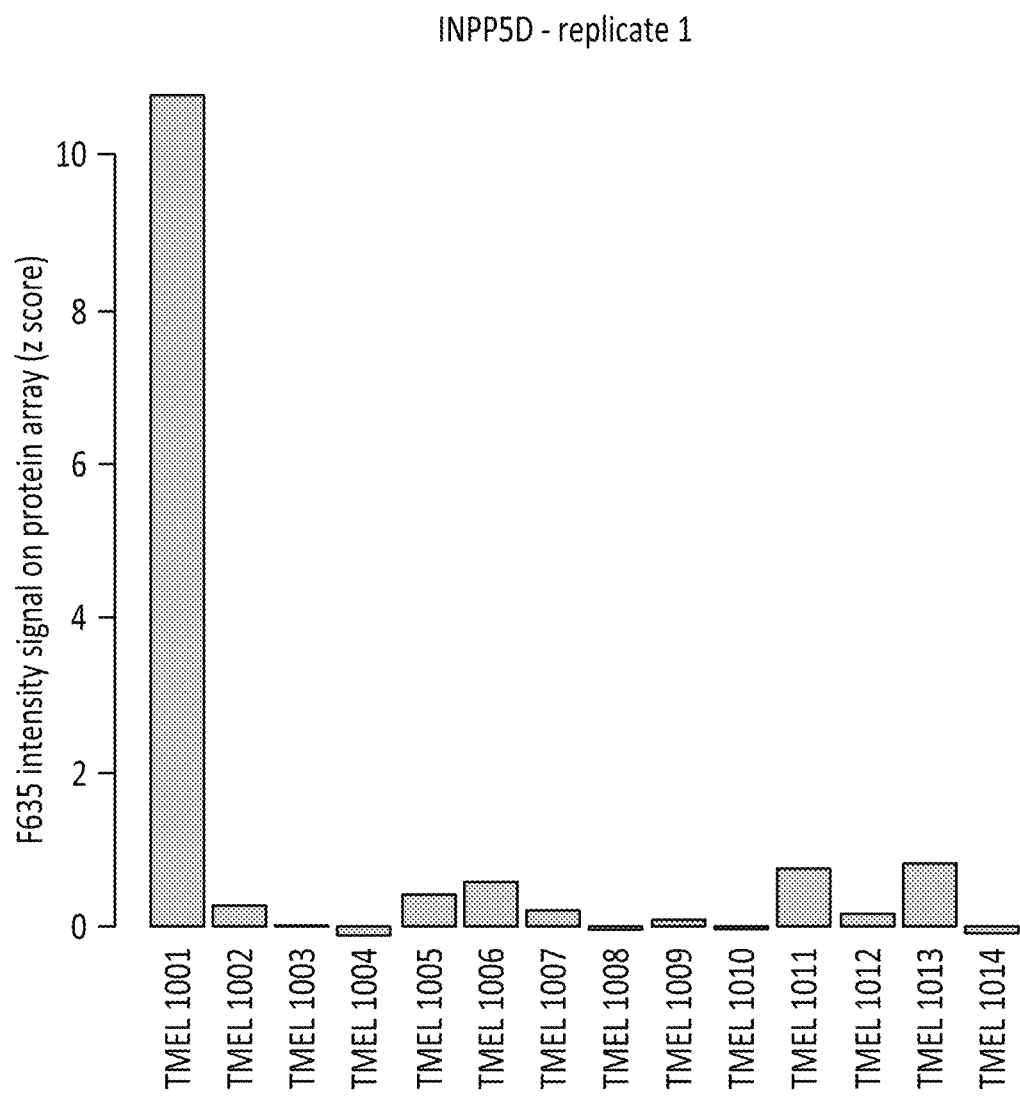
FIG. 15A and FIG. 15B is protein array data showing specific binding of antigen INPP5D also known as Src homology 2 (SH2) domain containing inositol polyphosphate 5-phosphatase 1 (SHIP1) by TMEL1001 antibody.
Figure 15B:
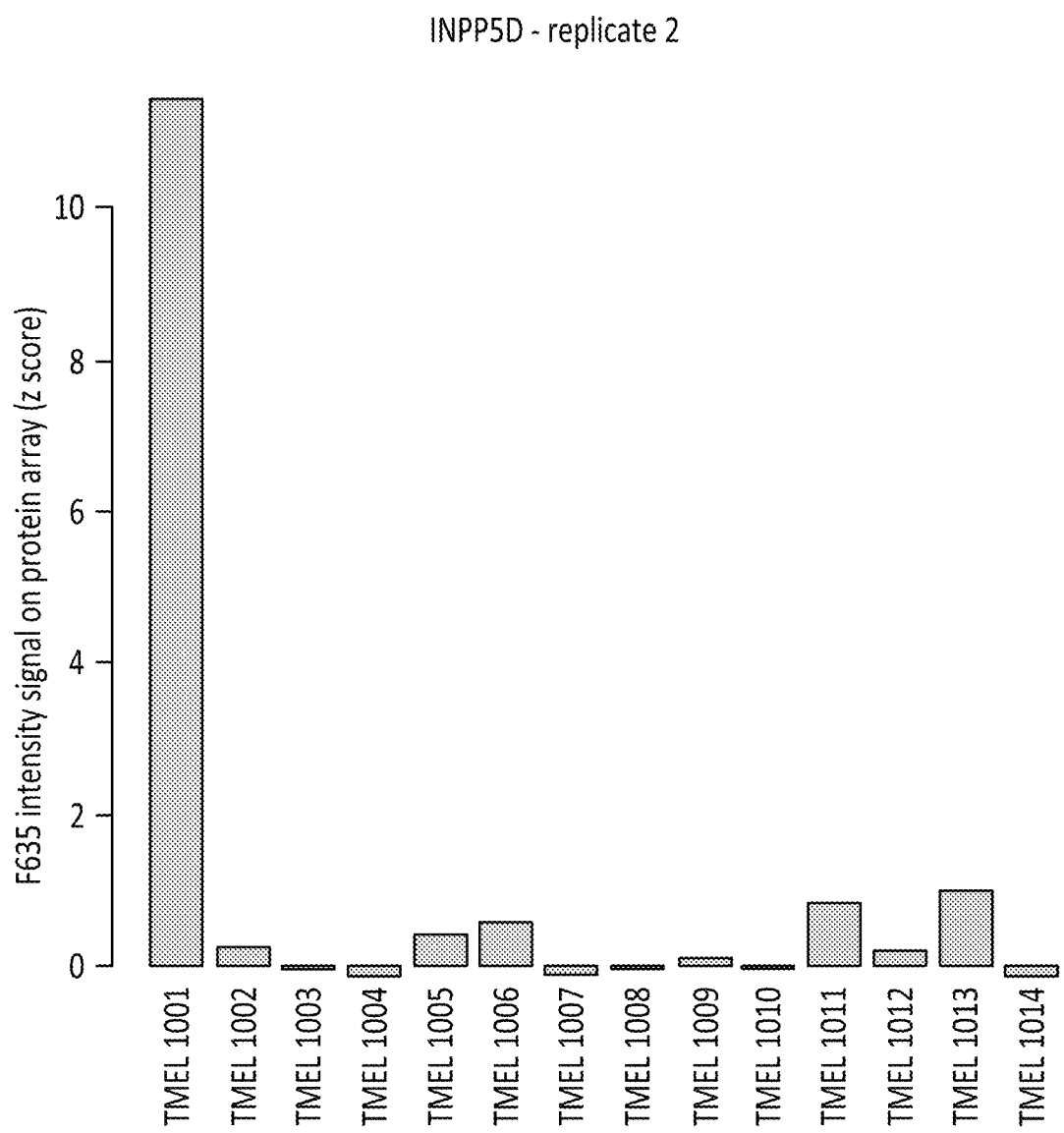
Figure 16A:
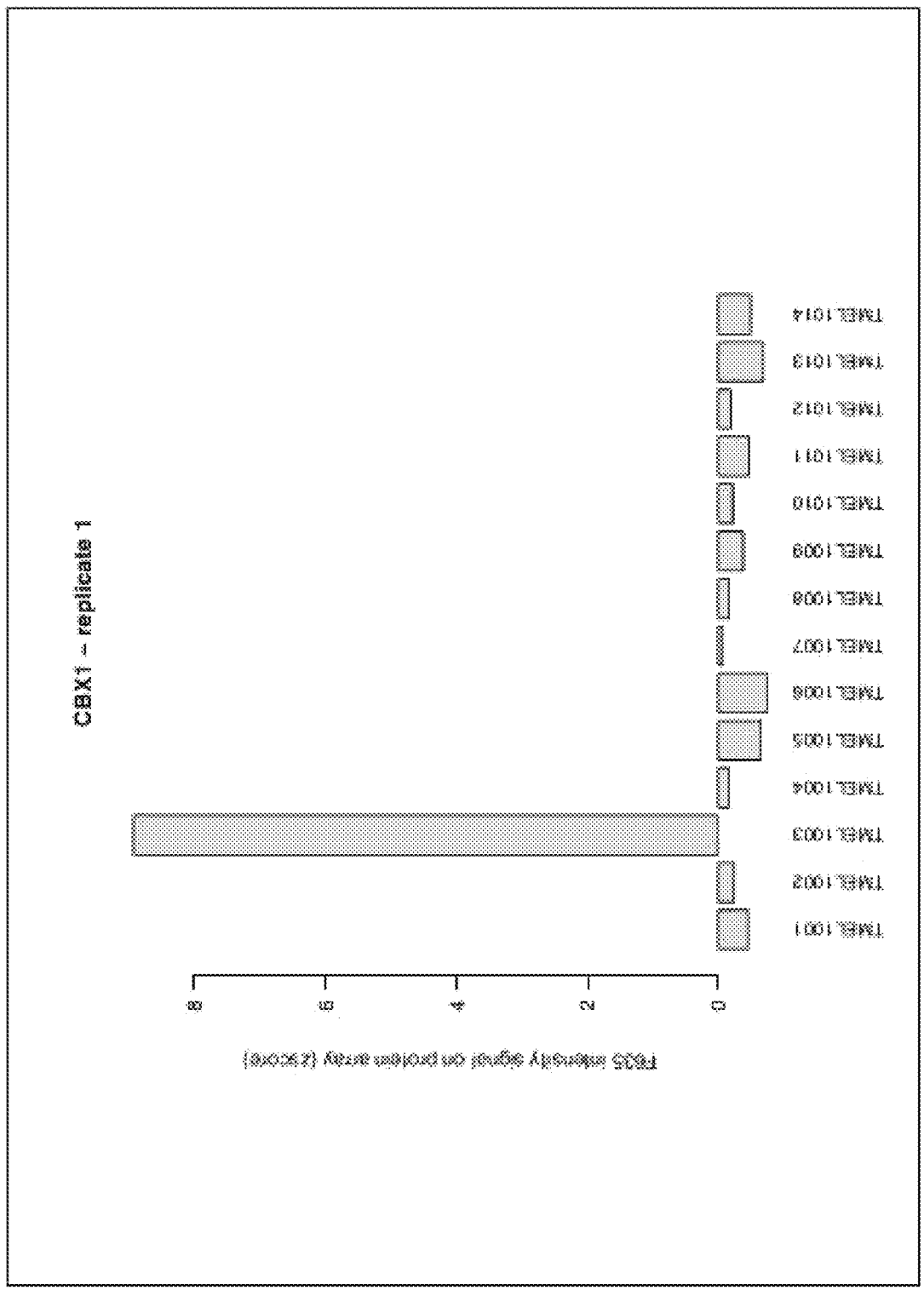
FIG. 16A and FIG. 16B is protein array data showing specific binding of antigen Chromobox protein homolog 1 (CBX1) by TMEL1003 antibody.
Figure 16B:
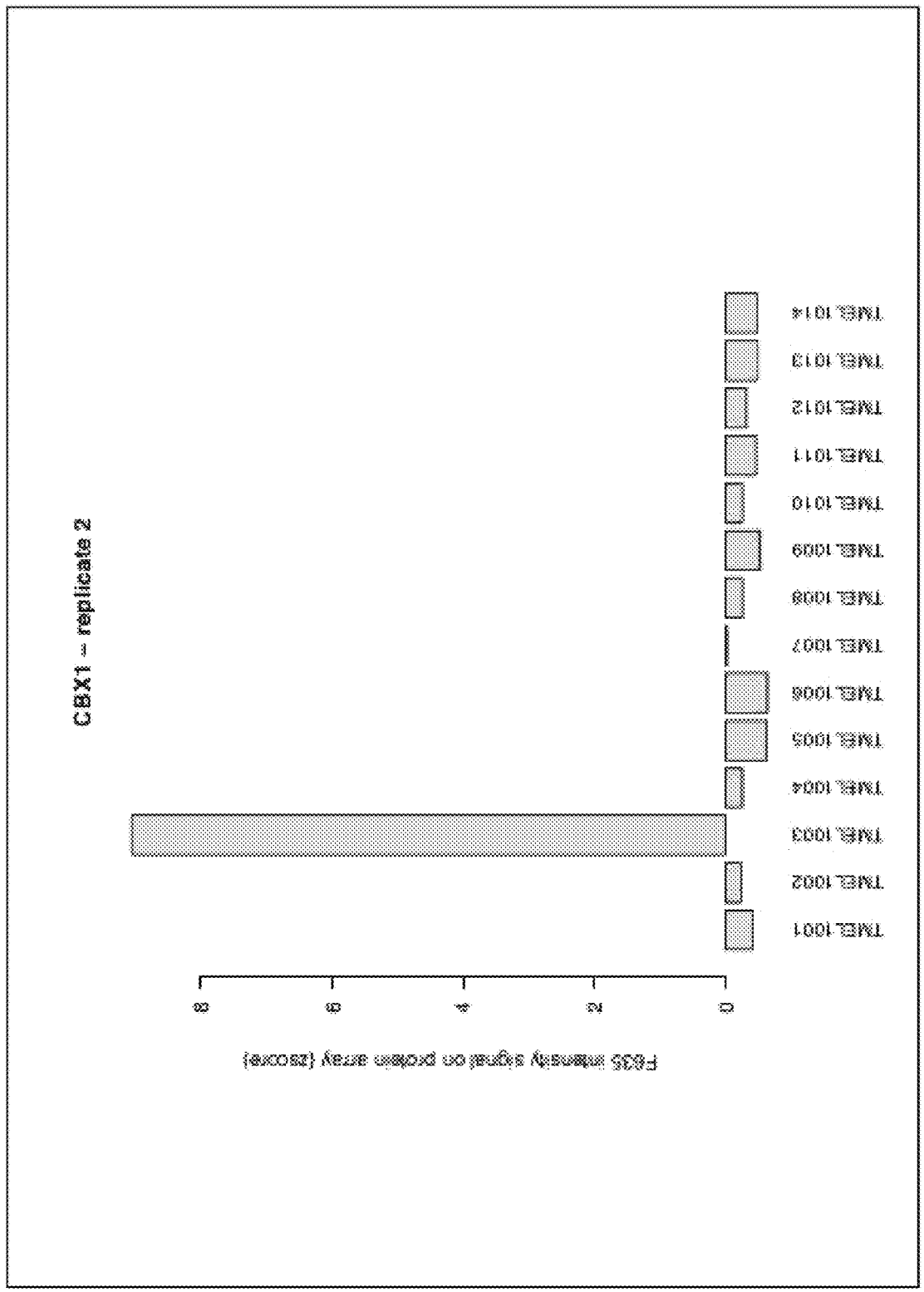
Figure 17A:
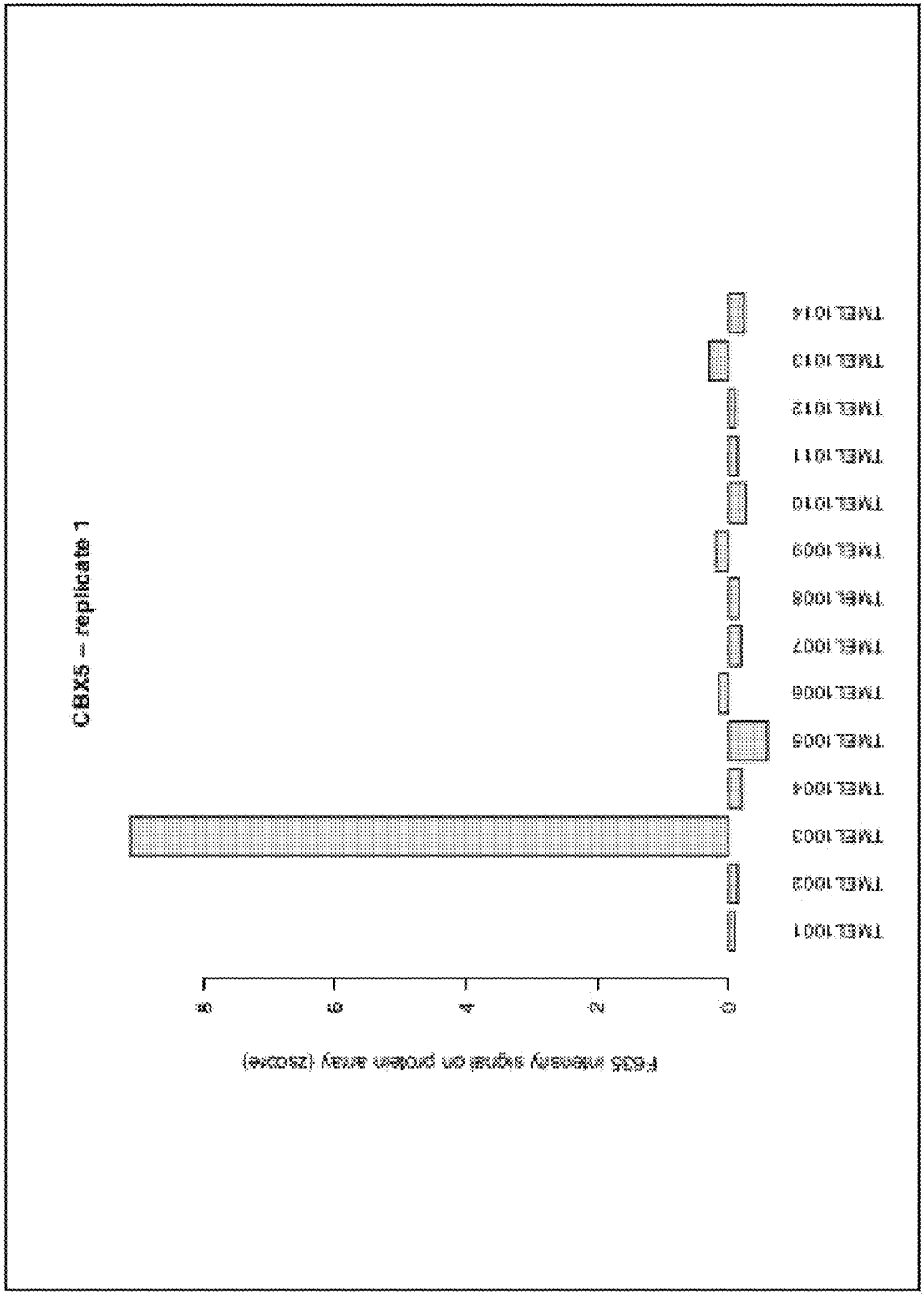
FIG. 17A and FIG. 17B is protein array data showing specific binding of antigen Chromobox protein homolog 5 (CBX5) by TMEL1003 antibody.
Figure 17B:
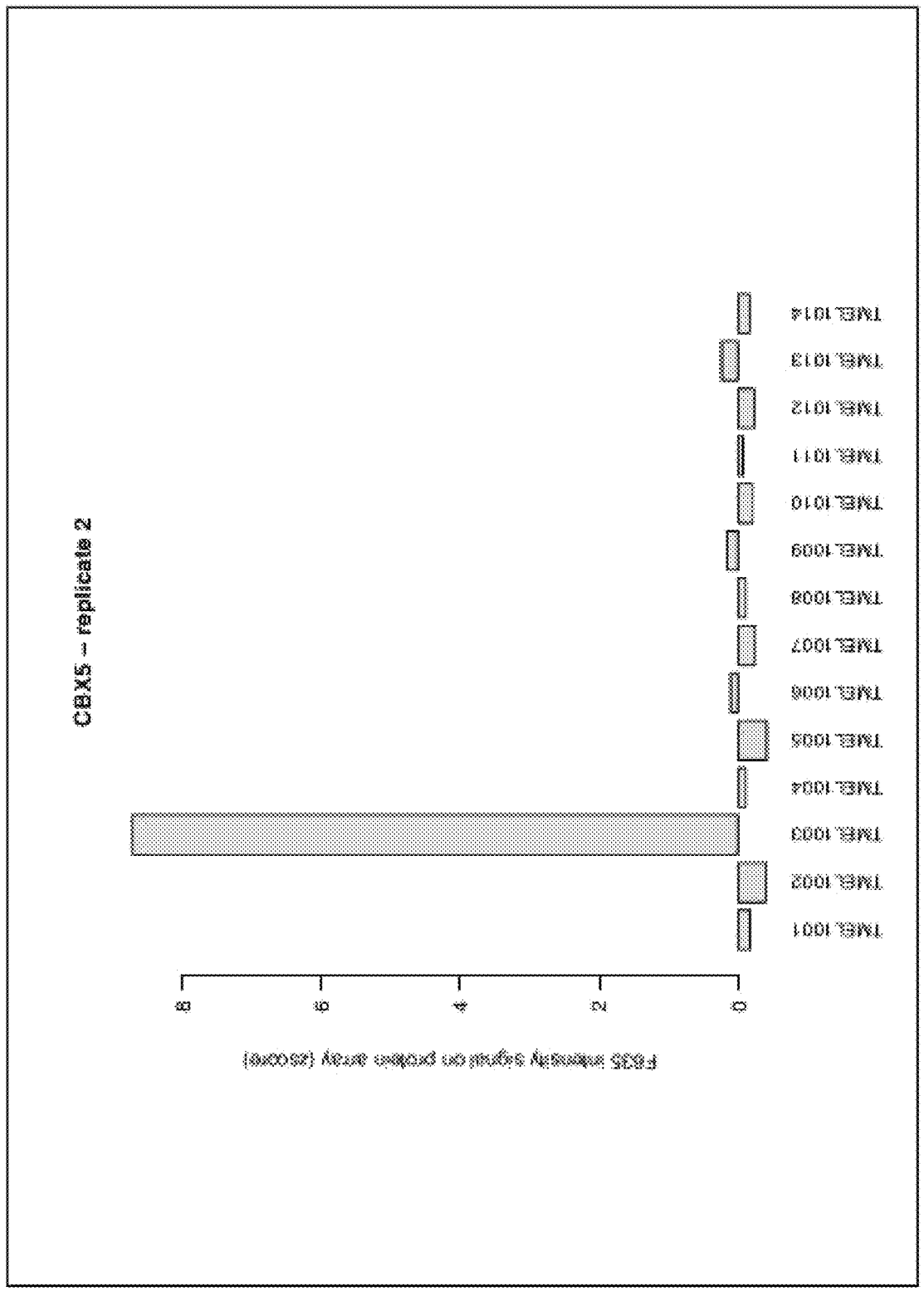
Figure 18A:
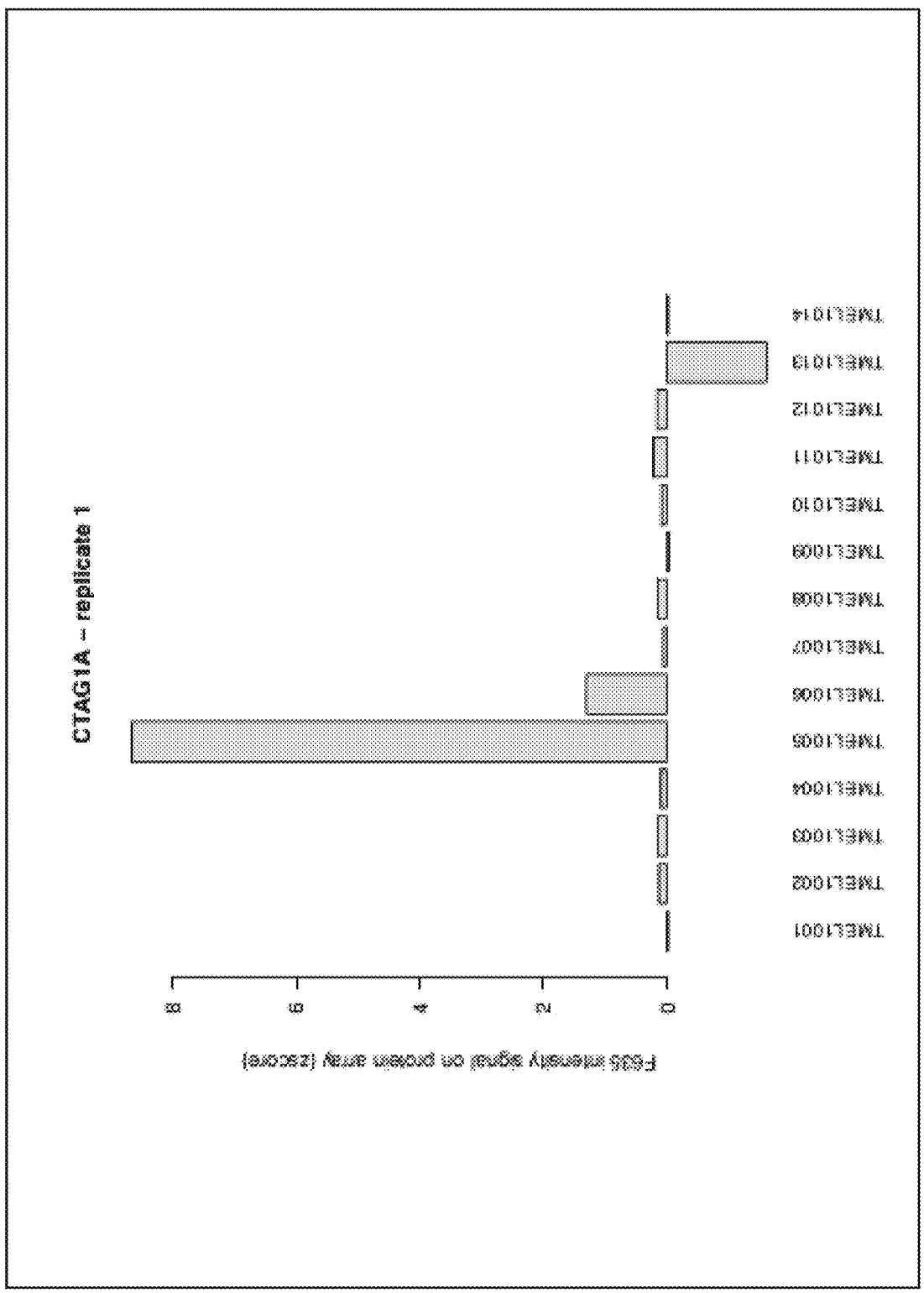
FIG. 18A and FIG. 18B is protein array data showing specific binding of antigen Cancer/testis antigen 1 (CTAG1A) also known as NY-ESO-1 by TMEL1005 antibody.
Figure 18B:
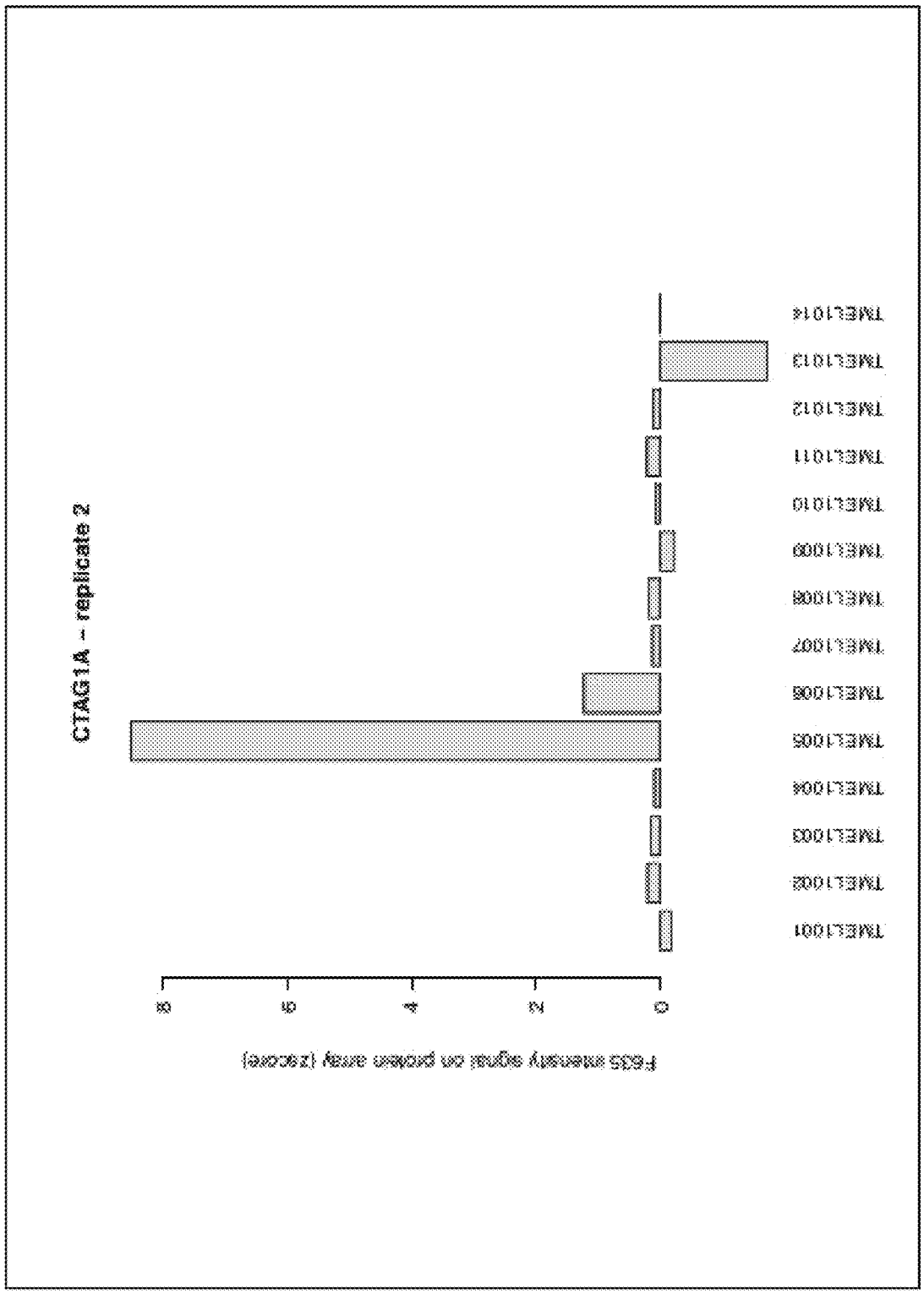
Figure 19A:
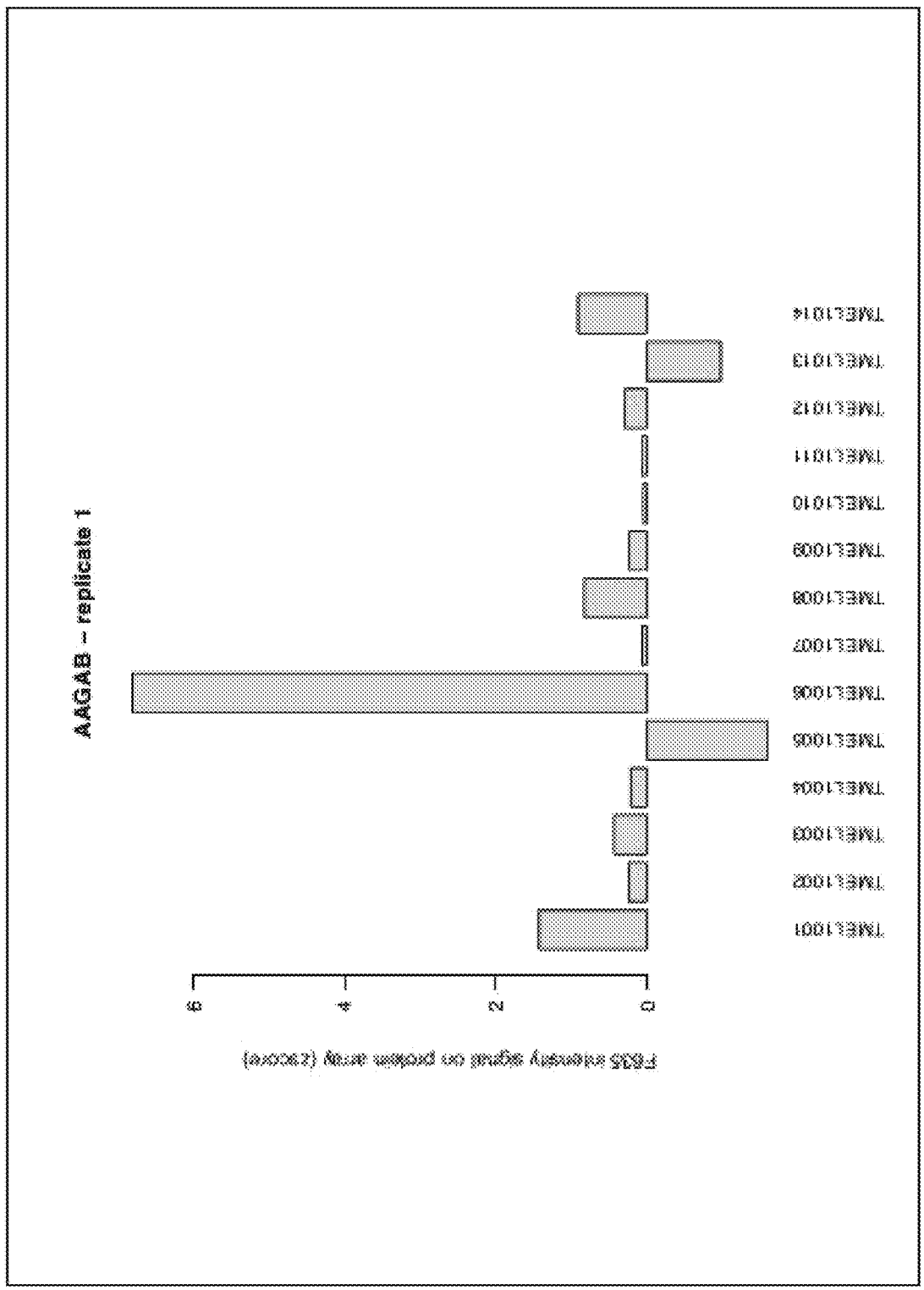
FIG. 19A and FIG. 19B is protein array data showing specific binding of antigen Alpha and Gamma Adaptin Binding Protein (AAGAB) by TMEL1006 antibody.
Figure 19B:
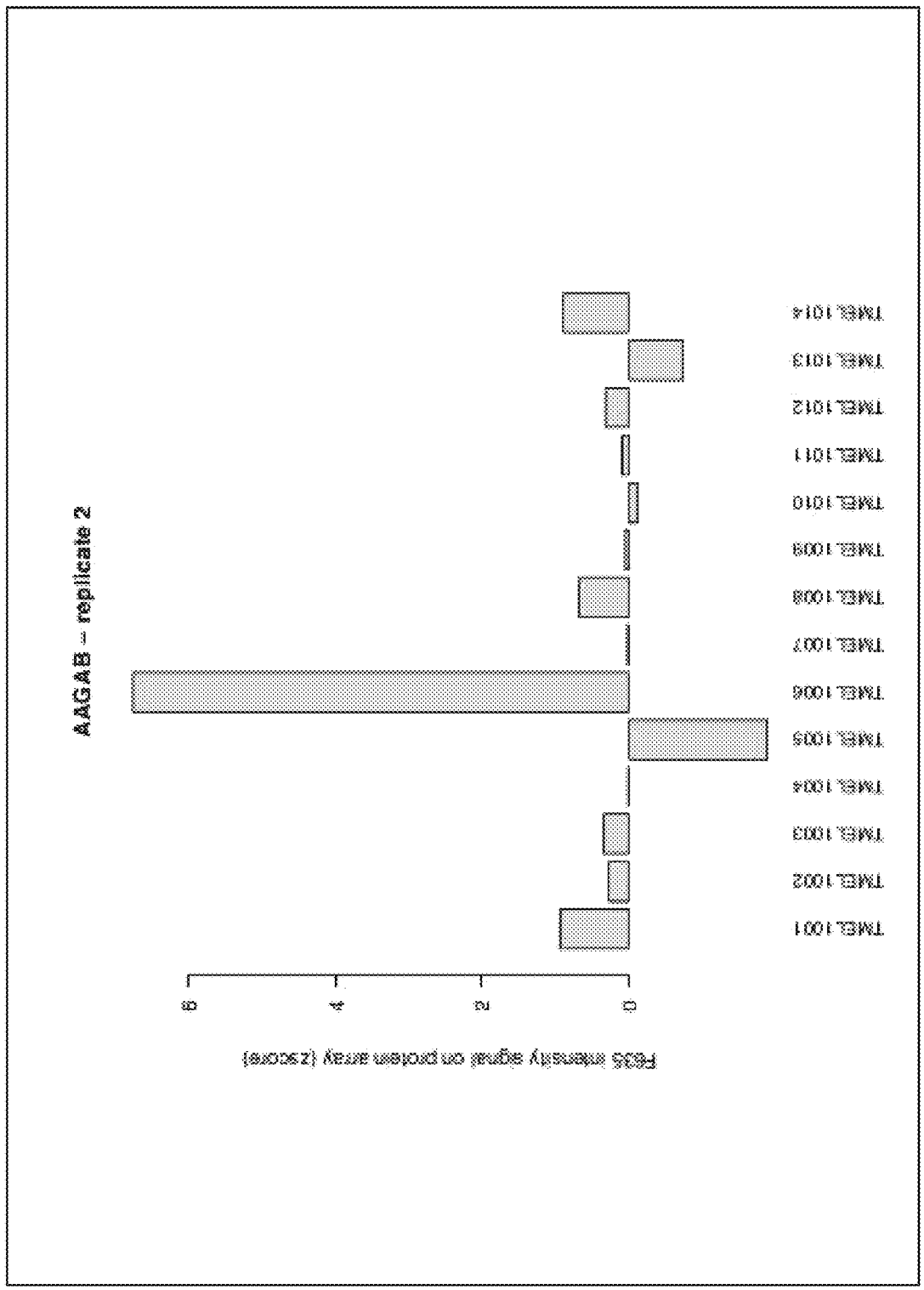
Figure 20A:
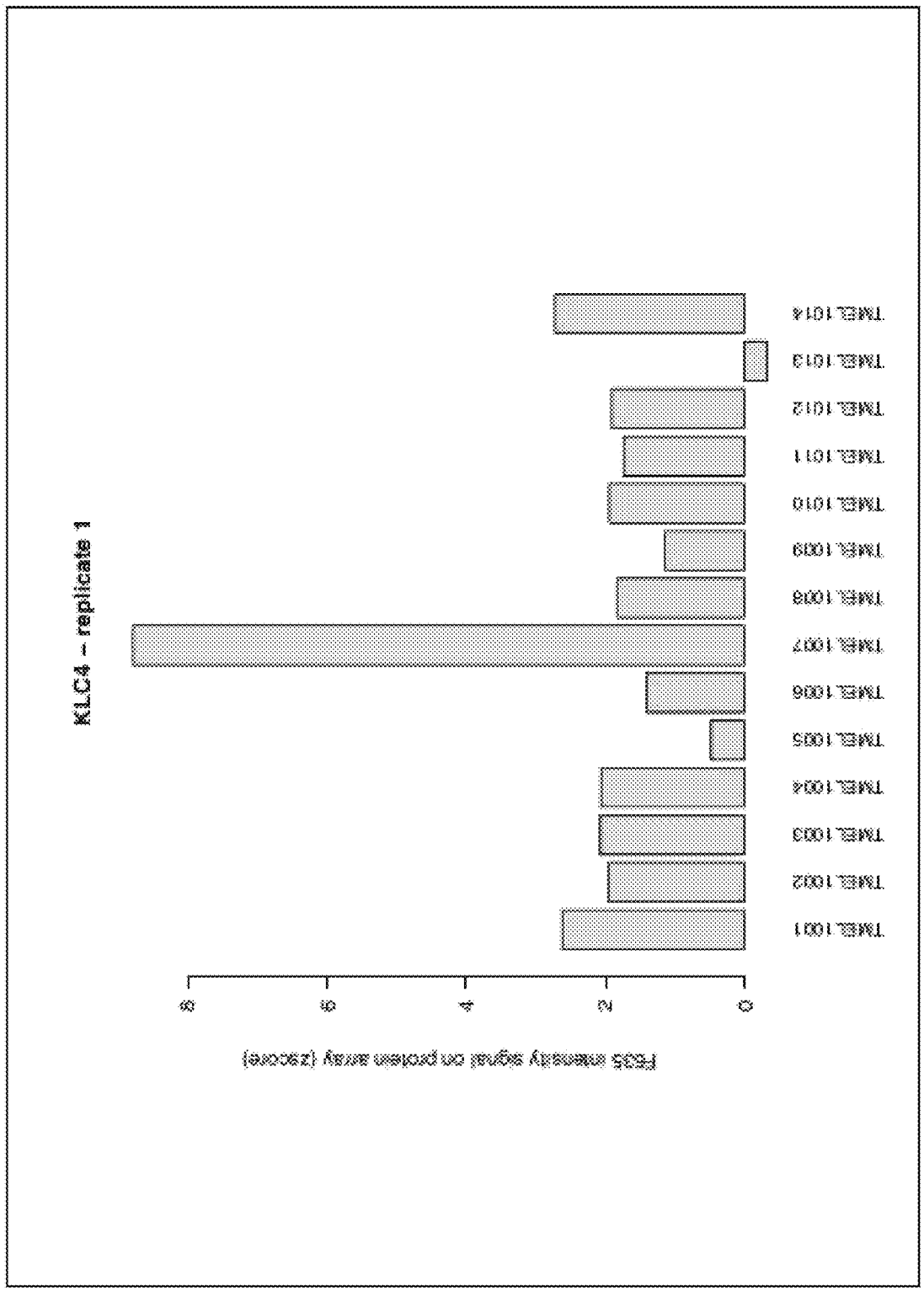
FIG. 20A and FIG. 20B is protein array data showing specific binding of antigen Kinesin light chain 4 protein (KLC4) by TMEL1007 antibody.
Figure 20B:
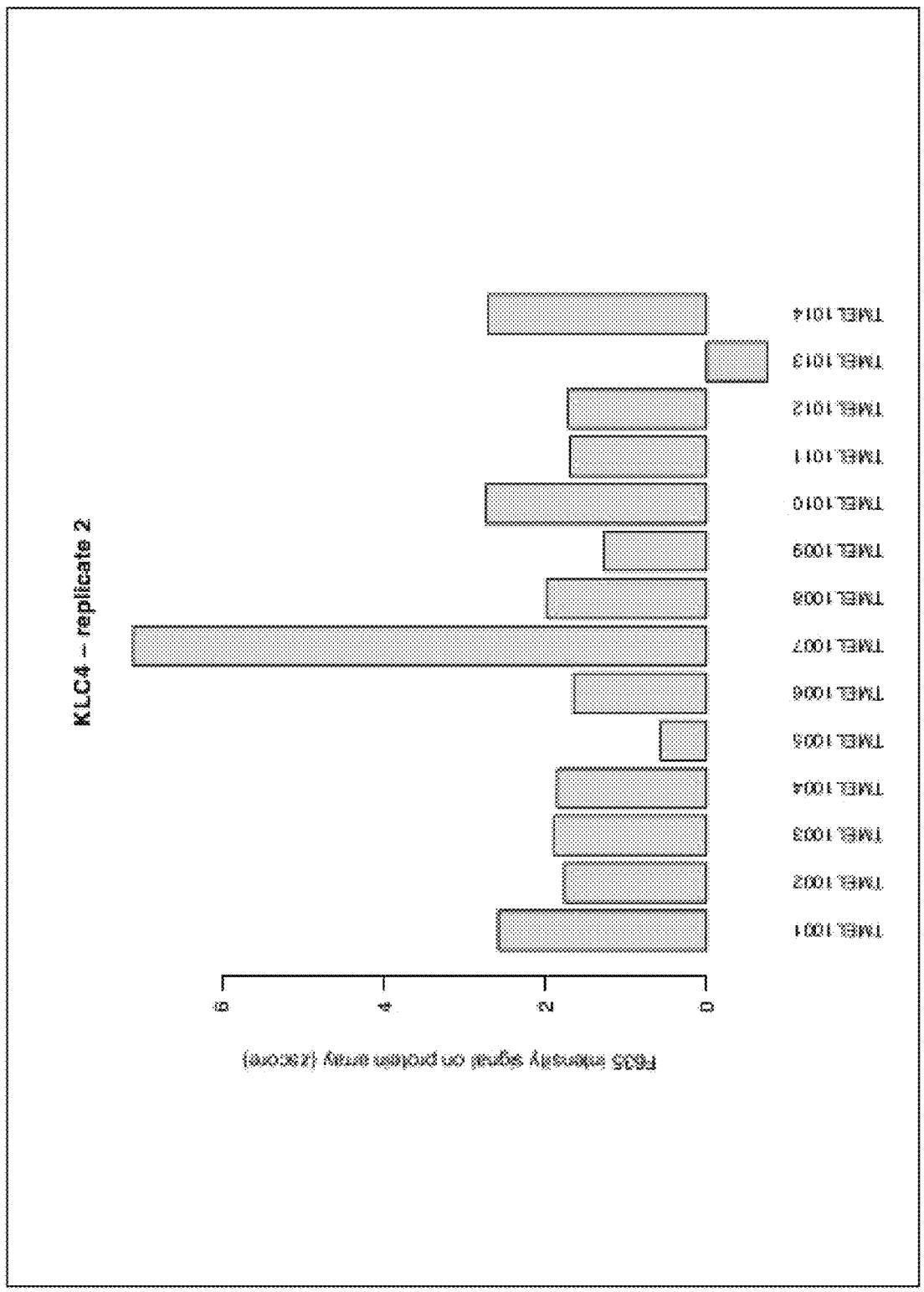
Figure 21A:
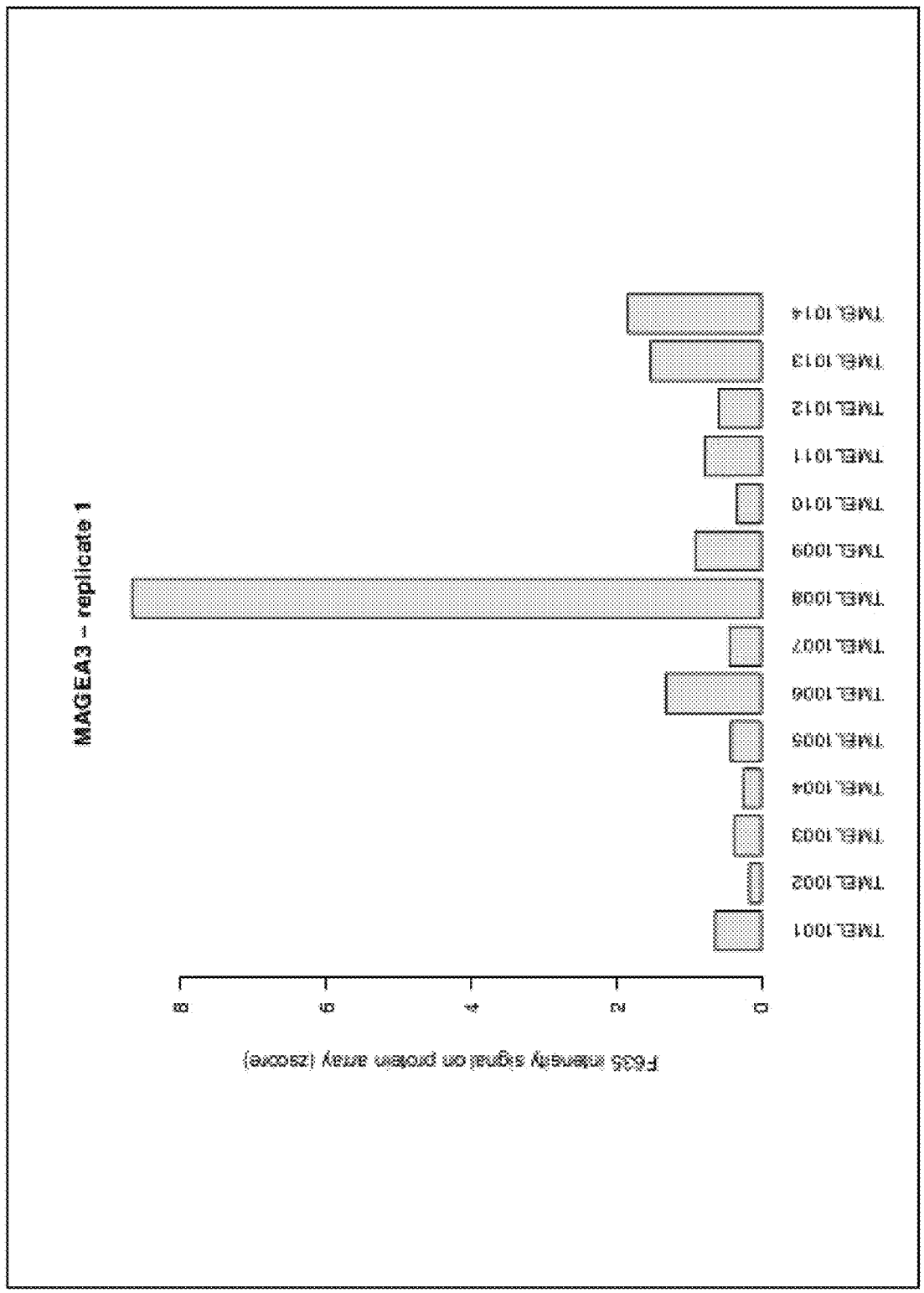
FIG. 21A and FIG. 21B is protein array data showing specific binding of antigen Melanoma-associated antigen 3 (MAGE-A3) by TMEL1008 antibody.
Figure 21B:
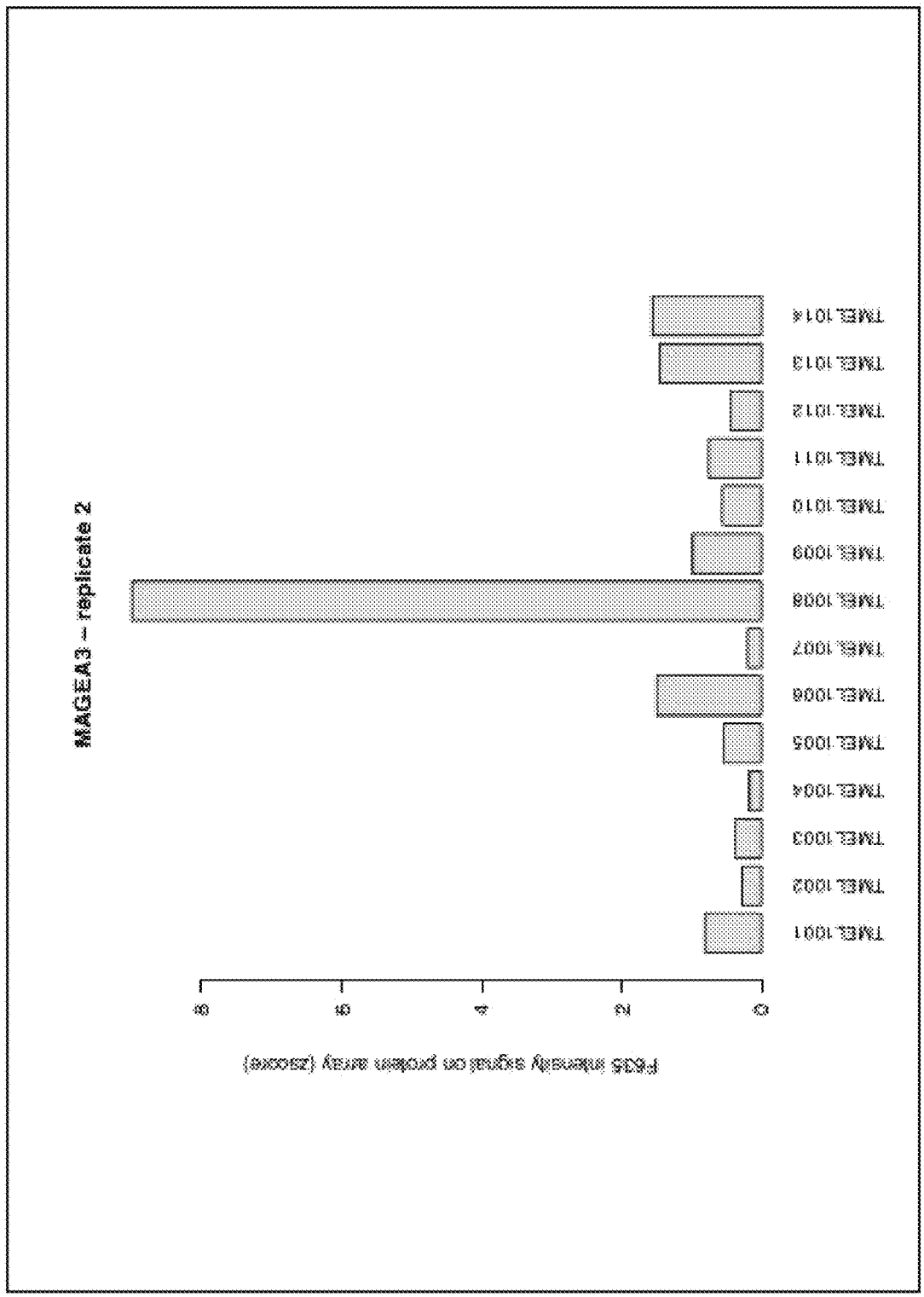
Figure 22A:
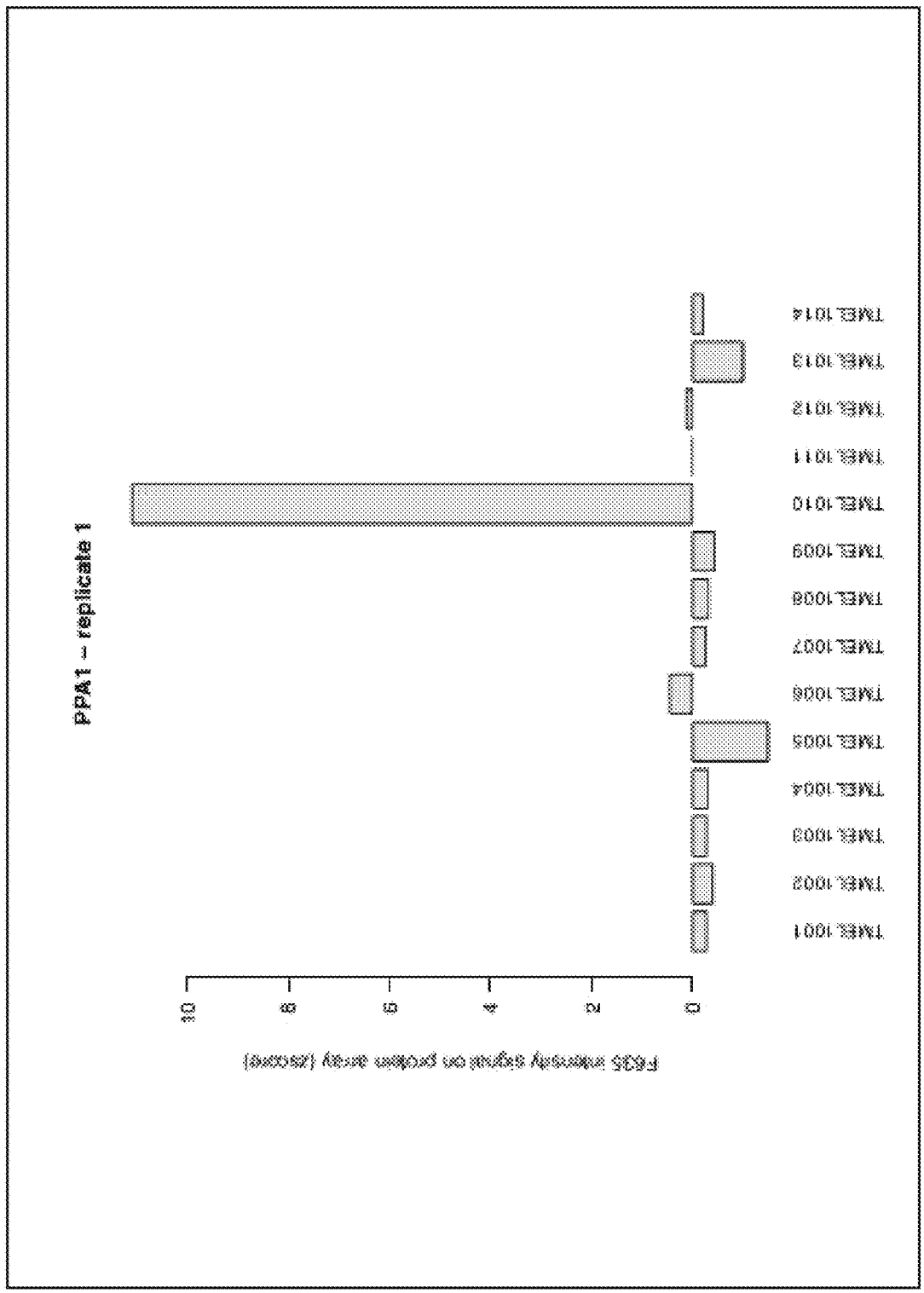
FIG. 22A and FIG. 22B is protein array data showing specific binding of antigen Inorganic pyrophosphatase (PPA1) by TMEL1010 antibody.
Figure 22B:
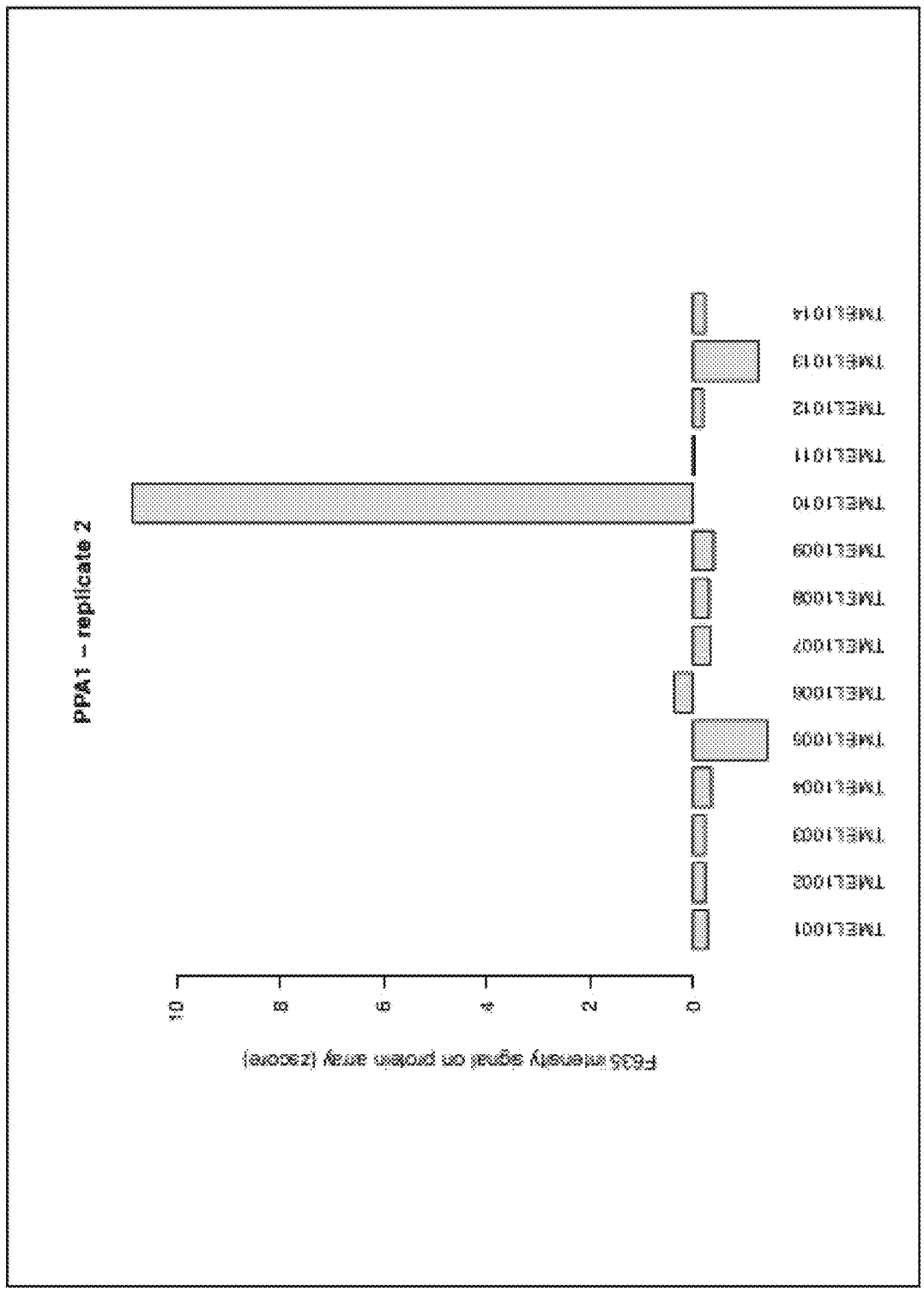
Figure 23A:
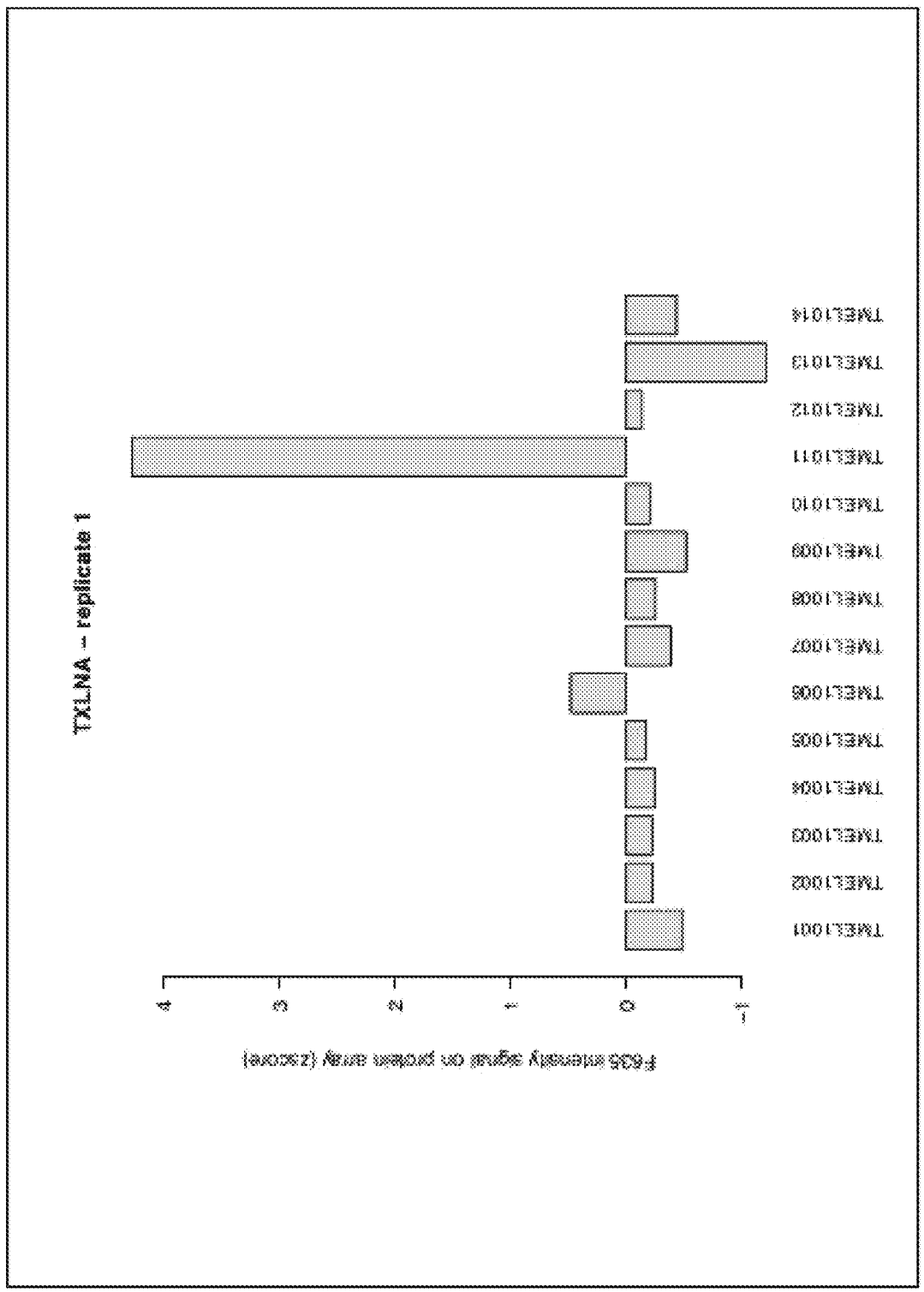
FIG. 23A and FIG. 23B is protein array data showing specific binding of antigen Alpha-taxilin (TXLNA) also known as interleukin-14A by TMEL1011 antibody.
Figure 23B:
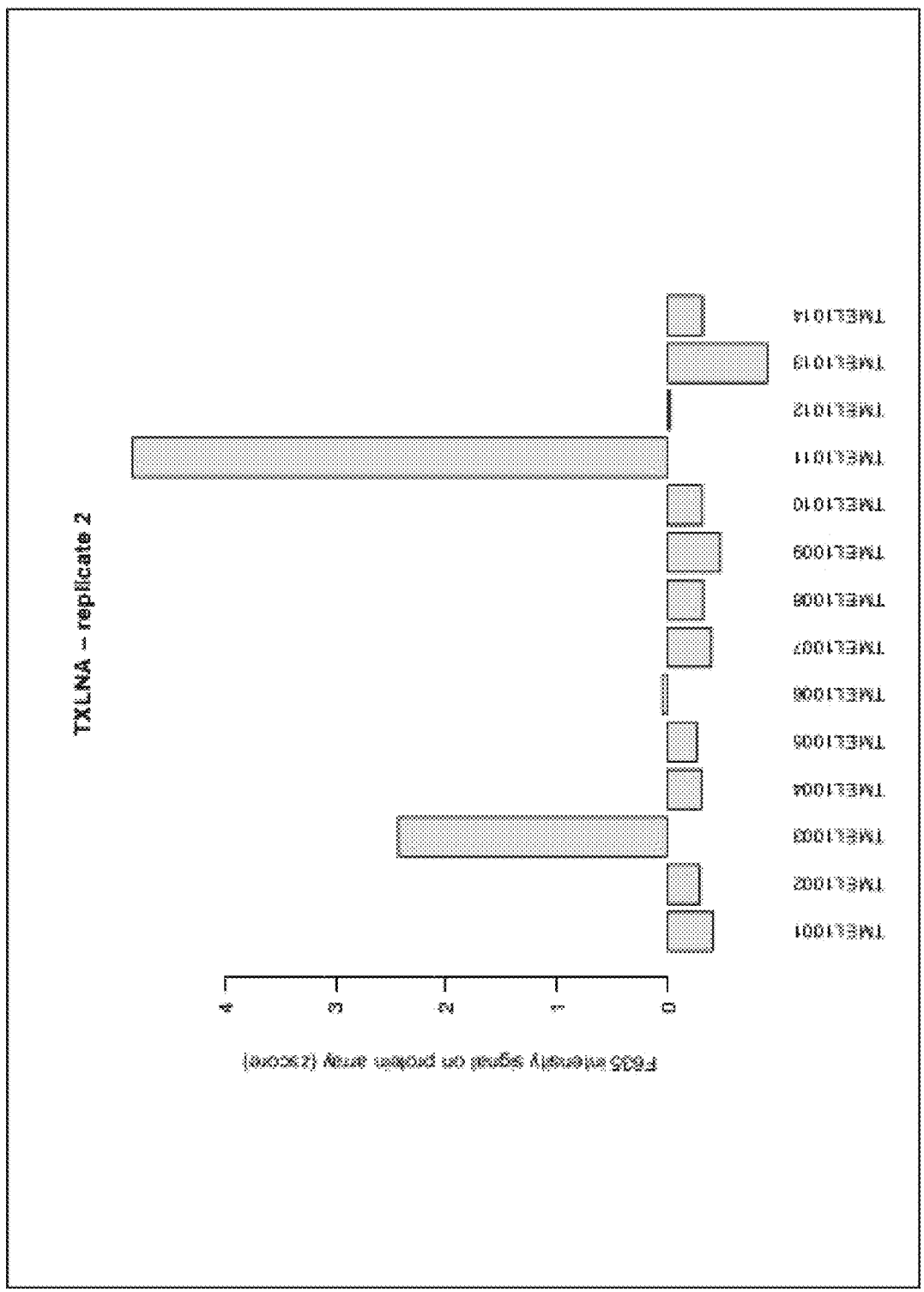
Figure 24A:
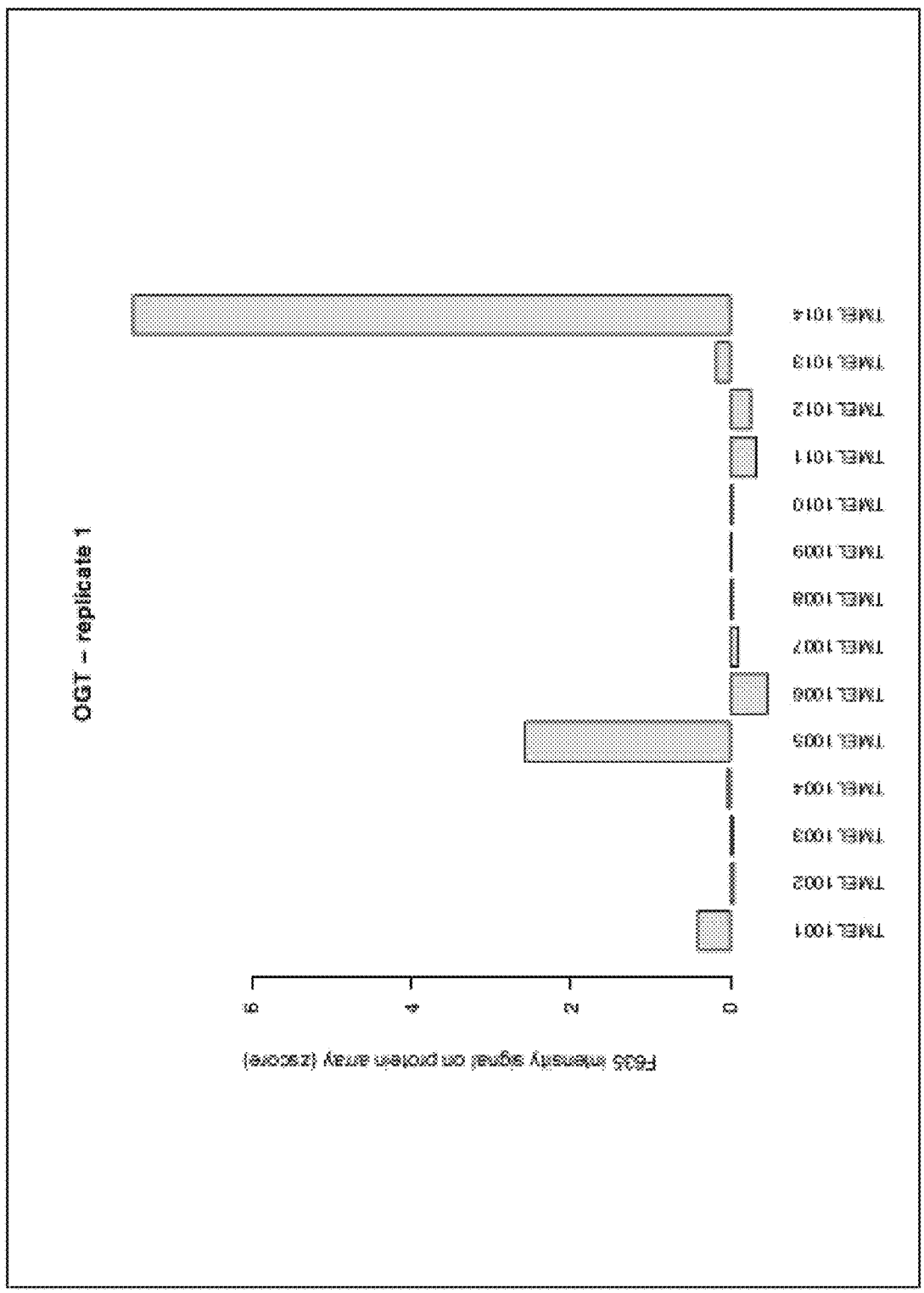
FIG. 24A and FIG. 24E is protein array data showing specific binding of antigen O-linked N-acetylglucosamine (GlcNAc) transferase (OGT) by TMEL1014 antibody.
Figure 24B:
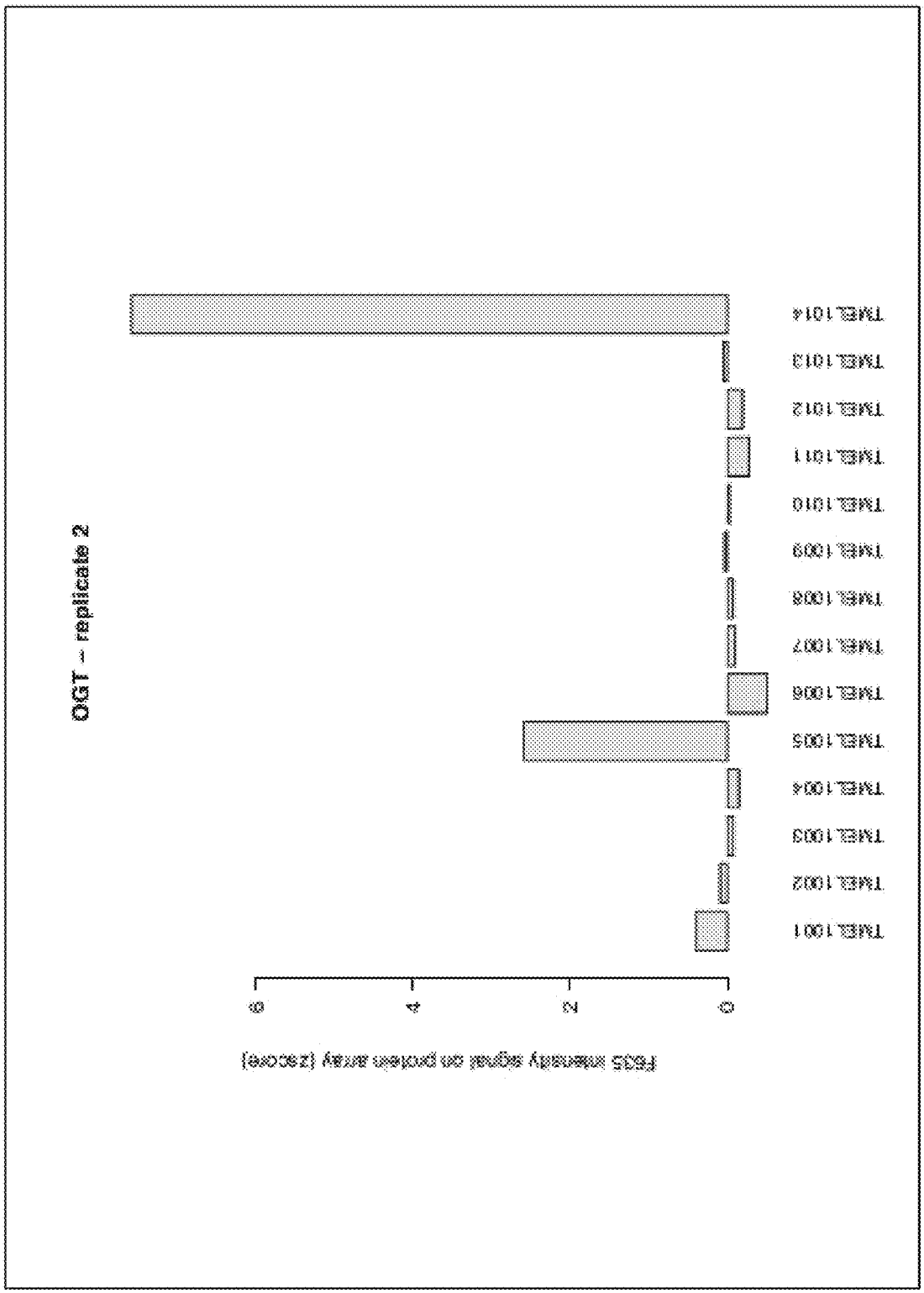
FIG. 24B shows experimental replicate 2.
Figure 24C:
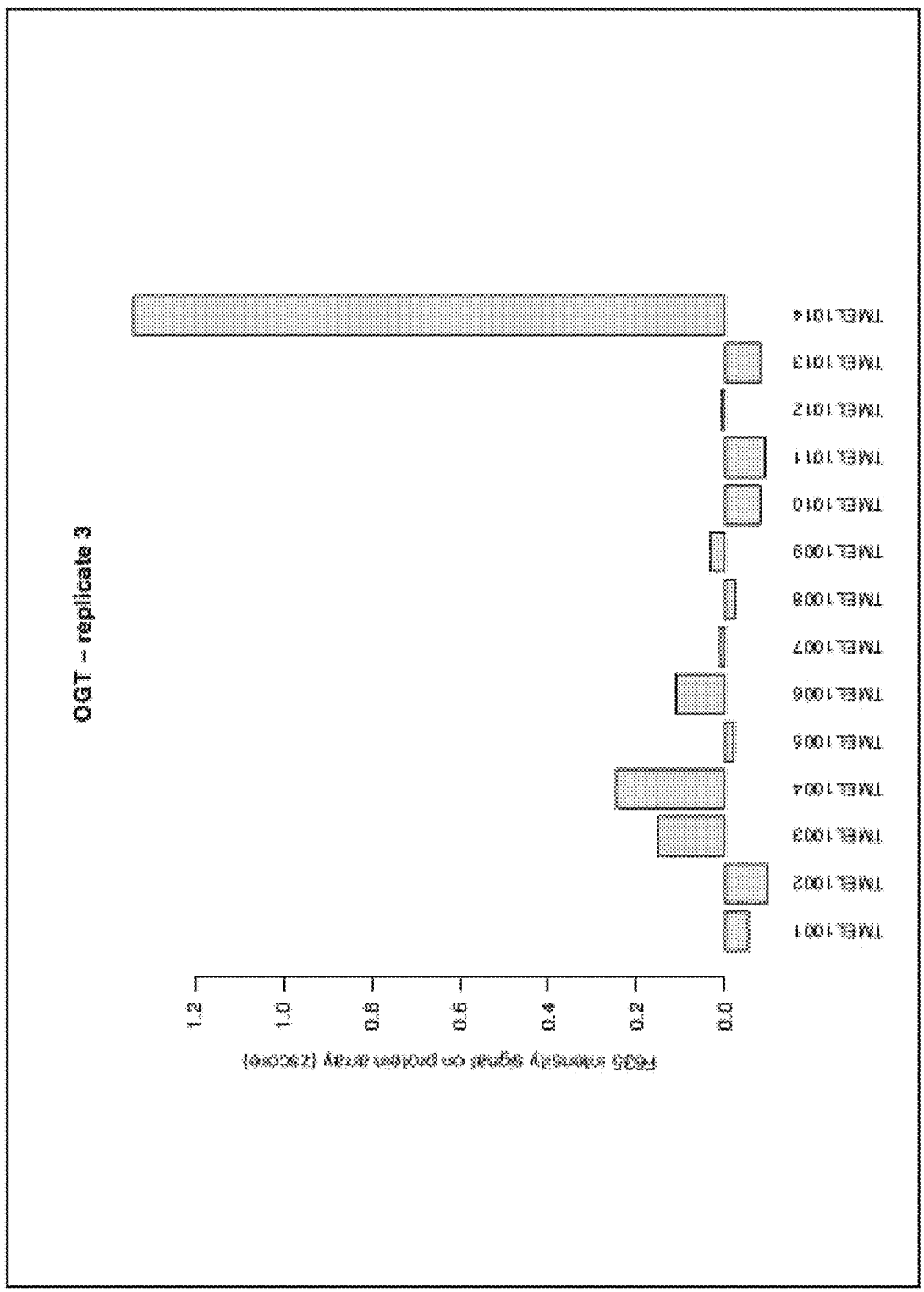
FIG. 24C shows experimental replicate 3.
Figure 24D:
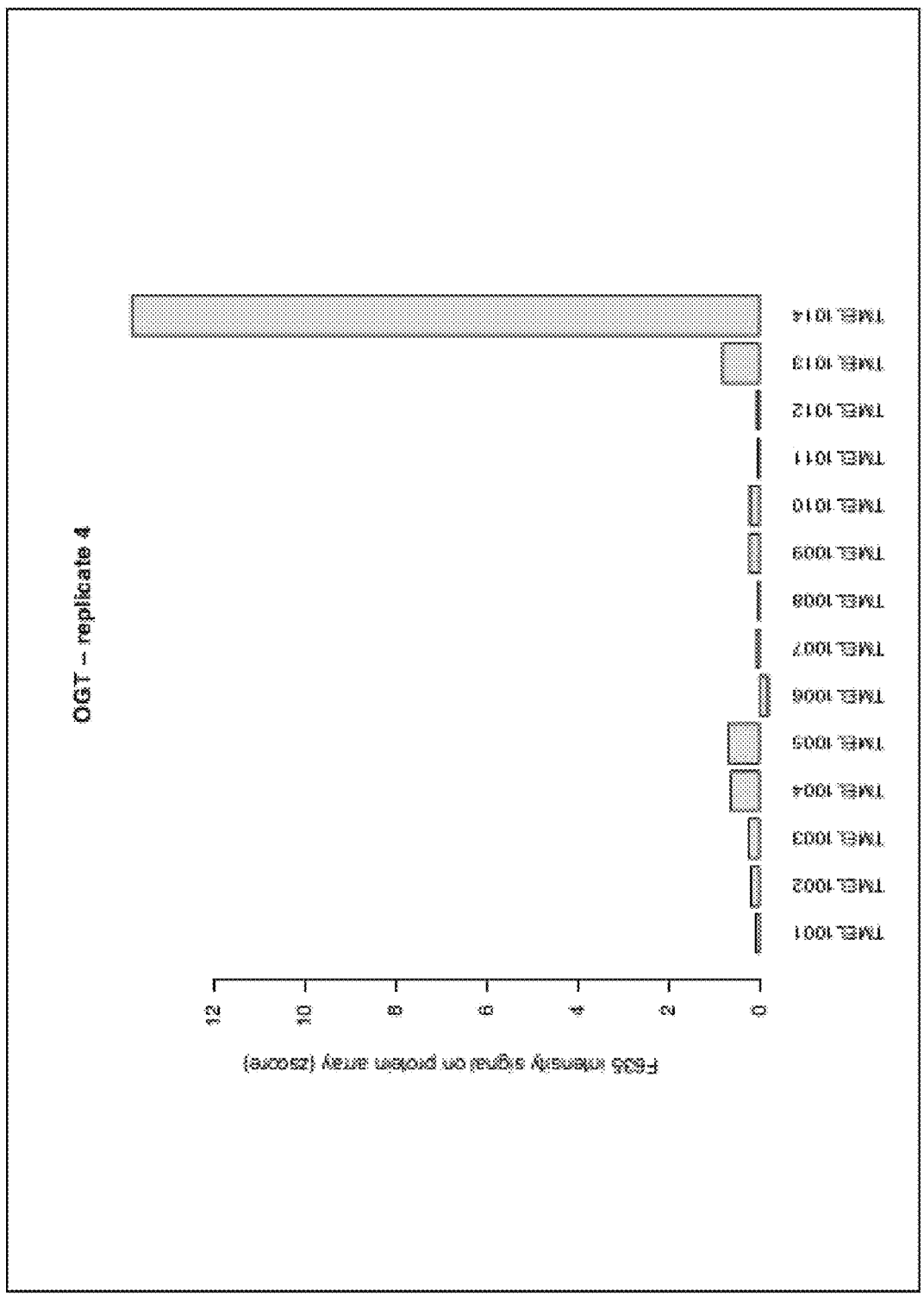
FIG. 24D shows experimental replicate 4.
Figure 24E:
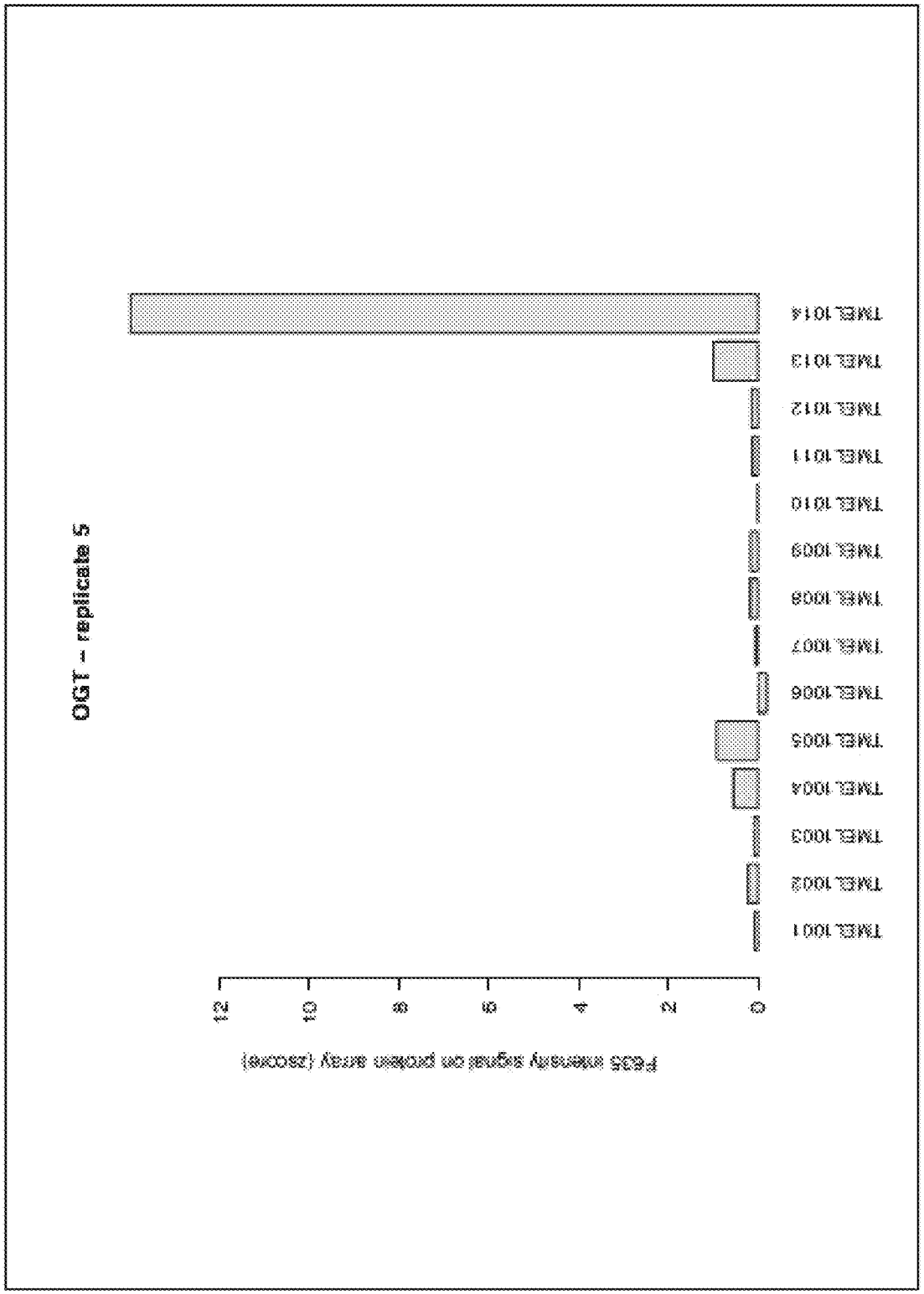

FIG. 9 illustrates detailed schema of Germline and CDR sequence identification. Once a final somatic sequence was identified in the first two steps, the reference was inputted to the IgBLAST tool to identify the closest segment ids from the IMGT database. Once the closest ids was identified, a germline sequence was generated by merging the sequences from IMGT database in V(D)JC form.

IgBLAST also reported the positions of the CDR1, CDR2 and CDR3 sequences of the exemplary antibodies. Using those positions, the somatic sequence was clipped and the CDR regions returned with their amino acid translations.

As a final step, the amino acid translation of reconstructed complete germline and somatic VDJ consensus sequences was produced.

Exemplary reconstructed amino acid and nucleic acid consensus sequences of variable heavy chain, variable light chain and their corresponding CDR3 are provided below.

Example 6: Identification of Target Cancer Antigen

Large scale protein arrays are versatile and sensitive platforms for antibody specificity evaluation. They can be used for the evaluation of protein binding or affinity reagents that are widely employed in research and clinical applications. The microarray used in our target identification experiment provides the largest number of unique, full-length, individually purified human proteins on a single microscope slide. This allows thousands of interactions to be profiled in a high-throughput manner. The hill-length recombinant proteins are expressed in the yeast S. cerevisiae, purified, and printed on glass slides in duplicate along with a set of control proteins (GST, BSA, histones, IgG, etc.). Such microarray is not restricted to a particular type of surface coating, although the default is glass coated with ultra-thin nitrocellulose film for the non-covalent, yet irreversible, capture of active proteins to the surface. Fourteen Protein arrays were used for the antibody cross-reactivity assay of the samples. The antibodies were probed at 1 µg/ml on the arrays and incubated at room temperature for 1 hour. After probing, the arrays were washed according to the protocol and probed with Alexa-647-anti-human IgG Fc gamma specific secondary antibodies under conditions optimized for signal detection. The antibody-antigen binding score was calculated for each protein represented on the array and expressed as z-scores. Results for each of the antibodies described in this document are shown in FIGS. 15A-24E.

To determine the target antigen and specificity and affinity for an identified target antigen, antibodies described herein are analyzed using the High-Spec® cross-reactivity assay on HuProt™ human proteome arrays, which contain the largest human protein collection on a single array. The HuProt™ Human Proteome Microarray allows interactions between antibodies and candidate antigen proteins to be profiled in a high-throughput manner. The full-length recombinant candidate antigen proteins are expressed in the yeast S. cerevisiae, purified, and printed on glass slides in duplicate along with a set of control proteins (GST, BSA, histones, IgG, etc.). The HuProt™ microarray is not restricted to a particular type of surface coating, although the default is glass coated with ultra-thin nitrocellulose film for the non-covalent, yet irreversible, capture of active proteins to the surface.

Antibody samples are probed on native HuProt arrays at 1 µg/ml and incubated at room temperature for 1 hour. After probing, the arrays are washed according to the standard protocols and probed with Alexa-647-anti-human IgG Fc gamma specific secondary antibodies under conditions optimized for signal detection.

Data Analysis

Non-specific hits that directly bind to the secondary antibodies are eliminated from the analysis of the samples. The specificity of each individual antibody sample to specific target antigen proteins on the array are quantified based on Z Scores.

Z score is the average Z score of the duplicate spots of a given protein (each protein is printed in duplicate on a HuProt™ array). The Z score of each spot on a given array is calculated according to the equation:

$$Z = [F635 - F635(avg)]/F635(std) \qquad \text{Equation 2.}$$

F635(avg) and F635(std) are the average and standard deviation of the F635 values of all spots on the array, respectively. S score is the difference of the Z Scores of a given protein and the one ranked next to it. If the S score of the top hit is >3, the antibody is considered as high specific against the top hit.

F635 is the average foreground signal intensity of 2 replicate spots of a given protein in the detection channel (635 nm). B635 is the average background signal intensity of 2 replicate spots of a given protein in the detection channel (635 nm). Range includes 3 numbers, the F635 values of the 2 replicate spots and the difference between them. If the difference is too high (compared to the F635 value), it indicates the 2 spots are not consistent and the hit may be less reliable. The non-specific hits bound by the secondary antibody are removed from the analysis of the samples.

TABLE 9 below lists exemplary target antigen identified for the antibodies disclosed herein.

| NO. | Antibody | Antigen hit | Specificity | Antigen name |
|---|---|---|---|---|
| 1 | TMEL1001 | INPP5D/SHIP1 | very high | Src homology 2 (SH2) domain containing inositol polyphosphate 5-phosphatase 1 (SHIP1) |
| 2 | TMEL1003 | CBX1, CBX3, CBX5 | very high | Chromobox protein homolog 1, 3, 5 |
| 3 | TMEL1005 | NY-ESO-1 | high | Cancer/Testis Antigen 1A |
| 4 | TMEL1006 | AAGAB | very high | Alpha And Gamma Adaptin Binding Protein |
| 5 | TMEL1007 | KLC4 | medium | Kinesin light chain 4 protein |
| 6 | TMEL1008 | MAGE-A3 | very high | Melanoma-associated antigen 3 |
| 7 | TMEL1010 | PPA1 | | Inorganic pyrophosphatase |
| 8 | TMEL1011 | TXLNA/IL-14A | high | interleukin-14A |
| 9 | TMEL1014 | OGT | very high | O-linked N-acetylglucosamine (GlcNAc) transferase |

TABLE 10 below lists exemplary amino acid sequences of target antigen

| Antigen name | SEQ ID NO: | NCBI reference sequence number | Amino acid sequence |
|---|---|---|---|
| human SHIP1 | 281 | NP_001017915.1 | MVPCWNHGNITRSKAEELLSRTGKDGSFLVRASESI SRAYALCVLYRNCVYTYRILPNEDDKFTVQASEGV SMRFFTKLDQLIEFYKKENMGLVTHLQYPVPLEEED TGDDPEEDTVESVVSPPELPPRNIPLTASSCEAKEVP FSNENPRATETSRPSLSETLFQRLQSMDTSGLPEEHL KAIQDYLSTQLAQDSEFVKTGSSSLPHLKKLTTLLC KELYGEVIRTLPSLESLQRLFDQQLSPGLRPRPQVPG EANPINMVSKLSQLTSLLSSIEDKVKALLHEGPESPH RPSLIPPVTFEVKAESLGIPQKMQLKVDVESGKLIIK KSKDGSEDKFYSHKKILQLIKSQKFLNKLVILVETEK EKILRKEYVFADSKKREGFCQLLQQMKNKHSEQPE PDMITIFIGTWNMGNAPPPKKITSWFLSKGQGKTRD DSADYIPHDIYVIGTQEDPLSEKEWLEILKHSLQEITS VTFKTVAIHTLWNIRIVVLAKPEHENRISHICTDNVK TGIANTLGNKGAVGVSFMFNGTSLGFVNSHLTSGSE KKLRRNQNYMNILRFLALGDKKLSPFNITHRFTHLF WFGDLNYRVDLPTWEAETIIQKIKQQQYADLLSHD QLLTERREQKVFLHFEEEEITFAPTYRFERLTRDKYA YTKQKATGMKYNLPSWCDRVLWKSYPLVHVVCQ SYGSTSDIMTSDHSPVFATFEAGVTSQFVSKNGPGT VDSQGQIEFLRCYATLKTKSQTKFYLEFHSSCLESFV KSQEGENEEGSEGELVVKFGETLPKLKPIISDPEYLL DQHILISIKSSDSDESYGEGCIALRLEATETQLPIYTP LTHHGELTGHFQGEIKLQTSQGKTREKLYDFVKTER DESSGPKTLKSLTSHDPMKQWEVTSRAPPCSGSSIT EIINPNYMGVGPFGPPMPLHVKQTLSPDQQPTAWSY DQPPKDSPLGPCRGESPPTPPGQPPISPKKFLPSTANR GLPPRTQESRPSDLGKNAGDTLPQEDLPLTKPEMFE NPLYGSLSSFPKPAPRKDQESPKMPRKEPPPCPEPGI LSPSIVLTKAQEADRGEGPGKQVPAPRLRSFTCSSSA EGRAAGGDKSQGKPKTPVSSQAPVPAKRPIKPSRSE INQQTPPTPTPRPPLPVKSPAVLHLQHSKGRDYRDN TELPHHGKHRPEEGPPGPLGRTAMQ |
| Human Chromobox protein homolog 1 | 286 | NP_001120700.1 | MGKKQNKKKVEEVLEEEEEYVVEKVLDRRVVKG KVEYLLKWKGFSDEDNTWEPEENLDCPDLIAEFLQ SQKTAHETDKSEGGKRKADSDSEDKGEESKPKKKK EESEKPRGFARGLEPERIIGATDSSGELMFLMKWKN SDEADLVPAKEANVKCPQVVISFYEERLTWHSYPSE DDDKKDDKN |
| Human Chromobox protein homolog 3 | 291 | NP_009207.2 | MASNKTTLQKMGKKQNGKSKKVEEAEPEEFVVEK VLDRRVVNGKVEYFLKWKGFTDADNTWEPEENLD CPELIEAFLNSQKAGKEKDGTKRKSLSDSESDDSKS KKKRDAADKPRGFARGLDPERIIGATDSSGELMFL MKWKDSDEADLVLAKEANMKCPQIVIAFYEERLT WHSCPEDEAQ |
| Human Chromobox protein homolog 5 | 296 | NP_001120793.1 | MGKKTKRTADSSSSEDEEEYVVEKVLDRRVVKGQ VEYLLKWKGFSEEHNTWEPEKNLDCPELISEFMKK YKKMKEGENNKPREKSESNKRKSNFSNSADDIKSK KKREQSNDIARGFERGLEPEKIIGATDSCGDLMFLM KWKDTDEADLVLAKEANVKCPQIVIAFYEERLTWH AYPEDAENKEKETAKS |

TABLE 10-continued below lists exemplary amino acid sequences of target antigen

| Antigen name | SEQ ID NO: | NCBI reference sequence number | Amino acid sequence |
|---|---|---|---|
| Human CTAG1A | 301 | NP_640343.1 | MQAEGRGTGGSTGDADGPGGPGIPDGPGGNAGGP GEAGATGGRGPRGAGAARASGPGGGAPRGPHGGAAS GLNGCCRCGARGPESRLLEFYLAMPFATPMEAELA RRSLAQDAPPLPVPGVLLKEFTVSGNILTIRLTAA DHRQLQLSISSCLQQLSLLMWITQCFLPVFLAQPPSG QRR |
| Human AAGAB | 303 | NP_001258814.1 | MILVCDRVSEDGINRQKAQEWCIKHGFELVELSPEE LPEEDDDFPESTGVKRIVQALNANVWSNVVMKND RNQGFSLLNSLTGTNHSIGSADPCHPEQPHLPAADS TESLSDHRGGASNTTDAQVDSIVDPMLDLDIQELAS LTTGGGDVENFERLFSKLKEMKDKAATLPHEQRKV HAEKVAKAFWMAIGGDRDEIEGLSSDEEH |
| Human KLC4 | 308 | NP_001275963.1 | MSGLVLGQRDEPAGHRLSQEEILGSTRLVSQGLEAL RSEHQAVLQSLSQTIECLQQGGHEEGLVHEKARQL RRSMENIELGLSEAQVMLALASHLSTVESEKQKLR AQVRRLCQENQWLRDELAGTQQRLQRSEQAVAQL EEEKKHLEFLGQLRQYDEDGHTSEEKEGDATKDSL DDLFPNEEEEDPSNGLSRGQGATAAQQGGYEIPARL RTLHNLVIQYAAQGRYEVAVPLCKQALEDLERTSG RGHPDVATMLNILALVYRDQNKYKEAAHLLNDAL SIRESTLGPDHPAVAATLNNLAVLYGKRGKYKEAE PLCQRALEIREKVLGTNHPDVAKQLNNLALLCQNQ GKYEAVERYYQRALAIYEGQLGPDNPNVARTKNN LASCYLKQGKYAEAETLYKEILTRAHVQEFGSVDD DHKPIWMHAEEREEMSKSRHHEGGTPYAEYGGWY KACKVSSPTVNTTLRNLGALYRRQGKLEAAETLEE CALRSRRQGTDPISQTKVAELLGESDGRRTSQEGPG DSVKFEGGEDASVAVEWSGDGSGTLQRSGSLGKIR DVLRRSSELLVRKLQGTEPRPSSSNMKRAASLNYLN QPSAAPLQVSRGLSASTMDLSSSS |
| Human MAGE-A3 | 313 | NP_005353.1 | MPLEQRSQHCKPEEGLEARGEALGLVGAQAPATEE QEAASSSSTLVEVTLGEVPAAESPDPPQSPQGASSLP TTMNYPLWSQSYEDSSNQEEEGPSTFPDLESEFQAA LSRKVAELVHFLLLKYRAREPVTKAEMLGSVVGN WQYFFPVIFSKASSSLQLVFGIELMEVDPIGHLYIFA TCLGLSYDGLLGDNQIMPKAGLLIIVLAIIAREGDCA PEEKIWEELSVLEVFEGREDSILGDPKKLLTQHFVQE NYLEYRQVPGSDPACYEFLWGPRALVETSYVKVLH HMVKISGGPHISYPPLHEWVLREGEE |
| Human PPA1 | 315 | NP_066952.1 | MSGFSTEERAAPFSLEYRVFLKNEKGQYISPFHDIPI YADKDVFHMVVEVPRWSNAKMEIATKDPLNPIKQ DVKKGKLRYVANLFPYKGYIWNYGAIPQTWEDPG HNDKHTGCCGDNDPIDVCEIGSKVCARGEIIGVKVL GILAMIDEGETDWKVIAINVDDPDAANYNDINDVK RLKPGYLEATVDWFRRYKVPDGKPENEFAFNAEFK DKDFAIDIIKSTHDHWKALVTKKTNGKGISCMNTTL SESPFKCDPDAARAIVDALPPPCESACTVPTDVDKW FHHQKN |
| Human IL-14A | 319 | NP_787048.1 | MKNQDKKNGAAKQSNPKSSPGQPEAGPEGAQERPS QAAPAVEAEGPGSSQAPRKPEGAQARTAQSGALRD VSEELSRQLEDILSTYCVDNNQGGPGEDGAQGEPAE PEDAEKSRTYVARNGEPEPTPVVNGEKEPSKGDPNT EEIRQSDEVGDRDHRRPQEKKKAKGLGKEITLLMQ TLNTLSTPEEKLAALCKKYAELLEEHRNSQKQMKL LQKKQSQLVQEKDHLRGEHSKAVLARSKLESLCRE LQRHNRSLKEEGVQRAREEEEKRKEVTSHFQVTLN DIQLQMEQHNERNSKLRQENMELAERLKKLIEQYE LREEHIDKVFKHKDLQQQLVDAKLQQAQEMLKEA EERHQREKDFLLKEAVESQRMCELMKQQETHLKQ QLALYTEKFEEFQNTLSKSSEVFTTFKQEMEKMTK KIKKLEKETTMYRSRWESSNKALLEMAEEKTVRDK ELEGLQVKIQRLEKLCRALQTERNDLNKRVQDLSA GGQGSLTDSGPERRPEGPGAQAPSSPRVTEAPCYPG APSTEASGQTGPQEPTSARA |
| Human OGT | 324 | NP_858058.1 | MASSVGNVADSTEPTKRMLSFQGLAELAHREYQA GDFEAAERHCMQLWRQEPDNTGVLLLLSSIHFQCR RLDRSAHFSTLAIKQNPLLAEAYSNLGNVYKERGQ LQEAIEHYRHALRLKPDFIDGYINLAAALVAAGDM |

TABLE 10-continued below lists exemplary amino acid sequences of target antigen

| Antigen name | SEQ ID NO: | NCBI reference sequence number | Amino acid sequence |
|---|---|---|---|
| | | | EGAVQAYVSALQYNPDLYCVRSDLGNLLKALGRL EEAKACYLKAIETQPNFAVAWSNLGCVFNAQGEIW LAIHHFEKAVTLDPNFLDAYINLGNVLKEARIFDRA VAAYLRALSLSPNHAVVHGNLACVYYEQGLIDLAI DTYRRAIELQPHFPDAYCNLANALKEKGSVAEAED CYNTALRLCPTHADSLNNLANIKREQGNIEEAVRLY RKALEVFPEFAAAHSNLASVLQQQGKLQEALMHY KEAIRISPTFADAYSNMGNTLKEMQDVQGALQCYT RAIQINPAFADAHSNLASIHKDSGNIPEAIASYRTAL KLKPDFPDAYCNLAHCLQIVCDWTDYDERMKKLV SIVADQLEKNRLPSVHPHHSMLYPLSHGFRKAIAER HGNLCLDKINVLHKPPYEHPKDLKLSDGRLRVGYV SSDFGNHPTSHLMQSIPGMHNPDKFEVFCYALSPDD GTNFRVKVMAEANHFIDLSQIPCNGKAADRIHQDGI HILVNMNGYTKGARNELFALRPAPIQAMWLGYPGT SGALFMDYIITDQETSPAEVAEQYSEKLAYMPHTFFI GDHANMFPHLKKKAVIDFKSNGHIYDNRIVLNGIDL KAFLDSLPDVKIVKMKCPDGGDNADSSNTALNMPV IPMNTIAEAVIEMINRGQIQITINGFSISNGLATTQINN KAATGEEVPRTIIVTTRSQYGLPEDAIVYCNFNQLY KIDPSTLQMWANILKRVPNSVLWLLRFPAVGEPNIQ QYAQNMGLPQNRIIFSPVAPKEEHVRRGQLADVCL DTPLCNGHTTGMDVLWAGTPMVTMPGETLASRVA ASQLTCLGCLELIAKNRQEYEDIAVKLGTDLEYLKK VRGKVWKQRISSPLFNTKQYTMELERLYLQMWEH YAAGNKPDHMIKPVEVTESA |

TABLE 1 lists exemplary reconstructed amino acid consensus sequences of variable heavy chain (VH) and Exemplary reconstructed amino acid consensus sequences variable light chain (VL)

| Name | Chain | SEQ ID NO: | Amino acid sequence |
|---|---|---|---|
| TMEL1001 | VH | 1 | CEVQLVESGGGLVKPGGSLRLSCAASGFTFRSYSMNWVRQ APGKGLEWVSSISSSGNYIYYADSVKGRFTLSRDNAKNSLY LQMNSLRAEDTAVYYCARGGGTSWSHYWGQGTLVTSS ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKSE |
| | VL | 15 | QFMLTQPHSVSESPGKTVTISCTRSSGSIASNYVQWYQQRP GSAPTTVIYEDNERPSGVPDRFSGSIDSSSNSASLTISGLKTE DEADYYCQSYDSNNRWVFGGGTKLTVLGQPKAAPSVTLF PPSSEELQANKATLVCLISDFYPGAVTVAWKADSSPVKAG VETTTPSKQSNNKYAASSYLSLTPEQWKSHKSYSCQVTHE GSTVEKTVAPTECS |
| TMEL1002 | VH | 2 | VVQLLESGGGLVQPGGSLRLSCAASGFTFSSYAMSWVRQA PGKGLEWVSAISGSGGSTYYADSVKGRFTISRDNSKNTLYL QMNSLRAEDTAVYYCAKDAYDSSGPDAFDIWGQGTMVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKRV |
| | VL | 16 | ASALTQPASVSGSPGQSITISCTGTSSDVGDYNYVSWYQQH PGKAPKLMIYDVSNRPSGVSNRFSGSKSGNTASLTISGLQA EDEADYYCSSYTSSSTLVFGGGTKLTVLGQPKAAPSVTLFP PSSEELQANKATLVCLISDFYPGAVTVAWKADSSPVKAGV ETTTPSKQSNNKYAASSYLSLTPEQWKSHRSYSCQVTHEGS TVEKTVAPTECS |
| TMEL1003 | VH | 3 | AVQLVQSGAEVKKPGESLRISCKGSGYSFTSYWISWVRQM PGKGLEWMGRIDPSDSYTNYSPSFQGHVTISADKSISTAYL QWSSLKTSDTAMYYCARPLQTYSIASVGHWGQGTLVTVSS GSASAPTLFPLVSCENSPSDTSSVAVGCLAQDFLPDSITFSW KYKNNSDISSTRGFPSVLRGGKYAATSQVLLPSKDVMQGT DEHVVCKVQHPNGNKEKNVPLP |
| | VL | 17 | ASALTQPASVSGSPGQSITISCTGTSSDVGSYNLVSWYQQH PGKAPKLMIYEGSKRPSGVSNRFSGSKSGNTASLTISGLQA EDEADYYCCSYAGSSTFAVFGGGTKLTVLGQPKAAPSVTL FPPSSEELQANKATLVCLISDFYPGAVTVAWKADSSPVKAG |

TABLE 1-continued lists exemplary reconstructed amino acid consensus sequences
of variable heavy chain (VH) and Exemplary reconstructed
amino acid consensus sequences variable light chain (VL)

| Name | Chain | SEQ ID NO: | Amino acid sequence |
|---|---|---|---|
| | | | VETTTPSKQSNNKYAASSYLSLTPEQWKSHRSYSCQVTHE GSTVEKTVAPTECS |
| TMEL1004 | VH | 4 | QITLKESGPTLVKPTQTLTLTCTFSGFSLNTPGVGVGWIRQP PGKALEWLALIYWDDDKRYRPSLESRLTITKDTSKNHVVL TMTNMDPVDTATYFCAHKNLQYSEWFDPWGQGTLVIVSS ASTKGPSVFPLAPCSRSTSESTAALGCLVKDYFPEPVTVSW NSGALTSGVHTFPAVLQSSGLYSLSSVVTVPSSSLGTKTYT CNVDHKPSNTKVDKRV |
| | VL | 18 | EMVLTQSPATLSLSPGERATLSCRASQSVSRNSLAWYQQRP GQTPRLLIYGASSRATGIPDRFSGSGSGTDFTLIISRLEPEDF AVYFCLQYDESPYTFGQGAKLEIKRTVAAPSVFIFPPSDEQL KSGTASVVCLLNNFYPREAKVQWKVDNALQSGNSQESVT EQDSKDSTYSLSSTLTLSKADYEKHKLYACEVTHQGLSSPV TKSFNRGEC |
| TMEL1005 | VH | 5 | PVQLQESGPGLVKPSETLSLTCTVSGGSMSIRSSYWGWIRQ SPGKGLEWIGHIFYSGSTYYNPSLQSRVTILVDTSKNQFSLR LSSVTAADTAVYYCVRSFGVARWDFWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKKV |
| | VL | 19 | DIQMTQSPSSLSASVGDRVTITCQASQNIRNYLNWYQQKPG KAPKLLIYDASNLETGVPSRFSGSGSGTDFTLTISSLQPEDIA TYYCQQYDNLLLFTFGPGTTVDIKRTVAAPSVFIFPPSDEQL KSGTASVVCLLNNFYPREAKVQWKVDNALQSGNSQESVT EQDSKDSTYSLSSTLTLSKADYEKHKVYACEVTHQGLSSP VTKSFNRGEC |
| TMEL1006 | VH | 6 | VVQLVESGGGLVQPGGSLRLSCAASGLTFRNYAMSWVRQ APGKGLEWVSAISGSGGRTHYADSVKGRFTISRDNSKNTLF LQMNSLRAEDTAVYYCAKEIGKYGTPTLFQHWGQGTLVT VSSASTKGPSVFPLAPSSKSTSGGTAALGCLVKDYFPEPVT VSWNSGALTSGVHTFPAVLQSSGLYSLSSVVTVPSSSLGTQ TYICNVNHKPSNTKVDKKV |
| | VL | 20 | DIQMTQSPSSLSASVGDRVTITCQASQDISNYLNWYQQKPG KAPKLLIYDASNLETGVPSRFSGSGSGTDFTFTISSLQPEDIA TYYCQQYDNLPITFGQGTRLEIKRTVAAPSVFIFPPSDEQLK SGTASVVCLLNNFYPREAKVQWKVDNALQSGNSQESVTE QDSKDSTYSLSSTLTLSKADYEKHKVYACEVTHQGLSSPV TKSFNRGEC |
| TMEL1007 | VH | 7 | HVHLVQSGAEVKKPGSSVKVSCTASGGSFSSNPISWVRQA PGHGLQWMGGFVPLFGTANYAPSFHGRLTITADESTSTTY MELNSLRSEDSAVYYCARDFNWNFDFWGQGTLVTVSSAS TKGPSVFPLAPSSKSTSGGTAALGCLVKDYFPEPVTVSWNS GALTSGVHTFPAVLQSSGLYSLSSVVTVPSSSLGTQTYICNV NHKPSNTKVDKSE |
| | VL | 21 | QSALTQPASVSGSPGQSITISCTGTSSDIGSYNLVSWYRQYP GKAPKLMIYEVNKRPSGVSNRFSGSKSGNTASLTISGLQAE DEADYYCCSYAGTTTFVIFGRGTKLTVLGQPKAAPSVTLFP PSSEELQANKATLVCLISDFYPGAVTVAWKADGSPVKAGV ETTTPSKQSNNKYAASSYLSLTPEQWKSHRSYSCQVTHEGS TVEKTVAPTECS |
| TMEL1008 | VH | 8 | QVQLVQSGAEVKKPGSSVKVSCKASGGTFNRDGIIWVRQA PGQGLEWMGRIIPILGIANYAQKFQGRVTIIADKSTSTAYM ELSSLRSEDTAVYYCARESEVGRGMDVWGQGTTVTVSSAS TKGPSVFPLAPSSKSTSGGTAALGCLVKDYFPEPVTVSWNS GALTSGVHTFPAVLQSSGLYSLSSVVTVPSSSLGTQTYICNV NHKPSNTKVDKSE |
| | VL | 22 | ASALTQPASVSGSPGQSITISCTGTSSDVGDYNYVSWYQQH PGKAPKLMIYDVSNRPSGVSHRFSGSKSGNTASLTISGLQA EDEADYYCSSYTISSTLGVFGPGTKVTVLGQPKANPTVTLF PPSSEELQANKATLVCLISDFYPGAVTVAWKADGSPVKAG VETTKPSKQSNNKYAASSYLSLTPEQWKSHRSYSCQVTHE GSTVEKTVAPTECS |

TABLE 1-continued lists exemplary reconstructed amino acid consensus sequences
of variable heavy chain (VH) and Exemplary reconstructed
amino acid consensus sequences variable light chain (VL)

| Name | Chain | SEQ ID NO: | Amino acid sequence |
|------|-------|------------|---------------------|
| TMEL1009 | VH | 9 | PVQLVQSGAEVKKPGSSVKVSCRASGGTFSNYGLNWVRQ APGQGLEWMGGIIPIFGSVNYAQKFQDRVTITADESTSTTY MDLNSLRSEDTAVYYCATERGHNMERAFDFWGQGTLVTV SSASTKGPSVFPLAPSSKSTSGGTAALGCLVKDYFPEPVTVS WNSGALTSGVHTFPAVLQSSGLYSLSSVVTVPSSSLGTQTY ICNVNHKPSNTKVDKKV |
| | VL | 23 | DIQMTQSPSTLSASVGDRVTITCRASQSIRRWLAWYQQKPG KAPKLLIYDASSLESGVPSRFSGSGSGTEFTLTISSLQPDDFA TYYCQQYNSYSYTFGQGTKLEIKRTVAAPSVFIFPPSDEQL KSGTASVVCLLNNFYPREAKVQWKVDNALQSGNSQESVT EQDSKDSTYSLSSTLTLSKADYEKHKVYACEVTHQGLSSP VTKSFNRGEC |
| TMEL1010 | VH | 10 | QVQLVQSGAEVKKPGASVKVSCKASGYTFSSYGISWVRQA PGQGLEWMGWISAYNGNTNYAKKLQGRVTMTTDTSTSTA YLELRSLRSDDTAVYYCARGDGPFDYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKKV |
| | VL | 24 | EIVMTQSPATLSVSPGERATLSCWASQSVSSSLAWYQQKP GQAPRLLMYGASNRATGIPARFSGSGSGTEFTLTISSLQSED FAVYYCQQYNKWPPDTFGQGTKLEIKRTVAAPSVFIFPPSD EQLKSGTASVVCLLNNFYPREAKVQWKVDNALQSGNSQE SVTEQDSKDSTYSLSSTLTLSKADYEKHKVYACEVTHQGL SSPVTKSFNRGEC |
| TMEL1011 | VH | 11 | PVQLVQSGAEVKKPGSSVKVSCKASGGTFSSYSFNWVRQA PGQGLEWMARIIPILGLANYAQKFQGRVTLTADESTSTAY MELSSLRSEDTAIFYCAGMVLGQLGFDPWGQGTLVTVSSA STKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKKV |
| | VL | 25 | QFMLTQPHSVSESPGRTVTISCTRSSGSIARNYVHWYQHRP GSSPTTVIYEDDQRPSGVPDRFSGSIDSSSNSASLTISGLKPE DEADYFCQSYDSNIWVFGGGTKLTVLGQPKAAPSVTLFPPS SEELQANKATLVCLISDFYPGAVTVAWKADSSPVKAGVET TTPSKQSNNKYAASSYLSLTPEQWKSHKSYSCQVTHEGST VEKTVAPTECS |
| TMEL1012 | VH | 12 | PLQLQESGPGLVKPSETLSLTCTVSGDSITTTYYWGWIRQPP GKGLEWIASIYFTGSTFHNPSLKSRVTMSVDTSKNQFSLNL SSVTAADTAVYYCARRVGNWNYVWFDPWGQGTLVSVSS ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKV |
| | VL | 26 | AYVLTQPPSVSVAPGQTARMTCGGNNIGSKSVHWYRQRP GQAPVLVVYDDTDRPSGIPERFSGSNSGNTATLTISRVEAG DEADYYCQVWDTNSDHVVFGGGTKLTVLGQPKAAPSVTL FPPSSEELQANKATLVCLISDFYPGAVTVAWKADSSPVKAG VETTTPSKQSNNKYAASSYLSLTPEQWKSHRSYSCQVTHE GSTVEKTVAPTECS |
| TMEL1013 | VH | 13 | PVQLVQSGAEVKKPGSSVKVSCKASGGTFSSYTINWVRQA PGQGLEWMGRIIPILGVANYAQKFQGRVTITADKSTSTAY MDLSSLRSEDTAVYYCAREWERAFDYWGQGTLVTVSSAS TKGPSVFPLAPSSKSTSGGTAALGCLVKDYFPEPVTVSWNS GALTSGVHTFPAVLQSSGLYSLSSVVTVPSSSLGTQTYICNV NHKPSNTKVDKKV |
| | VL | 27 | EIVLTQSPGTLSLSPGERATLSCRASQSVSSSYLAWYQQKP GQAPRLLIYGASSRATGIPDRFSGSGSGTDFTLTISRLEPEDF AVYYCQQYGNSPYTFGQGTKLEIKRTVAAPSVFIFPPSDEQ LKSGTASVVCLLNNFYPREAKVQWKVDNALQSGNSQESV TEQDSKDSTYSLSSTLTLSKADYEKHKVYACEVTHQGLSSP VTKSFNRGEC |
| TMEL1014 | VH | 14 | SVQLVESGGGVVQPGRSLRLSCAASGFTFSSYTMHWVRQA PGKGLEWVALISYDGSNKYYADSVKGRFTISRDNPKNTLY LQMNSLRVEDTAVYYCARDWTLGYWGQGTLVTVSSAST KGPSVFPLAPCSRSTSESTAALGCLVKDYFPEPVTVSWNSG ALTSGVHTFPAVLQSSGLYSLSSVVTVTSSNFGTQTYTCNV DHKPSNTKVDKTV |

TABLE 1-continued lists exemplary reconstructed amino acid consensus sequences of variable heavy chain (VH) and Exemplary reconstructed amino acid consensus sequences variable light chain (VL)

| Name | Chain | SEQ ID NO: | Amino acid sequence |
|---|---|---|---|
| | VL | 28 | VSSELTQDPAVSVALGQTVRITCQGDSLRNYYANWYQQKP GQAPILVIYDKNNRPSGIPDRFSGSSSGNTASLTITGAQAED EADYYCNSRDSSGYHLVFGGGTKLTVLGQPKAAPSVTLFP PSSEELQANKATLVCLISDFYPGAVTVAWKADSSPVKAGV ETTTPSKQSNNKYAASSYLSLTPEQWKSHRSYSCQVTHEGS TVEKTVAPTECS |

TABLE 2 below lists exemplary reconstructed amino acid consensus sequences of complementarity-determining region 3 from a variable heavy chain (CDR-H3) and exemplary reconstructed amino acid consensus sequences of complementarity-determining region from a variable light chain (CDR-L3)

| Name | Complementarity-determining region and Chain | SEQ ID NO: | Amino acid sequence of complementarity-determining region |
|---|---|---|---|
| TMEL1001 | CDR-H3 | 29 | ARGGGTSWSHY |
| | CDR-L3 | 43 | QSYDSNNRWV |
| TMEL1002 | CDR-H3 | 30 | AKDAYDSSGPDAFDI |
| | CDR-L3 | 44 | SSYTSSSTLV |
| TMEL1003 | CDR-H3 | 31 | ARPLQTYSIASVGH |
| | CDR-L3 | 45 | CSYAGSSTFAV |
| TMEL1004 | CDR-H3 | 32 | AHKNLQYSEWFDP |
| | CDR-L3 | 46 | LQYDESPYT |
| TMEL1005 | CDR-H3 | 33 | ARPEGSGYSADAFDI |
| | CDR-L3 | 47 | QQYDNLLLFT |
| TMEL1006 | CDR-H3 | 34 | AKEIGKYGTPTLFQH |
| | CDR-L3 | 48 | QQYDNLPIT |
| TMEL1007 | CDR-H3 | 35 | ARDFNWNFDF |
| | CDR-L3 | 49 | CSYAGTTTFVI |
| TMEL1008 | CDR-H3 | 36 | ARESEVGRGMDV |
| | CDR-L3 | 50 | SSYTISSTLGV |
| TMEL1009 | CDR-H3 | 37 | ATERGHNMERAFDF |
| | CDR-L3 | 51 | QQYNSYSYT |
| TMEL1010 | CDR-H3 | 38 | ARGDGPFDY |
| | CDR-L3 | 52 | QQYNKWPPDT |
| TMEL1011 | CDR-H3 | 39 | AGMVLGQLGFDP |
| | CDR-L3 | 53 | QSYDSNIWV |
| TMEL1012 | CDR-H3 | 40 | ARRVGNWNYVWFDP |
| | CDR-L3 | 54 | QVWDTNSDHVV |
| TMEL1013 | CDR-H3 | 41 | AREWERAFDY |
| | CDR-L3 | 55 | QQYGNSPYT |
| TMEL1014 | CDR-H3 | 42 | ARDWTLGY |
| | CDR-L3 | 56 | NSRDSSGYHLV |
| TMEL1001 | CDR-H2 | 57 | ISSSGNYI |
| | CDR-L2 | 71 | EDN |
| TMEL1002 | CDR-H2 | 58 | ISGSGGST |
| | CDR-L2 | 72 | DVS |
| TMEL1003 | CDR-H2 | 59 | IDPSDSYT |
| | CDR-L2 | 73 | EGS |

TABLE 2-continued below lists exemplary reconstructed amino acid consensus sequences of complementarity-determining region 3 from a variable heavy chain (CDR-H3) and exemplary reconstructed amino acid consensus sequences of complementarity-determining region from a variable light chain (CDR-L3)

| Name | Complementarity-determining region and Chain | SEQ ID NO: | Amino acid sequence of complementarity-determining region |
|---|---|---|---|
| TMEL1004 | CDR-H2 | 60 | IYWDDDK |
| | CDR-L2 | 74 | GAS |
| TMEL1005 | CDR-H2 | 61 | IFYSGST |
| | CDR-L2 | 75 | DAS |
| TMEL1006 | CDR-H2 | 62 | ISGSGGRT |
| | CDR-L2 | 76 | DAS |
| TMEL1007 | CDR-H2 | 63 | FVPLFGTA |
| | CDR-L2 | 77 | EVN |
| TMEL1008 | CDR-H2 | 64 | IIPILGIA |
| | CDR-L2 | 78 | DVS |
| TMEL1009 | CDR-H2 | 65 | IIPIFGSV |
| | CDR-L2 | 79 | DAS |
| TMEL1010 | CDR-H2 | 66 | ISAYNGNT |
| | CDR-L2 | 80 | GAS |
| TMEL1011 | CDR-H2 | 67 | IIPILGLA |
| | CDR-L2 | 81 | EDD |
| TMEL1012 | CDR-H2 | 68 | IYFTGST |
| | CDR-L2 | 82 | DDT |
| TMEL1013 | CDR-H2 | 69 | IIPILGVA |
| | CDR-L2 | 83 | GAS |
| TMEL1014 | CDR-H2 | 70 | ISYDGSNK |
| | CDR-L2 | 84 | DKN |
| TMEL1001 | CDR-H1 | 85 | GFTFRSYS |
| | CDR-L1 | 99 | SGSIASNY |
| TMEL1002 | CDR-H1 | 86 | GFTFSSYA |
| | CDR-L1 | 100 | SSDVGDYNY |
| TMEL1003 | CDR-H1 | 87 | GYSFTSYW |
| | CDR-L1 | 101 | SSDVGSYNL |
| TMEL1004 | CDR-H1 | 88 | GFSLNTPGVG |
| | CDR-L1 | 102 | QSVSRNS |
| TMEL1005 | CDR-H1 | 89 | GGSMSIRSSY |
| | CDR-L1 | 103 | QNIRNY |
| TMEL1006 | CDR-H1 | 90 | GLTFRNYA |
| | CDR-L1 | 104 | QDISNY |
| TMEL1007 | CDR-H1 | 91 | GGSFSSNP |
| | CDR-L1 | 105 | SSDIGSYNL |
| TMEL1008 | CDR-H1 | 92 | GGTFNRDG |
| | CDR-L1 | 106 | SSDVGDYNY |
| TMEL1009 | CDR-H1 | 93 | GGTFSNYG |
| | CDR-L1 | 107 | QSIRRW |
| TMEL1010 | CDR-H1 | 94 | GYTFSSYG |
| | CDR-L1 | 108 | QSVSSS |
| TMEL1011 | CDR-H1 | 95 | GGTFSSYS |
| | CDR-L1 | 109 | SGSIARNY |
| TMEL1012 | CDR-H1 | 96 | GDSITTTYY |
| | CDR-L1 | 110 | NIGSKS |

TABLE 2-continued below lists exemplary reconstructed amino acid consensus sequences of complementarity-determining region 3 from a variable heavy chain (CDR-H3) and exemplary reconstructed amino acid consensus sequences of complementarity-determining region from a variable light chain (CDR-L3)

| Name | Complementarity-determining region and Chain | SEQ ID NO: | Amino acid sequence of complementarity-determining region |
|---|---|---|---|
| TMEL1013 | CDR-H1 | 97 | GGTFSSYT |
|  | CDR-L1 | 111 | QSVSSSY |
| TMEL1014 | CDR-H1 | 98 | GFTFSSYT |
|  | CDR-L1 | 112 | SLRNYY |

TABLE 3 below lists exemplary reconstructed nucleic acid consensus sequences of variable heavy chain (VH) and exemplary reconstructed nucleic acid consensus sequences of variable light chain (VL)

| Name | Chain | SEQ ID No | Nucleic acid sequence |
|---|---|---|---|
| TMEL1001 | VH | 113 | GTGTGAGGTGCAGCTGGTGGAGTCTGGGGGAGGCCTGGTCAA GCCTGGGGGGTCCCTGAGACTCTCCTGTGCAGCCTCTGGATTC ACCTTCAGGAGCTATAGCATGAACTGGGTCCGCCAGGCTCCA GGGAAGGGGCTGGAGTGGGTCTCATCCATTAGTAGTAGTGGT AATTACATATACTACGCAGACTCAGTGAAGGGCCGATTCACC CTCTCCAGAGACAACGCCAAGAACTCACTGTATCTGCAAATG AACAGCCTGAGAGCCGAGGACACGGCTGTGTATTACTGTGCG AGAGGTGGGGTACCAGCTGGTCGCATTACTGGGGCCAGGGA ACCCTGGTCACCGTCTCCTCAGCCTCCACCAAGGGCCCATCG GTCTTCCCCCTGGCACCCTCCTCCAAGAGCACCTCTGGGGGCAC AGCGGCCCTGGGCTGCCTGGTCAAGGACTACTTCCCCGAACC GGTGACGGTGTCGTGGAACTCAGGCGCCCTGACCAGCGGCGT GCACACCTTCCCGGCTGTCCTACAGTCCTCAGGACTCTACTCC CTCAGCAGCGTGGTGACCGTGCCCTCCAGCAGCTTGGGCACC CAGACCTACATCTGCAACGTGAATCACAAGCCCAGCAACACC AAGGTGGACAAGAGTGAG |
|  | VL | 127 | CAATTTATGCTGACTCAGCCCCACTCTGTGTCGGAGTCTCCGG GGAAGACGGTAACCATCTCCTGCACCCGCAGCAGTGGCAGCA TTGCCAGCAACTATGTGCAGTGGTACCAGCAGCGCCCGGGCA GTGCCCCCACCACTGTGATCTATGAGGATAACGAAAGACCCT CTGGGGTCCCTGATCGGTTCTCTGGCTCCATCGACAGCTCCTC CAACTCTGCCTCCCTCACCATCTCTGGACTGAAGACTGAGGAC GAGGCTGACTACTACTGTCAGTCTTATGATAGCAACAATCGTT GGGTGTTCGGCGGAGGGACCAAGCTGACCGTCCTAGGTCAGC CCAAGGCTGCCCCCTCGGTCACTCTGTTCCCACCCTCCTCTGA GGAGCTTCAAGCCAACAAGGCCACACTGGTGTGTCTCATAAG TGACTTCTACCCGGGAGCCGTGACAGTGGCCTGGAAGGCAGA TAGCAGCCCCGTCAAGGCGGGAGTGGAGACCACCACACCCTC CAAACAAAGCAACAACAAGTACGCGGCCAGCAGCTACCTGA GCCTGACGCCTGAGCAGTGGAAGTCCCACAAAAGCTACAGCT GCCAGGTCACGCATGAAGGGAGCACCGTGGAGAAGACAGTG GCCCCTACAGAATGTTCA |
| TMEL1002 | VH | 114 | GTGGTGCAGCTGTTGGAGTCTGGGGGAGGCTTGGTACAGCCT GGGGGGTCCCTGAGACTCTCCTGTGCAGCCTCTGGATTCACCT TTAGCAGCTATGCCATGAGCTGGGTCCGCCAGGCTCCAGGGA AGGGGCTGGAGTGGGTCTCAGCTATTAGTGGTAGTGGTGGTA GCACATACTACGCAGACTCCGTGAAGGGCCGGTTCACCATCT CCAGAGACAATTCCAAGAACACGCTGTATCTGCAAATGAACA GCCTGAGAGCCGAGGACACGGCCGTATATTACTGTGCGAAAG ATGCATATGATAGTAGTGGCCCAGATGCTTTTGATATCTGGGG CCAAGGGACAATGGTCACCGTCTCCTCAGCCTCCACCAAGGG CCCATCGGTCTTCCCCCTGGCACCCTCCTCCAAGAGCACCTCT GGGGGCACAGCGGCCCTGGGCTGCCTGGTCAAGGACTACTTC CCCGAACCGGTGACGGTGTCGTGGAACTCAGGCGCCCTGACC AGCGGCGTGCACACCTTCCCGGCTGTCCTACAGTCCTCAGGAC TCTACTCCCTCAGCAGCGTGGTGACCGTGCCCTCCAGCAGCTT GGGCACCCAGACCTACATCTGCAACGTGAATCACAAGCCCAG CAACACCAAGGTGGACAAGAGAGTG |
|  | VL | 128 | GCCTCTGCCCTGACTCAGCCTGCCTCCGTGTCTGGGTCTCCTG GACAGTCGATCACCATCTCCTGCACTGGAACCAGCAGTGACG |

TABLE 3-continued below lists exemplary reconstructed nucleic acid consensus sequences of variable heavy chain (VH) and exemplary reconstructed nucleic acid consensus sequences of variable light chain (VL)

| Name | Chain | SEQ ID No | Nucleic acid sequence |
|---|---|---|---|
| | | | TTGGTGATTATAACTATGTCTCCTGGTACCAACAGCACCCAGG<br>CAAAGCCCCCAAACTCATGATTTATGATGTCAGTAATCGGCCC<br>TCAGGGGTTTCTAATCGCTTCTCTGGCTCCAAGTCTGGCAACA<br>CGGCCTCCCTGACCATCTCTGGGCTCCAGGCTGAGGACGAGG<br>CTGATTATTACTGCAGCTCATATACAAGCAGCAGCACTCTTGT<br>ATTCGGCGGAGGGACCAAGCTGACCGTCCTAGGTCAGCCCAA<br>GGCTGCCCCCTCGGTCACTCTGTTCCCGCCCTCCTCTGAGGAG<br>CTTCAAGCCAACAAGGCCACACTGGTGTGTCTCATAAGTGAC<br>TTCTACCCGGGAGCCGTGACAGTGGCCTGGAAGGCAGATAGC<br>AGCCCCGTCAAGGCGGGAGTGGAGACCACCACACCCTCCAAA<br>CAAAGCAACAACAAGTACGCGGCCAGCAGCTATCTGAGCCTG<br>ACGCCTGAGCAGTGGAAGTCCCACAGAAGCTACAGCTGCCAG<br>GTCACGCATGAAGGGAGCACCGTGGAGAAGACAGTGGCCCCT<br>ACAGAATGTTCA |
| TMEL1003 | VH | 115 | GCCGTGCAGCTGGTGCAGTCCGGAGCAGAGGTGAAAAAGCCC<br>GGGGAGTCTCTGAGGATCTCCTGTAAGGGTTCTGGATACAGC<br>TTTACCAGCTACTGGATCAGCTGGGTGCGCCAGATGCCCGGG<br>AAAGGCCTGGAGTGGATGGGGAGGATTGATCCTAGTGACTCT<br>TATACCAACTACAGCCCGTCCTTCCAAGGCCACGTCACCATCT<br>CAGCTGACAAGTCCATCAGCACTGCCTACCTACAGTGGAGCA<br>GCCTGAAGACCTCGGACACCGCCATGTATTACTGTGCGAGAC<br>CGCTACAAACTTATAGTATAGCATCAGTAGGACACTGGGGCC<br>AGGGAACCCTGGTCACCGTCTCCTCAGGGAGTGCATCCGCCC<br>CAACCCTTTTCCCCCTCGTCTCCTGTGAGAATTCCCCGTCGGA<br>TACGAGCAGCGTGGCCGTTGGCTGCCTCGCACAGGACTTCCTT<br>CCCGACTCCATCACTTTCTCCTGGAAATACAAGAACAACTCTG<br>ACATCAGCAGCACCCGGGGCTTCCCATCAGTCCTGAGAGGGG<br>GCAAGTACGCAGCCACCTCACAGGTGCTGCTGCCTTCCAAGG<br>ACGTCATGCAGGGCACAGACGAACACGTGGTGTGCAAAGTCC<br>AGCACCCCAACGGCAACAAAGAAAAGAACGTGCCTCTTCCG |
| | VL | 129 | GCCTCTGCCCTGACTCAGCCTGCCTCCGTGTCTGGGTCTCCTG<br>GACAGTCGATCACCATCTCCTGCACTGGAACCAGCAGTGATG<br>TTGGGAGTTATAACCTTGTCTCCTGGTACCAACAGCACCCAGG<br>CAAAGCCCCCAAACTCATGATTTATGAGGGCAGTAAGCGGCC<br>CTCAGGGGTTTCTAATCGCTTCTCTGGCTCCAAGTCTGGCAAC<br>ACGGCCTCCCTGACAATCTCTGGGCTCCAGGCTGAGGACGAG<br>GCTGATTATTACTGCTGCTCATATGCAGGTAGTAGCACTTTCG<br>CGGTATTCGGCGGAGGGACCAAGCTGACCGTCCTAGGTCAGC<br>CCAAGGCTGCCCCCTCGGTCACTCTGTTCCCGCCCTCCTCTGA<br>GGAGCTTCAAGCCAACAAGGCCACACTGGTGTGTCTCATAAG<br>TGACTTCTACCCGGGAGCCGTGACAGTGGCCTGGAAGGCAGA<br>TAGCAGCCCCGTCAAGGCGGGAGTGGAGACCACCACACCCTC<br>CAAACAAAGCAACAACAAGTACGCGGCCAGCAGCTACCTGA<br>GCCTGACGCCTGAGCAGTGGAAGTCCCACAGAAGCTACAGCT<br>GCCAGGTCACGCATGAAGGGAGCACCGTGGAGAAGACAGTG<br>GCCCCTACAGAATGTTCA |
| TMEL1004 | VH | 116 | CCCAGATCACCTTGAAGGAGTCTGGTCCGACGCTGGTGAAGC<br>CCACACAGACCCTCACGCTGACCTGCACCTTCTCTGGGTTCTC<br>ACTCAACACTCCTGGAGTGGGTGTGGGCTGGATCCGTCAGCC<br>CCCAGGAAAGGCCCTGGAATGGCTTGCACTCATTTATTGGGA<br>TGATGATAAGCGCTACAGGCCATCTCTGGAGAGCAGGCTCAC<br>CATCACCAAGGACACCTCCAAAAACCACGTTGTCCTTACGAT<br>GACCAACATGGACCCTGTGGACACAGCCACATATTTTTGTGC<br>ACACAAGAACCTTCAGTATTCGGAATGGTTCGACCCCTGGGG<br>CCAGGGCACCCTGGTCATTGTCTCCTCAGCCTCCACCAAGGGC<br>CCATCGGTCTTCCCCCTGGCGCCCTGCTCCAGGAGCACCTCCG<br>AGAGCACAGCGGCCCTGGGCTGCCTGGTCAAGGACTACTTCC<br>CCGAACCGGTGACGGTGTCGTGGAACTCAGGCGCCCTGACCA<br>GCGGCGTGCACACCTTCCCGGCTGTCCTACAGTCCTCAGGACT<br>CTACTCCCTCAGCAGCGTGGTGACCGTGCCCTCCAGCAGCTTG<br>GGCACGAAGACCTACACCTGCAATGTAGATCACAAGCCCAGC<br>AACACCAAGGTGGACAAGAGAGTT |
| | VL | 130 | GAAATGGTGTTGACGCAGTCTCCAGCCACCCTGTCTTTGTCTC<br>CAGGGGAAAGAGCCACCCTCTCCTGCAGGGCCAGTCAGAGTG<br>TTAGCAGAAACTCCTTAGCCTGGTACCAGCAGAGACCTGGCC<br>AGACTCCCAGGCTCCTCATCTATGGTGCCTCCAGCAGGGCCAC<br>TGGCATCCCAGACAGGTTCAGTGGCAGTGGGTCTGGGACAGA<br>CTTCACTCTCATCATCAGCAGACTGGAGCCTGAAGATTTTGCA<br>GTGTATTTCTGTCTCCAGTATGATGAGTCACCGTACACTTTTG<br>GCCAGGGGGCCAAGCTGGAGATCAAACGAACTGTGGCTGCAC<br>CATCTGTCTTCATCTTCCCGCCATCTGATGAGCAGTTGAAATC |

TABLE 3-continued below lists exemplary reconstructed nucleic acid consensus sequences of variable heavy chain (VH) and exemplary reconstructed nucleic acid consensus sequences of variable light chain (VL)

| Name | Chain | SEQ ID No | Nucleic acid sequence |
|---|---|---|---|
| | | | TGGAACTGCCTCTGTTGTGTGCCTGCTGAATAACTTCTATCCC AGAGAGGCCAAAGTACAGTGGAAGGTGGATAACGCCCTCCA ATCGGGTAACTCCCAGGAGAGTGTCACAGAGCAGGACAGCAA GGACAGCACCTACAGCCTCAGCAGCACCCTGACGCTGAGCAA AGCAGACTACGAGAAACACAAACTCTACGCCTGCGAAGTCAC CCATCAGGGCCTGAGCTCGCCCGTCACAAAGAGCTTCAACAG GGGAGAGTGT |
| TMEL1005 | VH | 117 | CCCGTGCAGCTGCAGGAGTCGGGCCCAGGACTGGTGAAGCCT TCGGAGACCCTGTCCCTCACCTGCACTGTCTCTGGTGGCTCCA TGAGCATTAGGAGTTCCTACTGGGGCTGGATCCGCCAGTCAC CAGGGAAGGGGCTGGAGTGGATTGGGCATATATTTTATAGTG GGAGCACCTACTACAACCCGTCCCTCCAGAGTCGAGTCACAA TATTAGTAGACACGTCCAAGAACCAATTCTCCCTGAGGCTGA GCTCTGTGACCGCAGCGGACACGGCCGTGTATTACTGTGTGA GAAGTTTTGGCGTGGCTCGATGGGACTTCTGGGGCCAGGGAA CCCTGGTCACCGTCTCCTCAGCCTCCACCAAGGGCCCATCGGT CTTCCCCCTGGCACCCTCCTCCAAGAGCACCTCTGGGGGCACA GCGGCCCTGGGCTGCCTGGTCAAGGACTACTTCCCCGAACCG GTGACGGTGTCGTGGAACTCAGGCGCCCTGACCAGCGGCGTG CACACCTTCCCGGCTGTCCTACAGTCCTCAGGACTCTACTCCC TCAGCAGCGTGGTGACCGTGCCCTCCAGCAGCTTGGGCACCC AGACCTACATCTGCAACGTGAATCACAAGCCCAGCAACACCA AGGTGGACAAGAAGGTG |
| | VL | 131 | GTGACATCCAGATGACCCAGTCTCCATCCTCCCTGTCTGCATC TGTAGGAGACAGAGTCACCATCACTTGCCAGGCGAGTCAGAA CATTAGGAATTATTTAAATTGGTATCAGCAGAAACCAGGGAA AGCCCCTAAGCTCCTGATCTACGATGCATCCAATTTGGAAACA GGGGTCCCATCAAGGTTCAGTGGAAGTGGATCTGGGACAGAT TTTACTCTCACCATCAGCAGCCTGCAGCCTGAAGATATTGCAA CATATTACTGTCAACAGTATGATAATCCTCCTATTCACTTTC GGCCCTGGGACCACAGTTGATATCAAACGAACTGTGGCTGCA CCATCTGTCTTCATCTTCCCGCCATCTGATGAGCAGTTGAAAT CTGGAACTGCCTCTGTTGTGTGCCTGCTGAATAACTTCTATCC CAGAGAGGCCAAAGTACAGTGGAAGGTGGATAACGCCCTCCA ATCGGGTAACTCCCAGGAGAGTGTCACAGAGCAGGACAGCAA GGACAGCACCTACAGCCTCAGCAGCACCCTGACGCTGAGCAA AGCAGACTACGAGAAACACAAAGTCTACGCCTGCGAAGTCAC CCATCAGGGCCTGAGCTCGCCCGTCACAAAGAGCTTCAACAG GGGAGAGTGT |
| TMEL1006 | VH | 118 | GTGGTGCAGCTGGTGGAGTCTGGGGGAGGCTTGGTACAGCCG GGGGGGTCCCTGAGACTCTCCTGTGCGGCCTCCGGATTAACCT TTCGCAACTACGCCATGAGCTGGGTCCGCCAGGCTCCAGGGA AGGGACTGGAGTGGGTCTCAGCTATTAGTGGTAGTGGTGGTC GCACACACTACGCAGACTCCGTGAAGGGCCGCTTCACCATCT CCAGAGACAATTCCAAGAACACGCTGTTTCTGCAAATGAACA GCCTGAGAGCCGAGGACACGGCCGTATATTACTGTGCGAAAG AGATTGGAAAATACGGGACTCCTACTCTTTTCCAGCACTGGG GCCAGGGCACCCTGGTCACCGTCTCCTCAGCCTCCACCAAGG GCCCATCGGTCTTCCCCCTGGCACCCTCCTCCAAGAGCACCTC TGGGGGCACAGCGGCCCTGGGCTGCCTGGTCAAGGACTACTT CCCCGAACCGGTGACGGTGTCGTGGAACTCAGGCGCCCTGAC CAGCGGCGTGCACACCTTCCCGGCTGTCCTACAGTCCTCAGGA CTCTACTCCCTCAGCAGCGTGGTGACCGTGCCCTCCAGCAGCT TGGGCACCCAGACCTACATCTGCAACGTGAATCACAAGCCCA GCAACACCAAGGTGGACAAGAAGGTG |
| | VL | 132 | GTGACATCCAGATGACCCAGTCTCCATCCTCCCTGTCTGCATC TGTAGGAGACAGAGTCACCATCACTTGCCAGGCGAGTCAGGA CATTAGCAACTATTTAAATTGGTATCAACAAAAACCAGGGAA AGCCCCTAAACTCCTGATCTACGATGCATCCAATTTGGAAACA GGGGTCCCATCAAGGTTCAGTGGAAGTGGATCTGGGACAGAT TTTACTTTCACCATCAGCAGCCTGCAGCCTGAAGATATTGCAA CATATTACTGTCAACAGTATGATAATCTCCCGATCACCTTCGG CCAAGGGACACGACTGGAGATTAAACGAACTGTGGCTGCACC ATCTGTCTTCATCTTCCCGCCATCTGATGAGCAGTTGAAATCT GGAACTGCCTCTGTTGTGTGCCTGCTGAATAACTTCTATCCCA GAGAGGCCAAAGTACAGTGGAAGGTGGATAACGCCCTCCAAT CGGGTAACTCCCAGGAGAGTGTCACAGAGCAGGACAGCAAG GACAGCACCTACAGCCTCAGCAGCACCCTGACGCTGAGCAAA GCAGACTACGAGAAACACAAAGTCTACGCCTGCGAAGTCACC CATCAGGGCCTGAGCTCGCCCGTCACAAAGAGCTTCAACAGG GGAGAGTGT |

TABLE 3-continued below lists exemplary reconstructed nucleic acid consensus sequences of variable heavy chain (VH) and exemplary reconstructed nucleic acid consensus sequences of variable light chain (VL)

| Name | Chain | SEQ ID No | Nucleic acid sequence |
|---|---|---|---|
| TMEL1007 | VH | 119 | CACGTGCATCTGGTGCAGTCTGGGGCTGAGGTGAAGAAACCT GGGTCCTCGGTGAAGGTCTCCTGCACGGCTTCTGGAGGCTCCT TCAGCAGTAATCCAATCAGCTGGGTGCGTCAGGCCCCTGGAC ACGGGCTTCAGTGGATGGGAGGATTCGTCCCTCTCTTTGGTAC AGCAAACTACGCACCGAGTTTCCACGGCAGACTCACGATTAC CGCGGACGAATCCACGAGCACAACTTACATGGAACTGAATAG CCTGAGATCTGAGGACTCGGCCGTCTATTATTGTGCGAGAGAT TTTAACTGGAACTTCGACTTCTGGGGCCAGGGAACCCTGGTCA CCGTCTCCTCGGCCTCCACCAAGGGCCCATCGGTCTTCCCCCT GGCACCCTCCTCCAAGAGCACCTCTGGGGGCACAGCGGCCCT GGGCTGCCTGGTCAAGGACTACTTCCCCGAACCGGTGACGGT GTCGTGGAACTCAGGCGCCCTGACCAGCGGCGTGCACACCTT CCCGGCTGTCCTACAGTCCTCAGGACTCTACTCCCTCAGCAGC GTGGTGACCGTGCCCTCCAGCAGCTTGGGCACCCAGACCTAC ATCTGCAACGTGAATCACAAGCCCAGCAACACCAAGGTGGAC AAGAGTGAG |
| | VL | 133 | CAGTCTGCCCTGACTCAGCCTGCCTCCGTGTCTGGGTCTCCTG GACAGTCGATCACCATCTCCTGCACTGGAACCAGCAGTGATA TTGGGAGTTATAACCTTGTCTCCTGGTACCGACAATACCCAGG CAAAGCCCCCAAACTCATGATTTATGAGGTCAATAAGCGGCC CTCAGGGGTTTCTAATCGCTTCTCTGGCTCCAAGTCTGGCAAC ACGGCCTCCCTGACGATCTCTGGGCTCCAGGCTGAGGACGAG GCTGATTATTACTGCTGCTCATATGCGGGTACTACTTTCG TGATTTTCGGCAGAGGGACCAAGCTGACCGTCCTAGGTCAGC CCAAGGCTGCCCCCTCGGTCACTCTGTTCCCGCCCTCCTCTGA GGAGCTTCAAGCCAACAAGGCCACACTGGTGTGTCTCATAAG TGACTTCTACCCGGGAGCCGTGACAGTGGCCTGGAAGGCAGA TGGCAGCCCCGTCAAGGCGGGAGTGGAGACCACCACACCCTC CAAACAAAGCAACAACAAGTACGCGGCCAGCAGCTATCTGAG CCTGACGCCTGAGCAGTGGAAGTCCCACAGAAGCTACAGCTG CCAGGTCACGCATGAAGGGAGCACCGTGGAGAAGACAGTGG CCCCTACAGAATGTTCA |
| TMEL1008 | VH | 120 | CCCAGGTCCAGCTGGTGCAGTCTGGGGCTGAGGTGAAGAAGC CTGGGTCCTCGGTGAAGGTCTCCTGCAAGGCTTCTGGAGGCA CCTTCAATAGGGATGGTATCATCTGGGTGCGACAGGCCCCTG GACAAGGGCTTGAGTGGATGGGAAGGATCATCCCTATCCTTG GTATAGCAAACTACGCACAGAAGTTCCAGGGCAGAGTCACGA TTATCGCGGACAAATCCACGAGCACAGCCTACATGGAACTGA GCAGCCTGAGATCTGAGGACACGGCCGTATATTACTGTGCGA GAGAATCGGAGGTGGGTCGCGGTATGGACGTCTGGGGCCAAG GGACCACGGTCACCGTCTCCTCAGCCTCCACCAAGGGCCCAT CGGTCTTCCCCCTGGCACCCTCCTCCAAGAGCACCTCTGGGGG CACAGCGGCCCTGGGCTGCCTGGTCAAGGACTACTTCCCCGA ACCGGTGACGGTGTCGTGGAACTCAGGCGCCCTGACCAGCGG CGTGCACACCTTCCCGGCTGTCCTACAGTCCTCAGGACTCTAC TCCCTCAGCAGCGTGGTGACCGTGCCCTCCAGCAGCTTGGGC ACCCAGACCTACATCTGCAACGTGAATCACAAGCCCAGCAAC ACCAAGGTGGACAAGAGTGAG |
| | VL | 134 | GCCTCTGCCCTGACTCAGCCTGCCTCCGTGTCTGGGTCTCCTG GACAGTCGATCACCATCTCCTGCACTGGAACCAGCAGTGACG TTGGTGATTATAACTATGTCTCCTGGTACCAACAGCACCCAGG CAAAGCCCCCAAACTCATGATTTATGATGTCAGTAATCGGCCC TCAGGGGTTTCTCATCGCTTCTCTGGCTCCAAGTCTGGCAACA CGGCCTCCCTGACCATCTCTGGGCTCCAGGCTGAGGACGAGG CTGATTATTACTGCAGCTCATATACAATCAGCAGTACTCTAGG AGTCTTCGGACCTGGGACCAAGGTCACCGTCCTAGGTCAGCC CAAGGCCAACCCCACTGTCACTCTGTTCCCGCCCTCCTCTGAG GAGCTCCAAGCCAACAAGGCCACACTAGTGTGTCTGATCAGT GACTTCTACCCGGGAGCTGTGACAGTGGCCTGGAAGGCAGAT GGCAGCCCCGTCAAGGCGGGAGTGGAGACCACCAAACCCTCC AAACAGAGCAACAACAAGTACGCGGCCAGCAGCTACCTGAG CCTGACGCCCGAGCAGTGGAAGTCCCACAGAAGCTACAGCTG CCAGGTCACGCATGAAGGGAGCACCGTGGAGAAGACAGTGG CCCCTACAGAATGTTCA |
| TMEL1009 | VH | 121 | CCCGTGCAGCTGGTGCAGTCTGGGGCTGAGGTGAAGAAGCCT GGGTCCTCGGTGAAGGTCTCCTGCAGGGCTTCTGGAGGCACC TTCAGCAACTATGGTCTCAACTGGGTGCGACAGGCCCCTGGA CAAGGGCTTGAGTGGATGGGAGGGATCATCCCTATCTTTGGTT CAGTAAATTATGCACAGAAGTTCCAGGACAGAGTCACGATTA CCGCGGACGAATCCACGAGCACTACCTACATGGACCTGAACA |

TABLE 3-continued below lists exemplary reconstructed nucleic acid consensus sequences of variable heavy chain (VH) and exemplary reconstructed nucleic acid consensus sequences of variable light chain (VL)

| Name | Chain | SEQ ID No | Nucleic acid sequence |
|---|---|---|---|
| | | | GCCTGAGATCTGAGGACACGGCCGTCTATTACTGTGCGACAG<br>AGCGTGGACACAACATGGAGAGGGCTTTTGATTTCTGGGGCC<br>AAGGGACACTGGTCACCGTCTCTTCAGCCTCCACCAAGGGCC<br>CATCGGTCTTCCCCCTGGCACCCTCCTCCAAGAGCACCTCTGG<br>GGGCACAGCGGCCCTGGGCTGCCTGGTCAAGGACTACTTCCC<br>CGAACCGGTGACGGTGTCATGGAACTCAGGCGCCCTGACCAG<br>CGGCGTGCACACCTTCCCGGCTGTCCTACAGTCCTCAGGACTC<br>TACTCCCTCAGCAGCGTGGTGACCGTGCCCTCCAGCAGCTTGG<br>GCACCCAGACCTACATCTGCAACGTGAATCACAAGCCCAGCA<br>ACACCAAGGTGGACAAGAAGGTG |
| | VL | 135 | GTGACATCCAGATGACCCAGTCTCCTTCCACCCTGTCTGCTTC<br>TGTAGGAGACAGAGTCACCATCACTTGCCGGGCCAGTCAGAG<br>TATTCGTAGGTGGTTGGCCTGGTATCAGCAGAAACCAGGGAA<br>AGCCCCTAAACTCCTGATCTATGATGCCTCAAGTTTGGAAAGT<br>GGGGTCCCATCAAGGTTCAGCGGCAGTGGATCTGGGACAGAA<br>TTCACTCTCACCATCAGCAGCCTGCAGCCTGATGATTTTGCAA<br>CTTATTACTGTCAACAGTATAATAGTTATTCGTACACTTTTGG<br>CCAGGGGACCAAGCTGGAGATCAAACGAACTGTGGCTGCACC<br>ATCTGTCTTCATCTTCCCGCCATCTGATGAGCAGTTGAAATCT<br>GGAACTGCCTCTGTTGTGTGCCTGCTGAATAACTTCTATCCCA<br>GAGAGGCCAAAGTACAGTGGAAGGTGGATAACGCCCTCCAAT<br>CGGGTAACTCCCAGGAGAGTGTCACAGAGCAGGACAGCAAG<br>GACAGCACCTACAGCCTCAGCAGCACCCTGACGCTGAGCAAA<br>GCAGACTACGAGAAACACAAAGTCTACGCCTGCGAAGTCACC<br>CATCAGGGCCTGAGCTCGCCCGTCACAAAGAGCTTCAACAGG<br>GGAGAGTGT |
| TMEL1010 | VH | 122 | CCCAGGTTCAGCTGGTGCAGTCTGGAGCTGAGGTGAAGAAGC<br>CTGGGGCCTCAGTGAAGGTCTCCTGCAAGGCTTCTGGTTACAC<br>CTTTAGCAGCTATGGTATCAGCTGGGTGCGACAGGCCCCTGG<br>ACAAGGGCTTGAGTGGATGGGATGGATCAGCGCTTACAATGG<br>TAACACAAACTATGCAAAGAAACTCCAGGGCAGAGTCACCAT<br>GACCACAGACACATCCACGAGTACAGCCTACTTGGAGTTGAG<br>GAGCCTGAGATCTGACGACACGGCCGTGTATTACTGTGCGAG<br>AGGCGACGGTCCCTTTGACTACTGGGGCCAGGGAACCCTGGT<br>CACCGTCTCCTCAGCCTCCACCAAGGGCCCATCGGTCTTCCCC<br>CTGGCACCCTCCTCCAAGAGCACCTCTGGGGGCACAGCGGCC<br>CTGGGCTGCCTGGTCAAGGACTACTTCCCCGAACCGGTGACG<br>GTGTCGTGGAACTCAGGCGCCCTGACCAGCGGCGTGCACACC<br>TTCCCGGCTGTCCTACAGTCCTCAGGACTCTACTCCCTCAGCA<br>GCGTGGTGACCGTGCCCTCCAGCAGCTTGGGCACCCAGACCT<br>ACATCTGCAACGTGAATCACAAGCCCAGCAACACCAAGGTGG<br>ACAAGAAAGTG |
| | VL | 136 | GAAATAGTGATGACGCAGTCTCCAGCCACCCTGTCTGTGTCTC<br>CAGGGGAAAGAGCCACCCTCTCCTGCTGGGCCAGTCAGAGTG<br>TTAGCAGCAGCTTAGCCTGGTACCAGCAGAAACCTGGCCAGG<br>CTCCCAGGCTCCTCATGTATGGTGCATCTAACAGGGCCACTGG<br>TATCCCAGCCAGGTTCAGTGGCAGTGGGTCTGGGACAGAGTT<br>CACTCTCACCATCAGCAGCCTGCAGTCTGAAGATTTTGCAGTT<br>TATTACTGTCAGCAGTATAATAAGTGGCCTCCGGACACTTTTG<br>GCCAGGGGACCAAGCTGGAGATCAAACGAACTGTGGCTGCAC<br>CATCTGTCTTCATCTTCCCGCCATCTGATGAGCAGTTGAAATC<br>TGGAACTGCCTCTGTTGTGTGCCTGCTGAATAACTTCTATCCC<br>AGAGAGGCCAAAGTACAGTGGAAGGTGGATAACGCCCTCCA<br>ATCGGGTAACTCCCAGGAGAGTGTCACAGAGCAGGACAGCAA<br>GGACAGCACCTACAGCCTCAGCAGCACCCTGACGCTGAGCAA<br>AGCAGACTACGAGAAACACAAAGTCTACGCCTGCGAAGTCAC<br>CCATCAGGGCCTGAGCTCGCCCGTCACAAAGAGCTTCAACAG<br>GGGAGAGTGT |
| TMEL1011 | VH | 123 | CCCGTCCAGCTGGTGCAATCTGGGGCTGAAGTGAAGAAGCCT<br>GGGTCCTCGGTGAAGGTCTCCTGCAAGGCTTCTGGAGGCACC<br>TTCAGCAGCTATAGTTTCAACTGGGTGCGACAGGCCCCTGGA<br>CAGGGGCTTGAGTGGATGGCAAGGATCATCCCTATCCTTGGT<br>CTGGCAAATTACGCACAGAAGTTCCAGGGCAGAGTCACACTT<br>ACCGCGGACGAATCCACGAGCACAGCCTACATGGAGCTGAGC<br>AGCCTGAGATCTGAAGACACGGCCATCTTTTACTGTGCGGGA<br>ATGGTCCTCGGCCAACTGGGGTTCGACCCCTGGGGCCAGGGA<br>ACCCTGGTCACCGTCTCCTCAGCCTCCACCAAGGGCCCATCGG<br>TCTTCCCCCTGGCACCCTCCTCAAGAGCACCTCTGGGGGCAC<br>AGCGGCCCTGGGCTGCCTGGTCAAGGACTACTTCCCCGAACC<br>GGTGACGGTGTCGTGGAACTCAGGCGCCCTGACCAGCGGCGT<br>GCACACCTTCCCGGCTGTCCTACAGTCCTCAGGACTCTACTCC |

TABLE 3-continued below lists exemplary reconstructed nucleic acid consensus sequences of variable heavy chain (VH) and exemplary reconstructed nucleic acid consensus sequences of variable light chain (VL)

| Name | Chain | SEQ ID No | Nucleic acid sequence |
|---|---|---|---|
| | | | CTCAGCAGCGTGGTGACCGTGCCCTCCAGCAGCTTGGGCACC CAGACCTACATCTGCAACGTGAATCACAAGCCCAGCAACACC AAGGTGGACAAGAAGGTG |
| | VL | 137 | CAATTTATGCTGACTCAGCCCCACTCTGTGTCGGAGTCTCCGG GGAGGACGGTAACCATCTCCTGCACCCGCAGCAGTGGCAGCA TTGCCCGCAACTATGTGCATTGGTACCAGCATCGCCCGGGCA GTTCCCCCACCACTGTGATCTATGAGGATGACCAAAGACCCTC TGGGGTCCCTGATCGGTTCTCTGGCTCCATCGACAGCTCCTCC AACTCTGCCTCCCTCACCATCTCTGGACTGAAACCTGAGGACG AGGCTGACTACTTCTGTCAGTCTTATGATAGCAACATTTGGGT GTTCGGCGGTGGGACCAAGCTGACCGTCCTAGGTCAGCCCAA GGCTGCCCCCTCGGTCACTCTGTTCCCACCCTCCTCTGAGGAG CTTCAAGCCAACAAGGCCACACTGGTGTGTCTCATAAGTGAC TTCTACCCGGGAGCCGTGACAGTGGCCTGGAAGGCAGATAGC AGCCCCGTCAAGGCGGGAGTGGAGACCACCACACCCTCCAAA CAAAGCAACAACAAGTACGCGGCCAGCAGCTACCTGAGCCTG ACGCCTGAGCAGTGGAAGTCCCACAAAAGCTACAGCTGCCAG GTCACGCATGAAGGGAGCACCGTGGAGAAGACAGTGGCCCCT ACAGAATGTTCA |
| TMEL1012 | VH | 124 | CCCCTGCAGCTGCAGGAGTCGGGCCCAGGACTGGTGAAGCCT TCGGAGACCCTGTCCCTCACCTGTACTGTCTCTGGTGACTCCA TCACTACTACTTACTACTGGGGCTGGATCCGCCAGCCCCCAGG GAAGGGGCTGGAGTGGATTGCCAGTATCTATTTTACTGGGAG CACCTTCCATAACCCGTCCCTCAAGAGTCGAGTCACAATGTCC GTGGACACGTCCAAGAACCAGTTCTCCCTGAACCTGAGCTCT GTGACAGCCGCAGACACGGCTGTGTATTACTGTGCGAGACGG GTGGGTAACTGGAACTACGTCTGGTTCGACCCCTGGGGCCAG GGAACCCTGGTCTCCGTCTCCTCAGCCTCCACCAAGGGCCCAT CGGTCTTCCCCCTGGCACCCTCCTCCAAGAGCACCTCTGGGGG CACAGCGGCCCTGGGCTGCCTGGTCAAGGACTACTTCCCCGA ACCGGTGACGGTGTCGTGGAACTCAGGCGCCCTGACCAGCGG CGTGCACACCTTCCCGGCTGTCCTACAGTCCTCAGGACTCTAC TCCCTCAGCAGCGTGGTGACCGTGCCCTCCAGCAGCTTGGGC ACCCAGACCTACATCTGCAACGTGAATCACAAGCCCAGCAAC ACCAAGGTGGACAAGAAAGTG |
| | VL | 138 | GCCTATGTGCTGACTCAGCCACCCTCGGTGTCAGTGGCCCCAG GGCAGACGGCCAGGATGACCTGTGGGGGAAACAACATTGGA AGTAAAAGTGTGCATTGGTACCGGCAGAGGCCAGGCCAGGCC CCTGTGCTGGTCGTCTATGATGATACCGACCGGCCCTCAGGGA TCCCTGAGCGATTCTCTGGCTCCAACTCTGGGAACACGGCCAC CCTGACCATCAGCAGGGTCGAGGCCGGGGATGAGGCCGACTA TTACTGTCAGGTGTGGGATACTAATAGTGATCATGTGGTATTC GGCGGAGGGACCAAGCTGACCGTCCTAGGTCAGCCCAAGGCT GCCCCCTCGGTCACTCTGTTCCCGCCCTCCTCTGAGGAGCTTC AAGCCAACAAGGCCACACTGGTGTGTCTCATAAGTGACTTCT ACCCGGGAGCCGTGACAGTGGCCTGGAAGGCAGATAGCAGCC CCGTCAAGGCGGGAGTGGAGACCACCACACCCTCCAAACAAA GCAACAACAAGTACGCGGCCAGCAGCTATCTGAGCCTGACGC CTGAGCAGTGGAAGTCCCACAGAAGCTACAGCTGCCAGGTCA CGCATGAAGGGAGCACCGTGGAGAAGACAGTGGCCCCTACA GAATGTTCA |
| TMEL1013 | VH | 125 | CCCGTCCAGCTGGTGCAATCTGGGGCTGAGGTGAAGAAGCCT GGGTCCTCGGTGAAGGTCTCCTGCAAGGCTTCTGGAGGCACC TTCAGCTACTATATCAACTGGGTGCGACAGGCCCCTGGA CAAGGGCTTGAGTGGATGGGAAGGATCATCCCTATCCTTGGT GTAGCAAACTACGCACAGAAGTTCCAGGGCAGAGTCACGATT ACCGCGGACAAATCCACGAGCACAGCCTACATGGACCTGAGC AGCCTGAGATCTGAGGACACGGCCGTGTATTACTGTGCGAGA GAGTGGGAGCGGGCCTTTGACTACTGGGGCCAGGGAACCCTG GTCACCGTCTCCTCAGCCTCCACCAAGGGCCCATCGGTCTTCC CCCTGGCACCCTCCTCCAAGAGCACCTCTGGGGGCACAGCGG CCCTGGGCTGCCTGGTCAAGGACTACTTCCCCGAACCGGTGA CGGTGTCGTGGAACTCAGGCGCCCTGACCAGCGGCGTGCACA CCTTCCCGGCTGTCCTACAGTCCTCAGGACTCTACTCCCTCAG CAGCGTGGTGACCGTGCCCTCCAGCAGCTTGGGCACCCAGAC CTACATCTGCAACGTGAATCACAAGCCCAGCAACACCAAGGT GGACAAGAAGGTG |
| | VL | 139 | GAGAAATTGTGTTGACGCAGTCTCCAGGCACCCTGTCTTTGTC TCCAGGGGAAAGAGCCACCCTCTCCTGCAGGGCCAGTCAGAG TGTTAGCAGCAGCTACTTAGCCTGGTACAGCAGAAACCTGG CCAGGCTCCCAGGCTCCTCATCTATGGTGCATCCAGCAGGGCC |

TABLE 3-continued below lists exemplary reconstructed nucleic acid consensus sequences of variable heavy chain (VH) and exemplary reconstructed nucleic acid consensus sequences of variable light chain (VL)

| Name | Chain | SEQ ID No | Nucleic acid sequence |
|---|---|---|---|
| | | | ACTGGCATCCCAGACAGGTTCAGTGGCAGTGGGTCTGGGACA GACTTCACTCTCACCATCAGCAGACTGGAGCCTGAAGATTTTG CAGTGTATTACTGTCAGCAGTATGGTAACTCACCGTACACTTT TGGCCAGGGGACCAAGCTGGAGATCAAACGAACTGTGGCTGC ACCATCTGTCTTCATCTTCCCGCCATCTGATGAGCAGTTGAAA TCTGGAACTGCCTCTGTTGTGTGCCTGCTGAATAACTTCTATC CCAGAGAGGCCAAAGTACAGTGGAAGGTGGATAACGCCCTCC AATCGGGTAACTCCCAGGAGAGTGTCACAGAGCAGGACAGCA AGGACAGCACCTACAGCCTCAGCAGCACCCTGACGCTGAGCA AAGCAGACTACGAGAAACACAAAGTCTACGCCTGCGAAGTCA CCCATCAGGGCCTGAGCTCGCCCGTCACAAAGAGCTTCAACA GGGGAGAGTGT |
| TMEL1014 | VH | 126 | TCAGTGCAGCTGGTGGAGTCTGGGGGAGGCGTGGTCCAGCCT GGGAGGTCCCTGAGACTCTCCTGTGCAGCCTCTGGATTCACCT TCAGTAGCTATACCATGCACTGGGTCCGCCAGGCTCCAGGCA AGGGGCTGGAGTGGGTGGCACTTATATCATATGATGGAAGCA ATAAATACTACGCAGACTCCGTGAAGGGCCGATTCACCATCT CCAGAGACAATCCCAAGAACACGCTGTATCTGCAAATGAACA GCCTGAGAGTTGAGGACACGGCTGTGTATTACTGTGCGAGAG ATTGGACCCTTGGGTACTGGGGCCAGGGAACCCTGGTCACCG TCTCCTCAGCCTCCACCAAGGGCCCATCGGTCTTCCCCCTGGC GCCCTGCTCCAGGAGCACCTCCGAGAGCACAGCGGCCCTGGG CTGCCTGGTCAAGGACTACTTCCCCGAACCGGTGACGGTGTC GTGGAACTCAGGCGCTCTGACCAGCGGCGTGCACACCTTCCC GGCTGTCCTACAGTCCTCAGGACTCTACTCCCTCAGCAGCGTG GTGACCGTGACCTCCAGCAACTTCGGCACCCAGACCTACACC TGCAACGTAGATCACAAGCCCAGCAACACCAAGGTGGACAAG ACAGTG |
| | VL | 140 | GTTTCTTCTGAGCTGACTCAGGACCCTGCTGTGTCTGTGGCCT TGGGACAGACAGTCAGGATCACATGCCAAGGAGACAGCCTCA GAAACTATTATGCAAACTGGTACCAGCAGAAGCCAGGACAGG CCCCTATACTTGTCATCTATGATAAAAACAACCGGCCCTCAGG GATCCCAGACCGATTCTCTGGCTCCAGCTCAGGAAACACAGC TTCCTTGACCATCACTGGGGCTCAGGCGGAAGATGAGGCTGA CTATTACTGTAATTCCCGGGACAGCAGTGGTTACCATCTGGTG TTCGGCGGAGGGACCAAGCTGACCGTCCTAGGTCAGCCCAAG GCTGCCCCCTCGGTCACTCTGTTCCCGCCCTCCTCTGAGGAGC TTCAAGCCAACAAGGCCACACTGGTGTGTCTCATAAGTGACTT CTACCCGGGAGCCGTGACAGTGGCCTGGAAGGCAGATAGCAG CCCCGTCAAGGCGGGAGTGGAGACCACCACACCCTCCAAACA AAGCAACAACAAGTACGCGGCCAGCAGCTACCTGAGCCTGAC GCCTGAGCAGTGGAAGTCCCACAGAAGCTACAGCTGCCAGGT CACGCATGAAGGGAGCACCGTGGAGAAGACAGTGGCCCCTAC AGAATGTTCA |

TABLE 4 below lists exemplary reconstructed nucleic acid consensus sequences of complementarity-determining region from a variable heavy chain (CDR-H3) and exemplary reconstructed nucleic acid consensus sequences of complementarity-determining region from a variable light chain (CDR-L3). The start and stop position of CDR3 on the corresponding isolated nucleic acid sequence is indicated.

| Name | Complementarity-determining region and chain | SEQ ID NO: | Start position | Stop position | Nucleic acid sequences of complementarity-determining regions |
|---|---|---|---|---|---|
| TMEL1001 | CDR-H3 | 141 | 293 | 325 | GCGAGAGGTGGGGGTAC CAGCTGGTCGCATTAC |
| | CDR-L3 | 155 | 274 | 303 | CAGTCTTATGATAGCAAC AATCGTTGGGTG |
| TMEL1002 | CDR-H3 | 142 | 289 | 333 | GCGAAAGATGCATATGAT AGTAGTGGCCCAGATGCT TTTGATATC |
| | CDR-L3 | 156 | 271 | 300 | AGCTCATATACAAGCAGC AGCACTCTTGTA |

TABLE 4-continued below lists exemplary reconstructed nucleic acid consensus sequences of complementarity-determining region from a variable heavy chain (CDR-H3) and exemplary reconstructed nucleic acid consensus sequences of complementarity-determining region from a variable light chain (CDR-L3). The start and stop position of CDR3 on the corresponding isolated nucleic acid sequence is indicated.

| Name | Complementarity-determining region and chain | SEQ ID NO: | Start position | Stop position | Nucleic acid sequences of complementarity-determining regions |
|---|---|---|---|---|---|
| TMEL1003 | CDR-H3 | 143 | 289 | 330 | GCGAGACCGCTACAAACT TATAGTATAGCATCAGTA GGACAC |
| | CDR-L3 | 157 | 271 | 303 | TGCTCATATGCAGGTAGT AGCACTTTCGCGGTA |
| TMEL1004 | CDR-H3 | 144 | 294 | 332 | GCACACAAGAACCTTCAG TATTCGGAATGGTTCGAC CCC |
| | CDR-L3 | 158 | 268 | 294 | CTCCAGTATGATGAGTCA CCGTACACT |
| TMEL1005 | CDR-H3 | 145 | 292 | 324 | GCGAGACCGGAAGGGAG CGGTTATTCCGCTGATGC TTTTGATATC |
| | CDR-L3 | 159 | 267 | 296 | CAACAGTATGATAATCTC CTCCTATTCACT |
| TMEL1006 | CDR-H3 | 146 | 289 | 333 | GCGAAAGAGATTGGAAA ATACGGGACTCCTACTCT TTTCCAGCAC |
| | CDR-L3 | 160 | 267 | 293 | CAACAGTATGATAATCTC CCGATCACC |
| TMEL1007 | CDR-H3 | 147 | 289 | 318 | GCGAGAGATTTTAACTGG AACTTCGACTTC |
| | CDR-L3 | 161 | 271 | 303 | TGCTCATATGCGGGTACT ACTACTTTCGTGATT |
| TMEL1008 | CDR-H3 | 148 | 291 | 326 | GCGAGAGAATCGGAGGT GGGTCGCGGTATGGACGT C |
| | CDR-L3 | 162 | 271 | 303 | AGCTCATATACAATCAGC AGTACTCTAGGAGTC |
| TMEL1009 | CDR-H3 | 149 | 289 | 330 | GCGACAGAGCGTGGACA CAACATGGAGAGGGCTTT TGATTTC |
| | CDR-L3 | 163 | 267 | 293 | CAACAGTATAATAGTTAT TCGTACACT |
| TMEL1010 | CDR-H3 | 150 | 291 | 317 | GCGAGAGGCGACGGTCC CTTTGACTAC |
| | CDR-L3 | 164 | 265 | 294 | CAGCAGTATAATAAGTGG CCTCCGGACACT |
| TMEL1011 | CDR-H3 | 151 | 289 | 324 | GCGGGAATGGTCCTCGGC CAACTGGGGTTCGACCCC |
| | CDR-L3 | 165 | 274 | 300 | CAGTCTTATGATAGCAAC ATTTGGGTG |
| TMEL1012 | CDR-H3 | 152 | 289 | 330 | GCGAGACGGGTGGGTAA CTGGAACTACGTCTGGTT CGACCCC |
| | CDR-L3 | 166 | 262 | 294 | CAGGTGTGGGATACTAAT AGTGATCATGTGGTA |
| TMEL1013 | CDR-H3 | 153 | 289 | 318 | GCGAGAGAGTGGGAGCG GGCCTTTGACTAC |
| | CDR-L3 | 167 | 270 | 296 | CAGCAGTATGGTAACTCA CCGTACACT |
| TMEL1014 | CDR-H3 | 154 | 289 | 312 | GCGAGAGATTGGACCCTT GGGTAC |
| | CDR-L3 | 168 | 265 | 297 | AATCCCGGGACAGCAGT GGTTACCATCTGGTG |

TABLE 4-continued below lists exemplary reconstructed nucleic acid consensus sequences of complementarity-determining region from a variable heavy chain (CDR-H3) and exemplary reconstructed nucleic acid consensus sequences of complementarity-determining region from a variable light chain (CDR-L3). The start and stop position of CDR3 on the corresponding isolated nucleic acid sequence is indicated.

| Name | Complementarity-determining region and chain | SEQ ID NO: | Start position | Stop position | Nucleic acid sequences of complementarity-determining regions |
|---|---|---|---|---|---|
| TMEL1001 | CDR-H2 | 169 | 155 | 178 | ATTAGTAGTAGTGGTAATTACATA |
|  | CDR-L2 | 183 | 151 | 159 | GAGGATAAC |
| TMEL1002 | CDR-H2 | 170 | 151 | 174 | ATTAGTGGTAGTGGTGGTAGCACA |
|  | CDR-L2 | 184 | 154 | 162 | GATGTCAGT |
| TMEL1003 | CDR-H2 | 171 | 151 | 174 | ATTGATCCTAGTGACTCTTATACC |
|  | CDR-L2 | 185 | 154 | 162 | GAGGGCAGT |
| TMEL1004 | CDR-H2 | 172 | 159 | 179 | ATTTATTGGGATGATGATAAG |
|  | CDR-L2 | 186 | 151 | 159 | GGTGCCTCC |
| TMEL1005 | CDR-H2 | 173 | 157 | 177 | ATATTTTATAGTGGGAGCACC |
|  | CDR-L2 | 187 | 150 | 158 | GATGCATCC |
| TMEL1006 | CDR-H2 | 174 | 151 | 174 | ATTAGTGGTAGTGGTGGTCGCACA |
|  | CDR-L2 | 188 | 150 | 158 | GATGCATCC |
| TMEL1007 | CDR-H2 | 175 | 151 | 174 | TTCGTCCCTCTCTTTGGTACAGCA |
|  | CDR-L2 | 189 | 154 | 162 | GAGGTCAAT |
| TMEL1008 | CDR-H2 | 176 | 153 | 176 | ATCATCCCTATCCTTGGTATAGCA |
|  | CDR-L2 | 190 | 154 | 162 | GATGTCAGT |
| TMEL1009 | CDR-H2 | 177 | 151 | 174 | ATCATCCCTATCTTTGGTTCAGTA |
|  | CDR-L2 | 191 | 150 | 158 | GATGCCTCA |
| TMEL1010 | CDR-H2 | 178 | 153 | 176 | ATCAGCGCTTACAATGGTAACACA |
|  | CDR-L2 | 192 | 148 | 156 | GGTGCATCT |
| TMEL1011 | CDR-H2 | 179 | 151 | 174 | ATCATCCCTATCCTTGGTCTGGCA |
|  | CDR-L2 | 193 | 151 | 159 | GAGGATGAC |
| TMEL1012 | CDR-H2 | 180 | 154 | 174 | ATCTATTTTACTGGGAGCACC |
|  | CDR-L2 | 194 | 145 | 153 | GATGATACC |
| TMEL1013 | CDR-H2 | 181 | 151 | 174 | ATCATCCCTATCCTTGGTGTAGCA |
|  | CDR-L2 | 195 | 153 | 161 | GGTGCATCC |
| TMEL1014 | CDR-H2 | 182 | 151 | 174 | ATATCATATGATGGAAGCAATAAA |
|  | CDR-L2 | 196 | 148 | 156 | GATAAAAAC |
| TMEL1001 | CDR-H1 | 197 | 80 | 103 | GGATTCACCTTCAGGAGCTATAGC |
|  | CDR-L1 | 211 | 76 | 99 | AGTGGCAGCATTGCCAGCAACTAT |
| TMEL1002 | CDR-H1 | 198 | 76 | 99 | GGATTCACCTTTAGCAGCATGCC |
|  | CDR-L1 | 212 | 76 | 102 | AGCAGTGACGTTGGTGATTATAACTAT |

TABLE 4-continued below lists exemplary reconstructed nucleic acid consensus sequences of complementarity-determining region from a variable heavy chain (CDR-H3) and exemplary reconstructed nucleic acid consensus sequences of complementarity-determining region from a variable light chain (CDR-L3). The start and stop position of CDR3 on the corresponding isolated nucleic acid sequence is indicated.

| Name | Complementarity-determining region and chain | SEQ ID NO: | Start position | Stop position | Nucleic acid sequences of complementarity-determining regions |
|---|---|---|---|---|---|
| TMEL1003 | CDR-H1 | 199 | 76 | 99 | GGATACAGCTTTACCAGCTACTGG |
| | CDR-L1 | 213 | 76 | 102 | AGCAGTGATGTTGGGAGTTATAACCTT |
| TMEL1004 | CDR-H1 | 200 | 78 | 107 | GGGTTCTCACTCAACACTCCTGGAGTGGGT |
| | CDR-L1 | 214 | 79 | 99 | CAGAGTGTTAGCAGAAACTCC |
| TMEL1005 | CDR-H1 | 201 | 76 | 105 | GGTGGCTCCATGAGCATTAGGAGTTCCTAC |
| | CDR-L1 | 215 | 81 | 98 | CAGAACATTAGGAATTAT |
| TMEL1006 | CDR-H1 | 202 | 76 | 99 | GGATTAACCTTTCGCAACTACGCC |
| | CDR-L1 | 216 | 81 | 98 | CAGGACATTAGCAACTAT |
| TMEL1007 | CDR-H1 | 203 | 76 | 99 | GGAGGCTCCTTCAGCAGTAATCCA |
| | CDR-L1 | 217 | 76 | 102 | AGCAGTGATATTGGGAGTTATAACCTT |
| TMEL1008 | CDR-H1 | 204 | 78 | 101 | GGAGGCACCTTCAATAGGGATGGT |
| | CDR-L1 | 218 | 76 | 102 | AGCAGTGACGTTGGTGATTATAACTAT |
| TMEL1009 | CDR-H1 | 205 | 76 | 99 | GGAGGCACCTTCAGCAACTATGGT |
| | CDR-L1 | 219 | 81 | 98 | CAGAGTATTCGTAGGTGG |
| TMEL1010 | CDR-H1 | 206 | 78 | 101 | GGTTACACCTTTAGCAGCTATGGT |
| | CDR-L1 | 220 | 79 | 96 | CAGAGTGTTAGCAGCAGC |
| TMEL1011 | CDR-H1 | 207 | 76 | 99 | GGAGGCACCTTCAGCAGCTATAGT |
| | CDR-L1 | 221 | 76 | 99 | AGTGGCAGCATTGCCCGCAACTAT |
| TMEL1012 | CDR-H1 | 208 | 76 | 102 | GGTGACTCCATCACTACTACTTACTAC |
| | CDR-L1 | 222 | 76 | 93 | AACATTGGAAGTAAAAGT |
| TMEL1013 | CDR-H1 | 209 | 76 | 99 | GGAGGCACCTTCAGCAGCTATACT |
| | CDR-L1 | 223 | 81 | 101 | CAGAGTGTTAGCAGCAGCTAC |
| TMEL1014 | CDR-H1 | 210 | 76 | 99 | GGATTCACCTTCAGTAGCTATACC |
| | CDR-L1 | 224 | 79 | 96 | AGCCTCAGAAACTATTAT |

TABLE 5 lists exemplary reconstructed germline amino acid consensus sequences of variable heavy chain (VH) and Exemplary reconstructed germline amino acid consensus sequences variable light chain (VL)

| Name | Chain | SEQ ID NO: | Amino acid sequence |
|---|---|---|---|
| TMEL1001 | VH | 225 | EVQLVESGGGLVKPGGSLRLSCAASGFTFSSYSMNWVRQAP GKGLEWVSSISSSSSYIYYADSVKGRFTISRDNAKNSLYLQM NSLRAEDTAVYYCAREGYCSSTSCYATTLTTGAREPWSPSPQ ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKKV |
|  | VL | 239 | NFMLTQPHSVSESPGKTVTISCTRSSGSIASNYVQWYQQRPG SSPTTVIYEDNQRPSGVPDRFSGSIDSSSNSASLTISGLKTEDE ADYYCQSYDSSNHWVFGGGTKLTVLAQGCPLGHSVPTLLG ASSQQGHTGVSHKLLPGSRDSCLEGRQPRQGGGGDFIHTLQT KQQQVRGQQLPEPDAAVEVPQKLQLPGHA- REHRGEDSCPYGMF |
| TMEL1002 | VH | 226 | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKEYYYDSSGYYYCFYLGPRDNGHRL FRPPPRAHRSSPWHPPPRAPLGAQRPWAAWSRTTSPNRRCRG TQAPPAACTPSRLSYSPQDSTPSAAWPCPPAAWAPRPTSATIT SPATPRWTRK |
|  | VL | 240 | QSALTQPASVSGSPGQSITISCTGTSSDVGGYNYVSWYQQHP GKAPKLMIYEVSNRPSGVSNRFSGSKSGNTASLTISGLQAEDE ADYYCSSYTSSSTLCGIRRRDQADRPRVSPRLPPRSLCSRPPL RSFKPTRPHWCVSVTSTREPQWLGKQIAAPSRREWRPPHPPN KATTSTRPAAIARLSSGSPTEATAARSRMKGAPWRRQWPLQ NV |
| TMEL1003 | VH | 227 | EVQLVQSGAEVKKPGESLRISCKGSGYSFTSYWISWVRQMP GKGLEWMGRIDPSDSYTNYSPSFQGHVTISADKSISTAYLQW SSLKASDTAMYYCARGYSSSWYTTLTTGAREPWSPSPQGSA SAPTLFPLVSCENSPSDTSSVAVGCLAQDFLPDSITLSWKYKN NSDISSTRGFPSVLRGGKYAATSQVLLPSKDVMQGTDEHVV CKVQHPNGNKEKNVPLP |
|  | VL | 241 | QSALTQPASVSGSPGQSITISCTGTSSDVGSYNLVSWYQQHPG KAPKLMIYEGSKRPSGVSNRFSGSKSGNTASLTISGLQAEDEA DYYCCSYAGSSTFCGIRRRDQADRPSPRLPPRSLCSHPPLRSF KPTRPHWCVSVTSTREPQLPGRQIAAPSRRGWRPPHPPNKAT TSTRPAATARLSSGSPTKATAARSRMKGAPWRRQLPLRNV |
| TMEL1004 | VH | 228 | QITLKESGPTLVKPTQTLTLTCTFSGFSLSTSGVGVGWIRQPP GKALEWLALIYWDDDKRYSPSLKSRLTITKDTSKNQVVLTM TNMDPVDTATYYCAHRRYNRNHTTGSTPGAREPWSPSPQAS TKGPSVFPLAPCSRSTSESTAALGCLVKDYFPEPVTVSWNSG ALTSGVHTFPAVLQSSGLYSLSSVVTVPSSNFGTQTYTCNVD HKPSNTKVDKTV |
|  | VL | 242 | EIVLTQSPGTLSLSPGERATLSCRASQSVSSSYLAWYQQKPGQ APRLLIYGASSRATGIPDRFSGSGSGTDFTLTISRLEPEDFAVY YCQQYGSSPPVHFWPGDQAGDQTELWLHHLSSSSRHLMSSN LELPLLCAC- ITSIPERPKYSGRWITPSNRVTPRRVSQSRTARTAPTASAAPRA KQTTRNTKSTPAKSPIRAARPSQRASTGES |
| TMEL1005 | VH | 229 | QLQLQESGPGLVKPSETLSLTCTVSGGSISSSSYYWGWIRQPP GKGLEWIGSIYYSGSTYYNPSLKSRVTISVDTSKNQFSLKLSS VTAADTAVYYCAREYYDFWSGYYTTLTTGAREPWSPSPQA STKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKV |
|  | VL | 243 | DIQMTQSPSSLSASVGDRVTITCQASQDISNYLNWYQQKPGK APKLLIYDASNLETGVPSRFSGSGSGTDFTFTISSLQPEDIATY YCQQYDNLPPFTFGPGTKVDIKPNCGCTICLHLPAIAVEIWNC LCCVPAELLSQRGQSTVEGGRPPIGLPGECHRAGQQGQHLQP QQHPDAEQSRLRETQSLRLRSHPSGPELARHKELQQGRV |
| TMEL1006 | VH | 230 | EVQLVESGGGLVQPGGSLRLSCAASGFTFSSYAMSWVRQAP GKGLEWVSAISGSGGSTYYADSVKGRFTISRDNSKNTLYLQ MNSLRAEDTAVYYCAKEGYCSGGSCYSAEYFQHWGQGTLV TVSSGLHQGPIGLPPGTLLQEHLWGHSGPGLPGQLLPRTGD GVVELRRPDQRRAHLPGCPTVLRTLLPQQRGDRALQQLGHP DLHLQRESAQQHQGQES |
|  | VL | 244 | DIQMTQSPSSLSASVGDRVTITCQASQDISNYLNWYQQKPGK APKLLIYDASNLETGVPSRFSGSGSGTDFTFTISSLQPEDIATY YCQQYDNLPPITFGQGTRLEIKPNCGCTICLHLPAI-- |

TABLE 5-continued lists exemplary reconstructed germline amino acid consensus sequences of variable heavy chain (VH) and Exemplary reconstructed germline amino acid consensus sequences variable light chain (VL)

| Name | Chain | SEQ ID NO: | Amino acid sequence |
|---|---|---|---|
| | | | AVEIWNCLCCVPAE-LLSQRGQSTVEGG-RPPIG-LPGECHRAGQQGQHLQPQQHPDAEQSRLRETQSLRLRSHPSG PELARHKELQQGRV |
| TMEL1007 | VH | 231 | QVQLVQSGAEVKKPGSSVKVSCKASGGTFSSYAISWVRQAP GQGLEWMGGIIPIFGTANYAQKFQGRVTITADESTSTAYMEL SSLRSEDTAVYYCAREV-LERHYFDYWGQGTLVTVSSGLHQGPIGLPPGTLLQEHLWGH SGPGLPGQGLLPRTGDGVVELRRPDQRRAHLPGCPTVLRTLL PQQRGDRALQQLGHPDLHLQRESQAQQHQGGQES |
| | VL | 245 | QSALTQPASVSGSPGQSITISCTGTSSDVGSYNLVSWYQQHPG KAPKLMIYEVSKRPSGVSNRFSGSKSGNTASLTISGLQAEDEA DYYCCSYAGSSTFCGIRRRDQADRPRVSPRLPPRSLCSRPPLR SFKPTRPHWCVS-VTSTREP-QWLGKQIAAPSRREWRPPHPPNKATTSTRPAAI-A-RLSSGSPTEATAARSRMKGAPWRRQWPLQNV |
| TMEL1008 | VH | 232 | QVQLVQSGAEVKKPGSSVKVSCKASGGTFSSYAISWVRQAP GQGLEWMGRIIPILGIANYAQKFQGRVTITADKSTSTAYMEL SSLRSEDTAVYYCAREV-WELLHYYYYGMDVWGQGTTVTVSSASTKGPSVFPLAPSSK STSGGTAALGCLVKDYFPEPVTVSWNSGALTSGVHTFPAVL QSSGLYSLSSVVTVPSSSLGTQTYICNVNHKPSNTKVDKKV |
| | VL | 246 | QSALTQPASVSGSPGQSITISCTGTSSDVGGYNYVSWYQQHP GKAPKLMIYEVSNRPSGVSNRFSGSKSGNTASLTISGLQAEDE ADYYCSSYTSSSTLLCLRNWDQGHRPSPRPTPRSLCSRPPLRS SKPTRPH-CV-SVTSTREL-QWLGRQMAAPSRREWRRPNPPNRATTSTRPAAT-A-RPSSGSPTEATAARSRMKGAPWRRQWPLQNV |
| TMEL1009 | VH | 233 | QVQLVQSGAEVKKPGSSVKVSCKASGGTFSSYAISWVRQAP GQGLEWMGGIIPIFGTANYAQKFQGRVTITADESTSTAYMEL SSLRSEDTAVYYCAREWIQLWLLMLLMSGAKGQWSPSLQAS TKGPSVFPLAPSSKSTSGGTAALGCLVKDYFPEPVTVSWNSG ALTSGVHTFPAVLQSSGLYSLSSVVTVPSSSLGTQTYICNVNH KPSNTKVDKKV |
| | VL | 247 | DIQMTQSPSTLSASVGDRVTITCRASQSISSWLAWYQQKPGK APKLLIYDASSLESGVPSRFSGSGSGTEFTLTISSLQPDDFATY YCQQYNSYSPVHFWPGDQAGDQTELWLHHLSSSSRHLMSS-NLELPLLCAC-ITSIPERPKYSGRWITPSNRVTPRRVSQSRTARTAPTASAAP-R-AKQTTRNTKSTPAKSPIRA-ARPSQRASTGES |
| TMEL1010 | VH | 234 | QVQLVQSGAEVKKPGASVKVSCKASGYTFTSYGISWVRQAP GQGLEWMGWISAYNGNTNYAQKLQGRVTMTTDTSTSTAY MELRSLRSDDTAVYYCARDDYGDYTTLTTGAREPWSPSPQA STKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKV |
| | VL | 248 | EIVMTQSPATLSVSPGERATLSCRASQSVSSNLAWYQQKPGQ APRLLIYGASTRATGIPARFSGSGSGTEFTLTISSLQSEDFAVY YCQQYNNWPPVHFWPGDQAGDQTELWLHHLSSSSRHLMSS-NLELPLLCAC-ITSIPERPKYSGRWITPSNRVTPRRVSQSRTARTAPTASAAP-R-AKQTTRNTKSTPAKSPIRA-ARPSQRASTGES |
| TMEL1011 | VH | 235 | QVQLVQSGAEVKKPGSSVKVSCKASGGTFSSYTISWVRQAP GQGLEWMGRIIPILGIANYAQKFQGRVTITADKSTSTAYMEL SSLRSEDTAVYYCARGTTGTTQLVRPLGPGNPGHRLLRPPPR AHRSSPWHPPPRAPLGAQRPWAAWSRTTSPNR-RCRGTQAP-PAACTPSRLSYSPQDSTPSAAW-PCPPAAWAPRPTSAT-ITSPATPRWTRK |
| | VL | 249 | NFMLTQPHSVSESPGKTVTISCTRSSGSIASNYVQWYQQRPGS SPTTVIYEDNQRPSGVPDRFSGSIDSSSNSASLTISGLKTEDEA DYYCQSYDSSNHWVFGGGTKLTVLAQGCPLGHSVPTLL-GASSQQGHTGVSHK-LLPGSRDSCLEGR-QPRQGGGGDHHTLQTKQQQVRGQQLPEPDA-AVEVPQKLQLPGHA-REHRGEDSCPYGMF |
| TMEL1012 | VH | 236 | QLQLQESGPGLVKPSETLSLTCTVSGGSISSSSYYWGWIRQPP GKGLEWIGSIYYSGSTYYNPSLKSRVTISVDTSKNQFSLKLSS VTAADTAVYYCARQV- |

TABLE 5-continued lists exemplary reconstructed germline amino acid consensus sequences of variable heavy chain (VH) and Exemplary reconstructed germline amino acid consensus sequences variable light chain (VL)

| Name | Chain | SEQ ID NO: | Amino acid sequence |
|---|---|---|---|
| | | | LELHNWFDPWGQGTLVTVSSGLHQGPIGLPPGTLLQEHLWG HSGPGLPGQGLLPRTGDGVVELRRPDQRRAHLPGCPTVLRTL LPQQRGDRALQQLGHPDLHLQRESQAQQHQGGQES |
| | VL | 250 | SYVLTQPPSVSVAPGQTARITCGGNNIGSKSVHWYQQKPGQ APVLVVYDDSDRPSGIPERFSGSNSGNTATLTISRVEAGDEAD YYCQVWDSSSDHPVVFGGGTKLTVLGSAQGCPLGHSVPALL -GASSQQGHTGVSHK-LLPGSRDSGLESR- QPRQGGSGDHHTLQTKQQQVRGQQLSEPDA- AVEVPQKLQLPGHA-REHRGEDSGPYRMF |
| TMEL1013 | VH | 237 | QVQLVQSGAEVKKPGSSVKVSCKASGGTFSSYTISWVRQAP GQGLEWMGRIIPILGTANYAQKFQGRVTITADKSTSTAYMEL SSLRSEDTAVYYCAREV- WELLHYFDYWGQGTLVTVSSGLHQGPIGLPPGTLLQEHLWG HSGPGLPGQGLLPRTGDGVVELRRPDQRRAHLPGCPTVLRTL LPQQRGDRALQQLGHPDLHLQRESQAQQHQGGQES |
| | VL | 251 | EIVLTQSPGTLSLSPGERATLSCRASQSVSSSYLAWYQQKPGQ APRLLIYGASSRATGIPDRFSGSGSGTDFTLTISRLEPEDFAVY YCQQYGSSPPVHFWPGDQAGDQTELWLHHLSSSSRHLMSS- NLELPLLCAC- ITSIPERPKYSGRWITPSNRVTPRRVSQSRTARTAPTASAAP-R- AKQTTRNTKSTPAKSPIRA-ARPSQRASTGES |
| TMEL1014 | VH | 238 | QVQLVESGGGVVQPGRSLRLSCAASGFTFSSYAMHWVRQAP GKGLEWVAVISYDGSNKYYADSVKGRFTISRDNSKNTLYLQ MNSLRAEDTAVYYCAREYYDFWTGYYTTTLTTGAREPWSPS PQASTKGPSVFPLAPCSRSTSESTAALGCLVKDYFPEPVTVSW NSGALTSGVHTFPAVLQSSGLYSLSSVVTVPSSNFGTQTYTC NVDHKPSNTKVDKTV |
| | VL | 252 | SSELTQDPAVSVALGQTVRITCQGDSLRSYYASWYQQKPGQ APVLVIYGKNNRPSGIPDRFSGSSSGNTASLTITGAQAEDEAD YYCNSRDSSGNHLWVFGGGTKLTVLAQGCPLGHSVPTLL- GASSQQGHTGVSHK-LLPGSRDSCLEGR- QPRQGGGGDHHTLQTKQQQVRGQQLPEPDA- AVEVPQKLQLPGHA-REHRGEDSCPYGMF |

TABLE 6 lists exemplary reconstructed germline nucleic acid consensus sequences of variable heavy chain (VH) and exemplary reconstructed germline nucleic acid consensus sequences of variable light chain (VL)

| Name | Chain | SEQ ID NO: | Nucleic acid sequences |
|---|---|---|---|
| TMEL1001 | VH | 253 | GAGGTGCAGCTGGTGGAGTCTGGGGGAGGCCTGGTCA AGCCTGGGGGGTCCCTGAGACTCTCCTGTGCAGCCTCT GGATTCACCTTCAGTAGCTATAGCATGAACTGGGTCCG CCAGGCTCCAGGGAAGGGGCTGGAGTGGGTCTCATCC ATTAGTAGTAGTAGTAGTTACATATACTACGCAGACTC AGTGAAGGGCCGATTCACCATCTCCAGAGACAACGCC AAGAACTCACTGTATCTGCAAATGAACAGCCTGAGAG CCGAGGACACGGCTGTGTATTACTGTGCGAGAGAAGG ATATTGTAGTAGTACCAGCTGCTATGCCACTACTTTGA CTACTGGGGCCAGGGAACCCTGGTCACCGTCTCCTCAG GCCTCCACCAAGGGCCCATCGGTCTTCCCCCTGGCACC CTCCTCCAAGAGCACCTCTGGGGGCACAGCGGCCCTG GGCTGCCTGGTCAAGGACTACTTCCCCGAACCGGTGAC GGTGTCGTGGAACTCAGGCGCCCTGACCAGCGGCGTG CACACCTTCCCGGCTGTCCTACAGTCCTCAGGACTCTA CTCCCTCAGCAGCGTGGTGACCGTGCCCTCCAGCAGCT TGGGCACCCAGACCTACATCTGCAACGTGAATCACAA GCCCAGCAACACCAAGGTGGACAAGAAAGTT |
| | VL | 267 | AATTTTATGCTGACTCAGCCCCACTCTGTGTCGGAGTC TCCGGGGAAGACGGTAACCATCTCCTGCACCCGCAGC AGTGGCAGCATTGCCAGCAACTATGTGCAGTGGTACC AGCAGCGCCCGGGCAGTTCCCCCACCACTGTGATCTAT GAGGATAACCAAAGACCCTCTGGGGTCCCTGATCGGTT CTCTGGCTCCATCGACAGCTCCTCCAACTCTGCCTCCCT |

TABLE 6-continued lists exemplary reconstructed germline nucleic acid consensus sequences of variable heavy chain (VH) and exemplary reconstructed germline nucleic acid consensus sequences of variable light chain (VL)

| Name | Chain | SEQ ID NO: | Nucleic acid sequences |
|---|---|---|---|
| | | | CACCATCTCTGGACTGAAGACTGAGGACGAGGCTGAC<br>TACTACTGTCAGTCTTATGATAGCAGCAATCATTGGGT<br>GTTCGGCGGAGGGACCAAGCTGACCGTCCTAGCCCAA<br>GGCTGCCCCCTCGGTCACTCTGTTCCCACCCTCCTCTGA<br>GGAGCTTCAAGCCAACAAGGCCACACTGGTGTGTCTC<br>ATAAGTGACTTCTACCCGGGAGCCGTGACAGTTGCCTG<br>GAAGGCAGATAGCAGCCCCGTCAAGGCGGGGTGGAG<br>ACCACCACACCCTCCAAACAAAGCAACAACAAGTACG<br>CGGCCAGCAGCTACCTGAGCCTGACGCCTGAGCAGTG<br>GAAGTCCCACAAAAGCTACAGCTGCCAGGTCACGCAT<br>GAAGGGAGCACCGTGGAGAAGACAGTTGCCCCTACGG<br>AATGTTCA |
| TMEL1002 | VH | 254 | GAGGTGCAGCTGTTGGAGTCTGGGGGAGGCTTGGTAC<br>AGCCTGGGGGGTCCCTGAGACTCTCCTGTGCAGCCTCT<br>GGATTCACCTTTAGCAGCTATGCCATGAGCTGGGTCCG<br>CCAGGCTCCAGGGAAGGGGCTGGAGTGGGTCTCAGCT<br>ATTAGTGGTAGTGGTGGTAGCACATACTACGCAGACTC<br>CGTGAAGGGCCGGTTCACCATCTCCAGAGACAATTCCA<br>AGAACACGCTGTATCTGCAAATGAACAGCCTGAGAGC<br>CGAGGACACGGCCGTATATTACTGTGCGAAAGAGTAT<br>TACTATGATAGTAGTGGTTATTACTACTGATGCTTTTG<br>ATATCTGGGGCCAAGGGACAATGGTCACCGTCTCTTCA<br>GGCCTCCACCAAGGGCCCATCGGTCTTCCCCCTGGCAC<br>CCTCCTCCAAGAGCACCTCTGGGGGCACAGCGGCCCTG<br>GGCTGCCTGGTCAAGGACTACTTCCCCGAACCGGTGAC<br>GGTGTCGTGGAACTCAGGCGCCCTGACCAGCGGCGTG<br>CACACCTTCCCGGCTGTCCTACAGTCCTCAGGACTCTA<br>CTCCCTCAGCAGCGTGGTGACCGTGCCCTCCAGCAGCT<br>TGGGCACCCAGACCTACATCTGCAACGTGAATCACAA<br>GCCCAGCAACACCAAGGTGGACAAGAAAGTT |
| | VL | 268 | CAGTCTGCCCTGACTCAGCCTGCCTCCGTGTCTGGGTC<br>TCCTGGACAGTCGATCACCATCTCCTGCACTGGAACCA<br>GCAGTGACGTTGGTGGTTATAACTATGTCTCCTGGTAC<br>CAACAGCACCCAGGCAAAGCCCCCAAACTCATGATTT<br>ATGAGGTCAGTAATCGGCCCTCAGGGGTTTCTAATCGC<br>TTCTCTGGCTCCAAGTCTGGCAACACGGCCTCCCTGAC<br>CATCTCTGGGCTCCAGGCTGAGGACGAGGCTGATTATT<br>ACTGCAGCTCATATACAAGCAGCAGCACTCTCTGTGGT<br>ATTCGGCGGAGGGACCAAGCTGACCGTCCTAGGGTCA<br>GCCCAAGGCTGCCCCCTCGGTCACTCTGTTCCCGCCCT<br>CCTCTGAGGAGCTTCAAGCCAACAAGGCCACACTGGT<br>GTGTCTCATAAGTGACTTCTACCCGGGAGCCGTGACAG<br>TGGCTTGGAAAGCAGATAGCAGCCCCGTCAAGGCGGG<br>AGTGGAGACCACCACACCCTCCAAACAAAGCAACAAC<br>AAGTACGCGGCCAGCAGCTATCTGAGCCTGACGCCTG<br>AGCAGTGGAAGTCCCACAGAAGCTACAGCTGCCAGGT<br>CACGCATGAAGGGAGCACCGTGGAGAAGACAGTGGCC<br>CCTACAGAATGTTCA |
| TMEL1003 | VH | 255 | GAAGTGCAGCTGGTGCAGTCCGGAGCAGAGGTGAAAA<br>AGCCCGGGGAGTCTCTGAGGATCTCCTGTAAGGGTTCT<br>GGATACAGCTTTACCAGCTACTGGATCAGCTGGGTGCG<br>CCAGATGCCCGGGAAAGGCCTGGAGTGGATGGGGAGG<br>ATTGATCCTAGTGACTCTTATACCAACTACAGCCCCGTC<br>CTTCCAAGGCCACGTCACCATCTCAGCTGACAAGTCCA<br>TCAGCACTGCCTACCTGCAGTGGAGCAGCCTGAAGGC<br>CTCGGACACCGCCATGTATTACTGTGCGAGAGGGTATA<br>GCAGCAGCTGGTACACTACTTTGACTACTGGGGCCAGG<br>GAACCCTGGTCACCGTCTCCTCAGGGGAGTGCATCCGC<br>CCCAACCCTTTTCCCCCTCGTCTCCTGTGAGAATTCCCC<br>GTCGGATACGAGCAGCGTGGCCGTTGGCTGCCTCGCAC<br>AGGACTTCCTTCCCGACTCCATCACTTTGTCCTGGAAA<br>TACAAGAACAACTCTGACATCAGCAGTACCCGGGGCT<br>TCCCATCAGTCCTGAGAGGGGGCAAGTACGCAGCCAC<br>CTCACAGGTGCTGCTGCCTTCCAAGGACGTCATGCAGG<br>GCACAGACGAACACGTGGTGTGCAAAGTCCAGCACCC<br>CAACGGCAACAAAGAAAGAACGTGCCTCTTCCA |
| | VL | 269 | CAGTCTGCCCTGACTCAGCCTGCCTCCGTGTCTGGGTC<br>TCCTGGACAGTCGATCACCATCTCCTGCACTGGAACCA<br>GCAGTGATGTTGGGAGTTATAACCTTGTCTCCTGGTAC<br>CAACAGCACCCAGGCAAAGCCCCCAAACTCATGATTT<br>ATGAGGGCAGTAAGCGGCCCTCAGGGGTTTCTAATCG |

TABLE 6-continued lists exemplary reconstructed germline nucleic acid consensus sequences of variable heavy chain (VH) and exemplary reconstructed germline nucleic acid consensus sequences of variable light chain (VL)

| Name | Chain | SEQ ID NO: | Nucleic acid sequences |
|---|---|---|---|
| | | | CTTCTCTGGCTCCAAGTCTGGCAACACGGCCTCCCTGA<br>CAATCTCTGGGCTCCAGGCTGAGGACGAGGCTGATTAT<br>TACTGCTGCTCATATGCAGGTAGTAGCACTTTCTGTGG<br>TATTCGGCGGAGGGACCAAGCTGACCGTCCTAGCCCA<br>AGGCTGCCCCCTCGGTCACTCTGTTCCCACCCTCCTCTG<br>AGGAGCTTCAAGCCAACAAGGCCACACTGGTGTGTCT<br>CATAAGTGACTTCTACCCGGGAGCCGTGACAGTTGCCT<br>GGAAGGCAGATAGCAGCCCCGTCAAGGCGGGGGTGGA<br>GACCACCACACCCTCCAAACAAAGCAACAACAAGTAC<br>GCGGCCAGCAGCTACCTGAGCCTGACGCCTGAGCAGT<br>GGAAGTCCCACAAAAGCTACAGCTGCCAGGTCACGCA<br>TGAAGGGAGCACCGTGGAGAAGACAGTTGCCCCTACG<br>GAATGTTCA |
| TMEL1004 | VH | 256 | CAGATCACCTTGAAGGAGTCTGGTCCTACGCTGGTGAA<br>ACCCACACAGACCCTCACGCTGACCTGCACCTTCTCTG<br>GGTTCTCACTCAGCACTAGTGGAGTGGGTGTGGGCTGG<br>ATCCGTCAGCCCCCAGGAAAGGCCCTGGAGTGGCTTG<br>CACTCATTTATTGGGATGATGATAAGCGCTACAGCCCA<br>TCTCTGAAGAGCAGGCTCACCATCACCAAGGACACCTC<br>CAAAAACCAGGTGGTCCTTACAATGACCAACATGGAC<br>CCTGTGGACACAGCCACATATTACTGTGCACACAGACG<br>GTATAACCGGAACCACACAACTGGTTCGACCCCTGGG<br>GCCAGGGAACCCTGGTCACCGTCTCCTCAGGCCTCCAC<br>CAAGGGCCCATCGGTCTTCCCCCTGGCGCCCTGCTCCA<br>GGAGCACCTCCGAGAGCACAGCCGCCCTGGGCTGCCT<br>GGTCAAGGACTACTTCCCCGAACCGGTGACGGTGTCGT<br>GGAACTCAGGCGCTCTGACCAGCGGCGTGCACACCTTC<br>CCAGCTGTCCTACAGTCCTCAGGACTCTACTCCCTCAG<br>CAGCGTGGTGACCGTGCCCTCCAGCAACTTCGGCACCC<br>AGACCTACACCTGCAACGTAGATCACAAGCCCAGCAA<br>CACCAAGGTGGACAAGACAGTT |
| | VL | 270 | GAAATTGTGTTGACGCAGTCTCCAGGCACCCTGTCTTT<br>GTCTCCAGGGGAAAGAGCCACCCTCTCCTGCAGGGCC<br>AGTCAGAGTGTTAGCAGCAGCTACTTAGCCTGGTACCA<br>GCAGAAACCTGGCCAGGCTCCCAGGCTCCTCATCTATG<br>GTGCATCCAGCAGGGCCACTGGCATCCCAGACAGGTT<br>CAGTGGCAGTGGGTCTGGGACAGACTTCACTCTCACCA<br>TCAGCAGACTGGAGCCTGAAGATTTTGCAGTGTATTAC<br>TGTCAGCAGTATGGTAGCTCACCTCCTGTACACTTTTG<br>GCCAGGGGACCAAGCTGGAGATCAAACCGAACTGTGG<br>CTGCACCATCTGTCTTCATCTTCCCGCCATCTGATGAGC<br>AGTTGAAATCTGGAACTGCCTCTGTTGTGTGCCTGCTG<br>AATAACTTCTATCCCAGAGAGGCCAAAGTACAGTGGA<br>AGGTGGATAACGCCCTCCAATCGGGTAACTCCCAGGA<br>GAGTGTCACAGAGCAGGACAGCAAGGACAGCACCTAC<br>AGCCTCAGCAGCACCCTGACGCTGAGCAAAGCAGACT<br>ACGAGAAACACAAAGTCTACGCCTGCGAAGTCACCCA<br>TCAGGGCCTGAGCTCGCCCGTCACAAAGAGCTTCAAC<br>AGGGGAGAGTGT |
| TMEL1005 | VH | 257 | CAGCTGCAGCTGCAGGAGTCGGGCCCAGGACTGGTGA<br>AGCCTTCGGAGACCCTGTCCCTCACCTGCACTGTCTCT<br>GGTGGCTCCATCAGCAGTAGTAGTTACTACTGGGGCTG<br>GATCCGCCAGCCCCCAGGGAAGGGGCTGGAGTGGATT<br>GGGAGTATCTATTATAGTGGGAGCACCTACTACAACCC<br>GTCCCTCAAGAGTCGAGTCACCATATCAGTAGACACGT<br>CCAAGAACCAGTTCTCCCTGAAGCTGAGCTCTGTGACC<br>GCCGCGGACACGGCCGTGTATTACTGTGCGAGAGAGT<br>ATTACGATTTTTGGAGTGGTTATTATACCACTACTTTGA<br>CTACTGGGGCCAGGGAACCCTGGTCACCGTCTCCTCAG<br>GCCTCCACCAAGGGCCCATCGGTCTTCCCCCTGGCACC<br>CTCCTCCAAGAGCACCTCTGGGGGCACAGCGGCCCTG<br>GGCTGCCTGGTCAAGGACTACTTCCCCGAACCGGTGAC<br>GGTGTCGTGGAACTCAGGCGCCCTGACCAGCGGCGTG<br>CACACCTTCCCGGCTGTCCTACAGTCCTCAGGACTCTA<br>CTCCCTCAGCAGCGTGGTGACCGTGCCCTCCAGCAGCT<br>TGGGCACCCAGACCTACATCTGCAACGTGAATCACAA<br>GCCCAGCAACACCAAGGTGGACAAGAAAGTT |
| | VL | 271 | GACATCCAGATGACCCAGTCTCCATCCTCCCTGTCTGC<br>ATCTGTAGGAGACAGAGTCACCATCACTTGCCAGGCG<br>AGTCAGGACATTAGCAACTATTTAAATTGGTATCAGCA<br>GAAACCAGGGAAAGCCCCTAAGCTCCTGATCTACGAT |

TABLE 6-continued lists exemplary reconstructed germline nucleic acid consensus sequences of variable heavy chain (VH) and exemplary reconstructed germline nucleic acid consensus sequences of variable light chain (VL)

| Name | Chain | SEQ ID NO: | Nucleic acid sequences |
|---|---|---|---|
| | | | GCATCCAATTTGGAAACAGGGGTCCCATCAAGGTTCA<br>GTGGAAGTGGATCTGGGACAGATTTTACTTTCACCATC<br>AGCAGCCTGCAGCCTGAAGATATTGCAACATATTACTG<br>TCAACAGTATGATAATCTCCCTCCATTCACTTTCGGCC<br>CTGGGACCAAAGTGGATATCAAACCGAACTGTGGCTG<br>CACCATCTGTCTTCATCTTCCCGCCATCTGATGAGCAG<br>TTGAAATCTGGAACTGCCTCTGTTGTGTGCCTGCTGAA<br>TAACTTCTATCCCAGAGAGGCCAAAGTACAGTGGAAG<br>GTGGATAACGCCCTCCAATCGGGTAACTCCCAGGAGA<br>GTGTCACAGAGCAGGACAGCAAGGACAGCACCTACAG<br>CCTCAGCAGCACCCTGACGCTGAGCAAAGCAGACTAC<br>GAGAAACACAAAGTCTACGCCTGCGAAGTCACCCATC<br>AGGGCCTGAGCTCGCCCGTCACAAAGAGCTTCAACAG<br>GGGAGAGTGT |
| TMEL1006 | VH | 258 | GAGGTGCAGCTGGTGGAGTCTGGGGGAGGCTTGGTAC<br>AGCCTGGGGGGTCCCTGAGACTCTCCTGTGCAGCCTCT<br>GGATTCACCTTTAGCAGCTATGCCATGAGCTGGGTCCG<br>CCAGGCTCCAGGGAAGGGGCTGGAGTGGGTCTCAGCT<br>ATTAGTGGTAGTGGTGGTAGCACATACTACGCAGACTC<br>CGTGAAGGGCCGGTTCACCATCTCCAGAGACAATTCCA<br>AGAACACGCTGTATCTGCAAATGAACAGCCTGAGAGC<br>CGAGGACACGGCCGTATATTACTGTGCGAAAGAAGGA<br>TATTGTAGTGGTGGTAGCTGCTACTCCGCTGAATACTT<br>CCAGCACTGGGGCCAGGGCACCCTGGTCACCGTCTCCT<br>CAGGCCTCCACCAAGGGCCCATCGGTCTTCCCCCTGGC<br>ACCCTCCTCCAAGAGCACCTCTGGGGGCACAGCGGCC<br>CTGGGCTGCCTGGTCAAGGACTACTTCCCCGAACCGGT<br>GACGGTGTCGTGGAACTCAGGCGCCCTGACCAGCGGC<br>GTGCACACCTTCCCGGCTGTCCTACAGTCCTCAGGACT<br>CTACTCCCTCAGCAGCGTGGTGACCGTGCCCTCCAGCA<br>GCTTGGGCACCCAGACCTACATCTGCAACGTGAATCAC<br>AAGCCCAGCAACACCAAGGTGGACAAGAAAGTT |
| | VL | 272 | GACATCCAGATGACCCAGTCTCCATCCTCCCTGTCTGC<br>ATCTGTAGGAGACAGAGTCACCATCACTTGCCAGGCG<br>AGTCAGGACATTAGCAACTATTTAAATTGGTATCAGCA<br>GAAACCAGGGAAAGCCCCTAAGCTCCTGATCTACGAT<br>GCATCCAATTTGGAAACAGGGGTCCCATCAAGGTTCA<br>GTGGAAGTGGATCTGGGACAGATTTTACTTTCACCATC<br>AGCAGCCTGCAGCCTGAAGATATTGCAACATATTACTG<br>TCAACAGTATGATAATCTCCCTCCGATCACCTTCGGCC<br>AAGGGACACGACTGGAGATTAAACCGAACTGTGGCTG<br>CACCATCTGTCTTCATCTTCCCGCCATCTGATGAGCAG<br>TTGAAATCTGGAACTGCCTCTGTTGTGTGCCTGCTGAA<br>TAACTTCTATCCCAGAGAGGCCAAAGTACAGTGGAAG<br>GTGGATAACGCCCTCCAATCGGGTAACTCCCAGGAGA<br>GTGTCACAGAGCAGGACAGCAAGGACAGCACCTACAG<br>CCTCAGCAGCACCCTGACGCTGAGCAAAGCAGACTAC<br>GAGAAACACAAAGTCTACGCCTGCGAAGTCACCCATC<br>AGGGCCTGAGCTCGCCCGTCACAAAGAGCTTCAACAG<br>GGGAGAGTGT |
| TMEL1007 | VH | 259 | CAGGTGCAGCTGGTGCAGTCTGGGGCTGAGGTGAAGA<br>AGCCTGGGTCCTCGGTGAAGGTCTCCTGCAAGGCTTCT<br>GGAGGCACCTTCAGCAGCTATGCTATCAGCTGGGTGCG<br>ACAGGCCCCTGGACAAGGGCTTGAGTGGATGGGAGGG<br>ATCATCCCTATCTTTGGTACAGCAAACTACGCACAGAA<br>GTTCCAGGGCAGAGTCACGATTACCGCGGACGAATCC<br>ACGAGCACAGCCTACATGGAGCTGAGCAGCCTGAGAT<br>CTGAGGACACGGCCGTGTATTACTGTGCGAGAGAGGT<br>ATAACTGGAACGACACTACTTTGACTACTGGGGCCAG<br>GGAACCCTGGTCACCGTCTCCTCAGGCCTCCACCAAGG<br>GCCCATCGGTCTTCCCCCTGGCACCCTCCTCCAAGAGC<br>ACCTCTGGGGGCACAGCGGCCCTGGGCTGCCTGGTCA<br>AGGACTACTTCCCCGAACCGGTGACGGTGTCGTGGAA<br>CTCAGGCGCCCTGACCAGCGGCGTGCACACCTTCCCGG<br>CTGTCCTACAGTCCTCAGGACTCTACTCCCTCAGCAGC<br>GTGGTGACCGTGCCCTCCAGCAGCTTGGGCACCCAGAC<br>CTACATCTGCAACGTGAATCACAAGCCCAGCAACACC<br>AAGGTGGACAAGAAAGTT |
| | VL | 273 | CAGTCTGCCCTGACTCAGCCTGCCTCCGTGTCTGGGTC<br>TCCTGGACAGTCGATCACCATCTCCTGCACTGGAACCA<br>GCAGTGATGTTGGGAGTTATAACCTTGTCTCCTGGTAC |

TABLE 6-continued lists exemplary reconstructed germline nucleic acid consensus sequences of variable heavy chain (VH) and exemplary reconstructed germline nucleic acid consensus sequences of variable light chain (VL)

| Name | Chain | SEQ ID NO: | Nucleic acid sequences |
|---|---|---|---|
| | | | CAACAGCACCCAGGCAAAGCCCCCAAACTCATGATTT ATGAGGTCAGTAAGCGGCCCTCAGGGGTTTCTAATCGC TTCTCTGGCTCCAAGTCTGGCAACACGGCCTCCCTGAC AATCTCTGGGCTCCAGGCTGAGGACGAGGCTGATTATT ACTGCTGCTCATATGCAGGTAGTAGCACTTTCTGTGGT ATTCGGCGGAGGGACCAAGCTGACCGTCCTAGGGTCA GCCCAAGGCTGCCCCCTCGGTCACTCTGTTCCCGCCCT CCTCTGAGGAGCTTCAAGCCAACAAGGCACACTGGT GTGTCTCATAAGTGACTTCTACCCGGGAGCCGTGACAG TGGCTTGGAAAGCAGATAGCAGCCCCGTCAAGGCGGG AGTGGAGACCACCACACCCTCCAAACAAAGCAACAAC AAGTACGCGGCCAGCAGCTATCTGAGCCTGACGCCTG AGCAGTGGAAGTCCCACAGAAGCTACAGCTGCCAGGT CACGCATGAAGGGAGCACCGTGGAGAAGACAGTGGCC CCTACAGAATGTTCA |
| TMEL1008 | VH | 260 | CAGGTCCAGCTGGTGCAGTCTGGGGCTGAGGTGAAGA AGCCTGGGTCCTCGGTGAAGGTCTCCTGCAAGGCTTCT GGAGGCACCTTCAGCAGCTATGCTATCAGCTGGGTGCG ACAGGCCCCTGGACAAGGGCTTGAGTGGATGGGAAGG ATCATCCCTATCCTTGGTATAGCAAACTACGCACAGAA GTTCCAGGGCAGAGTCACGATTACCGCGGACAAATCC ACGAGCACAGCCTACATGGAGCTGAGCAGCCTGAGAT CTGAGGACACGGCCGTGTATTACTGTGCGAGAGAGGT ATAGTGGGAGCTACTACATTACTACTACTACGGTA TGGACGTCTGGGGCCAAGGGACCACGGTCACCGTCTC CTCAGCCTCCACCAAGGGCCCATCGGTCTTCCCCCTGG CACCCTCCTCCAAGAGCACCTCTGGGGGCACAGCGGC CCTGGGCTGCCTGGTCAAGGACTACTTCCCCGAACCGG TGACGGTGTCGTGGAACTCAGGCGCCCTGACCAGCGG CGTGCACACCTTCCCGGCTGTCCTACAGTCCTCAGGAC TCTACTCCCTCAGCAGCGTGGTGACCGTGCCCTCCAGC AGCTTGGGCACCCAGACCTACATCTGCAACGTGAATCA CAAGCCCAGCAACACCAAGGTGGACAAGAAAGTT |
| | VL | 274 | CAGTCTGCCCTGACTCAGCCTGCCTCCGTGTCTGGGTC TCCTGGACAGTCGATCACCATCTCCTGCACTGGAACCA GCAGTGACGTTGGTGGTTATAACTATGTCTCCTGGTAC CAACAGCACCCAGGCAAAGCCCCCAAACTCATGATTT ATGAGGTCAGTAATCGGCCCTCAGGGGTTTCTAATCGC TTCTCTGGCTCCAAGTCTGGCAACACGGCCTCCCTGAC CATCTCTGGGCTCCAGGCTGAGGACGAGGCTGATTATT ACTGCAGCTCATATACAAGCAGCAGCACTCTCTTATGT CTTCGGAACTGGGACCAAGGTCACCGTCCTAGCCCAA GGCCAACCCCACGGTCACTCTGTTCCCGCCCTCCTCTG AGGAGCTCCAAGCCAACAAGGCCACACTAGTGTGTCT GATCAGTGACTTCTACCCGGGAGCTGTGACAGTGGCTT GGAAGGCAGATGGCAGCCCCGTCAAGGCGGGAGTGGA GACGACCAAACCCTCCAAACAGAGCAACAACAAGTAC GCGGCCAGCAGCTACCTGAGCCTGACGCCCGAGCAGT GGAAGTCCCACAGAAGCTACAGCTGCCAGGTCACGCA TGAAGGGAGCACCGTGGAGAAGACAGTGGCCCCTACA GAATGTTCA |
| TMEL1009 | VH | 261 | CAGGTGCAGCTGGTGCAGTCTGGGGCTGAGGTGAAGA AGCCTGGGTCCTCGGTGAAGGTCTCCTGCAAGGCTTCT GGAGGCACCTTCAGCAGCTATGCTATCAGCTGGGTGCG ACAGGCCCCTGGACAAGGGCTTGAGTGGATGGGAGGG ATCATCCCTATCTTTGGTACAGCAAACTACGCACAGAA GTTCCAGGGCAGAGTCACGATTACCGCGGACGAATCC ACGAGCACAGCCTACATGGAGCTGAGCAGCCTGAGAT CTGAGGACACGGCCGTGTATTACTGTGCGAGAGAGTG GATACAGCTATGGTTACTGATGCTTTTGATGTCTGGGG CCAAGGGACAATGGTCACCGTCTCTTCAGGCCTCCACC AAGGGCCCATCGGTCTTCCCCCTGGCACCCTCCTCCAA GAGCACCTCTGGGGGCACAGCGGCCCTGGGCTGCCTG GTCAAGGACTACTTCCCCGAACCGGTGACGGTGTCGTG GAACTCAGGCGCCCTGACCAGCGGCGTGCACACCTTCC CGGCTGTCCTACAGTCCTCAGGACTCTACTCCCTCAGC AGCGTGGTGACCGTGCCCTCCAGCAGCTTGGGCACCCA GACCTACATCTGCAACGTGAATCACAAGCCCAGCAAC ACCAAGGTGGACAAGAAAGTT |

TABLE 6-continued lists exemplary reconstructed germline nucleic acid consensus sequences of variable heavy chain (VH) and exemplary reconstructed germline nucleic acid consensus sequences of variable light chain (VL)

| Name | Chain | SEQ ID NO: | Nucleic acid sequences |
|---|---|---|---|
| | VL | 275 | GACATCCAGATGACCCAGTCTCCTTCCACCCTGTCTGC<br>ATCTGTAGGAGACAGAGTCACCATCACTTGCCGGGCC<br>AGTCAGAGTATTAGTAGCTGGTTGGCCTGGTATCAGCA<br>GAAACCAGGGAAAGCCCCTAAGCTCCTGATCTATGAT<br>GCCTCCAGTTTGGAAAGTGGGGTCCCATCAAGGTTCAG<br>CGGCAGTGGATCTGGGACAGAATTCACTCTCACCATCA<br>GCAGCCTGCAGCCTGATGATTTTGCAACTTATTACTGC<br>CAACAGTATAATAGTTATTCTCCTGTACACTTTTGGCC<br>AGGGGACCAAGCTGGAGATCAAACCGAACTGTGGCTG<br>CACCATCTGTCTTCATCTTCCCGCCATCTGATGAGCAG<br>TTGAAATCTGGAACTGCCTCTGTTGTGTGCCTGCTGAA<br>TAACTTCTATCCCAGAGAGGCCAAAGTACAGTGGAAG<br>GTGGATAACGCCCTCCAATCGGGTAACTCCCAGGAGA<br>GTGTCACAGAGCAGGACAGCAAGGACAGCACCTACAG<br>CCTCAGCAGCACCCTGACGCTGAGCAAAGCAGACTAC<br>GAGAAACACAAAGTCTACGCCTGCGAAGTCACCCATC<br>AGGGCCTGAGCTCGCCCGTCACAAAGAGCTTCAACAG<br>GGGAGAGTGT |
| TMEL1010 | VH | 262 | CAGGTTCAGCTGGTGCAGTCTGGAGCTGAGGTGAAGA<br>AGCCTGGGGCCTCAGTGAAGGTCTCCTGCAAGGCTTCT<br>GGTTACACCTTTACCAGCTATGGTATCAGCTGGGTGCG<br>ACAGGCCCCTGGACAAGGGCTTGAGTGGATGGGATGG<br>ATCAGCGCTTACAATGGTAACACAAACTATGCACAGA<br>AGCTCCAGGGCAGAGTCACCATGACCACAGACACATC<br>CACGAGCACAGCCTACATGGAGCTGAGGAGCCTGAGA<br>TCTGACGACACGGCCGTGTATTACTGTGCGAGAGATGA<br>CTACGGTGACTACACTACTTTGACTACTGGGGCCAGGG<br>AACCCTGGTCACCGTCTCCTCAGGCCTCCACCAAGGGC<br>CCATCGGTCTTCCCCCTGGCACCCTCCTCCAAGAGCAC<br>CTCTGGGGGCACAGCGGCCCTGGGCTGCCTGGTCAAG<br>GACTACTTCCCCGAACCGGTGACGGTGTCGTGGAACTC<br>AGGCGCCCTGACCAGCGGCGTGCACACCTTCCCGGCTG<br>TCCTACAGTCCTCAGGACTCTACTCCCTCAGCAGCGTG<br>GTGACCGTGCCCTCCAGCAGCTTGGGCACCCAGACCTA<br>CATCTGCAACGTGAATCACAAGCCCAGCAACACCAAG<br>GTGGACAAGAAAGTT |
| | VL | 276 | GAAATAGTGATGACGCAGTCTCCAGCCACCCTGTCTGT<br>GTCTCCAGGGGAAAGAGCCACCCTCTCCTGCAGGGCC<br>AGTCAGAGTGTTAGCAGCAACTTAGCCTGGTACCAGC<br>AGAAACCTGGCCAGGCTCCCAGGCTCCTCATCTATGGT<br>GCATCCACCAGGGCCACTGGTATCCCAGCCAGGTTCAG<br>TGGCAGTGGGTCTGGGACAGAGTTCACTCTCACCATCA<br>GCAGCCTGCAGTCTGAAGATTTTGCAGTTTATTACTGT<br>CAGCAGTATAATAACTGGCCTCCTGTACACTTTTGGCC<br>AGGGGACCAAGCTGGAGATCAAACCGAACTGTGGCTG<br>CACCATCTGTCTTCATCTTCCCGCCATCTGATGAGCAG<br>TTGAAATCTGGAACTGCCTCTGTTGTGTGCCTGCTGAA<br>TAACTTCTATCCCAGAGAGGCCAAAGTACAGTGGAAG<br>GTGGATAACGCCCTCCAATCGGGTAACTCCCAGGAGA<br>GTGTCACAGAGCAGGACAGCAAGGACAGCACCTACAG<br>CCTCAGCAGCACCCTGACGCTGAGCAAAGCAGACTAC<br>GAGAAACACAAAGTCTACGCCTGCGAAGTCACCCATC<br>AGGGCCTGAGCTCGCCCGTCACAAAGAGCTTCAACAG<br>GGGAGAGTGT |
| TMEL1011 | VH | 263 | CAGGTCCAGCTGGTGCAATCTGGGGCTGAGGTGAAGA<br>AGCCTGGGTCCTCGGTGAAGGTCTCCTGCAAGGCTTCT<br>GGAGGCACCTTCAGCAGCTATACTATCAGCTGGGTGCG<br>ACAGGCCCCTGGACAAGGGCTTGAGTGGATGGGAAGG<br>ATCATCCCTATCCTTGGTATAGCAAACTACGCACAGAA<br>GTTCCAGGGCAGAGTCACGATTACCGCGGACAAATCC<br>ACGAGCACAGCCTACATGGAGCTGAGCAGCCTGAGAT<br>CTGAGGACACGGCCGTGTATTACTGTGCGAGAGGTAC<br>AACTGGAACGACACAACTGGTTCGACCCCTGGGGCCA<br>GGGAACCCTGGTCACCGTCTCCTCAGGCCTCCACCAAG<br>GGCCCATCGGTCTTCCCCCTGGCACCCTCCTCCAAGAG<br>CACCTCTGGGGGCACAGCGGCCCTGGGCTGCCTGGTCA<br>AGGACTACTTCCCCGAACCGGTGACGGTGTCGTGGAA<br>CTCAGGCGCCCTGACCAGCGGCGTGCACACCTTCCCGG<br>CTGTCCTACAGTCCTCAGGACTCTACTCCCTCAGCAGC |

TABLE 6-continued lists exemplary reconstructed germline nucleic acid consensus sequences of variable heavy chain (VH) and exemplary reconstructed germline nucleic acid consensus sequences of variable light chain (VL)

| Name | Chain | SEQ ID NO: | Nucleic acid sequences |
|---|---|---|---|
| | | | GTGGTGACCGTGCCCTCCAGCAGCTTGGGCACCCAGAC CTACATCTGCAACGTGAATCACAAGCCCAGCAACACC AAGGTGGACAAGAAAGTT |
| | VL | 277 | AATTTTATGCTGACTCAGCCCCACTCTGTGTCGGAGTC TCCGGGGAAGACGGTAACCATCTCCTGCACCCGCAGC AGTGGCAGCATTGCCAGCAACTATGTGCAGTGGTACC AGCAGCGCCCGGGCAGTTCCCCCACCACTGTGATCTAT GAGGATAACCAAAGACCCTCTGGGGTCCCTGATCGGTT CTCTGGCTCCATCGACAGCTCCTCCAACTCTGCCTCCCT CACCATCTCTGGACTGAAGACTGAGGACGAGGCTGAC TACTACTGTCAGTCTTATGATAGCAGCAATCATTGGGT GTTCGGCGGAGGGACCAAGCTGACCGTCCTAGCCCAA GGCTGCCCCCTCGGTCACTCTGTTCCCACCCTCCTCTGA GGAGCTTCAAGCCAACAAGGCCACACTGGTGTGTCTC ATAAGTGACTTCTACCCGGGAGCCGTGACAGTTGCCTG GAAGGCAGATAGCAGCCCCGTCAAGGCGGGGGTGGAG ACCACCACACCCTCCAAACAAAGCAACAACAAGTACG CGGCCAGCAGCTACCTGAGCCTGACGCCTGAGCAGTG GAAGTCCCACAAAAGCTACAGCTGCCAGGTCACGCAT GAAGGGAGCACCGTGGAGAAGACAGTTGCCCCTACGG AATGTTCA |
| TMEL1012 | VH | 264 | CAGCTGCAGCTGCAGGAGTCGGGCCCAGGACTGGTGA AGCCTTCGGAGACCCTGTCCCTCACCTGCACTGTCTCT GGTGGCTCCATCAGCAGTAGTAGTTACTACTGGGGCTG GATCCGCCAGCCCCCAGGGAAGGGGCTGGAGTGGATT GGGAGTATCTATTATAGTGGGAGCACCTACTACAACCC GTCCCTCAAGAGTCGAGTCACCATATCCGTAGACACGT CCAAGAACCAGTTCTCCCTGAAGCTGAGCTCTGTGACC GCCGCAGACACGGCTGTGTATTACTGTGCGAGACAGG TATAACTGGAACTACACAACTGGTTCGACCCCTGGGGC CAGGGAACCCTGGTCACCGTCTCCTCAGGCCTCCACCA AGGGCCCATCGGTCTTCCCCCTGGCACCCTCCTCCAAG AGCACCTCTGGGGGCACAGCGGCCCTGGGCTGCCTGG TCAAGGACTACTTCCCCGAACCGGTGACGGTGTCGTGG AACTCAGGCGCCCTGACCAGCGGCGTGCACACCTTCCC GGCTGTCCTACAGTCCTCAGGACTCTACTCCCTCAGCA GCGTGGTGACCGTGCCCTCCAGCAGCTTGGGCACCCAG ACCTACATCTGCAACGTGAATCACAAGCCCAGCAACA CCAAGGTGGACAAGAAAGTT |
| | VL | 278 | TCCTATGTGCTGACTCAGCCACCCTCGGTGTCAGTGGC CCCAGGACAGACGGCCAGGATTACCTGTGGGGGAAAC AACATTGGAAGTAAAAGTGTGCACTGGTACCAGCAGA AGCCAGGCCAGGCCCCTGTGCTGGTCGTCTATGATGAT AGCGACCGGCCCTCAGGGATCCCTGAGCGATTCTCTGG CTCCAACTCTGGGAACACGGCCACCCTGACCATCAGCA GGGTCGAAGCCGGGGATGAGGCCGACTATTACTGTCA GGTGTGGGATAGTAGTAGTGATCATCCTGTGGTATTCG GCGGAGGGACCAAGCTGACCGTCCTAGGGTCAGCCCA AGGCTGCCCCCTCGGTCACTCTGTTCCCGCCCTCCTCTG AGGAGCTTCAAGCCAACAAGGCCACACTGGTGTGTCT CATAAGTGACTTCTACCCGGGAGCCGTGACAGTGGCTT GGAAAGCAGATAGCAGCCCCGTCAAGGCGGGAGTGGA GACCACCACACCCTCCAAACAAAGCAACAACAAGTAC GCGGCCAGCAGCTATCTGAGCCTGACGCCTGAGCAGT GGAAGTCCCACAGAAGCTACAGCTGCCAGGTCACGCA TGAAGGGAGCACCGTGGAGAAGACAGTGGCCCCTACA GAATGTTCA |
| TMEL1013 | VH | 265 | CAGGTCCAGCTGGTGCAATCTGGGGCTGAGGTGAAGA AGCCTGGGTCCTCGGTGAAGGTCTCCTGCAAGGCTTCT GGAGGCACCTTCAGCAGCTATACTATCAGCTGGGTGCG ACAGGCCCCTGGACAAGGGCTTGAGTGGATGGGAAGG ATCATCCCTATCCTTGGTACAGCAAACTACGCACAGAA GTTCCAGGGCAGAGTCACGATTACCGCGGACAAATCC ACGAGCACAGCCTACATGGAGCTGAGCAGCCTGAGAT CTGAGGACACGGCCGTGTATTACTGTGCGAGAGAGGT ATAGTGGGAGCTACTACACTACTTTGACTACTGGGGCC AGGGAACCCTGGTCACCGTCTCCTCAGGCCTCCACCAA GGGCCCATCGGTCTTCCCCCTGGCACCCTCCTCCAAGA GCACCTCTGGGGGCACAGCGGCCCTGGGCTGCCTGGTC AAGGACTACTTCCCCGAACCGGTGACGGTGTCGTGGA ACTCAGGCGCCCTGACCAGCGGCGTGCACACCTTCCCG |

TABLE 6-continued lists exemplary reconstructed germline nucleic acid consensus sequences of variable heavy chain (VH) and exemplary reconstructed germline nucleic acid consensus sequences of variable light chain (VL)

| Name | Chain | SEQ ID NO: | Nucleic acid sequences |
|---|---|---|---|
| | VL | 279 | GCTGTCCTACAGTCCTCAGGACTCTACTCCCTCAGCAG CGTGGTGACCGTGCCCTCCAGCAGCTTGGGCACCCAGA CCTACATCTGCAACGTGAATCACAAGCCCAGCAACAC CAAGGTGGACAAGAAAGTT GAAATTGTGTTGACGCAGTCTCCAGGCACCCTGTCTTT GTCTCCAGGGGAAAGAGCCACCCTCTCCTGCAGGGCC AGTCAGAGTGTTAGCAGCAGCTACTTAGCCTGGTACCA GCAGAAACCTGGCCAGGCTCCCAGGCTCCTCATCTATG GTGCATCCAGCAGGGCCACTGGCATCCCAGACAGGTT CAGTGGCAGTGGGTCTGGGACAGACTTCACTCTCACCA TCAGCAGACTGGAGCCTGAAGATTTTGCAGTGTATTAC TGTCAGCAGTATGGTAGCTCACCTCCTGTACACTTTTG GCCAGGGGACCAAGCTGGAGATCAAACCGAACTGTGG CTGCACCATCTGTCTTCATCTTCCCGCCATCTGATGAGC AGTTGAAATCTGGAACTGCCTCTGTTGTGTGCCTGCTG AATAACTTCTATCCCAGAGAGGCCAAAGTACAGTGGA AGGTGGATAACGCCCTCCAATCGGGTAACTCCCAGGA GAGTGTCACAGAGCAGGACAGCAAGGACAGCACCTAC AGCCTCAGCAGCACCCTGACGCTGAGCAAAGCAGACT ACGAGAAACACAAAGTCTACGCCTGCGAAGTCACCCA TCAGGGCCTGAGCTCGCCCGTCACAAAGAGCTTCAAC AGGGGAGAGTGT |
| TMEL1014 | VH | 266 | CAGGTGCAGCTGGTGGAGTCTGGGGGAGGCGTGGTCC AGCCTGGGAGGTCCCTGAGACTCTCCTGTGCAGCCTCT GGATTCACCTTCAGTAGCTATGCTATGCACTGGGTCCG CCAGGCTCCAGGCAAGGGGCTGGAGTGGGTGGCAGTT ATATCATATGATGGAAGCAATAAATACTACGCAGACT CCGTGAAGGGCCGATTCACCATCTCCAGAGACAATTCC AAGAACACGCTGTATCTGCAAATGAACAGCCTGAGAG CTGAGGACACGGCTGTGTATTACTGTGCGAGAGAGTAT TATGATTTTTGGACTGGTTATTATACCACTACTTTGACT ACTGGGGCCAGGGAACCCTGGTCACCGTCTCCTCAGGC CTCCACCAAGGGCCCATCGGTCTTCCCCCTGGCGCCCT GCTCCAGGAGCACCTCCGAGAGCACAGCCGCCCTGGG CTGCCTGGTCAAGGACTACTTCCCCGAACCGGTGACGG TGTCGTGGAACTCAGGCGCTCTGACCAGCGGCGTGCAC ACCTTCCCAGCTGTCCTACAGTCCTCAGGACTCTACTC CCTCAGCAGCGTGGTGACCGTGCCCTCCAGCAACTTCG GCACCCAGACCTACACCTGCAACGTAGATCACAAGCC CAGCAACACCAAGGTGGACAAGACAGTT |
| | VL | 280 | TCTTCTGAGCTGACTCAGGACCCTGCTGTGTCTGTGGC CTTGGGACAGACAGTCAGGATCACATGCCAAGGAGAC AGCCTCAGAAGCTATTATGCAAGCTGGTACCAGCAGA AGCCAGGACAGGCCCCTGTACTTGTCATCTATGGTAAA AACAACCGGCCCTCAGGGATCCCAGACCGATTCTCTGG CTCCAGCTCAGGAAACACAGCTTCCTTGACCATCACTG GGGCTCAGGCGGAAGATGAGGCTGACTATTACTGTAA CTCCCGGGACAGCAGTGGTAACCATCTTTGGGTGTTCG GCGGAGGGACCAAGCTGACCGTCCTAGCCCAAGGCTG CCCCCTCGGTCACTCTGTTCCCACCCTCCTCTGAGGAG CTTCAAGCCAACAAGGCCACACTGGTGTGTCTCATAAG TGACTTCTACCCGGGAGCCGTGACAGTTGCCTGGAAGG CAGATAGCAGCCCCGTCAAGGCGGGGGTGGAGACCAC CACACCCTCCAAACAAAGCAACAACAAGTACGCGGCC AGCAGCTACCTGAGCCTGACGCCTGAGCAGTGGAAGT CCCACAAAAGCTACAGCTGCCAGGTCACGCATGAAGG GAGCACCGTGGAGAAGACAGTTGCCCCTACGGAATGT TCA |

Table 7 Lists Exemplary Heavy and Light Chain Pairings

| | SEQ ID NOs: | | | | | | | |
|---|---|---|---|---|---|---|---|---|
| | Variable Region | | CDR3 | | CDR2 | | CDR1 | |
| Name | Heavy Chain (VH) | Light Chain (VL) | Heavy Chain (CDR-H3) | Light chain (CDR-L3) | Heavy Chain (CDR-H2) | Light chain (CDR-L2) | Heavy Chain (CDR-H1) | Light chain (CDR-L1) |
| TMEL 1001 | 1 | 15 | 29 | 43 | 57 | 71 | 85 | 99 |
| TMEL 1002 | 2 | 16 | 30 | 44 | 58 | 72 | 86 | 100 |
| TMEL 1003 | 3 | 17 | 31 | 45 | 59 | 73 | 87 | 101 |
| TMEL 1004 | 4 | 18 | 32 | 46 | 60 | 74 | 88 | 102 |
| TMEL 1005 | 5 | 19 | 33 | 47 | 61 | 75 | 89 | 103 |
| TMEL 1006 | 6 | 20 | 34 | 48 | 62 | 76 | 90 | 104 |
| TMEL 1007 | 7 | 21 | 35 | 49 | 63 | 77 | 91 | 105 |
| TMEL 1008 | 8 | 22 | 36 | 50 | 64 | 78 | 92 | 106 |
| TMEL 1009 | 9 | 23 | 37 | 51 | 65 | 79 | 93 | 107 |
| TMEL 1010 | 10 | 24 | 38 | 52 | 66 | 80 | 94 | 108 |
| TMEL 1011 | 11 | 25 | 39 | 53 | 67 | 81 | 95 | 109 |
| TMEL 1012 | 12 | 26 | 40 | 54 | 68 | 82 | 96 | 110 |
| TMEL 1013 | 13 | 27 | 41 | 55 | 69 | 83 | 97 | 111 |
| TMEL 1014 | 14 | 28 | 42 | 56 | 70 | 84 | 98 | 112 |

What is claimed is:

1. An antibody or antigen-binding fragment thereof comprising:
   a complementarity-determining region heavy chain 1 (CDR-H1), a CDR-H2 and a CDR-H3, wherein the CDR-H1 comprises the reconstructed polypeptide consensus sequence set out in SEQ ID NO: 95, the CDR-H2 comprises the reconstructed polypeptide consensus sequence set out in SEQ ID NO: 67, and the CDR-H3 comprises the reconstructed polypeptide consensus sequence set out in SEQ ID NO: 39; and
   a complementarity-determining region light chain 1 (CDR-L1), a CDR-L2 and a CDR-L3, wherein the CDR-L1 comprises the reconstructed polypeptide consensus sequence set out in SEQ ID NO: 109, the CDR-L2 comprises the reconstructed polypeptide consensus sequence set out in SEQ ID NO: 81, and the CDR-L3 comprises the reconstructed polypeptide consensus sequence set out in SEQ ID NO: 53.

2. The antibody or antigen-binding fragment thereof of claim 1, wherein the antibody is an IgG, IgA, or IgM antibody.

3. The antibody or antigen-binding fragment thereof of claim 2, wherein the IgG is IgG1, IgG2, IgG3, IgG4, IgA1, or IgA2.

4. The antibody or antigen-binding fragment thereof of claim 1, wherein the antibody is a chimeric antibody, a humanized antibody, a monoclonal antibody, a deimmunized antibody, a bispecific antibody, a multispecific antibody, a multivalent antibody, or a combination thereof.

5. The antibody or antigen-binding fragment thereof of claim 1, wherein the antigen-binding fragment comprises a Fab, Fab', Fab'-SH, Fv, scFv, F(ab')2, a diabody, or a linear antibody.

6. The antibody or antigen-binding fragment thereof of claim 1, wherein the antibody or antigen-binding fragment thereof is recombinant or synthetic.

7. The antibody or antigen-binding fragment thereof of claim 1, wherein the antibody or antigen-binding fragment thereof further comprises an enzyme, a substrate, cofactor, a fluorescent marker, a chemiluminescent marker, a peptide tag, a magnetic particle, a drug, a toxin, a radionuclide, a binding site for secondary antibodies, a metal binding domain, or a combination thereof.

8. The An antibody or antigen-binding fragment of claim 1 thereof comprising:
   (a) a variable heavy chain, wherein the variable heavy chain comprises a reconstructed polypeptide consensus sequence having at least 95% identity to the amino acid sequence set out in SEQ ID NO: 11;
   (b) a variable light chain, wherein the variable light chain comprises a reconstructed polypeptide consensus sequence having at least 95% sequence identity to the amino acid sequence set out in SEQ ID NO: 25; or
   (c) the variable heavy chain as in (a) and the variable light chain as in (b).

9. A hybridoma that produces the antibody or antigen-binding fragment thereof of claim 1.

10. A pharmaceutical composition or a medicament comprising the antibody or antigen-binding fragment thereof of claim 1 and a pharmaceutically acceptable carrier.

11. The pharmaceutical composition of claim 10, further comprising a second therapeutic agent.

12. The pharmaceutical composition of claim 11, wherein the second therapeutic agent comprises an anti-cancer agent, a cytotoxic agent, a NSAID, a corticosteroid, a dietary supplement such as an antioxidant, or a combination thereof.

13. The pharmaceutical composition of claim 12, wherein the anti-cancer agent is an anti-cancer antibody or a chemotherapeutic agent.

14. A method for treating a subject suffering from a cancer associated with IL-14A, the method comprising administering to the subject a therapeutically effective amount of the antibody or antigen-binding fragment thereof of claim 1.

15. An isolated nucleic acid molecule comprising at least one of;
   (a) a nucleic acid sequence encoding a CDR-H1, wherein the nucleic acid sequence is set out in SEQ ID NO: 207;
   (b) a nucleic acid sequence encoding a CDR-H2, wherein the nucleic acid sequence is set out in SEQ ID NO: 179;
   (c) a nucleic acid sequence encoding a CDR-H3, wherein the nucleic acid sequence is set out in SEQ ID NO: 151;
   (d) a nucleic acid sequence encoding a CDR-L1, wherein the nucleic acid sequence is set out in SEQ ID NO: 221;
   (e) a nucleic acid sequence encoding a CDR-L2, wherein the nucleic acid sequence is set out in SEQ ID NO: 193; and
   (f) a nucleic acid sequence encoding a CDR-L3, wherein the nucleic acid sequence is set out in SEQ ID NO: 165.

16. An isolated nucleic acid molecule comprising a nucleic acid sequence encoding a heavy chain polypeptide of an antibody, wherein the nucleic acid sequence is set out in SEQ ID NO: 123.

17. An isolated nucleic acid molecule comprising a nucleic acid sequence encoding a light chain polypeptide of an antibody, wherein the nucleic acid sequence is set out in SEQ ID NO: 137.

\* \* \* \* \*